United States Patent
Jang et al.

(10) Patent No.: US 9,640,766 B2
(45) Date of Patent: May 2, 2017

(54) ORGANIC LIGHT EMITTING DIODE

(71) Applicant: LG CHEM, LTD., Seoul (KR)

(72) Inventors: Boonjae Jang, Daejeon (KR); Dong Hoon Lee, Daejeon (KR); Jungoh Huh, Daejeon (KR); Minyoung Kang, Daejeon (KR); Dong Uk Heo, Daejeon (KR); Miyeon Han, Daejeon (KR); Min Woo Jung, Daejeon (KR); Wooyung Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/769,717

(22) PCT Filed: Apr. 2, 2015

(86) PCT No.: PCT/KR2015/003273
§ 371 (c)(1),
(2) Date: Aug. 21, 2015

(87) PCT Pub. No.: WO2015/152644
PCT Pub. Date: Oct. 8, 2015

(65) Prior Publication Data
US 2016/0276596 A1     Sep. 22, 2016

(30) Foreign Application Priority Data

| Apr. 4, 2014 | (KR) | 10-2014-0040818 |
| Jan. 23, 2015 | (KR) | 10-2015-0011540 |
| Jan. 23, 2015 | (KR) | 10-2015-0011559 |

(51) Int. Cl.
*H01L 51/50* (2006.01)
*H01L 51/00* (2006.01)
(Continued)

(52) U.S. Cl.
CPC ........ *H01L 51/0067* (2013.01); *C07C 255/51* (2013.01); *C07D 209/86* (2013.01); *C07D 251/12* (2013.01); *C07D 251/24* (2013.01); *C09K 11/025* (2013.01); *C09K 11/06* (2013.01); *H01B 1/04* (2013.01); *H01L 51/005* (2013.01); *H01L 51/006* (2013.01); *H01L 51/0052* (2013.01); *H01L 51/0054* (2013.01); *H01L 51/0056* (2013.01); *H01L 51/0058* (2013.01); *H01L 51/0061* (2013.01);
(Continued)

(58) Field of Classification Search
None
See application file for complete search history.

(56) References Cited

U.S. PATENT DOCUMENTS

| 6,821,643 B1 * | 11/2004 | Hu | C09K 11/06 |
| | | | 252/301.23 |
| 2005/0221124 A1 * | 10/2005 | Hwang | C07F 9/5728 |
| | | | 428/690 |

(Continued)

FOREIGN PATENT DOCUMENTS

| KR | 10-2011-0085174 A | 7/2011 |
| KR | 10-2014-0008126 A | 1/2014 |
| WO | 2009/072587 A1 | 6/2009 |
| WO | 2010/126270 A1 | 11/2010 |
| WO | 2011/021520 A1 | 2/2011 |

*Primary Examiner* — Gregory Clark
(74) *Attorney, Agent, or Firm* — Dentons US LLP

(57) ABSTRACT

The present specification relates to an organic light emitting diode having high light emitting efficiency.

24 Claims, 4 Drawing Sheets

(51) Int. Cl.
*C07D 251/12* (2006.01)
*C09K 11/06* (2006.01)
*H01B 1/04* (2006.01)
*C07C 255/51* (2006.01)
*C07D 209/86* (2006.01)
*C07D 251/24* (2006.01)
*C09K 11/02* (2006.01)

(52) U.S. Cl.
CPC ...... H01L 51/0072 (2013.01); H01L 51/5004 (2013.01); *C07C 2101/02* (2013.01); *C09K 2211/1007* (2013.01); *C09K 2211/1011* (2013.01); *C09K 2211/1014* (2013.01); *C09K 2211/1059* (2013.01); *C09K 2211/1092* (2013.01); *H01L 51/5012* (2013.01); *H01L 51/5016* (2013.01); *H01L 51/5072* (2013.01); *H01L 51/5092* (2013.01); *H01L 2251/552* (2013.01)

(56) References Cited

U.S. PATENT DOCUMENTS

| | | |
|---|---|---|
| 2009/0160323 A1 | 6/2009 | Nomura et al. |
| 2012/0146014 A1 | 6/2012 | Kato |
| 2013/0248830 A1 | 9/2013 | Welsh et al. |
| 2014/0014927 A1 | 1/2014 | Kim et al. |

* cited by examiner

ORGANIC LIGHT EMITTING DIODE

This application is a National Stage Entry of International Application No. PCT/KR2015/003273, filed Apr. 2, 2015, which claims the benefit of priority of Korean Application No. 10-2014-0040818, filed Apr. 4, 2014, Korean Application No. 10-2015-0011540, filed Jan. 23, 2015, and Korean Application No. 10-2015-0011559, filed Jan. 23, 2015, all of which are incorporated by reference in their entirety for all purposes as if fully set forth herein.

TECHNICAL FIELD

The present specification relates to an organic light emitting diode.

BACKGROUND ART

An organic light emission phenomenon is one of the examples of converting current into visible rays through an internal process of a specific organic molecule. The principle of the organic light emission phenomenon is as follows.

When an organic material layer is disposed between an anode and a cathode, if voltage is applied between the two electrodes, electrons and holes are injected from the cathode and the anode, respectively, into the organic material layer. The electrons and the holes which are injected into the organic material layer are recombined to form an exciton, and the exciton falls down again to the ground state to emit light. An organic light emitting diode using this principle may be composed of a cathode, an anode, and an organic material layer disposed therebetween, for example, an organic material layer including a hole injection layer, a hole transporting layer, a light emitting layer, and an electron transporting layer.

The materials used in the organic light emitting diode are mostly pure organic materials or complex compounds in which organic materials and metals form a complex, and may be classified into a hole injection material, a hole transporting material, a light emitting material, an electron transporting material, an electron injection material, and the like according to the use thereof. Here, an organic material having a p-type property, that is, an organic material, which is easily oxidized and electrochemically stable when the material is oxidized, is usually used as the hole injection material or the hole transporting material. Meanwhile, an organic material having an n-type property, that is, an organic material, which is easily reduced and electrochemically stable when the material is reduced, is usually used as the electron injection material or the electron transporting material. As the light emitting layer material, a material having both p-type and n-type properties, that is, a material, which is stable during both the oxidation and reduction states, is preferred, and when an exciton is formed, a material having high light emitting efficiency for converting the exciton into light is preferred.

There is a need for developing an organic light emitting diode having high efficiency in the art.

CITATION LIST

[Patent Document]

Official Gazette of Korean Patent Application Laid-Open No. 2000-0051826

DETAILED DESCRIPTION OF THE INVENTION

Technical Problem

An object of the present specification is to provide an organic light emitting diode having high light emitting efficiency and/or low driving voltage.

Technical Solution

The present specification provides an organic light emitting diode including: a cathode; an anode; a light emitting layer provided between the cathode and the anode; an organic material layer including a heterocyclic compound represented by the following Formula 1 and provided between the cathode and the light emitting layer; and an organic material layer including a carbazole derivative represented by the following Formula 3 and provided between the anode and the light emitting layer.

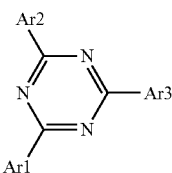

[Formula 1]

in Formula 1,

Ar1 to Ar3 are different from each other,

Ar1 and Ar2 are each independently a substituted or unsubstituted aryl group; or a substituted or unsubstituted heterocyclic group, Ar3 is represented by the following Formula 2,

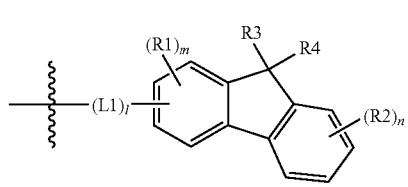

[Formula 2]

in Formula 2,

R1 to R4 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted hydrocarbon ring or a substituted or unsubstituted hetero ring, L1 is a direct bond; a substituted or unsubstituted arylene group; or a substituted or unsubstituted divalent heterocyclic group, l is an integer of 1 to 5, m is an integer of 1 to 3, n is an integer of 1 to 4, and when l, m, and n are each an integer of 2 or more, two or more structures in the parenthesis are the same as or different from each other,

[Formula 3]

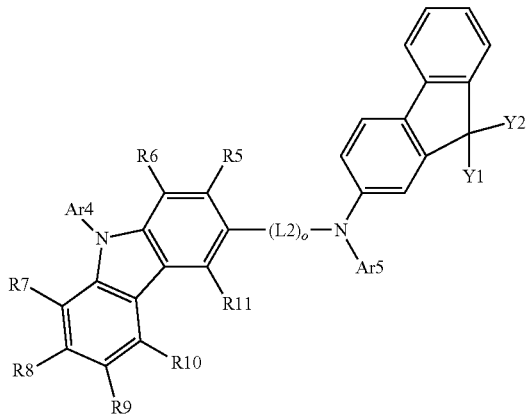

in Formula 3.

Ar4 and Ar5 are the same as or different from each other, and hydrogen; deuterium; a substituted or unsubstituted aryl group; or a substituted or unsubstituted heterocyclic group, L2 is a direct bond; or a substituted or unsubstituted arylene group, o is an integer of 0 to 5, and when o is an integer of 2 or more, two or more L2's are the same as or different from each other, R5 to R11 are the same as or different from each other, and each independently hydrogen; deuterium; a substituted or unsubstituted alkyl group; a substituted or unsubstituted aryl group, or a substituted or unsubstituted heterocyclic group, or combine with an adjacent group to form a substituted or unsubstituted hydrocarbon ring or a substituted or unsubstituted hetero ring, and Y1 and Y2 are the same as or different from each other, and each independently hydrogen; deuterium; a substituted or unsubstituted alkyl group; a substituted or unsubstituted aryl group; or a substituted or unsubstituted heterocyclic group, or Y1 and Y2 combine with each other to form a substituted or unsubstituted hydrocarbon ring or a substituted or unsubstituted hetero ring.

Advantageous Effects

The organic light emitting diode according to an exemplary embodiment of the present specification provides low driving voltage and/or high light emitting efficiency.

EXPLANATION OF REFERENCE NUMERALS AND SYMBOLS

Figure 1:
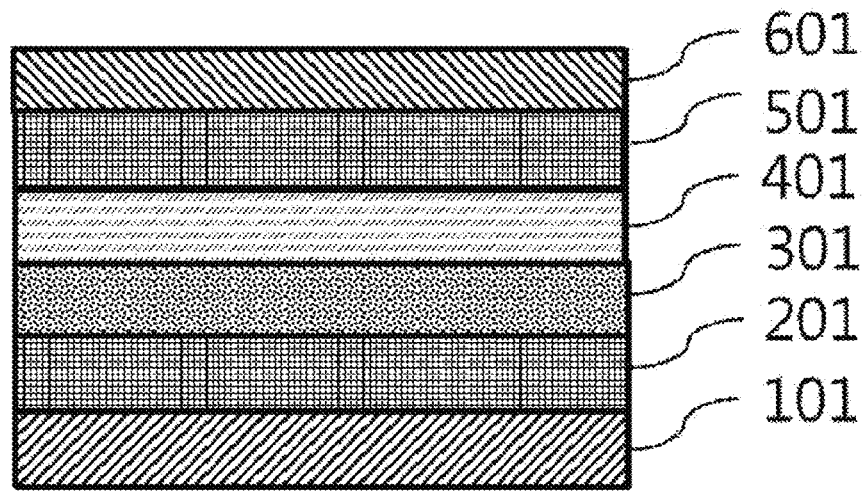
FIG. 1 is a view illustrating an organic light emitting diode according to an exemplary embodiment of the present specification.

101: Substrate
201: Anode
301: Hole transporting layer
401: Light emitting layer
501: Electron transporting layer
601: Cathode
701: Acceptor layer

BEST MODE

Hereinafter, the present specification will be described in more detail.

When one member is disposed "on" another member in the present specification, this includes not only a case where the one member is in contact with the another member, but also a case where still another member is present between the two members.

When one part "includes" one constituent element in the present specification, unless otherwise specifically described, this does not mean that another constituent element is excluded, but means that another constituent element may be further included.

The present specification provides an organic light emitting diode including: a cathode; an anode; a light emitting layer provided between the cathode and the anode; an organic material layer including the heterocyclic compound represented by the Formula 1 and provided between the cathode and the light emitting layer; and an organic material layer including the carbazole derivative represented by Formula 3 and provided between the anode and the light emitting layer.

In an exemplary embodiment of the present specification, the organic material layer including the heterocyclic compound represented by Formula 1 is an electron transporting layer, an electron injection layer, or a layer which simultaneously transports and injects electrons.

In an exemplary embodiment of the present specification, the organic material layer including the heterocyclic compound represented by Formula 1 is an electron transporting layer.

In an exemplary embodiment of the present specification, the organic material layer including the carbazole derivative represented by Formula 3 is a hole transporting layer, a hole injection layer, or a layer which simultaneously transports and injects holes.

In another exemplary embodiment, the organic material layer including the carbazole derivative represented by Formula 3 is a hole transporting layer.

In an exemplary embodiment of the present specification, the organic light emitting diode emits blue fluorescent light.

In an exemplary embodiment of the present specification, the HOMO energy level of the heterocyclic compound represented by Formula 1 is 6 eV or more. In an exemplary embodiment of the present specification, the HOMO energy level of the heterocyclic compound represented by Formula 1 is 6.0 eV or more and 7.0 eV or less. According to an exemplary embodiment of the present specification, in the case of having a deep HOMO energy level as in the compound represented by Formula 1, holes may be effectively blocked from a light emitting layer, and thus, high light emitting efficiency may be provided, and the stability of the diode may be improved, and thus, a diode having a long service life may be provided.

In an exemplary embodiment of the present specification, the light emitting layer includes a host and a dopant, and the difference between the HOMO energy level of the host and the HOMO energy level of the heterocyclic compound represented by Formula 1 is 0.2 eV or more. As described above, when the difference in HOMO energy level between the host material of the light emitting layer and the heterocyclic compound represented by Formula 1 is 0.2 eV or more, holes may be further effectively blocked from the light emitting layer, and thus, it is possible to provide an organic light emitting diode having high light emitting efficiency and a long service life.

In an exemplary embodiment of the present specification, an organic material layer including the heterocyclic compound represented by Formula 1 is provided to be adjacent to the light emitting layer. In this case, holes may be effectively blocked by having a deeper HOMO energy level than that of the host compound of the light emitting layer.

In the case of an organic light emitting diode which emits blue fluorescent light as in an exemplary embodiment of the present specification, an anthracene derivative is usually used as a host material, and in this case, the host material has a HOMO energy level of less than 6 eV. Accordingly, when an organic material layer including the heterocyclic compound represented by Formula 1 is provided between the cathode and the light emitting layer, it is possible to simultaneously play a role of blocking a hole along with the transfer of an electron.

In the present specification, the energy level means the size of energy. Accordingly, even when the energy level is expressed in the negative (−) direction from the vacuum level, it is interpreted that the energy level means an absolute value of the corresponding energy value. For example, the HOMO energy level means the distance from the vacuum level to the highest occupied molecular orbital.

In an exemplary embodiment of the present specification, the HOMO level may be measured by using an atmospheric pressure photoelectron spectrometer AC3 (manufactured by Riken Keiki Co., Ltd.). Specifically, the HOMO level may be measured by irradiating light on a material, and measuring the amount of electron produced due to separation of a charge at that time.

In an exemplary embodiment of the present specification, the triplet energy of the heterocyclic compound represented by Formula 1 is 2.2 eV or more.

According to an exemplary embodiment of the present specification, in the case of including the heterocyclic compound represented by Formula 1, which has the triplet energy in various ranges, it is possible to expect a diode having high efficiency and/or a long service life by effectively blocking the triplet exciton of the light emitting layer in the organic light emitting diode.

In an exemplary embodiment of the present specification, the light emitting layer includes a host and a dopant, and the triplet energy of the heterocyclic compound represented by Formula 1 is larger than that of the host.

In the case of having a larger triplet energy than the triplet energy of the host compound of the light emitting layer, it is possible to effectively block the triplet excitons of the light emitting layer. Specifically, since anthracene host derivatives of the light emitting layer generally used have a triplet energy level of less than 1.9 eV and the organic material layer including the compound represented by Formula 1 between the cathode and the light emitting layer has a triplet energy level of 2.2 eV or more, an effect of blocking the triplet excitons is high, and thus the diode efficiency may be improved. All of the following compounds [ET-A], [ET-B], [ET-D], and [ET-J], which are the anthracene derivatives suggested as the Comparative Examples to be described below, have a triplet energy of less than 1.9 eV, and it can be confirmed that the compound having a low triplet energy has low diode efficiency. This is because an effect of the triplet-triplet annihilation (TTA) is reduced when a compound having a triplet energy of less than 2.2 eV is used.

In an exemplary embodiment of the present specification, when a plurality of layers is provided between the cathode and the light emitting layer, the organic material layer including the heterocyclic compound represented by Formula 1 is provided to be relatively adjacent to the light emitting layer. In this case, the triplet excitons may be more effectively blocked.

In an exemplary embodiment of the present specification, the triplet energy ($E_T$) may be measured by using the low temperature photoluminescence method. The triplet energy may be obtained by measuring the $\lambda_{edge}$ value and using the following conversion formula.

$$E_T(eV)=1239.85/(\lambda_{edge})$$

When a phosphorescence spectrum is expressed by taking the phosphorescence intensity in the longitudinal axis and the wavelength in the lateral axis, "$\lambda_{edge}$" in the conversion formula means a wavelength value of a cross-section of a tangent line and the lateral axis by drawing the tangent line with respect to an increase at the short wavelength side of the phosphorescence spectrum, and the unit thereof is nm.

In another exemplary embodiment of the present specification, the triplet energy ($E_T$) may also be obtained by the quantum chemical calculation. The quantum chemical calculation may be performed by using a quantum chemical calculation program Gaussian 03 manufactured by U.S. Gaussian Corporation. In the calculation, the density functional theory (DFT) is used, and a calculated value of the triplet energy may be obtained by the time-dependent-density functional theory (TD-DFT) with respect to a structure optimized using B3LYP as a functional and 6-31G* as a basis function.

In another exemplary embodiment of the present specification, the phosphorescence spectrum is not observed in a specific organic compound in some cases, and in the organic compound, it is possible to assume and use the triplet energy ($E_T$) obtained by using the quantum chemical calculation as shown above.

In an exemplary embodiment of the present specification, the dipole moment of the heterocyclic compound represented by Formula 1 is 2 debye or less. Preferably, the dipole moment of the heterocyclic compound represented by Formula 1 is 1 debye or less.

The dipole moment in the present specification is a physical quantity which indicates the degree of polarity, and may be calculated by the following Equation 1.

$$p(r) = \int_V \rho(r_0)(r_0 - r)d^3 r_0 \qquad \text{[Equation 1]}$$

ρ (r₀): molecular density
V: volume
r: the point of observation
d³r₀: an elementary volume The value of the dipole moment may be obtained by calculating the molecular density in Equation 1. For example, the molecular density may be obtained by using a method called Hirshfeld Charge Analysis to obtain a charge and a dipole for each atom and performing the calculation according to the following equations, and the dipole moment may be obtained by substituting Equation 1 with the calculation result.

Weight Function $$W_\alpha(r) = \rho_\alpha(r - R_\alpha)\left[\sum_\beta \rho_\beta(r - R_\beta)\right]^{-1}$$

$\rho_\alpha(r - R_\alpha)$: spherically averaged ground-state amomic density $\sum_\beta \rho_\beta(r - R_\beta)$: promolecule density Deformation Density $$\rho_d(r) = \rho(r) - \sum_\alpha \rho_\alpha(r - R_\alpha)$$

$\rho(r)$: molecular density $\rho_\alpha(r - R_\alpha)$: density of the free atom $\alpha$ located at coordinates $R_\alpha$ Atomic Charge $$q(\alpha) = -\int \rho_d(r) W_\alpha(r) d^3 r$$

$W_\alpha(r)$: weight function

The organic light emitting diode, which includes the organic material layer including the compound having the aforementioned dipole moment value range, has an improved capability of transporting electrons or holes injected from an organic material layer such as an adjacent electron injection layer or an adjacent hole injection layer. Accordingly, it is possible to provide an organic light emitting diode having low driving voltage and high light emitting efficiency. Further, the arrangement of the molecules in the organic light emitting diode is excellent, thereby providing a dense and compact film. Accordingly, an organic light emitting diode including the electron transporting material is excellent in stability, and thus, may provide an organic light emitting diode having a long service life.

According to an exemplary embodiment of the present specification, when the organic material layer including the compound having the aforementioned dipole moment value range further includes the above-described n-type dopant, the dipole moment of the organic material layer may be greatly increased and a capability of injecting and transporting electrons from the cathode may be improved, thereby providing an organic light emitting diode having low driving voltage and/or high light emitting efficiency.

Accordingly, an organic light emitting diode, which satisfies the dipole moment value range according to an exemplary embodiment of the present specification and includes the heterocyclic compound represented by Formula 1, may provide an organic light emitting diode having a long service life, which is highly stable and efficient.

In an exemplary embodiment of the present specification, the electron mobility of the heterocyclic compound represented by Formula 1 is $10^{-6}$ cm²/Vs or more.

In another exemplary embodiment, the electron mobility of the heterocyclic compound represented by Formula 1 is $10^{-6}$ cm²/Vs or more under an electric field condition of 0.1 to 0.5 MV/cm. In still another exemplary embodiment, the electron mobility of the heterocyclic compound represented by Formula 1 is $10^{-6}$ cm²/Vs or more under an electric field condition of 0.1 MV/cm. In this case, the number of excitons produced in the light emitting layer is increased, and thus, high efficiency may be expected.

In the present specification, the electron mobility may be measured by a method used in the art. Specifically, a time of flight (TOF) or a method of measuring a space charge limited current (SCLC) may be used, and the method is not limited thereto.

Specifically, in an exemplary embodiment of the present specification, bathophenanthroline and lithium (2%) were heated under vacuum on an ITO substrate and deposited to have a thickness of 20 nm, and then the compound was deposited to have a thickness of 200 nm. Bathophenanthroline and lithium (2%) were heated under vacuum on the layer and deposited to have a film having a thickness of 20 nm, and then aluminum was deposited to have a thickness of 100 nm or more, thereby preparing a sample. The electron mobility in the space charge limited current (SCLC) region may be calculated by measuring the currently density (mA/cm²) for the voltage of the sample.

In an exemplary embodiment of the present specification, the heterocyclic compound represented by Formula 1 has a glass transition temperature of 80° C. or more. More preferably, the heterocyclic compound represented by Formula 1 has a glass transition temperature of 100° C. Bphen, which is generally known as a hole blocking material, has a glass transition temperature of less than 70° C. and thus has a problem in that Bphen may not be applied to an environment of 70° C. or more. Accordingly, when a compound having a glass transition temperature in the aforementioned range is used, an organic light emitting diode having excellent thermal stability may be applied.

In an exemplary embodiment of the present specification, the organic material layer including the heterocyclic compound represented by Formula 1 further includes an n-type dopant.

Specifically, in one exemplary embodiment of the present specification, the organic material layer including the heterocyclic compound represented by Formula 1 further includes an n-type dopant represented by the following Formula 10.

[Formula 10]

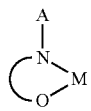

A is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, the curved line represents a bond required for forming a 5-membered or 6-membered ring having M, and two or three atoms, and the atom is unsubstituted or substituted with a substituent which is the same as the definition of one or two or more A's, and M is an alkali metal or an alkaline earth metal.

In an exemplary embodiment of the present specification, the n-type dopant represented by Formula 10 is represented by the following Formula 10-1 or 10-2.

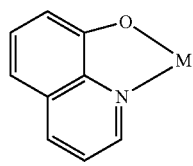

[Formula 10-1]

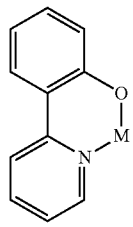

[Formula 10-2]

In Formulae 10-1 and 10-2,

M is the same as that defined in Formula 10, and

Formulae 10-1 and 10-2 are each independently unsubstituted or substituted with one or two or more substituents selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents combine with each other to form a substituted or unsubstituted hydrocarbon ring or a substituted or unsubstituted hetero ring.

In an exemplary embodiment of the present specification, the n-type dopant represented by Formula 10 may be any one of the following structures.

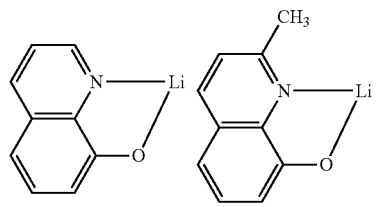

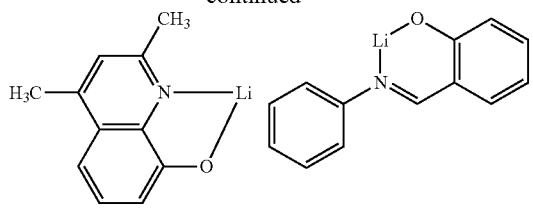

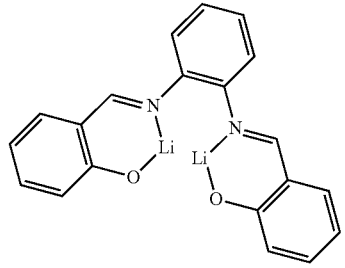

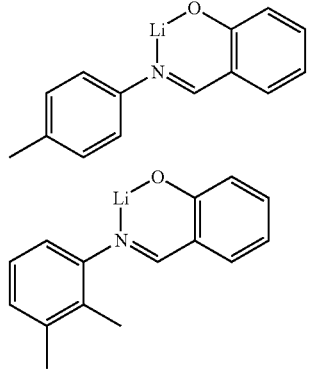


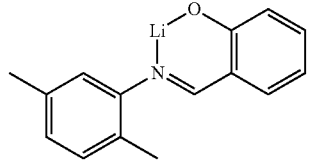

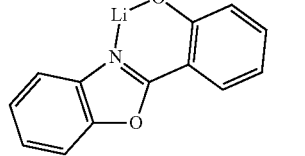

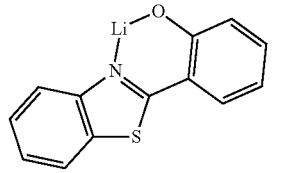

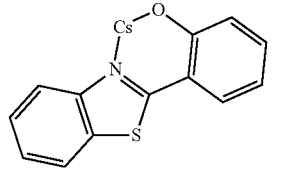

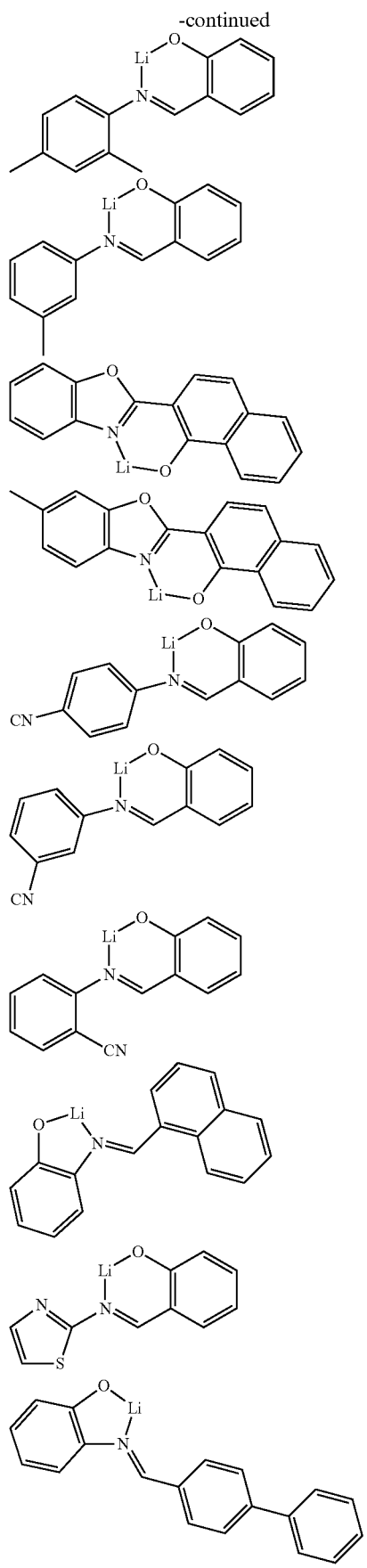
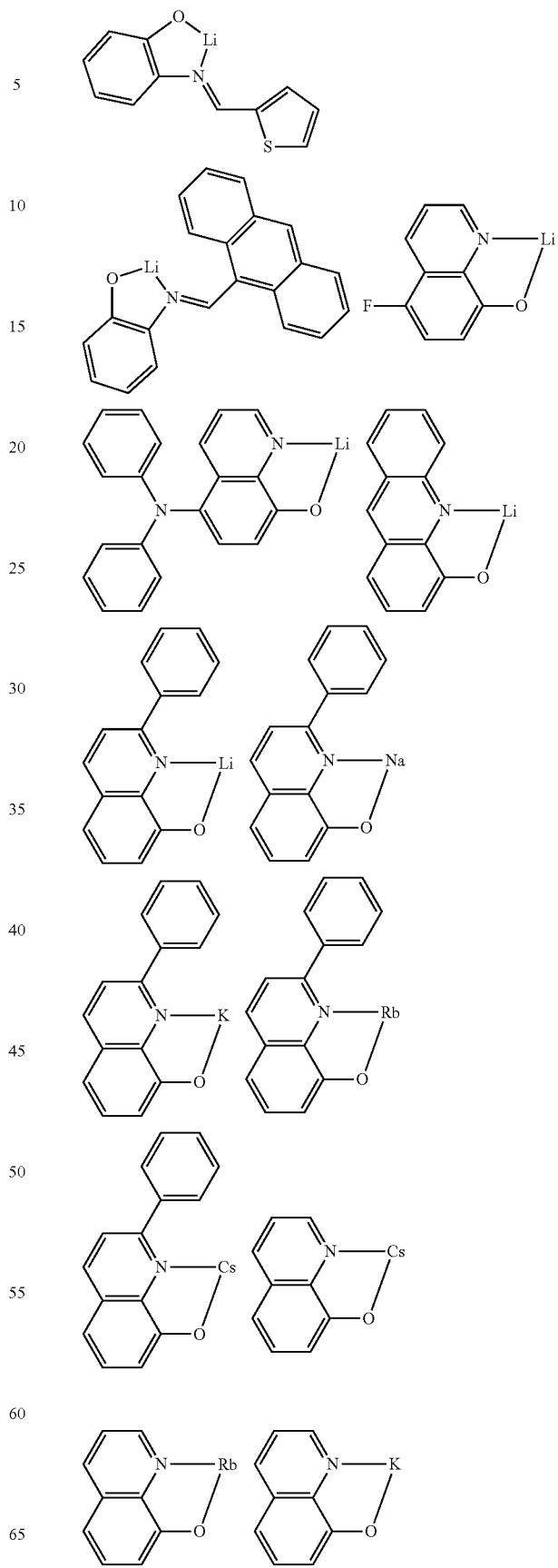

-continued

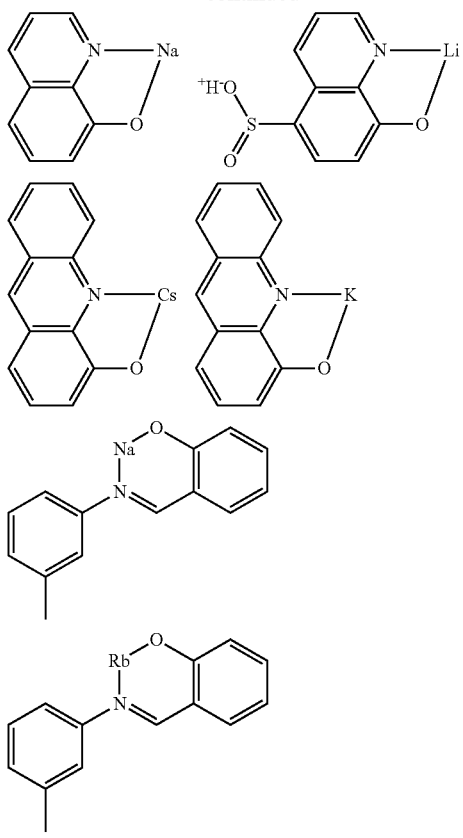

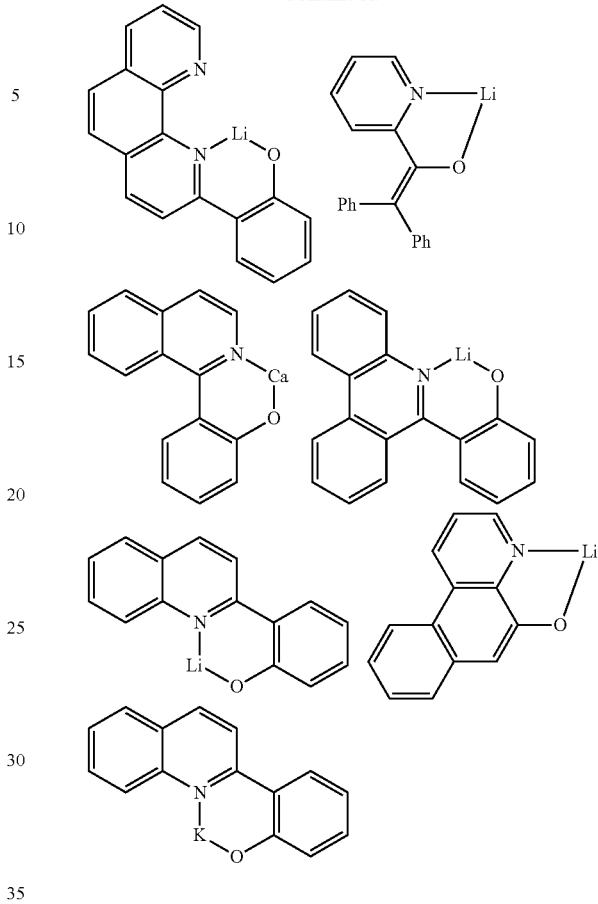

The structure may be unsubstituted or substituted with one or two or more substituents selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

In the present specification, the n-dopant means a material which allows a host material to have n-semiconductor characteristics. The n-semiconductor characteristics means characteristics that electrons are injected or transported at the lowest unoccupied molecular orbit (LUMO) energy level, that is, characteristics of a material having large electron conductivity.

In the present specification, the n-type dopant is for facilitating extraction of electrons from the cathode by doping an electron transporting layer with a donor represented by an alkali metal, and may include one or more selected from the group consisting of a donor metal compound and a donor metal complex.

In an exemplary embodiment of the present specification, the n-type dopant of the organic alkali metal compound or the organic alkaline earth metal compound, which is represented by Formula 10, is present in an amount of 20 wt % to 80 wt % based on the total weight of the organic material layer including the heterocyclic compound represented by Formula 1.

According to an exemplary embodiment of the present specification, the n-type dopants may be either alone or in combination of two or more thereof.

The organic light emitting diode according to an exemplary embodiment of the present specification includes an electron transporting layer which includes the heterocyclic compound represented by Formula 1 as the host between the light emitting layer and the cathode, and an n-type dopant.

In an exemplary embodiment of the present specification, the organic light emitting diode may further include a hole blocking layer between the aforementioned electron transporting layer and the light emitting layer.

Examples of the substituents will be described below, but the present specification is not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In an exemplary embodiment of the present specification, the "substituted or unsubstituted" may be interpreted as being unsubstituted or substituted with one or more substituents selected from the group consisting of deuterium; a halogen group; a nitrile group; a hydroxy group; a carbonyl group; an ester group; an alkoxy group; an aryloxy group; an alkylthioxy group; an arylthioxy group; an alkylsulfoxy group; an arylsulfoxy group; a silyl group; an alkyl group; a cycloalkyl group; an alkenyl group; an aryl group; an aralkyl group; an aralkenyl group; and an alkylaryl group.

According to an exemplary embodiment of the present specification, it is more preferred that the expression "substituted or unsubstituted" is substituted or unsubstituted with one or more substituents selected from the group consisting of deuterium; an alkyl group; and an aryl group.

In an exemplary embodiment of the present specification, the hydrogen atom of the heterocyclic compound represented by Formula 1 may be substituted by deuterium. That is, the heterocyclic compound represented by Formula 1 according to an exemplary embodiment of the present specification may include one or more deuteriums. The meaning of including deuterium also includes the case where the substituent of the heterocyclic compound itself may also be deuterium, and the case where the substituent of the heterocyclic compound is substituted with deuterium.

In the present specification, the halogen group may be fluorine, chlorine, bromine or iodine.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specifically, examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of the boron group include a trimethylboron group, a triethylboron group, a t-butyldimethylboron group, a triphenylboron group, a phenylboron group, and the like, but are not limited thereto.

In the present specification, the aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, the aryl group may be a phenyl group, a biphenyl group, a terphenyl group, a quarterphenyl group, and the like, but is not limited thereto. When the aryl group is a polycyclic aryl group, the aryl group may be a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and two substituents may combine with each other to form a spiro structure.

When the fluorenyl group is substituted, the fluorenyl group may be

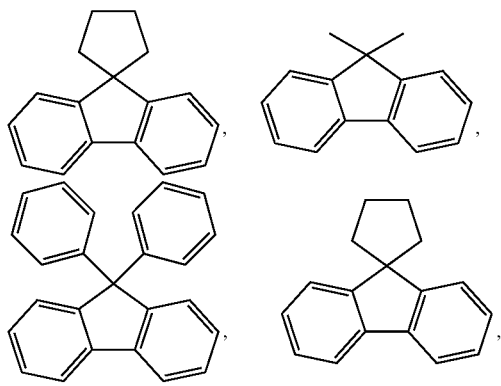

and the like, but is not limited thereto.

In the present specification, the heterocyclic group is a heterocyclic group including one or more of O, N, S, Si, and Se as a hetero element, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

The heterocyclic group may be monocyclic or polycyclic, and may be an aromatic ring, an aliphatic ring, or a condensed ring of the aromatic ring and the aliphatic ring.

In the present specification, the description on the above-described aryl group may be applied to an aryl group of an aryloxy group, an arylthioxy group, and an arylsulfoxy group.

In the present specification, the description on the above-described alkyl group may be applied to an alkyl group of an alkylthioxy group and an alkylsulfoxy group.

In the present specification, the description on the above-described aryl group may be applied to an arylene group except for a divalent arylene group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, an alkylene, which is unsubstituted or substituted with two adjacent hydrocarbons or hetero rings, or an alkenylene, which is unsubstituted or substituted with a hydrocarbon or a hetero ring, may combine with each other to form a ring. In the present specification, the ring formed by combining the adjacent groups with each other may be monocyclic or polycyclic, may be any of an aliphatic ring, an aromatic ring, or a condensed ring of the aliphatic ring and the aromatic ring, and may form a hydrocarbon ring or hetero ring.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; and a condensed ring thereof.

The hydrocarbon ring may be selected from the example of the cycloalkyl group or the aryl group, except for the hydrocarbon ring which is not monovalent. The hetero ring may be any of an aromatic ring, an aliphatic ring, or a condensed ring of the aromatic ring and the aliphatic ring, and may be selected from the example of the heterocyclic group, except for the hetero ring which is not monovalent.

In the present specification, the "spiro bond" may mean a structure in which substituents in the same carbon combined with each other, and two ring compounds are linked to each other through one atom.

In an exemplary embodiment of the present specification, the heterocyclic compound represented by Formula 1 may be represented by the following Formula 1-A.

[Formula 1-A]

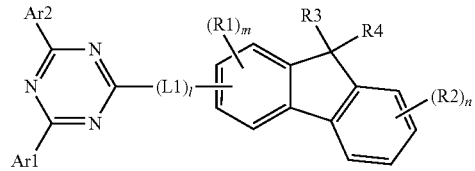

In Formula 1-A, the definition of Ar1, Ar2, L1, R1 to R4, l, m, and n is the same as defined in Formula 1.

One of the important characteristics of an organic material used in the organic light emitting diode is that an amorphous deposition film needs to be formed. An organic material having high crystallinity has a disadvantage in that a film is non-uniformly deposited during the deposition, and thus, the driving voltage is largely increased when a diode is driven, and the service life of the diode is decreased, and thus the diode quickly deteriorates. In order to alleviate the disadvantage, an amorphous film needs to be formed.

Thus, the present inventors have confirmed that an asymmetric material in a triazine derivative structure does not exhibit crystallinity. In an exemplary embodiment of the present specification, for the heterocyclic compound represented by Formula 1, Ar1 to Ar3, which are a substituent of triazine, are different from each other. In this case, the heterocyclic compound may provide a diode which is capable of forming an amorphous deposition film because the substituents of triazine are asymmetric, and has a low driving voltage and long service life.

According to an exemplary embodiment of the present specification, Formula 1 may be represented by any one of the following Formulae 1-A-1 to 1-A-4.

[Formula 1-A-1]

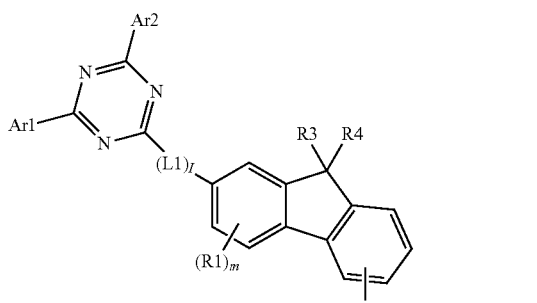

[Formula 1-A-2]

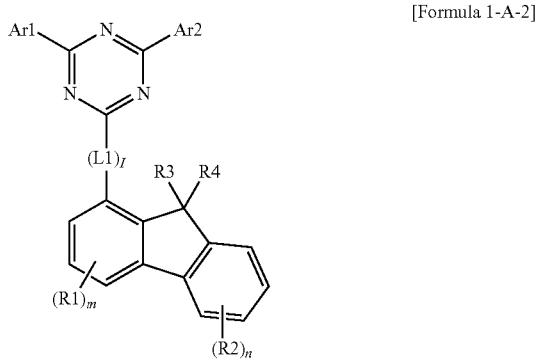

[Formula 1-A-3]

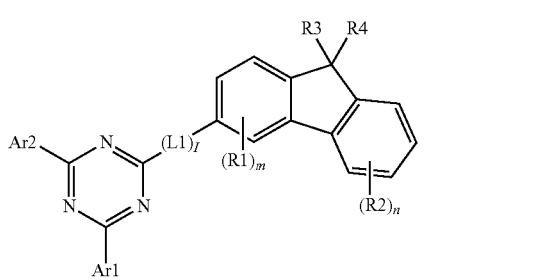

[Formula 1-A-4]

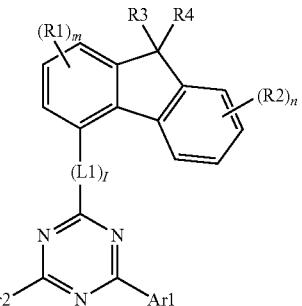

In Formulae 1-A-1 to 1-A-4, the definition of Ar1, Ar2, L1, R1 to R4, l, m, and n is the same as defined in Formula 1.

In an exemplary embodiment of the present specification, the heterocyclic compound represented by Formula 1 is represented by Formula 1-A-1.

In another exemplary embodiment, the heterocyclic compound represented by Formula 1 is represented by Formula 1-A-2.

In still another exemplary embodiment, the heterocyclic compound represented by Formula 1 is represented by Formula 1-A-4.

The heterocyclic compound serving as an electron transporting layer in the present specification is preferably the compound represented by Formula 1-A-4 in terms of light emitting efficiency and service life.

In an exemplary embodiment of the present specification, the heterocyclic compound represented by Formula 1 is represented by the following Formula 1-B.

[Formula 1-B]

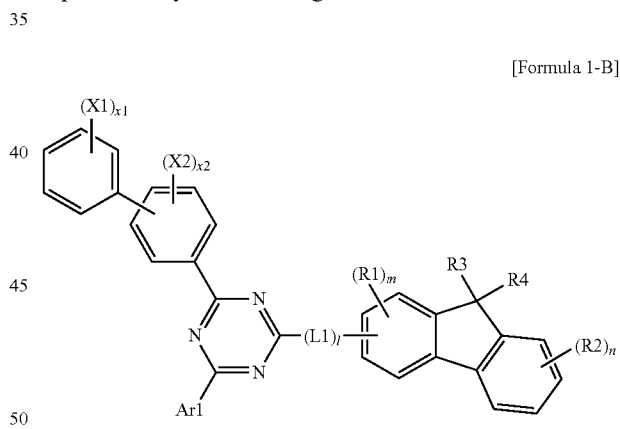

R1 to R4, Ar1, L1, l, m, and n are the same as those defined in Formula 1.

x1 is an integer of 1 to 5, and x2 is an integer of 1 to 4, and when x1 and x2 are an integer of 2 or more, two or more structures in the parenthesis are the same as or different from each other, and X1 and X2 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or two or more adjacent groups combine with each other to form a substituted or unsubstituted hydrocarbon ring; or a substituted or unsubstituted hetero ring.

In an exemplary embodiment of the present specification, the heterocyclic compound represented by Formula 1 is represented by the following Formula 1-B-1.

[Formula 1-B-1]

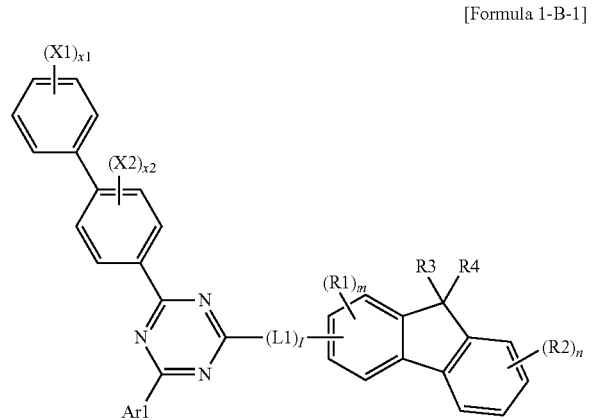

In Formula 1-B-1,

R1 to R4, Ar1, L1, l, m, n, x1, x2, X1, and X2 are the same as those defined in Formula 1-B.

In an exemplary embodiment of the present specification, X1 is hydrogen.

In another exemplary embodiment, X2 is hydrogen.

When Ar1 or Ar2 includes a biphenyl group as in an exemplary embodiment of the present specification, there is an excellent effect in terms of service life of the diode.

According to an exemplary embodiment of the present specification, Ar1 and Ar2 are different from each other, and each independently a substituted or unsubstituted aryl group.

According to an exemplary embodiment of the present specification, Ar1 and Ar2 are different from each other, and each independently an aryl group of substituted or unsubstituted 1-membered to 4-membered ring.

According to an exemplary embodiment of the present specification, Ar1 and Ar2 are different from each other, and each independently an aryl group, which is unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group.

According to an exemplary embodiment of the present specification, Ar1 and Ar2 are different from each other, and each independently an aryl group, which is unsubstituted or substituted with one or more substituents selected from the group consisting of deuterium, an alkyl group, and an aryl group.

According to an exemplary embodiment of the present specification, Ar1 and Ar2 are different from each other, and each independently a substituted or unsubstituted aryl group, and at least one of Ar1 and Ar2 is an aryl group, which is unsubstituted or substituted with deuterium.

According to an exemplary embodiment of the present specification, Ar1 and Ar2 are different from each other, and each independently an aryl group, which is unsubstituted or substituted with deuterium.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; a substituted or unsubstituted fluorenyl group; or a substituted or unsubstituted heteroaryl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; a chrysenyl group; a fluorenyl group; or a heteroaryl group.

According to an exemplary embodiment of the present specification, Ar1 and Ar2 are different from each other, and each independently a substituted or unsubstituted phenyl group; a substituted or unsubstituted naphthyl group; a substituted or unsubstituted biphenyl group; a substituted or unsubstituted terphenyl group; a substituted or unsubstituted quarterphenyl group; a substituted or unsubstituted phenanthryl group; a substituted or unsubstituted chrysenyl group; or a substituted or unsubstituted heteroaryl group.

In an exemplary embodiment of the present specification, Ar1 and Ar2 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 and Ar2 are different from each other, and each independently a phenyl group; a naphthyl group; a biphenyl group; a terphenyl group; a quarterphenyl group; a phenanthryl group; a chrysenyl group; or a heteroaryl group.

According to an exemplary embodiment of the present specification, Ar1 is a substituted or unsubstituted phenyl group; a substituted or unsubstituted biphenyl group; a substituted or unsubstituted naphthyl group; or a substituted or unsubstituted phenanthryl group.

According to an exemplary embodiment of the present specification, Ar1 is a phenyl group; a biphenyl group; a naphthyl group; or a phenanthryl group.

According to an exemplary embodiment of the present specification, Ar1 is a substituted or unsubstituted phenyl group.

According to an exemplary embodiment of the present specification, Ar1 is a substituted or unsubstituted biphenyl group.

According to an exemplary embodiment of the present specification, Ar1 is a substituted or unsubstituted naphthyl group.

According to an exemplary embodiment of the present specification, Ar1 is a substituted or unsubstituted phenanthryl group.

According to an exemplary embodiment of the present specification, when Ar1 is a substituted or unsubstituted phenyl group, Ar2 is a substituted or unsubstituted biphenyl group; a substituted or unsubstituted terphenyl group; a substituted or unsubstituted quarterphenyl group; a substituted or unsubstituted naphthyl group; a substituted or unsubstituted phenanthryl group; or a substituted phenyl group.

According to an exemplary embodiment of the present specification, when Ar1 is a phenyl group, Ar2 is a biphenyl group; a terphenyl group; a terphenyl group substituted with a phenyl group; a quarterphenyl group; a naphthyl group; a phenanthryl group; or a phenyl group substituted with a naphthyl group.

According to an exemplary embodiment of the present specification, when Ar1 is a substituted or unsubstituted biphenyl group, Ar2 is a substituted or unsubstituted terphenyl group; a substituted or unsubstituted biphenyl group; a substituted phenyl group; a substituted or unsubstituted naphthyl group; or a substituted or unsubstituted phenanthryl group.

According to an exemplary embodiment of the present specification, when Ar1 is a biphenyl group, Ar2 is a terphenyl group; a biphenyl group; a phenyl group substituted with a naphthyl group; a phenyl group substituted with a phenanthryl group; a biphenyl group substituted with a naphthyl group; a naphthyl group; a naphthyl group substituted with a phenyl group; or a phenanthryl group.

According to an exemplary embodiment of the present specification, when Ar1 is a substituted or unsubstituted naphthyl group, Ar2 is a substituted or unsubstituted biphenyl group; a substituted phenyl group; a substituted or unsubstituted terphenyl group; a substituted or unsubstituted phenanthryl group; or a substituted or unsubstituted quarterphenyl group.

According to an exemplary embodiment of the present specification, when Ar1 is a naphthyl group, Ar2 is a biphenyl group; a phenyl group substituted with a naphthyl group; a phenyl group substituted with a phenanthryl group; a terphenyl group; a biphenyl group substituted with a naphthyl group; a phenanthryl group substituted with a phenyl group; a phenanthryl group; a quarterphenyl group; or a terphenyl group substituted with a phenyl group.

According to an exemplary embodiment of the present specification, when Ar1 is a substituted or unsubstituted phenanthryl group, Ar2 is a substituted or unsubstituted biphenyl group; a substituted phenyl group; a substituted or unsubstituted terphenyl group; or a substituted or unsubstituted quarterphenyl group.

According to an exemplary embodiment of the present specification, when Ar1 is a phenanthryl group, Ar2 is a biphenyl group; a phenyl group substituted with a phenanthryl group; a phenyl group substituted with a naphthyl group; a terphenyl group; a quarterphenyl group; or a terphenyl group substituted with a phenyl group.

According to an exemplary embodiment of the present specification, Ar2 is a substituted or unsubstituted phenyl group; a substituted or unsubstituted biphenyl group; a substituted or unsubstituted terphenyl group; a substituted or unsubstituted quarterphenyl group; a substituted or unsubstituted naphthyl group; or a substituted or unsubstituted phenanthryl group.

According to an exemplary embodiment of the present specification, Ar2 is a phenyl group; a biphenyl group; a terphenyl group; a quarterphenyl group; a naphthyl group; or a phenanthryl group.

According to an exemplary embodiment of the present specification, at least one of Ar1 and Ar2 is a substituted or unsubstituted biphenyl group.

According to an exemplary embodiment of the present specification, Ar1 is a phenyl group, which is unsubstituted or substituted with an aryl group; a biphenyl group, which is unsubstituted or substituted with an aryl group; a naphthyl group, which is unsubstituted or substituted with an aryl group; or a phenanthryl group, which is unsubstituted or substituted with an aryl group, and Ar2 is a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

According to an exemplary embodiment of the present specification, Ar1 is a phenyl group, and Ar2 is a biphenyl group.

According to an exemplary embodiment of the present specification, Ar1 and Ar2 are different from each other, and each independently a phenyl group; a biphenyl group; a naphthyl group; a phenanthrenyl group; a terphenyl group; a phenyl group substituted with a naphthyl group; or a phenyl group substituted with a terphenyl group.

According to an exemplary embodiment of the present specification, R1 is hydrogen; a substituted or unsubstituted alkyl group; or a substituted or unsubstituted aryl group.

According to an exemplary embodiment of the present specification, R1 is hydrogen; a substituted or unsubstituted alkyl group having 1 to 30 carbon atoms; or a substituted or unsubstituted aryl group having 6 to 40 carbon atoms.

According to an exemplary embodiment of the present specification, R1 is hydrogen; a substituted or unsubstituted alkyl group having 1 to 6 carbon atoms; or a substituted or unsubstituted aryl group having 6 to 20 carbon atoms, or two or more adjacent R1's combine with each other to form a substituted or unsubstituted hydrocarbon ring or a substituted or unsubstituted hetero ring.

According to an exemplary embodiment of the present specification, R1 is hydrogen; deuterium; an alkyl group having 1 to 6 carbon atoms; or an aryl group having 6 to 20 carbon atoms, or two or more adjacent R1's combine with each other to form a substituted or unsubstituted hydrocarbon ring or a substituted or unsubstituted hetero ring.

According to an exemplary embodiment of the present specification, R1 is hydrogen; deuterium; or an alkyl group.

According to an exemplary embodiment of the present specification, R1 is hydrogen.

In an exemplary embodiment of the present specification, two or more R1's combine with each other to form a substituted or unsubstituted hydrocarbon ring.

In another exemplary embodiment, the two or more adjacent R1's combine with each other to form a substituted or unsubstituted benzene ring.

In an exemplary embodiment of the present specification, the two or more adjacent R1's combine with each other to form a benzene ring.

According to an exemplary embodiment of the present specification, R2 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; a substituted or unsubstituted monocyclic or bicyclic heterocyclic group including one or more of O and S atoms; a substituted or unsubstituted pyrrole group; a substituted or unsubstituted imidazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazole group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted benzimidazole group; or a substituted or unsubstituted phenanthroline group, or two or more adjacent R2's combine with each other to form a substituted or unsubstituted hydrocarbon ring or a substituted or unsubstituted hetero ring.

According to an exemplary embodiment of the present specification, R2 is hydrogen; a substituted or unsubstituted alkyl group; a substituted or unsubstituted aryl group; or a substituted or unsubstituted heterocyclic group, or two or more adjacent R2's combine with each other to form a substituted or unsubstituted hydrocarbon ring.

According to an exemplary embodiment of the present specification, R2 is hydrogen; deuterium; a substituted or unsubstituted alkyl group having 1 to 20 carbon atoms; a substituted or unsubstituted aryl group having 6 to 20 carbon atoms; or a substituted or unsubstituted heterocyclic group having 2 to 20 carbon atoms, or two or more adjacent R2's combine with each other to form a substituted or unsubstituted hydrocarbon ring.

According to an exemplary embodiment of the present specification, R2 is hydrogen; deuterium; or a substituted or unsubstituted aryl group having 6 to 40 carbon atoms.

According to an exemplary embodiment of the present specification, R2 is hydrogen; deuterium; or a substituted or unsubstituted aryl group having 6 to 20 carbon atoms.

According to an exemplary embodiment of the present specification, R2 is hydrogen; or an aryl group having 6 to 20 carbon atoms.

According to an exemplary embodiment of the present specification, R2 is hydrogen; or a substituted or unsubstituted phenyl group.

According to an exemplary embodiment of the present specification, R2 is hydrogen; deuterium; or a phenyl group.

According to an exemplary embodiment of the present specification, R2 is hydrogen; or deuterium.

According to an exemplary embodiment of the present specification, R2 is hydrogen.

In an exemplary embodiment of the present specification, R2 is a substituted or unsubstituted phenyl group.

In another exemplary embodiment, R2 is a phenyl group.

In an exemplary embodiment of the present specification, the two or more R2's combine with each other to form a substituted or unsubstituted hydrocarbon ring.

In another exemplary embodiment, the two or more adjacent R2's combine with each other to form a substituted or unsubstituted benzene ring.

In an exemplary embodiment of the present specification, the two or more adjacent R2's combine with each other to form a benzene ring.

In another exemplary embodiment, R1 is hydrogen; or adjacent groups combine with each other to form a benzene ring.

In still another exemplary embodiment, R2 is hydrogen.

According to an exemplary embodiment of the present specification, R3 and R4 are the same as or different from each other, and each independently hydrogen; deuterium; a halogen group; a substituted or unsubstituted, straight-chained alkyl group having 1 to 40 carbon atoms; a substituted or unsubstituted, straight-chained alkoxy group having 1 to 40 carbon atoms; a substituted or unsubstituted, straight-chained thioalkyl group having 1 to 40 carbon atoms; a substituted or unsubstituted, branched mono or poly cycloalkyl group having 3 to 40 carbon atoms; a substituted or unsubstituted, branched alkenyl group having 3 to 40 carbon atoms; a substituted or unsubstituted, branched alkoxy group having 3 to 40 carbon atoms; a substituted or unsubstituted, branched thioalkoxy group having 3 to 40 carbon atoms; a 6 to 40-membered substituted or unsubstituted aryl group; a 5 to 40-membered substituted or unsubstituted heterocyclic group; a 5 to 40-membered substituted or unsubstituted aryloxy group; or a 5 to 40-membered substituted or unsubstituted heteroaryloxy group, or combine with each other to form a substituted or unsubstituted hydrocarbon ring, or the substituents in the same carbon combine with each other to form a substituted or unsubstituted spiro bond.

According to an exemplary embodiment of the present specification, R3 and R4 are the same as or different from each other, and each independently a substituted or unsubstituted alkyl group; a substituted or unsubstituted aryl group; or a substituted or unsubstituted heterocyclic group, or combine with each other to form a substituted or unsubstituted hydrocarbon ring, or the substituents in the same carbon combine with each other to form a substituted or unsubstituted Spiro bond.

In an exemplary embodiment of the present specification, it is more preferred that R3 and R4 are a substituted or unsubstituted alkyl group; a substituted or unsubstituted aryl group; or a substituted or unsubstituted heterocyclic group. According to the document (J. AM. CHEM. SOC. 2003, 125, 3710-3711), it can be confirmed that a disubstituted fluorenyl group has a higher electron mobility than that of a spirobifluorenyl group. Accordingly, it can be confirmed that the compound represented by Formula 1 may transport electrons more efficiently than Formula [ET-J] or Formula [ET-K] used in the Comparative Examples to be described below and thus exhibits high efficiency, and also improves the service life.

According to an exemplary embodiment of the present specification, R3 and R4 are the same as or different from each other, and each independently a substituted or unsubstituted alkyl group; or a substituted or unsubstituted aryl group.

According to an exemplary embodiment of the present specification, R3 and R4 are the same as or different from each other, and each independently a substituted or unsubstituted alkyl group; a substituted or unsubstituted aryl group having 6 to 20 carbon atoms; or a substituted or unsubstituted heterocyclic group.

According to an exemplary embodiment of the present specification, R3 and R4 are the same as or different from each other, and each independently an alkyl group; an aryl group having 6 to 20 carbon atoms; or a heterocyclic group.

According to an exemplary embodiment of the present specification, R3 and R4 are the same as or different from each other, and each independently an alkyl group; a substituted or unsubstituted phenyl group; a substituted or unsubstituted biphenyl group; or a substituted or unsubstituted naphthyl group, or R3 and R4 combine with each other to form a 5-membered aliphatic ring.

According to an exemplary embodiment of the present specification, R3 and R4 are the same as or different from each other, and each independently a methyl group; a substituted or unsubstituted phenyl group; a substituted or unsubstituted biphenyl group; or a substituted or unsubstituted naphthyl group, or R3 and R4 combine with each other to form a 5-membered aliphatic ring.

According to an exemplary embodiment of the present specification, R3 and R4 are the same as or different from each other, and each independently a methyl group; an unsubstituted phenyl group; a phenyl group substituted with a methyl group; a biphenyl group; or a naphthyl group, or R3 and R4 combine with each other to form a 5-membered aliphatic ring.

In an exemplary embodiment of the present specification, R3 and R4 are the same as or different from each other, and each independently an alkyl group; or an aryl group.

In another exemplary embodiment, R3 and R4 are a methyl group; or a phenyl group.

In an exemplary embodiment of the present specification, R1 to R4 are the same as or different from each other, and each independently hydrogen; a substituted or unsubstituted alkyl group; or a substituted or unsubstituted aryl group, or two or more adjacent substituents combine with each other to form a substituted or unsubstituted hydrocarbon ring, or the substituents in the same carbon combine with each other to form a spiro bond.

In an exemplary embodiment of the present specification, R1 to R4 are the same as or different from each other, and each independently hydrogen; a substituted or unsubstituted alkyl group; or a substituted or unsubstituted aryl group, or two or more adjacent substituents combine with each other to form a substituted or unsubstituted hydrocarbon ring, or the substituents in the same carbon combine with each other to form a substituted or unsubstituted Spiro bond.

In an exemplary embodiment of the present specification, L1 is a direct bond; or a substituted or unsubstituted arylene group.

In another exemplary embodiment, L1 is a direct bond; or an arylene group having 6 to 20 carbon atoms.

According to an exemplary embodiment of the present specification, L1 is a direct bond; or any one selected from the following structures.

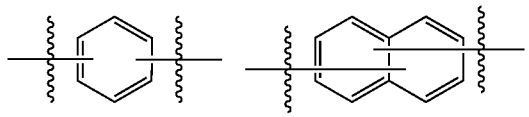

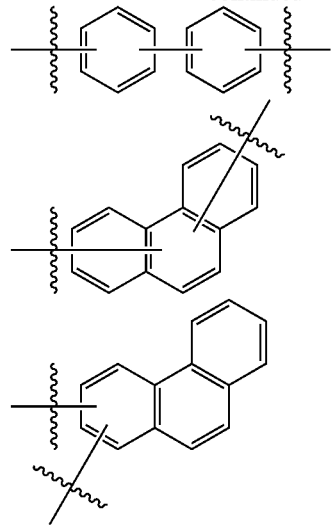

The structures may be unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an amine group; an arylphosphine group; or a heterocyclic group.

In an exemplary embodiment of the present specification, L1 is a direct bond; a substituted or unsubstituted phenylene group; a substituted or unsubstituted biphenylylene group; a substituted or unsubstituted naphthalene group; or a substituted or unsubstituted phenanthrenylene group.

In an exemplary embodiment of the present specification, (L1)$_1$ is a direct bond; a substituted or unsubstituted phenylene group; a substituted or unsubstituted biphenylylene group; a substituted or unsubstituted naphthalene group; or a substituted or unsubstituted phenanthrenylene group.

In an exemplary embodiment of the present specification, L1 is a direct bond.

In another exemplary embodiment, L1 is a substituted or unsubstituted phenylene group.

In still another exemplary embodiment, L1 is a phenylene group.

In an exemplary embodiment of the present specification, L1 is a substituted or unsubstituted biphenylylene group.

In one exemplary embodiment, L1 is a biphenylylene group.

In an exemplary embodiment of the present specification, L1 is a substituted or unsubstituted naphthalene group.

In an exemplary embodiment of the present specification, L1 is a naphthalene group.

In an exemplary embodiment of the present specification, L1 is a substituted or unsubstituted phenanthrenylene group.

In another exemplary embodiment, L1 is a phenanthrenylene group.

In one exemplary embodiment of the present specification, L1 is a direct bond; a phenylene group; or a naphthalene group.

In one exemplary embodiment of the present specification, L1 is unsubstituted or substituted with one or more deuteriums.

In an exemplary embodiment of the present specification, Formula 2 may be selected from any one of the following structures.

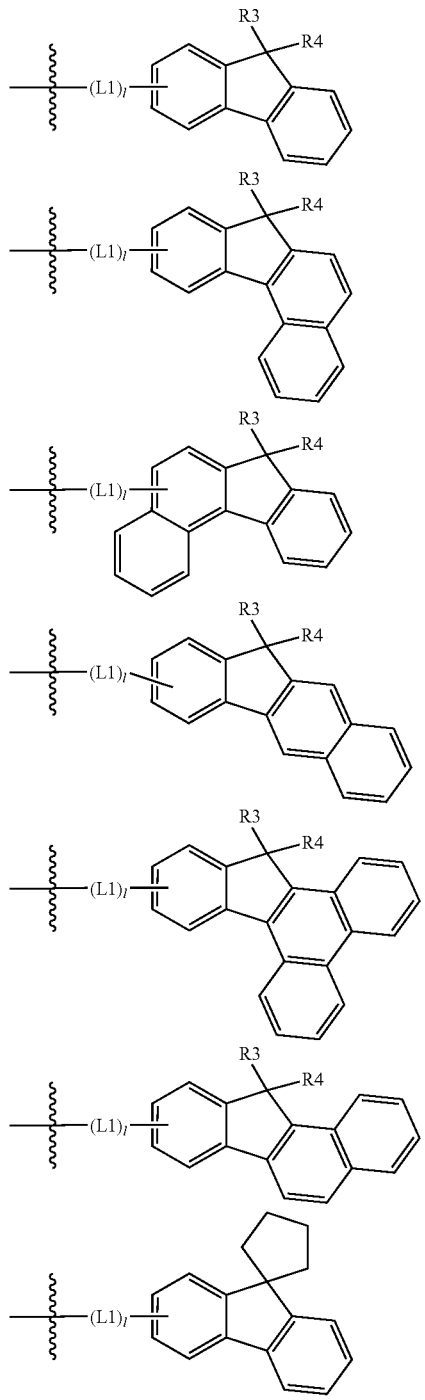

In the structures, R3, R4, L1, and l are the same as those described above, and the structures may be unsubstituted or substituted with one or more substituents selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group.

In an exemplary embodiment of the present specification, Ar3 may be selected from the following structures.

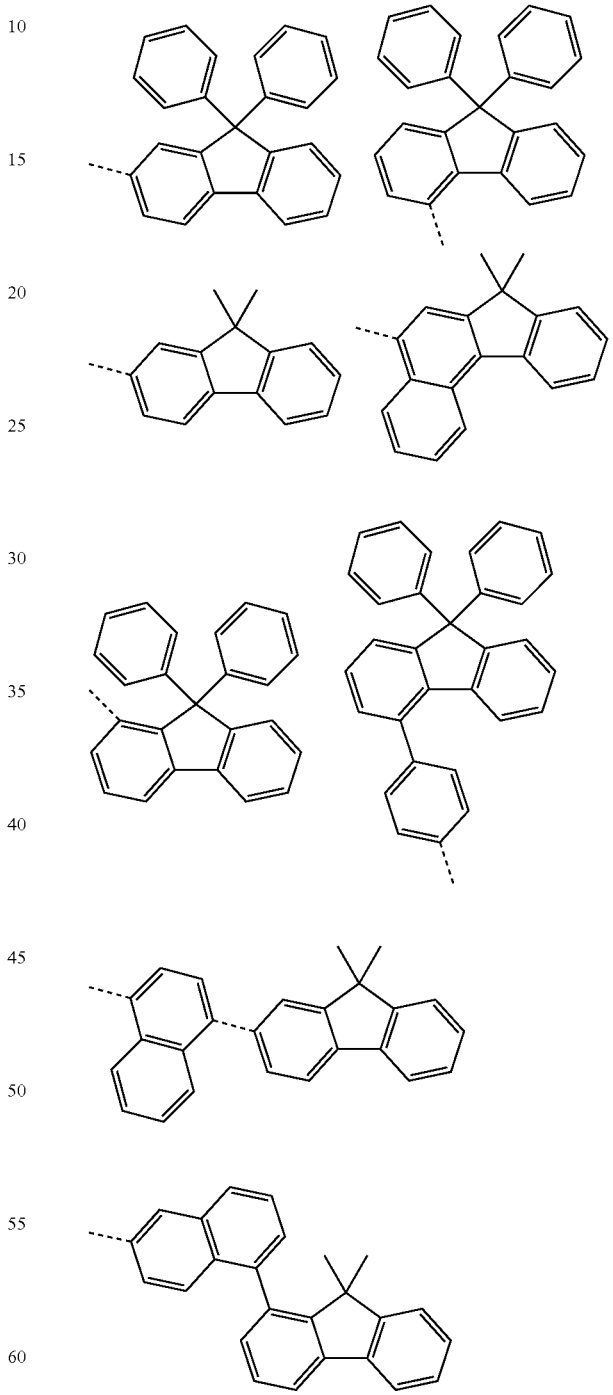

In an exemplary embodiment of the present specification, the heterocyclic compound represented by Formula 1 is represented by any one of the following Formulae 1-1 to 1-627 and 2-1 to 2-363.

| Formula | ---Ar1 | ---Ar2 | ---Ar3 |
|---|---|---|---|
| 1-1 | phenyl | biphenyl | 9,9-dimethylfluoren-1-yl |
| 1-2 | phenyl | biphenyl | 9,9-dimethylfluoren-2-yl |
| 1-3 | phenyl | biphenyl | 9,9-dimethylfluoren-3-yl |
| 1-4 | phenyl | biphenyl | 9,9-dimethylfluoren-4-yl |
| 1-5 | phenyl | biphenyl | 9,9-diphenylfluoren-1-yl |
| 1-6 | phenyl | biphenyl | 9,9-diphenylfluoren-2-yl |
| 1-7 | phenyl | biphenyl | 9,9-dimethylbenzofluorenyl |
| 1-8 | phenyl | biphenyl | 9,9-diphenylfluoren-4-yl |

| Formula | ---Ar1 | ---Ar2 | ---Ar3 |
|---------|--------|--------|--------|
| 1-9 | 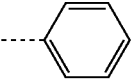 | 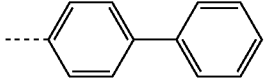 | 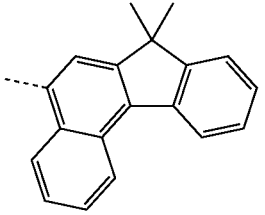 |
| 1-10 | 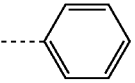 | 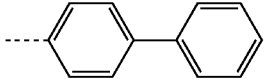 | 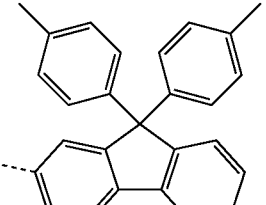 |
| 1-11 | 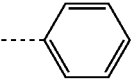 | 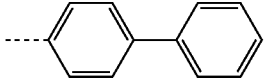 | 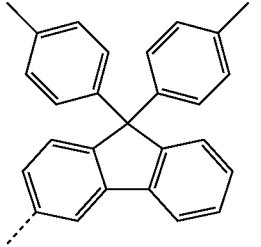 |
| 1-12 | 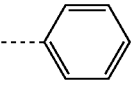 | 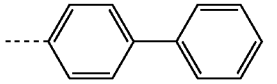 | 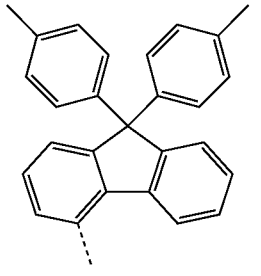 |
| 1-13 | 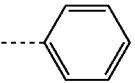 | 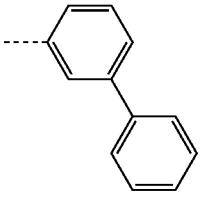 | 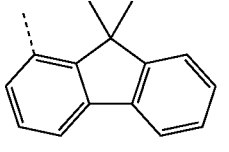 |
| 1-14 | 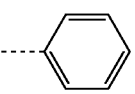 | 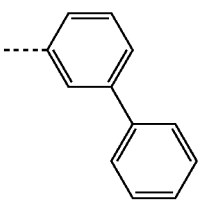 | 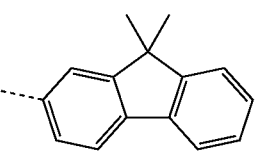 |

-continued

| Formula | - - -Ar1 | - - -Ar2 | - - -Ar3 |
|---|---|---|---|
| 1-15 | phenyl | biphenyl | 9,9-dimethyl-2-phenylfluorenyl (3-position) |
| 1-16 | phenyl | biphenyl | 9,9-dimethyl-2-phenylfluorenyl (4-position) |
| 1-17 | phenyl | biphenyl | 9,9-diphenylfluorenyl (1-position) |
| 1-18 | phenyl | biphenyl | 9,9-diphenylfluorenyl (2-position) |
| 1-19 | phenyl | biphenyl | 9,9-diphenylfluorenyl (3-position) |
| 1-20 | phenyl | biphenyl | 9,9-diphenylfluorenyl (4-position) |
| 1-21 | phenyl | biphenyl | 9,9-di(p-tolyl)fluorenyl |

-continued

| Formula | ---Ar1 | ---Ar2 | ---Ar3 |
|---|---|---|---|
| 1-22 | phenyl | biphenyl (meta) | 9,9-di(p-tolyl)fluorene |
| 1-23 | phenyl | biphenyl (meta) | 9,9-dimethyl-benzo-fluorene |
| 1-24 | phenyl | biphenyl (meta) | 9,9-di(p-tolyl)fluorene (4-linked) |
| 1-25 | phenyl | biphenyl (ortho) | 9,9-dimethylfluorene (1-linked) |
| 1-26? | phenyl | biphenyl (ortho) | 2-phenyl-9,9-dimethylfluorene |
| 1-27 | phenyl | biphenyl (ortho) | 9-methyl-9-phenylfluorene |
| 1-28 | phenyl | biphenyl (ortho) | 9,9-dimethylfluorene (4-linked) |

-continued
| Formula | - - -Ar1 | - - -Ar2 | - - -Ar3 |
|---|---|---|---|
| 1-29 | 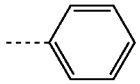 | 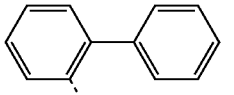 | 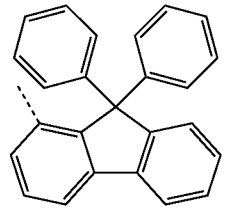 |
| 1-30 | 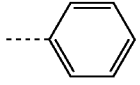 | 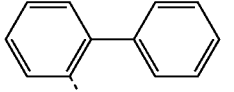 | 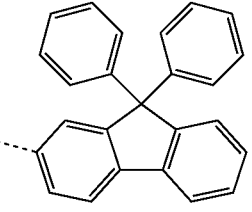 |
| 1-31 | 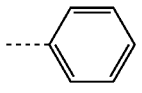 | 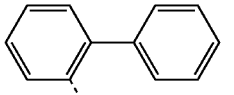 | 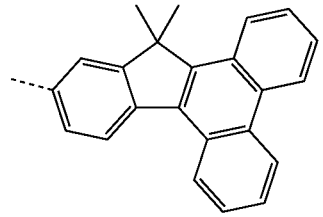 |
| 1-32 | 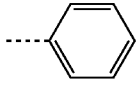 | 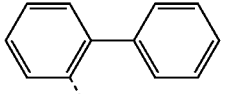 | 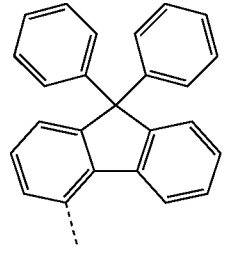 |
| 1-33 | 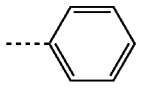 | 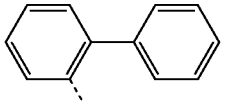 | 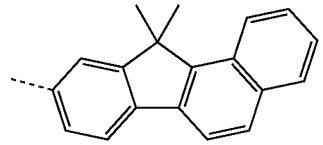 |
| 1-34 | 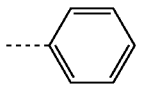 | 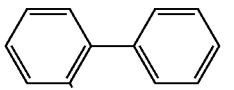 | 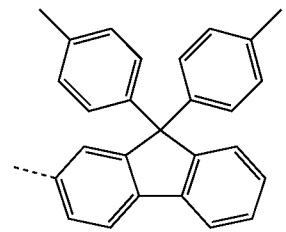 |

-continued
| Formula | - - -Ar1 | - - -Ar2 | - - -Ar3 |
|---|---|---|---|
| 1-35 | 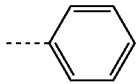 | 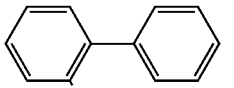 | 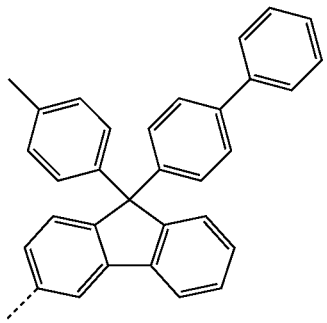 |
| 1-36 | 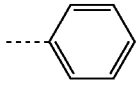 | 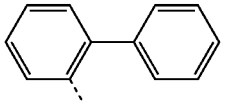 | 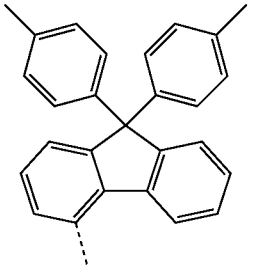 |
| 1-37 | 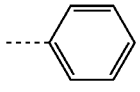 | 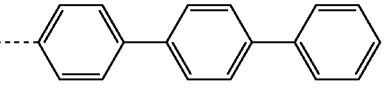 | 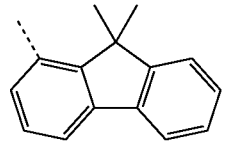 |
| 1-38 | 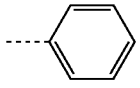 | 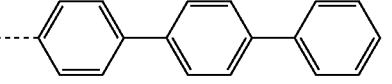 | 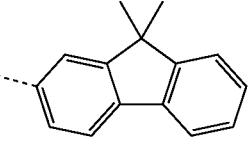 |
| 1-39 | 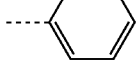 | 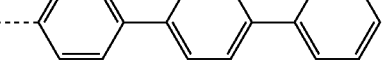 | 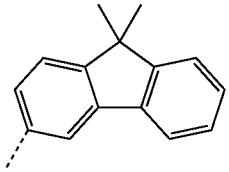 |
| 1-40 | 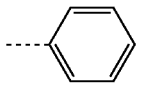 | 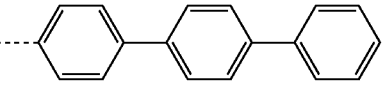 | 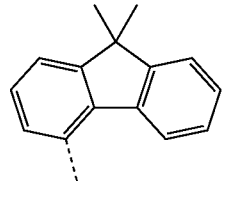 |
| 1-41 | 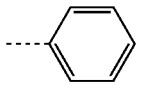 | 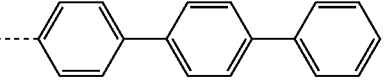 | 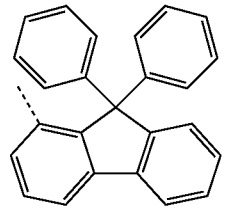 |

-continued
| Formula | ---Ar1 | ---Ar2 | ---Ar3 |
|---|---|---|---|
| 1-42 | 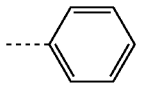 | 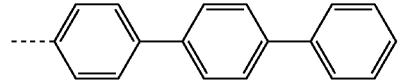 | 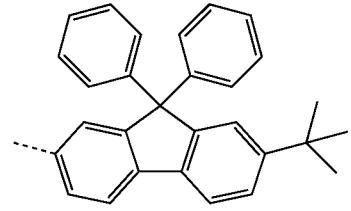 |
| 1-43 | 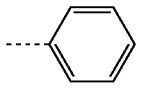 | 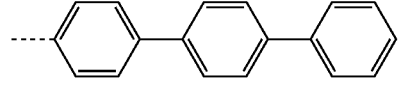 | 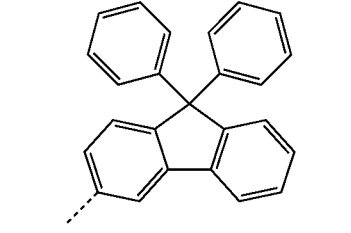 |
| 1-44 | 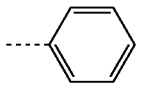 | 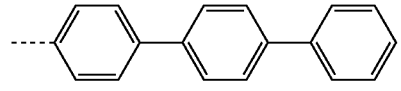 | 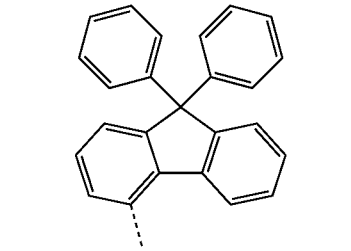 |
| 1-45 | 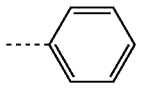 | 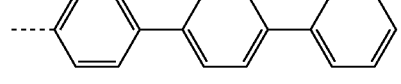 | 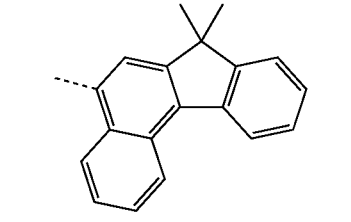 |
| 1-46 | 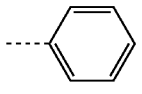 | 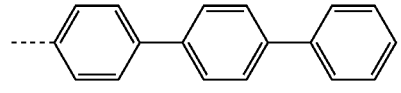 | 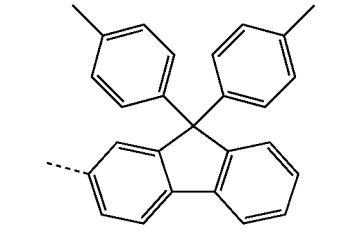 |
| 1-47 | 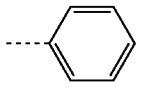 | 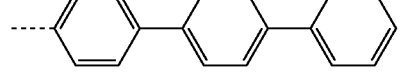 | 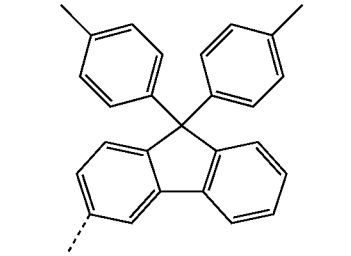 |

| Formula | ---Ar1 | ---Ar2 | ---Ar3 |
|---------|--------|--------|--------|
| 1-48 | 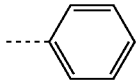 | 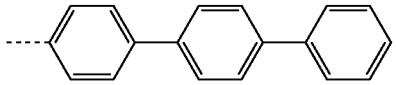 | 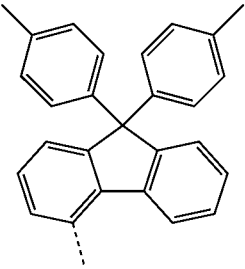 |
| 1-49 | 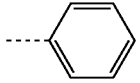 | 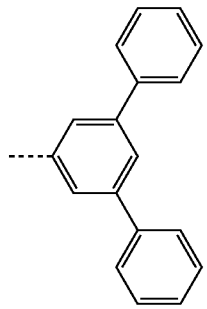 | 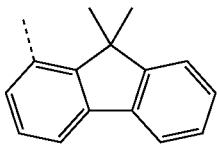 |
| 1-50 | 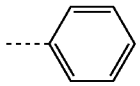 | 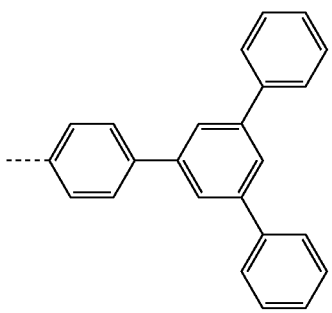 | 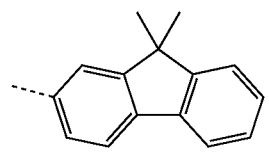 |
| 1-51 | 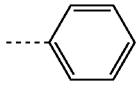 | 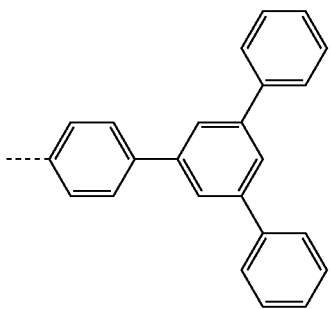 | 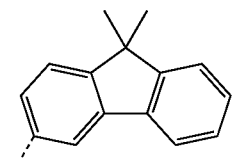 |
| 1-52 | 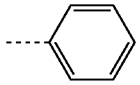 | 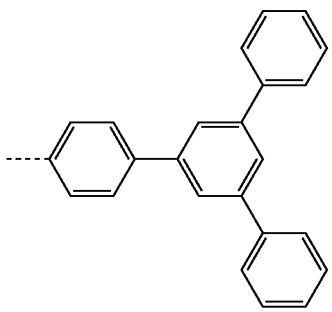 | 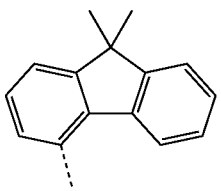 |

-continued

| Formula | ---Ar1 | ---Ar2 | ---Ar3 |
|---|---|---|---|
| 1-53 | phenyl | 3,5-diphenylphenyl | 9,9-diphenylfluoren-1-yl |
| 1-54 | phenyl | 3,5-diphenylphenyl | 9,9-diphenylfluoren-2-yl |
| 1-55 | phenyl | 3,5-diphenylphenyl | 9,9-diphenylfluoren-3-yl |
| 1-56 | phenyl | 3,5-diphenylphenyl | 9,9-diphenylfluoren-4-yl |
| 1-57 | phenyl | 3,5-diphenylphenyl | 9,9-dimethyl-9H-benzo[b]fluorenyl |

-continued
| Formula | - - -Ar1 | - - -Ar2 | - - -Ar3 |
|---|---|---|---|
| 1-58 | 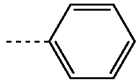 | 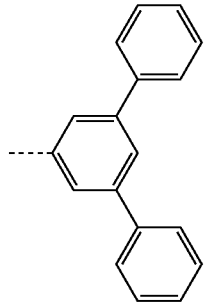 | 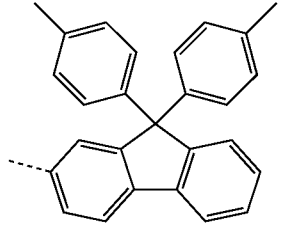 |
| 1-59 | 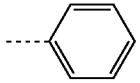 | 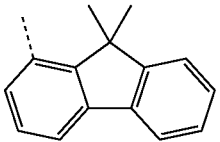 | 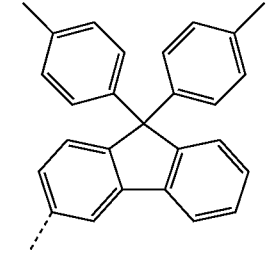 |
| 1-60 | 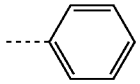 | 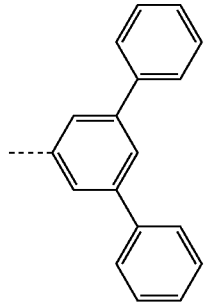 | 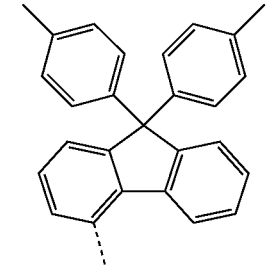 |
| 1-61 | 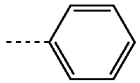 | 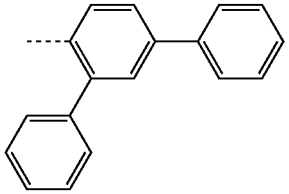 | 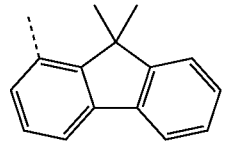 |
| 1-62 | 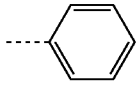 | 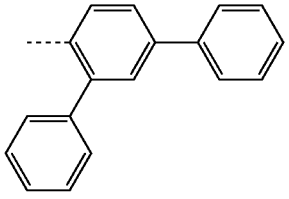 | 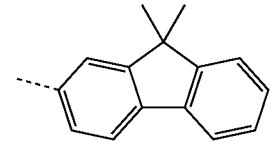 |
| 1-63 | 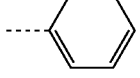 | 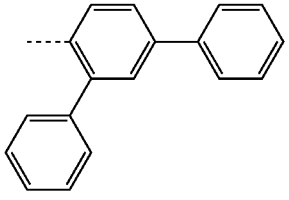 | 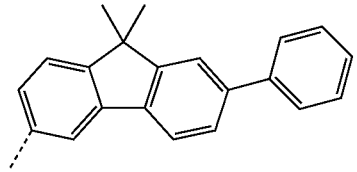 |

-continued
| Formula | - - -Ar1 | - - -Ar2 | - - -Ar3 |
|---|---|---|---|
| 1-64 | 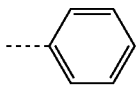 | 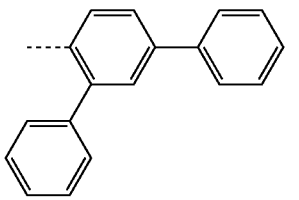 | 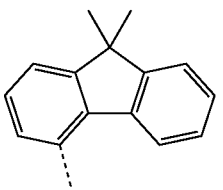 |
| 1-65 | 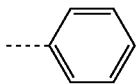 | 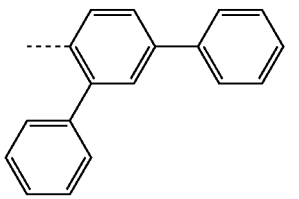 | 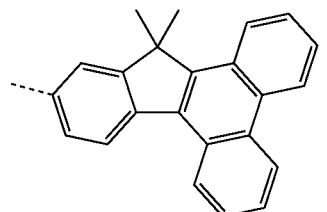 |
| 1-66 | 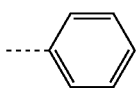 | 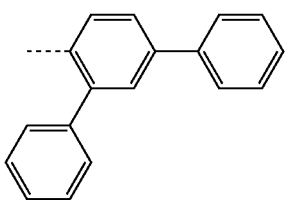 | 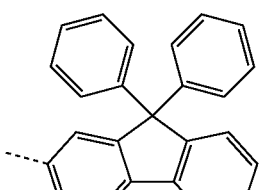 |
| 1-67 | 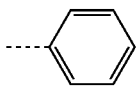 | 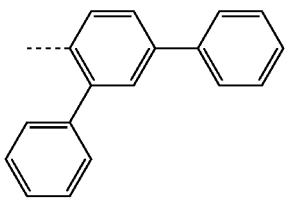 | 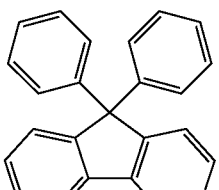 |
| 1-68 | 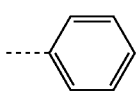 | 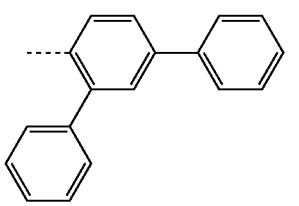 | 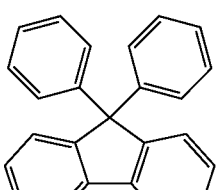 |
| 1-69 | 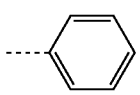 | 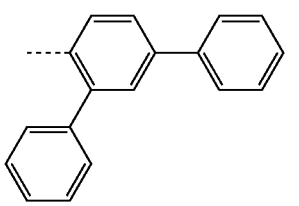 | 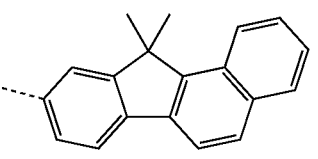 |
| 1-70 | 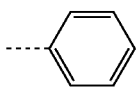 | 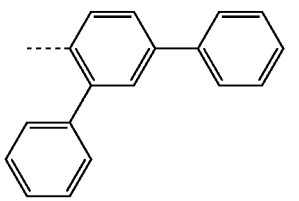 | 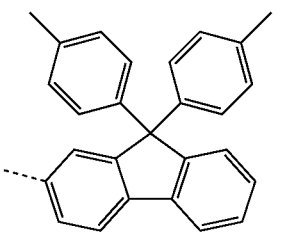 |

-continued

| Formula | ---Ar1 | ---Ar2 | ---Ar3 |
|---|---|---|---|
| 1-71 | phenyl | m-terphenyl (1,2,4-trisubstituted benzene variant) | 3-(9,9-di-p-tolyl)fluorenyl |
| 1-72 | phenyl | m-terphenyl | 4-(9,9-di-p-tolyl)fluorenyl |
| 1-73 | phenyl | 2-naphthyl | 1-(9,9-dimethyl)fluorenyl |
| 1-74 | phenyl | 2-naphthyl | 7-(9,9-dimethyl-2-phenyl)fluorenyl |
| 1-75 | phenyl | 2-naphthyl | 4-(9-methyl-9-phenyl)fluorenyl |
| 1-76 | phenyl | 2-naphthyl | 4-(9,9-dimethyl)fluorenyl |
| 1-77 | phenyl | 2-naphthyl | 1-(9,9-diphenyl)fluorenyl |

-continued
| Formula | ---Ar1 | ---Ar2 | ---Ar3 |
|---|---|---|---|
| 1-78 | 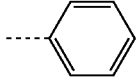 | 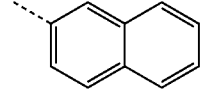 | 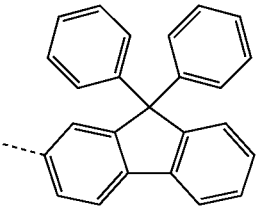 |
| 1-79 | 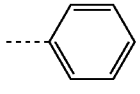 | 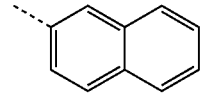 | 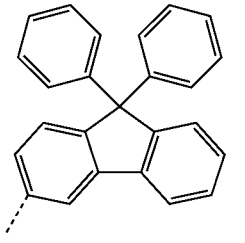 |
| 1-80 | 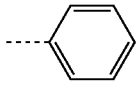 | 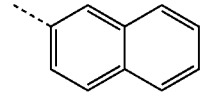 | 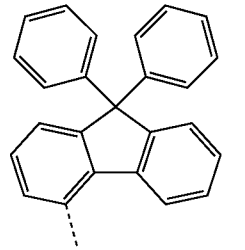 |
| 1-81 | 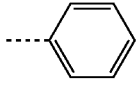 | 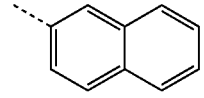 | 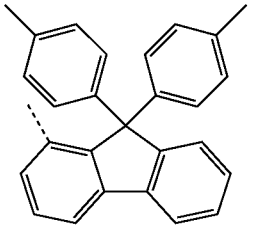 |
| 1-82 | 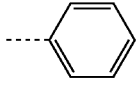 | 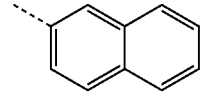 | 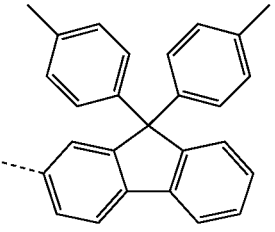 |
| 1-83 | 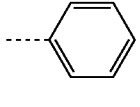 | 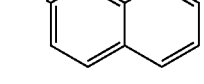 | 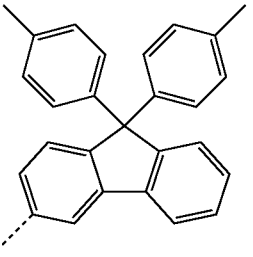 |

-continued
| Formula | ---Ar1 | ---Ar2 | ---Ar3 |
|---|---|---|---|
| 1-84 | 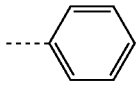 | 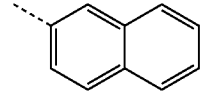 | 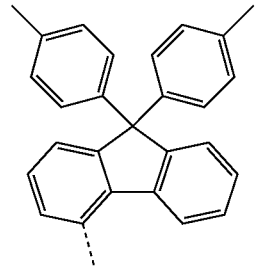 |
| 1-85 | 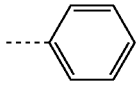 | 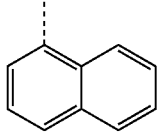 | 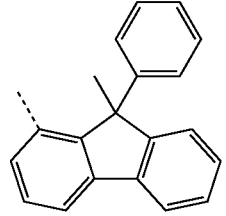 |
| 1-86 | 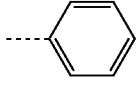 | 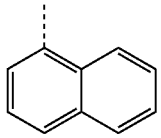 | 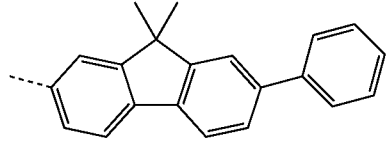 |
| 1-87 | 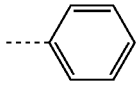 | 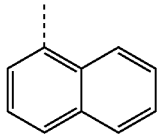 | 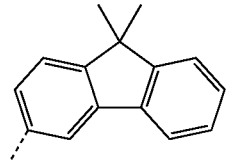 |
| 1-88 | 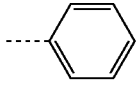 | 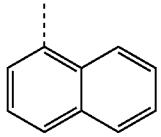 | 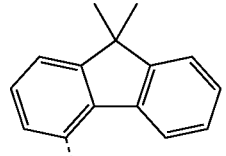 |
| 1-89 | 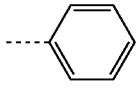 | 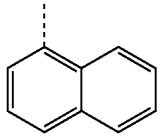 | 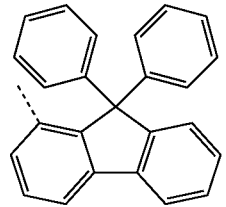 |
| 1-90 | 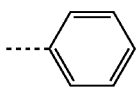 | 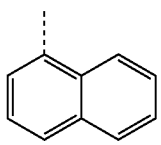 | 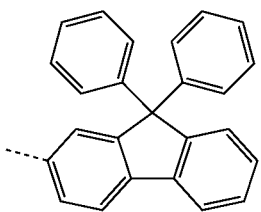 |

-continued

| Formula | - - -Ar1 | - - -Ar2 | - - -Ar3 |
| --- | --- | --- | --- |
| 1-91 | phenyl | 1-naphthyl | 3-(9,9-diphenylfluorenyl) |
| 1-92 | phenyl | 1-naphthyl | 4-(9,9-diphenylfluorenyl) |
| 1-93 | phenyl | 1-naphthyl | 1-(9,9-di-p-tolylfluorenyl) |
| 1-94 | phenyl | 1-naphthyl | 2-(9,9-di-p-tolylfluorenyl) |
| 1-95 | phenyl | 1-naphthyl | 3-(9-phenyl-9-(2-naphthyl)fluorenyl) |
| 1-96 | phenyl | 1-naphthyl | 4-(9,9-di-p-tolylfluorenyl) |

-continued
| Formula | ---Ar1 | ---Ar2 | ---Ar3 |
|---|---|---|---|
| 1-97 | 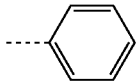 | 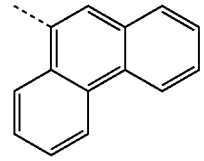 | 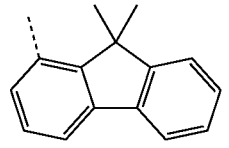 |
| 1-98 | 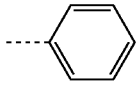 | 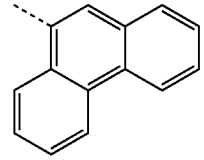 | 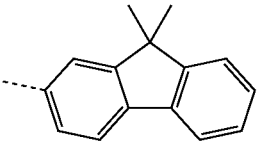 |
| 1-99 | 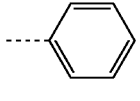 | 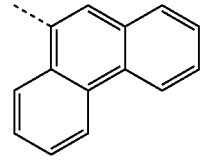 | 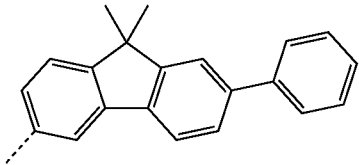 |
| 1-100 | 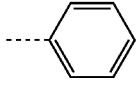 | 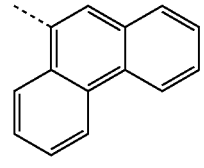 | 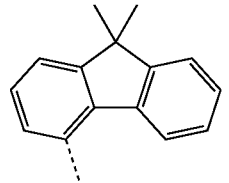 |
| 1-101 | 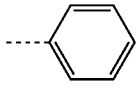 | 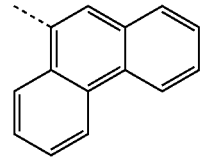 | 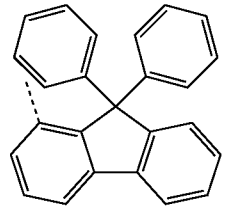 |
| 1-102 | 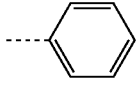 | 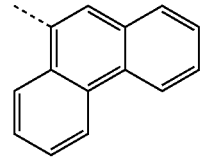 | 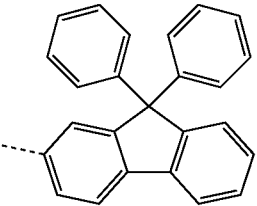 |
| 1-103 | 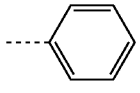 | 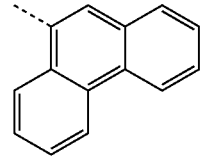 | 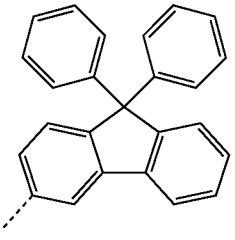 |

-continued
| Formula | ---Ar1 | ---Ar2 | ---Ar3 |
|---|---|---|---|
| 1-104 | 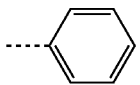 | 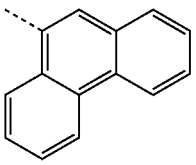 | 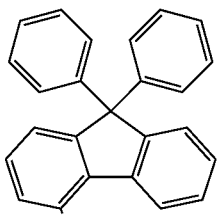 |
| 1-105 | 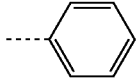 | 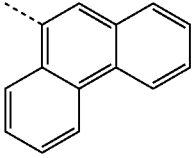 | 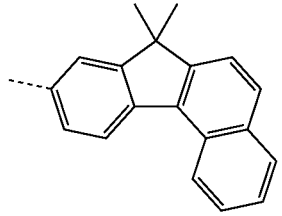 |
| 1-106 | 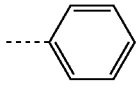 | 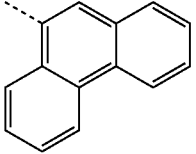 | 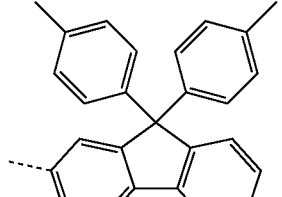 |
| 1-107 | 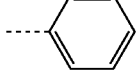 | 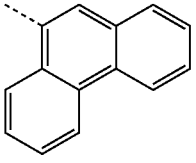 | 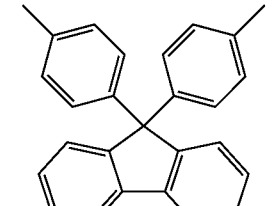 |
| 1-108 | 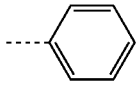 | 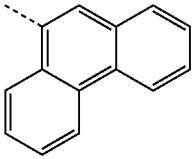 | 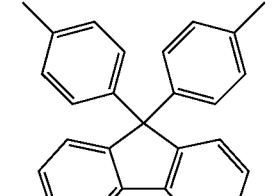 |
| 1-109 | 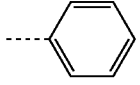 | 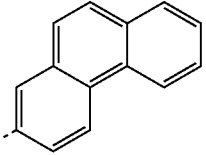 | 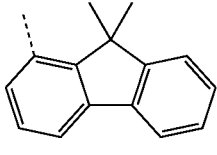 |
| 1-110 | 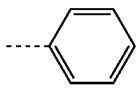 | 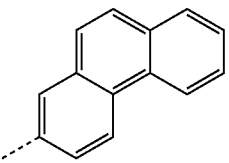 | 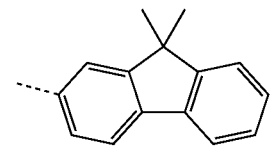 |

-continued
| Formula | ---Ar1 | ---Ar2 | ---Ar3 |
|---|---|---|---|
| 1-111 | 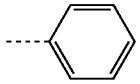 | 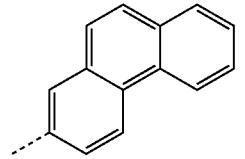 | 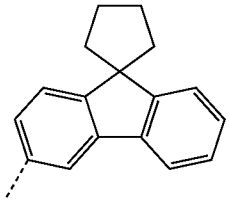 |
| 1-112 | 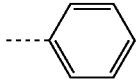 | 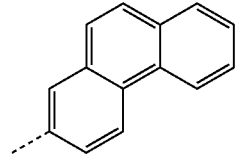 | 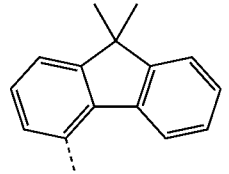 |
| 1-113 | 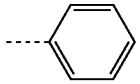 | 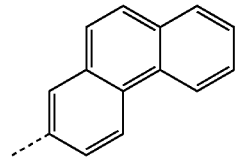 | 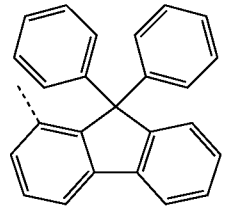 |
| 1-114 | 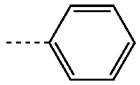 | 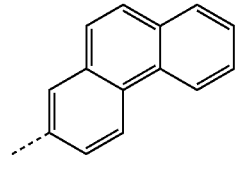 | 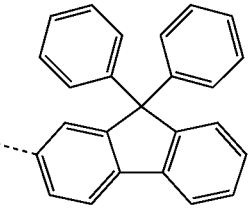 |
| 1-115 | 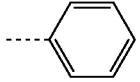 | 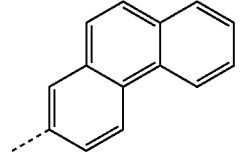 | 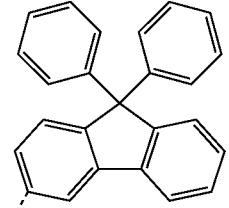 |
| 1-116 | 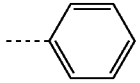 | 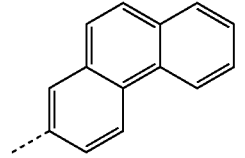 | 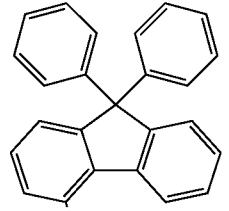 |
| 1-117 | 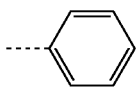 | 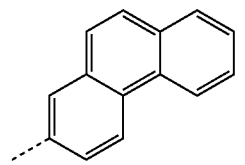 | 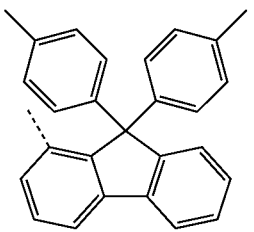 |

-continued
| Formula | ---Ar1 | ---Ar2 | ---Ar3 |
|---|---|---|---|
| 1-118 | 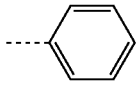 | 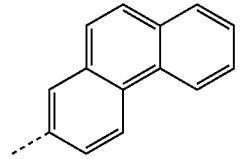 | 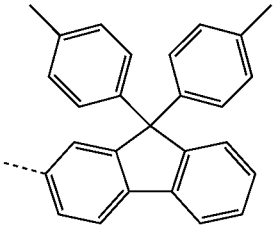 |
| 1-119 | 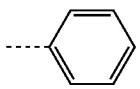 | 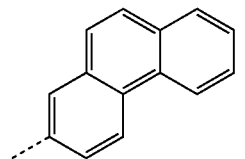 | 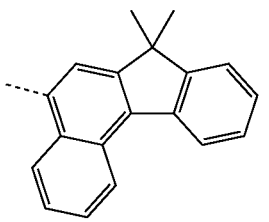 |
| 1-120 | 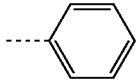 | 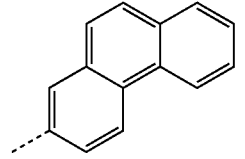 | 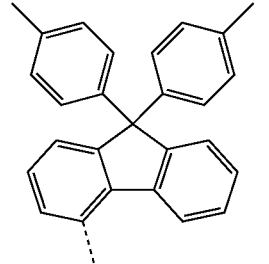 |
| 1-121 | 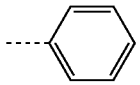 | 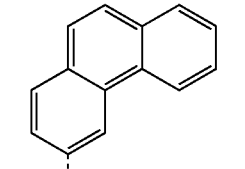 | 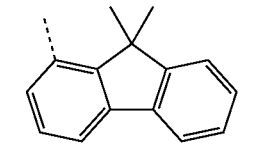 |
| 1-122 | 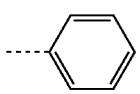 | 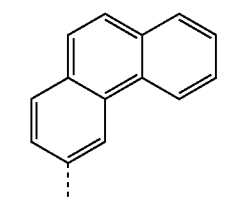 | 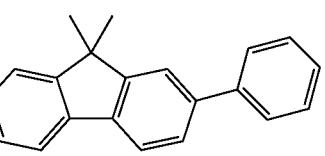 |
| 1-123 | 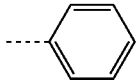 | 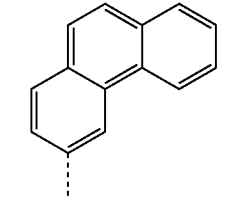 | 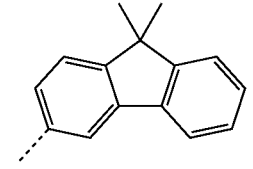 |
| 1-124 | 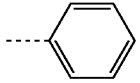 | 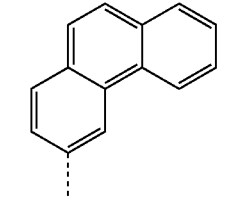 | 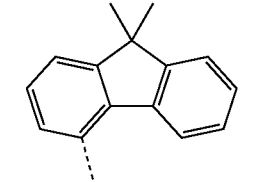 |

US 9,640,766 B2
| Formula | ---Ar1 | ---Ar2 | ---Ar3 |
|---|---|---|---|
| 1-125 | 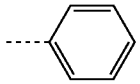 | 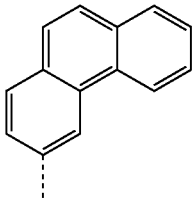 | 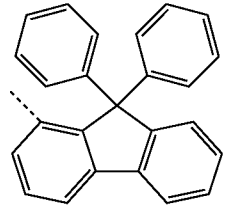 |
| 1-126 | 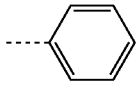 | 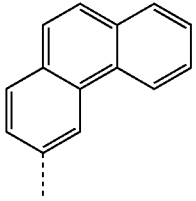 | 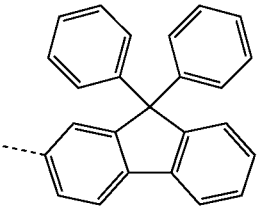 |
| 1-127 | 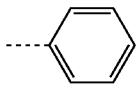 | 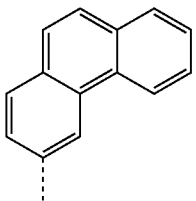 | 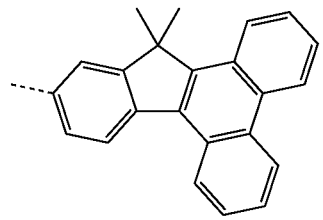 |
| 1-128 | 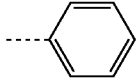 | 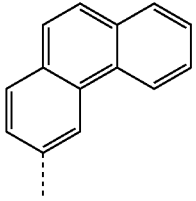 | 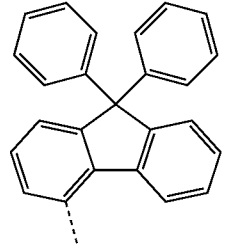 |
| 1-129 | 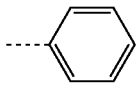 | 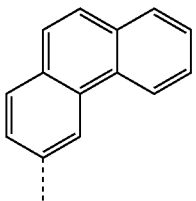 | 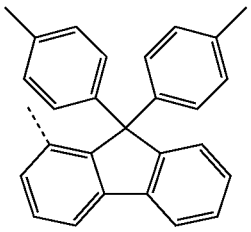 |
| 1-130 | 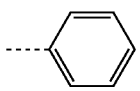 | 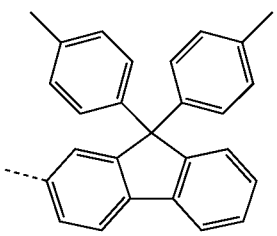 | 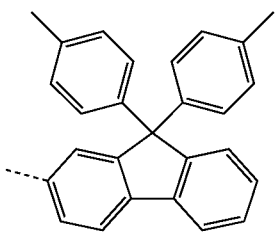 |

-continued
| Formula | ---Ar1 | ---Ar2 | ---Ar3 |
|---|---|---|---|
| 1-131 | 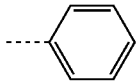 | 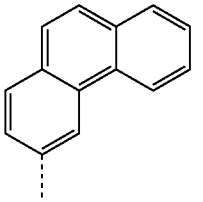 | 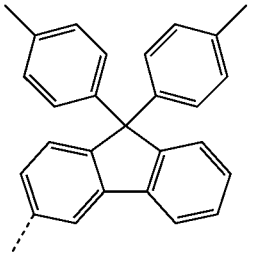 |
| 1-132 | 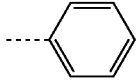 | 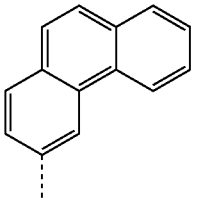 | 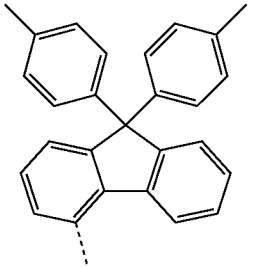 |
| 1-133 | 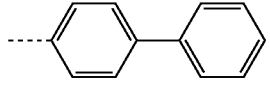 | 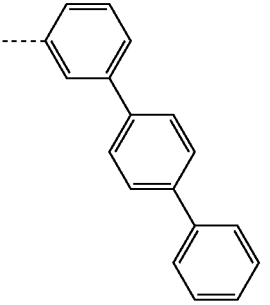 | 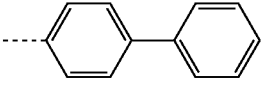 |
| 1-134 | 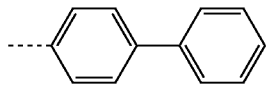 | 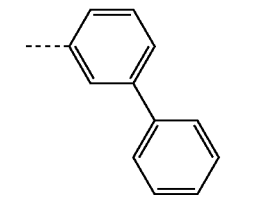 | 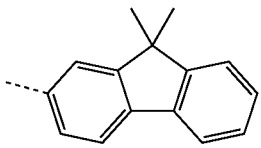 |
| 1-135 | 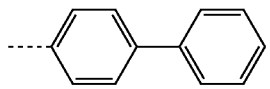 | 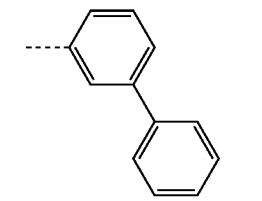 | 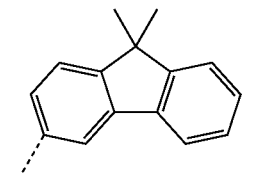 |
| 1-136 | 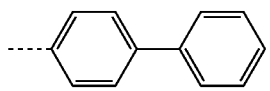 | 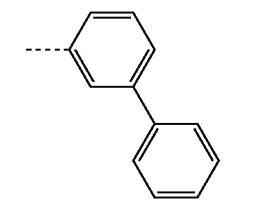 | 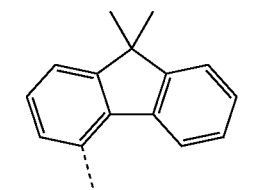 |

-continued

| Formula | ---Ar1 | ---Ar2 | ---Ar3 |
| --- | --- | --- | --- |
| 1-137 | 4-biphenyl | 3-biphenyl | 9,9-diphenylfluoren-1-yl |
| 1-138 | phenyl | 4-(2-naphthyl)phenyl | 9,9-diphenylfluoren-2-yl |
| 1-139 | 4-biphenyl | 3-biphenyl | 9,9-diphenylfluoren-3-yl |
| 1-140 | 4-biphenyl | 3-biphenyl | 9,9-diphenylfluoren-4-yl |
| 1-141 | 4-biphenyl | 3-biphenyl | 9,9-di(p-tolyl)fluoren-1-yl |
| 1-142 | 4-biphenyl | 3-biphenyl | 9,9-di(p-tolyl)fluoren-2-yl |

-continued

| Formula | ---Ar1 | ---Ar2 | ---Ar3 |
| --- | --- | --- | --- |
| 1-143 | 4-biphenyl | 3-(1-naphthyl)phenyl | 9,9-diphenyl-2-fluorenyl |
| 1-144 | 4-biphenyl | 3-biphenyl | 9,9-di(p-tolyl)-4-fluorenyl |
| 1-145 | 4-biphenyl | 2-biphenyl | 9,9-dimethyl-1-fluorenyl |
| 1-146 | 4-biphenyl | 2-biphenyl | 9,9-dimethyl-2-fluorenyl |
| 1-147 | 4-biphenyl | 2-biphenyl | 9,9-dimethyl-3-fluorenyl |
| 1-148 | 4-biphenyl | 2-biphenyl | 9,9-dimethyl-4-fluorenyl |
| 1-149 | 4-biphenyl | 2-biphenyl | 9,9-diphenyl-7-tert-butyl-2-fluorenyl |

-continued
| Formula | ---Ar1 | ---Ar2 | ---Ar3 |
|---|---|---|---|
| 1-150 | 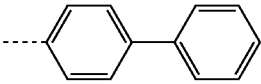 | 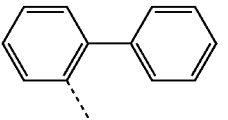 | 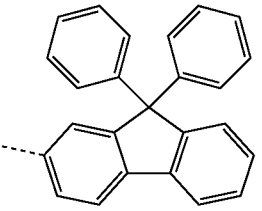 |
| 1-151 | 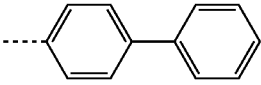 | 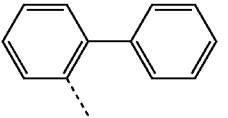 | 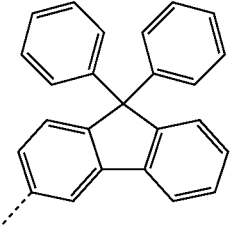 |
| 1-152 | 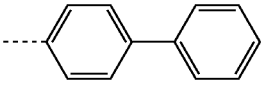 | 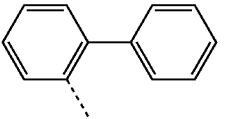 | 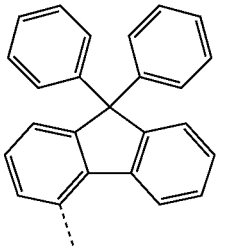 |
| 1-153 | 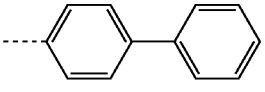 | 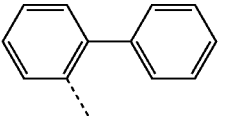 | 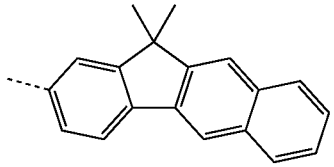 |
| 1-154 | 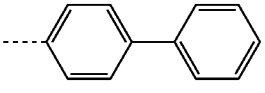 | 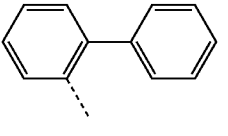 | 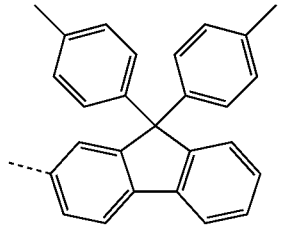 |
| 1-155 | 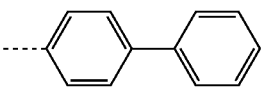 | 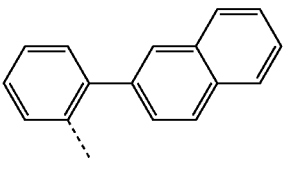 | 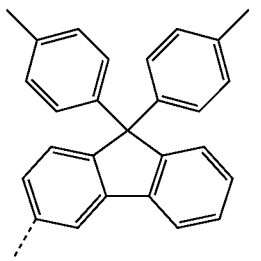 |

-continued

| Formula | ---Ar1 | ---Ar2 | ---Ar3 |
|---|---|---|---|
| 1-156 | | | |
| 1-157 | | | |
| 1-158 | | | |
| 1-159 | | | |
| 1-160 | | | |
| 1-161 | | | |
| 1-162 | | | |

-continued

| Formula | ---Ar1 | ---Ar2 | ---Ar3 |
|---|---|---|---|
| 1-163 | | | |
| 1-164 | | | |
| 1-165 | | | |
| 1-166 | | | |
| 1-167 | | | |
| 1-168 | | | |

-continued
| Formula | ---Ar1 | ---Ar2 | ---Ar3 |
|---|---|---|---|
| 1-169 | 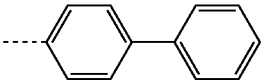 | 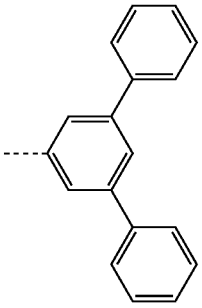 | 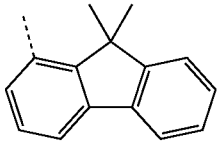 |
| 1-170 | 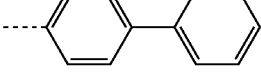 | 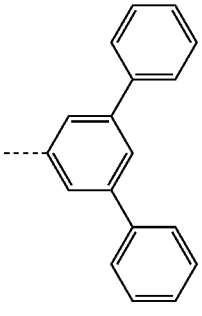 | 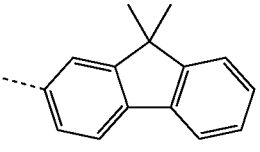 |
| 1-171 | 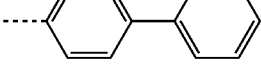 | 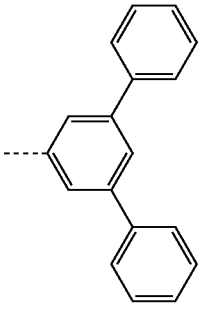 | 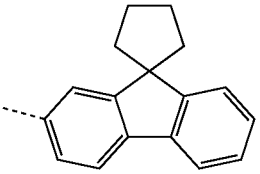 |
| 1-172 | 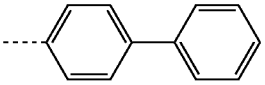 | 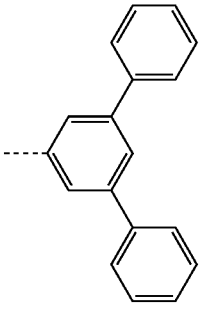 | 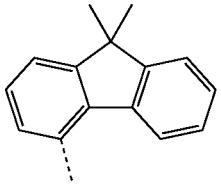 |
| 1-173 | 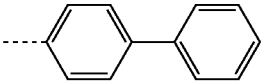 | 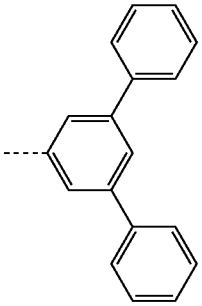 | 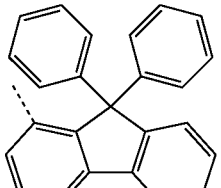 |

-continued

| Formula | ---Ar1 | ---Ar2 | ---Ar3 |
| --- | --- | --- | --- |
| 1-174 | | | |
| 1-175 | | | |
| 1-176 | | | |
| 1-177 | | | |
| 1-178 | | | |

-continued

| Formula | ---Ar1 | ---Ar2 | ---Ar3 |
|---|---|---|---|
| 1-179 | | | |
| 1-180 | | | |
| 1-181 | | | |
| 1-182 | | | |
| 1-183 | | | |
| 1-184 | | | |

-continued

| Formula | ---Ar1 | ---Ar2 | ---Ar3 |
| --- | --- | --- | --- |
| 1-185 | | | |
| 1-186 | | | |
| 1-187 | | | |
| 1-188 | | | |
| 1-189 | | | |
| 1-190 | | | |

-continued

| Formula | ---Ar1 | ---Ar2 | ---Ar3 |
|---|---|---|---|
| 1-191 | | | |
| 1-192 | | | |
| 1-193 | | | |
| 1-194 | | | |
| 1-195 | | | |
| 1-196 | | | |
| 1-197 | | | |

-continued

| Formula | ---Ar1 | ---Ar2 | ---Ar3 |
| --- | --- | --- | --- |
| 1-198 | biphenyl | 2-naphthyl | 9,9-diphenylfluoren-2-yl |
| 1-199 | biphenyl | 6-phenylnaphthalen-2-yl | 9,9-diphenylfluoren-3-yl |
| 1-200 | biphenyl | 6-phenylnaphthalen-2-yl | 9,9-diphenylfluoren-4-yl |
| 1-201 | biphenyl | 2-naphthyl | 9,9-di(p-tolyl)fluoren-1-yl |
| 1-202 | biphenyl | 2-naphthyl | 9,9-di(p-tolyl)fluoren-2-yl |
| 1-203 | biphenyl | 2-naphthyl | 9,9-di(p-tolyl)fluoren-3-yl |

-continued

| Formula | ---Ar1 | ---Ar2 | ---Ar3 |
|---|---|---|---|
| 1-204 | | | |
| 1-205 | | | |
| 1-207 | | | |
| 1-208 | | | |
| 1-209 | | | |
| 1-210 | | | |
| 1-211 | | | |

-continued

| Formula | - - -Ar1 | - - -Ar2 | - - -Ar3 |
|---|---|---|---|
| 1-212 | biphenyl | naphthyl | 9,9-diphenylfluorenyl |
| 1-213 | biphenyl | 4-phenylnaphthyl | 9,9-di(p-tolyl)fluorenyl |
| 1-214 | biphenyl | naphthyl | 9,9-di(p-tolyl)fluorenyl |
| 1-215 | biphenyl | naphthyl | 9,9-di(p-tolyl)fluorenyl |
| 1-216 | biphenyl | naphthyl | biphenyl |
| 1-217 | biphenyl | phenanthrenyl | 9,9-dimethylfluorenyl |
| 1-218 | biphenyl | phenanthrenyl | 9,9-dimethylfluorenyl |

-continued

| Formula | ---Ar1 | ---Ar2 | ---Ar3 |
| --- | --- | --- | --- |
| 1-219 | biphenyl | phenanthrenyl | 9,9-dimethylfluorenyl |
| 1-220 | biphenyl | phenyl-phenanthrenyl | 9,9-dimethylfluorenyl |
| 1-221 | biphenyl | phenanthrenyl | 9,9-diphenylfluorenyl |
| 1-222 | biphenyl | phenanthrenyl | 9,9-diphenylfluorenyl |
| 1-223 | biphenyl | phenanthrenyl | 9,9-diphenylfluorenyl |
| 1-224 | biphenyl | phenanthrenyl | 9,9-diphenylfluorenyl |

-continued

| Formula | ---Ar1 | ---Ar2 | ---Ar3 |
|---|---|---|---|
| 1-225 | biphenyl | phenanthrene | 9,9-di(p-tolyl)fluorene |
| 1-226 | biphenyl | phenanthrene | 9,9-di(p-tolyl)fluorene |
| 1-227 | biphenyl | phenanthrene | 9,9-dimethylbenzo[a]fluorene |
| 1-228 | biphenyl | phenanthrene | 9,9-di(p-tolyl)fluorene |
| 1-229 | biphenyl | phenanthrene | 9,9-dimethylfluorene |
| 1-230 | biphenyl | phenanthrene | 9,9-dimethylfluorene |
| 1-231 | biphenyl | phenanthrene | 9,9-dimethylfluorene |

-continued

| Formula | ---Ar1 | ---Ar2 | ---Ar3 |
|---|---|---|---|
| 1-232 | | | |
| 1-233 | | | |
| 1-234 | | | |
| 1-235 | | | |
| 1-236 | | | |
| 1-237 | | | |

-continued

| Formula | ---Ar1 | ---Ar2 | ---Ar3 |
| --- | --- | --- | --- |
| 1-238 | | | |
| 1-239 | | | |
| 1-240 | | | |
| 1-241 | | | |
| 1-242 | | | |
| 1-243 | | | |

-continued

| Formula | - - -Ar1 | - - -Ar2 | - - -Ar3 |
|---|---|---|---|
| 1-244 | | | |
| 1-245 | | | |
| 1-246 | | | |
| 1-247 | | | |
| 1-248 | | | |
| 1-249 | | | |
| 1-250 | | | |

-continued
| Formula | ---Ar1 | ---Ar2 | ---Ar3 |
|---|---|---|---|
| 1-251 | 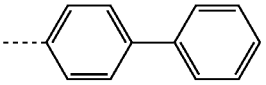 | 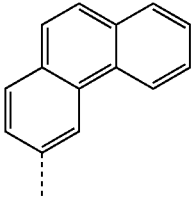 | 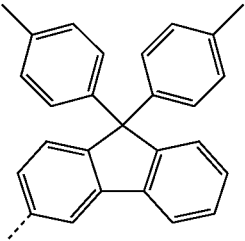 |
| 1-252 | 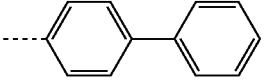 | 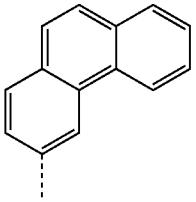 | 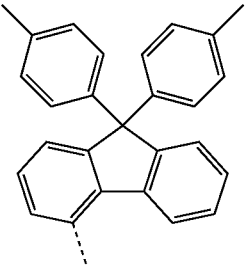 |
| 1-253 | 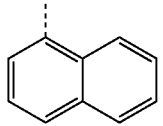 | 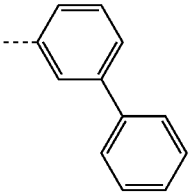 | 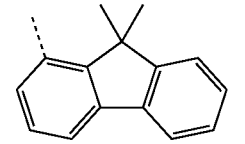 |
| 1-254 | 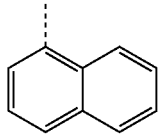 | 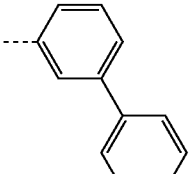 | 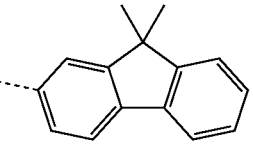 |
| 1-255 | 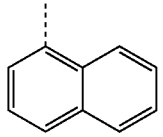 | 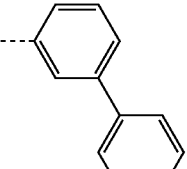 | 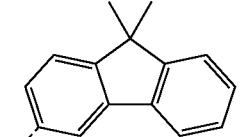 |
| 1-256 | 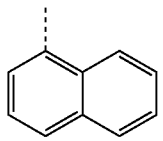 | 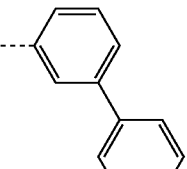 | 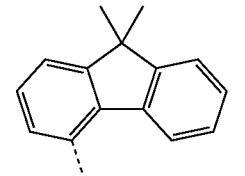 |
| 1-257 | 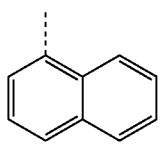 | 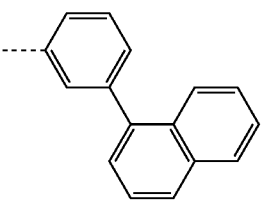 | 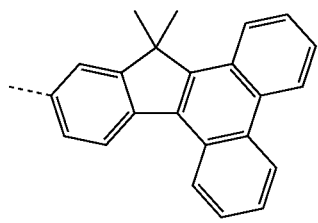 |

-continued
| Formula | ---Ar1 | ---Ar2 | ---Ar3 |
|---|---|---|---|
| 1-258 | 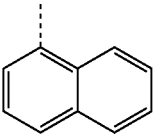 | 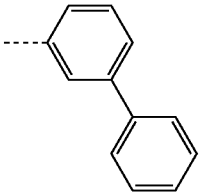 | 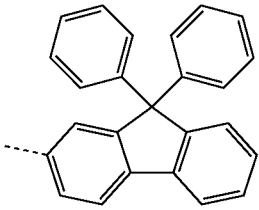 |
| 1-259 | 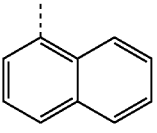 | 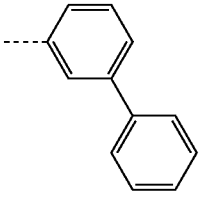 | 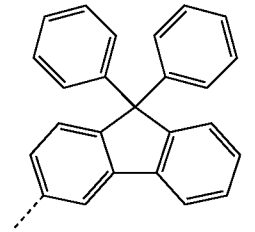 |
| 1-260 | 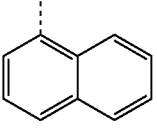 | 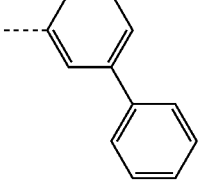 | 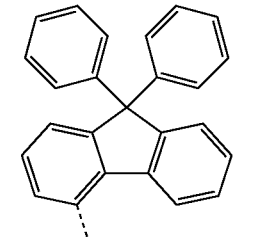 |
| 1-261 | 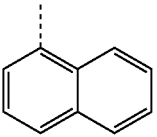 | 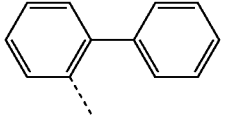 | 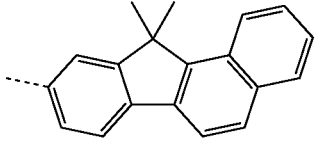 |
| 1-262 | 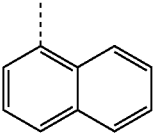 | 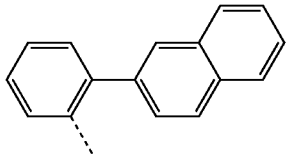 | 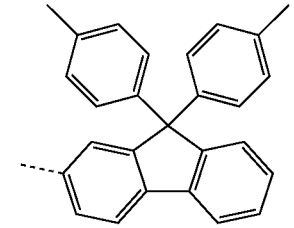 |
| 1-263 | 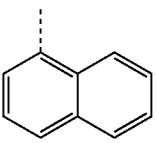 | 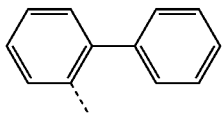 | 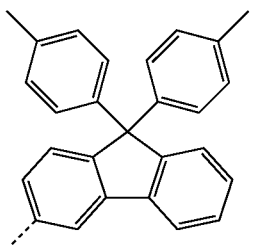 |

-continued

| Formula | ---Ar1 | ---Ar2 | ---Ar3 |
| --- | --- | --- | --- |
| 1-264 | 1-naphthyl | 2-biphenyl | 9,9-di(p-tolyl)fluoren-4-yl |
| 1-265 | 1-naphthyl | 2-(1-naphthyl)phenyl | 9,9-dimethylfluoren-1-yl |
| 1-266 | 1-naphthyl | 2-biphenyl | 9,9-dimethylfluoren-2-yl |
| 1-267 | 1-naphthyl | 2-biphenyl | 9,9-dimethylfluoren-3-yl |
| 1-268 | 1-naphthyl | 2-biphenyl | 9,9-dimethylfluoren-4-yl |
| 1-269 | 1-naphthyl | 2-biphenyl | 9,9-diphenylfluoren-1-yl |
| 1-270 | 1-naphthyl | 2-biphenyl | 9,9-diphenylfluoren-2-yl |

115                                                                                                                     116
-continued
| Formula | ---Ar1 | ---Ar2 | ---Ar3 |
|---|---|---|---|
| 1-271 | 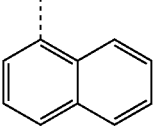 | 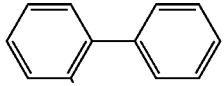 | 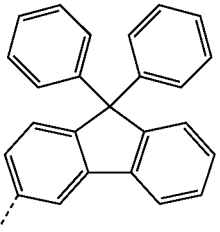 |
| 1-272 | 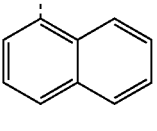 | 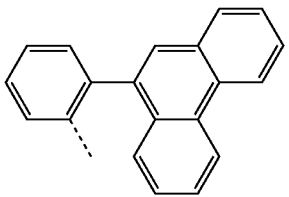 | 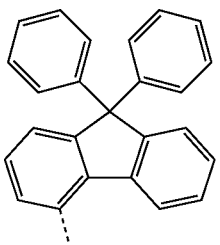 |
| 1-273 | 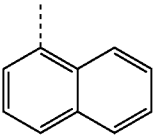 | 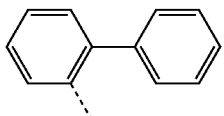 | 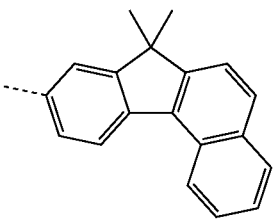 |
| 1-274 | 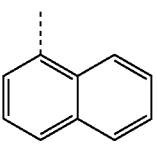 | 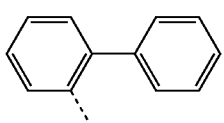 | 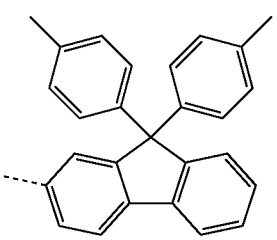 |
| 1-275 | 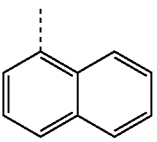 | 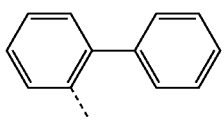 | 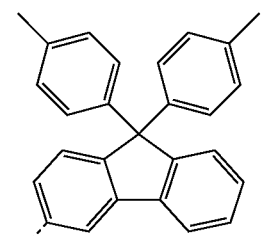 |
| 1-276 | 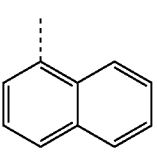 | 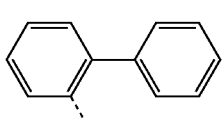 | 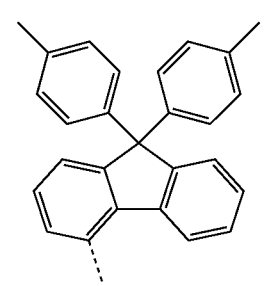 |

-continued
| Formula | ---Ar1 | ---Ar2 | ---Ar3 |
|---|---|---|---|
| 1-277 | 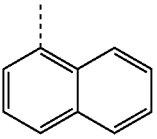 | 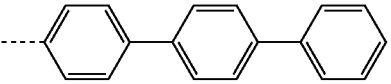 | 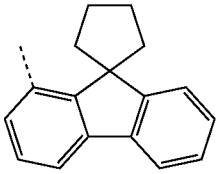 |
| 1-278 | 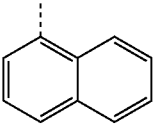 | 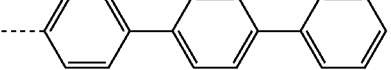 | 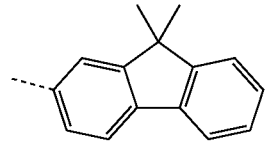 |
| 1-279 | 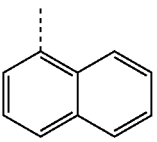 | 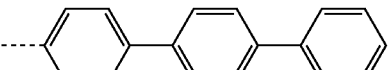 | 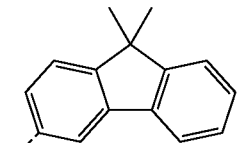 |
| 1-280 | 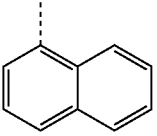 | 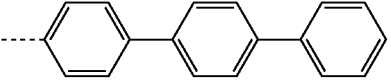 | 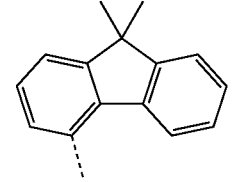 |
| 1-281 | 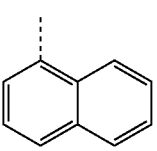 | 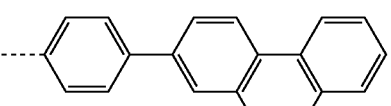 | 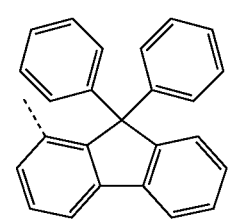 |
| 1-282 | 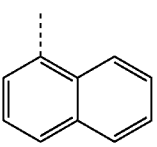 | 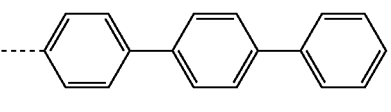 | 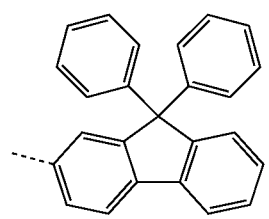 |
| 1-283 | 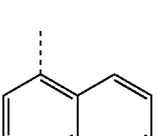 | 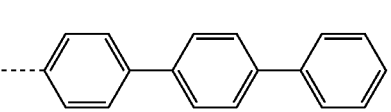 | 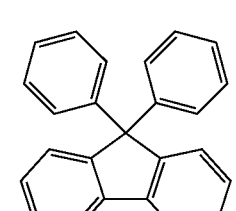 |

-continued
| Formula | ---Ar1 | ---Ar2 | ---Ar3 |
|---|---|---|---|
| 1-284 | 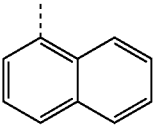 | 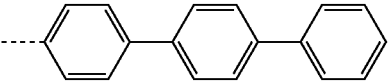 | 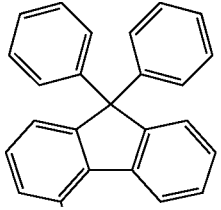 |
| 1-285 | 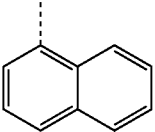 | 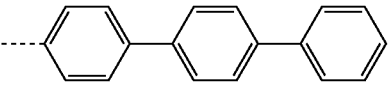 | 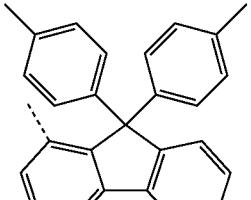 |
| 1-286 | 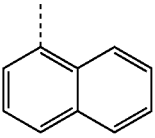 | 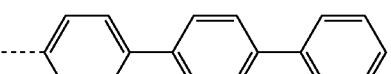 | 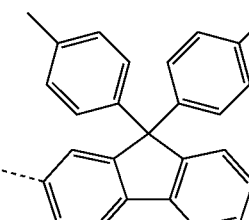 |
| 1-287 | 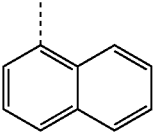 | 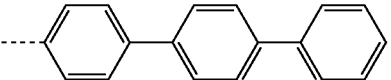 | 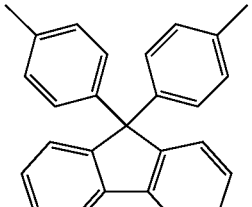 |
| 1-288 | 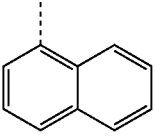 | 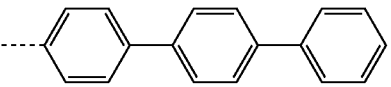 | 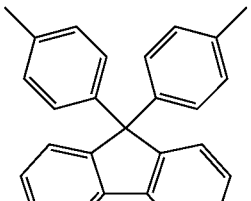 |
| 1-289 | 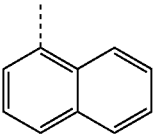 | 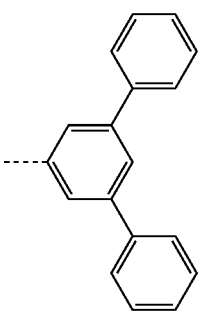 | 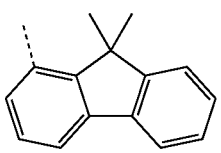 |

-continued
| Formula | ---Ar1 | ---Ar2 | ---Ar3 |
|---|---|---|---|
| 1-290 | 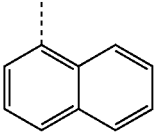 | 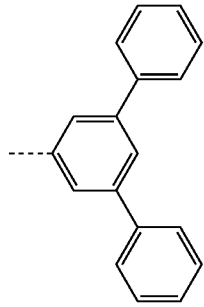 | 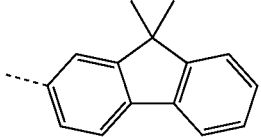 |
| 1-291 | 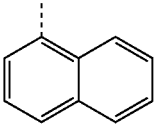 | 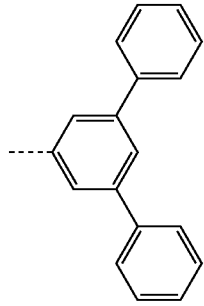 | 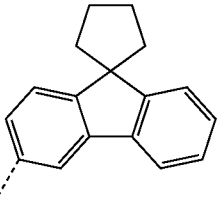 |
| 1-292 | 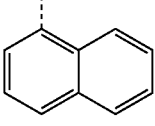 | 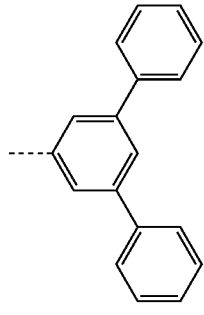 | 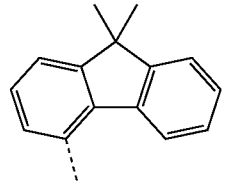 |
| 1-293 | 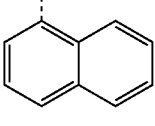 | 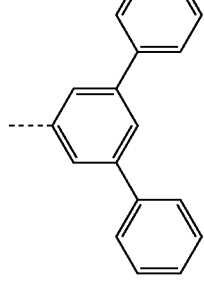 | 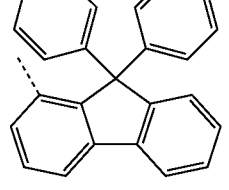 |
| 1-294 | 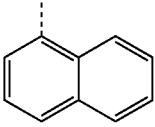 | 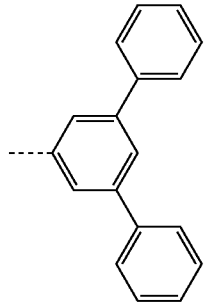 | 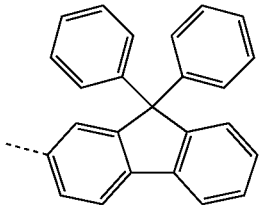 |

| Formula | ---Ar1 | ---Ar2 | ---Ar3 |
|---|---|---|---|
| 1-295 | 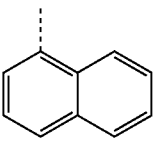 | 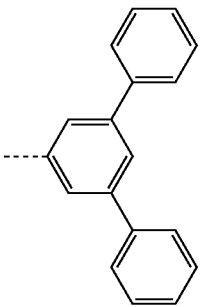 | 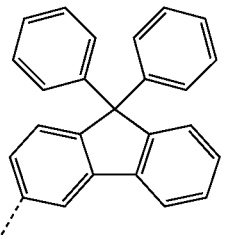 |
| 1-296 | 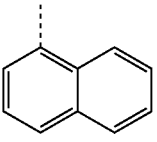 | 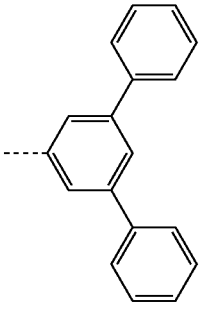 | 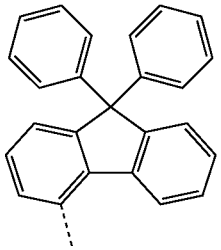 |
| 1-297 | 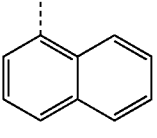 | 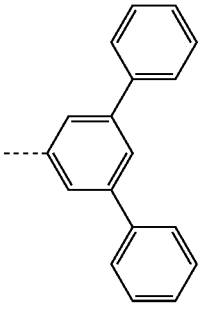 | 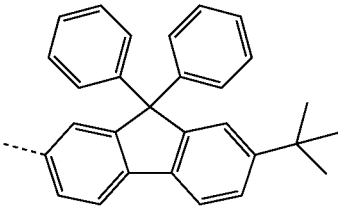 |
| 1-298 | 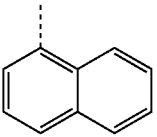 | 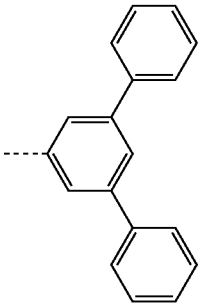 | 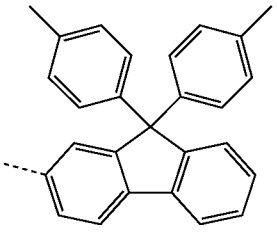 |
| 1-299 | 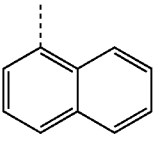 | 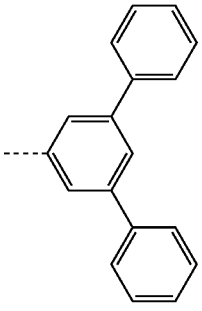 | 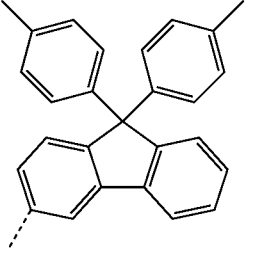 |

-continued
| Formula | ---Ar1 | ---Ar2 | ---Ar3 |
|---|---|---|---|
| 1-300 | 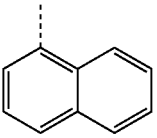 | 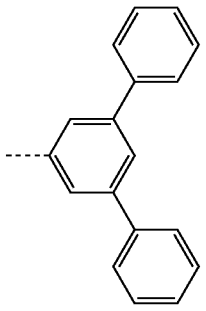 | 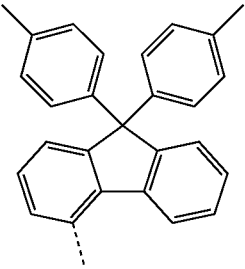 |
| 1-301 | 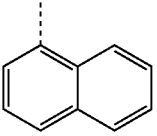 | 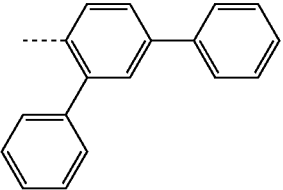 | 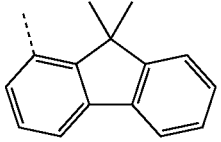 |
| 1-302 | 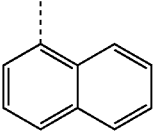 | 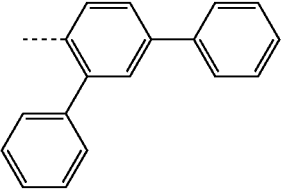 | 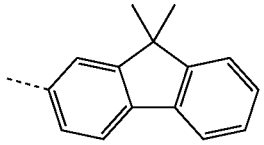 |
| 1-303 | 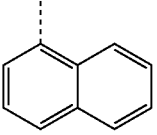 | 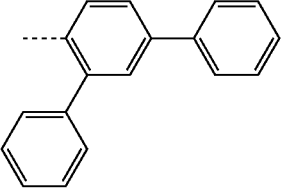 | 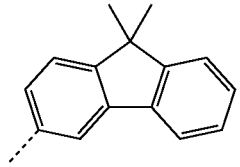 |
| 1-304 | 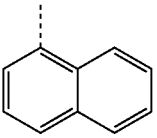 | 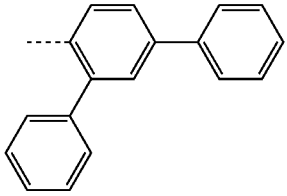 | 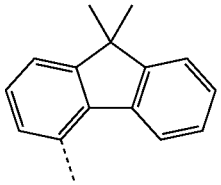 |
| 1-305 | 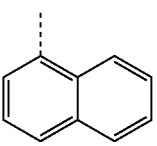 | 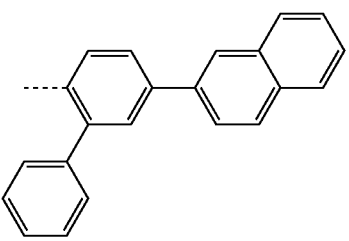 | 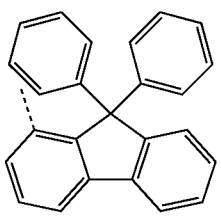 |

-continued
| Formula | ---Ar1 | ---Ar2 | ---Ar3 |
|---|---|---|---|
| 1-306 | 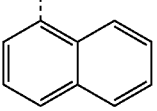 | 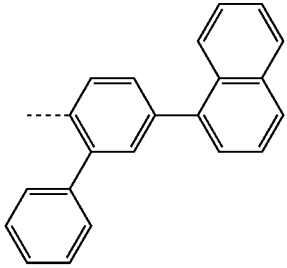 | 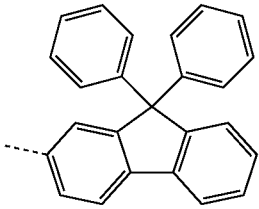 |
| 1-307 | 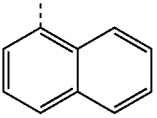 | 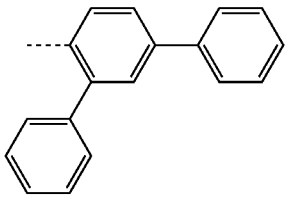 | 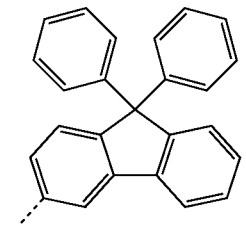 |
| 1-308 | 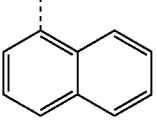 | 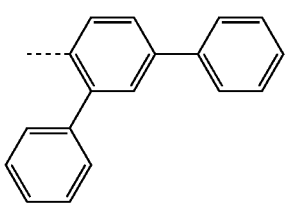 | 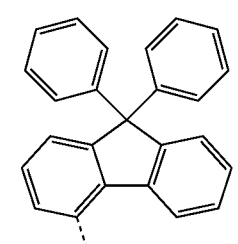 |
| 1-309 | 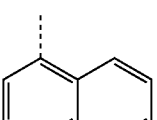 | 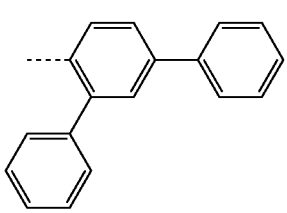 | 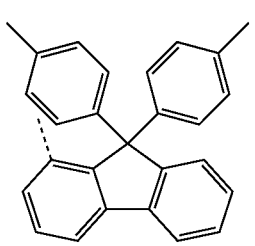 |
| 1-310 | 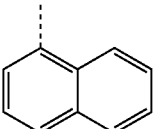 | 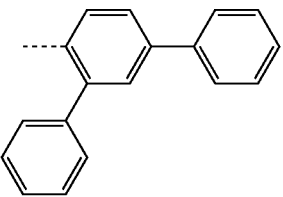 | 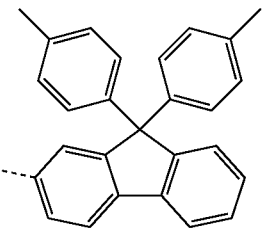 |
| 1-311 | 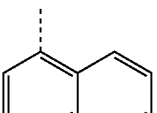 | 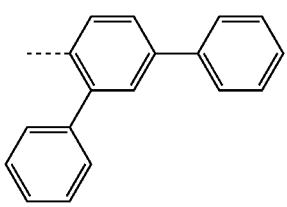 | 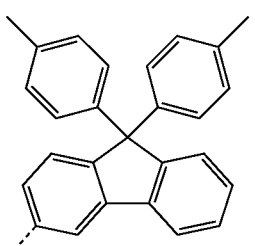 |

-continued
| Formula | - - -Ar1 | - - -Ar2 | - - -Ar3 |
|---|---|---|---|
| 1-312 | 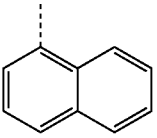 | 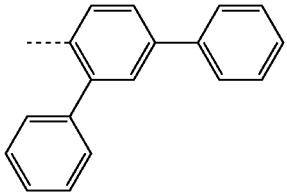 | 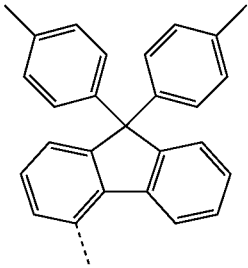 |
| 1-313 | 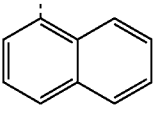 | 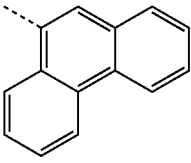 | 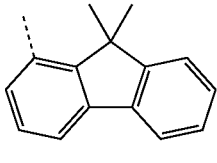 |
| 1-314 | 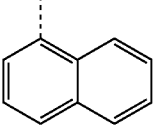 | 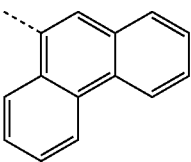 | 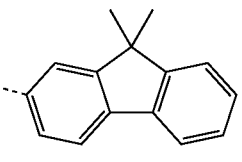 |
| 1-315 | 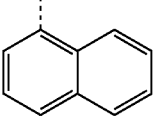 | 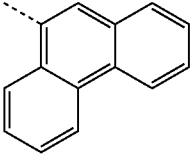 | 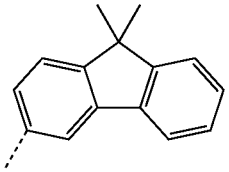 |
| 1-316 | 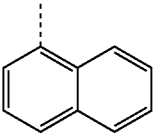 | 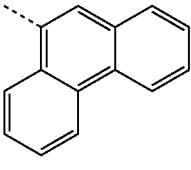 | 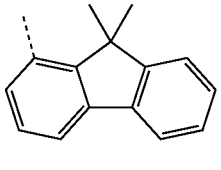 |
| 1-317 | 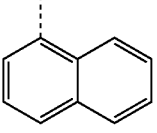 | 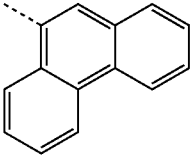 | 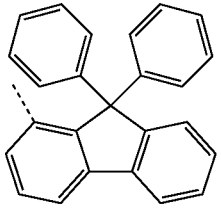 |
| 1-318 | 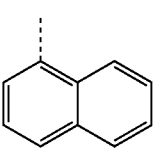 | 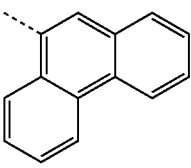 | 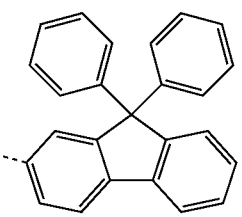 |

-continued
| Formula | ---Ar1 | ---Ar2 | ---Ar3 |
|---|---|---|---|
| 1-319 | 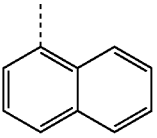 | 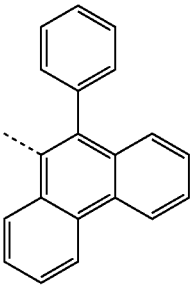 | 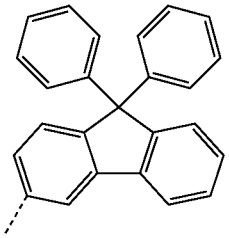 |
| 1-320 | 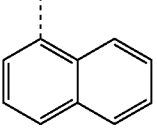 | 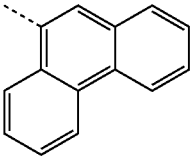 | 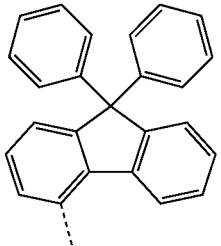 |
| 1-321 | 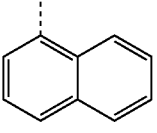 | 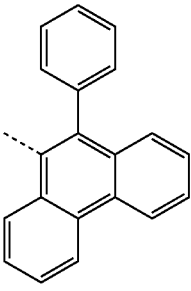 | 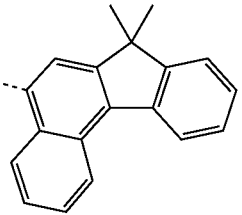 |
| 1-322 | 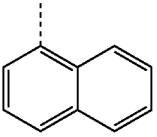 | 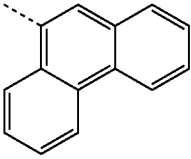 | 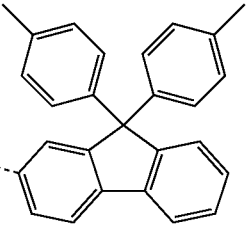 |
| 1-323 | 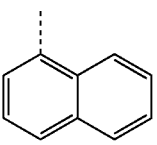 | 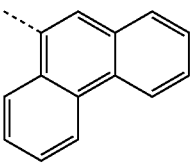 | 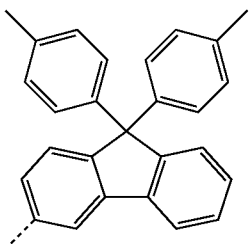 |

-continued
| Formula | - - -Ar1 | - - -Ar2 | - - -Ar3 |
|---|---|---|---|
| 1-324 | 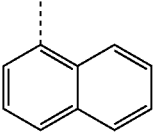 | 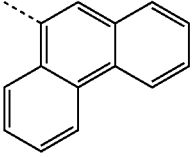 | 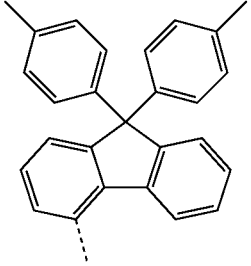 |
| 1-325 | 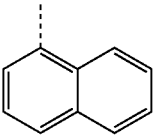 | 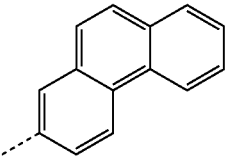 | 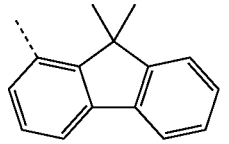 |
| 1-326 | 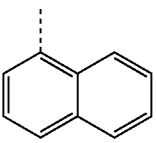 | 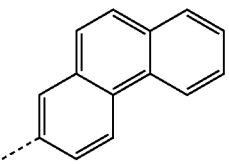 | 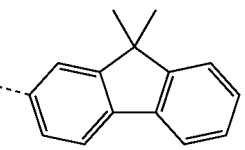 |
| 1-327 | 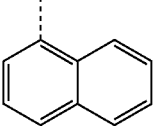 | 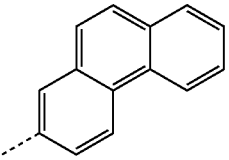 | 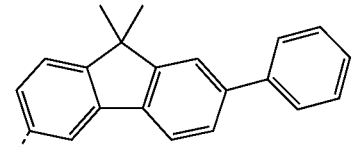 |
| 1-328 | 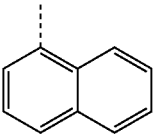 | 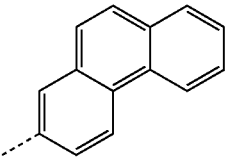 | 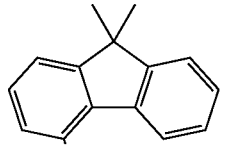 |
| 1-329 | 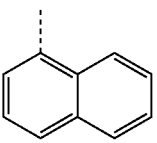 | 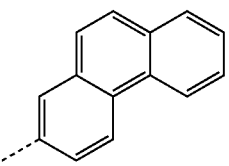 |  |
| 1-330 | 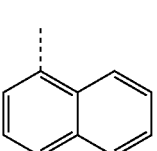 | 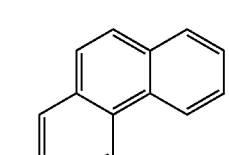 | 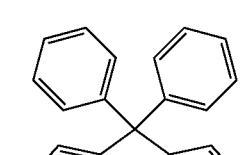 |

-continued
| Formula | ---Ar1 | ---Ar2 | ---Ar3 |
| --- | --- | --- | --- |
| 1-331 | 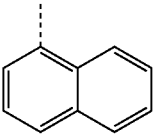 | 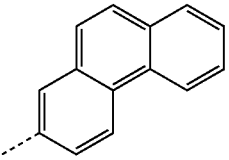 | 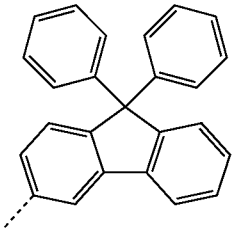 |
| 1-332 | 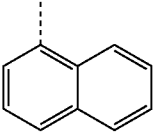 | 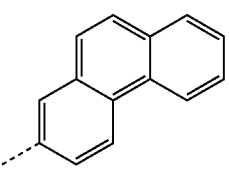 | 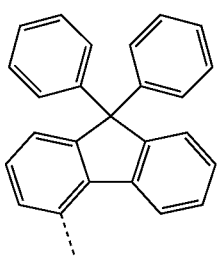 |
| 1-333 | 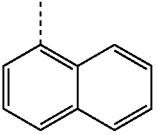 | 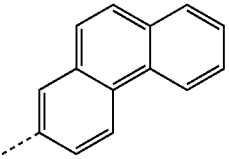 | 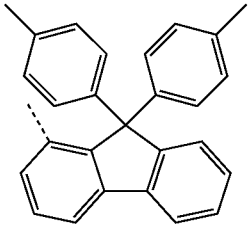 |
| 1-334 | 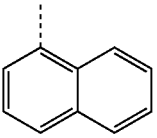 | 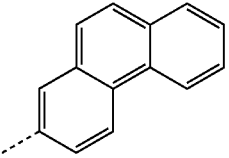 | 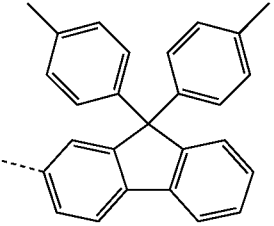 |
| 1-335 | 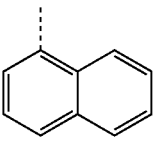 | 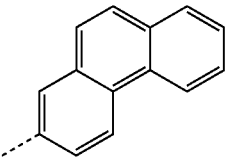 | 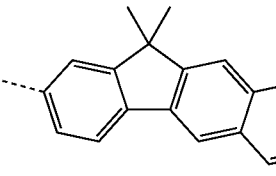 |
| 1-336 | 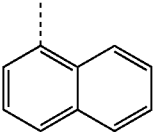 | 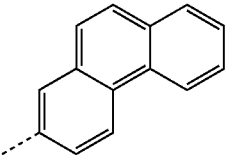 | 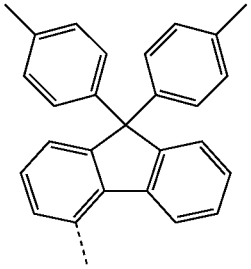 |

-continued
| Formula | ---Ar1 | ---Ar2 | ---Ar3 |
|---|---|---|---|
| 1-337 | 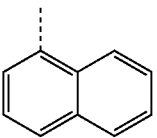 | 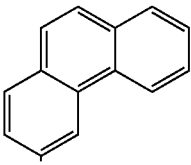 | 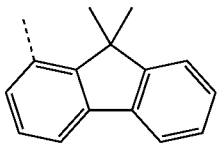 |
| 1-338 | 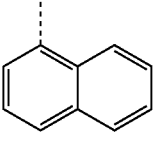 | 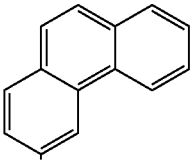 | 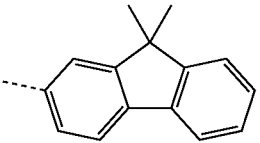 |
| 1-339 | 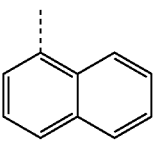 | 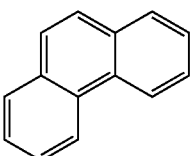 | 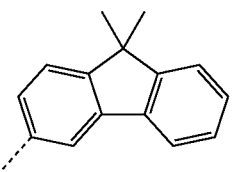 |
| 1-340 | 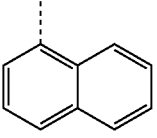 | 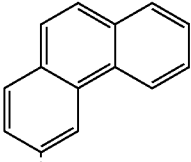 | 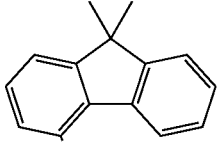 |
| 1-341 | 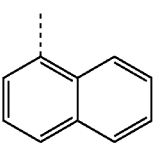 | 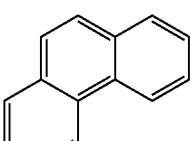 | 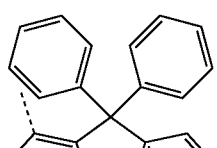 |
| 1-342 | 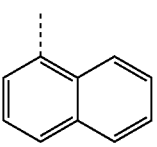 | 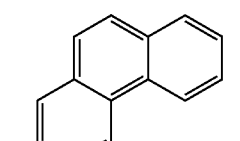 | 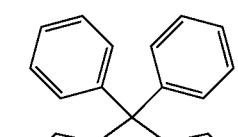 |
| 1-343 | 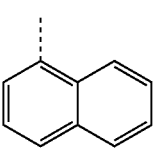 | 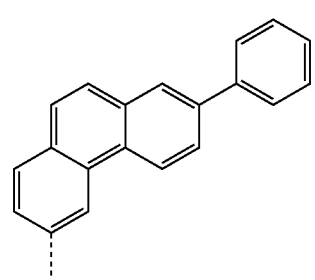 | 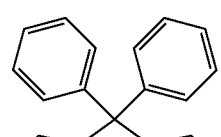 |

-continued
| Formula | ---Ar1 | ---Ar2 | ---Ar3 |
|---|---|---|---|
| 1-344 | 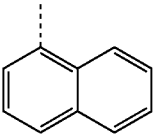 | 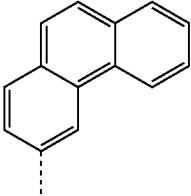 | 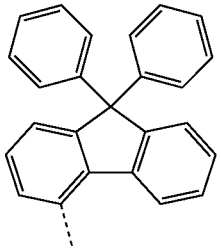 |
| 1-345 | 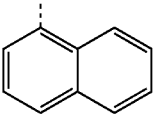 | 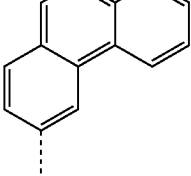 | 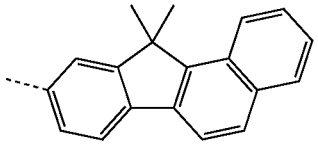 |
| 1-346 | 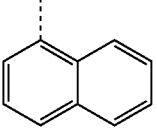 | 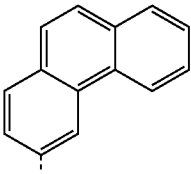 | 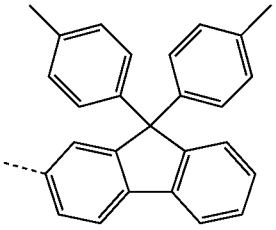 |
| 1-347 | 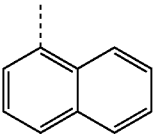 | 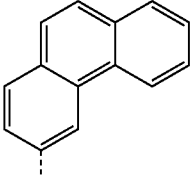 | 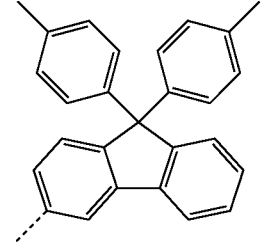 |
| 1-348 | 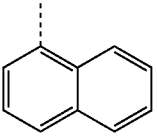 | 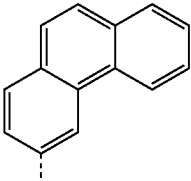 | 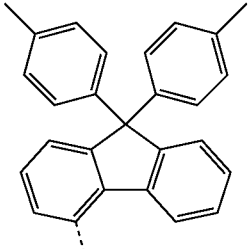 |
| 1-349 | 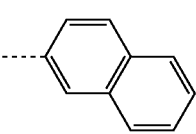 | 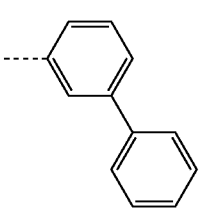 | 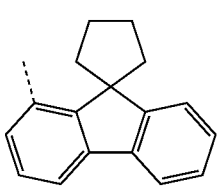 |

-continued
| Formula | ---Ar1 | ---Ar2 | ---Ar3 |
|---|---|---|---|
| 1-350 |  |  | 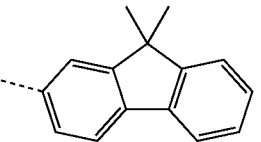 |
| 1-351 |  | 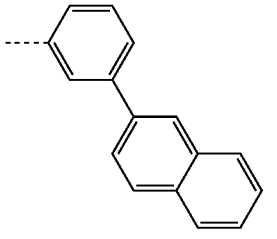 | 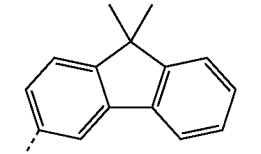 |
| 1-352 |  |  | 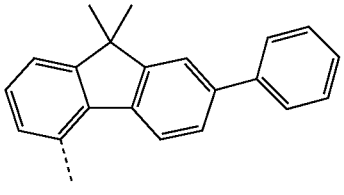 |
| 1-353 |  |  | 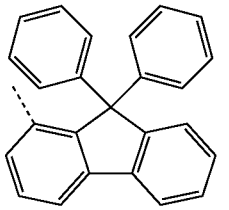 |
| 1-354 |  |  |  |
| 1-355 | 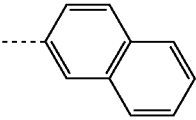 | 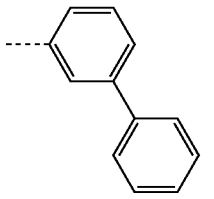 | 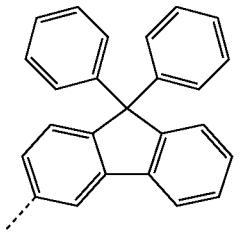 |
| 1-356 | 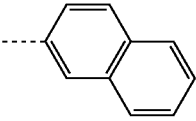 | 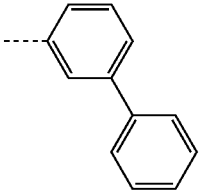 | 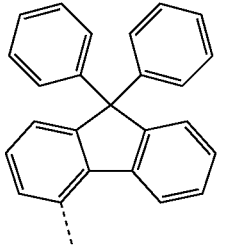 |

-continued
| Formula | - - -Ar1 | - - -Ar2 | - - -Ar3 |
|---|---|---|---|
| 1-357 | 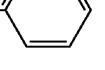 | 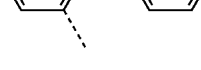 | 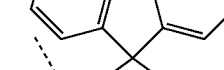 |
| 1-358 | 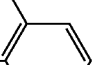 | 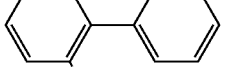 | 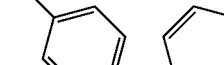 |
| 1-359 | 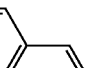 | 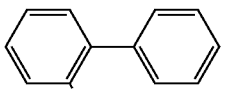 | 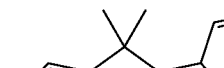 |
| 1-360 | 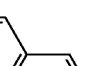 | 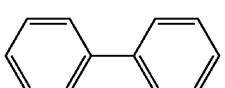 | 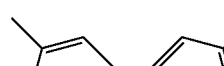 |
| 1-361 | 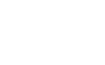 | 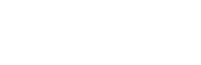 | 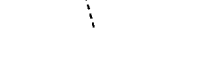 |
| 1-362 | 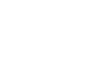 | 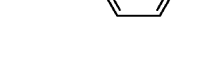 | 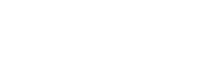 |

-continued
| Formula | ---Ar1 | ---Ar2 | ---Ar3 |
|---|---|---|---|
| 1-363 | 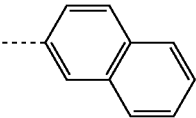 | 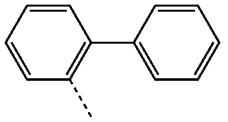 | 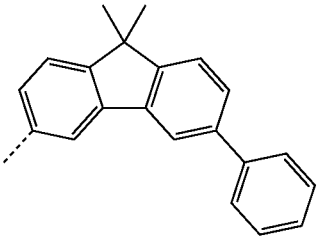 |
| 1-364 | 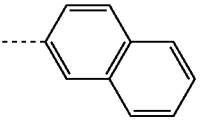 | 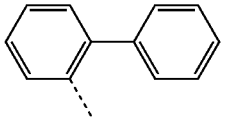 | 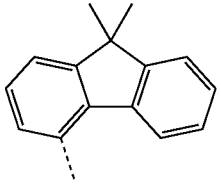 |
| 1-365 | 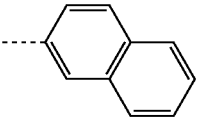 | 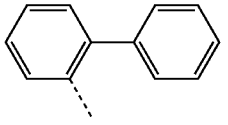 | 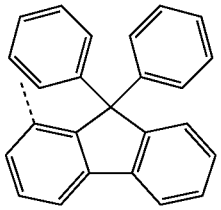 |
| 1-366 | 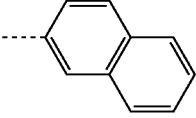 | 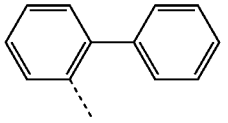 | 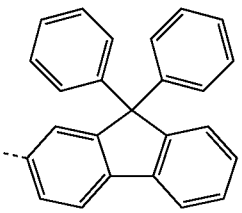 |
| 1-367 | 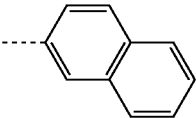 | 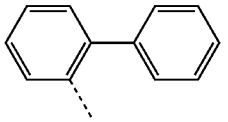 |  |
| 1-368 | 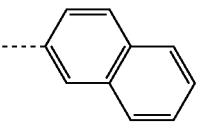 | 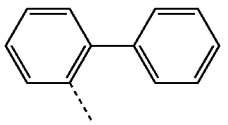 | 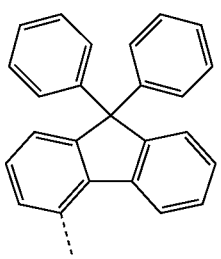 |

-continued
| Formula | - - -Ar1 | - - -Ar2 | - - -Ar3 |
|---|---|---|---|
| 1-369 | 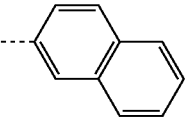 | 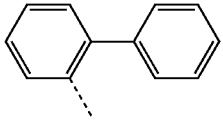 | 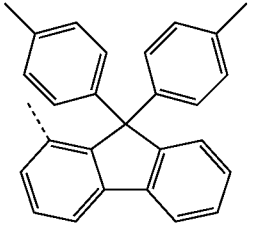 |
| 1-370 | 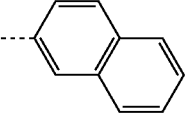 | 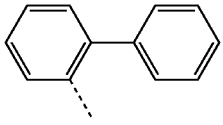 | 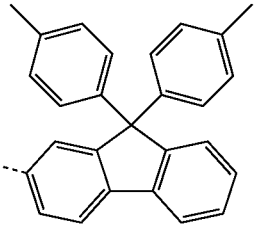 |
| 1-371 | 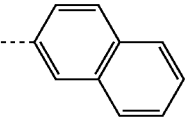 | 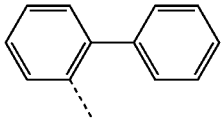 | 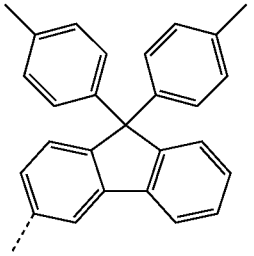 |
| 1-372 | 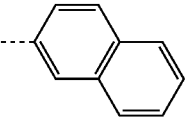 | 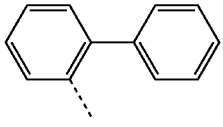 | 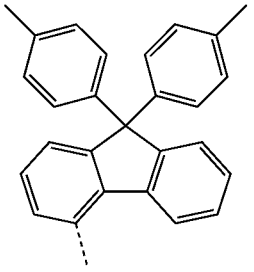 |
| 1-373 | 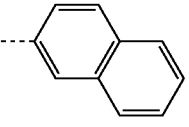 | 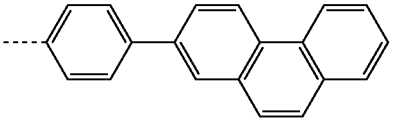 | 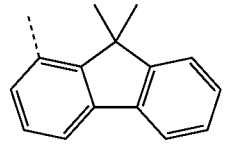 |
| 1-374 | 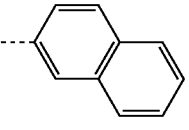 | 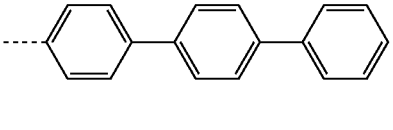 | 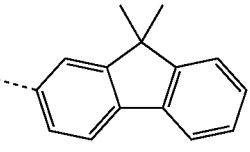 |
| 1-375 | 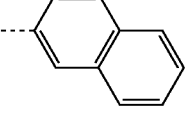 | 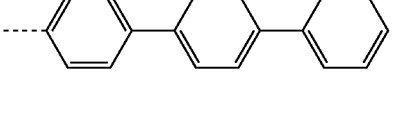 | 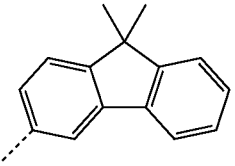 |

-continued
| Formula | ---Ar1 | ---Ar2 | ---Ar3 |
|---|---|---|---|
| 1-376 | 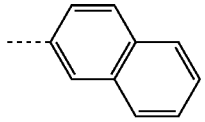 | 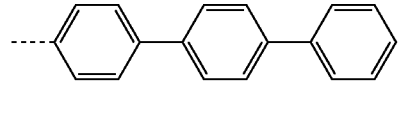 | 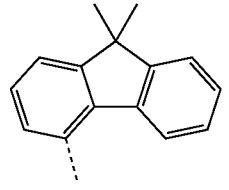 |
| 1-377 | 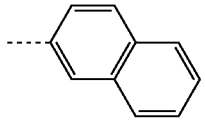 | 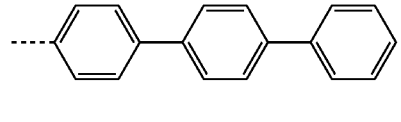 | 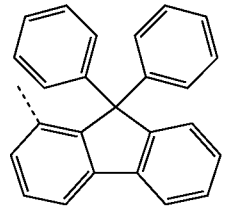 |
| 1-378 | 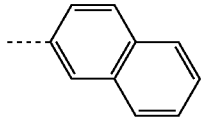 | 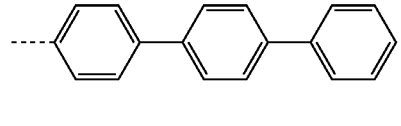 | 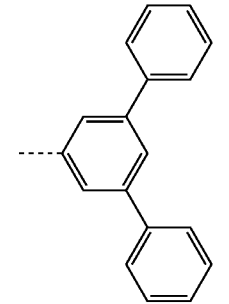 |
| 1-379 | 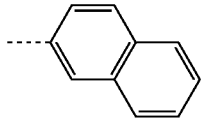 | 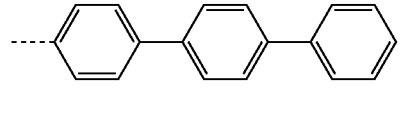 | 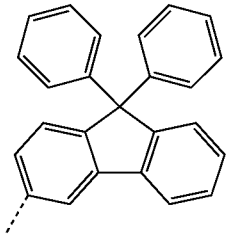 |
| 1-380 | 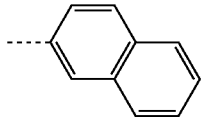 | 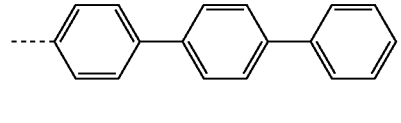 | 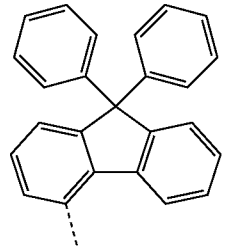 |
| 1-381 | 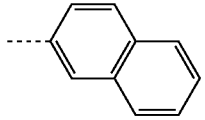 | 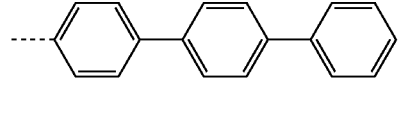 | 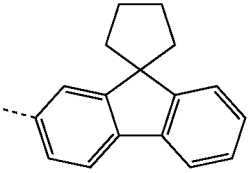 |

| Formula | ---Ar1 | ---Ar2 | ---Ar3 |
|---|---|---|---|
| 1-382 | 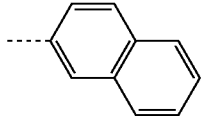 | 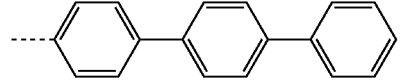 | 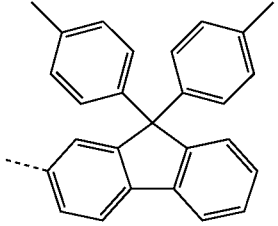 |
| 1-383 | 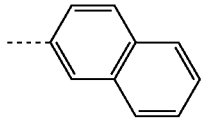 | 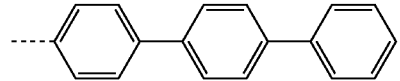 | 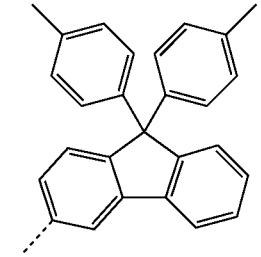 |
| 1-384 | 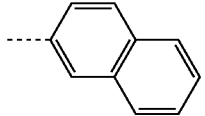 | 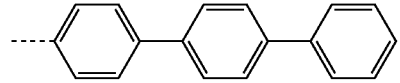 | 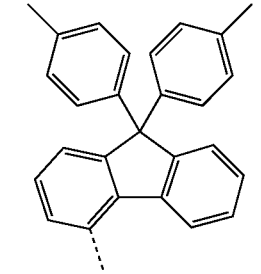 |
| 1-385 | 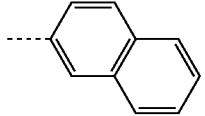 | 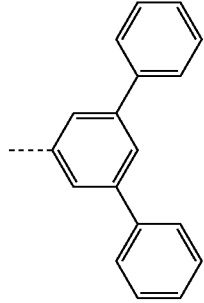 | 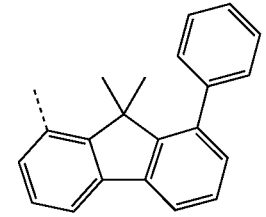 |
| 1-386 | 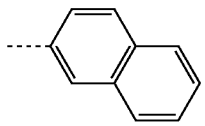 | 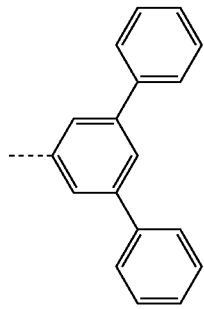 | 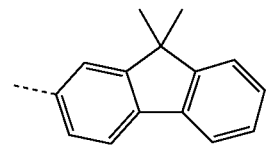 |

-continued
| Formula | - - -Ar1 | - - -Ar2 | - - -Ar3 |
|---|---|---|---|
| 1-387 | 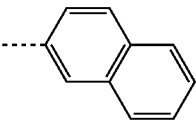 | 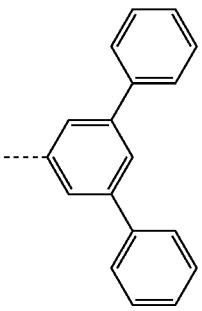 | 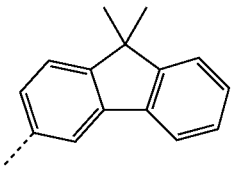 |
| 1-388 | 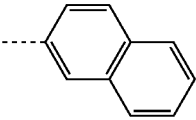 | 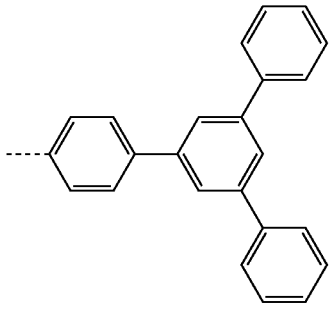 | 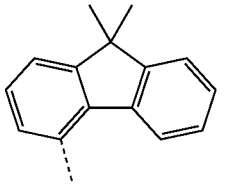 |
| 1-389 | 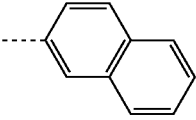 | 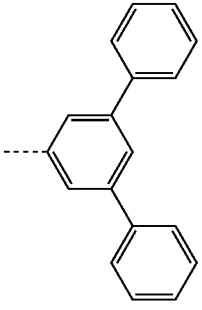 | 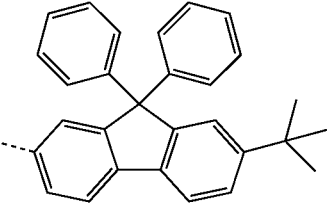 |
| 1-390 | 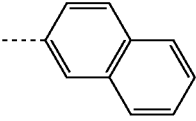 | 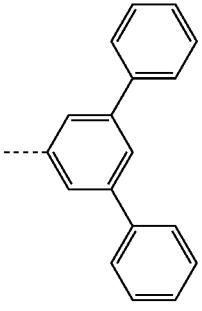 | 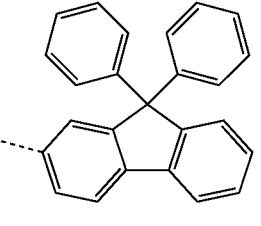 |
| 1-391 | 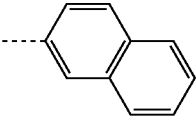 | 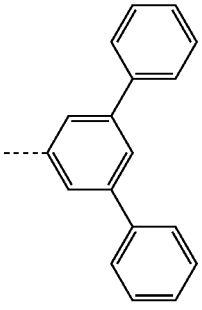 | 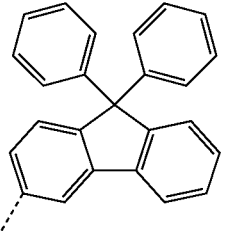 |

-continued
| Formula | ---Ar1 | ---Ar2 | ---Ar3 |
|---|---|---|---|
| 1-392 | 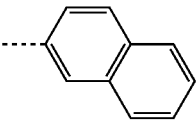 | 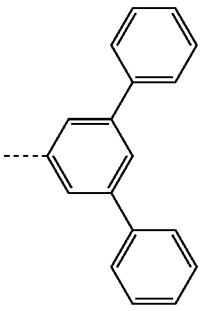 | 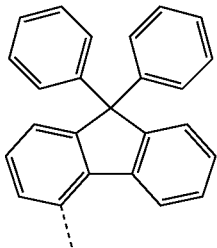 |
| 1-393 | 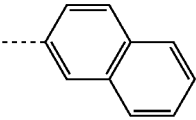 | 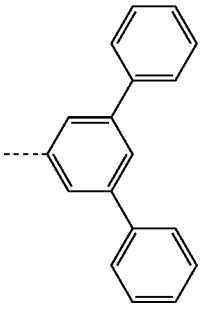 | 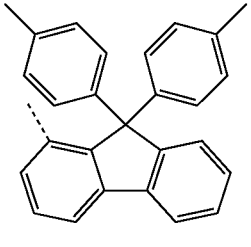 |
| 1-394 | 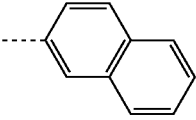 | 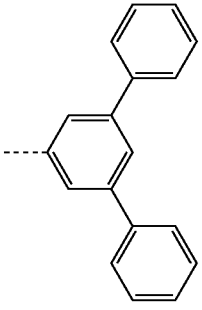 | 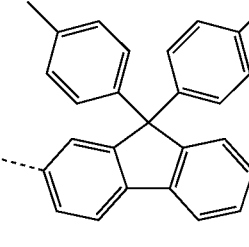 |
| 1-395 | 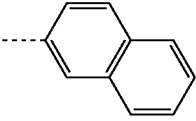 | 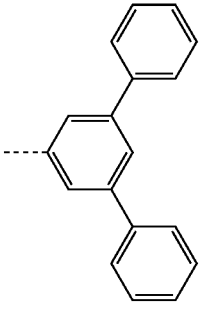 | 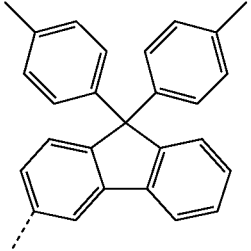 |
| 1-396 | 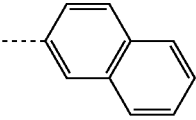 | 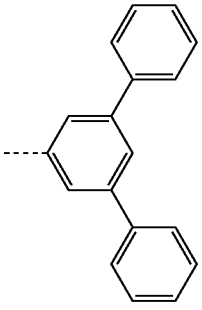 | 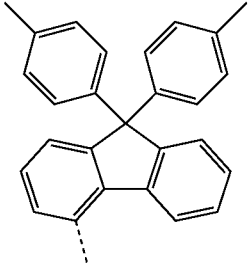 |

-continued
| Formula | - - -Ar1 | - - -Ar2 | - - -Ar3 |
|---|---|---|---|
| 1-397 | 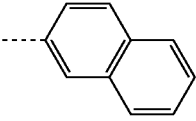 | 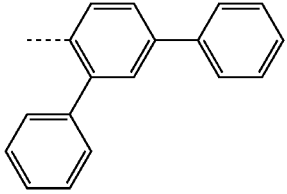 | 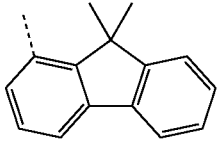 |
| 1-398 | 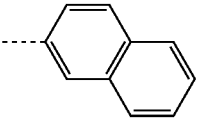 | 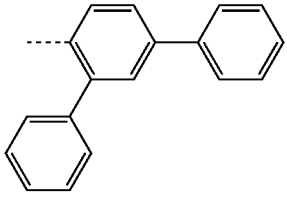 | 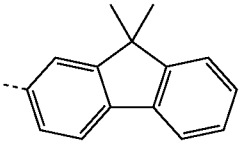 |
| 1-399 | 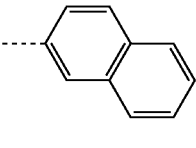 | 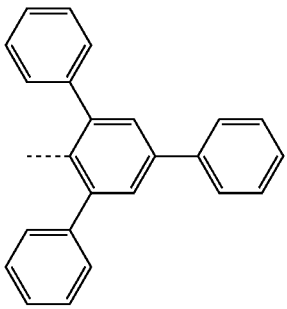 | 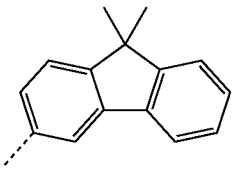 |
| 1-400 | 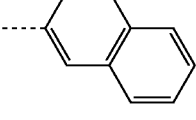 | 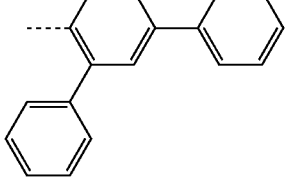 | 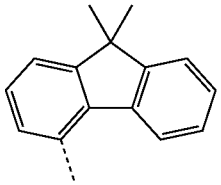 |
| 1-401 | 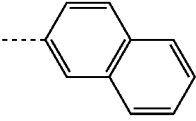 | 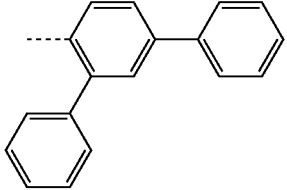 | 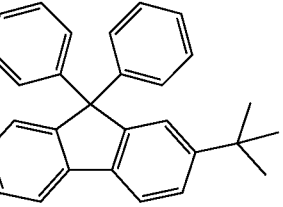 |
| 1-402 | 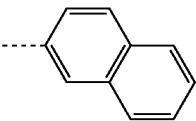 | 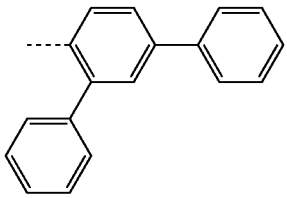 | 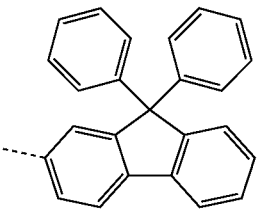 |
| 1-403 | 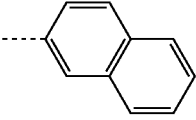 | 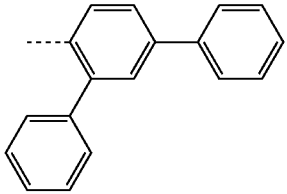 | 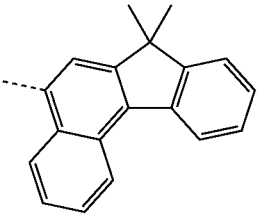 |

-continued
| Formula | ---Ar1 | ---Ar2 | ---Ar3 |
|---|---|---|---|
| 1-404 | 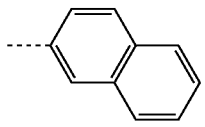 | 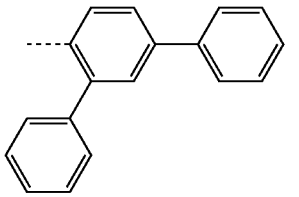 | 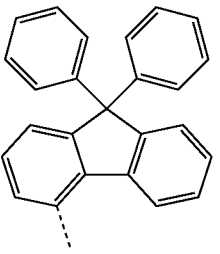 |
| 1-405 | 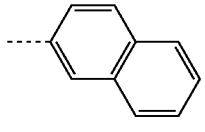 | 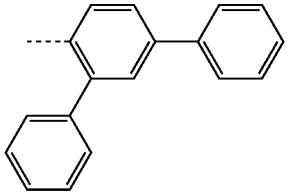 | 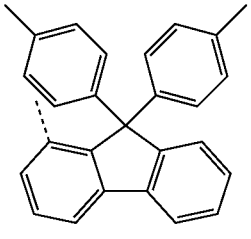 |
| 1-406 | 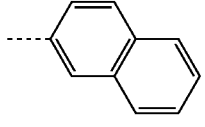 | 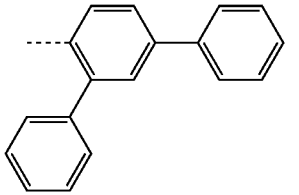 | 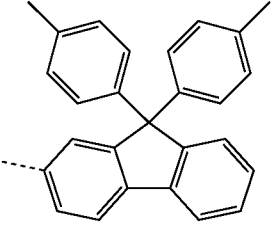 |
| 1-407 | 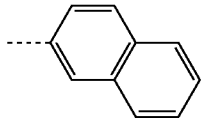 | 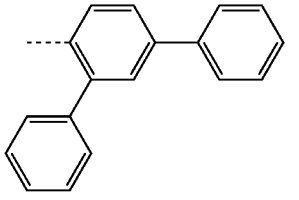 | 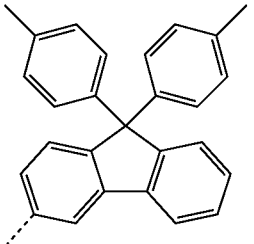 |
| 1-408 | 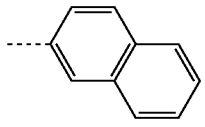 | 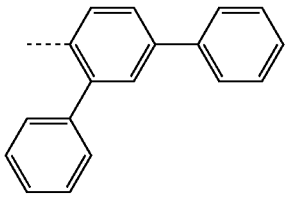 | 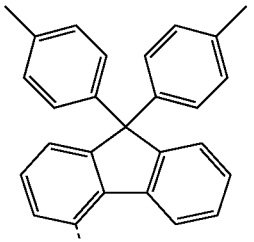 |
| 1-409 | 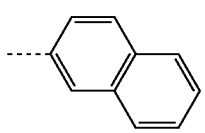 | 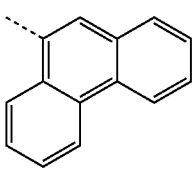 | 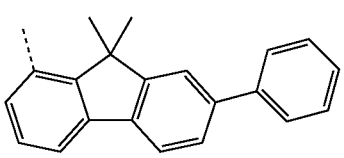 |

-continued
| Formula | ---Ar1 | ---Ar2 | ---Ar3 |
|---|---|---|---|
| 1-410 | 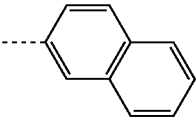 | 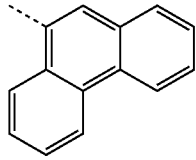 | 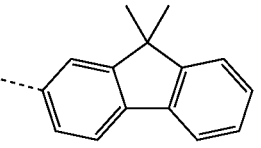 |
| 1-411 | 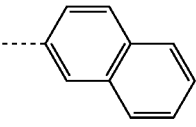 | 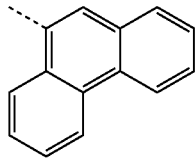 | 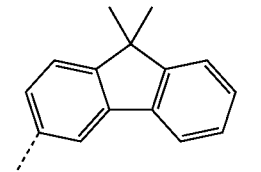 |
| 1-412 | 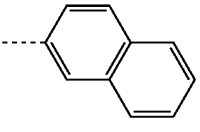 | 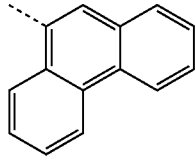 | 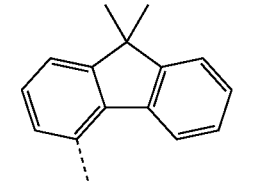 |
| 1-413 | 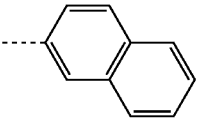 | 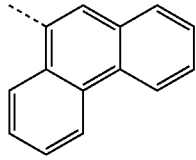 |  |
| 1-414 | 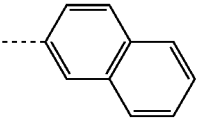 | 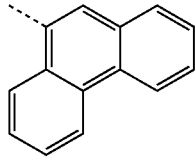 |  |
| 1-415 | 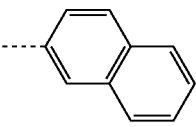 | 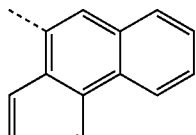 | 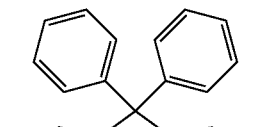 |
| 1-416 | 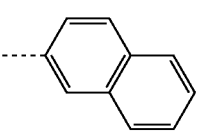 | 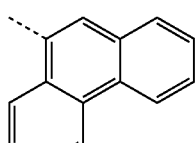 | 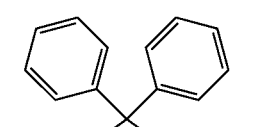 |

-continued
| Formula | ---Ar1 | ---Ar2 | ---Ar3 |
|---|---|---|---|
| 1-417 | 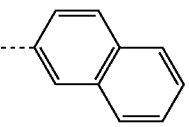 | 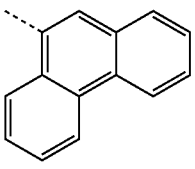 | 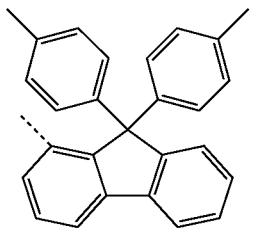 |
| 1-418 | 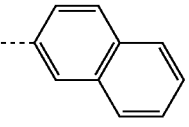 | 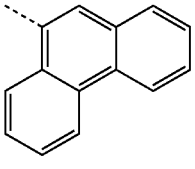 | 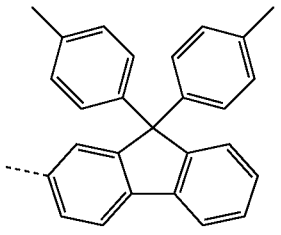 |
| 1-419 | 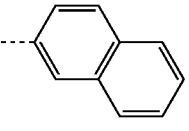 | 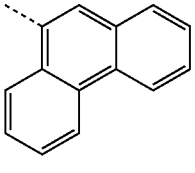 | 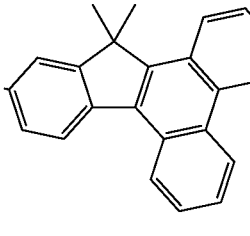 |
| 1-420 | 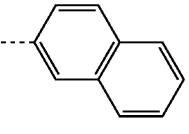 | 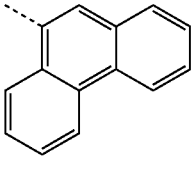 | 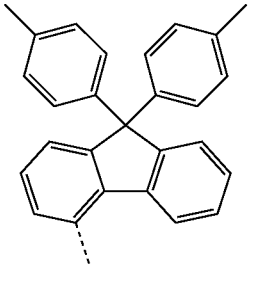 |
| 1-421 | 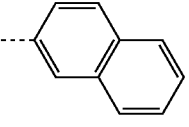 | 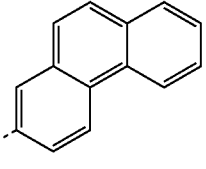 | 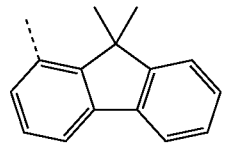 |
| 1-422 | 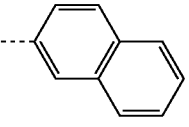 | 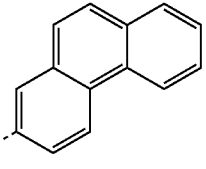 | 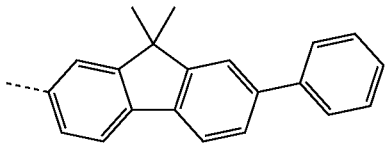 |
| 1-423 | 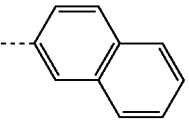 | 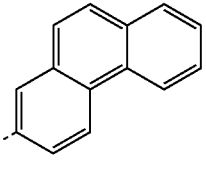 | 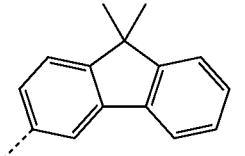 |

-continued

| Formula | ---Ar1 | ---Ar2 | ---Ar3 |
|---|---|---|---|
| 1-424 | naphthyl | phenanthrenyl | 9,9-dimethylfluorenyl |
| 1-425 | naphthyl | phenanthrenyl | 9,9-diphenylfluorenyl |
| 1-426 | naphthyl | phenanthrenyl | 9,9-diphenylfluorenyl |
| 1-427 | naphthyl | phenanthrenyl | 9,9-diphenylfluorenyl |
| 1-428 | naphthyl | phenanthrenyl | 9,9-diphenylfluorenyl |
| 1-429 | naphthyl | phenanthrenyl | 9,9-dimethylbenzofluorenyl |

-continued

| Formula | ---Ar1 | ---Ar2 | ---Ar3 |
|---|---|---|---|
| 1-430 | | | |
| 1-431 | | | |
| 1-432 | | | |
| 1-433 | | | |
| 1-434 | | | |
| 1-435 | | | |

-continued

| Formula | ---Ar1 | ---Ar2 | ---Ar3 |
|---|---|---|---|
| 1-436 | 2-naphthyl | phenanthrenyl | 9,9-dimethylfluoren-4-yl |
| 1-437 | 2-naphthyl | phenanthrenyl | 9,9-diphenylfluoren-1-yl |
| 1-438 | 2-naphthyl | phenanthrenyl | 9,9-diphenylfluoren-2-yl |
| 1-439 | 2-naphthyl | phenanthrenyl | 9,9-diphenylfluoren-3-yl |
| 1-440 | 2-naphthyl | phenanthrenyl | 9,9-diphenylfluoren-4-yl |
| 1-441 | 2-naphthyl | phenanthrenyl | 9,9-di(p-tolyl)fluoren-1-yl |

-continued

| Formula | ---Ar1 | ---Ar2 | ---Ar3 |
|---|---|---|---|
| 1-442 | | | |
| 1-443 | | | |
| 1-444 | | | |
| 1-445 | | | |
| 1-446 | | | |
| 1-447 | | | |

-continued

| Formula | ---Ar1 | ---Ar2 | ---Ar3 |
| --- | --- | --- | --- |
| 1-448 | phenanthrene | biphenyl | 9,9-dimethylfluorene |
| 1-449 | phenanthrene | biphenyl | 9,9-dimethylbenzofluorene |
| 1-450 | phenanthrene | biphenyl | 9,9-diphenylfluorene |
| 1-451 | phenanthrene | biphenyl | 9,9-diphenylfluorene |
| 1-452 | phenanthrene | biphenyl | 9,9-diphenylfluorene |
| 1-453 | phenanthrene | biphenyl | 9,9-di(p-tolyl)fluorene |

-continued

| Formula | ---Ar1 | ---Ar2 | ---Ar3 |
|---|---|---|---|
| 1-454 | | | |
| 1-455 | | | |
| 1-456 | | | |
| 1-457 | | | |
| 1-458 | | | |
| 1-459 | | | |
| 1-460 | | | |

-continued
| Formula | ---Ar1 | ---Ar2 | ---Ar3 |
|---|---|---|---|
| 1-461 | 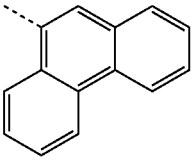 | 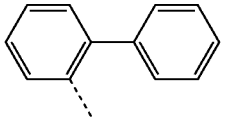 | 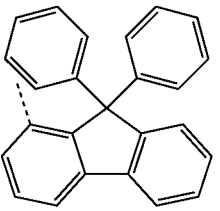 |
| 1-462 | 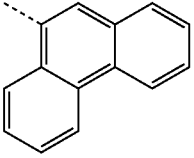 | 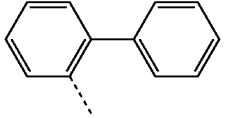 | 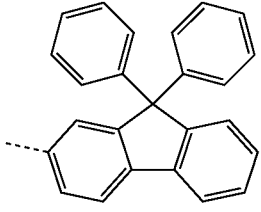 |
| 1-463 | 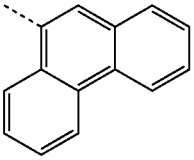 | 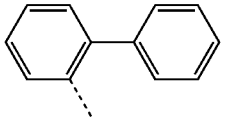 | 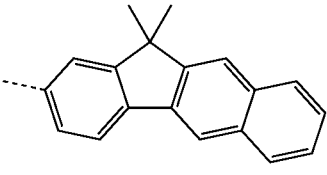 |
| 1-464 | 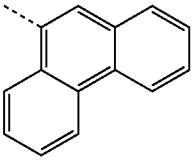 | 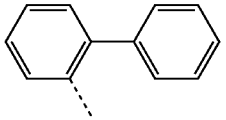 | 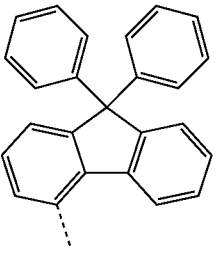 |
| 1-465 | 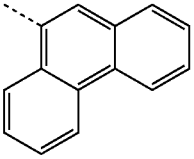 | 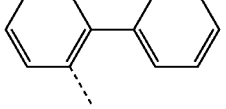 | 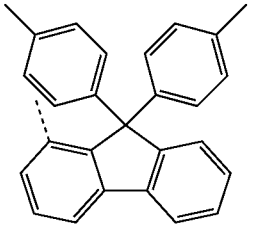 |
| 1-466 | 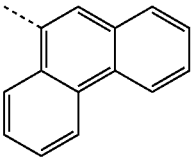 | 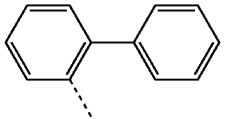 | 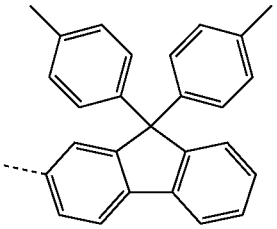 |

-continued
| Formula | ---Ar1 | ---Ar2 | ---Ar3 |
|---|---|---|---|
| 1-467 | 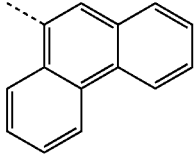 | 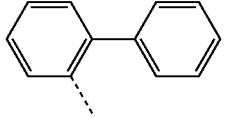 | 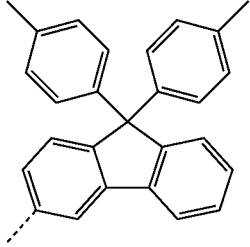 |
| 1-468 | 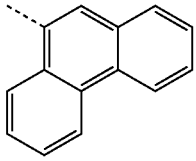 | 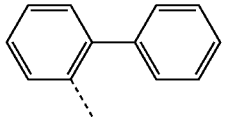 | 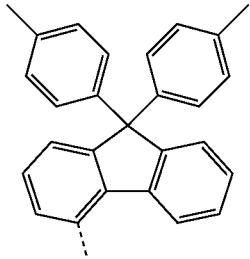 |
| 1-469 | 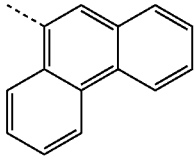 | 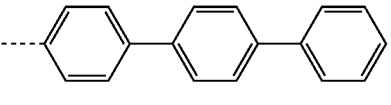 | 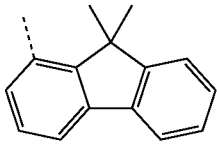 |
| 1-470 | 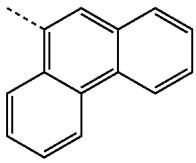 | 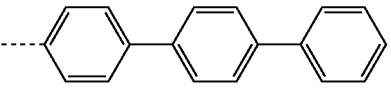 | 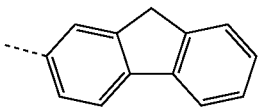 |
| 1-471 | 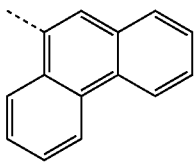 | 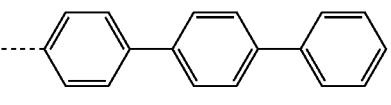 | 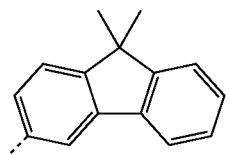 |
| 1-472 | 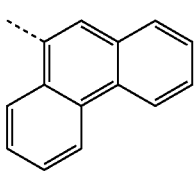 | 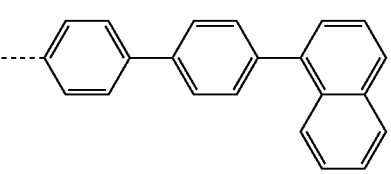 | 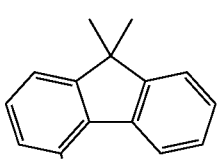 |
| 1-473 | 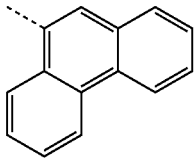 | 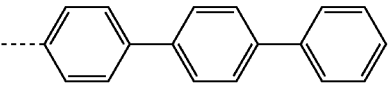 | 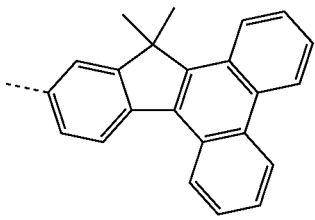 |

-continued

| Formula | ---Ar1 | ---Ar2 | ---Ar3 |
|---|---|---|---|
| 1-474 | phenanthrenyl | p-terphenyl | 9,9-diphenylfluoren-2-yl |
| 1-475 | phenanthrenyl | p-terphenyl | 9,9-diphenylfluoren-3-yl |
| 1-476 | phenanthrenyl | p-terphenyl | 9,9-diphenylfluoren-4-yl |
| 1-477 | phenanthrenyl | p-terphenyl | 9,9-di(p-tolyl)fluoren-1-yl |
| 1-478 | phenanthrenyl | p-terphenyl | 9,9-di(p-tolyl)fluoren-2-yl |
| 1-479 | phenanthrenyl | p-terphenyl | 9,9-di(p-tolyl)fluoren-3-yl |

-continued

| Formula | ---Ar1 | ---Ar2 | ---Ar3 |
|---|---|---|---|
| 1-480 | phenanthrene | p-terphenyl | 9,9-bis(p-tolyl)fluorene |
| 1-481 | phenanthrene | 1,1':3',1''-terphenyl-5'-yl | 9,9-dimethylfluorene |
| 1-482 | phenanthrene | 1,1':3',1''-terphenyl-4'-yl | 9,9-dimethylfluorene |
| 1-483 | phenanthrene | 1,1':3',1''-terphenyl-5'-yl | spiro[cyclopentane-1,9'-fluorene] |
| 1-484 | phenanthrene | 1,1':3',1''-terphenyl-5'-yl | 9,9-dimethylfluorene |

-continued

| Formula | ---Ar1 | ---Ar2 | ---Ar3 |
|---|---|---|---|
| 1-485 | | | |
| 1-486 | | | |
| 1-487 | | | |
| 1-488 | | | |
| 1-489 | | | |

-continued

| Formula | ---Ar1 | ---Ar2 | ---Ar3 |
|---|---|---|---|
| 1-490 | phenanthrene | 1,3,5-terphenyl (meta attach) | 9,9-di(p-tolyl)fluorene (2-yl) |
| 1-491 | phenanthrene | 1,3,5-terphenyl (meta attach) | 9,9-di(p-tolyl)fluorene (3-yl) |
| 1-492 | phenanthrene | 1,3,5-terphenyl (meta attach) | 9,9-di(p-tolyl)fluorene (4-yl) |
| 1-493 | phenanthrene | 1,2,4-triphenylbenzene | 9,9-dimethylfluoren-1-yl |
| 1-494 | phenanthrene | 2,3-diphenyl (biphenyl) | 9,9-dimethylfluoren-2-yl |

-continued
| Formula | ---Ar1 | ---Ar2 | ---Ar3 |
|---|---|---|---|
| 1-495 | 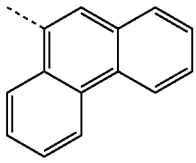 | 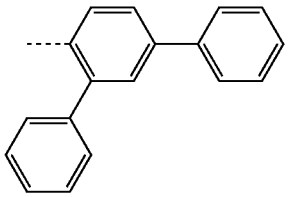 | 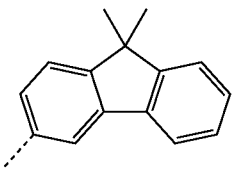 |
| 1-496 | 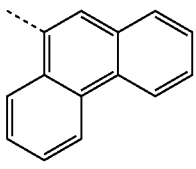 | 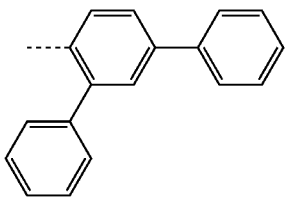 | 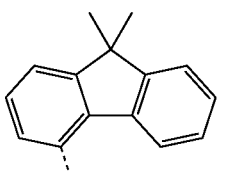 |
| 1-497 | 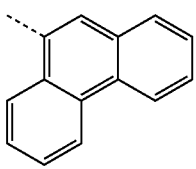 | 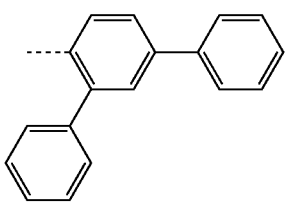 | 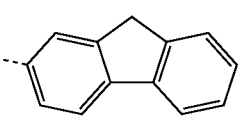 |
| 1-498 | 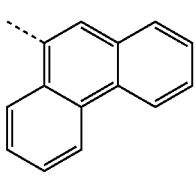 | 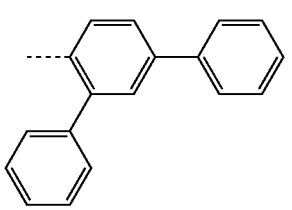 | 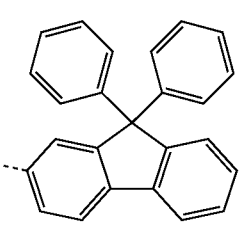 |
| 1-499 | 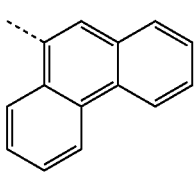 | 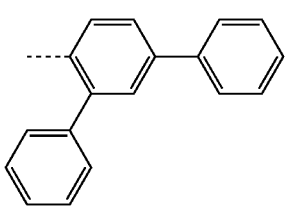 | 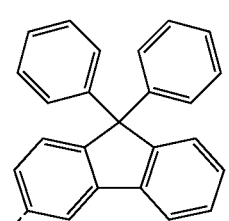 |
| 1-500 | 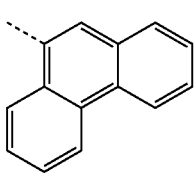 | 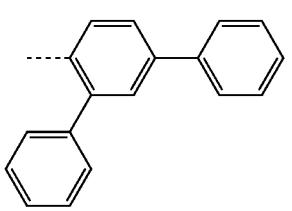 | 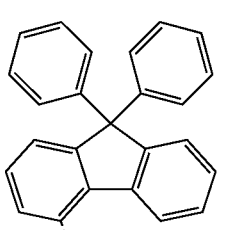 |
| 1-501 | 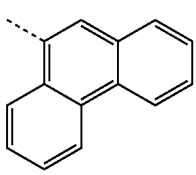 | 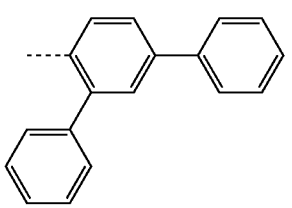 | 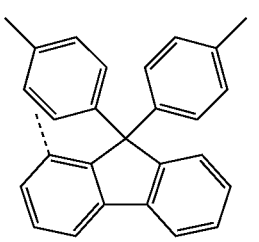 |

-continued
| Formula | ---Ar1 | ---Ar2 | ---Ar3 |
|---|---|---|---|
| 1-502 | 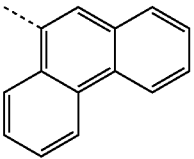 | 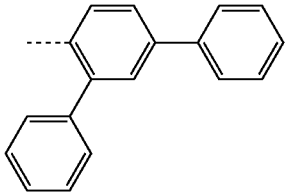 | 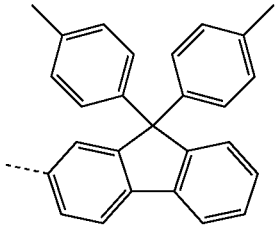 |
| 1-503 | 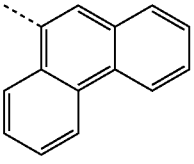 | 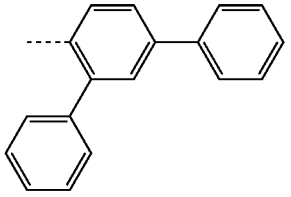 | 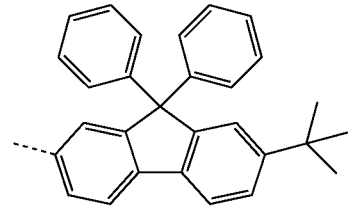 |
| 1-504 | 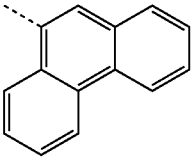 | 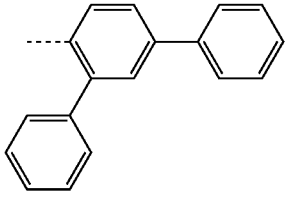 | 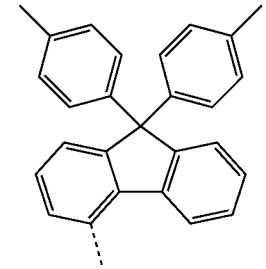 |
| 1-505 | 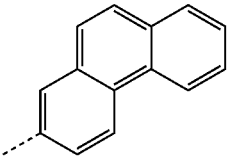 | 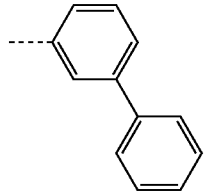 | 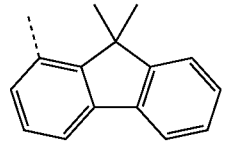 |
| 1-506 | 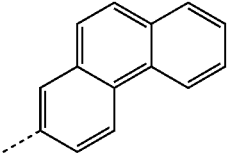 | 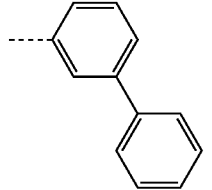 | 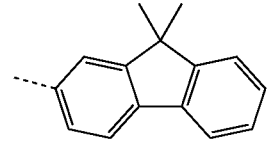 |
| 1-507 | 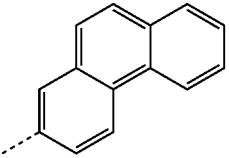 | 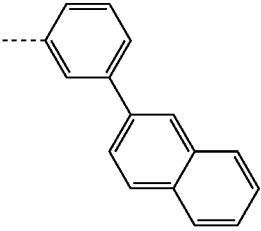 | 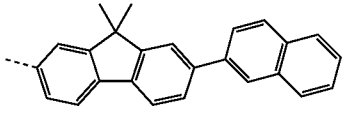 |
| 1-508 | 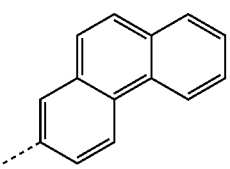 | 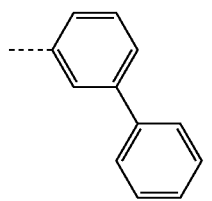 | 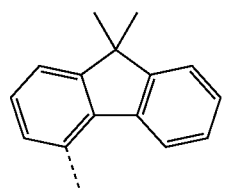 |

-continued
| Formula | ---Ar1 | ---Ar2 | ---Ar3 |
|---|---|---|---|
| 1-509 | 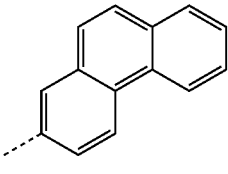 | 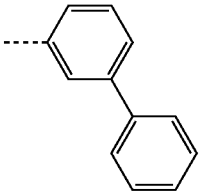 | 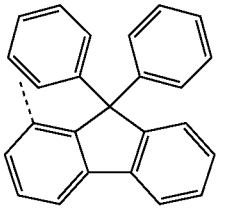 |
| 1-510 | 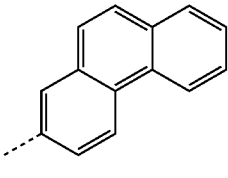 | 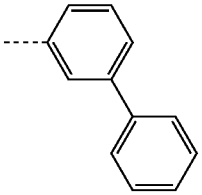 | 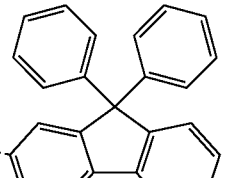 |
| 1-511 | 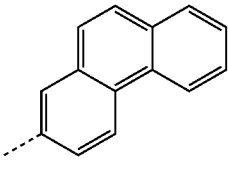 | 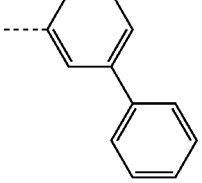 | 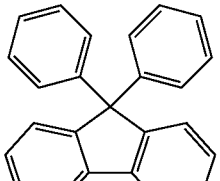 |
| 1-512 | 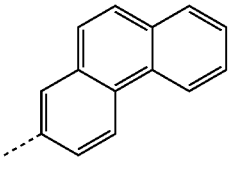 | 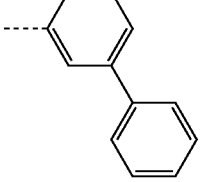 | 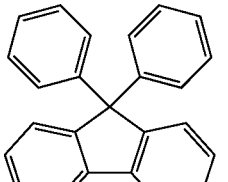 |
| 1-513 | 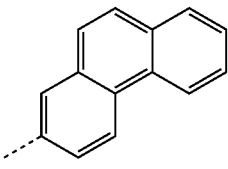 | 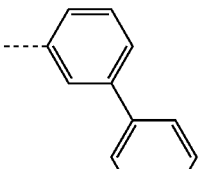 | 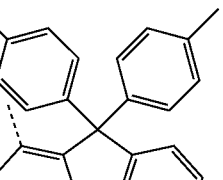 |
| 1-514 | 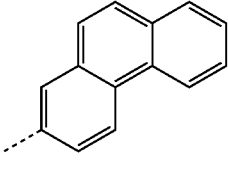 | 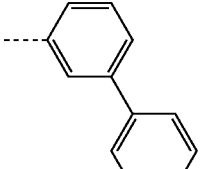 | 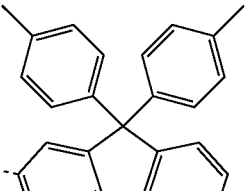 |

-continued

| Formula | ---Ar1 | ---Ar2 | ---Ar3 |
|---|---|---|---|
| 1-515 | | | |
| 1-516 | | | |
| 1-517 | | | |
| 1-518 | | | |
| 1-519 | | | |
| 1-520 | | | |
| 1-521 | | | |

-continued
| Formula | - - -Ar1 | - - -Ar2 | - - -Ar3 |
|---|---|---|---|
| 1-522 | 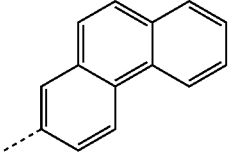 | 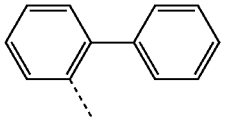 | 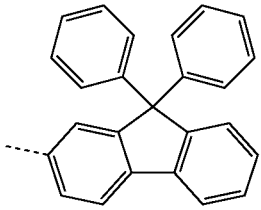 |
| 1-523 | 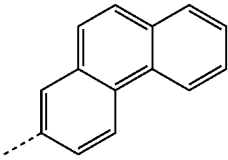 | 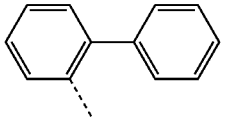 | 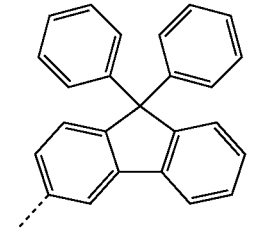 |
| 1-524 | 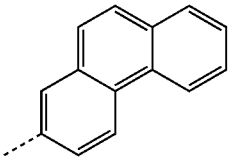 | 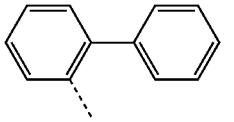 | 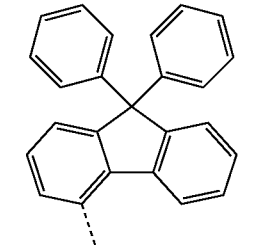 |
| 1-525 | 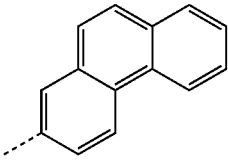 | 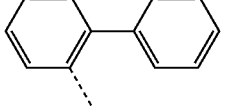 | 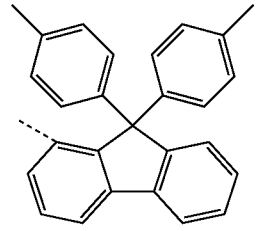 |
| 1-526 | 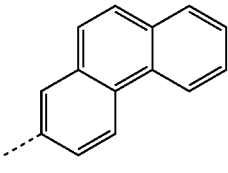 | 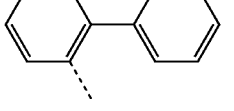 | 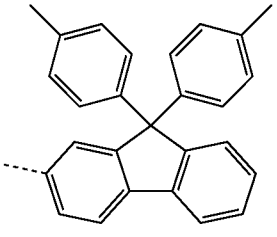 |
| 1-527 | 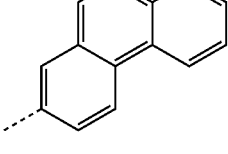 | 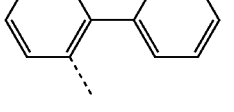 | 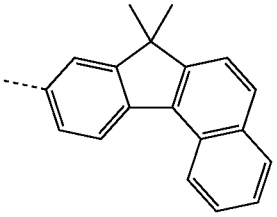 |

US 9,640,766 B2
-continued
| Formula | ---Ar1 | ---Ar2 | ---Ar3 |
|---|---|---|---|
| 1-528 | 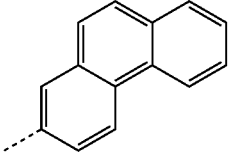 | 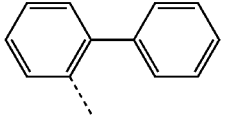 | 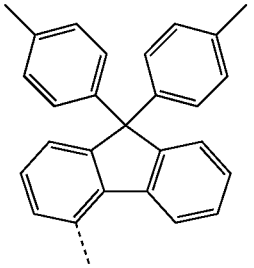 |
| 1-529 | 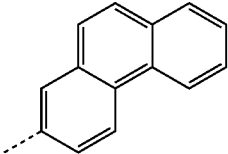 | 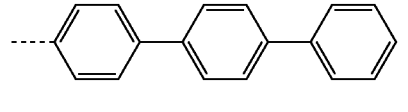 | 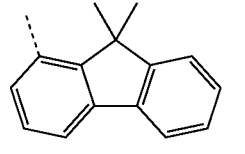 |
| 1-530 | 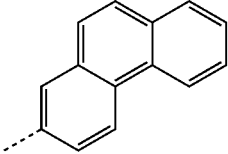 | 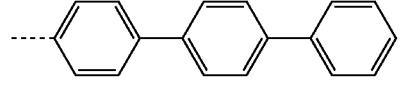 | 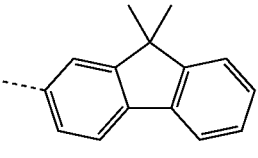 |
| 1-531 | 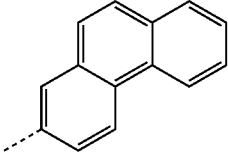 | 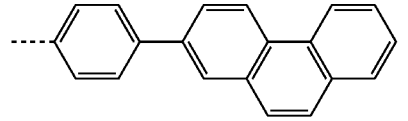 | 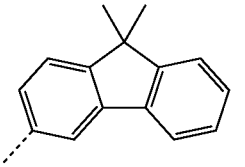 |
| 1-532 | 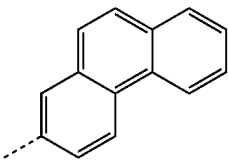 | 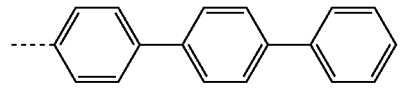 | 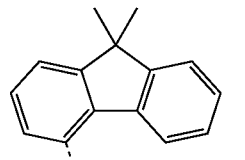 |
| 1-533 | 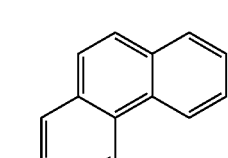 | 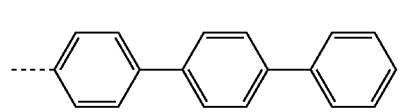 | 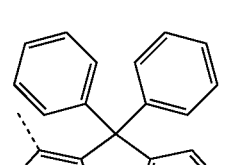 |
| 1-534 | 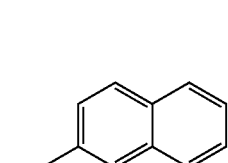 |  | 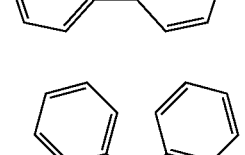 |

201 202
-continued
| Formula | - - -Ar1 | - - -Ar2 | - - -Ar3 |
|---|---|---|---|
| 1-535 | 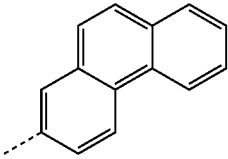 | 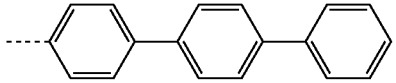 | 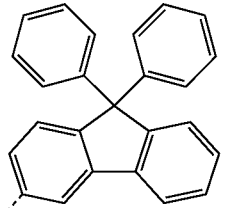 |
| 1-536 | 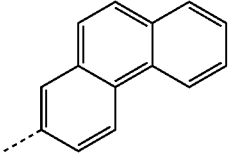 | 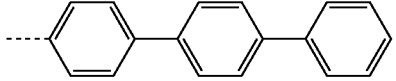 | 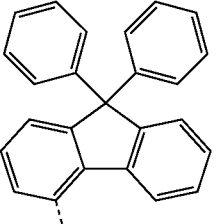 |
| 1-537 | 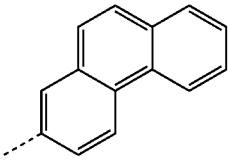 | 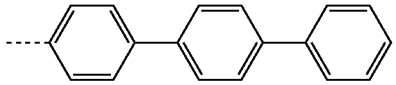 | 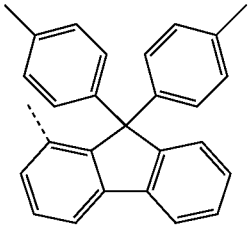 |
| 1-538 | 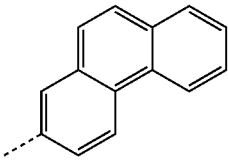 | 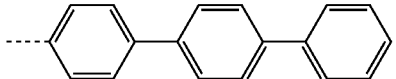 | 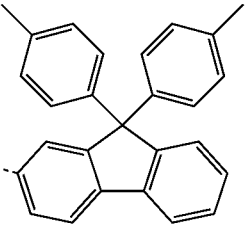 |
| 1-539 | 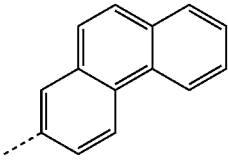 | 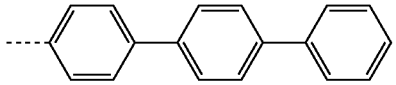 | 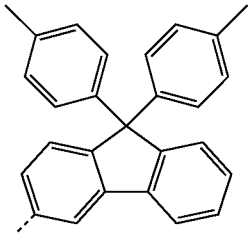 |
| 1-540 | 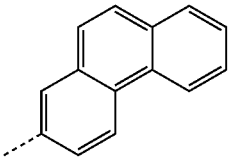 | 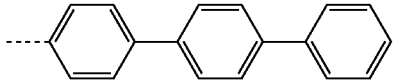 | 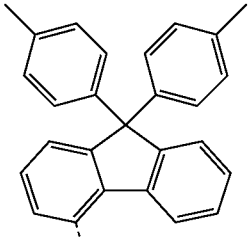 |

-continued

| Formula | ---Ar1 | ---Ar2 | ---Ar3 |
|---|---|---|---|
| 1-541 | phenanthrene | m-terphenyl | 9,9-dimethylfluorene |
| 1-542 | phenanthrene | m-terphenyl | 9,9-dimethylfluorene |
| 1-543 | phenanthrene | m-terphenyl | 9,9-dimethylfluorene |
| 1-544 | phenanthrene | m-terphenyl | 9,9-dimethylfluorene |
| 1-545 | phenanthrene | m-terphenyl | 9,9-diphenylfluorene |

-continued
| Formula | ---Ar1 | ---Ar2 | ---Ar3 |
|---|---|---|---|
| 1-546 | 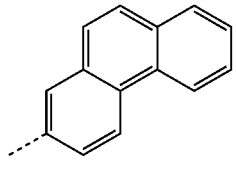 | 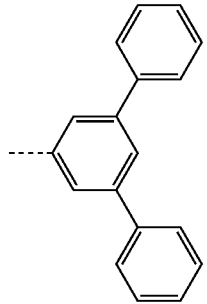 | 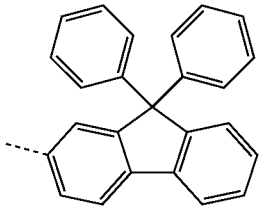 |
| 1-547 | 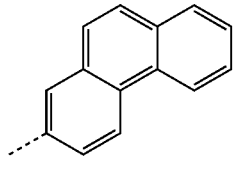 | 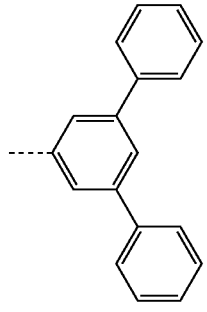 | 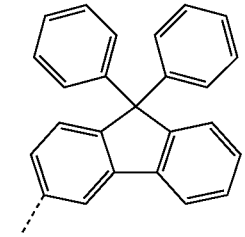 |
| 1-548 | 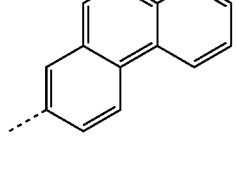 | 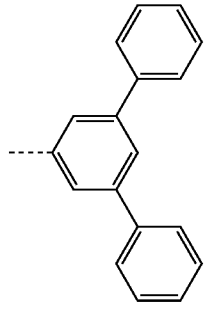 | 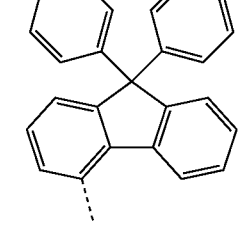 |
| 1-549 | 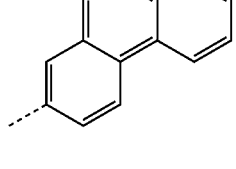 | 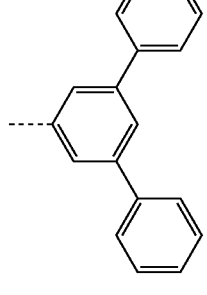 | 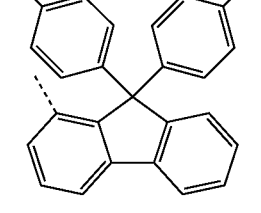 |
| 1-550 | 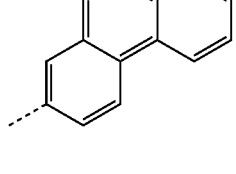 | 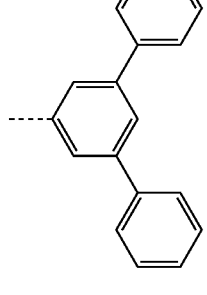 | 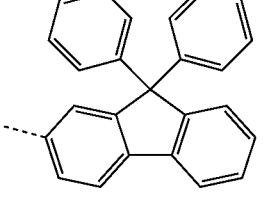 |

-continued

| Formula | ---Ar1 | ---Ar2 | ---Ar3 |
|---|---|---|---|
| 1-551 | | | |
| 1-552 | | | |
| 1-553 | | | |
| 1-554 | | | |
| 1-555 | | | |
| 1-556 | | | |

-continued
| Formula | - - -Ar1 | - - -Ar2 | - - -Ar3 |
|---|---|---|---|
| 1-557 | 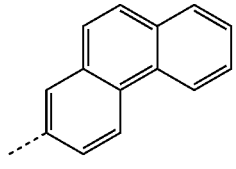 | 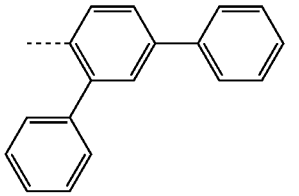 | 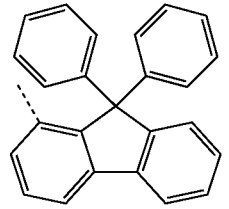 |
| 1-558 | 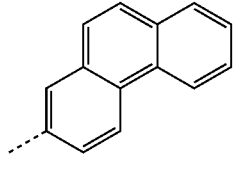 | 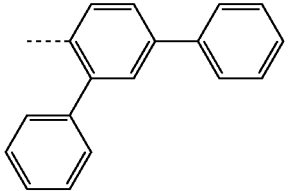 | 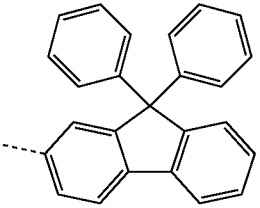 |
| 1-559 | 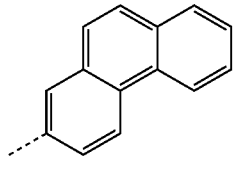 | 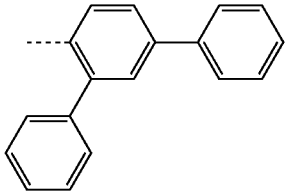 | 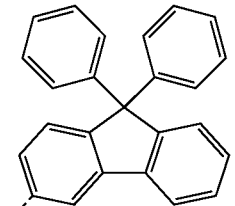 |
| 1-560 | 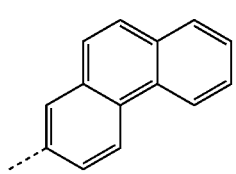 | 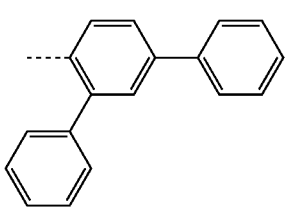 | 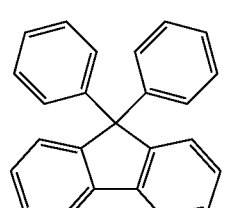 |
| 1-561 | 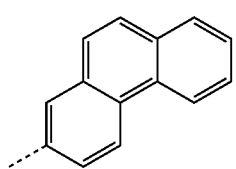 | 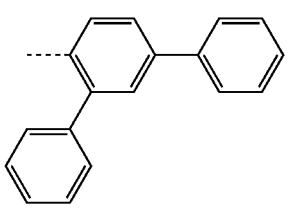 | 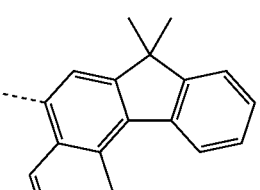 |
| 1-562 | 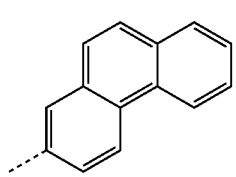 | 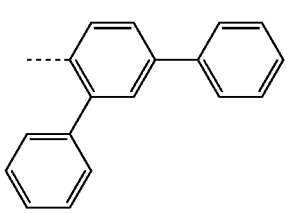 | 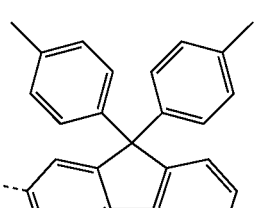 |

-continued

| Formula | ---Ar1 | ---Ar2 | ---Ar3 |
|---|---|---|---|
| 1-563 | | | |
| 1-564 | | | |
| 1-565 | | | |
| 1-566 | | | |
| 1-567 | | | |
| 1-568 | | | |

-continued
| Formula | - - -Ar1 | - - -Ar2 | - - -Ar3 |
|---|---|---|---|
| 1-569 | 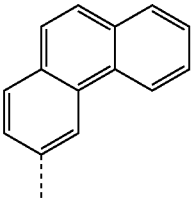 | 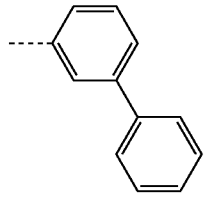 | 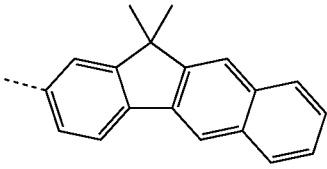 |
| 1-570 | 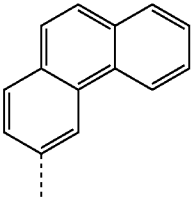 | 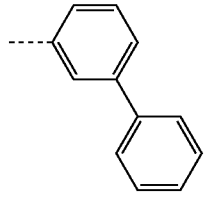 | 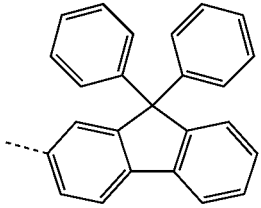 |
| 1-571 | 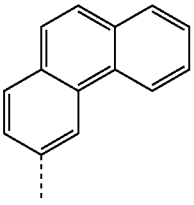 | 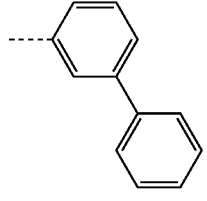 | 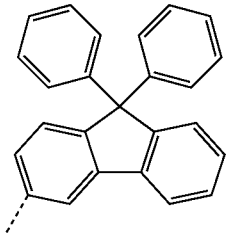 |
| 1-572 | 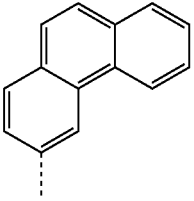 | 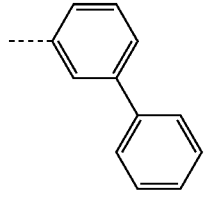 | 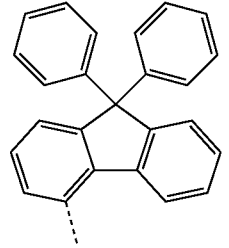 |
| 1-573 | 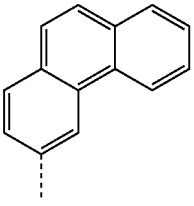 | 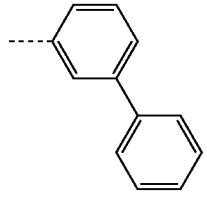 | 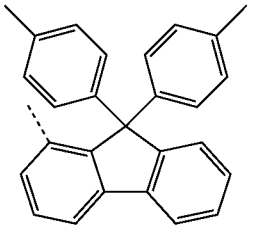 |
| 1-574 | 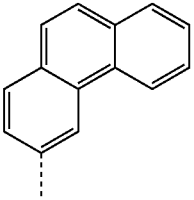 | 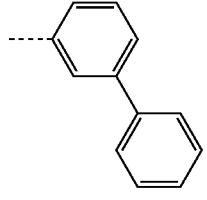 | 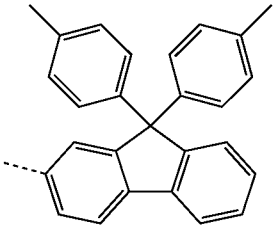 |

US 9,640,766 B2
-continued
| Formula | - - -Ar1 | - - -Ar2 | - - -Ar3 |
|---|---|---|---|
| 1-575 | 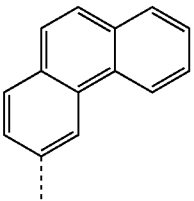 | 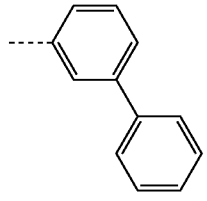 | 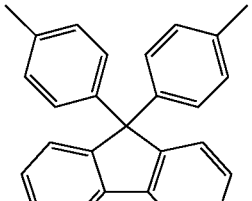 |
| 1-576 | 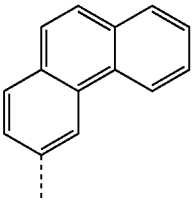 | 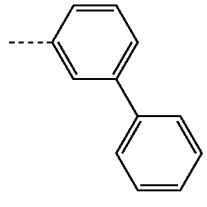 | 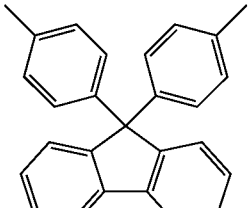 |
| 1-577 | 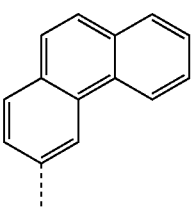 | 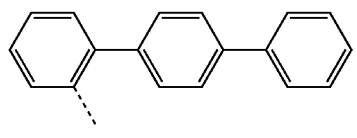 | 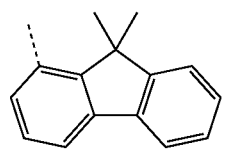 |
| 1-578 | 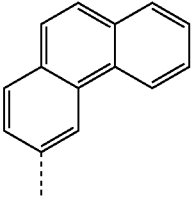 | 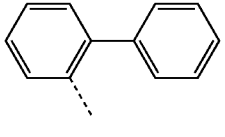 | 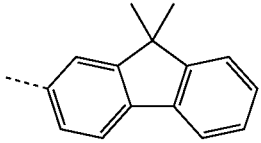 |
| 1-579 | 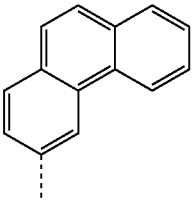 | 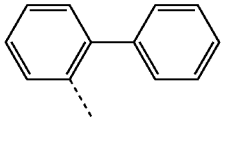 | 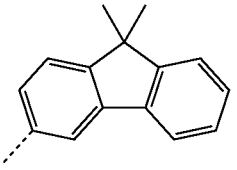 |
| 1-580 | 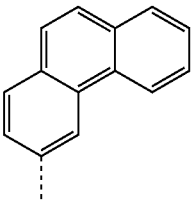 | 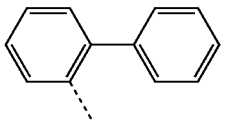 | 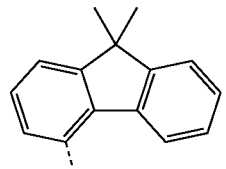 |
| 1-581 | 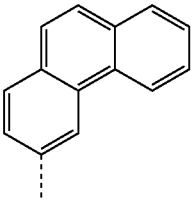 | 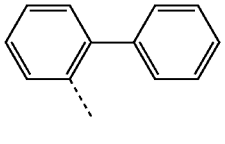 | 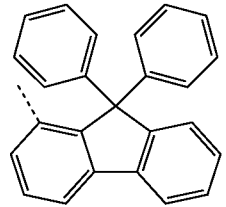 |

-continued
| Formula | ---Ar1 | ---Ar2 | ---Ar3 |
|---|---|---|---|
| 1-582 | 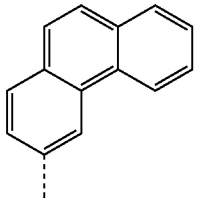 | 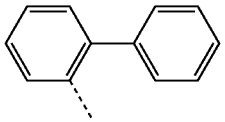 | 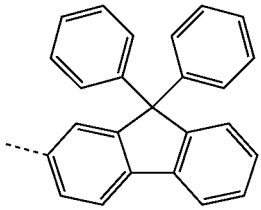 |
| 1-583 | 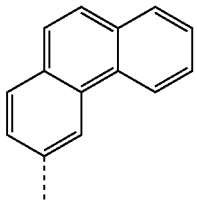 | 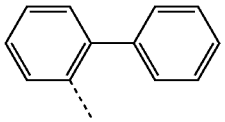 | 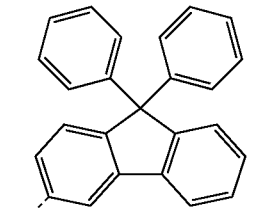 |
| 1-584 | 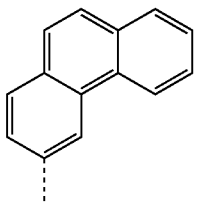 | 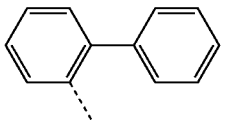 | 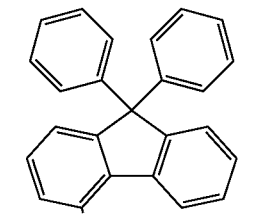 |
| 1-585 | 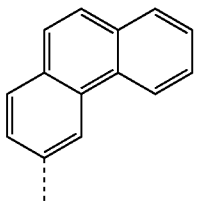 | 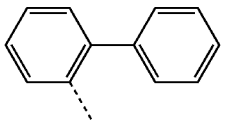 | 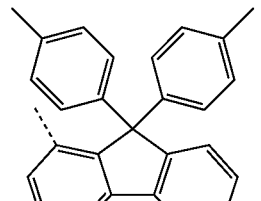 |
| 1-586 | 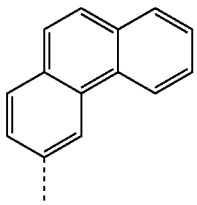 | 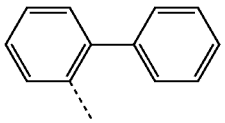 | 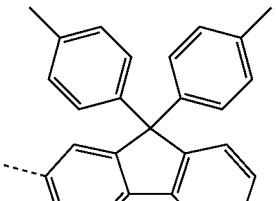 |
| 1-587 | 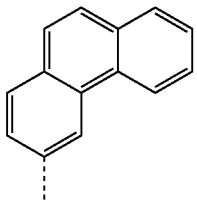 | 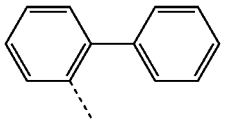 | 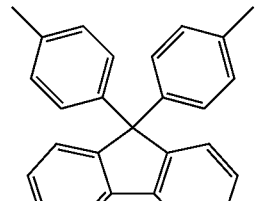 |

-continued
| Formula | - - -Ar1 | - - -Ar2 | - - -Ar3 |
|---|---|---|---|
| 1-588 | 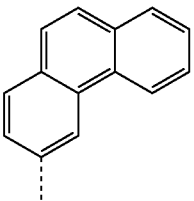 | 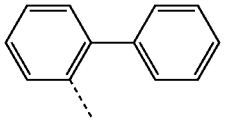 | 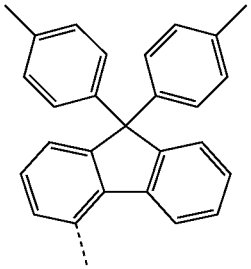 |
| 1-589 | 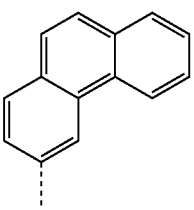 | 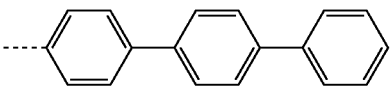 | 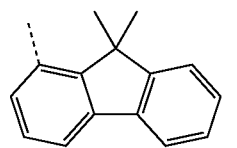 |
| 1-590 | 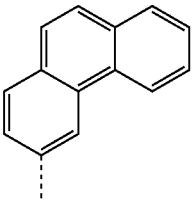 | 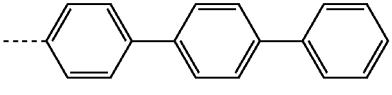 | 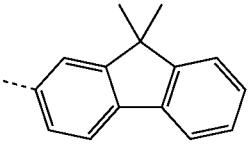 |
| 1-591 | 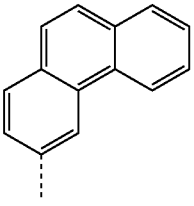 | 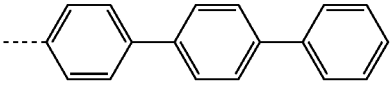 | 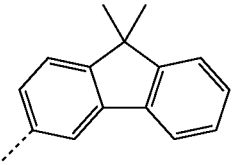 |
| 1-592 | 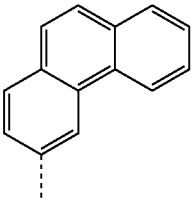 | 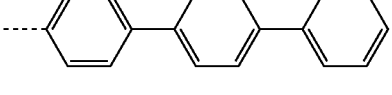 | 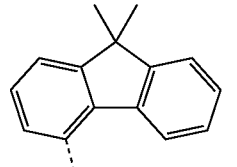 |
| 1-593 | 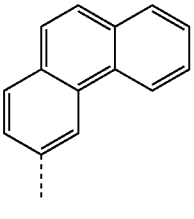 | 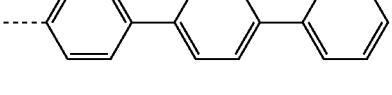 | 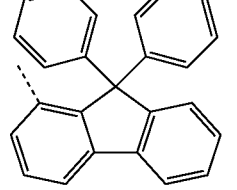 |
| 1-594 | 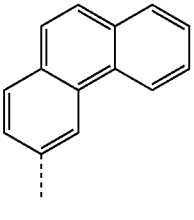 | 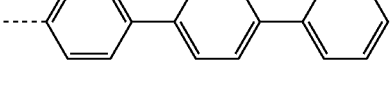 | 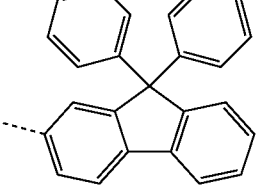 |

-continued

| Formula | ---Ar1 | ---Ar2 | ---Ar3 |
|---|---|---|---|
| 1-595 | phenanthrene | terphenyl | 9,9-diphenylfluorene |
| 1-596 | phenanthrene | terphenyl | 9,9-diphenylfluorene |
| 1-597 | phenanthrene | terphenyl | methyl-substituted benzofluorene |
| 1-598 | phenanthrene | terphenyl | 9,9-di(p-tolyl)fluorene |
| 1-599 | phenanthrene | terphenyl | tert-butyl-9,9-diphenylfluorene |
| 1-600 | phenanthrene | terphenyl | 9,9-di(p-tolyl)fluorene |

-continued

| Formula | ---Ar1 | ---Ar2 | ---Ar3 |
| --- | --- | --- | --- |
| 1-601 | | | |
| 1-602 | | | |
| 1-603 | | | |
| 1-604 | | | |
| 1-605 | | | |

-continued

| Formula | ---Ar1 | ---Ar2 | ---Ar3 |
|---|---|---|---|
| 1-606 | phenanthrene | 1,3,5-triphenylbenzene | 9,9-diphenylfluorene (2-yl) |
| 1-607 | phenanthrene | 1,3,5-triphenylbenzene | 9,9-diphenylfluorene (3-yl) |
| 1-608 | phenanthrene | 1,3,5-triphenylbenzene | 9,9-diphenylfluorene (4-yl) |
| 1-609 | phenanthrene | 1,3,5-triphenylbenzene | 9,9-dimethylbenzo[a]fluorene |
| 1-610 | phenanthrene | 1,3,5-triphenylbenzene | 9,9-di(p-tolyl)fluorene |

227                                                                 228
-continued
| Formula | - - -Ar1 | - - -Ar2 | - - -Ar3 |
|---|---|---|---|
| 1-611 | 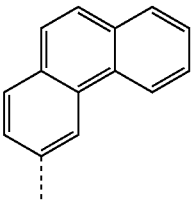 | 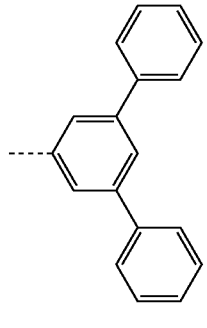 | 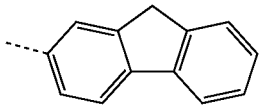 |
| 1-612 | 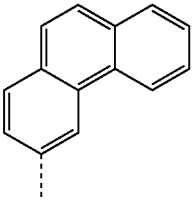 | 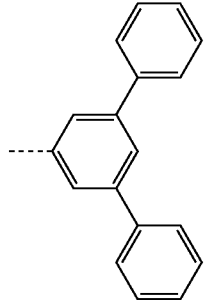 | 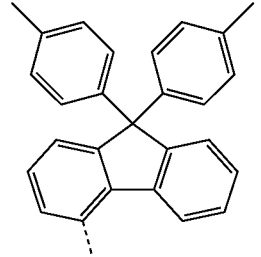 |
| 1-613 | 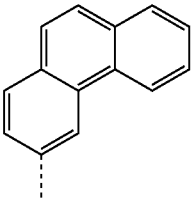 | 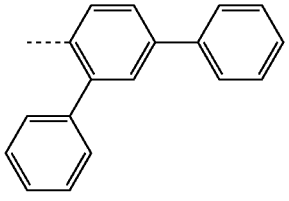 | 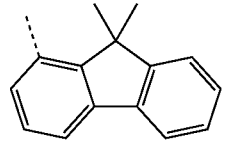 |
| 1-614 | 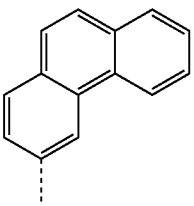 | 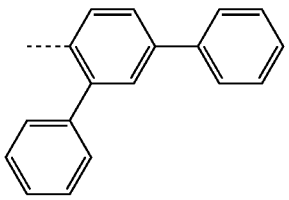 | 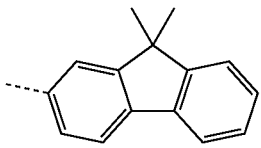 |
| 1-615 | 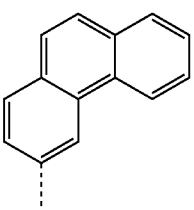 | 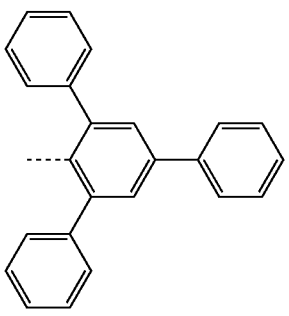 | 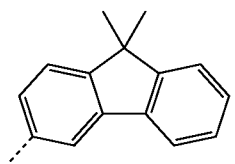 |
| 1-616 | 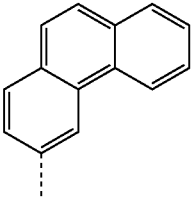 | 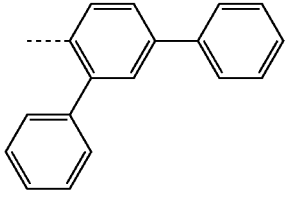 | 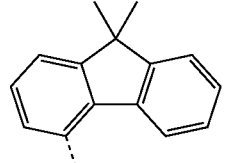 |

-continued
| Formula | ---Ar1 | ---Ar2 | ---Ar3 |
|---|---|---|---|
| 1-617 | 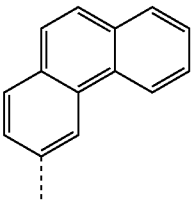 | 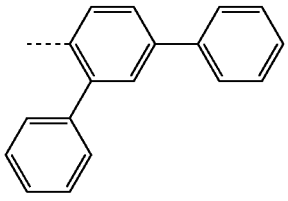 | 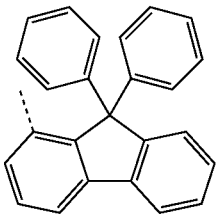 |
| 1-618 | 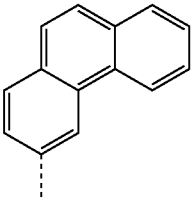 | 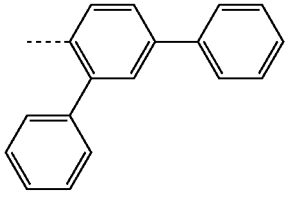 | 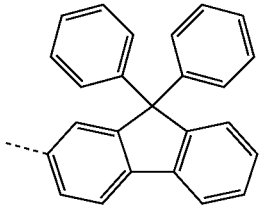 |
| 1-619 | 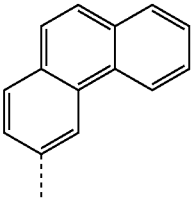 | 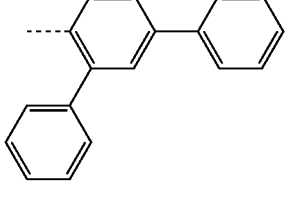 | 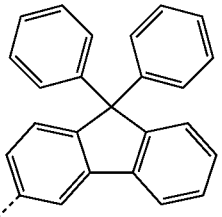 |
| 1-620 | 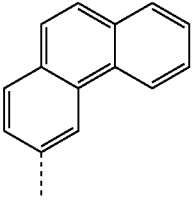 | 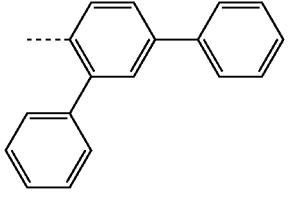 | 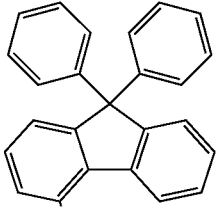 |
| 1-621 | 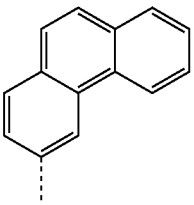 | 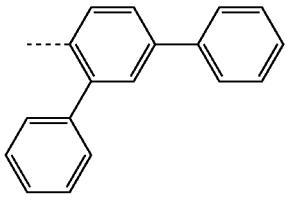 | 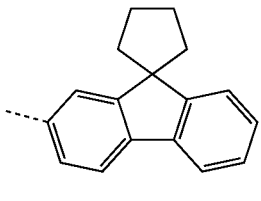 |
| 1-622 | 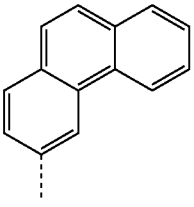 | 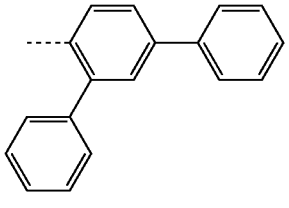 | 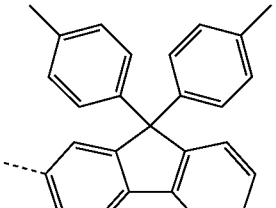 |
| 1-623 | 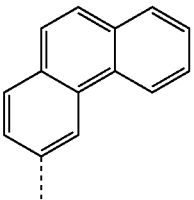 | 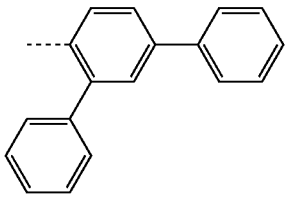 | 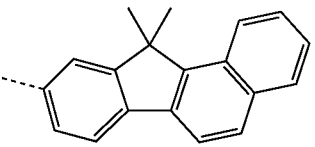 |

-continued
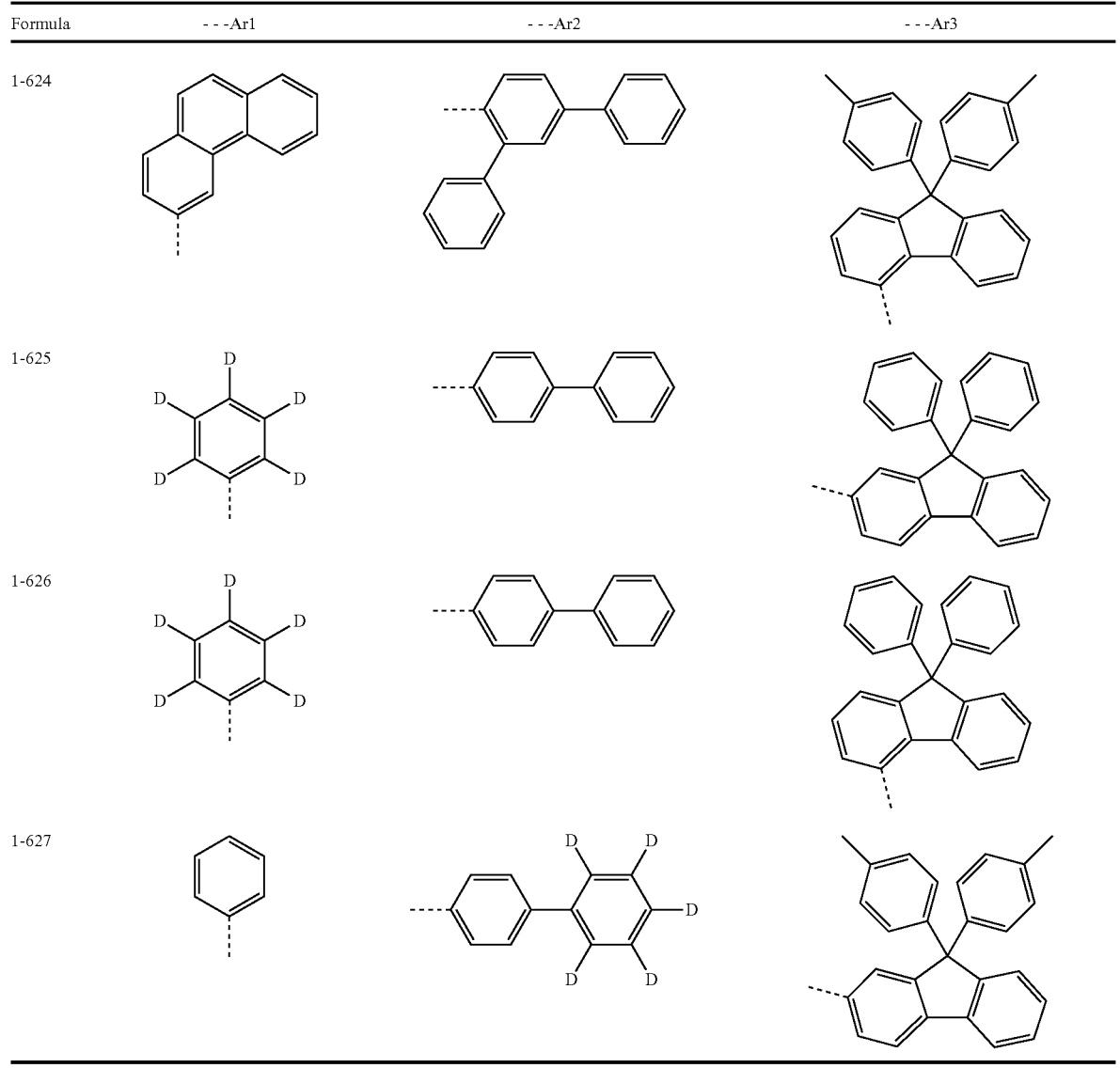
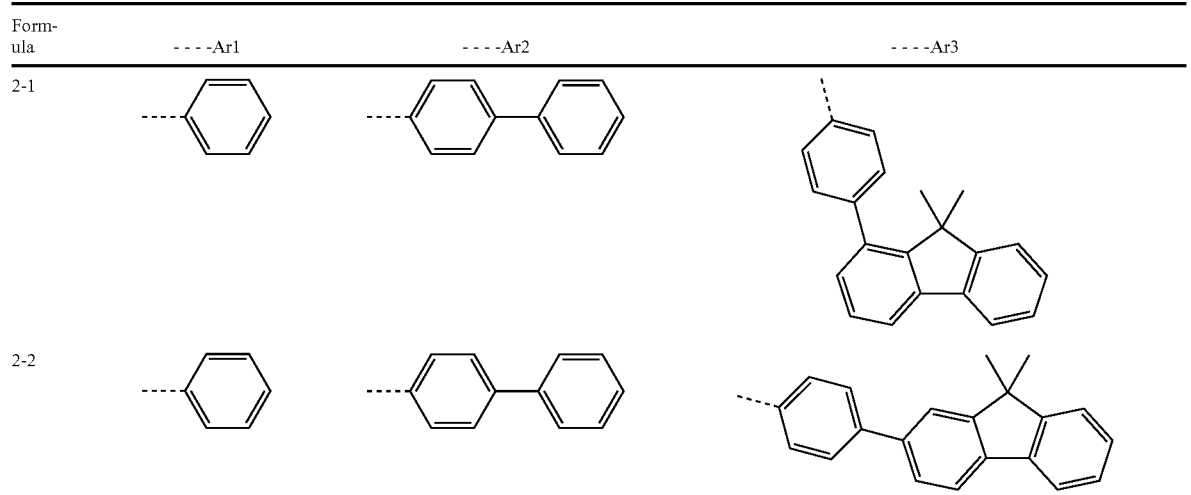

-continued
| Formula | ----Ar1 | ----Ar2 | ----Ar3 |
|---|---|---|---|
| 2-3 | 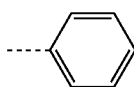 | 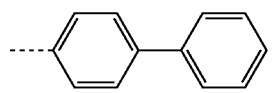 | 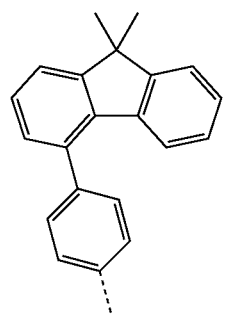 |
| 2-4 | 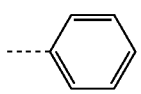 | 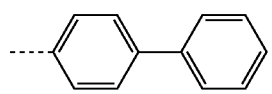 | 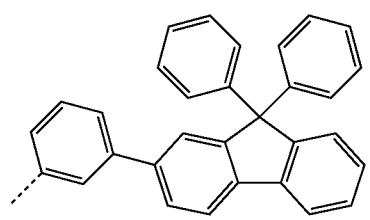 |
| 2-5 | 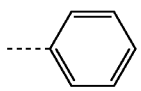 | 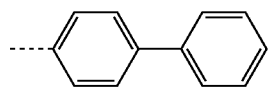 | 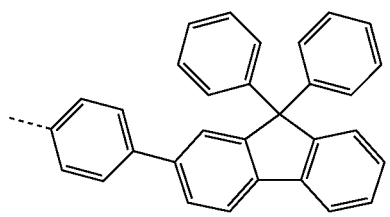 |
| 2-6 | 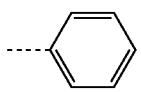 | 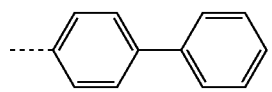 | 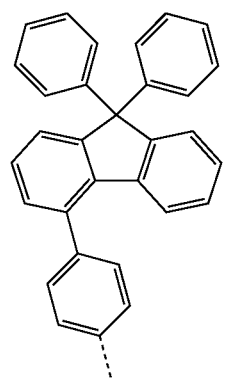 |
| 2-7 | 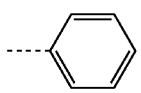 | 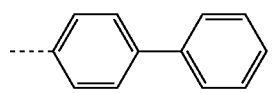 | 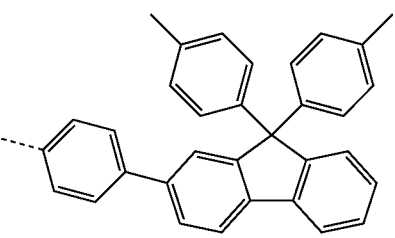 |

-continued
| Formula | ----Ar1 | ----Ar2 | ----Ar3 |
|---|---|---|---|
| 2-8 | 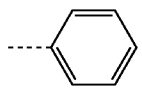 | 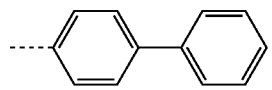 | 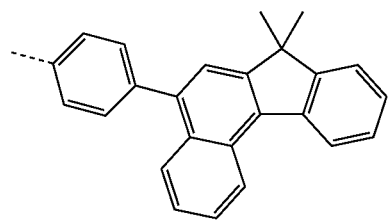 |
| 2-9 | 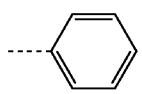 | 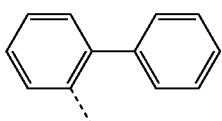 | 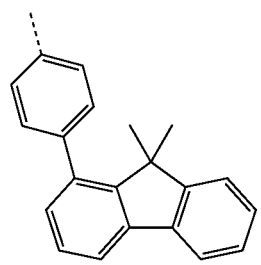 |
| 2-10 | 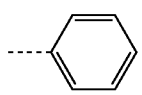 | 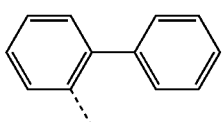 | 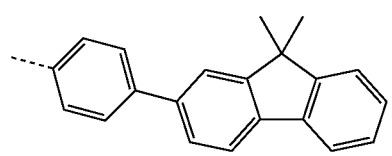 |
| 2-11 | 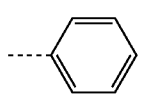 | 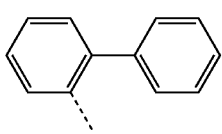 | 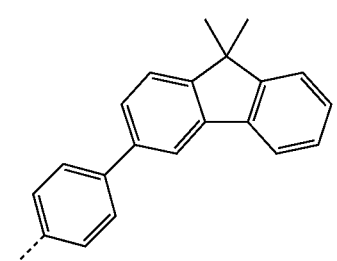 |
| 2-12 | 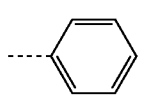 | 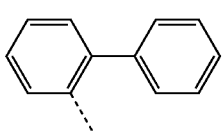 | 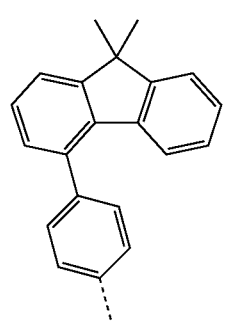 |
| 2-13 | 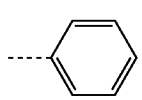 | 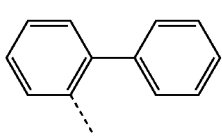 | 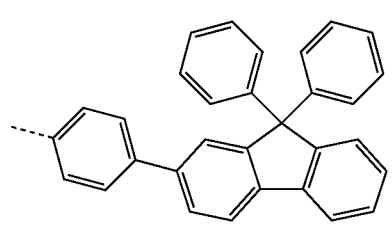 |

-continued
| Formula | ----Ar1 | ----Ar2 | ----Ar3 |
|---|---|---|---|
| 2-14 | 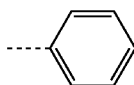 | 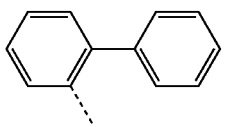 | 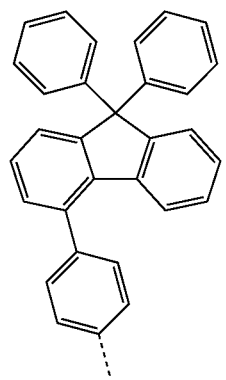 |
| 2-15 | 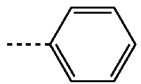 | 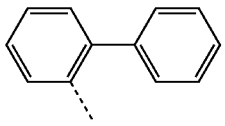 | 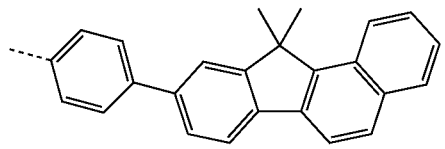 |
| 2-16 | 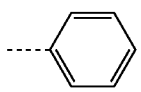 | 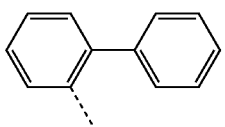 | 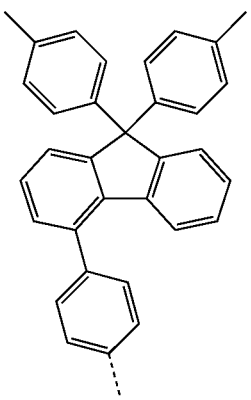 |
| 2-17 | 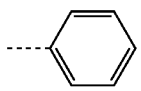 | 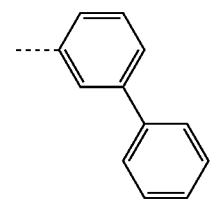 | 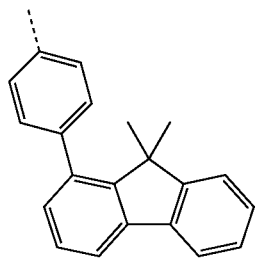 |
| 2-18 | 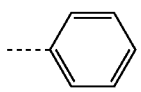 | 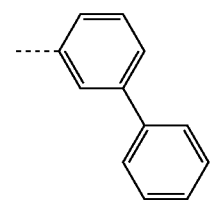 | 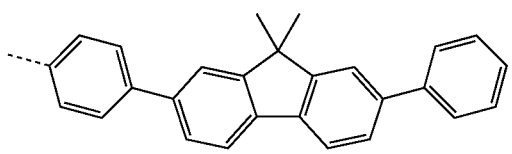 |

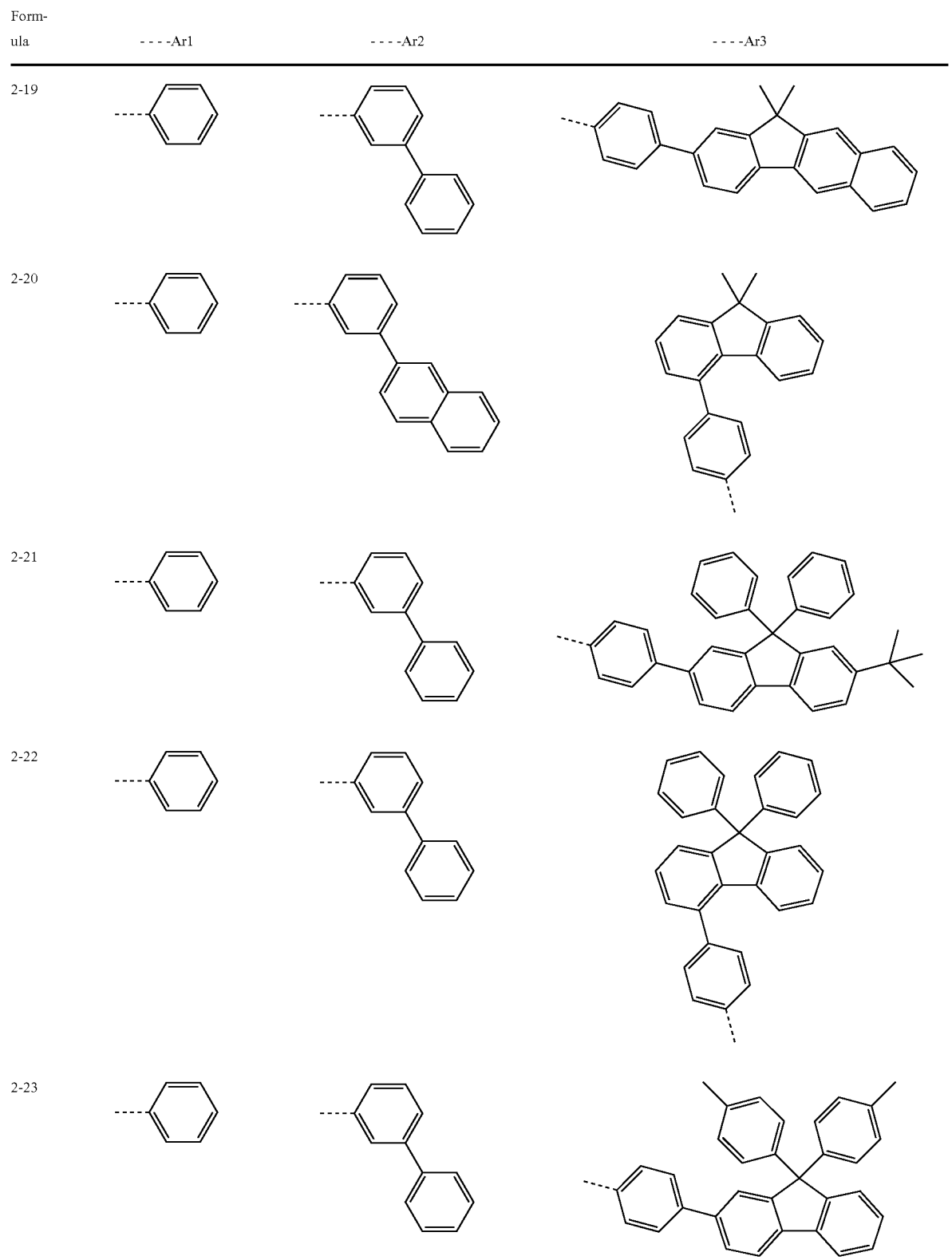

| Formula | ----Ar1 | ----Ar2 | ----Ar3 |
|---|---|---|---|
| 2-24 | 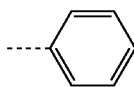 | 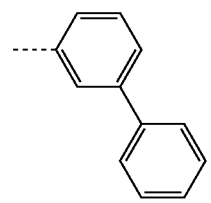 | 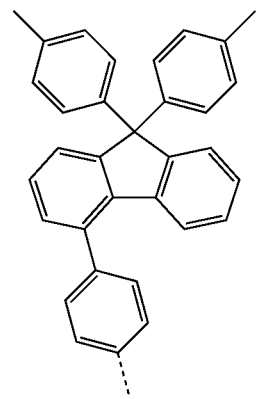 |
| 2-25 | 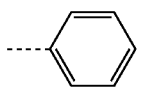 | 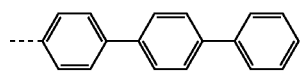 | 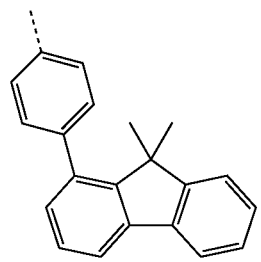 |
| 2-26 | 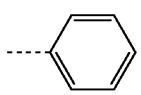 | 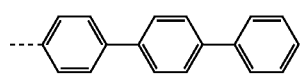 | 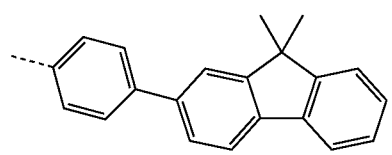 |
| 2-27 | 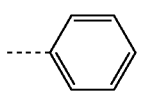 | 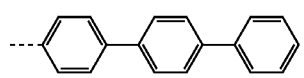 | 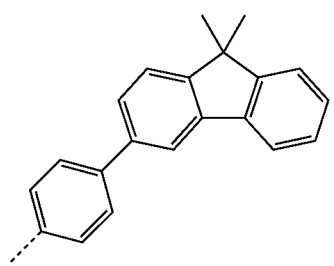 |
| 2-28 | 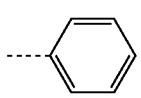 | 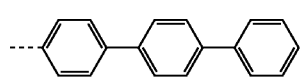 | 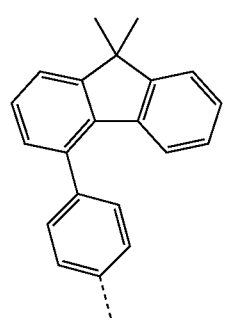 |

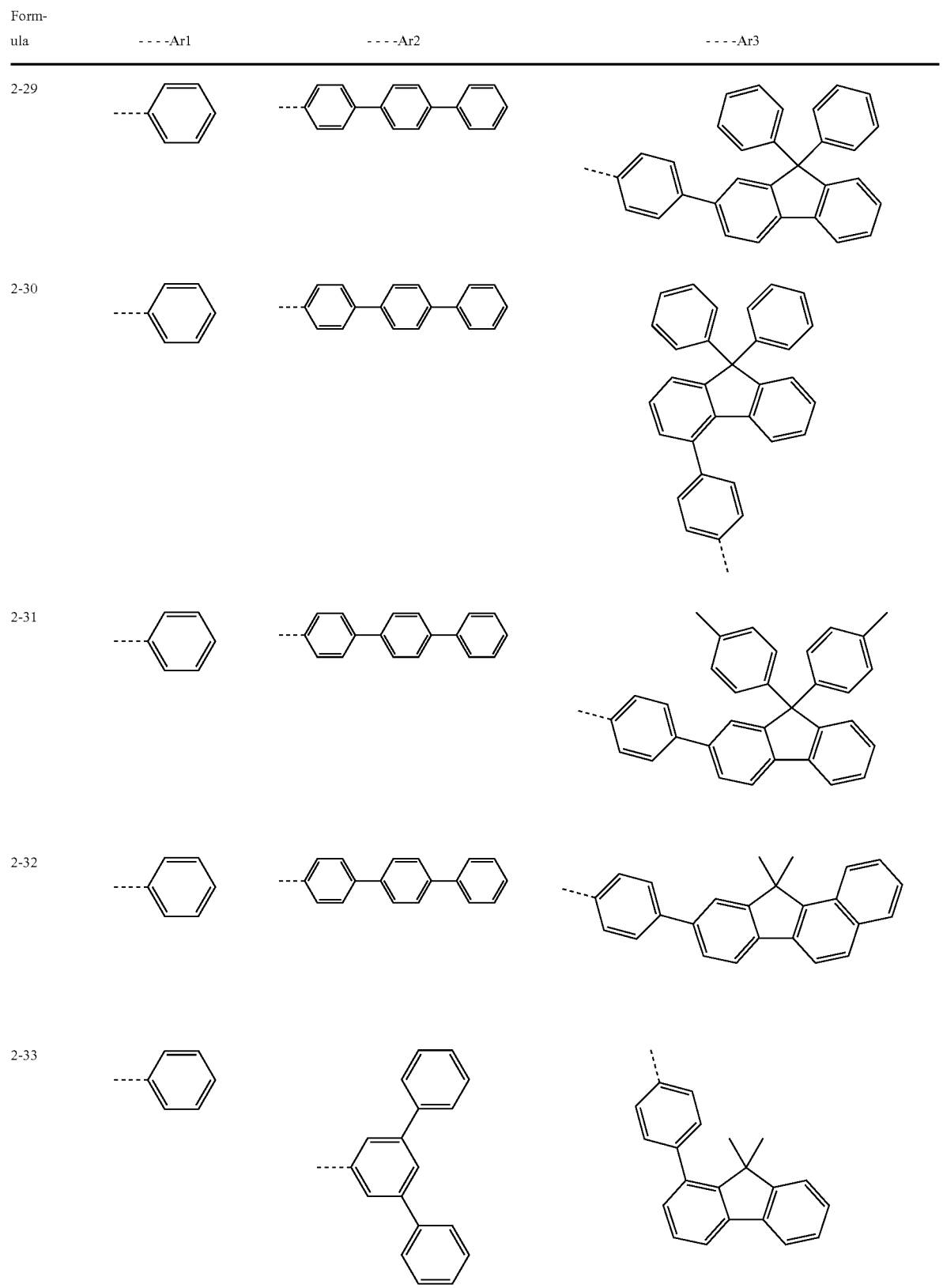

| Formula | ----Ar1 | ----Ar2 | ----Ar3 |
|---|---|---|---|
| 2-34 | 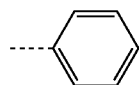 | 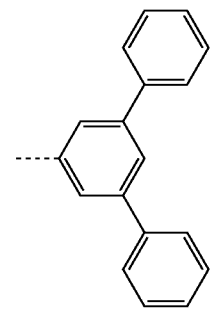 | 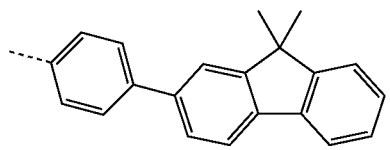 |
| 2-35 | 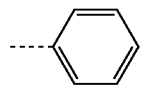 | 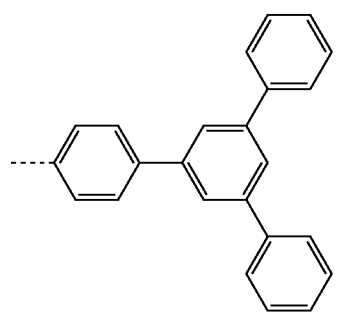 | 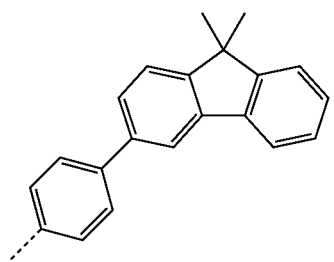 |
| 2-36 | 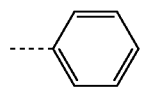 | 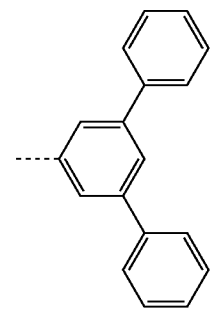 | 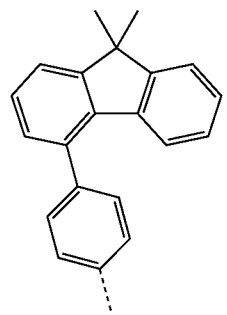 |
| 2-37 | 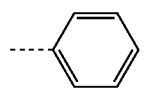 | 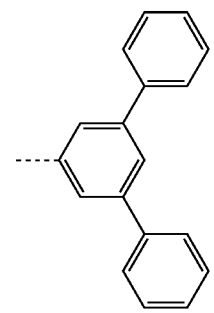 | 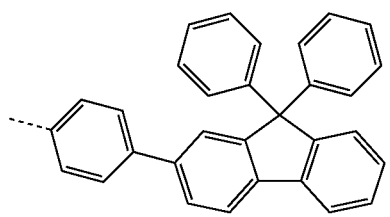 |

-continued

| Formula | ----Ar1 | ----Ar2 | ----Ar3 |
|---|---|---|---|
| 2-38 | | | |
| 2-39 | | | |
| 2-40 | | | |
| 2-41 | | | |
| 2-42 | | | |

-continued
| Formula | ----Ar1 | ----Ar2 | ----Ar3 |
|---|---|---|---|
| 2-43 | 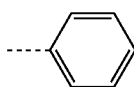 | 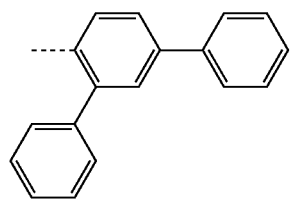 | 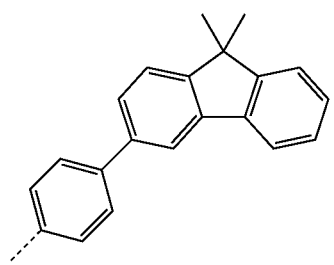 |
| 2-44 | 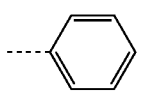 | 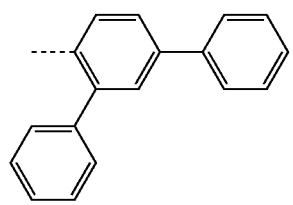 | 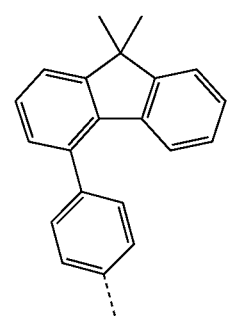 |
| 2-45 | 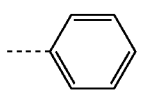 | 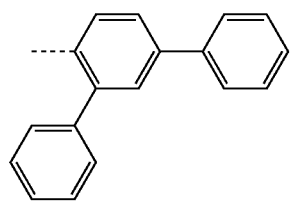 | 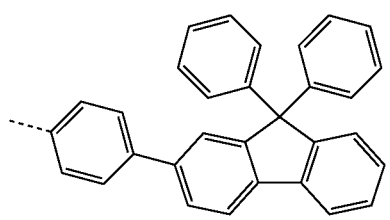 |
| 2-46 | 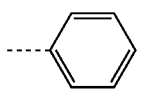 | 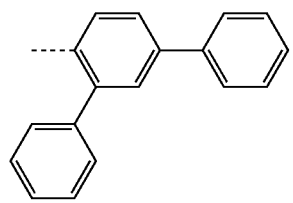 | 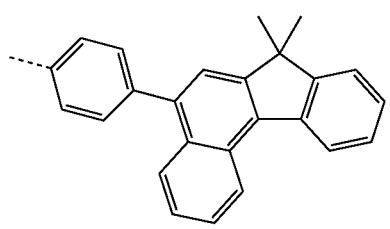 |
| 2-47 | 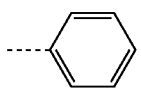 | 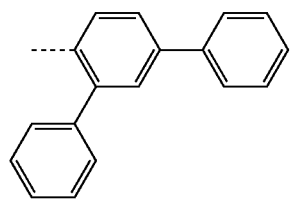 | 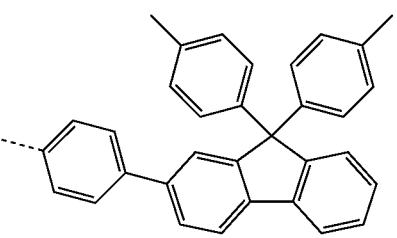 |

| Formula | ----Ar1 | ----Ar2 | ----Ar3 |
|---|---|---|---|
| 2-48 | 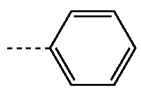 | 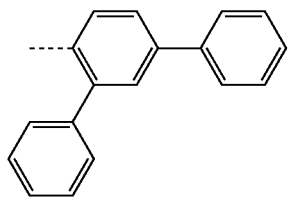 | 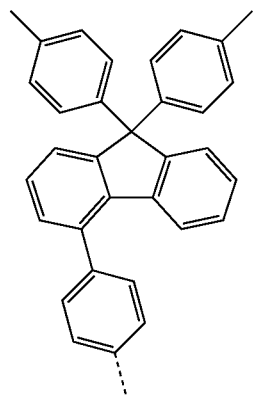 |
| 2-49 | 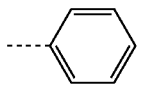 | 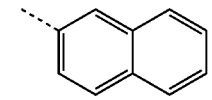 | 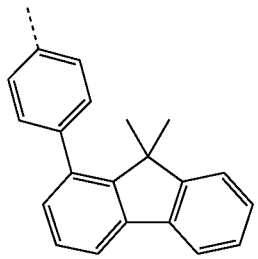 |
| 2-50 | 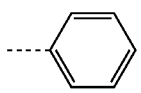 | 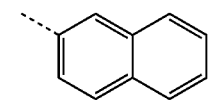 | 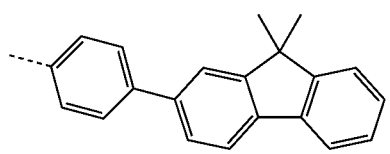 |
| 2-51 | 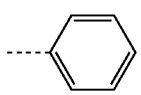 | 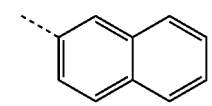 | 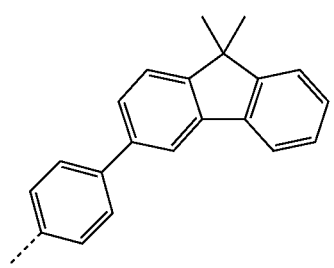 |
| 2-52 | 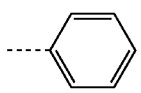 | 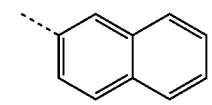 | 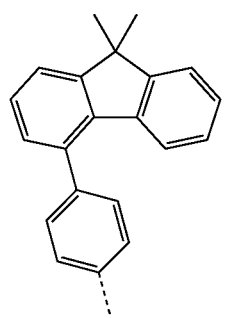 |

-continued
| Formula | ----Ar1 | ----Ar2 | ----Ar3 |
|---|---|---|---|
| 2-53 | 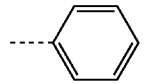 | 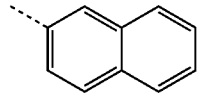 | 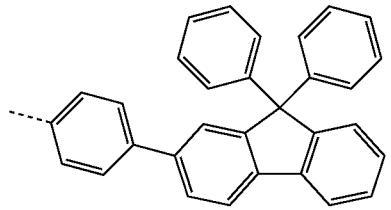 |
| 2-54 | 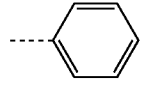 | 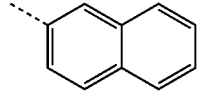 | 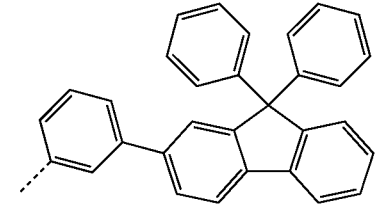 |
| 2-55 | 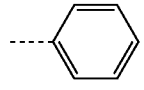 | 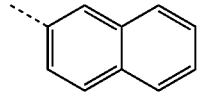 | 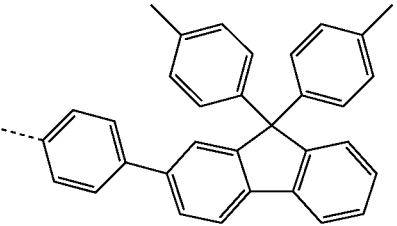 |
| 2-56 | 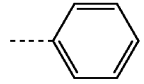 | 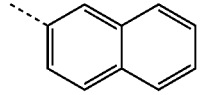 | 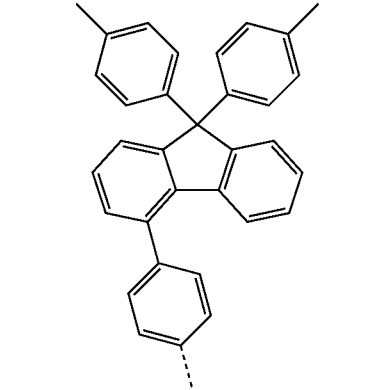 |
| 2-57 | 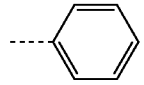 | 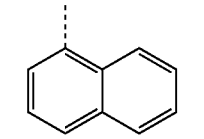 | 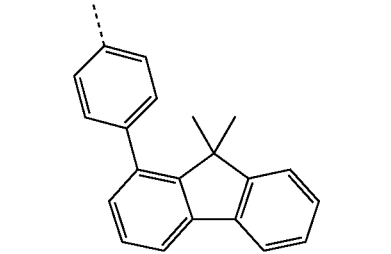 |
| 2-58 | 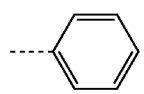 | 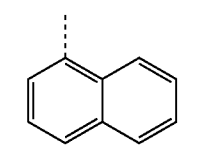 | 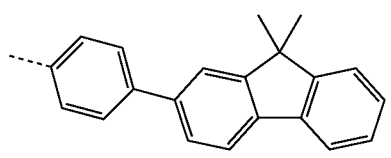 |

-continued

| Formula | ----Ar1 | ----Ar2 | ----Ar3 |
|---|---|---|---|
| 2-59 | phenyl | 1-naphthyl | 9,9-dimethylfluorene-2-yl-(4-phenylene)- |
| 2-60 | phenyl | 1-naphthyl | 9,9-dimethylfluorene-4-yl-biphenyl- |
| 2-61 | phenyl | 1-naphthyl | 9,9-diphenylfluorene-2-yl-(4-phenylene)- |
| 2-62 | phenyl | 1-naphthyl | 9,9-diphenylfluorene-4-yl-(4-phenylene)- |
| 2-63 | phenyl | 1-naphthyl | 9,9-di(p-tolyl)fluorene-2-yl-(4-phenylene)- |

-continued
| Formula | ----Ar1 | ----Ar2 | ----Ar3 |
|---|---|---|---|
| 2-64 | 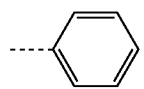 | 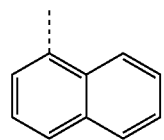 | 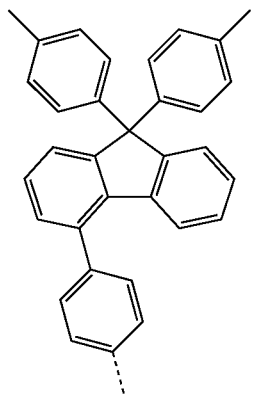 |
| 2-65 | 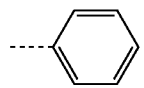 | 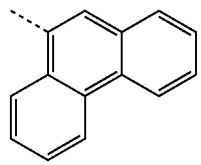 | 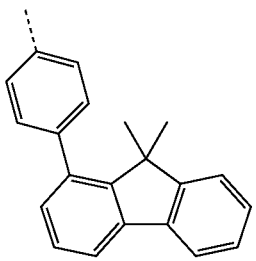 |
| 2-66 | 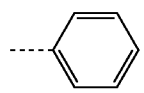 | 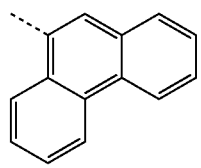 | 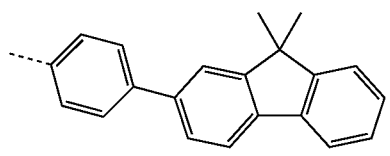 |
| 2-67 | 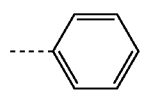 | 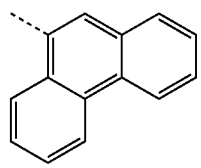 | 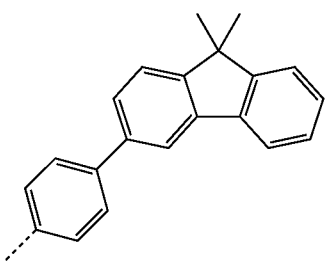 |
| 2-68 | 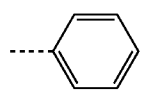 | 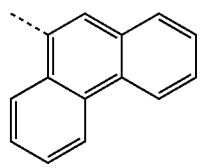 | 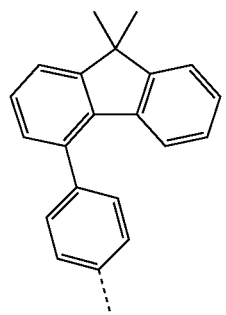 |

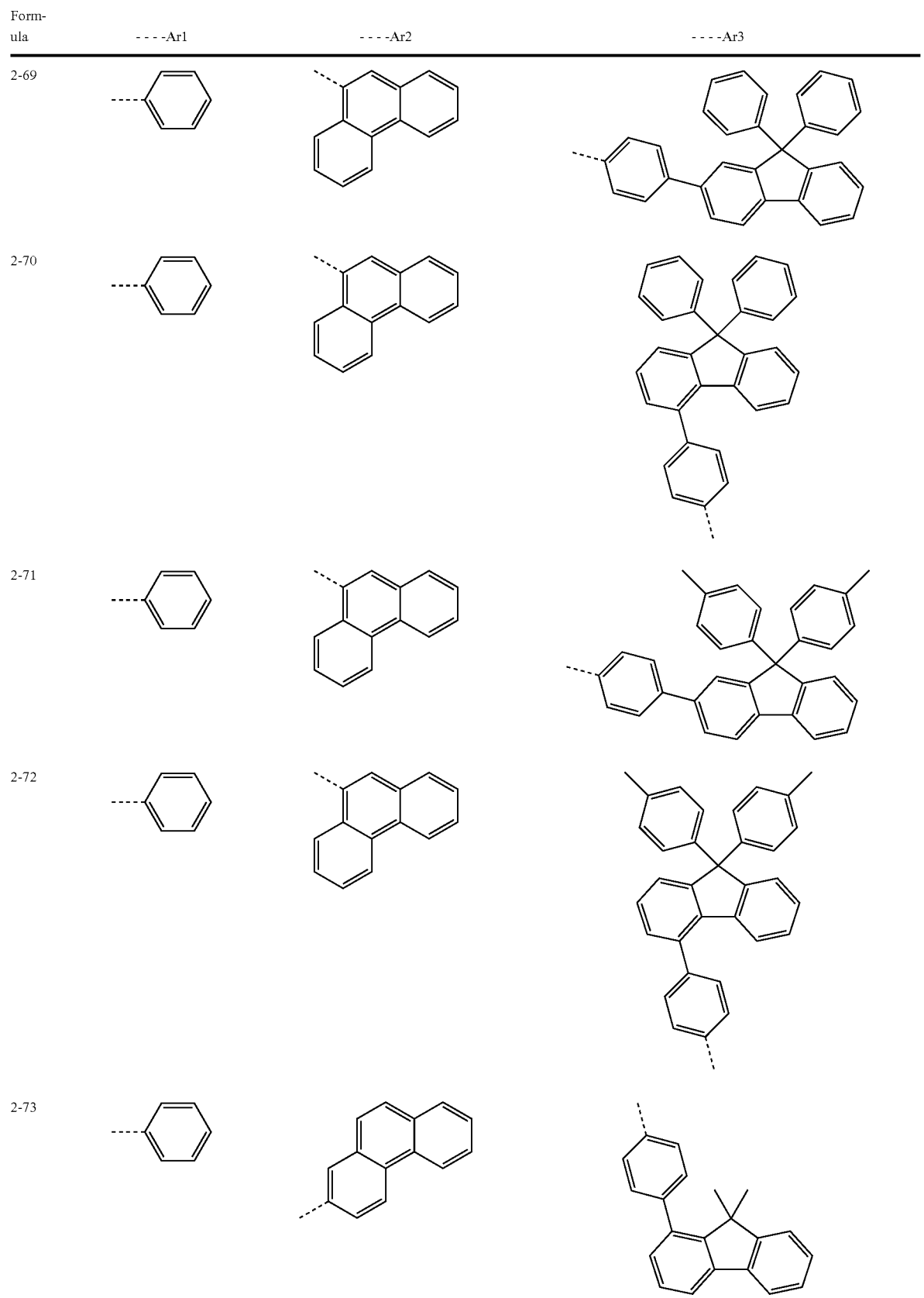

-continued
| Formula | ----Ar1 | ----Ar2 | ----Ar3 |
|---|---|---|---|
| 2-74 | 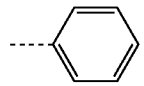 | 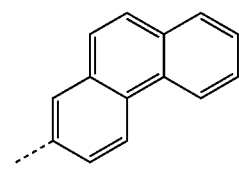 | 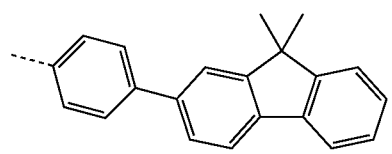 |
| 2-75 | 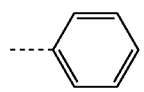 | 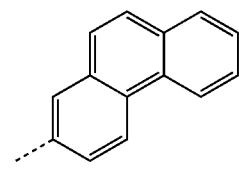 | 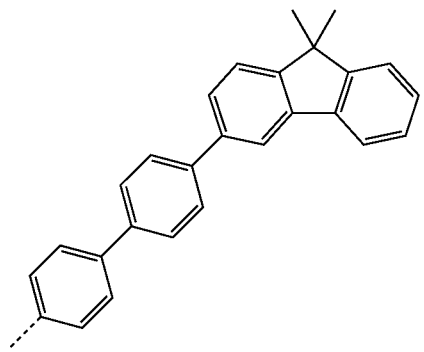 |
| 2-76 | 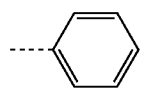 | 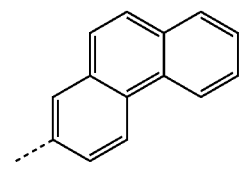 | 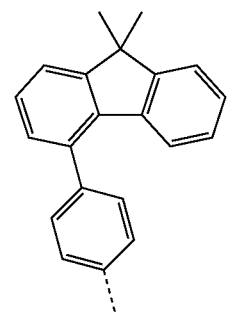 |
| 2-77 | 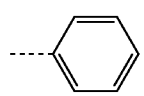 | 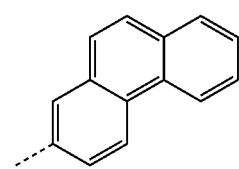 | 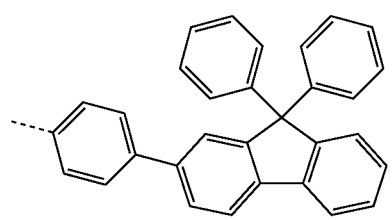 |
| 2-78 | 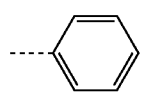 | 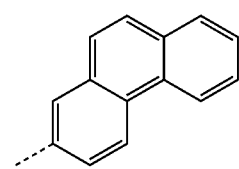 | 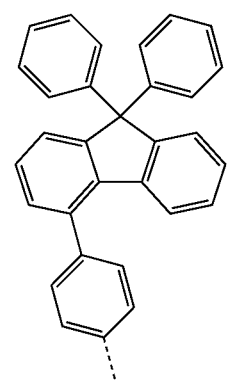 |

-continued
| Formula | ----Ar1 | ----Ar2 | ----Ar3 |
|---|---|---|---|
| 2-79 | 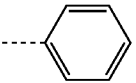 | 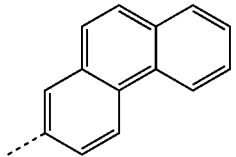 | 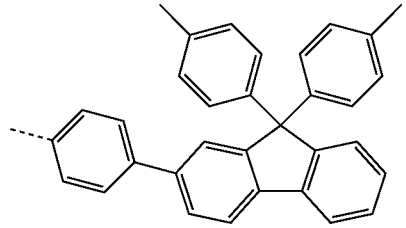 |
| 2-80 | 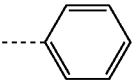 | 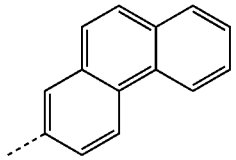 | 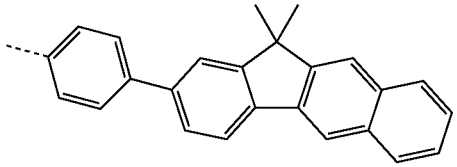 |
| 2-81 | 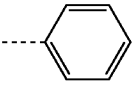 | 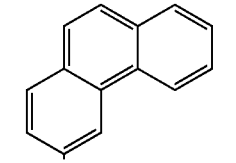 | 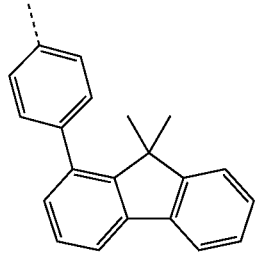 |
| 2-82 | 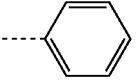 | 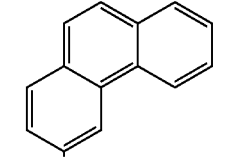 | 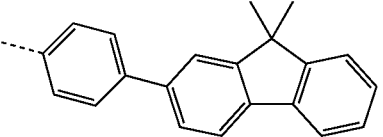 |
| 2-83 | 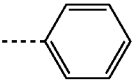 | 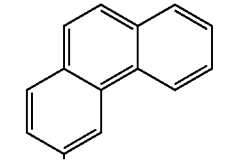 | 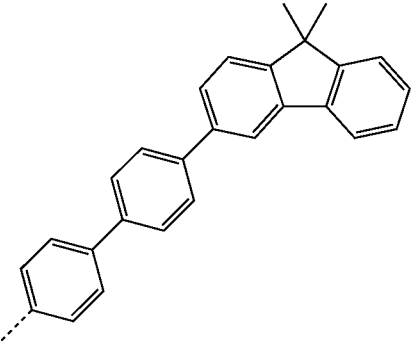 |
| 2-84 | 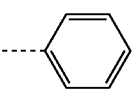 | 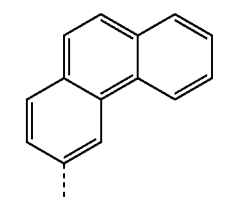 | 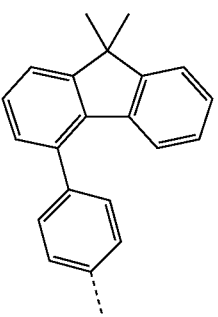 |

| Formula | ----Ar1 | ----Ar2 | ----Ar3 |
|---|---|---|---|
| 2-85 | 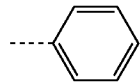 | 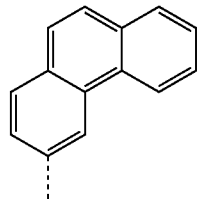 | 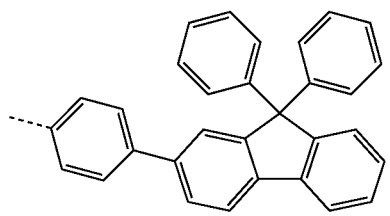 |
| 2-86 | 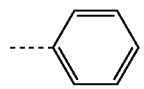 | 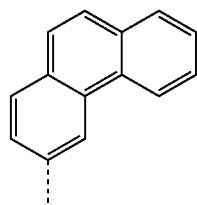 | 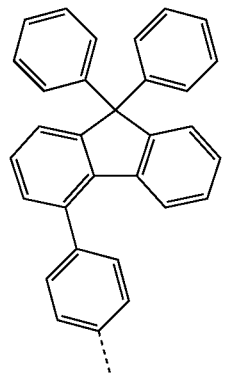 |
| 2-87 | 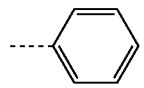 | 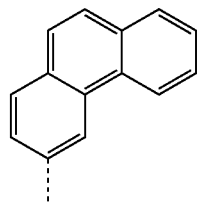 | 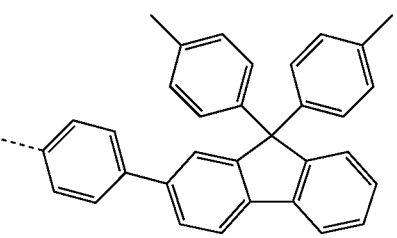 |
| 2-88 | 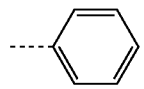 | 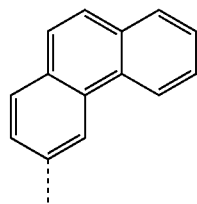 | 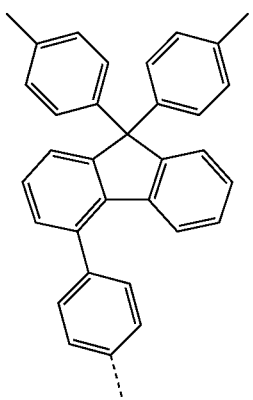 |
| 2-89 | 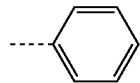 | 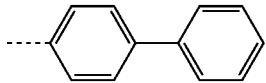 | 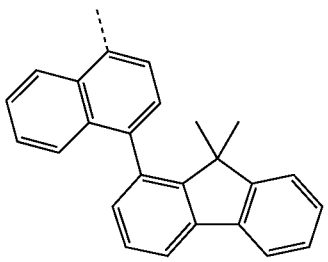 |

-continued
| Formula | ----Ar1 | ----Ar2 | ----Ar3 |
|---|---|---|---|
| 2-90 | 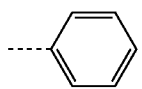 | 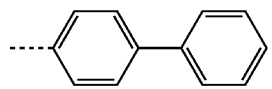 | 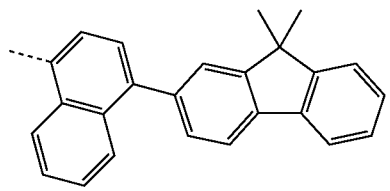 |
| 2-91 | 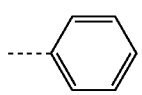 | 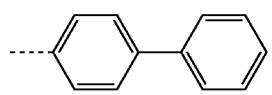 | 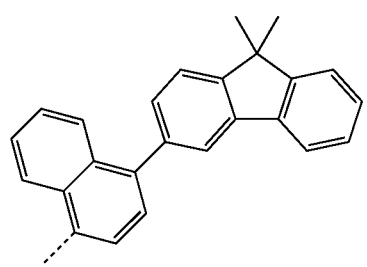 |
| 2-92 | 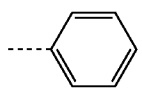 | 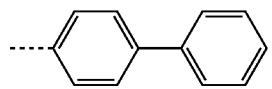 | 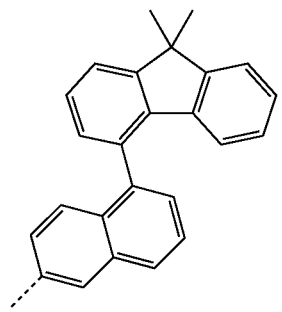 |
| 2-93 | 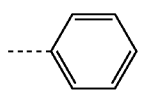 | 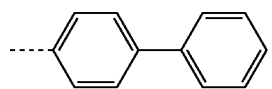 | 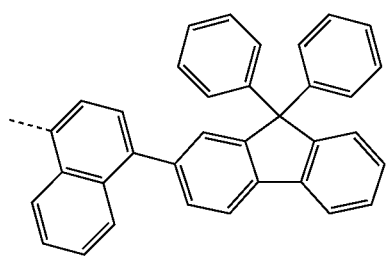 |
| 2-94 | 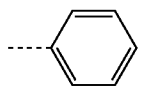 | 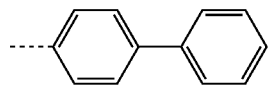 | 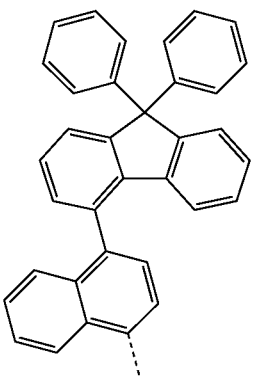 |

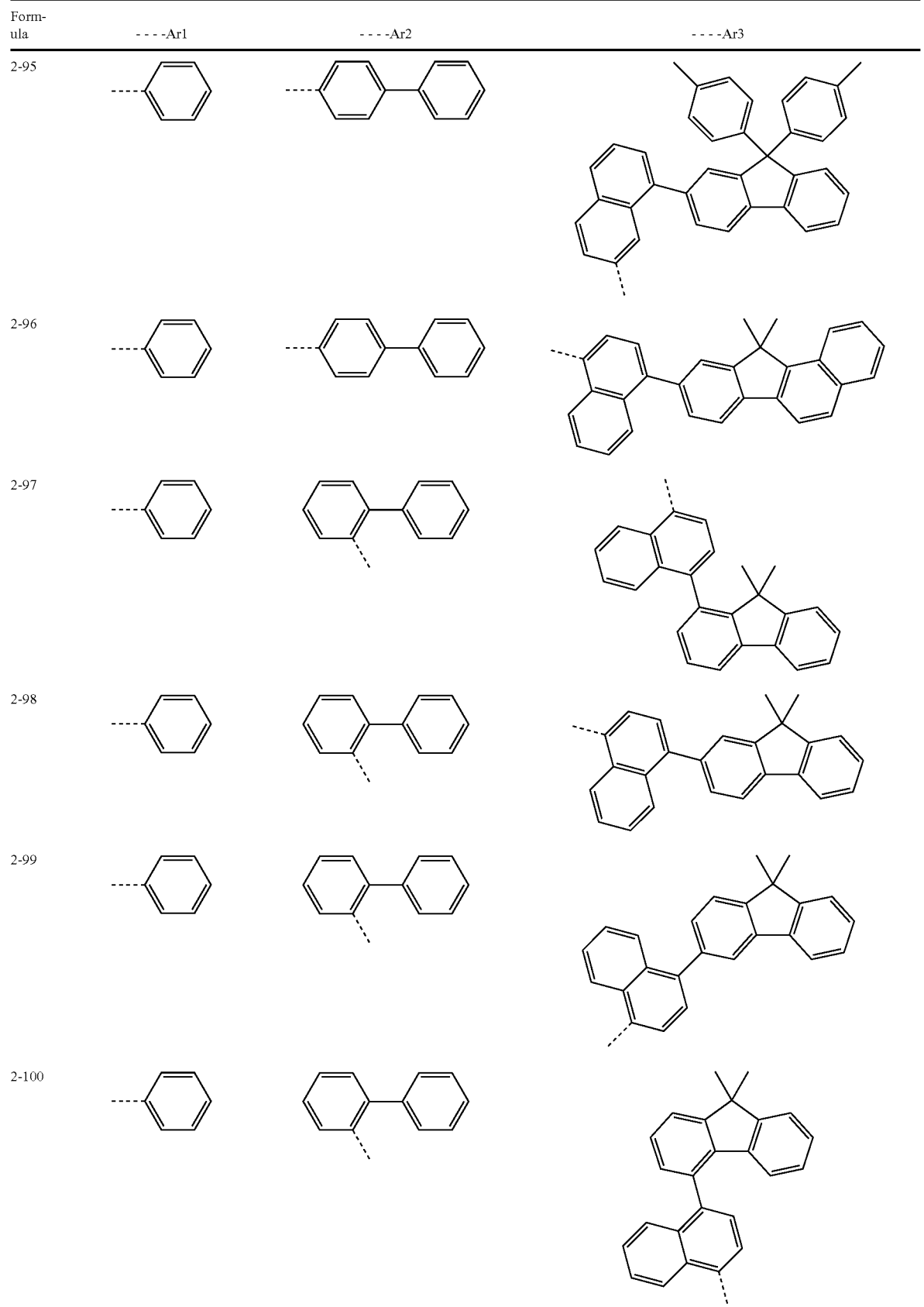

-continued
| Formula | ----Ar1 | ----Ar2 | ----Ar3 |
|---|---|---|---|
| 2-101 | 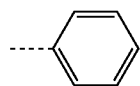 | 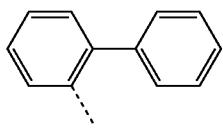 | 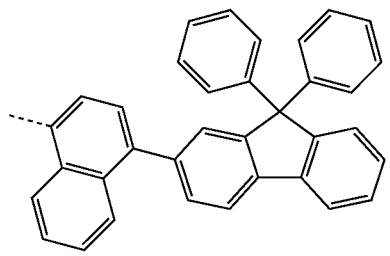 |
| 2-102 | 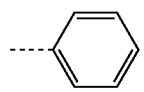 | 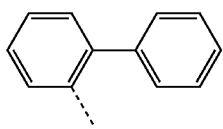 | 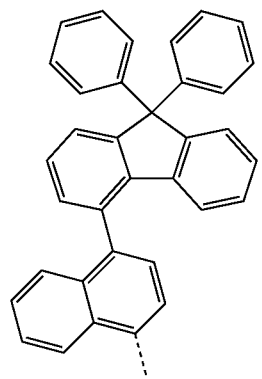 |
| 2-103 | 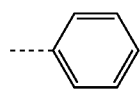 | 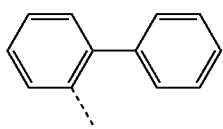 | 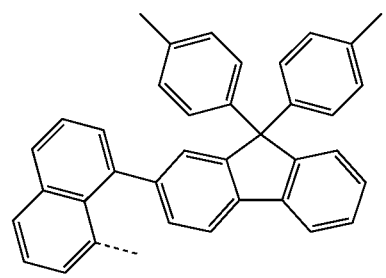 |
| 2-104 | 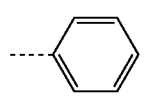 | 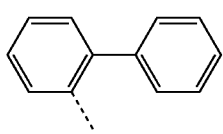 | 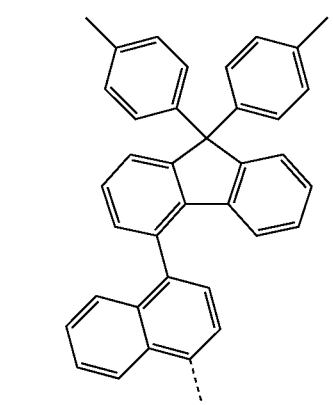 |

| Formula | ----Ar1 | ----Ar2 | ----Ar3 |
|---|---|---|---|
| 2-105 | 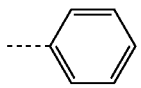 | 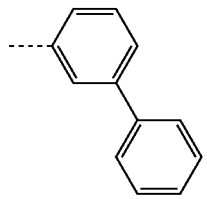 | 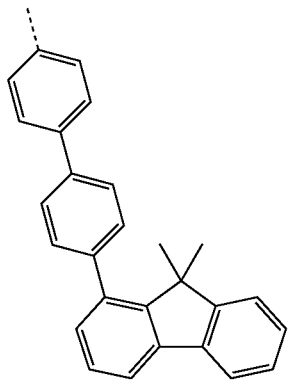 |
| 2-106 | 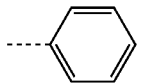 | 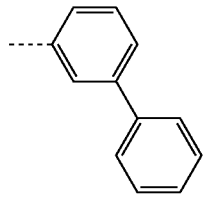 | 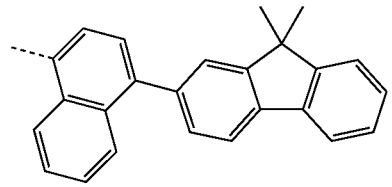 |
| 2-107 | 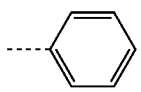 | 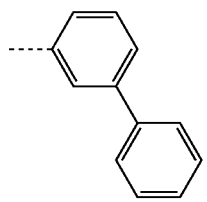 | 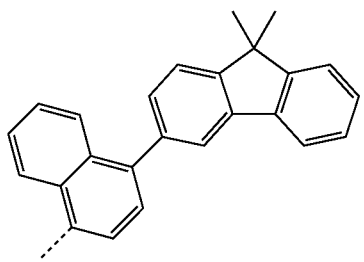 |
| 2-108 | 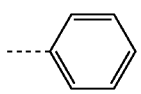 | 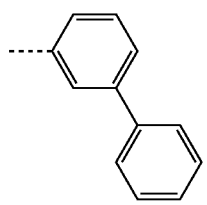 | 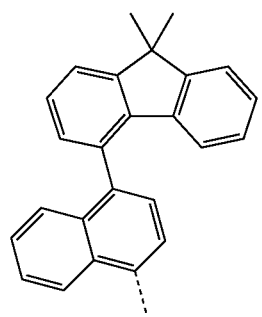 |
| 2-109 | 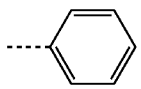 | 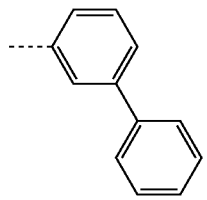 | 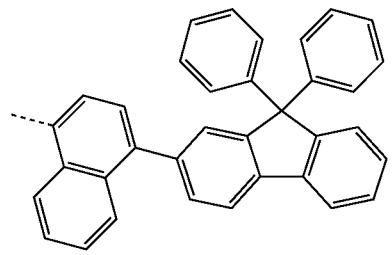 |

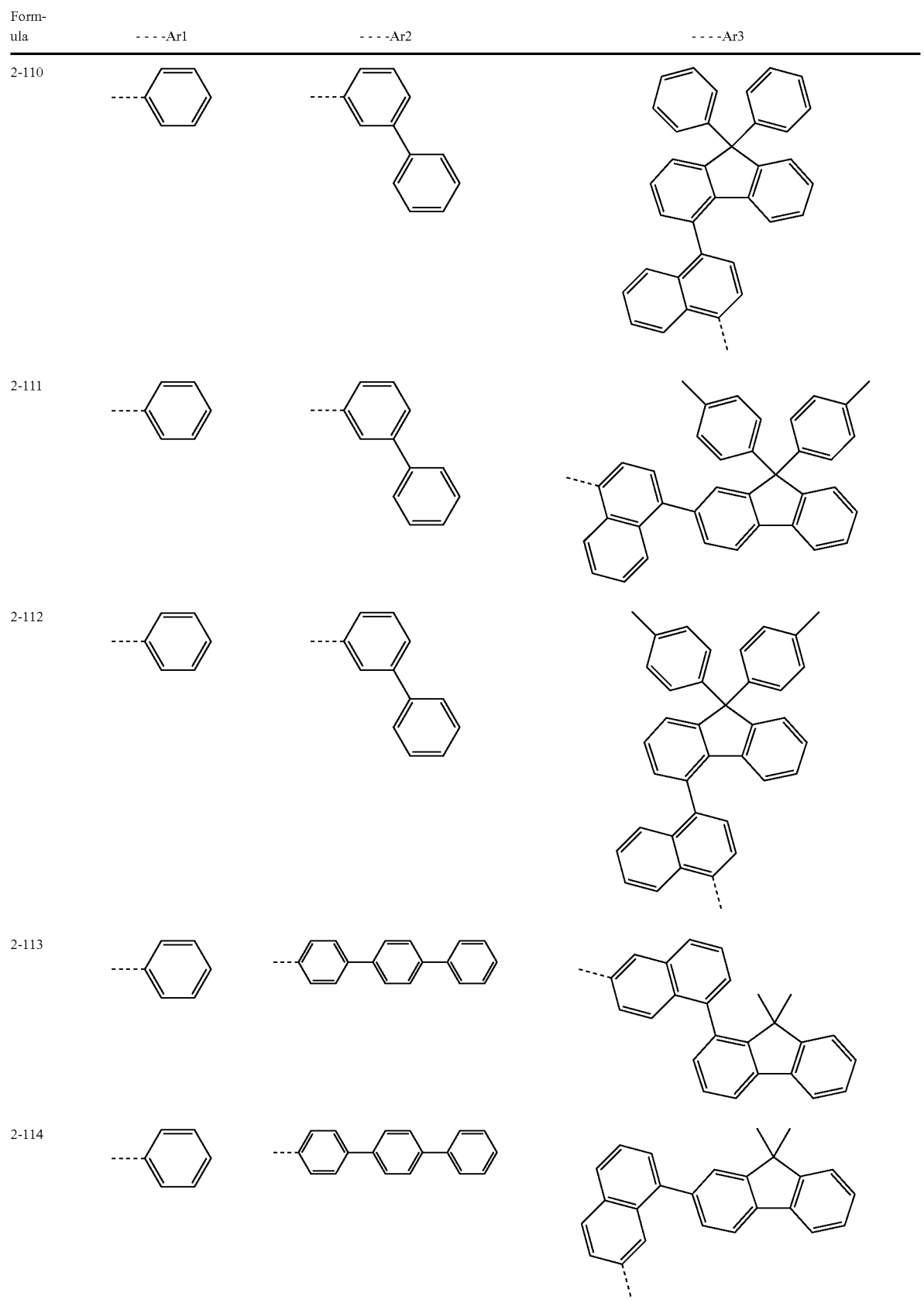

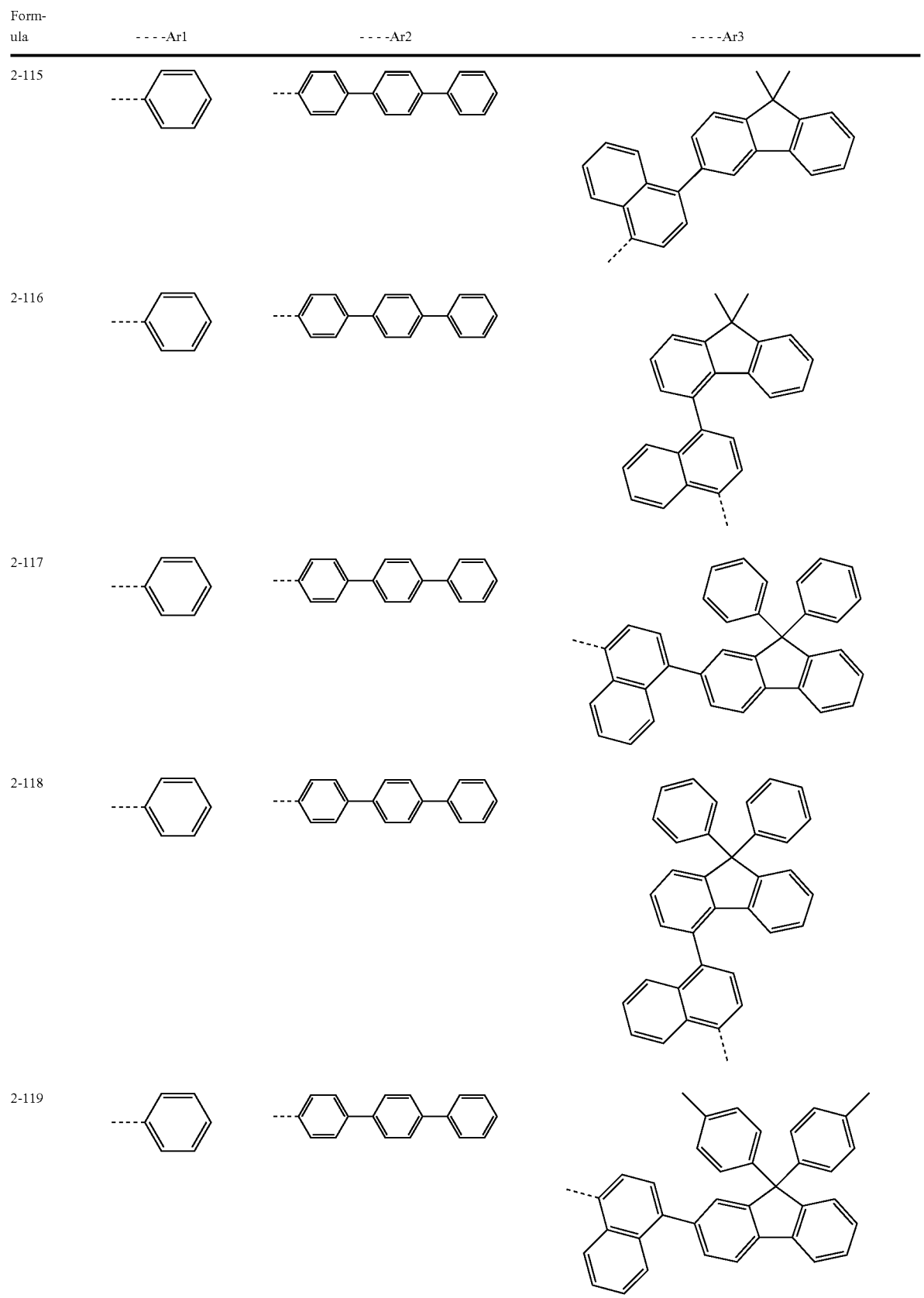

-continued
| Formula | ----Ar1 | ----Ar2 | ----Ar3 |
|---|---|---|---|
| 2-120 | 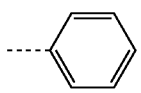 | 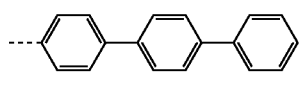 | 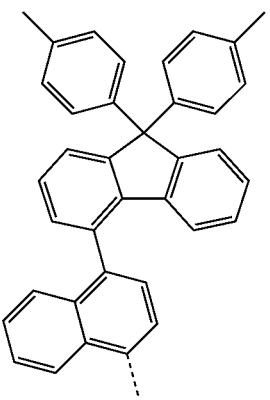 |
| 2-121 | 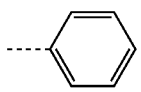 | 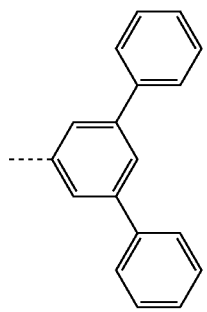 | 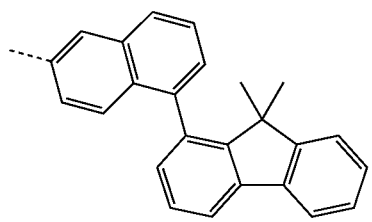 |
| 2-122 | 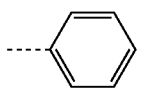 | 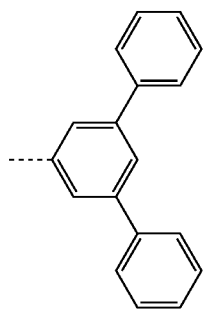 | 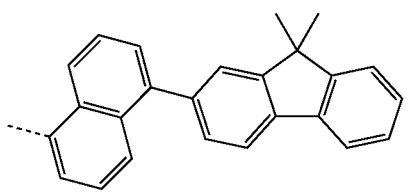 |
| 2-123 | 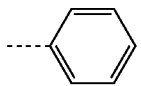 | 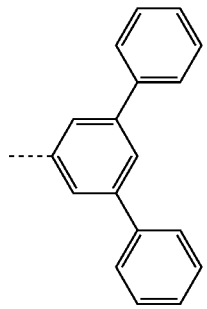 | 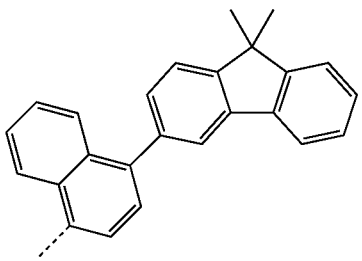 |

-continued
| Formula | ----Ar1 | ----Ar2 | ----Ar3 |
|---|---|---|---|
| 2-124 | 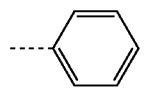 | 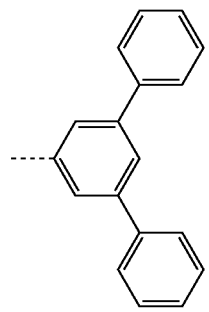 | 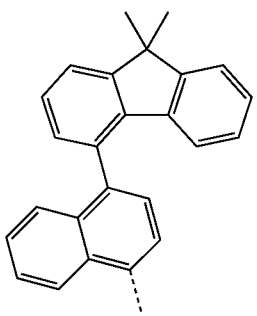 |
| 2-125 | 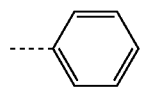 | 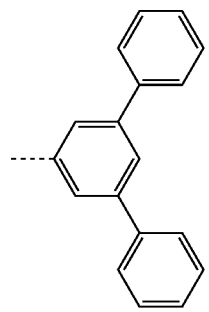 | 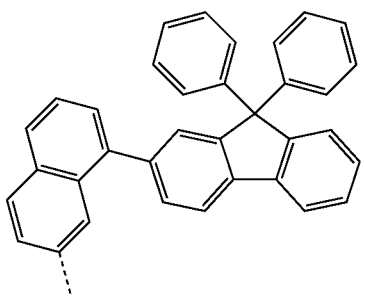 |
| 2-126 | 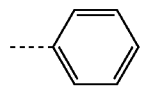 | 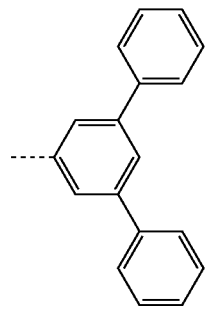 | 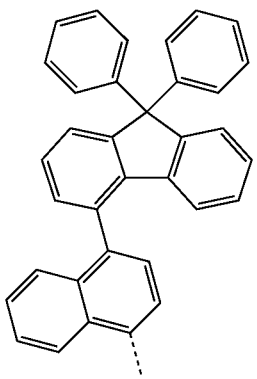 |
| 2-127 | 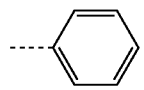 | 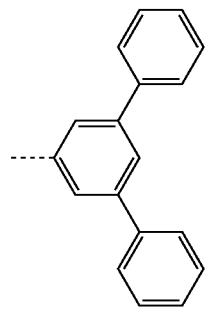 | 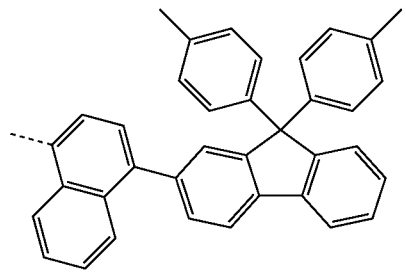 |

-continued
| Formula | ----Ar1 | ----Ar2 | ----Ar3 |
|---|---|---|---|
| 2-128 | | | |
| 2-129 | | | |
| 2-130 | | | |
| 2-131 | | | |
| 2-132 | | | |
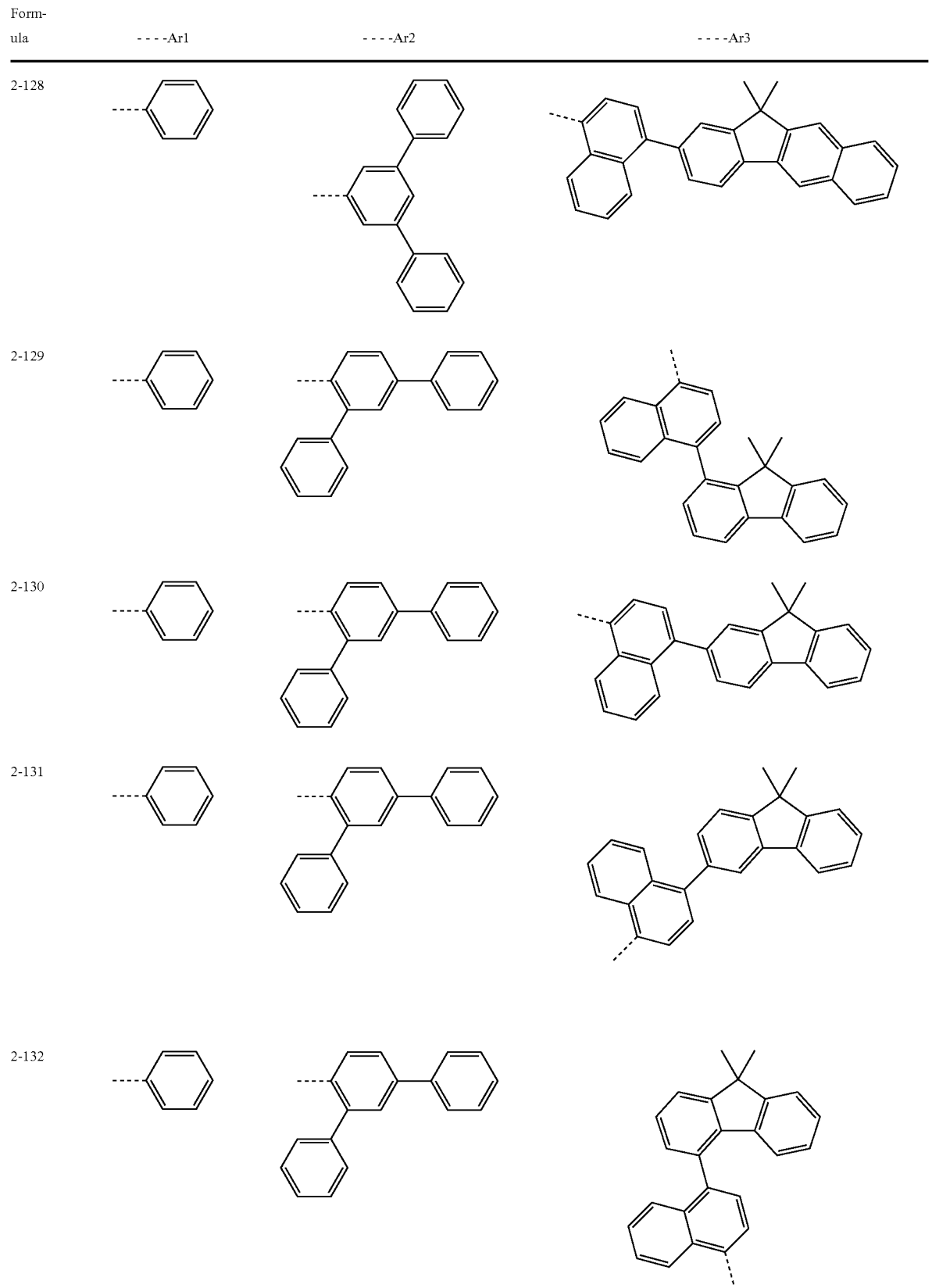

-continued
| Formula | ----Ar1 | ----Ar2 | ----Ar3 |
|---|---|---|---|
| 2-133 | 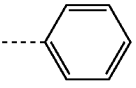 | 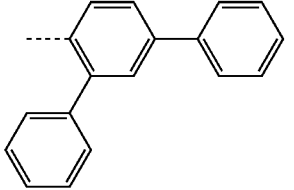 | 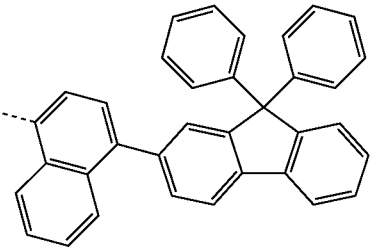 |
| 2-134 | 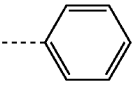 | 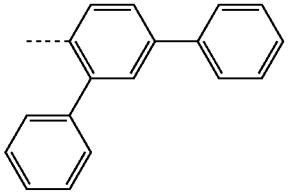 | 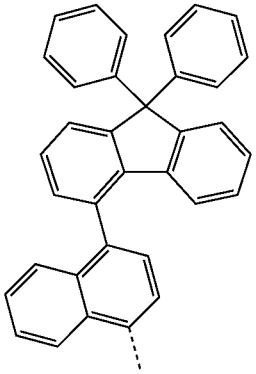 |
| 2-135 | 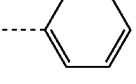 | 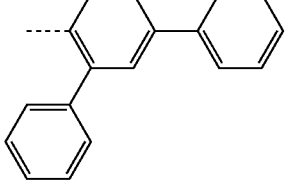 | 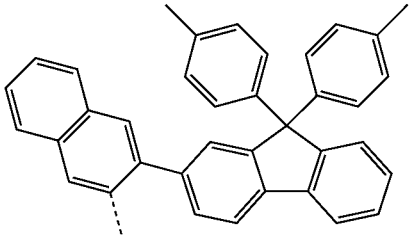 |
| 2-136 | 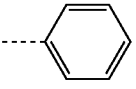 | 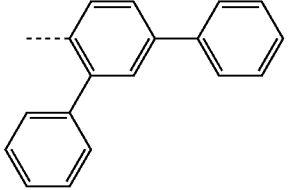 | 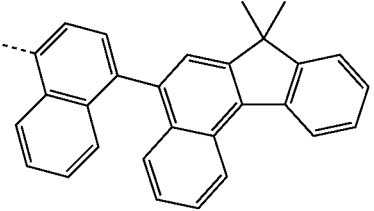 |
| 2-137 | 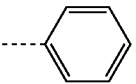 | 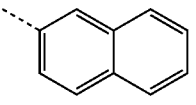 | 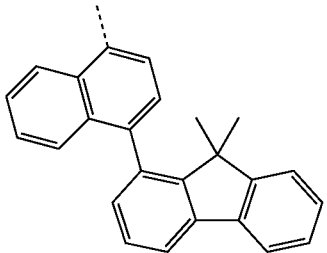 |
| 2-138 | 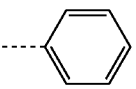 | 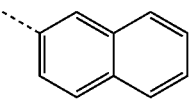 | 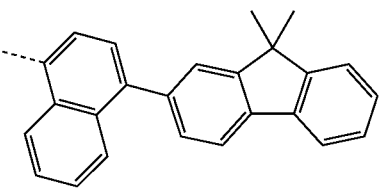 |

| Formula | ----Ar1 | ----Ar2 | ----Ar3 |
|---|---|---|---|
| 2-139 | 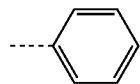 | 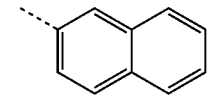 | 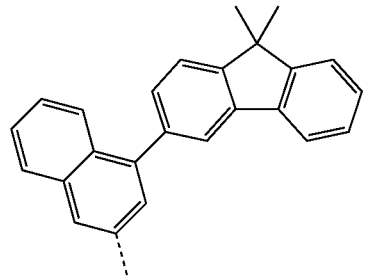 |
| 2-140 | 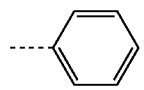 | 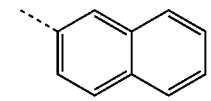 | 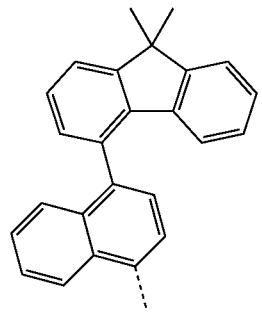 |
| 2-141 | 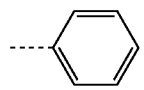 | 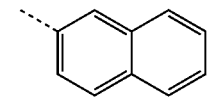 | 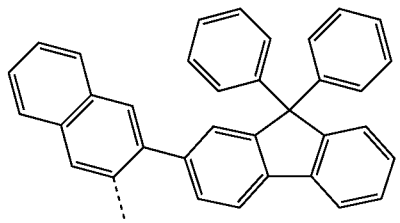 |
| 2-142 | 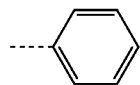 | 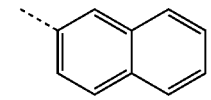 | 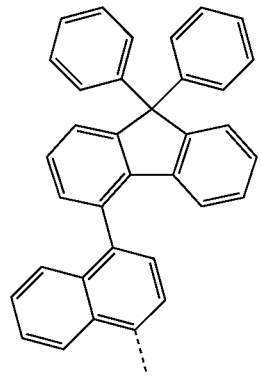 |
| 2-143 | 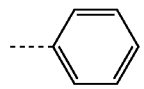 | 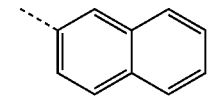 | 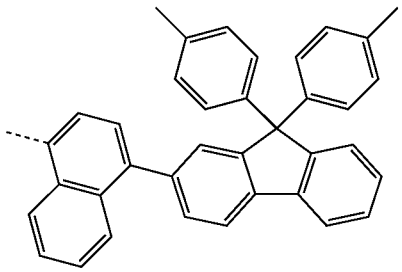 |

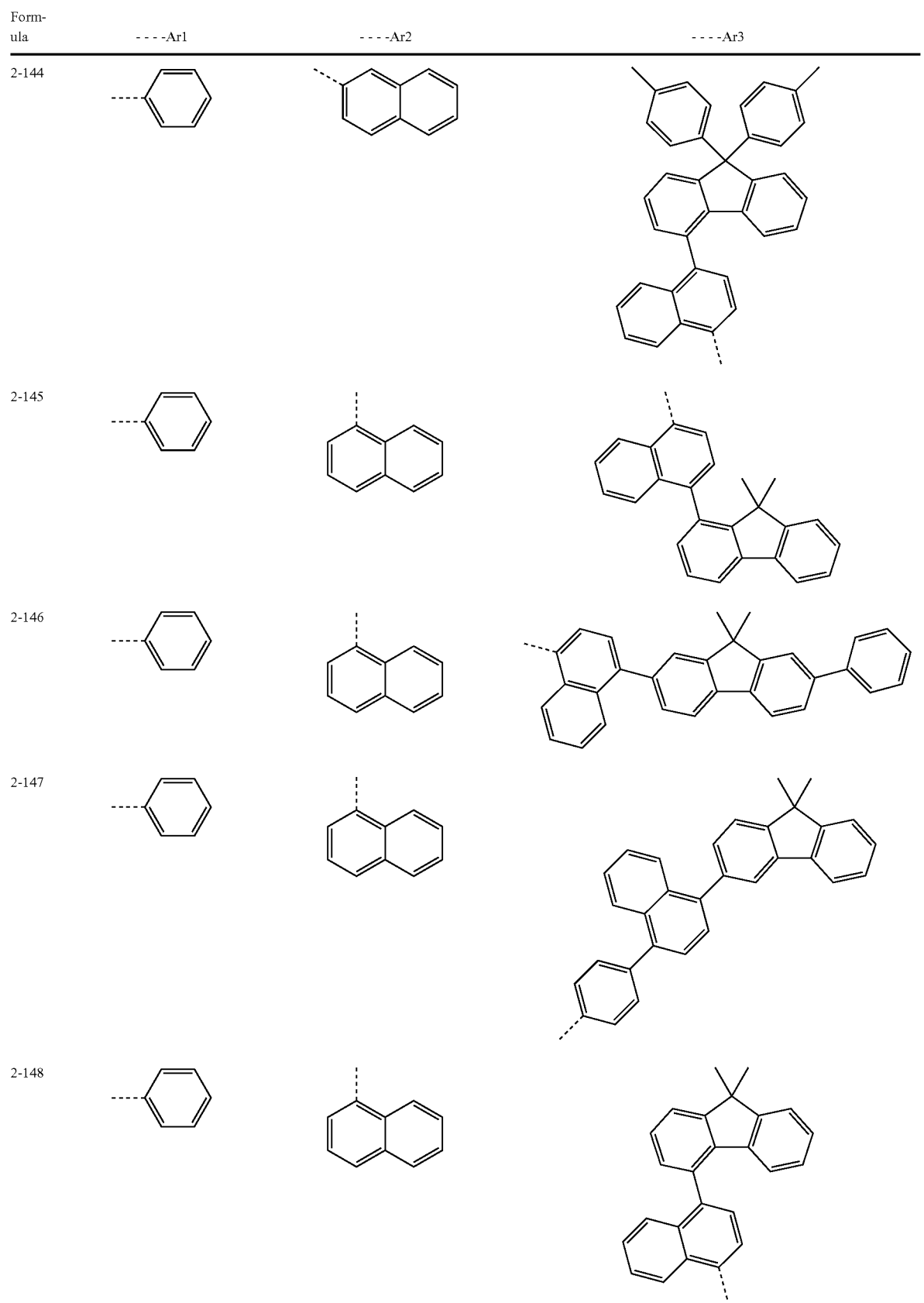

291 292
-continued
| Formula | ----Ar1 | ----Ar2 | ----Ar3 |
|---|---|---|---|
| 2-149 | 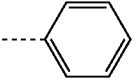 | 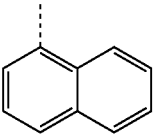 | 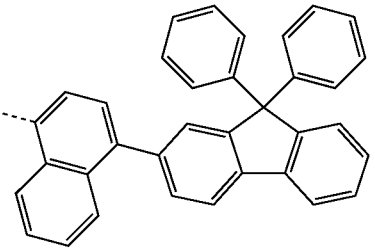 |
| 2-150 | 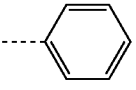 | 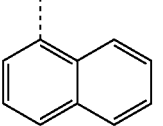 | 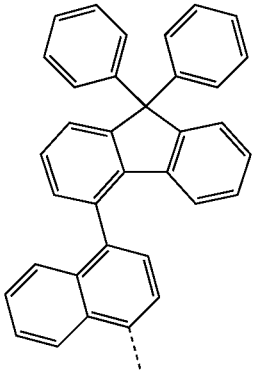 |
| 2-151 | 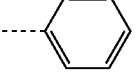 | 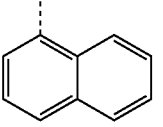 | 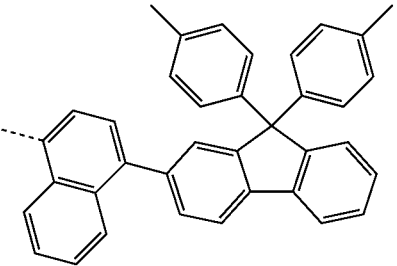 |
| 2-152 | 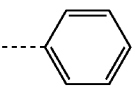 | 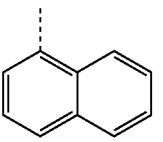 | 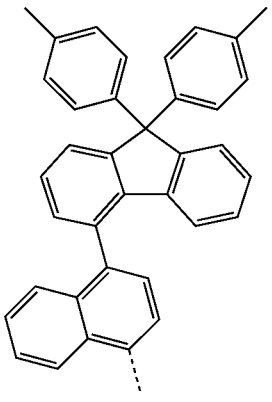 |
| 2-153 | 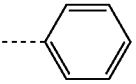 | 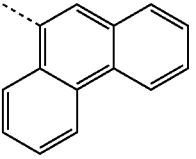 | 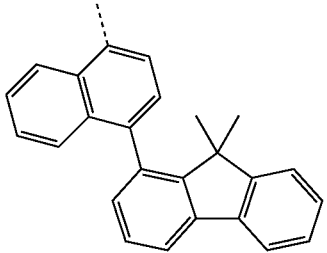 |

-continued
| Formula | ----Ar1 | ----Ar2 | ----Ar3 |
|---|---|---|---|
| 2-154 | 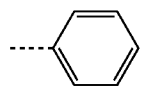 | 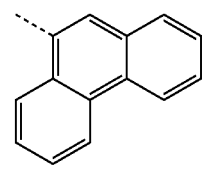 | 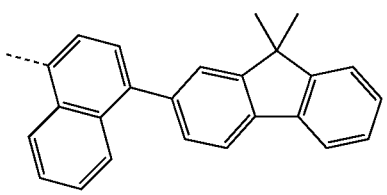 |
| 2-155 | 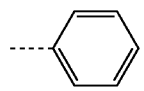 | 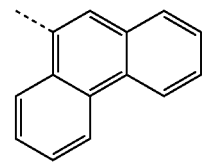 | 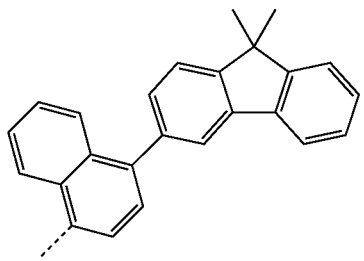 |
| 2-156 | 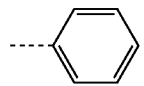 | 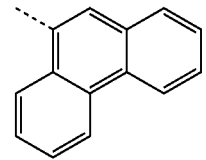 | 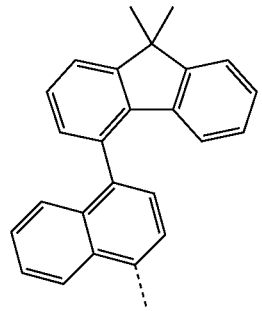 |
| 2-157 | 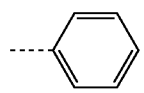 | 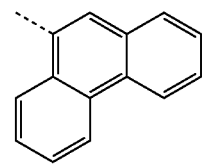 | 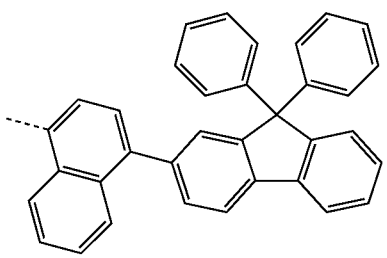 |
| 2-158 | 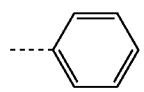 | 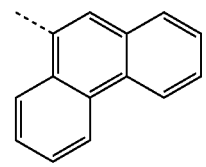 | 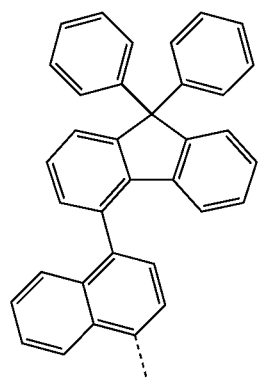 |

-continued
| Formula | ----Ar1 | ----Ar2 | ----Ar3 |
|---|---|---|---|
| 2-159 | 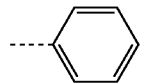 | 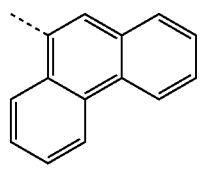 | 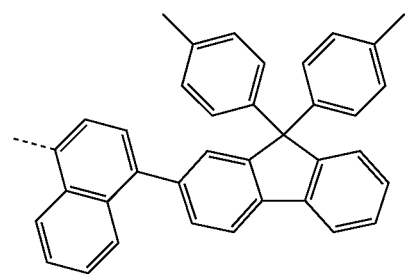 |
| 2-160 | 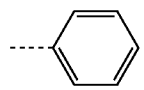 | 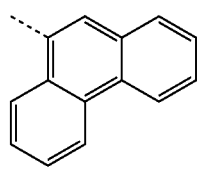 | 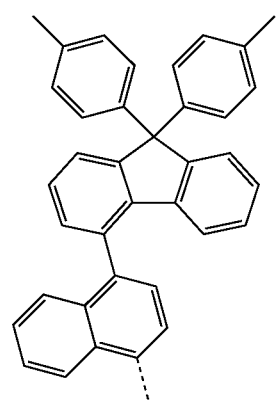 |
| 2-161 | 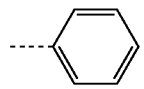 | 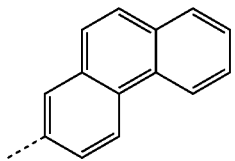 | 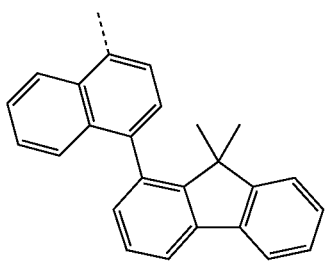 |
| 2-162 | 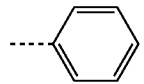 | 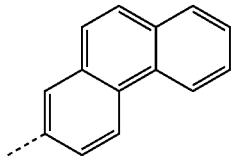 | 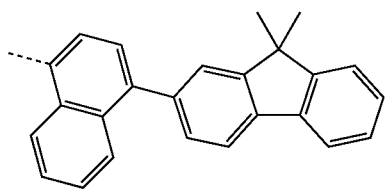 |
| 2-163 | 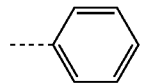 | 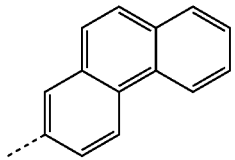 | 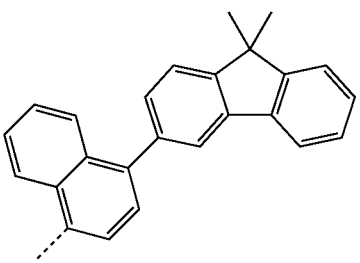 |

| Formula | ----Ar1 | ----Ar2 | ----Ar3 |
|---|---|---|---|
| 2-164 | 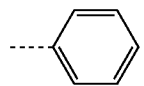 | 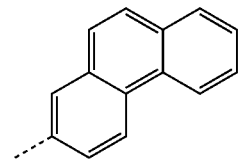 | 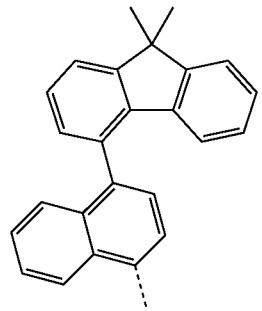 |
| 2-165 | 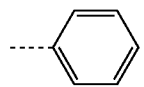 | 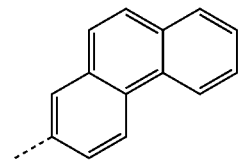 | 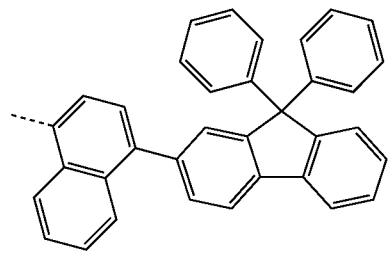 |
| 2-166 | 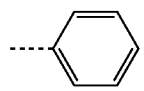 | 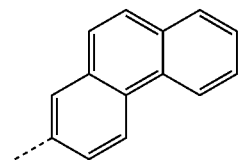 | 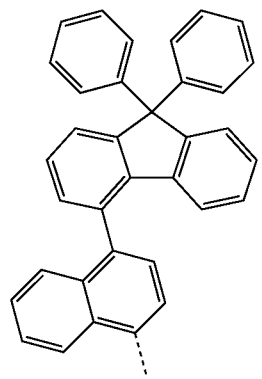 |
| 2-167 | 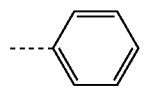 | 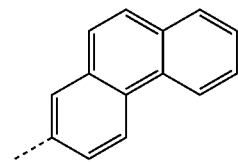 | 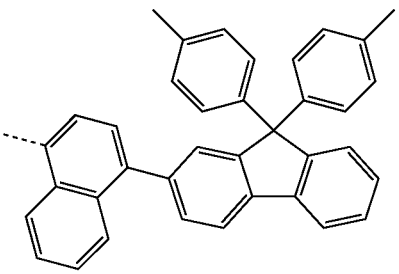 |

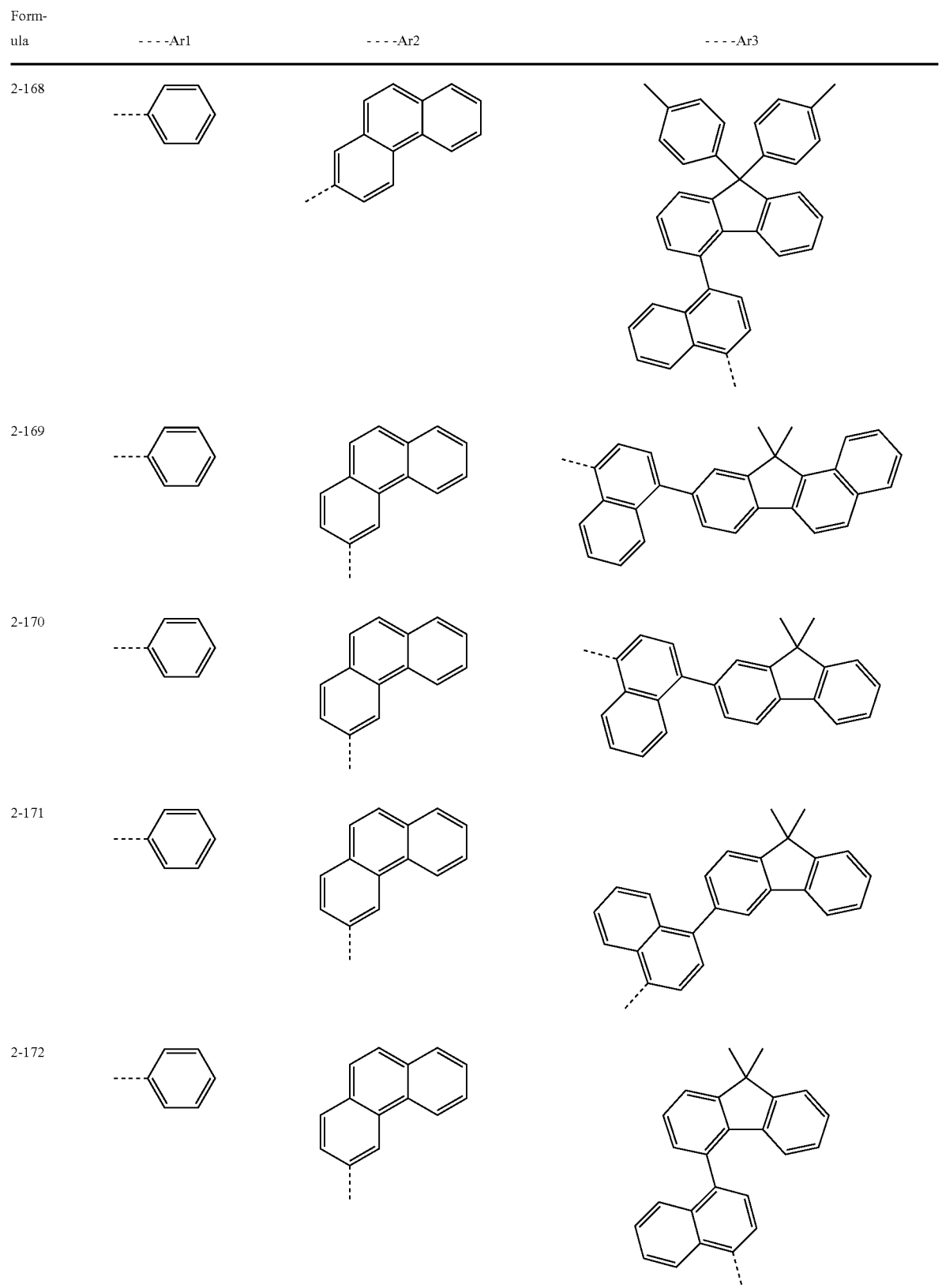

301 302
-continued
| Formula | ----Ar1 | ----Ar2 | ----Ar3 |
|---|---|---|---|
| 2-173 | 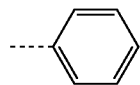 | 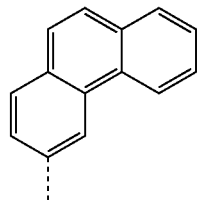 | 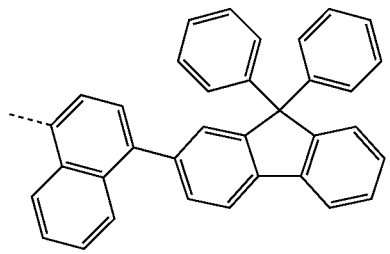 |
| 2-174 | 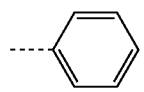 | 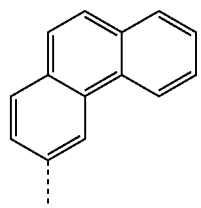 | 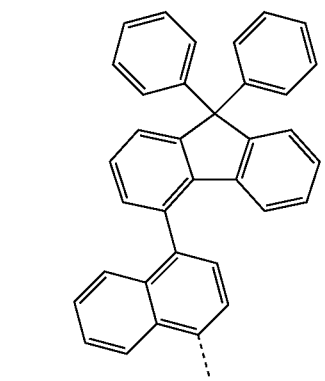 |
| 2-175 | 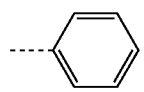 | 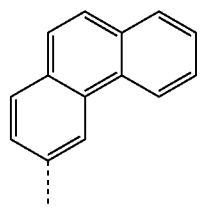 | 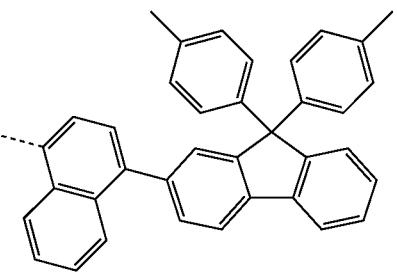 |
| 2-176 | 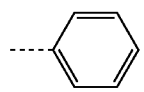 | 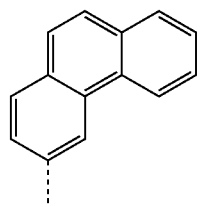 | 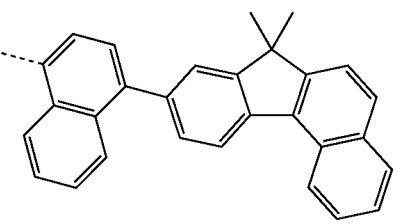 |
| 2-177 | 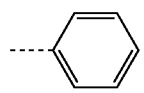 | 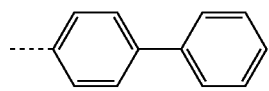 | 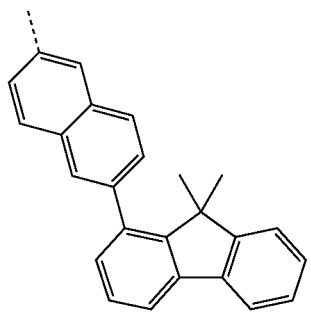 |

-continued
| Formula | ----Ar1 | ----Ar2 | ----Ar3 |
|---|---|---|---|
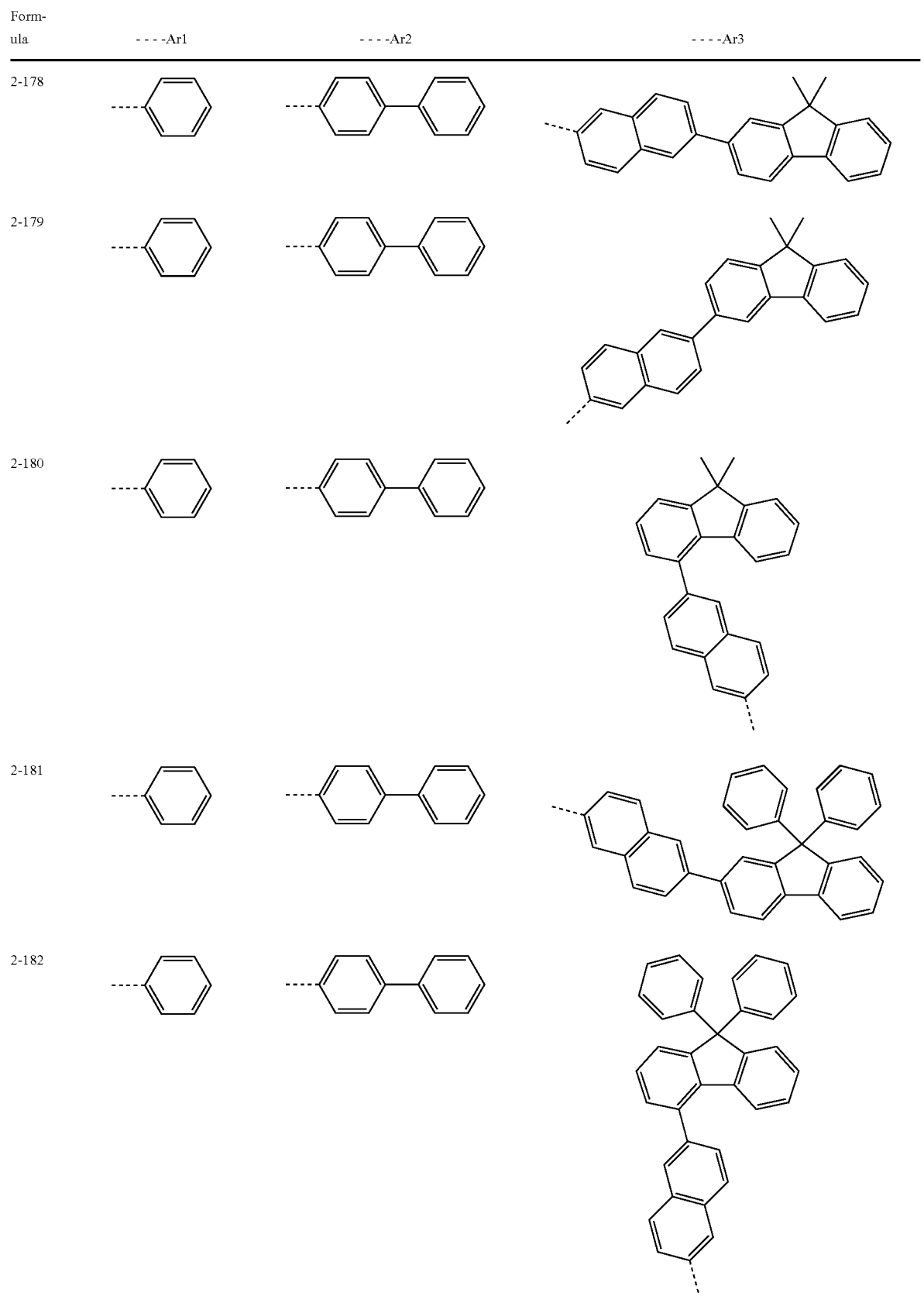

-continued
| Formula | ----Ar1 | ----Ar2 | ----Ar3 |
|---|---|---|---|
| 2-183 | 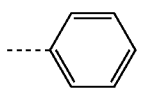 | 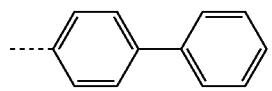 | 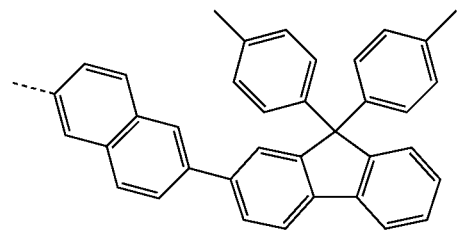 |
| 2-184 | 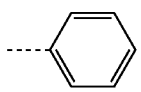 | 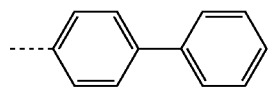 | 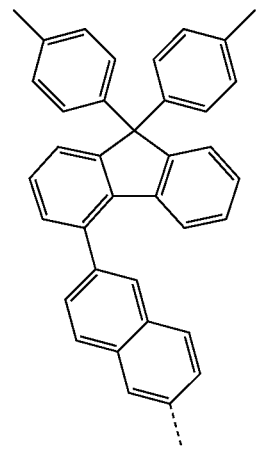 |
| 2-185 | 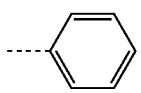 | 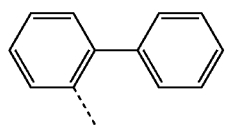 | 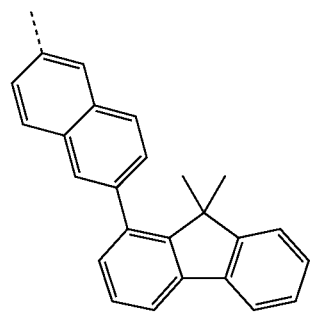 |
| 2-186 | 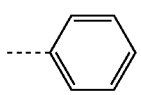 | 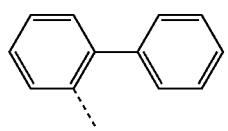 | 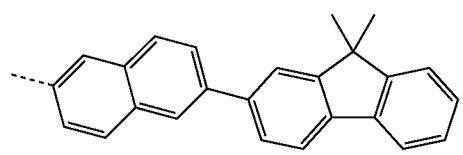 |
| 2-187 | 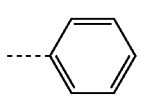 | 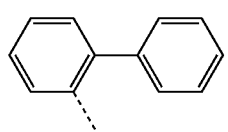 | 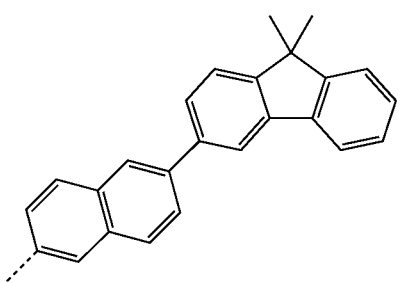 |

-continued

| Formula | ----Ar1 | ----Ar2 | ----Ar3 |
|---|---|---|---|
| 2-188 | | | |
| 2-189 | | | |
| 2-190 | | | |
| 2-191 | | | |
| 2-192 | | | |

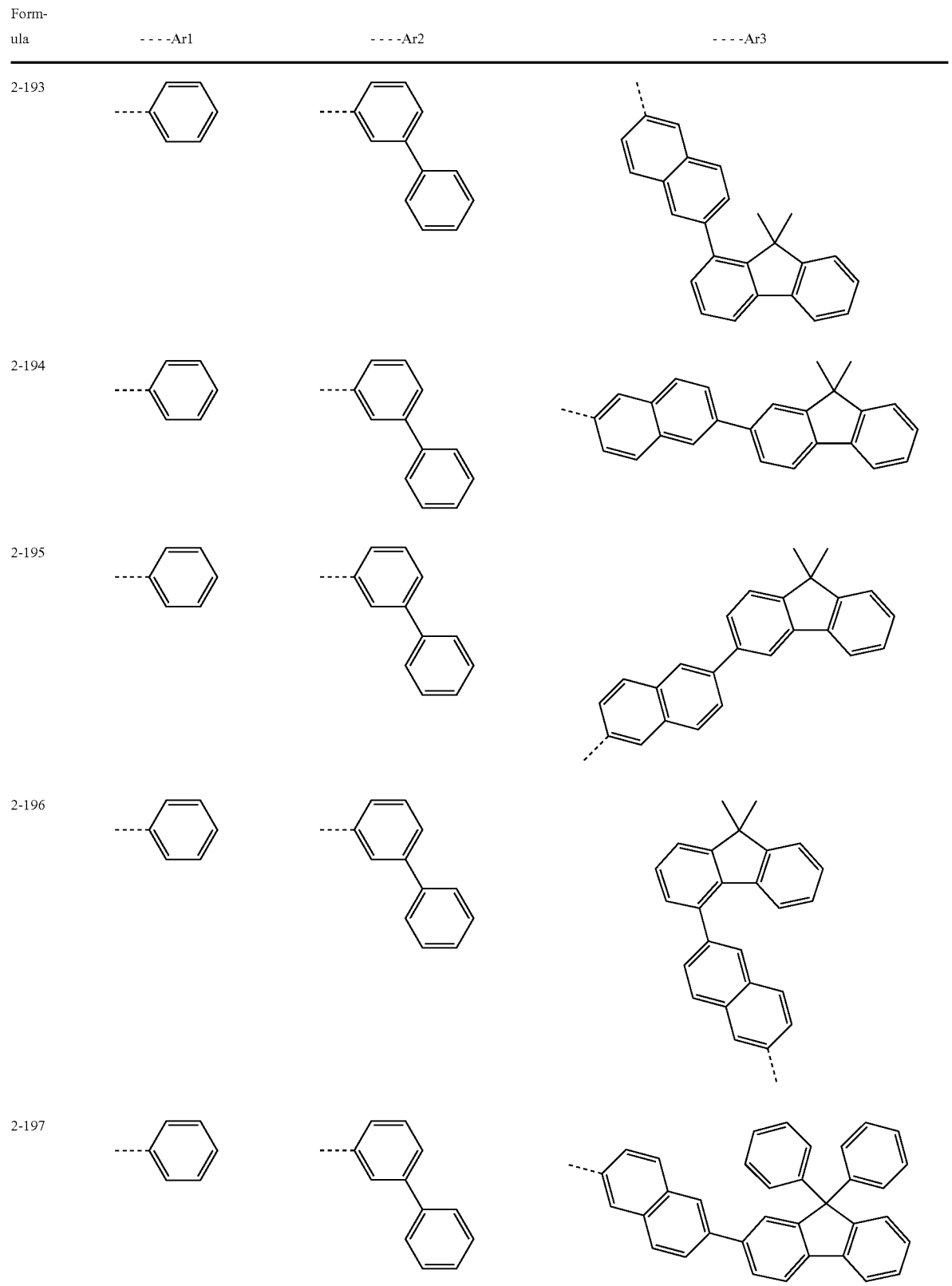

-continued

| Formula | ----Ar1 | ----Ar2 | ----Ar3 |
|---|---|---|---|
| 2-198 | | | |
| 2-199 | | | |
| 2-200 | | | |
| 2-201 | | | |
| 2-202 | | | |

-continued
| Formula | ----Ar1 | ----Ar2 | ----Ar3 |
|---|---|---|---|
| 2-203 | 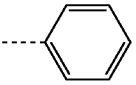 | 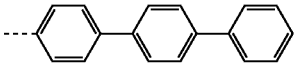 | 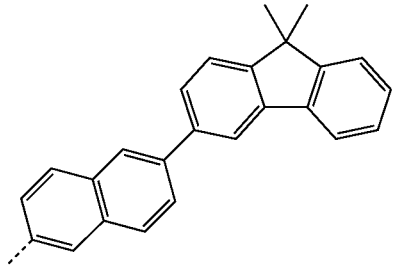 |
| 2-204 | 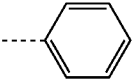 | 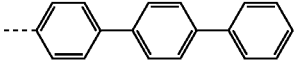 | 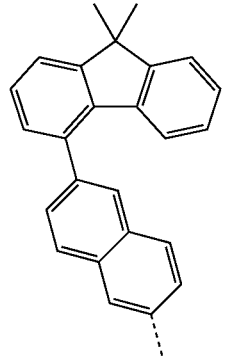 |
| 2-205 | 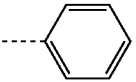 | 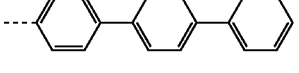 | 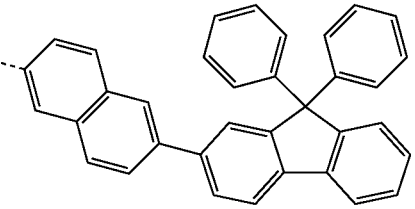 |
| 2-206 | 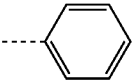 | 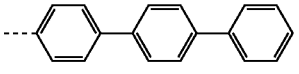 | 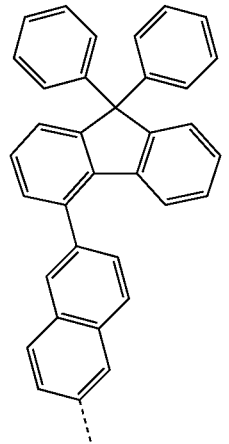 |
| 2-207 | 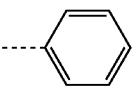 | 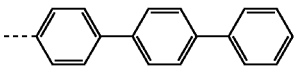 | 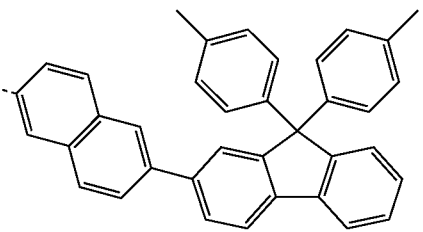 |

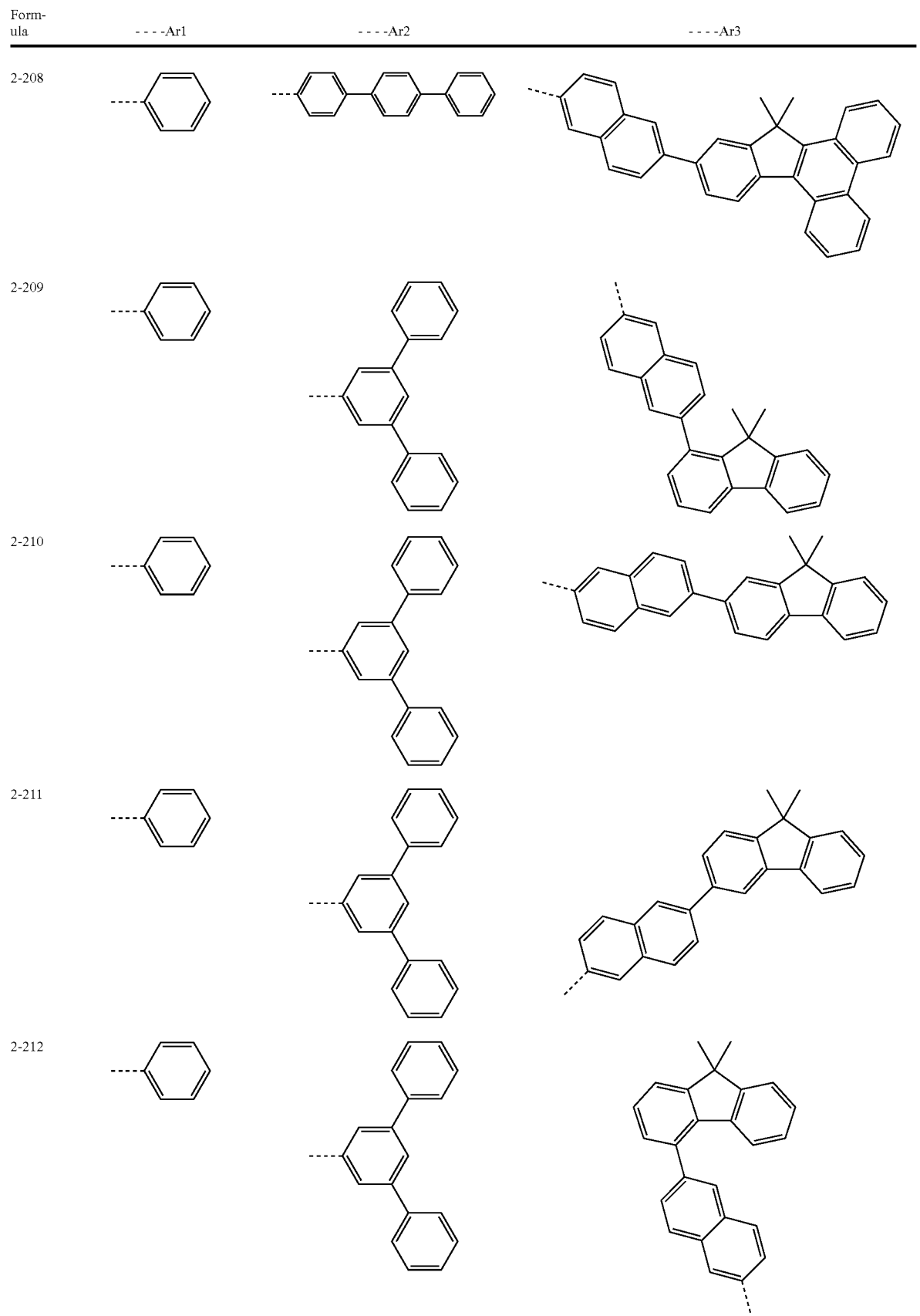

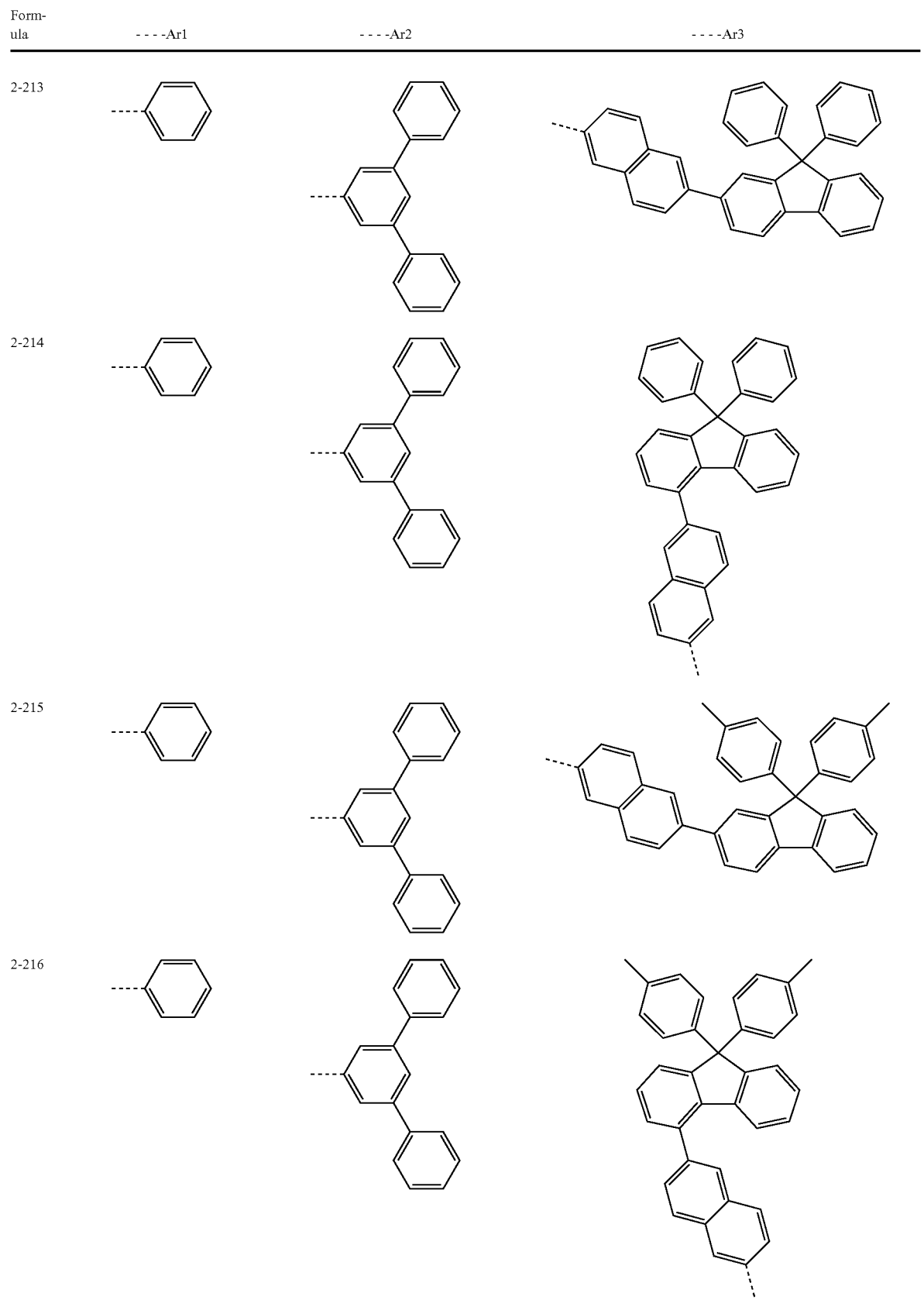

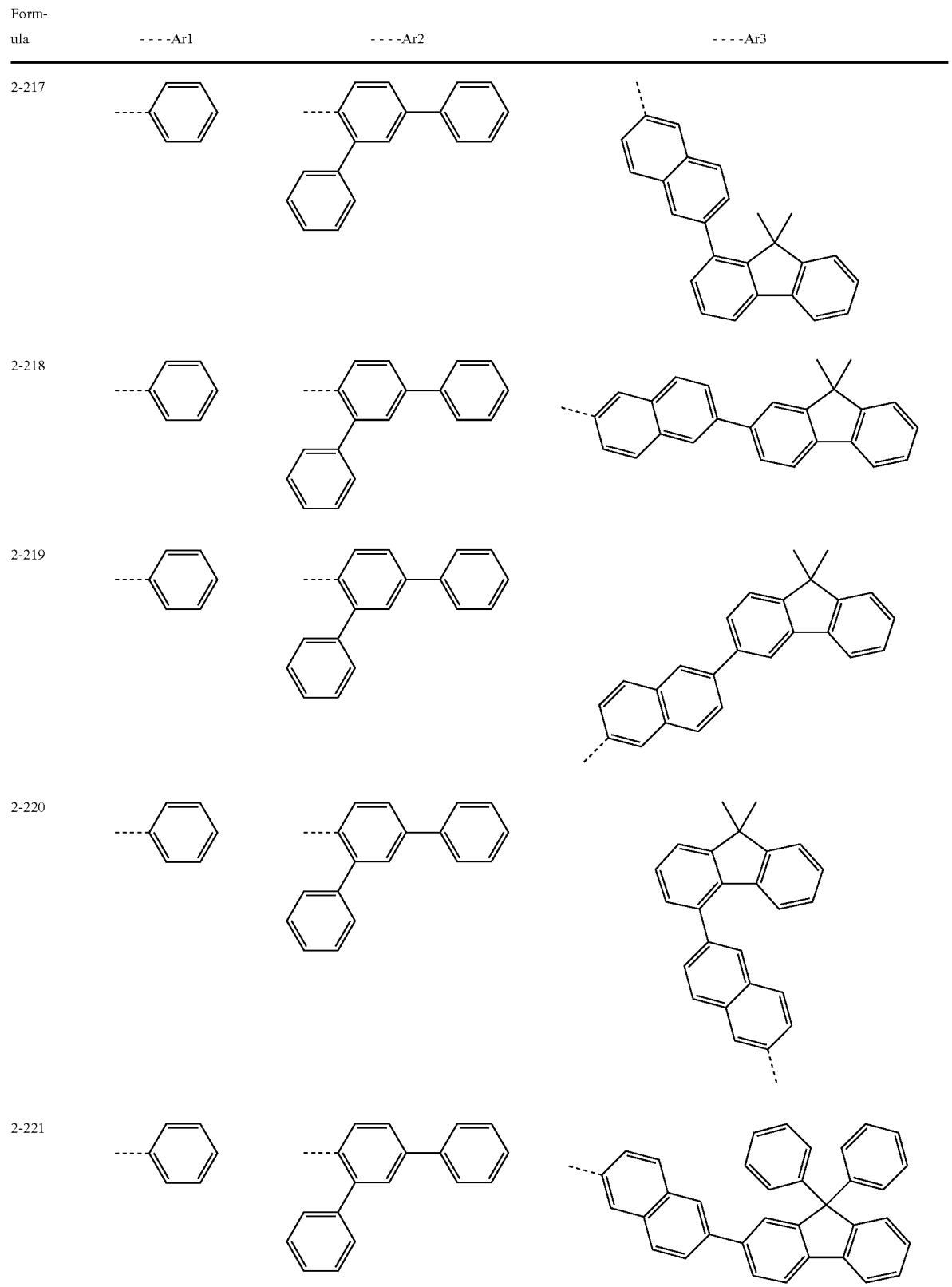

-continued
| Formula | ----Ar1 | ----Ar2 | ----Ar3 |
|---|---|---|---|
| 2-222 | 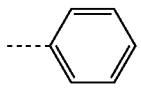 | 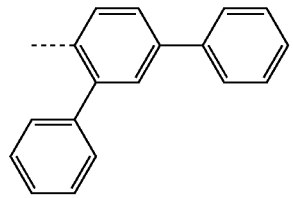 | 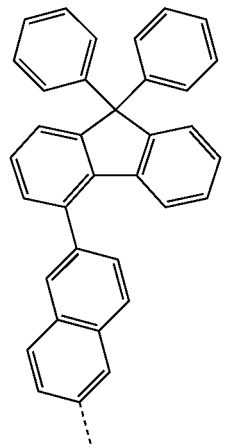 |
| 2-223 | 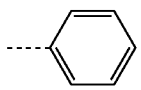 | 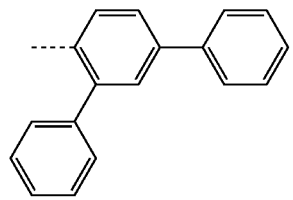 | 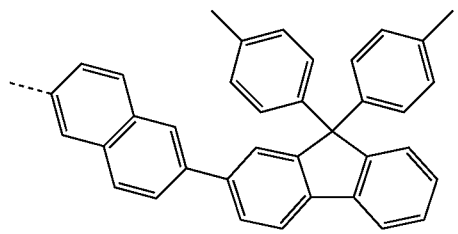 |
| 2-224 | 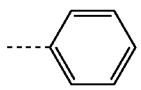 | 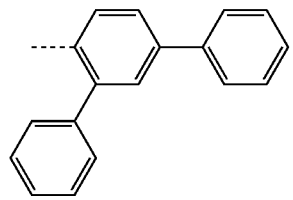 | 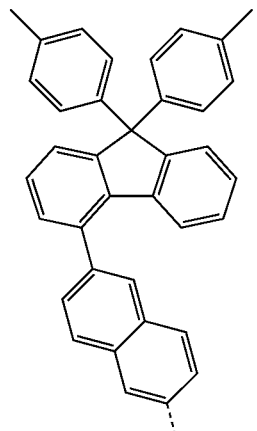 |
| 2-225 | 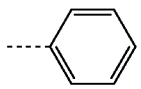 | 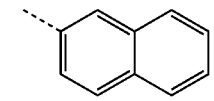 | 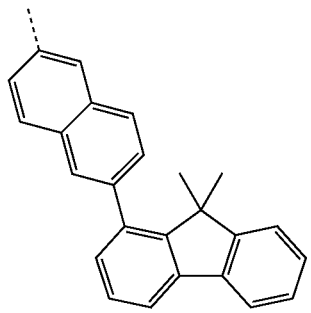 |

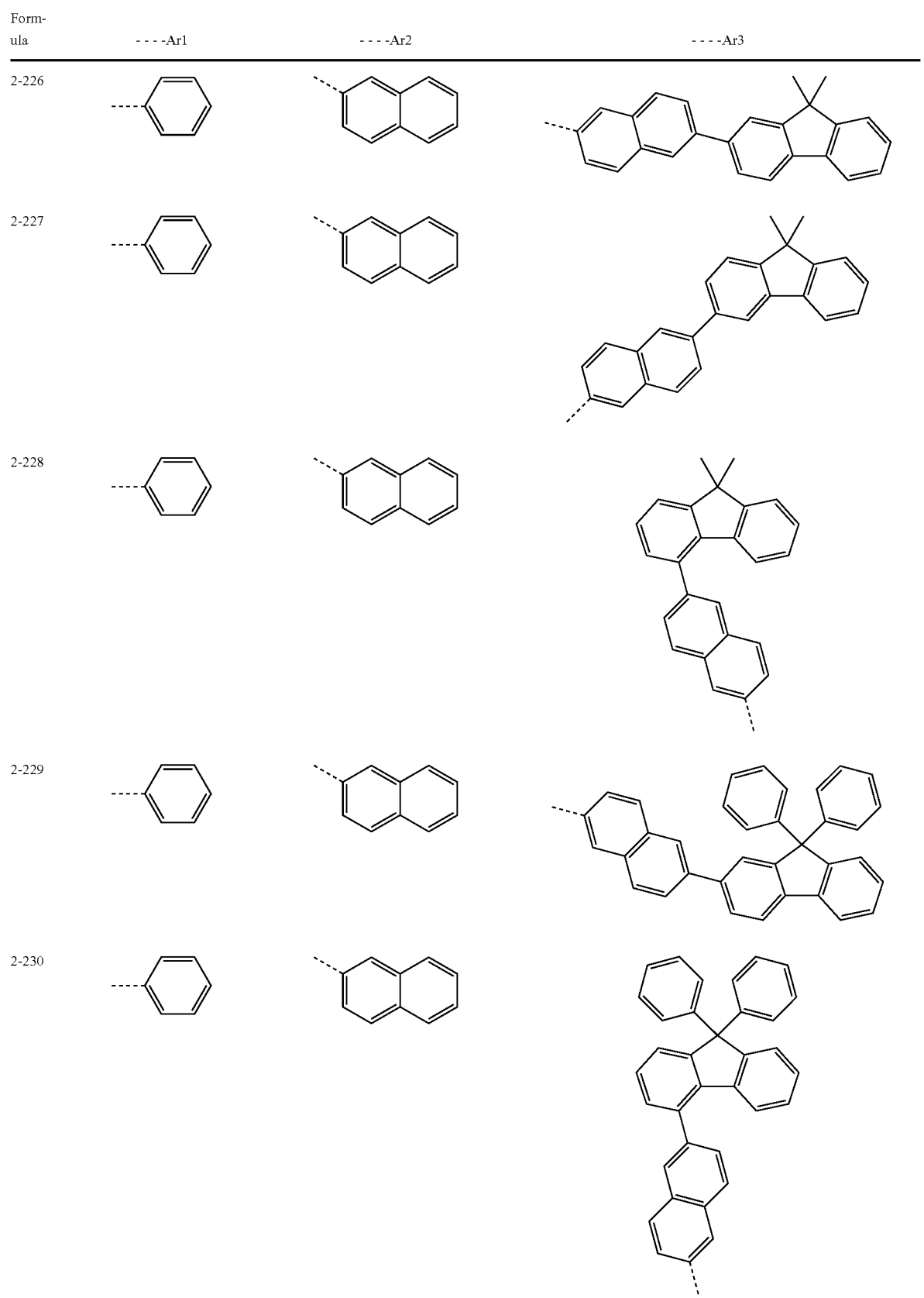

-continued
| Formula | ----Ar1 | ----Ar2 | ----Ar3 |
|---|---|---|---|
| 2-231 | 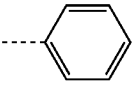 | 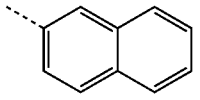 | 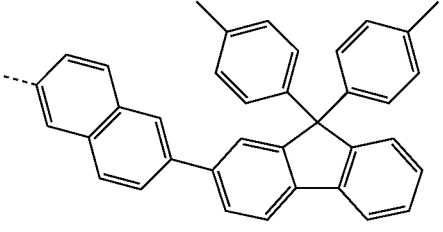 |
| 2-232 | 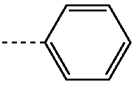 | 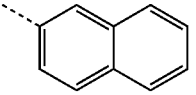 | 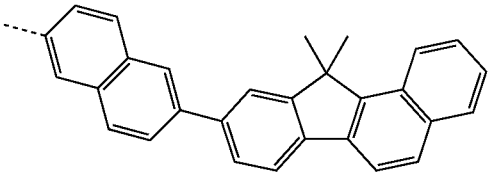 |
| 2-233 | 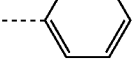 | 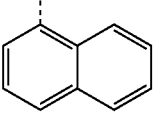 | 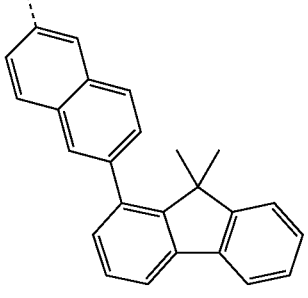 |
| 2-234 | 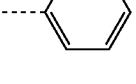 | 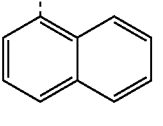 | 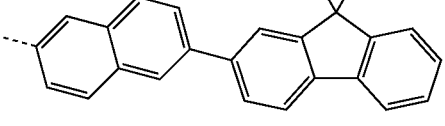 |
| 2-235 | 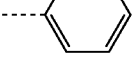 | 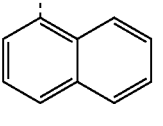 | 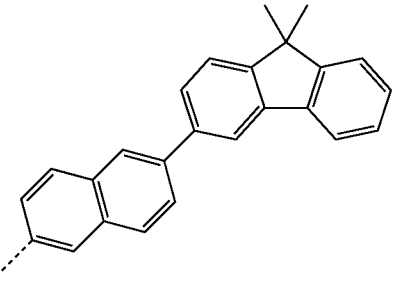 |
| 2-236 | 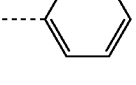 | 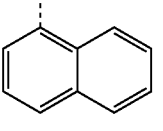 | 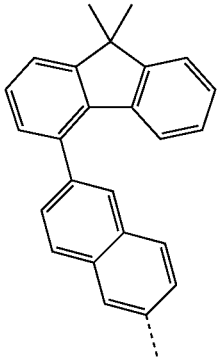 |

-continued
| Formula | ----Ar1 | ----Ar2 | ----Ar3 |
|---|---|---|---|
| 2-237 | 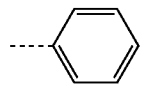 | 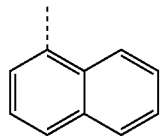 | 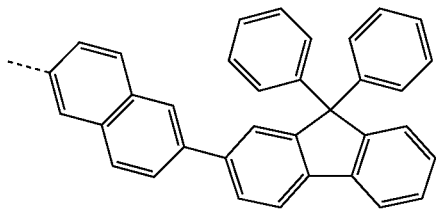 |
| 2-238 | 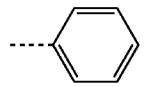 | 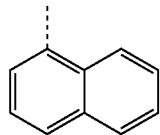 | 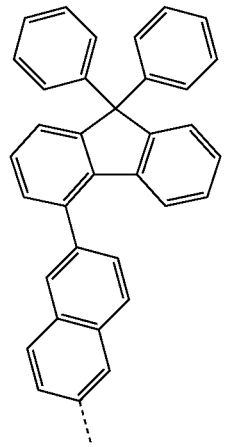 |
| 2-239 | 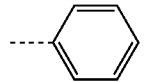 | 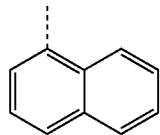 | 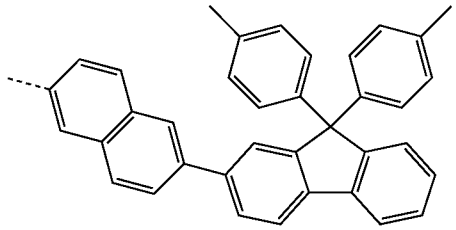 |
| 2-240 | 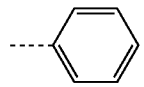 | 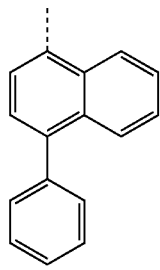 | 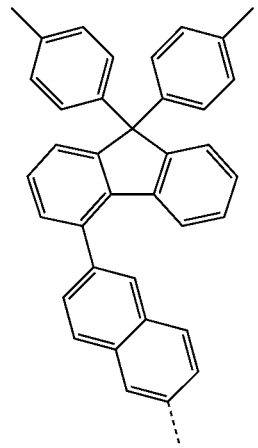 |

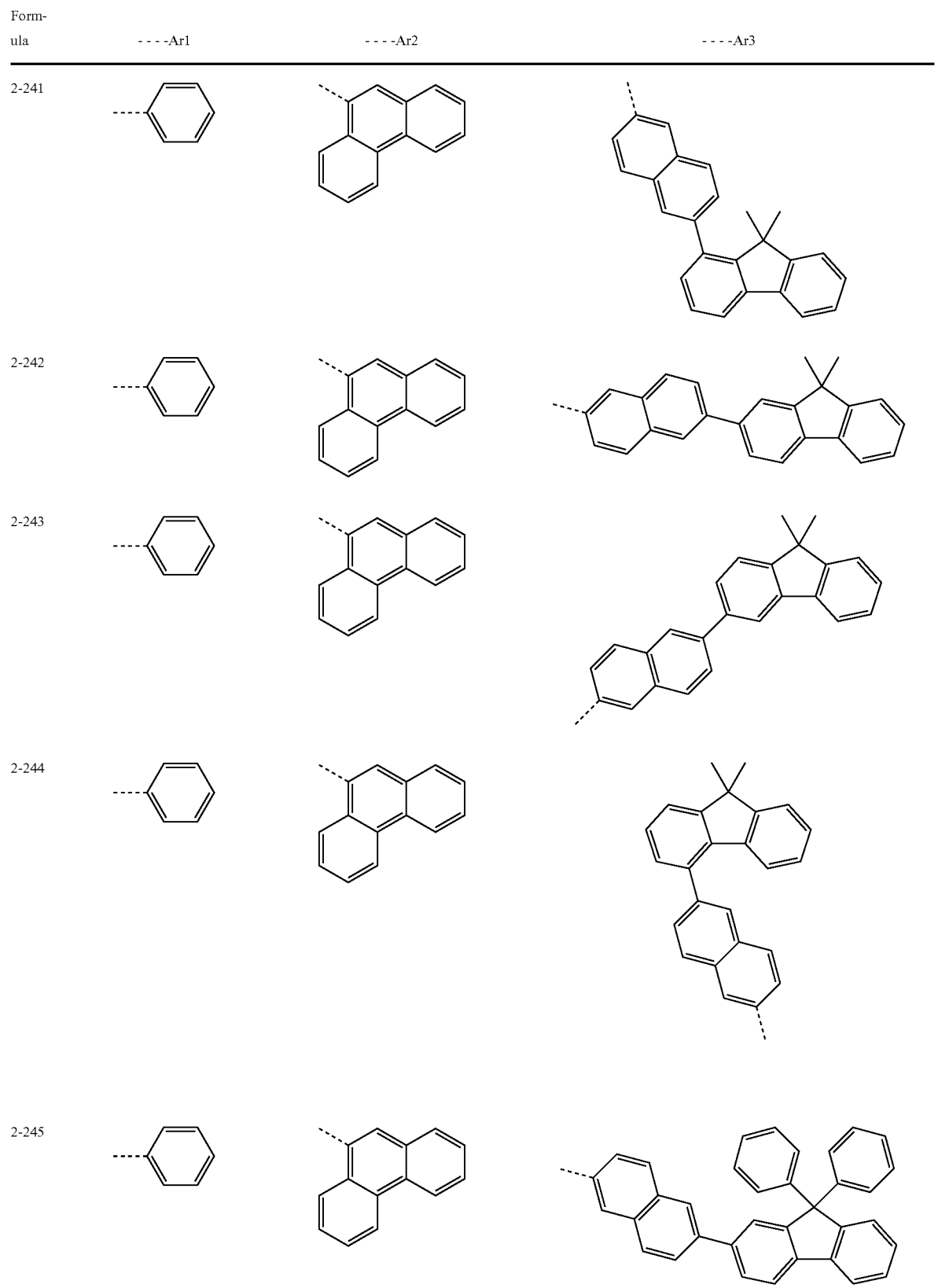

| Formula | ----Ar1 | ----Ar2 | ----Ar3 |
|---|---|---|---|
| 2-246 | 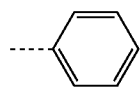 | 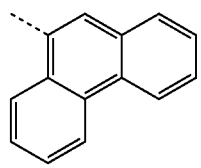 | 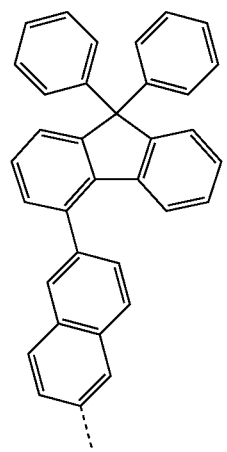 |
| 2-247 | 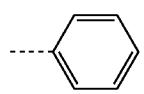 | 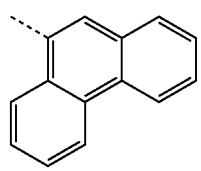 | 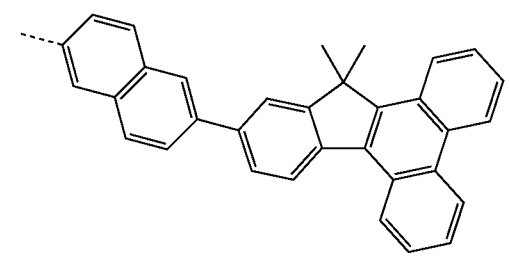 |
| 2-248 | 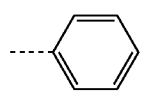 | 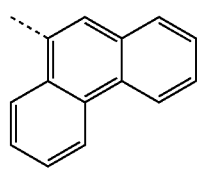 | 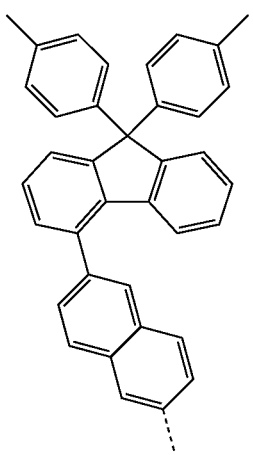 |
| 2-249 | 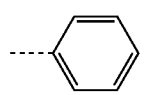 | 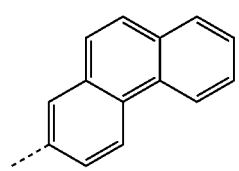 | 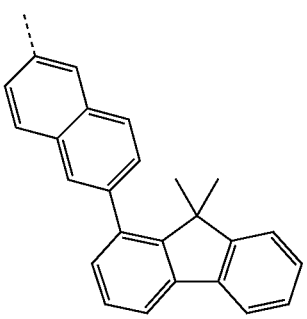 |

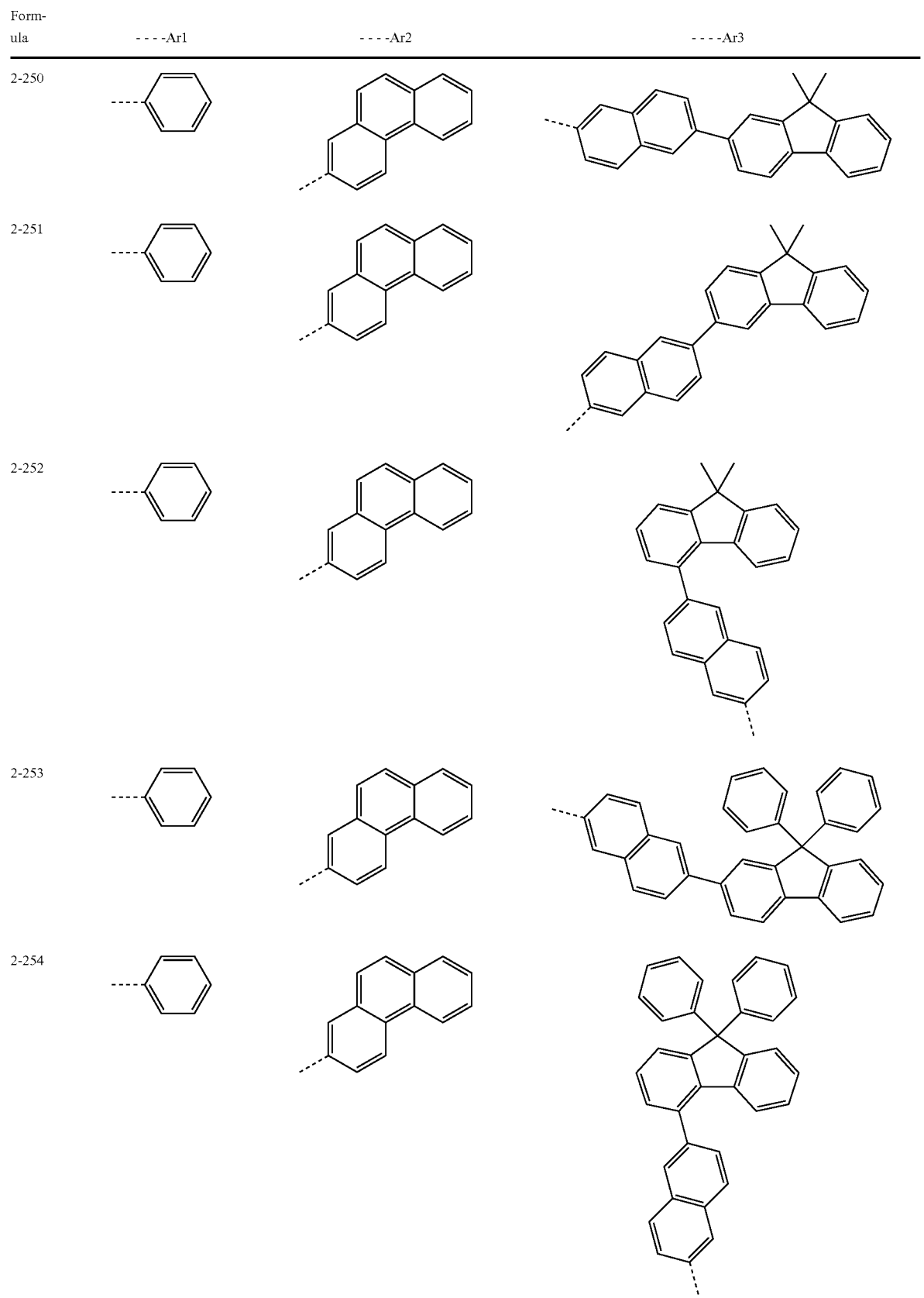

-continued
| Formula | ----Ar1 | ----Ar2 | ----Ar3 |
|---|---|---|---|
| 2-255 | 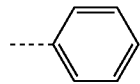 | 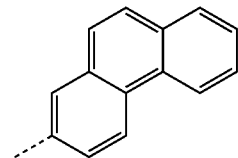 | 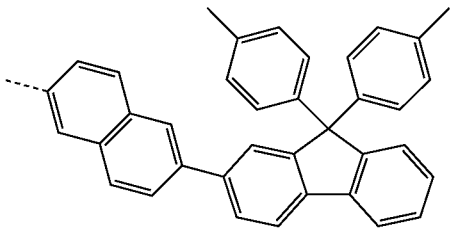 |
| 2-256 | 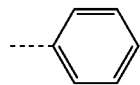 | 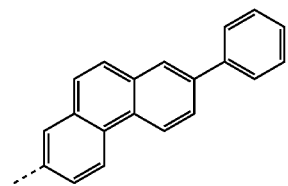 | 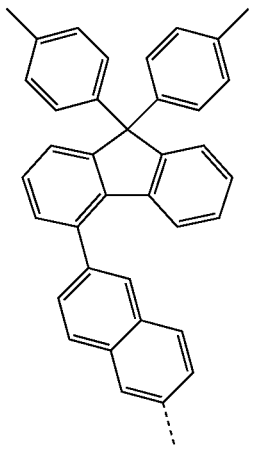 |
| 2-257 | 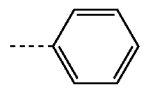 | 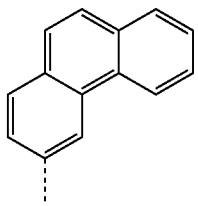 | 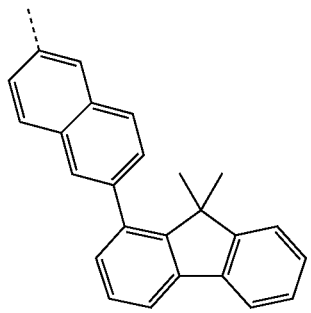 |
| 2-258 | 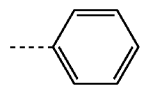 | 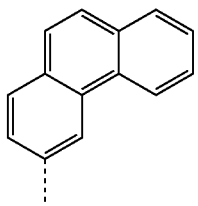 | 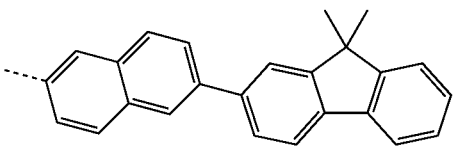 |
| 2-259 | 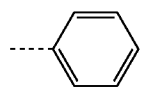 | 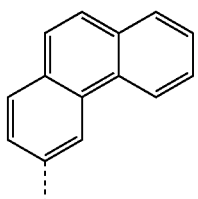 | 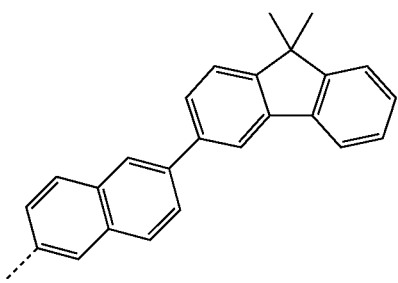 |

| Formula | ----Ar1 | ----Ar2 | ----Ar3 |
|---|---|---|---|
| 2-260 | 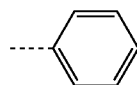 | 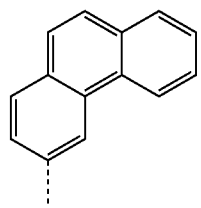 | 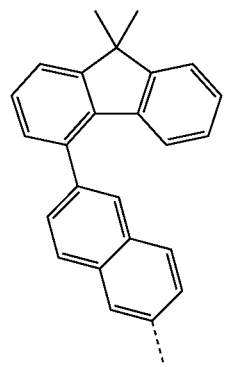 |
| 2-261 | 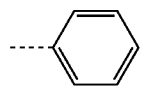 | 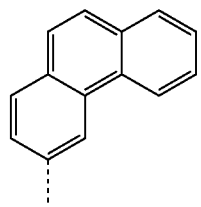 | 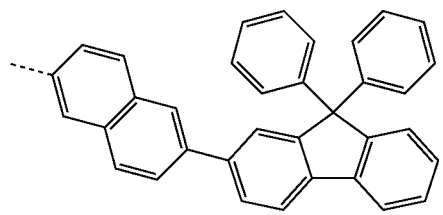 |
| 2-262 | 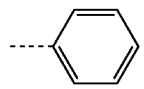 | 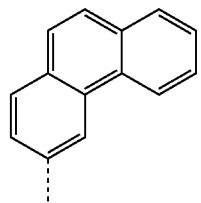 | 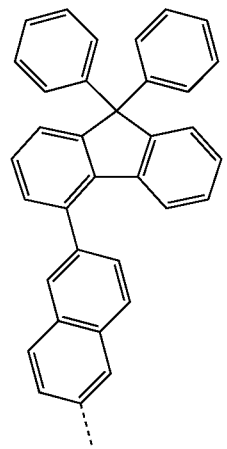 |
| 2-263 | 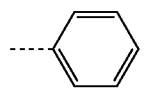 | 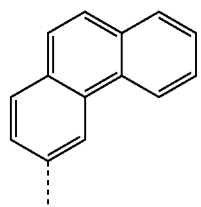 | 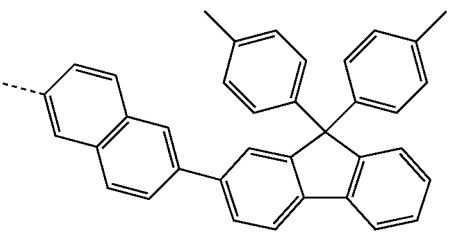 |

| Formula | ----Ar1 | ----Ar2 | ----Ar3 |
|---|---|---|---|
| 2-264 | 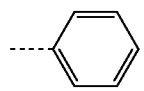 | 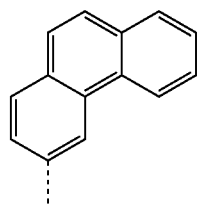 | 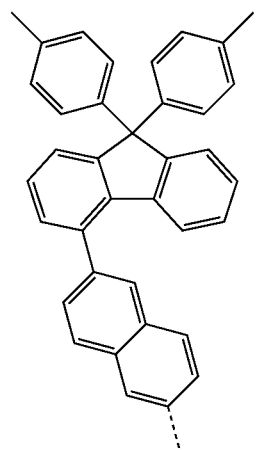 |
| 2-265 | 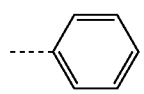 | 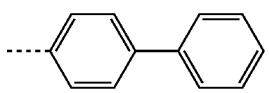 | 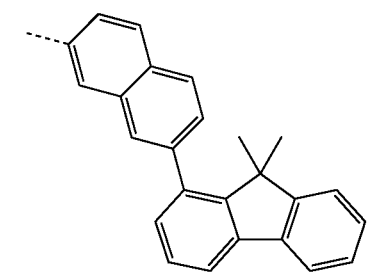 |
| 2-266 | 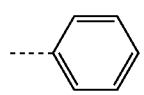 | 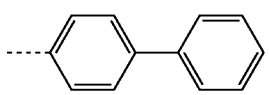 | 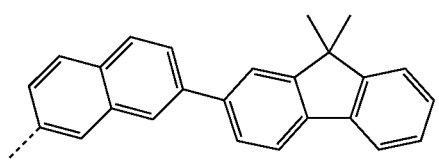 |
| 2-267 | 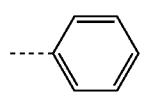 | 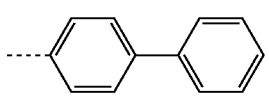 | 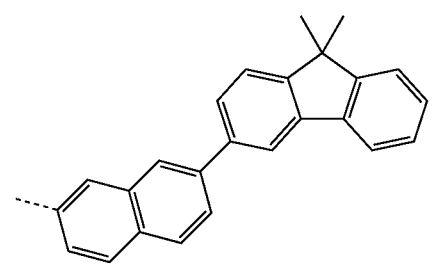 |
| 2-268 | 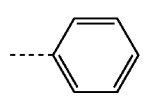 | 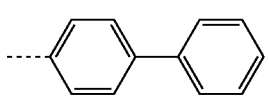 | 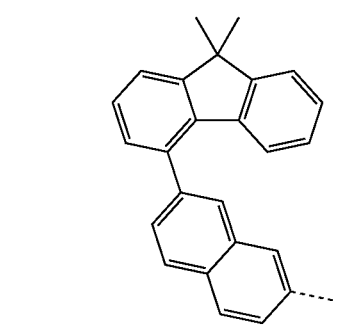 |

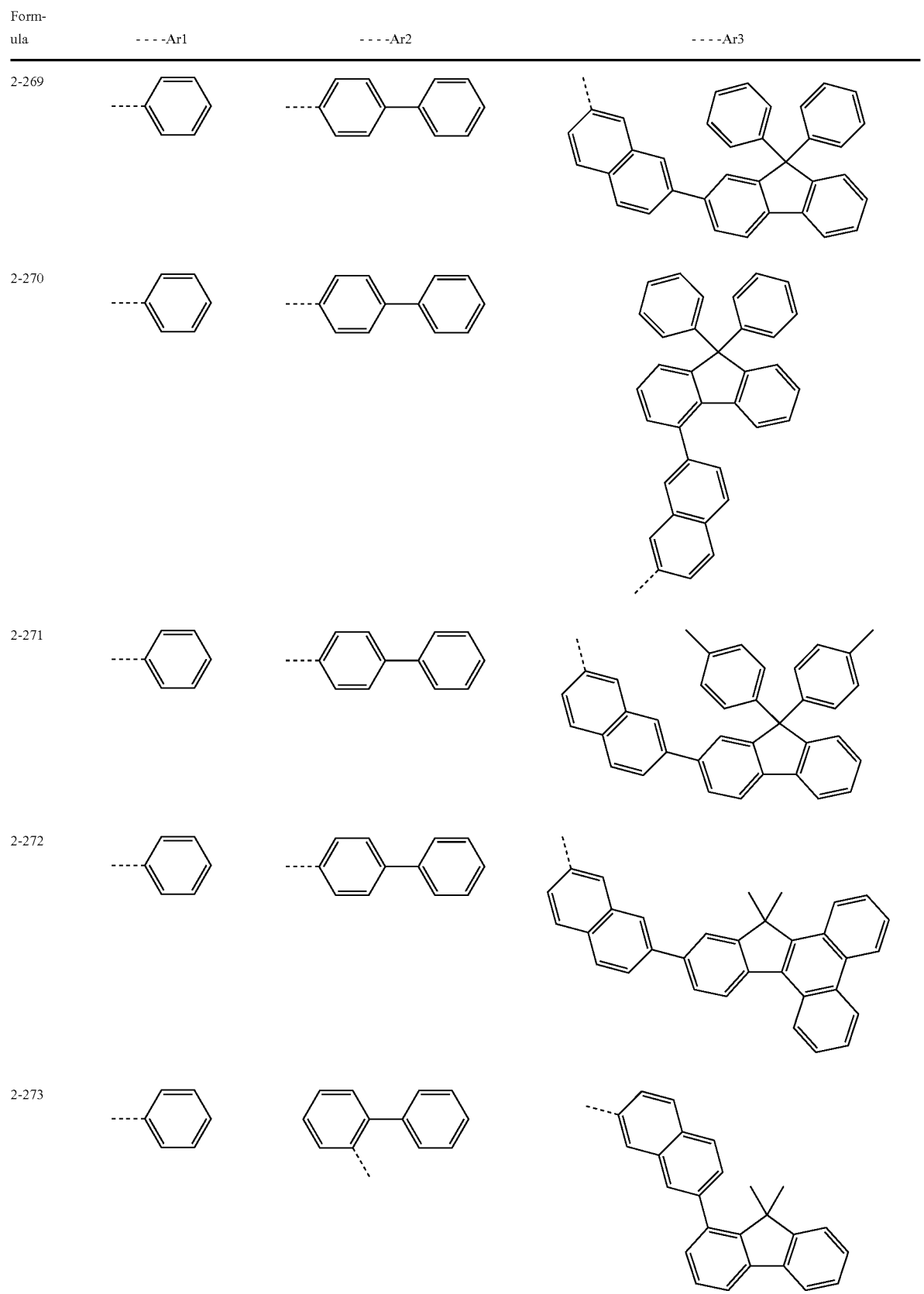

| Formula | ----Ar1 | ----Ar2 | ----Ar3 |
|---|---|---|---|
| 2-274 | 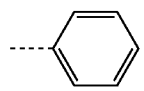 | 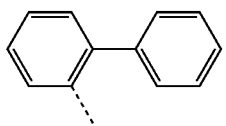 | 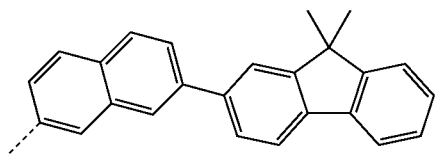 |
| 2-275 | 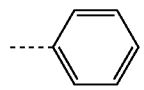 | 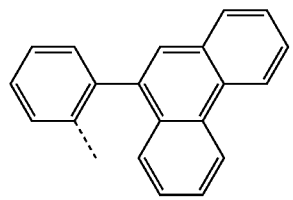 | 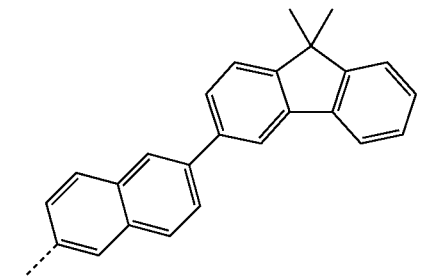 |
| 2-276 | 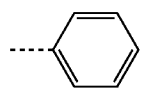 | 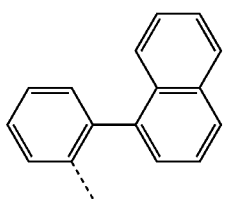 | 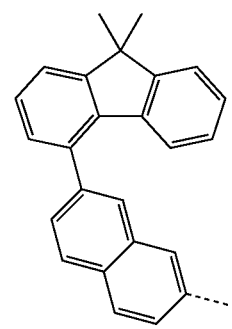 |
| 2-277 | 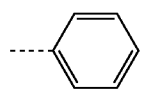 | 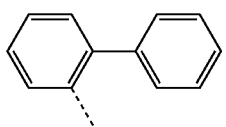 | 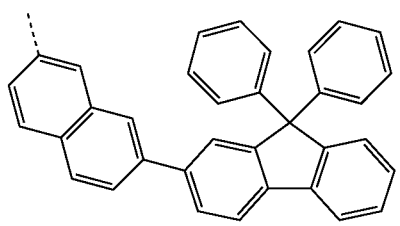 |
| 2-278 | 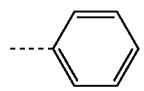 | 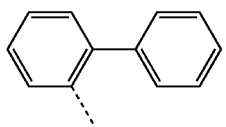 | 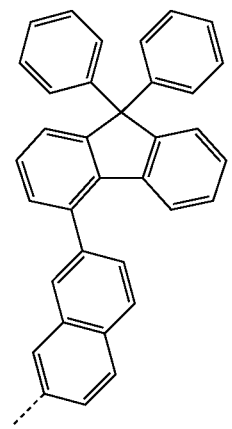 |

| Formula | ----Ar1 | ----Ar2 | ----Ar3 |
|---|---|---|---|
| 2-279 | 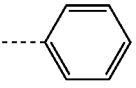 | 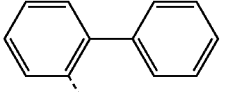 | 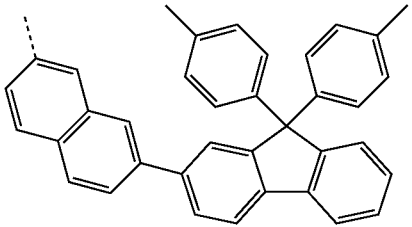 |
| 2-280 | 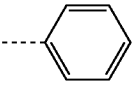 | 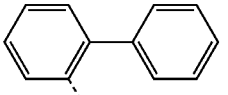 | 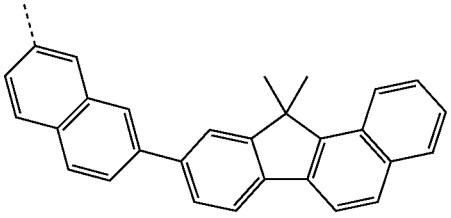 |
| 2-281 | 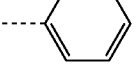 | 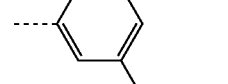 | 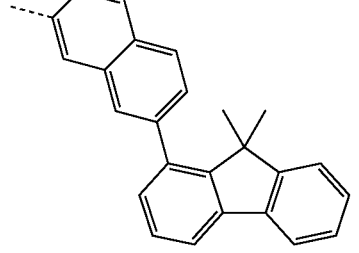 |
| 2-282 | 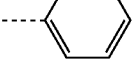 | 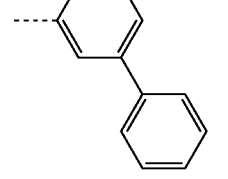 | 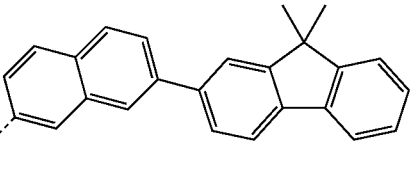 |
| 2-283 | 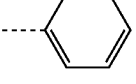 | 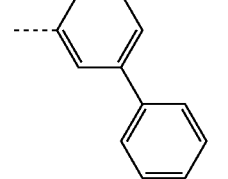 |  |
| 2-284 | 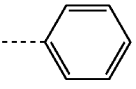 | 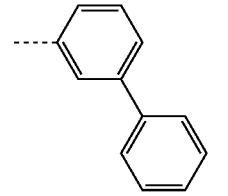 | 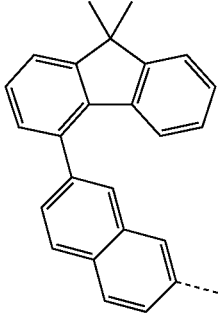 |

-continued
| Formula | ----Ar1 | ----Ar2 | ----Ar3 |
|---|---|---|---|
| 2-285 | 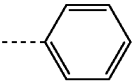 | 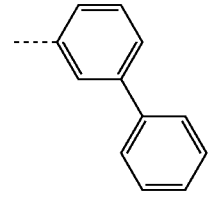 | 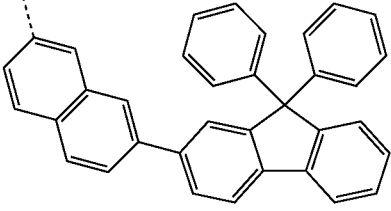 |
| 2-286 | 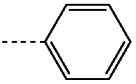 | 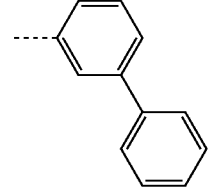 | 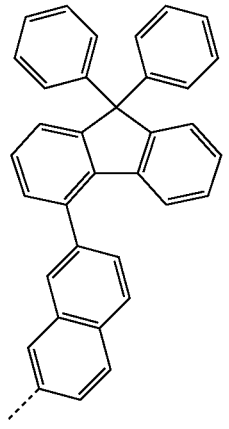 |
| 2-287 | 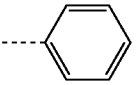 | 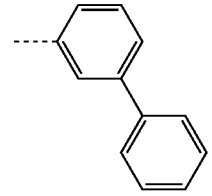 | 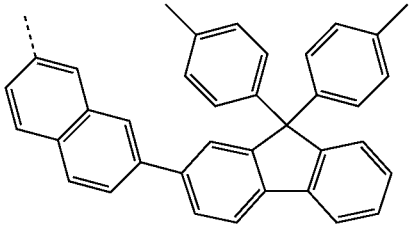 |
| 2-288 | 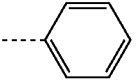 | 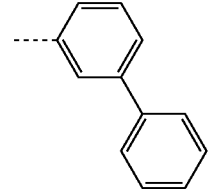 | 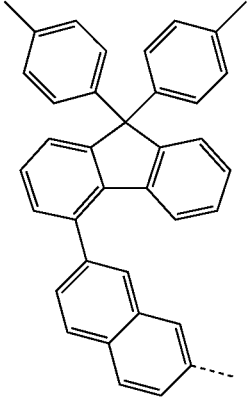 |
| 2-289 | 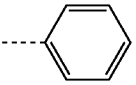 | 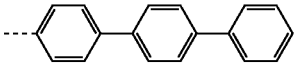 | 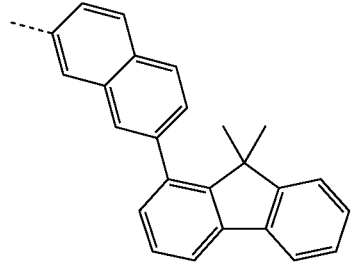 |

-continued
| Formula | ----Ar1 | ----Ar2 | ----Ar3 |
|---|---|---|---|
| 2-290 | 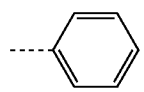 | 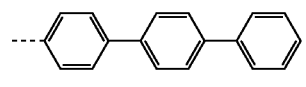 | 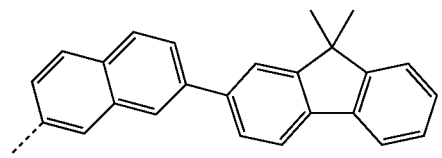 |
| 2-291 | 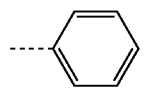 | 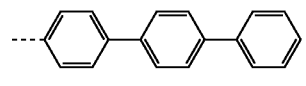 | 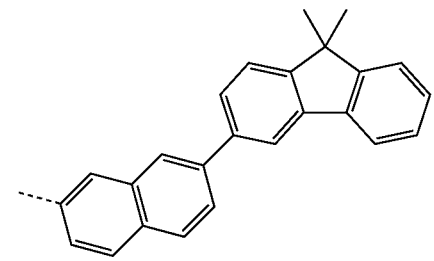 |
| 2-292 | 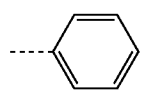 | 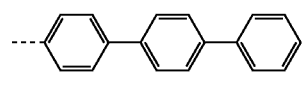 | 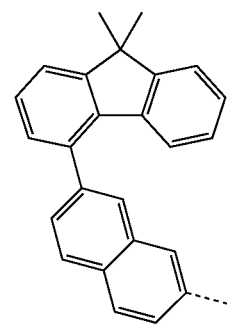 |
| 2-293 | 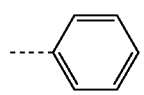 | 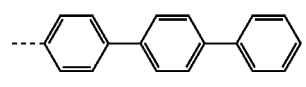 | 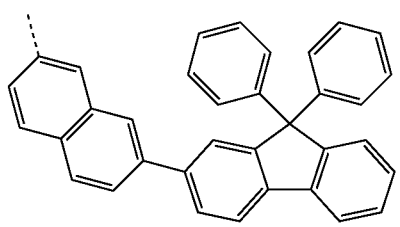 |
| 2-294 | 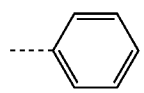 | 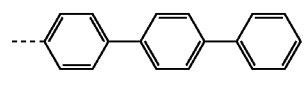 | 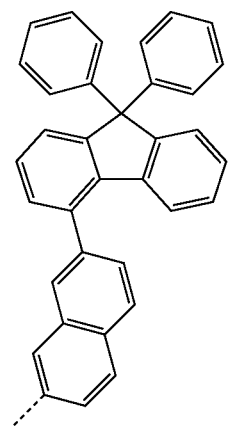 |

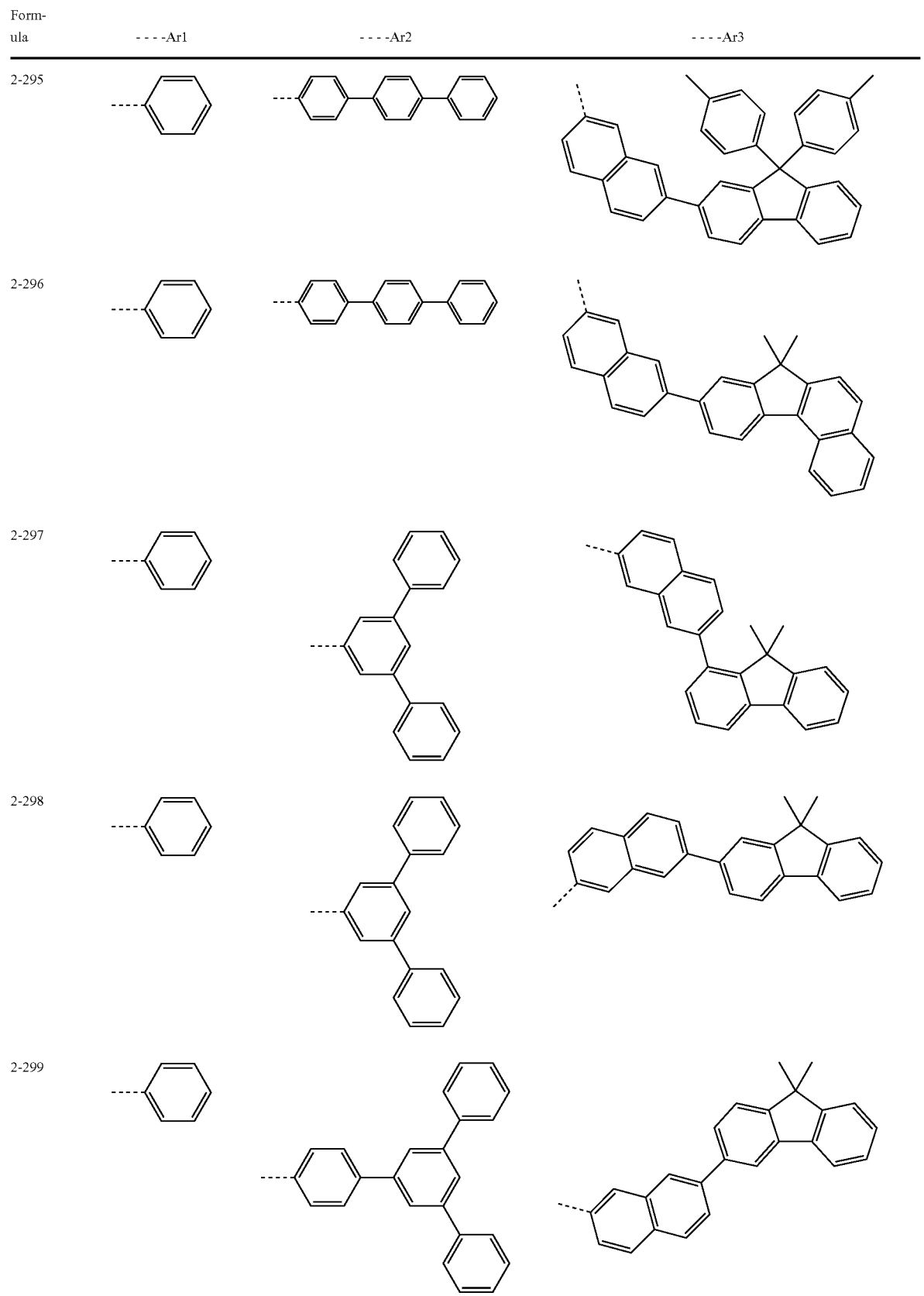

-continued
| Formula | ----Ar1 | ----Ar2 | ----Ar3 |
|---|---|---|---|
| 2-300 | 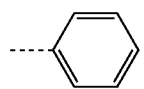 | 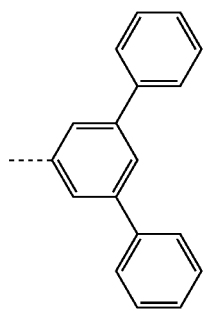 | 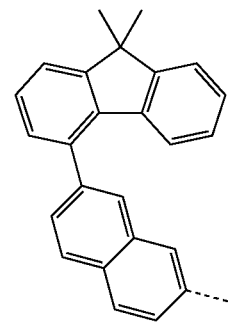 |
| 2-301 | 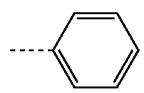 | 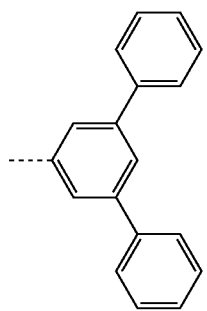 | 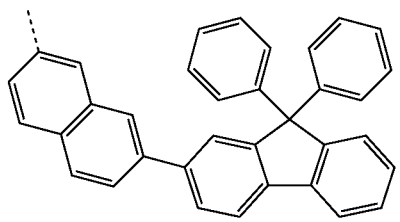 |
| 2-302 | 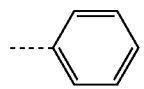 | 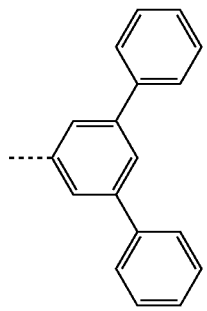 | 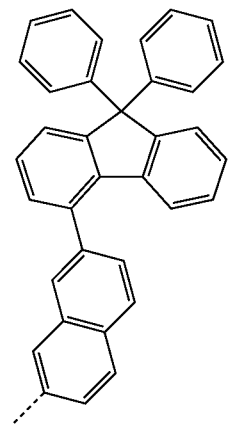 |
| 2-303 | 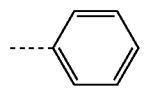 | 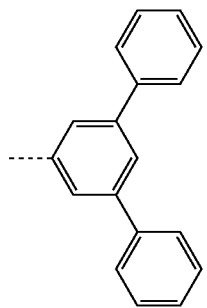 | 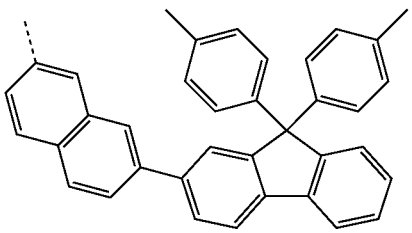 |

-continued
| Formula | ----Ar1 | ----Ar2 | ----Ar3 |
|---|---|---|---|
| 2-304 | 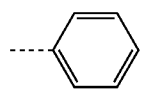 | 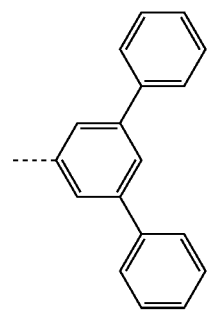 | 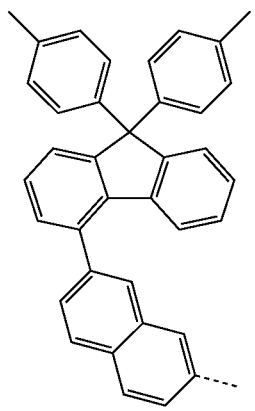 |
| 2-305 | 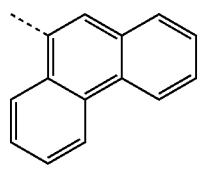 | 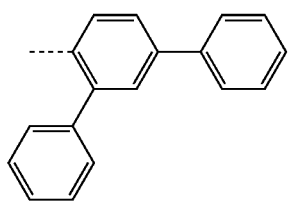 | 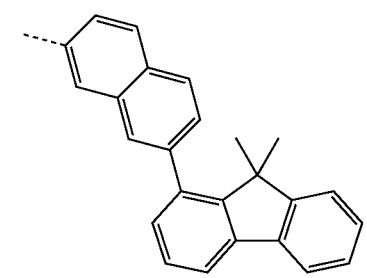 |
| 2-306 | 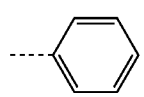 | 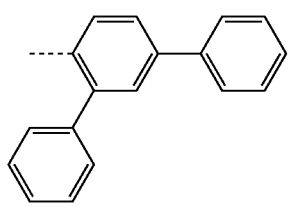 | 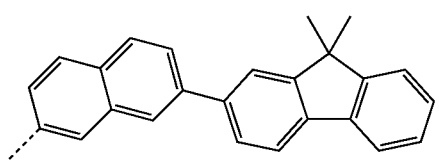 |
| 2-307 | 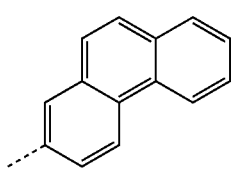 | 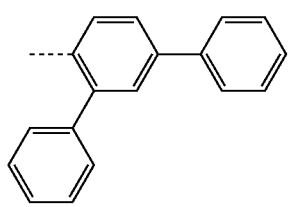 | 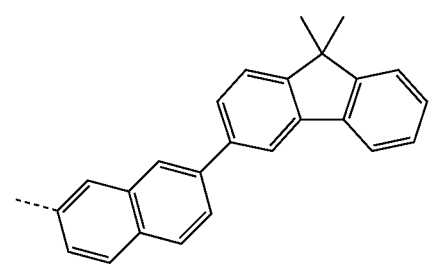 |
| 2-308 | 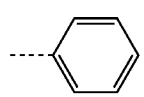 | 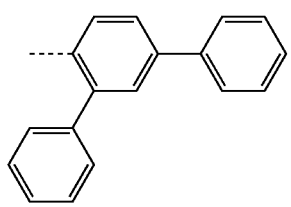 | 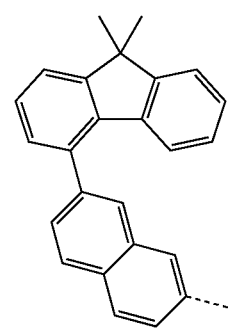 |

US 9,640,766 B2
357                                                                   358
-continued
| Formula | ----Ar1 | ----Ar2 | ----Ar3 |
|---|---|---|---|
| 2-309 | 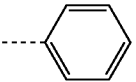 | 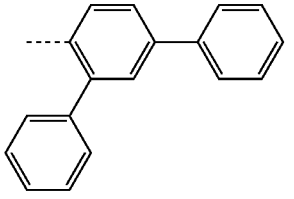 | 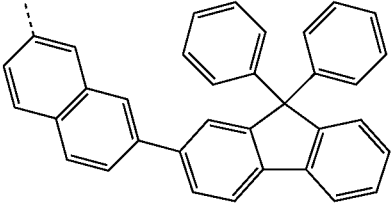 |
| 2-310 | 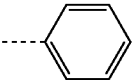 | 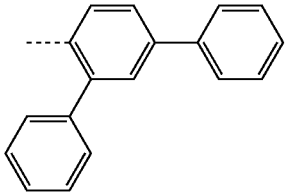 | 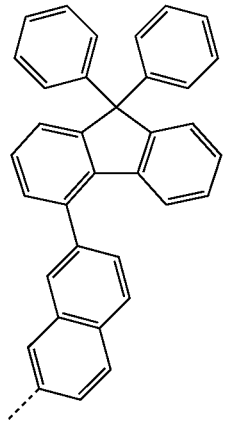 |
| 2-311 | 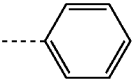 | 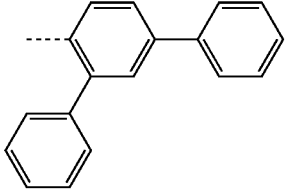 | 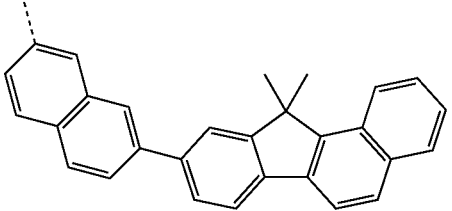 |
| 2-312 | 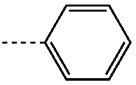 | 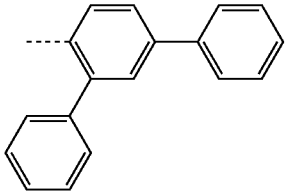 | 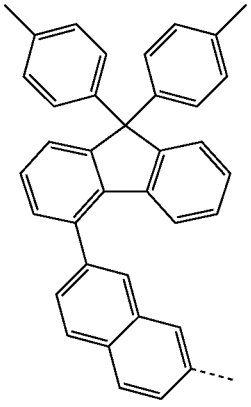 |
| 2-313 | 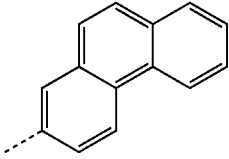 | 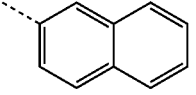 | 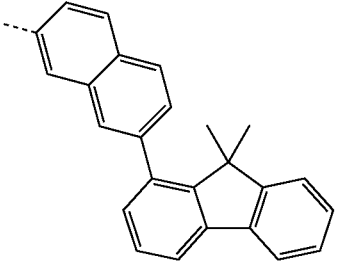 |

-continued
| Formula | ----Ar1 | ----Ar2 | ----Ar3 |
|---|---|---|---|
| 2-314 | 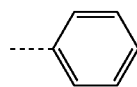 | 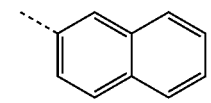 | 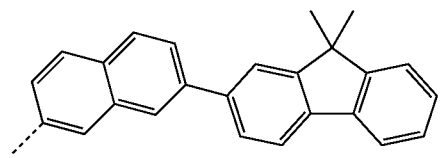 |
| 2-315 | 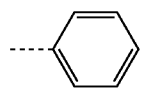 | 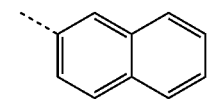 | 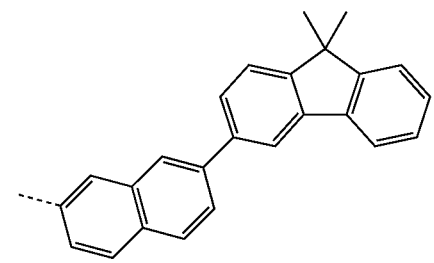 |
| 2-316 | 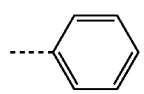 | 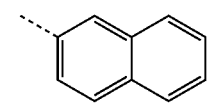 | 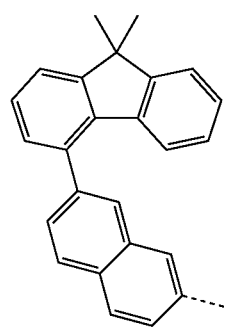 |
| 2-317 | 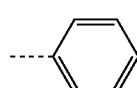 | 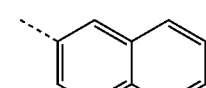 | 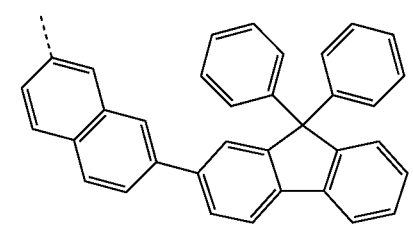 |
| 2-318 | 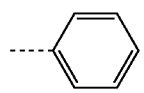 | 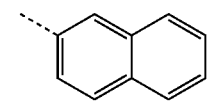 | 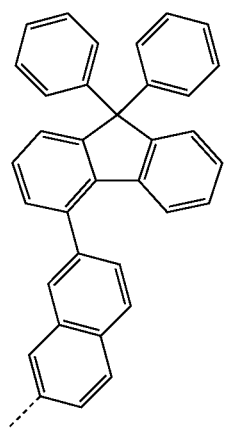 |

| Formula | ----Ar1 | ----Ar2 | ----Ar3 |
|---|---|---|---|
| 2-319 | 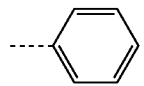 | 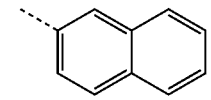 | 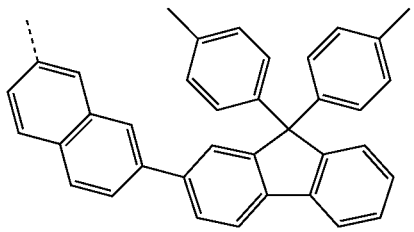 |
| 2-320 | 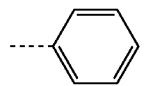 | 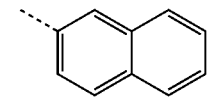 | 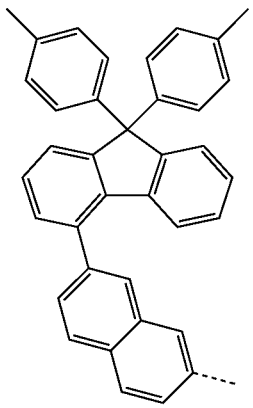 |
| 2-321 | 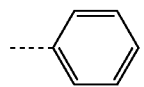 | 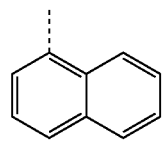 | 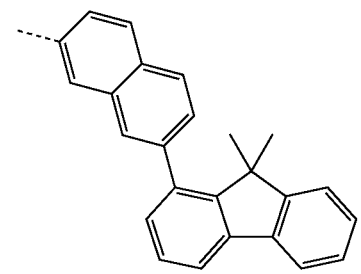 |
| 2-322 | 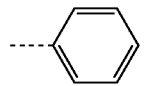 | 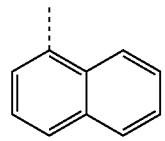 | 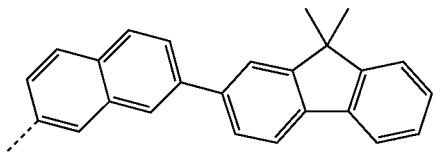 |
| 2-323 | 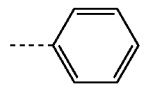 | 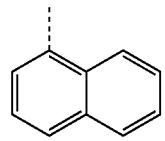 | 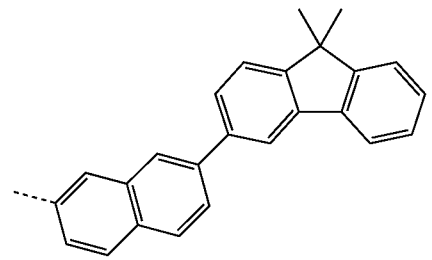 |

-continued
| Formula | ----Ar1 | ----Ar2 | ----Ar3 |
|---|---|---|---|
| 2-324 | 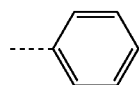 | 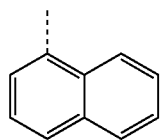 | 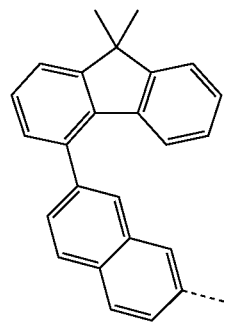 |
| 2-325 | 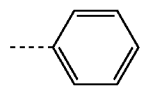 | 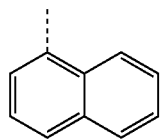 | 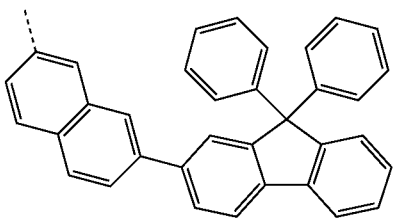 |
| 2-326 | 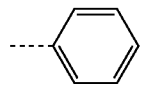 | 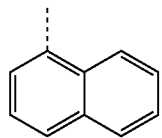 | 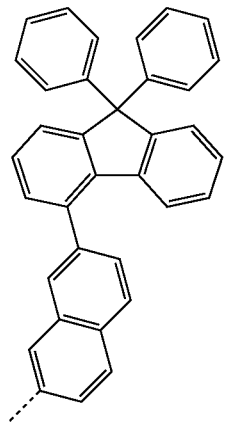 |
| 2-327 | 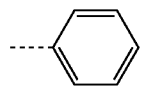 | 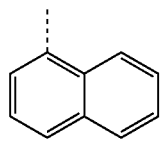 | 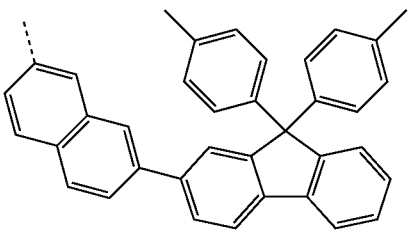 |

-continued
| Formula | ----Ar1 | ----Ar2 | ----Ar3 |
|---|---|---|---|
| 2-328 | 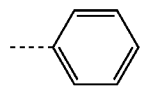 | 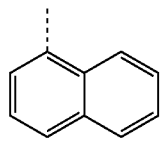 | 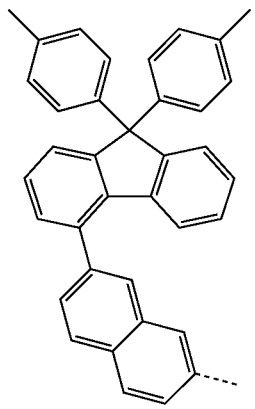 |
| 2-329 | 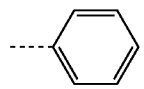 | 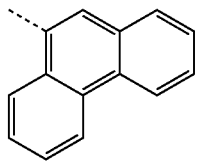 | 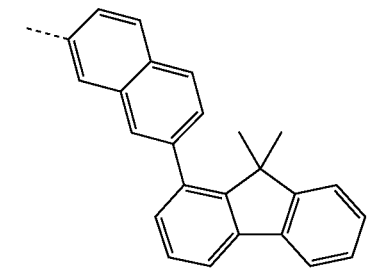 |
| 2-330 | 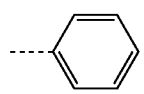 | 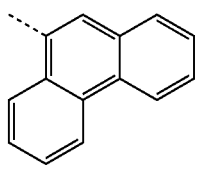 | 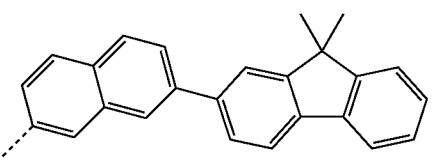 |
| 2-331 | 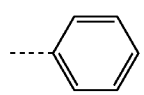 | 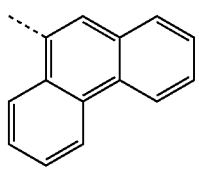 | 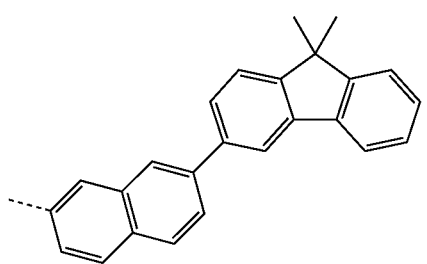 |
| 2-332 | 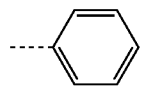 | 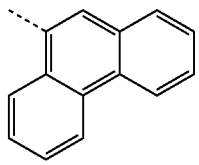 | 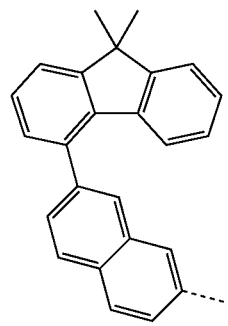 |

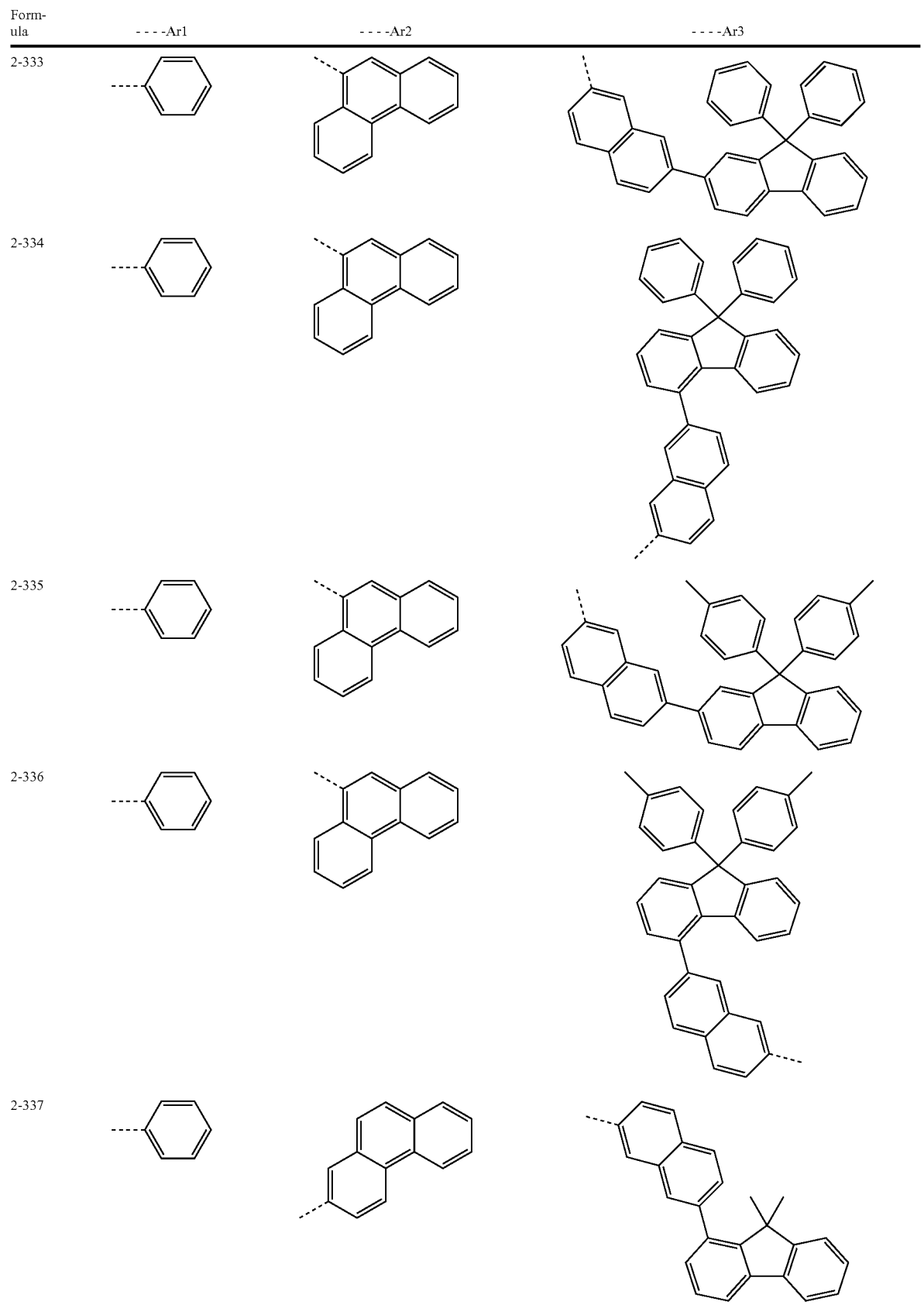

-continued
| Formula | ----Ar1 | ----Ar2 | ----Ar3 |
|---|---|---|---|
| 2-338 | 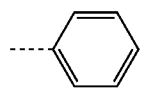 | 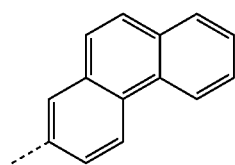 | 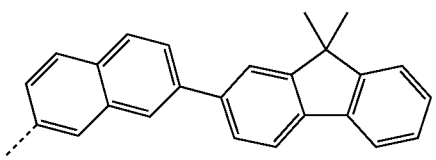 |
| 2-339 | 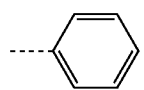 | 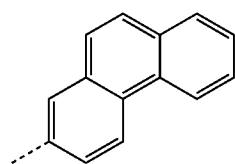 | 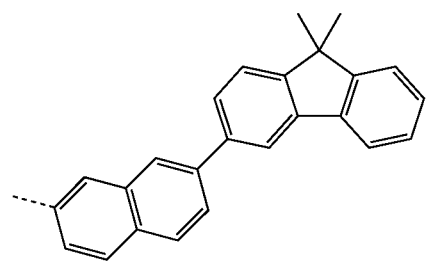 |
| 2-340 | 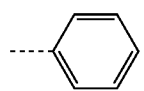 | 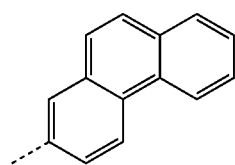 | 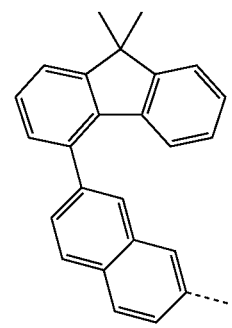 |
| 2-341 | 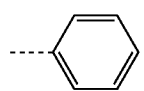 | 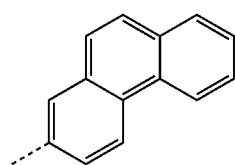 | 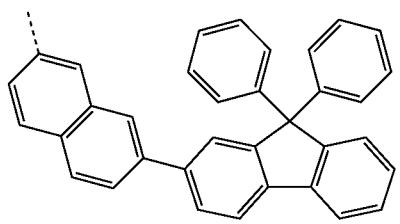 |
| 2-342 | 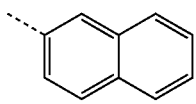 | 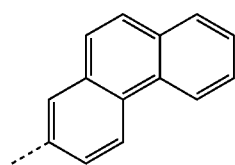 | 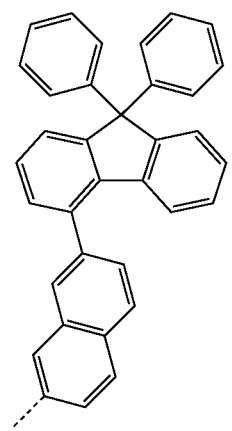 |

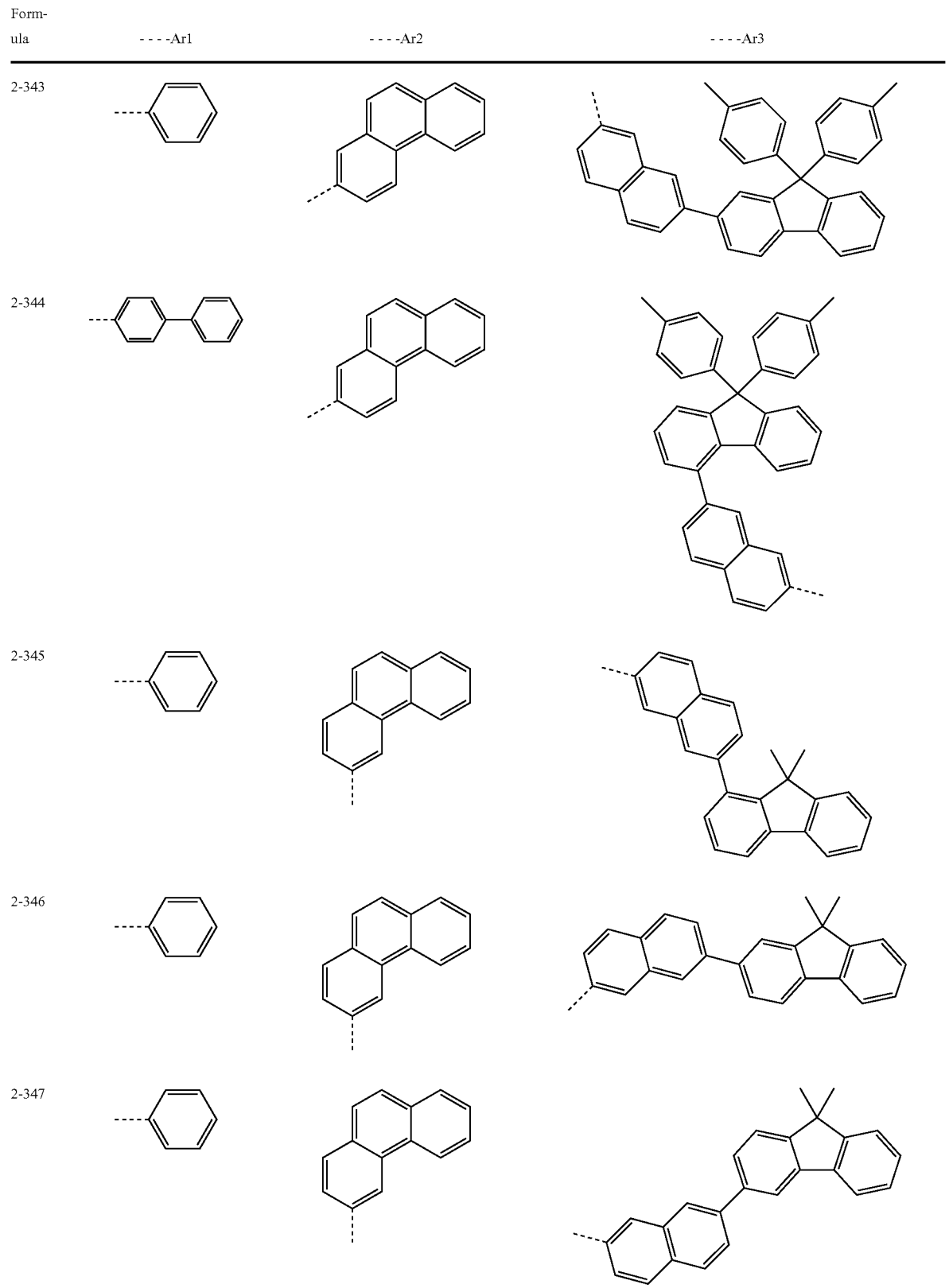

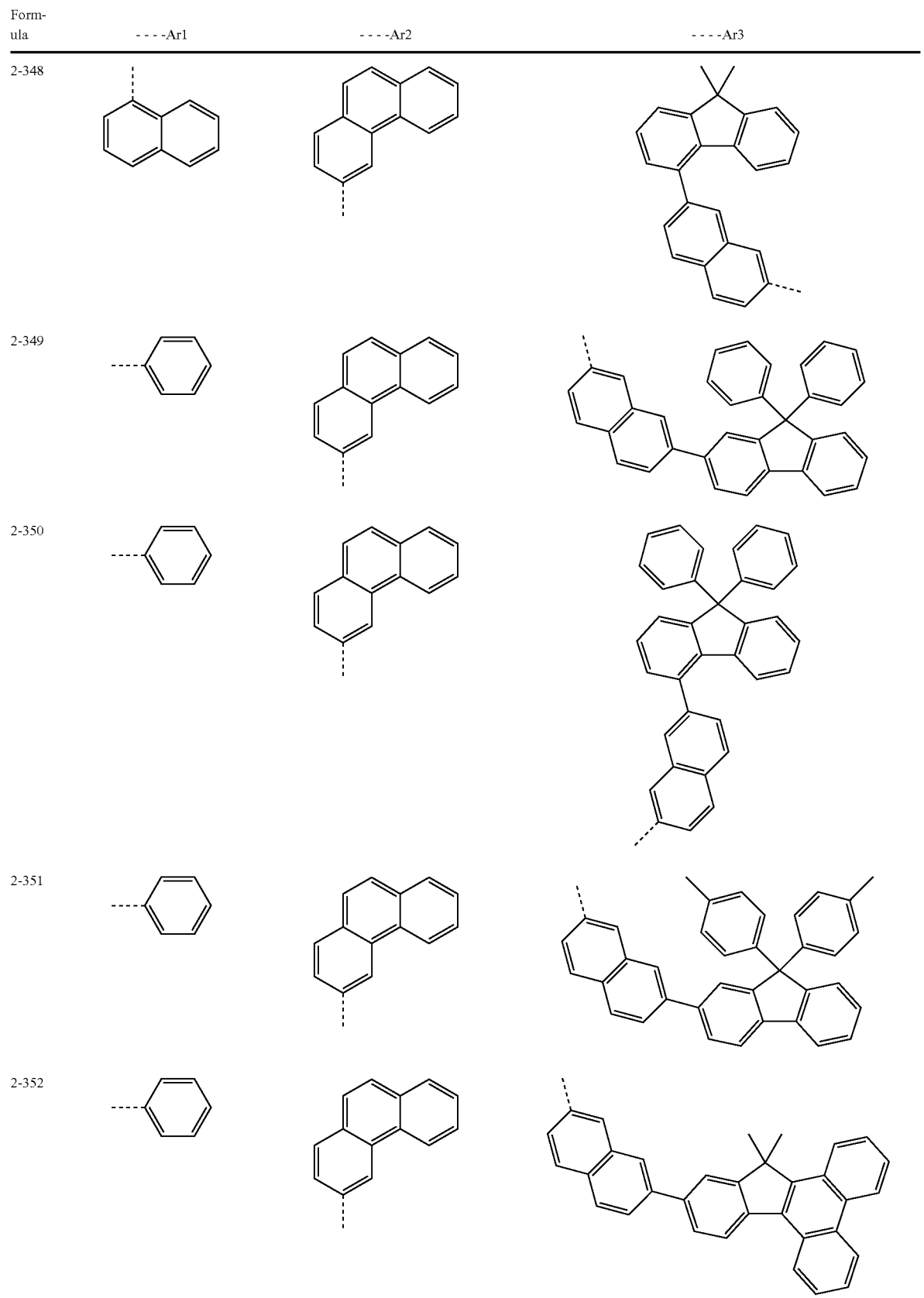

-continued
| Formula | ----Ar1 | ----Ar2 | ----Ar3 |
|---|---|---|---|
| 2-353 | 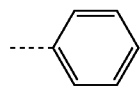 | 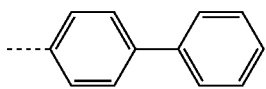 | 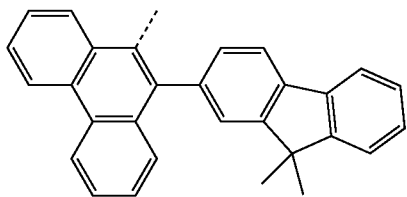 |
| 2-354 | 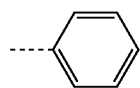 | 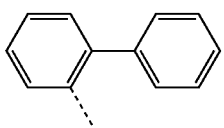 | 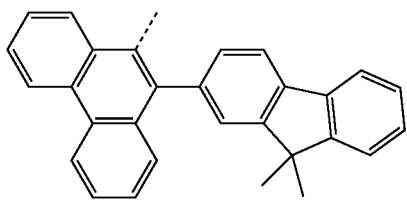 |
| 2-355 | 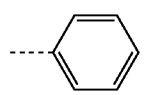 | 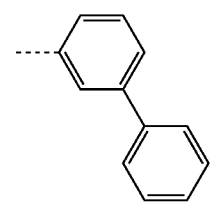 | 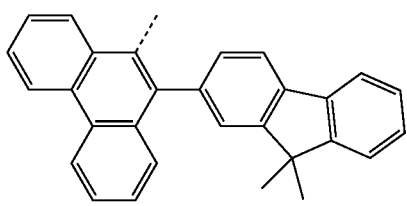 |
| 2-356 | 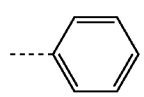 | 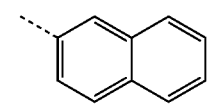 | 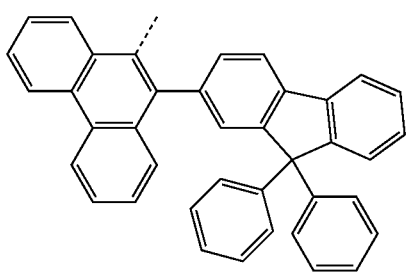 |
| 2-357 | 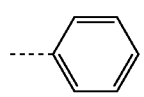 | 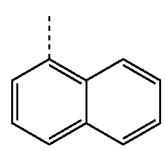 | 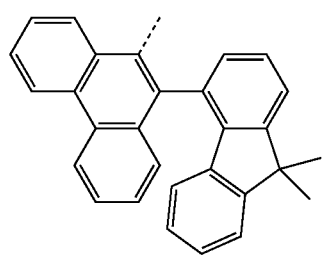 |
| 2-358 | 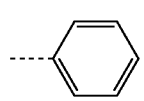 | 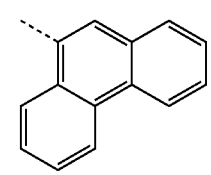 | 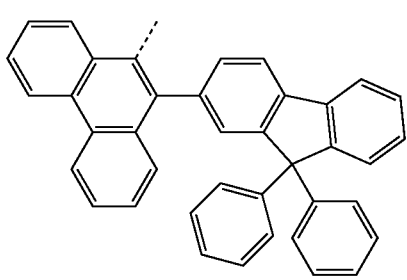 |

| Formula | ----Ar1 | ----Ar2 | ----Ar3 |
|---|---|---|---|
| 2-359 | | | |
| 2-360 | | | |
| 2-361 | | | |
| 2-362 | | | |
| 2-363 | | | |

In an exemplary embodiment of the present specification, the hole mobility of the compound represented by Formula 3 is $5\times10^{-6}$ cm$^2$/Vs or more. In another exemplary embodiment, the hole mobility of the compound represented by Formula 3 is $5\times10^{-6}$ cm$^2$/Vs or more under an electric field condition of 0.1 to 0.5 MV/cm. In still another exemplary embodiment, the hole mobility of the compound represented by Formula 3 is $5\times10^{-6}$ cm$^2$/Vs or more under an electric field condition of 0.1 MV/cm. In other exemplary embodiments, the hole mobility of the compound represented by Formula 3 is $10^{-6}$ cm$^2$/Vs or more.

The compound represented by Formula 3 according to an exemplary embodiment of the present specification has a hole mobility of $5\times10^{-6}$ cm$^2$/Vs or more under an electric field condition of 0.1 to 0.5 MV/cm, and the hole mobility is faster than that of the hole transporting material in the related art. Accordingly, the number of excitons produced in the light emitting layer may be increased, and thus high efficiency may be expected, but leakage of holes toward the cathode may be caused. However, when the organic material layer including the heterocyclic compound represented by Formula 1 according to an exemplary embodiment of the present specification is provided between a light emitting layer and a cathode, there is an advantage in that not only the efficiency, but also the service life may be maximized because not only holes leaked, but also excitons produced may be effectively confined in the light emitting layer by Formula 3, and an exciton, that is, a hole-electron pair may maintain a stable form from the chemical attack.

In the present specification, the hole mobility may be measured by a method used in the art. Specifically, a time of flight (TOF) or a method of measuring a space charge limited current (SCLC) may be used, and the method is not limited thereto. In the present specification, the hole mobility may be measured by setting the film thickness of the material to 100 nm or more in order to measure the space charge limited current (SCLC).

In an exemplary embodiment of the present specification, the hole mobility of the compound represented by Formula 3, which is measured by time of flight (TOF), is $5 \times 10^{-6}$ cm$^2$/Vs or more.

In one exemplary embodiment of the present specification, the compound represented by Formula 3 and the compound represented by Formula 4 were heated under vacuum at a weight ratio of 20:1 on an ITO substrate and deposited to have a thickness of 10 nm, and then the hole transporting material represented by Formula 3 was deposited to have a thickness of 200 nm, and then the compound represented by Formula 3 and the compound represented by Formula 4 were deposited at a weight ratio of 20:1 to have a thickness of 10 nm, and then aluminum was deposited thereon to have a thickness of 10 nm or more, thereby preparing a sample. The hole mobility in the space charge limited current (SCLC) region may be calculated by measuring the currently density (mA/cm$^2$) for the voltage of the sample.

According to an exemplary embodiment of the present specification, Ar4 and Ar5 in Formula 3 are the same as or different from each other, and a substituted or unsubstituted monocyclic or polycyclic aryl group having 6 to 20 carbon atoms; or a substituted or unsubstituted monocyclic or polycyclic heteroaryl group having 2 to 20 carbon atoms.

According to another exemplary embodiment of the present specification, Ar4 and Ar5 are the same as or different from each other, and a substituted or unsubstituted monocyclic or polycyclic aryl group having 6 to 15 carbon atoms; or a substituted or unsubstituted monocyclic or polycyclic heteroaryl group having 2 to 15 carbon atoms.

According to still another exemplary embodiment of the present specification, Ar4 and Ar5 are the same as or different from each other, and a substituted or unsubstituted phenyl group; a substituted or unsubstituted biphenyl group; or a substituted or unsubstituted fluorenyl group.

According to yet another exemplary embodiment of the present specification, Ar4 and Ar5 are the same as or different from each other, and a phenyl group; a phenyl group substituted with a phenyl group; a phenyl group substituted with a pyridine group; a biphenyl group; or a fluorenyl group substituted with a methyl group.

According to an exemplary embodiment of the present specification, Ar4 is a substituted or unsubstituted phenyl group; a substituted or unsubstituted biphenyl group; or a substituted or unsubstituted fluorenyl group.

In one exemplary embodiment of the present specification, Ar4 is a substituted or unsubstituted phenyl group.

In another exemplary embodiment, Ar4 is a phenyl group substituted with an aryl group.

In an exemplary embodiment of the present specification, Ar4 is a phenyl group substituted with a phenyl group.

In another exemplary embodiment, Ar4 is a phenyl group.

In an exemplary embodiment of the present specification, Ar4 is a phenyl group substituted with a heterocyclic group.

In another exemplary embodiment, Ar4 is a phenyl group substituted with a nitrogen-containing heterocyclic group.

In still another exemplary embodiment, Ar4 is a phenyl group substituted with a pyridine group.

In an exemplary embodiment of the present specification, the phenyl group substituted with a pyridine group is

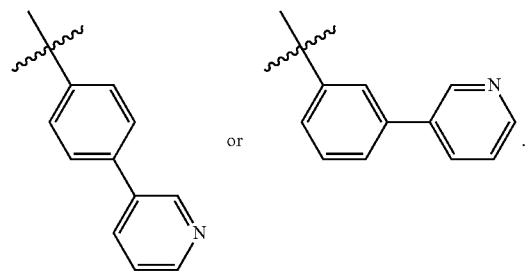 [SMILES: *c1ccc(-c2cccnc2)cc1 ; *c1cccc(-c2cccnc2)c1]

In another exemplary embodiment, Ar4 is a substituted or unsubstituted biphenyl group.

In still another exemplary embodiment, Ar4 is a biphenyl group.

In an exemplary embodiment of the present specification, the biphenyl group is

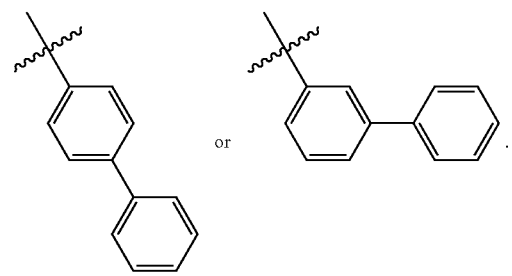 [SMILES: *c1ccc(-c2ccccc2)cc1 ; *c1cccc(-c2ccccc2)c1]

In an exemplary embodiment of the present specification, Ar4 is a substituted or unsubstituted fluorenyl group.

In another exemplary embodiment, Ar4 is a fluorenyl group substituted with an alkyl group.

In an exemplary embodiment of the present specification, Ar4 is a fluorenyl group substituted with a methyl group.

According to one exemplary embodiment of the present specification, Ar5 is a substituted or unsubstituted phenyl group; or a substituted or unsubstituted biphenyl group.

In one exemplary embodiment, Ar5 is a substituted or unsubstituted phenyl group.

In another exemplary embodiment, Ar5 is a phenyl group.

In still another exemplary embodiment, Ar5 is a substituted or unsubstituted biphenyl group.

In yet another exemplary embodiment, Ar5 is a biphenyl group.

According to an exemplary embodiment of the present specification, in Formula 3, L2 is a direct bond; or a substituted or unsubstituted monocyclic or polycyclic arylene group having 6 to 20 carbon atoms.

According to another exemplary embodiment of the present specification, L2 is a direct bond; or a substituted or unsubstituted monocyclic or polycyclic arylene group having 6 to 10 carbon atoms.

In still another exemplary embodiment, L2 is a direct bond; a substituted or unsubstituted phenylene group; a substituted or unsubstituted biphenylylene group; or a substituted or unsubstituted naphthalene group.

According to an exemplary embodiment of the present specification, $(L2)_o$ is a direct bond; a substituted or unsubstituted phenylene group; a substituted or unsubstituted biphenylene group; or a substituted or unsubstituted naphthalene group.

According to an exemplary embodiment of the present specification, in Formula 3, R5 to R11 are the same as or different from each other, and each independently selected from the group consisting of hydrogen; deuterium; a substituted or unsubstituted straight-chained or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms.

According to another exemplary embodiment of the present specification, R5 to R11 are the same as or different from each other, and each independently selected from the group consisting of hydrogen; deuterium; a substituted or unsubstituted straight-chained or branched alkyl group having 1 to 10 carbon atoms; a substituted or unsubstituted monocyclic or polycyclic aryl group having 6 to 10 carbon atoms; and a substituted or unsubstituted monocyclic or polycyclic heteroaryl group having 2 to 10 carbon atoms.

According to one exemplary embodiment of the present specification, R5 to R11 are the same as or different from each other, and are each independently hydrogen; or a substituted or unsubstituted monocyclic or polycyclic aryl group having 6 to 30 carbon atoms.

According to another exemplary embodiment, R5 to R11 are the same as or different from each other, and each independently hydrogen; or a substituted or unsubstituted phenyl group.

In an exemplary embodiment of the present specification, R5 is hydrogen.

In another exemplary embodiment, R6 is hydrogen.

In an exemplary embodiment of the present specification, R7 is hydrogen.

In an exemplary embodiment of the present specification, R8 is hydrogen.

In an exemplary embodiment of the present specification, R9 is hydrogen.

In another exemplary embodiment, R9 is a substituted or unsubstituted monocyclic or polycyclic aryl group having 6 to 30 carbon atoms.

In still another exemplary embodiment, R9 is a substituted or unsubstituted phenyl group.

In yet another exemplary embodiment, R9 is a phenyl group.

In an exemplary embodiment of the present specification, R10 is hydrogen.

In another exemplary embodiment, R11 is hydrogen.

According to an exemplary embodiment of the present specification, in Formula 3, Y1 and Y2 are the same as or different from each other, and each independently a substituted or unsubstituted straight-chained or branched alkyl group having 1 to 20 carbon atoms; a substituted or unsubstituted monocyclic or polycyclic aryl group having 6 to 20 carbon atoms; or a substituted or unsubstituted monocyclic or polycyclic heteroaryl group having 2 to 20 carbon atoms, or Y1 and Y2 combine with each other to form a substituted or unsubstituted aromatic ring.

According to another exemplary embodiment of the present specification, Y1 and Y2 are the same as or different from each other, and each independently a substituted or unsubstituted straight-chained or branched alkyl group having 1 to 15 carbon atoms; a substituted or unsubstituted monocyclic or polycyclic aryl group having 6 to 15 carbon atoms; or a substituted or unsubstituted monocyclic or polycyclic heteroaryl group having 2 to 15 carbon atoms, or Y1 and Y2 combine with each other to form a substituted or unsubstituted aromatic ring.

According to still another exemplary embodiment of the present specification, Y1 and Y2 are the same as or different from each other, and each independently a substituted or unsubstituted alkyl group having 1 to 10 carbon atoms; or a substituted or unsubstituted phenyl group, or combine with each other to form a substituted or unsubstituted fluorene structure.

According to another exemplary embodiment of the present specification, Y1 and Y2 are the same as or different from each other, and each independently a methyl group; or a phenyl group, or combine with each other to form a fluorene structure.

According to one exemplary embodiment of the present specification, when Y1 and Y2 combine with each other to form a fluorene structure, the fluorenyl group including Y1 and Y2 in Formula 3 may be a spirobifluorene structure.

According to an exemplary embodiment of the present specification, the compound represented by Formula 3 is represented by any one of the following Formulae 3-1 to 3-22.

Formula 3-1

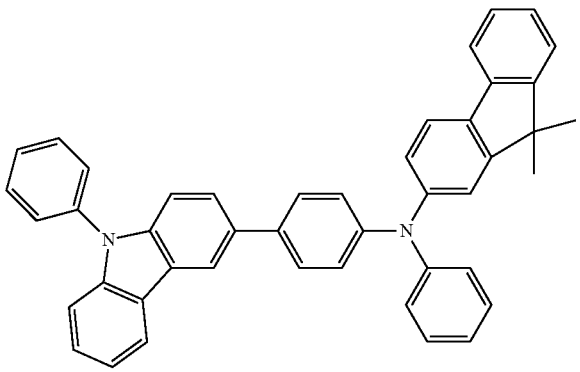

Formula 3-2

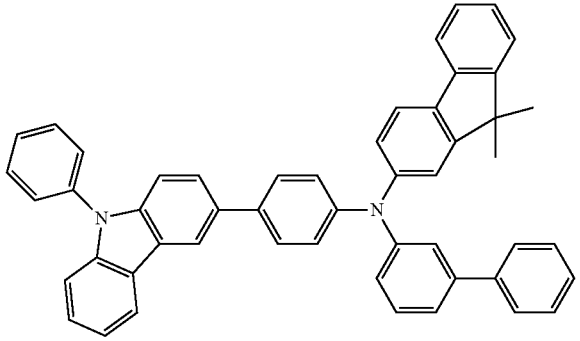

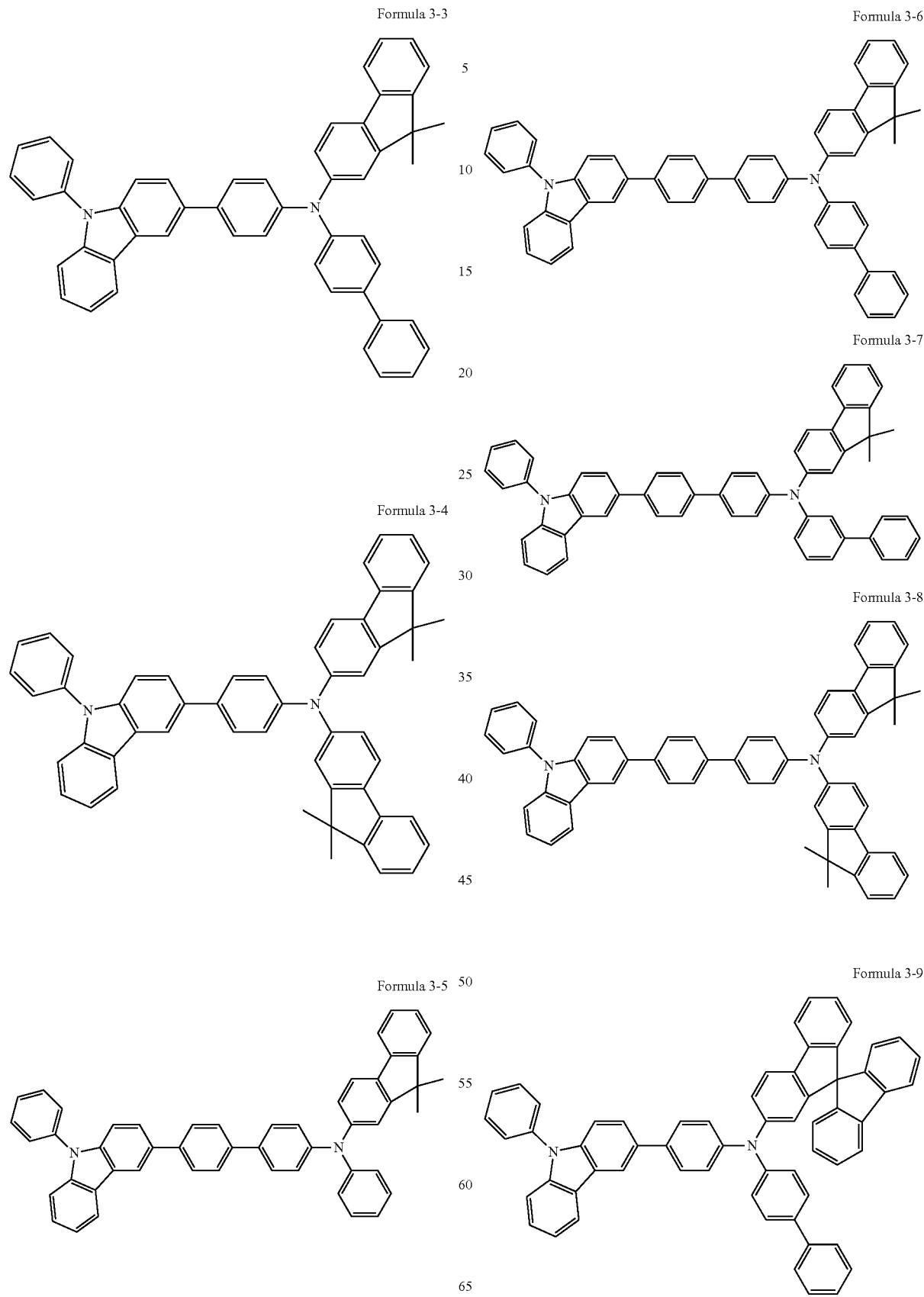

Formula 3-10
Formula 3-13
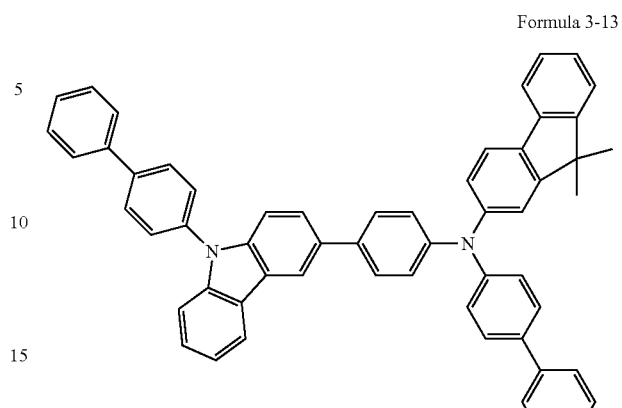
Formula 3-11
Formula 3-14
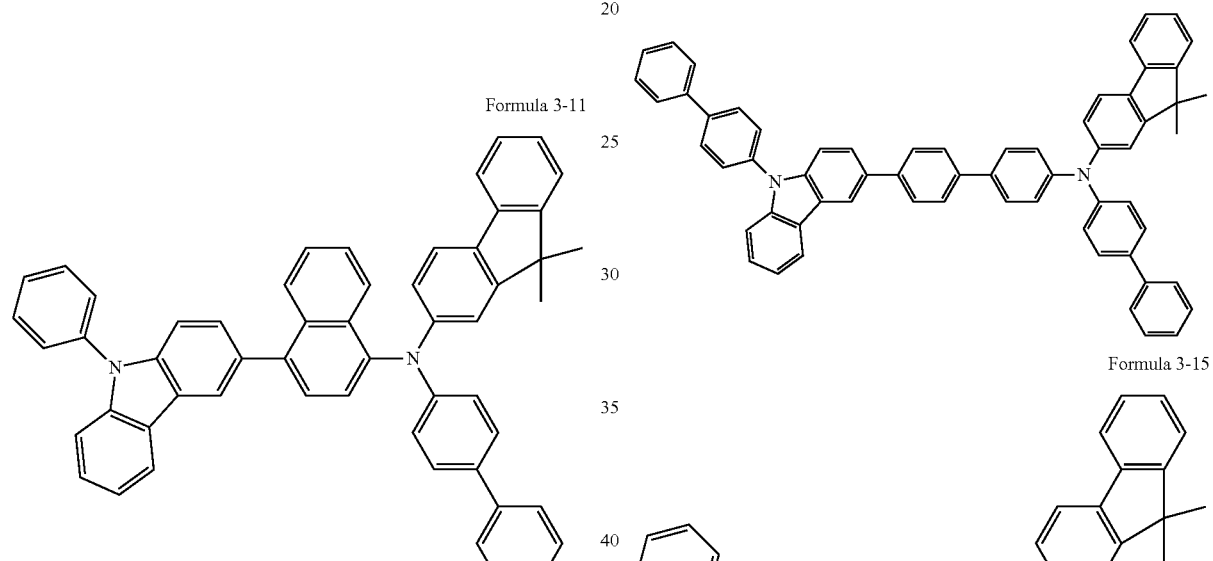
Formula 3-12
Formula 3-15
Formula 3-16
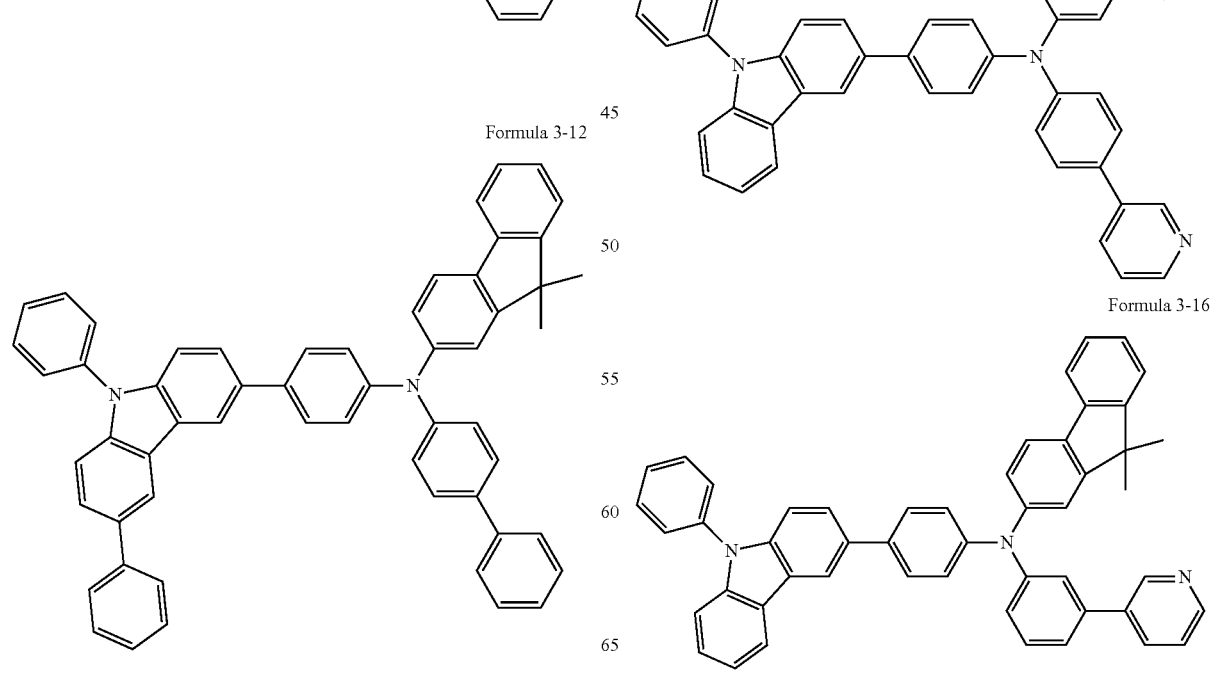

-continued

Formula 3-17

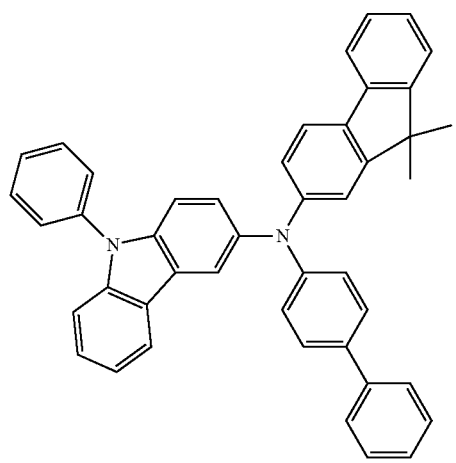

Formula 3-18

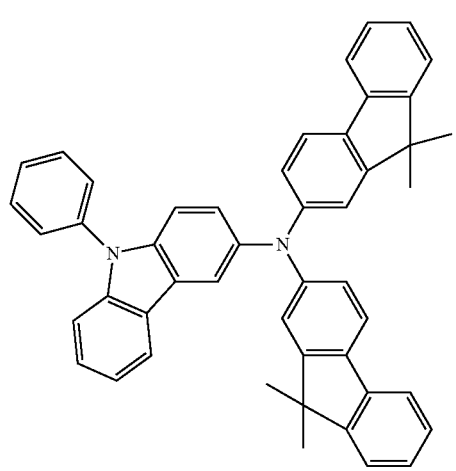

Formula 3-19

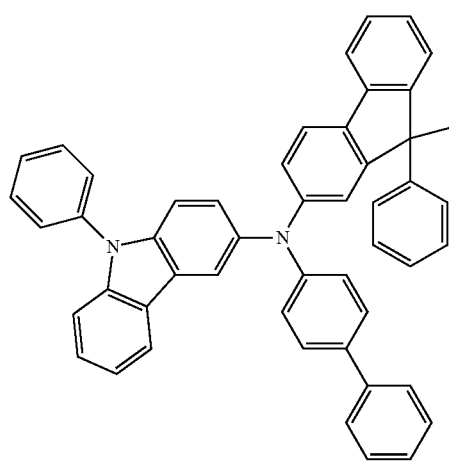

-continued

Formula 3-20

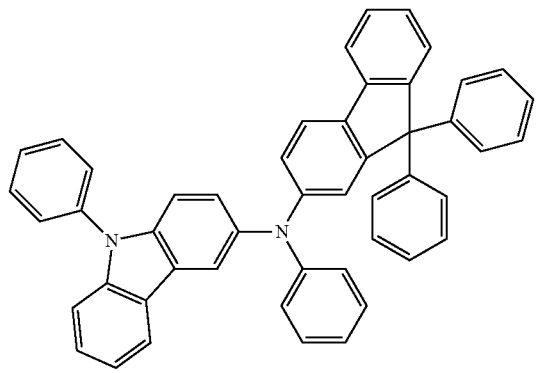

Formula 3-21

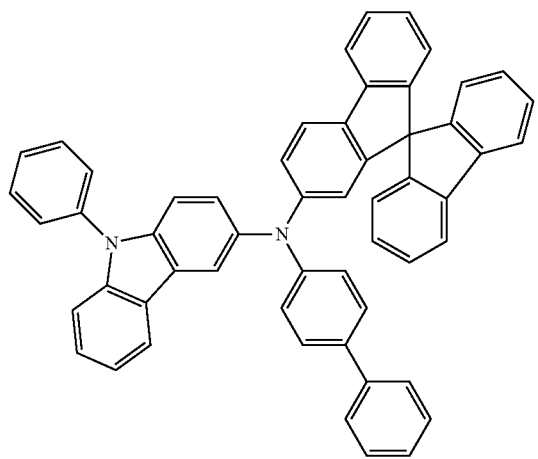

Formula 3-22

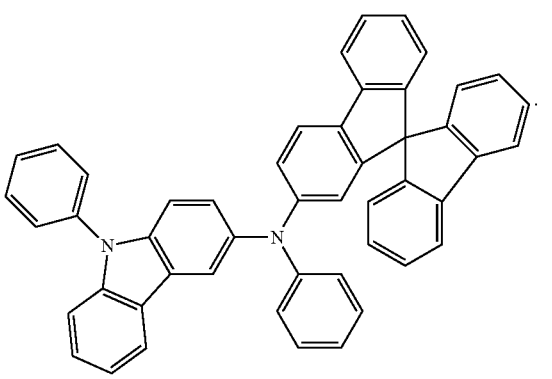

In one exemplary embodiment of the present specification, the organic light emitting diode further includes an acceptor layer including an acceptor material represented by the following Formula 4 between the anode and an organic material layer including the carbazole derivative represented by Formula 3.

[Formula 4]

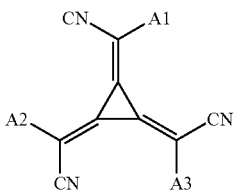

In Formula 4,

A1 to A3 are the same as or different from each other, and each independently an aryl group, which is unsubstituted or substituted with one or two or more substituents selected from the group consisting of a cyano group, a halogen group, and a haloalkyl group; or a heterocyclic group, which is unsubstituted or substituted with one or two or more substituents selected from the group consisting of a cyano group, a halogen group, and a haloalkyl group.

In an exemplary embodiment of the present specification, the acceptor layer further includes the carbazole derivative represented by Formula 3.

In another exemplary embodiment, the acceptor material represented by Formula 4 is present in an amount of 1 wt % to 30 wt % based on the total weight of the acceptor layer.

According to an exemplary embodiment of the present specification, the acceptor layer may serve as an electron injection layer.

In an exemplary embodiment of the present specification, a hole transporting layer including the carbazole derivative represented by Formula 3 is provided between the light emitting layer and the anode, and an acceptor layer including the acceptor material represented by Formula 4 and the carbazole derivative represented by Formula 3 may be provided between the hole transporting layer and the anode.

In the present specification, the acceptor layer may serve as a hole injection layer.

In one exemplary embodiment of the present specification, the hole transporting layer which does not include the acceptor material is provided to be adjacent to the light emitting layer.

In another exemplary embodiment, the organic light emitting diode may further include an electron blocking layer between the aforementioned hole transporting layer and the light emitting layer.

Further, when the aforementioned acceptor material is included in the organic material layer including the carbazole derivative represented by Formula 3 according to an exemplary embodiment of the present specification, holes are smoothly injected from the anode. This is because the capability of injecting holes is improved while the difference between the Fermi energy level of the anode and the Fermi energy level of the hole transporting layer is adjusted within 0.2 eV due to the doping of the acceptor material. Due to the improvement in the capability of injecting holes, many holes are transported from the anode to the light emitting layer to lower the driving voltage of the organic light emitting diode, and enhance the efficiency of the diode.

In an exemplary embodiment of the present specification, the organic material layer including the carbazole derivative represented by Formula 3 contains a fluorene group and thus has a relatively high molecular planarity, thereby leading to high hole mobility. Accordingly, due to excellent interaction with the acceptor material represented by Formula 4, generation of carriers is increased. Accordingly, there is an effect in that many holes may be transported and injected into the light emitting layer.

In an exemplary embodiment of the present specification, the organic light emitting diode may include two or more hole transporting layers between the anode and the light emitting layer. In this case, one or more layers of the two or more hole transporting layers include the carbazole derivative represented by Formula 3.

In an exemplary embodiment of the present specification, materials for the two or more hole transporting layers are the same as or different from each other.

In an exemplary embodiment of the present specification, when the organic light emitting diode includes two or more hole transporting layers, the hole transporting layer including the carbazole derivative represented by Formula 3 is provided to be adjacent to the light emitting layer.

In addition, the two or more hole transporting layers may include the carbazole derivative represented by Formula 3, and the other materials except for the carbazole derivative may be the same as or different from each other.

The "adjacent" in the present specification means being relatively closely disposed. In this case, the present specification may include a case of being in physical contact with each other, and may also include a case where an additional organic material layer is provided between the adjacent organic material layers.

In an exemplary embodiment of the present specification, A1 to A3 are the same as or different from each other, and each independently a phenyl group; a naphthyl group; a pyridine group; a pyrazine group; a pyrimidine group; a quinoline group; or an isoquinoline group, and the phenyl group; the naphthyl group; the pyridine group; the pyrazine group; the pyrimidine group; the quinoline group; and the isoquinoline group may be unsubstituted or substituted with one or two or more substituents selected from the group consisting of a cyano group, a halogen group, and a haloalkyl group.

A1 to A3 include an electron withdrawing group of the group consisting of a cyano group, a halogen group, and a haloalkyl group and thus may further enhance the effect of the acceptor.

In an exemplary embodiment of the present specification, A1 to A3 are the same as or different from each other, and each independently a phenyl group substituted with fluorine and a cyano group.

In an exemplary embodiment of the present specification, the acceptor material represented by Formula 4 is represented by the following Formula 4-1.

[Formula 4-1]

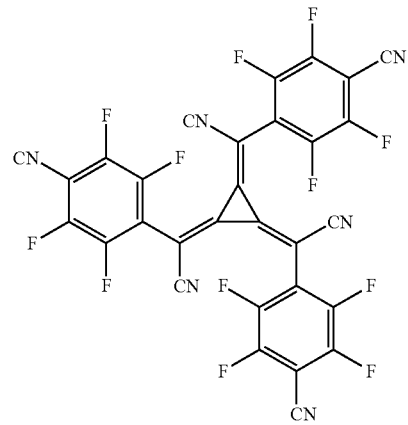

The organic light emitting diode according to an exemplary embodiment of the present specification may be manufactured by materials and methods known in the art, except that the organic light emitting diode includes the aforementioned heterocyclic compound represented by Formula 1 between the cathode and the light emitting layer, and the aforementioned carbazole derivative represented by Formula 3 between the anode and the light emitting layer.

For example, the organic light emitting diode of the present specification may be manufactured by sequentially stacking an anode, an organic material layer, and a cathode on a substrate. In this case, the organic light emitting diode may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, an electron blocking layer, a light emitting layer, an electron transporting layer, and an electron injection layer thereon, and then depositing a material which may be used as a cathode thereon. In addition to the method described above, an organic light emitting diode may be made by subsequently depositing a cathode material, an organic material layer, and an anode material on a substrate. In addition to the method described above, an organic light emitting diode may be made by subsequently depositing an anode material, an organic material layer, and a cathode material on a substrate.

The organic material layer of the organic light emitting diode of the present specification may be composed of a multi-layered structure in which an organic material layer having one or more layers is stacked.

In an exemplary embodiment of the present specification, the organic light emitting diode may further include one or more layers selected from the group consisting of a hole injection layer, a hole transporting layer, an electron transporting layer, an electron injection layer, an electron blocking layer, and a hole blocking layer.

Figure 2:
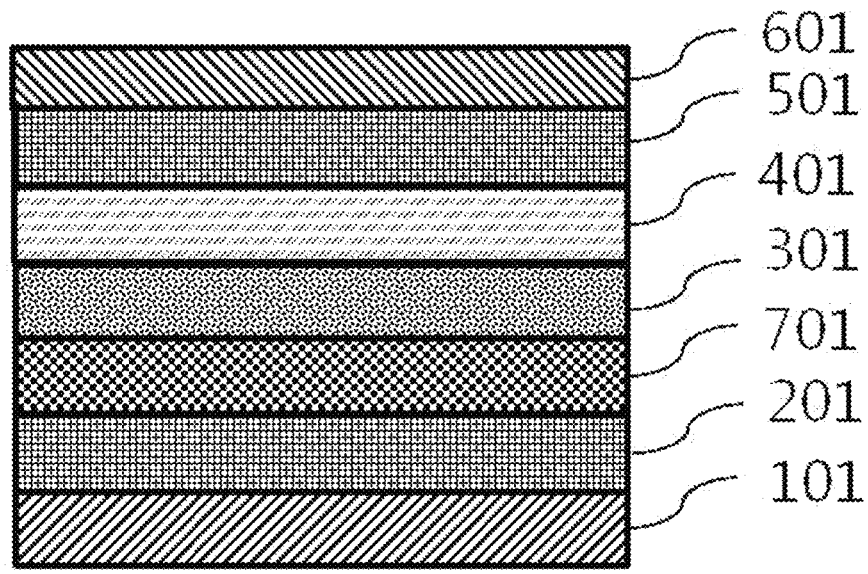
FIG. 2 is a view illustrating an organic light emitting diode according to an exemplary embodiment of the present specification.
Figure 3:
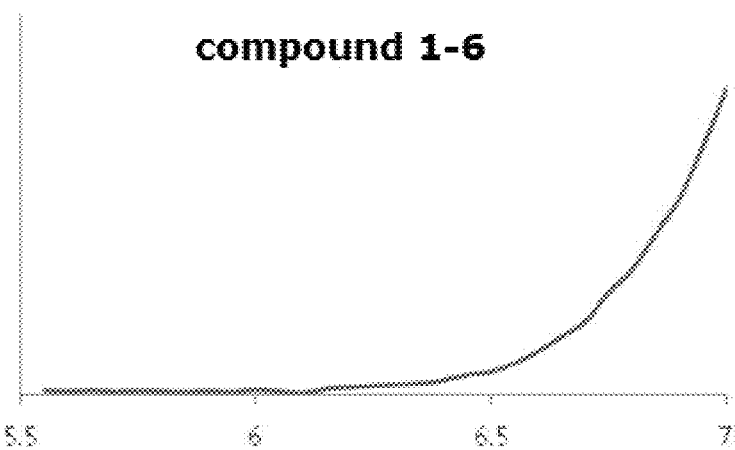
FIG. 3 is a view illustrating a result of measurement data of the HOMO(AC3) levels of Compound 1-6.
Figure 4:
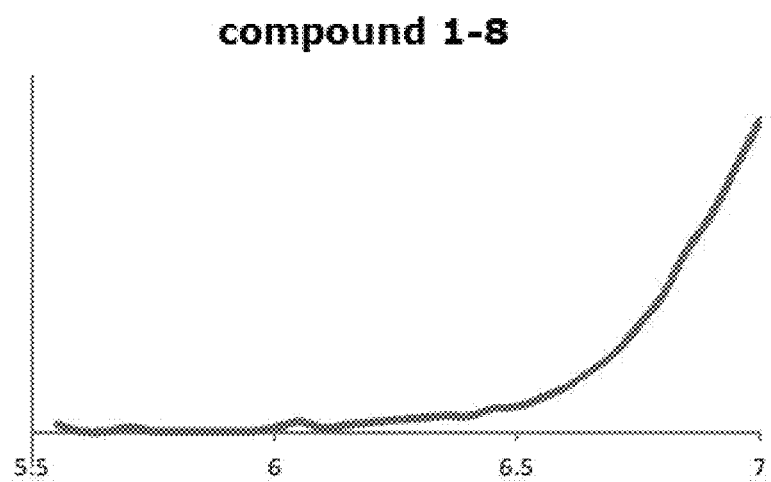
FIG. 4 is a view illustrating a result of measurement data of the HOMO(AC3) levels of Compound 1-8.
Figure 5:
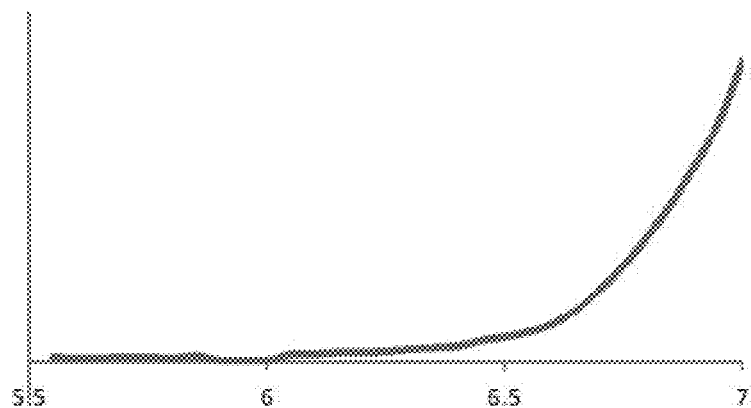
FIG. 5 is a view illustrating a result of measurement data of the HOMO(AC3) levels of Compound 1-30.
Figure 6:
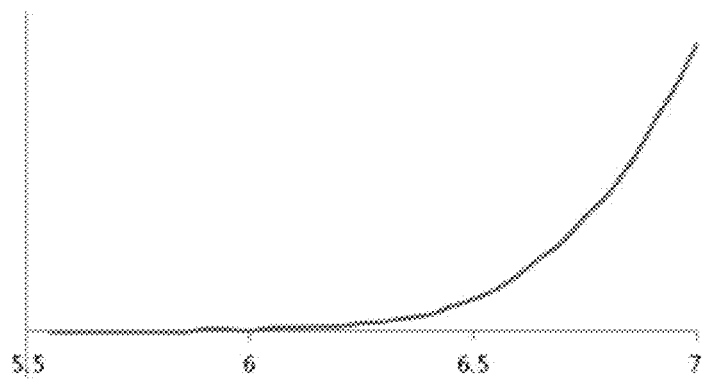
FIG. 6 is a view illustrating a result of measurement data of the HOMO(AC3) levels of Compound 1-138.
Figure 7:
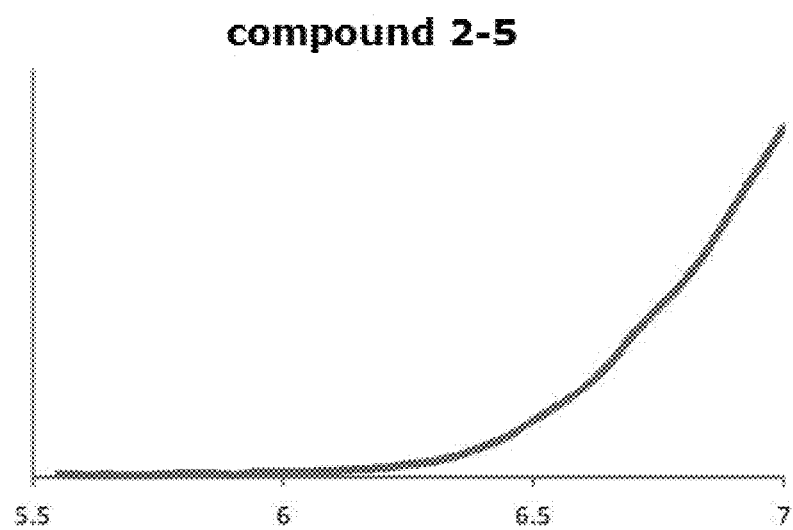
FIG. 7 is a view illustrating a result of measurement data of the HOMO(AC3) levels of Compound 2-5.

For example, the structure of the organic light emitting diode of the present specification may have the same structures as those illustrated in FIGS. 1 and 2, but is not limited thereto.

FIG. 1 illustrates the structure of an organic light emitting diode in which an anode 201, a hole transporting layer 301, a light emitting layer 401, an electron transporting layer 501, and a cathode 601 are sequentially stacked on a substrate 101. In FIG. 1, the heterocyclic compound represented by Formula 1 is included in the electron transporting layer 501, and the carbazole derivative represented by Formula 3 is included in the hole transporting layer 301.

FIG. 2 illustrates the structure of an organic light emitting diode in which an anode 201, an acceptor layer 701, a hole transporting layer 301, a light emitting layer 401, an electron transporting layer 501, and a cathode 601 are sequentially stacked on a substrate 101. In FIG. 1, the heterocyclic compound represented by Formula 1 may be included in the electron transporting layer 501, the carbazole derivative represented by Formula 3 may be included in the hole transporting layer 301, and the acceptor material represented by Formula 4 may be included in the acceptor layer 701.

FIGS. 1 and 2 are exemplified structures according to exemplary embodiments of the present specification, and may further include other organic material layers.

When the organic light emitting diode includes a plurality of organic material layers, the organic material layer may be formed of the same material or different materials.

As the anode material, a material having a large work function is usually preferred so as to smoothly inject holes into an organic material layer. Examples of an anode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly (3-methylthiophene), poly[3,4-(ethylene-1,2-dioxy)thiophene] (PEDOT), polypyrrole, and polyaniline, and the like, but are not limited thereto.

As the cathode material, a material having a small work function is usually preferred so as to smoothly inject electrons into an organic material layer. Specific examples of a cathode material include: a metal, such as magnesium, calcium, sodium, potassium, titanium, indium, yttrium, lithium, gadolinium, aluminum, silver, tin, or lead, or alloys thereof; a multi-layered structural material, such as LiF/Al or $LiO2/Al$, and the like, but are not limited thereto.

As the hole injection material, a compound is preferred, in which the hole injection material has a capability of transporting holes to a layer which injects holes from an electrode, and thus has an effect of injecting holes at the anode and an excellent effect of injecting holes for the light emitting layer or the light emitting material, prevents excitons produced from the light emitting layer from moving to an electron injection layer or an electron injection material, and has excellent capability of forming a thin film. It is preferred that the highest occupied molecular orbital (HOMO) of the hole injection material is between the work function of the anode material and the HOMO of the organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The electron transporting layer is a layer which receives holes from the hole injection layer and transports holes to the light emitting layer, and a hole transporting material is suitably a material which may receive holes from an anode or a hole injection layer and may transfer holes to a light emitting layer, and has large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from the hole transporting layer and the electron transporting layer, respectively, and combine the holes and the electrons to emit light in a visible ray region, and is preferably a material having good quantum efficiency to fluorescence or phosphorescence. Specific examples thereof comprise a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but are not limited thereto.

In the fluorescence light emitting layer, as the host material, one or two or more are selected from the group consisting of distyrylarylene (DSA), a distyrylarylene derivative, distyrylbenzene (DSB), a distyrylbenzene derivative, 4,4'-bis(2,2'-diphenyl vinyl)-1,1'-biphenyl (DPVBi), a DPVBi derivative, spiro-DPVBi, and spiro-6P.

In the fluorescence light emitting layer, as the dopant material, one or two or more are selected from the group consisting of styrylamine-based, pherylene-based, and distyrylbiphenyl (DSBP)-based dopant materials.

The electron injection layer is a layer which injects electrons from an electrode, and a compound is preferred, which has a capability of transporting electrons, has an effect of injecting electrons from a cathode and an excellent effect of injecting electrons into a light emitting layer or a light emitting material, prevents excitons produced from the light emitting layer from moving to the hole injection layer, and is also highly capable of forming a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a cathode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting diode according to the present specification may be a top emission type, a bottom emission type, or a dual emission type according to the material to be used.

In addition, the organic light emitting diode according to the present specification may be a normal type in which a lower electrode is an anode and an upper electrode is a cathode, and may also be an inverted type in which a lower electrode is a cathode and an upper electrode is an anode.

The structure according to an exemplary embodiment of the present specification may be operated by a principle which is similar to the principle applied to an organic light emitting diode, even in an organic electronic diode including an organic solar cell, an organic photoconductor, an organic transistor, and the like.

MODE FOR INVENTION

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided for more completely explaining the present specification to the person with ordinary skill in the art.

Example 1

The values of the HOMO energy level and the triplet energy ($E_T$) of the heterocyclic compound represented by Formula 1 according to an exemplary embodiment of the present specification, the compounds represented by the following Formulae ET-B and ET-J are shown in the following Table 1.

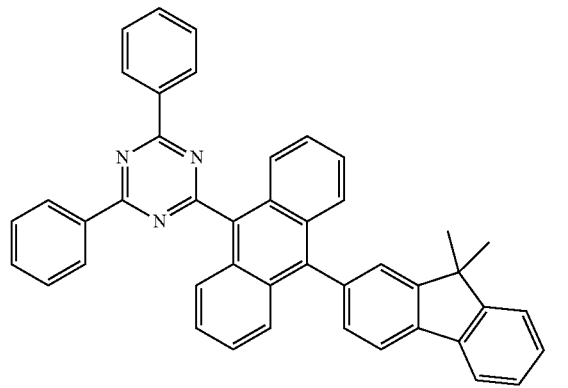

[ET-B]

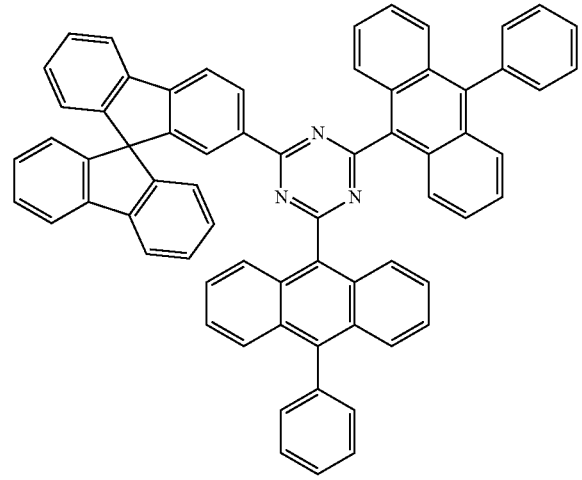

[ET-J]

In the Examples of the present specification, the HOMO level was measured by using an atmospheric pressure photoelectron spectrometer AC3 (manufactured by Riken Keiki Co., Ltd.).

Further, the triplet energy ($E_T$) was calculated by using a quantum chemical calculation program Gaussian 03 manufactured by U.S. Gaussian Corporation, and a density functional theory (DFT) was used and the calculated value of the triplet energy was obtained by the time-dependent-density functional theory (TD-DFT) with respect to a structure optimized using B3LYP as a functional and 6-31G* as a basis function.

TABLE 1

| Formula | HOMO (eV) | $E_T$ (eV) |
|---|---|---|
| 1-6 | 6.37 | 2.62 |
| 1-8 | 6.38 | 2.78 |
| 1-22 | 6.35 | 2.61 |
| 1-30 | 6.44 | 2.62 |
| 1-40 | 6.35 | 2.79 |
| 1-53 | 6.39 | 2.79 |
| 1-54 | 6.35 | 2.62 |
| 1-55 | 6.38 | 2.77 |
| 1-56 | 6.37 | 2.78 |
| 1-92 | 6.30 | 2.46 |
| 1-102 | 6.27 | 2.46 |
| 1-116 | 6.29 | 2.57 |
| 1-126 | 6.31 | 2.46 |
| 1-138 | 6.29 | 2.47 |
| 1-160 | 6.37 | 2.79 |
| 1-170 | 6.36 | 2.64 |
| 1-198 | 6.30 | 2.46 |
| 1-237 | 6.28 | 2.46 |
| 1-279 | 6.31 | 2.46 |
| 1-341 | 6.27 | 2.43 |
| 1-345 | 6.20 | 2.43 |
| 1-482 | 6.31 | 2.46 |
| 2-5 | 6.22 | 2.62 |
| 2-6 | 6.25 | 2.70 |
| 2-38 | 6.30 | 2.70 |
| 2-70 | 6.22 | 2.46 |
| 2-90 | 6.20 | 2.46 |
| 2-113 | 6.25 | 2.44 |
| 2-141 | 6.15 | 2.43 |
| 2-178 | 6.20 | 2.43 |
| 2-269 | 6.13 | 2.44 |
| 2-353 | 6.15 | 2.44 |
| ET-B | 5.81 | 1.67 |
| ET-J | 5.84 | 1.68 |

Example 2

The dipole moment values of the heterocyclic compound represented by Formula 1 according to an exemplary embodiment of the present specification are shown in Table 2.

TABLE 2

| Formula | Dipole moment (Debye) |
|---|---|
| 1-6 | 0.85 |
| 1-8 | 0.51 |
| 1-30 | 0.8 |
| 1-198 | 0.64 |

Example 1-1

A glass substrate thinly coated with indium tin oxide (ITO) to have a thickness of 500 Å was put into distilled water in which a detergent was dissolved, and ultrasonically washed. In this case, a product manufactured by Fischer Co. was used as the detergent, and distilled water twice filtered using a filter manufactured by Millipore Co., was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transported to a plasma washing machine. In addition, the substrate was washed using oxygen plasma for 5 minutes, and then transported to a vacuum evaporator.

Formula 3-3 and Formula 4-1 were thermally vacuum deposited at a weight ratio of 98:2 to have a thickness of 100 Å on a transparent ITO electrode, which was prepared as described above, thereby forming a hole injection layer. Formula 3-3 was vacuum deposited to have a thickness of 1,300 Å on the hole injection layer, thereby forming a hole transporting layer.

Subsequently, the following compounds [BH] and [BD] were vacuum deposited at a weight ratio of 25:1 to have a film thickness of 350 Å on the hole transporting layer, thereby forming a light emitting layer.

The compound of Formula 1-6 and the following compound [LiQ] were vacuum deposited at a weight ratio of 1:1 on the light emitting layer, thereby forming an electron transporting layer having a thickness of 350 Å. Lithium fluoride (LiF) and aluminum were subsequently deposited to have a thickness of 10 Å and 1,000 Å, respectively, on the electron transporting layer, thereby forming a cathode.

In the aforementioned procedure, the deposition rate of the organic material was maintained at 0.4 to 0.9 Å/sec, the deposition rate of lithium fluoride of the cathode was maintained at 0.3 Å/sec, and the deposition rate of aluminum was maintained at 2 Å/sec, and the degree of vacuum during the deposition was maintained at 1×10-7 to 5×10-8 torr, thereby manufacturing an organic light emitting diode.

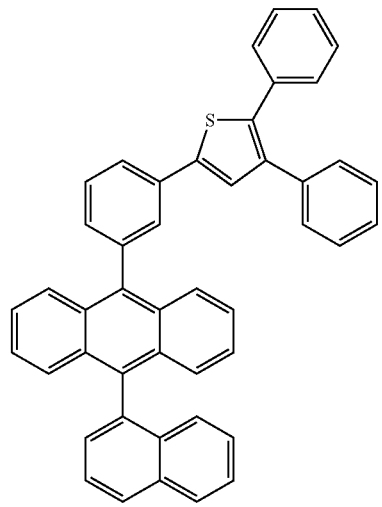

[BH]

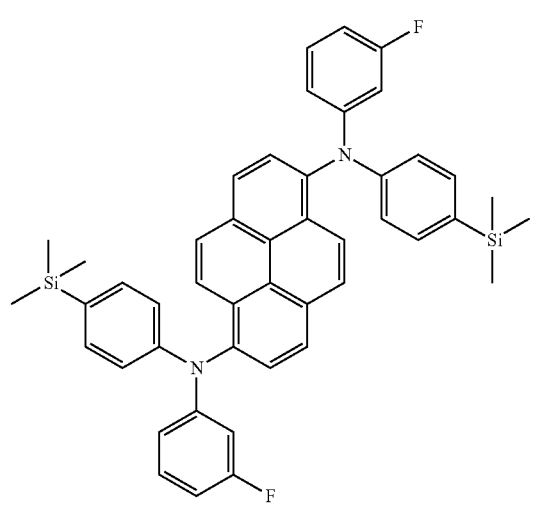

[BD]

[Liq] 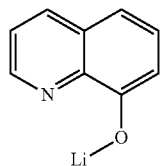
[NPB] 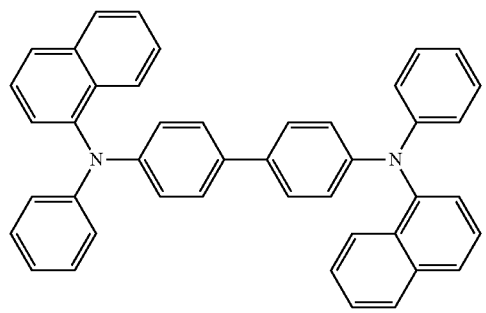
[TCTA] 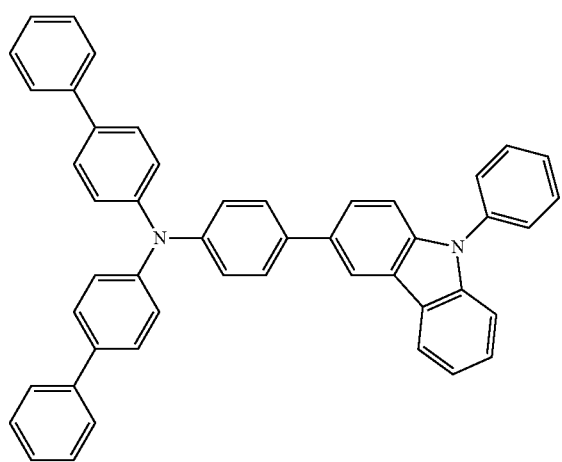
[HT-A] 
[ET-A] 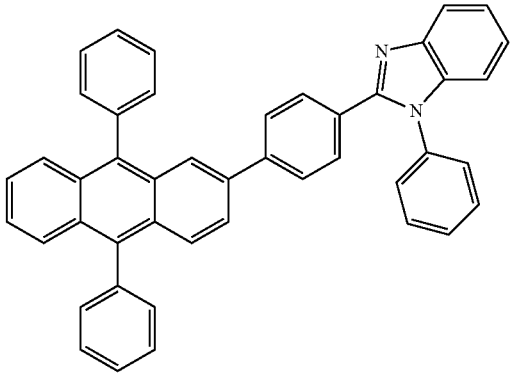
[ET-B] 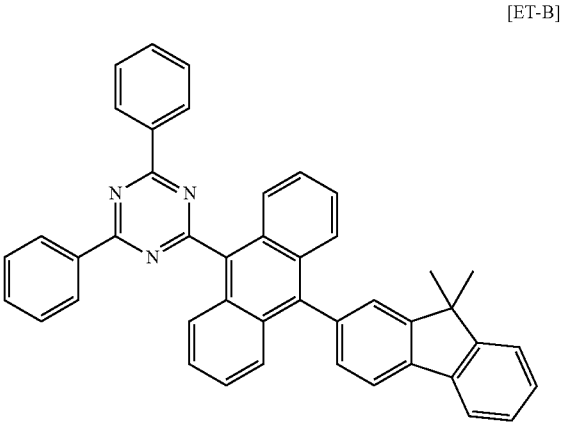
[ET-C] 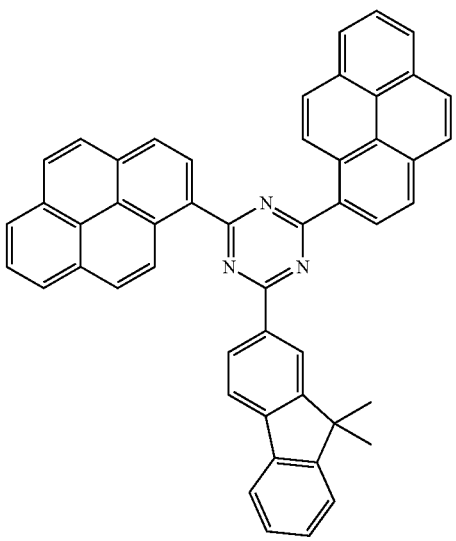

[ET-D]
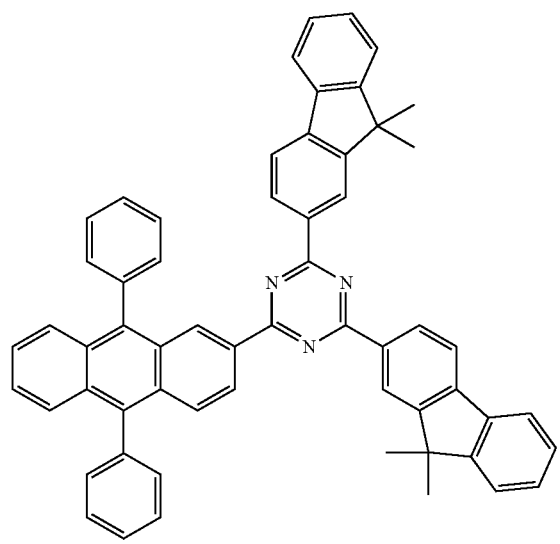
[ET-E]
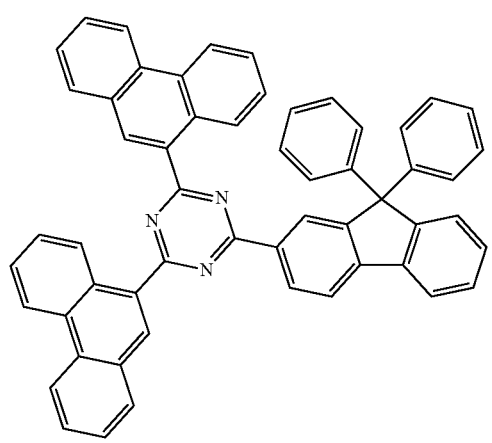
[ET-F]
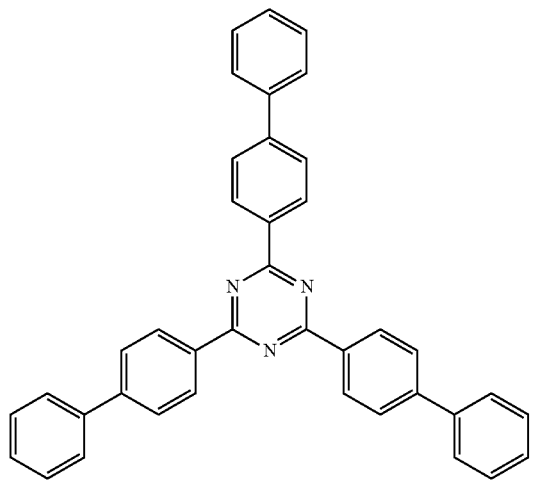
[ET-G]
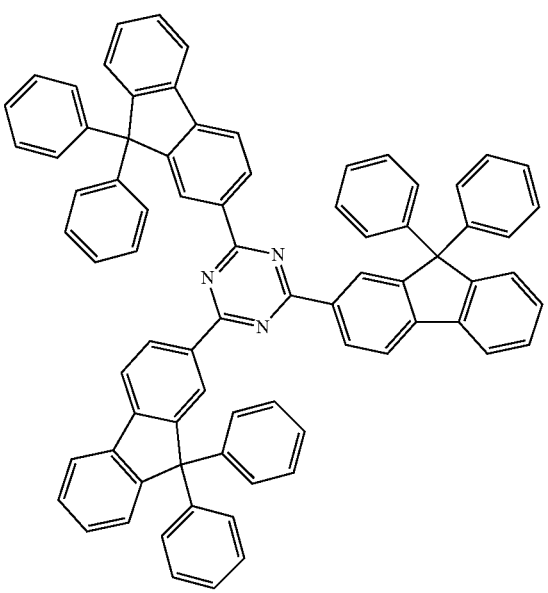
[ET-H]
[ET-I]
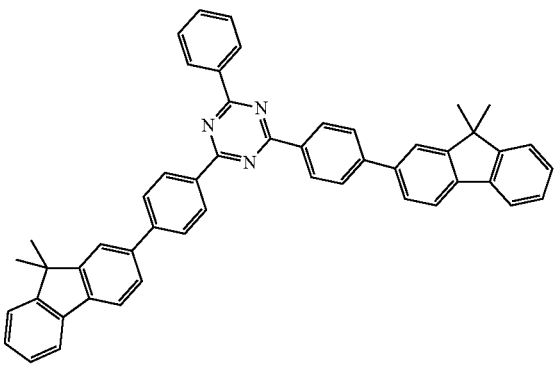

401

-continued

[ET-J]

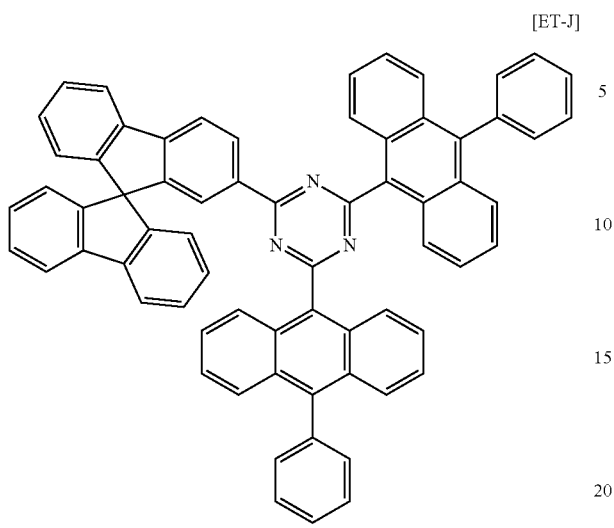

[ET-K]

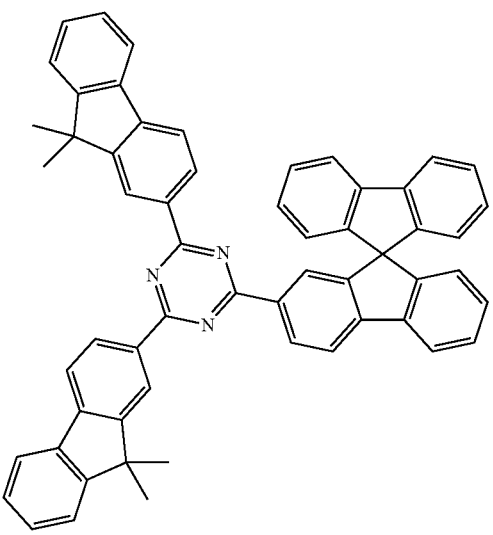

[Alq₃]

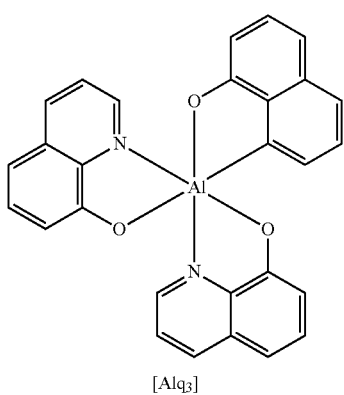

402

-continued

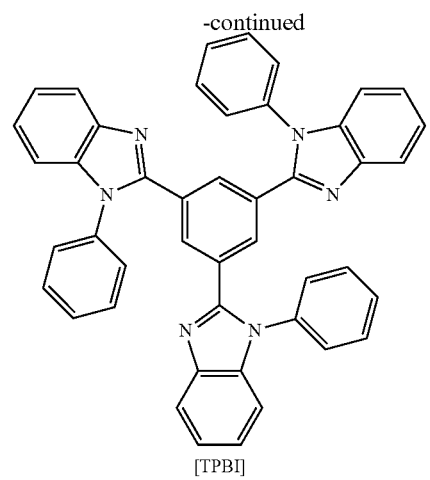

[TPBI]

Example 1-2

An organic light emitting diode was manufactured in the same manner as in [Example 1-1], except that [Formula 1-8] was used instead of [Formula 1-6] of [Example 1-1].

Example 1-3

An organic light emitting diode was manufactured in the same manner as in [Example 1-1], except that [Formula 1-30] was used instead of [Formula 1-6] of [Example 1-1].

Example 1-4

An organic light emitting diode was manufactured in the same manner as in [Example 1-1], except that [Formula 1-56] was used instead of [Formula 1-6] of [Example 1-1].

Example 1-5

An organic light emitting diode was manufactured in the same manner as in [Example 1-1], except that [Formula 1-102] was used instead of [Formula 1-6] of [Example 1-1].

Example 1-6

An organic light emitting diode was manufactured in the same manner as in [Example 1-1], except that [Formula 1-116] was used instead of [Formula 1-6] of [Example 1-1].

Example 1-7

An organic light emitting diode was manufactured in the same manner as in [Example 1-1], except that [Formula 1-138] was used instead of [Formula 1-6] of [Example 1-1].

Example 1-8

An organic light emitting diode was manufactured in the same manner as in [Example 1-1], except that [Formula 1-170] was used instead of [Formula 1-6] of [Example 1-1].

Example 1-9

An organic light emitting diode was manufactured in the same manner as in [Example 1-1], except that [Formula 1-198] was used instead of [Formula 1-6] of [Example 1-1].

Example 1-10

An organic light emitting diode was manufactured in the same manner as in [Example 1-1], except that [Formula 1-237] was used instead of [Formula 1-6] of [Example 1-1].

Example 1-11

An organic light emitting diode was manufactured in the same manner as in [Example 1-1], except that [Formula 1-341] was used instead of [Formula 1-6] of [Example 1-1].

Example 1-12

An organic light emitting diode was manufactured in the same manner as in [Example 1-1], except that [Formula 1-482] was used instead of [Formula 1-6] of [Example 1-1].

Example 1-13

An organic light emitting diode was manufactured in the same manner as in [Example 1-1], except that [Formula 1-126] was used instead of [Formula 1-6] of [Example 1-1].

Example 1-14

An organic light emitting diode was manufactured in the same manner as in [Example 1-1], except that [Formula 2-6] was used instead of [Formula 1-6] of [Example 1-1].

Example 1-15

An organic light emitting diode was manufactured in the same manner as in [Example 1-1], except that [Formula 2-38] was used instead of [Formula 1-6] of [Example 1-1].

Example 1-16

An organic light emitting diode was manufactured in the same manner as in [Example 1-1], except that [Formula 2-90] was used instead of [Formula 1-6] of [Example 1-1].

Example 1-17

An organic light emitting diode was manufactured in the same manner as in [Example 1-1], except that [Formula 2-113] was used instead of [Formula 1-6] of [Example 1-1].

Example 1-18

An organic light emitting diode was manufactured in the same manner as in [Example 1-1], except that [Formula 2-141] was used instead of [Formula 1-6] of [Example 1-1].

Example 1-19

An organic light emitting diode was manufactured in the same manner as in [Example 1-1], except that [Formula 2-269] was used instead of [Formula 1-6] of [Example 1-1].

Example 1-20

An organic light emitting diode was manufactured in the same manner as in [Example 1-1], except that [Formula 1-40] and [Formula 3-6] were used instead of [Formula 1-6] and [Formula 3-3] of [Example 1-1], respectively.

Example 1-21

An organic light emitting diode was manufactured in the same manner as in [Example 1-20], except that [Formula 1-160] was used instead of [Formula 1-40] of [Example 1-20].

Example 1-22

An organic light emitting diode was manufactured in the same manner as in [Example 1-20], except that [Formula 1-345] was used instead of [Formula 1-40] of [Example 1-20].

Example 1-23

An organic light emitting diode was manufactured in the same manner as in [Example 1-20], except that [Formula 2-5] was used instead of [Formula 1-40] of [Example 1-20].

Example 1-24

An organic light emitting diode was manufactured in the same manner as in [Example 1-20], except that [Formula 2-353] was used instead of [Formula 1-40] of [Example 1-20].

Example 1-25

An organic light emitting diode was manufactured in the same manner as in [Example 1-1], except that [Formula 1-22] and [Formula 3-12] were used instead of [Formula 1-6] and [Formula 3-3] of [Example 1-1], respectively.

Example 1-26

An organic light emitting diode was manufactured in the same manner as in [Example 1-25], except that [Formula 1-92] was used instead of [Formula 1-22] of [Example 1-25].

Example 1-27

An organic light emitting diode was manufactured in the same manner as in [Example 1-25], except that [Formula 1-279] was used instead of [Formula 1-22] of [Example 1-25].

Example 1-28

An organic light emitting diode was manufactured in the same manner as in [Example 1-25], except that [Formula 2-70] was used instead of [Formula 1-22] of [Example 1-25].

Example 1-29

An organic light emitting diode was manufactured in the same manner as in [Example 1-25], except that [Formula 2-178] was used instead of [Formula 1-22] of [Example 1-25].

Example 1-30

An organic light emitting diode was manufactured in the same manner as in [Example 1-1], except that [Formula 1-53] was used instead of [Formula 1-6] of [Example 1-1].

Example 1-31

An organic light emitting diode was manufactured in the same manner as in [Example 1-1], except that [Formula 1-54] was used instead of [Formula 1-6] of [Example 1-1].

Example 1-32

An organic light emitting diode was manufactured in the same manner as in [Example 1-1], except that [Formula 1-55] was used instead of [Formula 1-6] of [Example 1-1].

Comparative Example 1-1

An organic light emitting diode was manufactured in the same manner as in [Example 1-1], except that Formula [NPB] was used instead of [Formula 3-3] of [Example 1-1].

Comparative Example 1-2

An organic light emitting diode was manufactured in the same manner as in [Example 1-2], except that Formula [NPB] was used instead of [Formula 3-3] of [Example 1-2].

Comparative Example 1-3

An organic light emitting diode was manufactured in the same manner as in [Example 1-4], except that Formula [NPB] was used instead of [Formula 3-3] of [Example 1-4].

Comparative Example 1-4

An organic light emitting diode was manufactured in the same manner as in [Example 1-12], except that Formula [NPB] was used instead of [Formula 3-3] of [Example 1-12].

Comparative Example 1-5

An organic light emitting diode was manufactured in the same manner as in [Example 1-18], except that Formula [TCTA] was used instead of [Formula 3-3] of [Example 1-18].

Comparative Example 1-6

An organic light emitting diode was manufactured in the same manner as in [Example 1-22], except that Formula [TCTA] was used instead of [Formula 3-6] of [Example 1-22].

Comparative Example 1-7

An organic light emitting diode was manufactured in the same manner as in [Example 1-28], except that Formula [TCTA] was used instead of [Formula 3-12] of [Example 1-28].

Comparative Example 1-8

An organic light emitting diode was manufactured in the same manner as in [Example 1-9], except that Formula [TCTA] was used instead of [Formula 3-3] of [Example 1-9].

Comparative Example 1-9

An organic light emitting diode was manufactured in the same manner as in [Example 1-6], except that Formula [HT-A] was used instead of [Formula 3-3] of [Example 1-6].

Comparative Example 1-10

An organic light emitting diode was manufactured in the same manner as in [Example 1-8], except that Formula [HT-A] was used instead of [Formula 3-3] of [Example 1-8].

Comparative Example 1-11

An organic light emitting diode was manufactured in the same manner as in [Example 1-26], except that Formula [HT-A] was used instead of [Formula 3-3] of [Example 1-26].

Comparative Example 1-12

An organic light emitting diode was manufactured in the same manner as in [Example 1-1], except that Formula [ET-A] was used instead of [Formula 1-6] of [Example 1-1].

Comparative Example 1-13

An organic light emitting diode was manufactured in the same manner as in [Example 1-1], except that Formula [ET-B] was used instead of [Formula 1-6] of [Example 1-1].

Comparative Example 1-14

An organic light emitting diode was manufactured in the same manner as in [Example 1-1], except that Formula [ET-C] was used instead of [Formula 1-6] of [Example 1-1].

Comparative Example 1-15

An organic light emitting diode was manufactured in the same manner as in [Example 1-1], except that Formula [ET-D] was used instead of [Formula 1-6] of [Example 1-1].

Comparative Example 1-16

An organic light emitting diode was manufactured in the same manner as in [Example 1-1], except that Formula [ET-E] was used instead of [Formula 1-6] of [Example 1-1].

Comparative Example 1-17

An organic light emitting diode was manufactured in the same manner as in [Example 1-1], except that Formula [ET-F] was used instead of [Formula 1-6] of [Example 1-1].

Comparative Example 1-18

An organic light emitting diode was manufactured in the same manner as in [Example 1-20], except that Formula [ET-G] was used instead of [Formula 1-40] of [Example 1-20].

Comparative Example 1-19

An organic light emitting diode was manufactured in the same manner as in [Example 1-20], except that Formula [ET-H] was used instead of [Formula 1-40] of [Example 1-20].

Comparative Example 1-20

An organic light emitting diode was manufactured in the same manner as in [Example 1-20], except that Formula [ET-I] was used instead of [Formula 1-40] of [Example 1-20].

Comparative Example 1-21

An organic light emitting diode was manufactured in the same manner as in [Example 1-25], except that Formula [ET-J] was used instead of [Formula 1-22] of [Example 1-25].

Comparative Example 1-22

An organic light emitting diode was manufactured in the same manner as in [Example 1-25], except that Formula [ET-K] was used instead of [Formula 1-22] of [Example 1-25].

Comparative Example 1-23

An organic light emitting diode was manufactured in the same manner as in [Example 1-1], except that Formula [Alq3] was used instead of [Formula 1-6] of [Example 1-1].

Comparative Example 1-24

An organic light emitting diode was manufactured in the same manner as in [Example 1-1], except that Formula [TPBI] was used instead of [Formula 1-6] of [Example 1-1].

For the organic light emitting diodes manufactured by the above-described method, the driving voltage and the light emitting efficiency were measured at a current density of 10 mA/cm$^2$, and a time T90 for reaching a 90% value compared to the initial luminance was measured at a current density of 20 mA/cm$^2$. The results are shown in the following Table 3.

TABLE 3

| | Voltage (V) | Efficiency (Cd/A) | Color coordinate (x,y) | Service life (h) T$_{90}$ at 20 mA/cm$^2$ |
|---|---|---|---|---|
| Example 1-1 | 4.30 | 6.65 | (0.138, 0.111) | 201 |
| Example 1-2 | 4.02 | 7.05 | (0.138, 0.109) | 223 |
| Example 1-3 | 4.42 | 6.82 | (0.138, 0.112) | 174 |
| Example 1-4 | 4.26 | 6.74 | (0.138, 0.109) | 207 |
| Example 1-5 | 4.48 | 6.25 | (0.138, 0.113) | 181 |
| Example 1-6 | 4.21 | 6.52 | (0.138, 0.110) | 193 |
| Example 1-7 | 4.53 | 6.38 | (0.138, 0.112) | 172 |
| Example 1-8 | 4.42 | 6.38 | (0.138, 0.110) | 170 |
| Example 1-9 | 4.52 | 6.33 | (0.138, 0.111) | 168 |
| Example 1-10 | 4.67 | 6.28 | (0.138, 0.111) | 175 |
| Example 1-11 | 4.55 | 6.19 | (0.138, 0.114) | 171 |
| Example 1-12 | 4.66 | 6.33 | (0.138, 0.112) | 173 |
| Example 1-13 | 4.61 | 6.21 | (0.138, 0.112) | 164 |
| Example 1-14 | 4.22 | 6.67 | (0.138, 0.109) | 191 |
| Example 1-15 | 4.71 | 6.26 | (0.138, 0.110) | 169 |
| Example 1-16 | 4.39 | 6.49 | (0.138, 0.112) | 184 |
| Example 1-17 | 4.62 | 6.35 | (0.138, 0.112) | 185 |
| Example 1-18 | 4.55 | 6.31 | (0.138, 0.114) | 163 |
| Example 1-19 | 4.35 | 6.53 | (0.138, 0.112) | 192 |
| Example 1-20 | 4.25 | 6.81 | (0.138, 0.109) | 187 |
| Example 1-21 | 4.51 | 6.51 | (0.138, 0.111) | 183 |
| Example 1-22 | 4.62 | 6.55 | (0.138, 0.112) | 176 |
| Example 1-23 | 4.51 | 6.51 | (0.138, 0.112) | 182 |
| Example 1-24 | 4.68 | 6.48 | (0.138, 0.112) | 189 |
| Example 1-25 | 4.43 | 6.69 | (0.138, 0.12) | 175 |
| Example 1-26 | 4.61 | 6.31 | (0.138, 0.111) | 163 |
| Example 1-27 | 4.77 | 6.15 | (0.138, 0.113) | 161 |
| Example 1-28 | 4.68 | 6.28 | (0.138, 0.112) | 177 |
| Example 1-29 | 4.42 | 6.52 | (0.138, 0.112) | 185 |
| Example 1-30 | 4.62 | 6.22 | (0.138, 0.111) | 182 |
| Example 1-31 | 4.45 | 6.42 | (0.138, 0.111) | 169 |
| Example 1-32 | 4.53 | 6.35 | (0.138, 0.110) | 173 |
| Comparative Example 1-1 | 5.19 | 5.34 | (0.138, 0.116) | 120 |
| Comparative Example 1-2 | 5.04 | 5.62 | (0.138, 0.115) | 130 |
| Comparative Example 1-3 | 5.32 | 4.95 | (0.138, 0.117) | 135 |
| Comparative Example 1-4 | 5.27 | 5.13 | (0.138, 0.116) | 122 |
| Comparative Example 1-5 | 5.82 | 4.63 | (0.138, 0.117) | 114 |
| Comparative Example 1-6 | 5.79 | 5.24 | (0.138, 0.115) | 125 |
| Comparative Example 1-7 | 5.73 | 4.71 | (0.138, 0.114) | 87 |
| Comparative Example 1-8 | 5.85 | 4.80 | (0.138, 0.112) | 99 |
| Comparative Example 1-9 | 4.81 | 5.81 | (0.138, 0.114) | 132 |
| Comparative Example 1-10 | 4.92 | 5.70 | (0.138, 0.113) | 123 |
| Comparative Example 1-11 | 5.10 | 5.65 | (0.138, 0.112) | 117 |
| Comparative Example 1-12 | 4.82 | 5.70 | (0.138, 0.112) | 133 |
| Comparative Example 1-13 | 5.22 | 4.37 | (0.138, 0.110) | 111 |
| Comparative Example 1-14 | 5.18 | 4.72 | (0.138, 0.114) | 124 |
| Comparative Example 1-15 | 5.29 | 4.51 | (0.138, 0.111) | 141 |
| Comparative Example 1-16 | 4.92 | 5.60 | (0.138, 0.112) | 137 |
| Comparative Example 1-17 | 5.10 | 5.51 | (0.138, 0.110) | 115 |
| Comparative Example 1-18 | 5.31 | 5.32 | (0.138, 0.114) | 117 |
| Comparative Example 1-19 | 4.82 | 5.73 | (0.138, 0.111) | 143 |
| Comparative Example 1-20 | 4.97 | 5.42 | (0.138, 0.110) | 151 |
| Comparative Example 1-21 | 5.39 | 4.21 | (0.138, 0.111) | 120 |
| Comparative Example 1-22 | 4.99 | 5.62 | (0.138, 0.113) | 137 |
| Comparative Example 1-23 | 5.65 | 5.41 | (0.138, 0.113) | 117 |
| Comparative Example 1-24 | 5.33 | 5.17 | (0.138, 0.112) | 132 |

From the result of Table 3, it can be confirmed that the compound represented by Formula 1 according to an exemplary embodiment of the present specification may be used for an organic layer which may simultaneously inject and transport electrons of the organic light emitting diode.

In the case of an organic light emitting diode using the same, it can be confirmed that the diode has a higher efficiency, a lower driving voltage, and a longer service life than the case where a triazine compound, in which at least two or more of Ar1 to Ar3 have the same symmetry, is used for an organic layer which may simultaneously inject and transport electrons.

In particular, the compound represented by Formula 1 according to the present invention was excellent in thermal stability, and had a deep HOMO level of 6.0 eV or more, and high triplet energy ($E_T$) and hole stability, thereby exhibiting excellent characteristics. When the compound is used in the organic layer which may simultaneously inject and transport electrons, the compound may be used in a mixture with an n-type dopant. Accordingly, the compound represented by Formula 1 has low driving voltage and high efficiency, and stability of the diode may be improved by hole stability of the compound.

As a result of Table 1, it can be confirmed that both the compounds represented by Formulae [ET-B] and [ET-J] have a triplet energy of less than 1.9 eV, and as a result of the Examples and the Comparative Examples of Table 3, it can be confirmed that a compound having a triplet energy of less than 2.2 eV has low diode efficiency. These results are because an effect of the triplet-triplet annihilation (TTA) is reduced when a compound having a triplet energy of less than 2.2 eV is used.

Further, it can be confirmed through Table 1 that the compounds represented by Formulae [ET-B] and [ET-J] have a HOMO level of less than 6 eV, and referring to the result of Table 3 obtained by evaluating the diodes, it can be confirmed that the diode has a short service life when the diode includes the compound. The result as described above is exhibited because an effect of blocking holes transferred from the light emitting layer is reduced in the organic light emitting diode including the compound having a HOMO energy level of less than 6 eV.

The ranges of the triplet energy and HOMO energy level values may be confirmed particularly in compounds including anthracene, and the effects with respect to the same may be confirmed in the Comparative Examples to which [ET-A], [ET-B], [ET-D], and [ET-J] are applied.

Accordingly, the compound, which is the heterocyclic compound represented by Formula 1 according to an exemplary embodiment of the present invention and has a HOMO energy level of 6 eV or more and a triplet energy of 2.2 eV, is more preferred in terms of driving voltage, efficiency, and/or service life of the diode.

Further, according to the document (J. AM. CHEM. SOC. 2003, 125, 3710-3711), it can be confirmed that a disubstituted fluorenyl group has higher electron mobility than that of a spirobifluorenyl group. Accordingly, it can be confirmed that the compound represented by Formula 1 transports electrons more efficiently than Formula [ET-J] or Formula [ET-K] used in the Comparative Examples and thus exhibits high efficiency, and also improves the service life.

In addition, it can be confirmed that when the results of Comparative Examples 1-1 to 1-24 are compared to those of Examples 1-1 to 1-32, an organic light emitting diode, in which the heterocyclic compound represented by Formula 1 is provided between the cathode and the light emitting layer, and the carbazole derivative represented by Formula 3 is provided between the anode and the light emitting layer, may provide an organic light emitting diode having low driving voltage, high light emitting efficiency, and/or a long service life.

In an exemplary embodiment of the present specification, the hole mobility of the compound represented by Formula 3 is $5 \times 10^{-6}$ cm$^2$/Vs or more. In another exemplary embodiment, the hole mobility of the compound represented by Formula 3 is $5 \times 10^{-6}$ cm$^2$/Vs or more under an electric field condition of 0.1 to 0.5 MV/cm. In still another exemplary embodiment, the hole mobility of the compound represented by Formula 3 is $5 \times 10^{-6}$ cm$^2$/Vs or more under an electric field condition of 0.1 MV/cm. In other exemplary embodiments, the hole mobility of the compound represented by Formula 3 is $10^{-6}$ cm$^2$/Vs or more.

The compound represented by Formula 3 according to an exemplary embodiment of the present specification has a hole mobility of $5 \times 10^{-6}$ cm$^2$/Vs or more under an electric field condition of 0.1 to 0.5 MV/cm, and the hole mobility is faster than that of the hole transporting material in the related art. Accordingly, the number of excitons produced in the light emitting layer may be increased, and thus high efficiency may be expected, but leakage of holes toward the cathode may be caused. However, when the organic material layer including the heterocyclic compound represented by Formula 1 according to an exemplary

The invention claimed is:
1. An organic light emitting diode comprising:
a cathode;
an anode;
a light emitting layer provided between the cathode and the anode;
an organic material layer comprising a heterocyclic compound represented by the following Formula 1 and provided between the cathode and the light emitting layer; and
an organic material layer comprising a carbazole derivative represented by the following Formula 3 and provided between the anode and the light emitting layer:

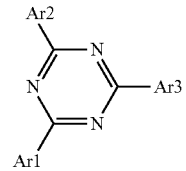

[Formula 1]

in Formula 1,
Ar1 to Ar3 are different from each other,
Ar1 and Ar2 are each independently a substituted or unsubstituted aryl group; or a substituted or unsubstituted heterocyclic group,
Ar3 is represented by the following Formula 2,

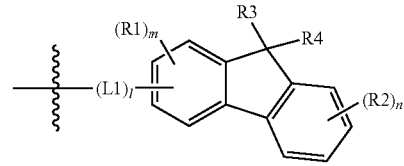

[Formula 2]

in Formula 2,
R1 to R4 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or combine with an adjacent group to form a substituted or unsubstituted hydrocarbon ring or a substituted or unsubstituted hetero ring, or the substituents in the same carbon combine with each other to form a substituted or unsubstituted spiro bond, L1 is a direct bond; a substituted or unsubstituted arylene group; or a substituted or unsubstituted divalent heterocyclic group, l is an integer of 1 to 5, m is an integer of 1 to 3, n is an integer of 1 to 4, and when l, m, and n are each an integer of 2 or more, two or more structures in the parenthesis are the same as or different from each other,

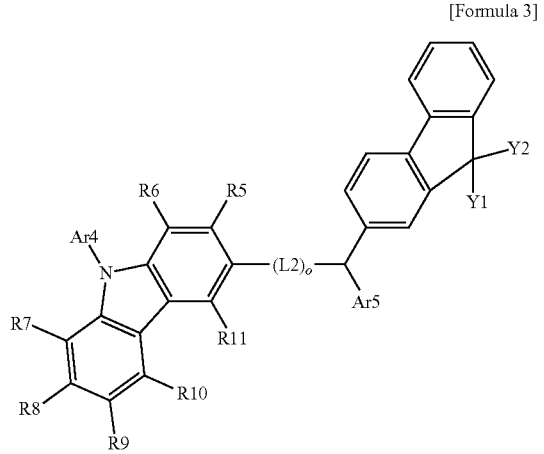

[Formula 3]

in Formula 3,

Ar4 and Ar5 are the same as or different from each other, and hydrogen; deuterium; a substituted or unsubstituted aryl group; or a substituted or unsubstituted heterocyclic group, L2 is a direct bond; or a substituted or unsubstituted arylene group, o is an integer of 0 to 5, and when o is an integer of 2 or more, two or more L2's are the same as or different from each other, R5 to R11 are the same as or different from each other, and each independently hydrogen; deuterium; a substituted or unsubstituted alkyl group; substituted or unsubstituted aryl group or a substituted or unsubstituted heterocyclic group, or combine with an adjacent group to form a substituted or unsubstituted hydrocarbon ring or a substituted or unsubstituted hetero ring, and Y1 and Y2 are the same as or different from each other, and each independently hydrogen; deuterium; a substituted or unsubstituted alkyl group; a substituted or unsubstituted aryl group; or a substituted or unsubstituted heterocyclic group, or Y1 and Y2 combine with each other to form a substituted or unsubstituted hydrocarbon ring or a substituted or unsubstituted hetero ring, wherein a HOMO energy level of the heterocyclic compound represented by Formula 1 is 6 eV or more.

2. The organic light emitting diode of claim 1, wherein the organic material layer comprising the heterocyclic compound represented by Formula 1 is an electron transporting layer, an electron injection layer, or a layer which simultaneously transports and injects electrons.

3. The organic light emitting diode of claim 1, wherein a triplet energy of the heterocyclic compound represented by Formula 1 is 2.2 eV or more.

4. The organic light emitting diode of claim 1, wherein a dipole moment of the heterocyclic compound represented by Formula 1 is 2 debye or less.

5. The organic light emitting diode of claim 1, wherein an electron mobility of the heterocyclic compound represented by Formula 1 is $10^{-6}$ cm$^2$/Vs or more.

6. The organic light emitting diode of claim 1, wherein the light emitting layer comprises a host and a dopant, and a difference between a HOMO energy level of the host and a HOMO energy level of the heterocyclic compound represented by Formula 1 is 0.2 eV or more.

7. The organic light emitting diode of claim 1, wherein the light emitting layer comprises a host and a dopant, and a triplet energy of the heterocyclic compound represented by Formula 1 is larger than that of the host.

8. The organic light emitting diode of claim 1, wherein the organic material layer comprising the heterocyclic compound represented by Formula 1 further comprises an n-type dopant represented by the following Formula 10:

[Formula 10]

A is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, a curved line represents a bond required for forming a 5-membered or 6-membered ring having M, and two or three atoms, and the atom is unsubstituted or substituted with a substituent which is the same as the definition of one or two or more A's, and M is an alkali metal or an alkaline earth metal.

9. The organic light emitting diode of claim 8, wherein the n-type dopant represented by Formula 10 is represented by the following Formula 10-1 or 10-2:

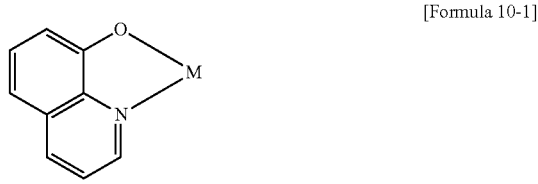

[Formula 10-1]

-continued

[Formula 10-2]

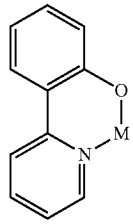

in Formulae 10-1 and 10-2,

M is the same as that defined in Formula 10, and

Formulae 10-1 and 10-2 are each independently unsubstituted or substituted with one or two or more substituents selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituents combine with each other to form a substituted or unsubstituted hydrocarbon ring or a substituted or unsubstituted hetero ring.

10. The organic light emitting diode of claim 1, wherein Ar1 and Ar2 are different from each other, and each independently a phenyl group, which is unsubstituted or substituted with an aryl group; a biphenyl group, which is unsubstituted or substituted with an aryl group; a terphenyl group, which is unsubstituted or substituted with an aryl group; a quarterphenyl group, which is unsubstituted or substituted with an aryl group; a naphthyl group, which is unsubstituted or substituted with an aryl group; or a phenanthryl group, which is unsubstituted or substituted with an aryl group.

11. The organic light emitting diode of claim 1, wherein R1 to R4 are the same as or different from each other, and each independently hydrogen; a substituted or unsubstituted alkyl group; or a substituted or unsubstituted aryl group, or combine with an adjacent group to form a substituted or unsubstituted hydrocarbon ring, or the substituents in the same carbon combine with each other to form a substituted or unsubstituted spiro bond.

12. The organic light emitting diode of claim 1, wherein L1 is a direct bond; a substituted or unsubstituted phenylene group; a substituted or unsubstituted biphenylylene group; a substituted or unsubstituted naphthalene group; or a substituted or unsubstituted phenanthrenylene group.

13. The organic light emitting diode of claim 1, wherein the heterocyclic compound represented by Formula 1 is represented by the following Formula 1-B:

[Formula 1-B]

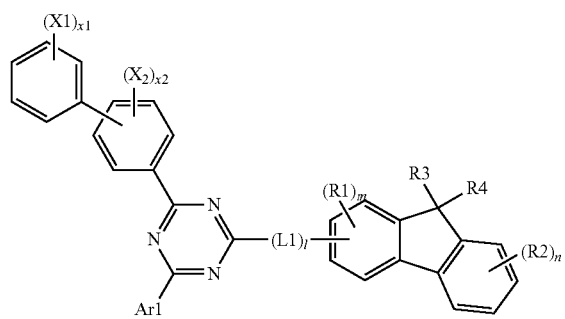

R1 to R4, Ar1, L1, l, m, and n are the same as those defined in Formula 1, x1 is an integer of 1 to 5, and x2 is an integer of 1 to 4, and when x1 and x2 are an integer of 2 or more, two or more structures in the parenthesis are the same as or different from each other, and X1 and X2 are the same as or different from each other, and each independently hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, or two or more adjacent groups combine with each other to form a substituted or unsubstituted hydrocarbon ring; or a substituted or unsubstituted hetero ring.

14. The organic light emitting diode of claim 1, wherein the heterocyclic compound represented by Formula 1 is represented by any one of the following Formulae 1-1 to 1-627 and 2-1 to 2-363

| Formula | ----Ar1 | ----Ar2 | ----Ar3 |
|---|---|---|---|
| 1-1 | ----⟨phenyl⟩ | ----⟨biphenyl⟩ | ⟨fluorenyl⟩ |

-continued
| Formula | ----Ar1 | ----Ar2 | ----Ar3 |
|---|---|---|---|
| 1-2 | 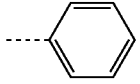 | 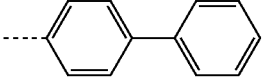 | 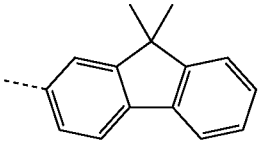 |
| 1-3 | 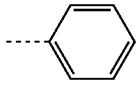 | 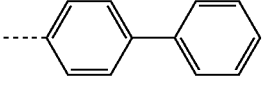 | 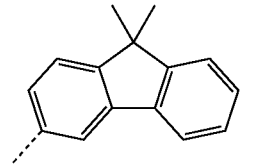 |
| 1-4 | 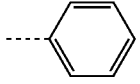 | 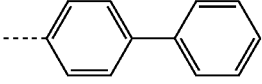 | 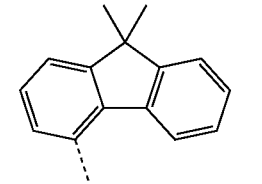 |
| 1-5 | 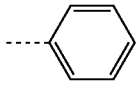 | 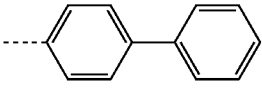 | 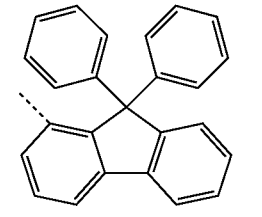 |
| 1-6 | 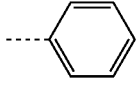 | 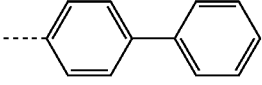 | 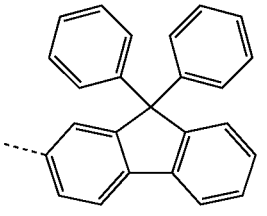 |
| 1-7 | 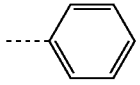 | 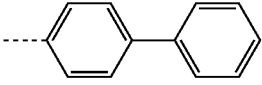 | 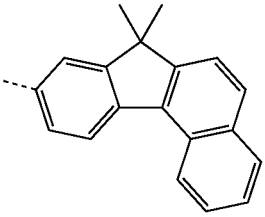 |
| 1-8 | 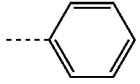 | 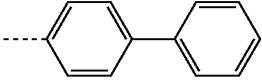 | 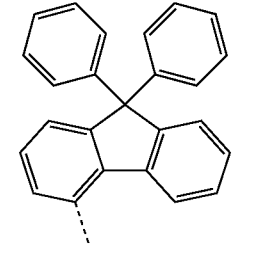 |

-continued
| Formula | ----Ar1 | ----Ar2 | ----Ar3 |
|---|---|---|---|
| 1-9 | 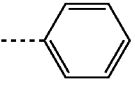 | 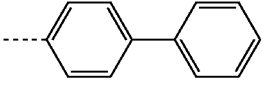 | 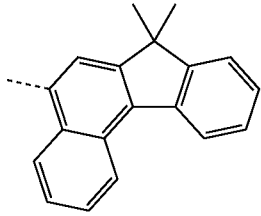 |
| 1-10 | 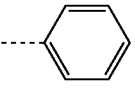 | 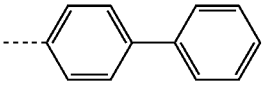 | 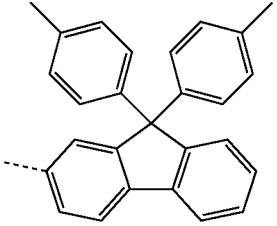 |
| 1-11 | 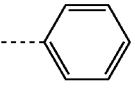 | 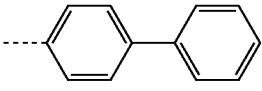 | 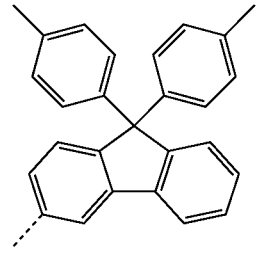 |
| 1-12 | 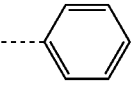 | 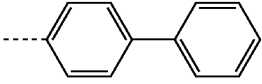 | 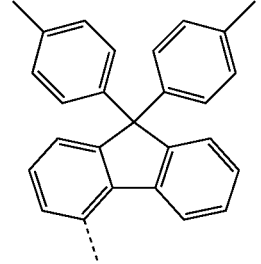 |
| 1-13 | 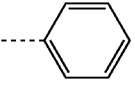 | 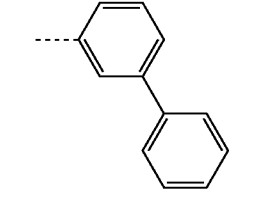 | 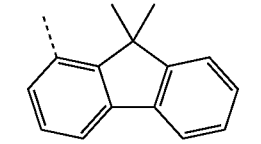 |
| 1-14 | 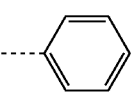 | 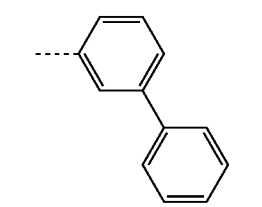 | 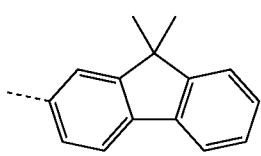 |

-continued

| Formula | ----Ar1 | ----Ar2 | ----Ar3 |
|---|---|---|---|
| 1-15 | phenyl | biphenyl | 9,9-dimethyl-2-phenylfluorene |
| 1-16 | phenyl | biphenyl | 9,9-dimethyl-2-phenylfluorene |
| 1-17 | phenyl | biphenyl | 9,9-diphenylfluorene |
| 1-18 | phenyl | biphenyl | 9,9-diphenylfluorene |
| 1-19 | phenyl | biphenyl | 9,9-diphenylfluorene |
| 1-20 | phenyl | biphenyl | 9,9-diphenylfluorene |
| 1-21 | phenyl | biphenyl | 9,9-di(p-tolyl)fluorene |

-continued

| Formula | ----Ar1 | ----Ar2 | ----Ar3 |
|---|---|---|---|
| 1-22 | phenyl | 3-biphenyl | 9,9-di(p-tolyl)fluoren-2-yl |
| 1-23 | phenyl | 3-biphenyl | 9,9-dimethyl-9H-benzo[b]fluoren-2-yl |
| 1-24 | phenyl | 3-biphenyl | 9,9-di(p-tolyl)fluoren-4-yl |
| 1-25 | phenyl | 2-biphenyl | 9,9-dimethylfluoren-1-yl |
| 1-26 | phenyl | 2-biphenyl | 9,9-dimethyl-7-phenylfluoren-2-yl |
| 1-27 | phenyl | 2-biphenyl | 9-methyl-9-phenylfluoren-3-yl |
| 1-28 | phenyl | 2-biphenyl | 9,9-dimethylfluoren-4-yl |

-continued

| Formula | ----Ar1 | ----Ar2 | ----Ar3 |
|---|---|---|---|
| 1-29 | phenyl | 2-biphenyl | 9,9-diphenyl-fluoren-1-yl |
| 1-30 | phenyl | 2-biphenyl | 9,9-diphenyl-fluoren-2-yl |
| 1-31 | phenyl | 2-biphenyl | 9,9-dimethyl-dibenzo[g]fluorenyl |
| 1-32 | phenyl | 2-biphenyl | 9,9-diphenyl-fluoren-4-yl |
| 1-33 | phenyl | 2-biphenyl | 9,9-dimethyl-benzo[b]fluorenyl |
| 1-34 | phenyl | 2-biphenyl | 9,9-di(p-tolyl)-fluoren-2-yl |

-continued
| Formula | ----Ar1 | ----Ar2 | ----Ar3 |
|---|---|---|---|
| 1-35 | 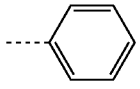 | 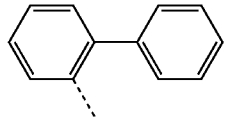 | 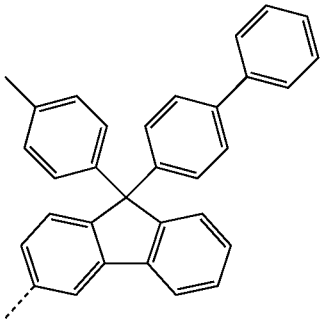 |
| 1-36 | 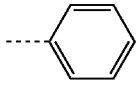 | 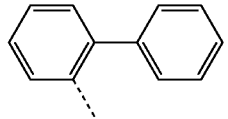 | 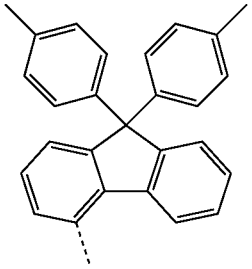 |
| 1-37 | 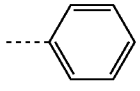 | 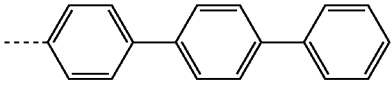 | 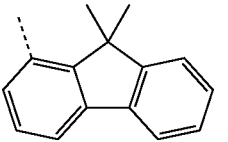 |
| 1-38 | 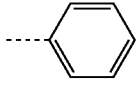 | 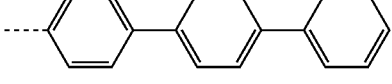 | 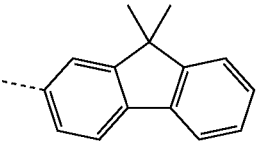 |
| 1-39 | 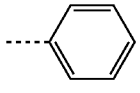 | 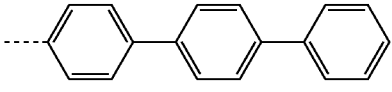 | 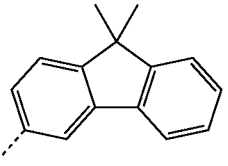 |
| 1-40 | 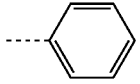 | 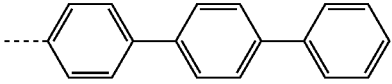 | 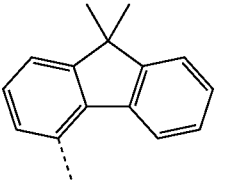 |
| 1-41 | 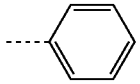 | 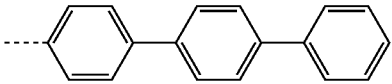 | 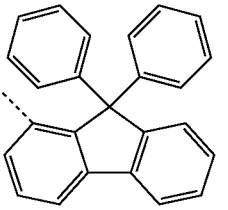 |

-continued
| Formula | ----Ar1 | ----Ar2 | ----Ar3 |
|---|---|---|---|
| 1-42 | 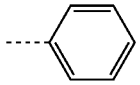 | 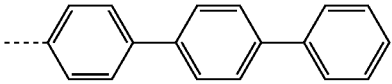 | 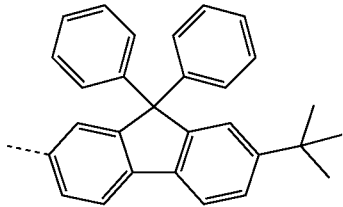 |
| 1-43 | 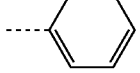 | 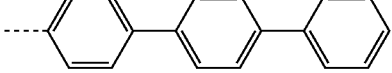 | 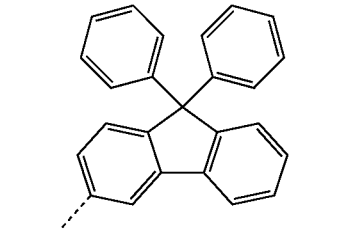 |
| 1-44 | 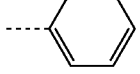 | 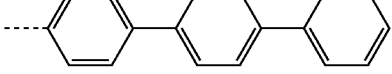 | 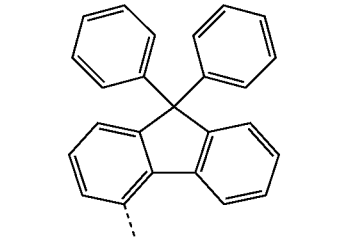 |
| 1-45 | 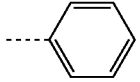 | 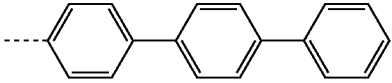 | 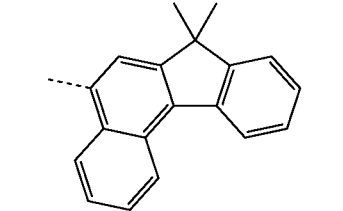 |
| 1-46 | 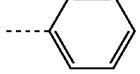 | 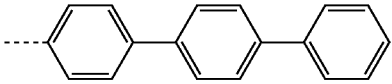 | 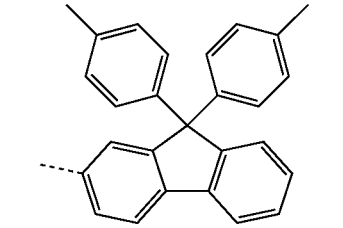 |
| 1-47 | 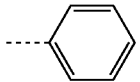 | 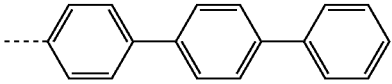 | 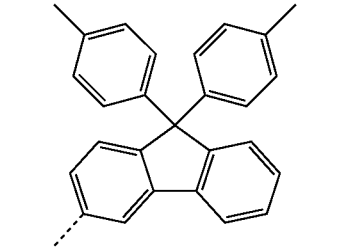 |

-continued

| Formula | ----Ar1 | ----Ar2 | ----Ar3 |
|---|---|---|---|
| 1-48 | | | |
| 1-49 | | | |
| 1-50 | | | |
| 1-51 | | | |
| 1-52 | | | |

-continued
| Formula | ----Ar1 | ----Ar2 | ----Ar3 |
|---|---|---|---|
| 1-53 | 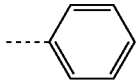 | 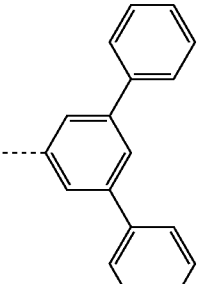 | 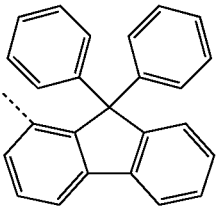 |
| 1-54 | 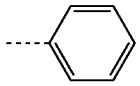 | 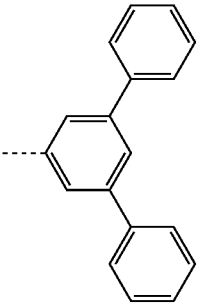 | 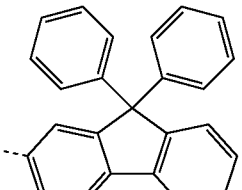 |
| 1-55 | 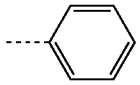 | 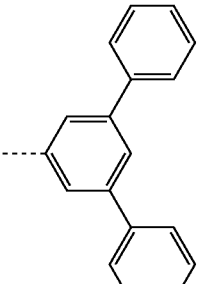 | 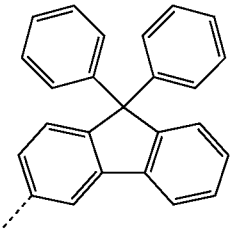 |
| 1-56 | 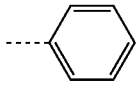 | 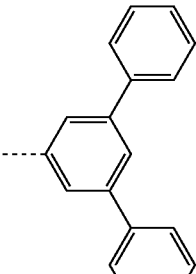 | 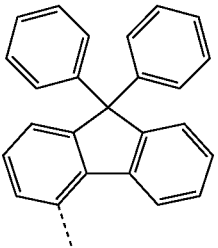 |
| 1-57 | 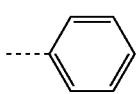 | 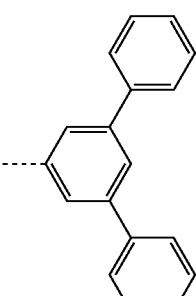 | 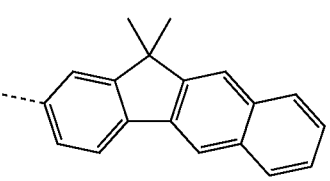 |

-continued

| Formula | ----Ar1 | ----Ar2 | ----Ar3 |
|---|---|---|---|
| 1-58 | | | |
| 1-59 | | | |
| 1-60 | | | |
| 1-61 | | | |
| 1-62 | | | |
| 1-63 | | | |

-continued
| Formula | ----Ar1 | ----Ar2 | ----Ar3 |
|---|---|---|---|
| 1-64 | 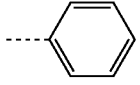 | 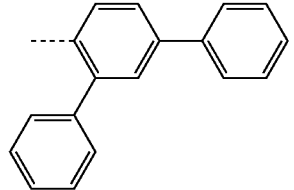 | 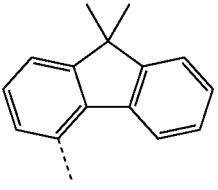 |
| 1-65 | 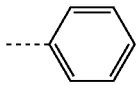 | 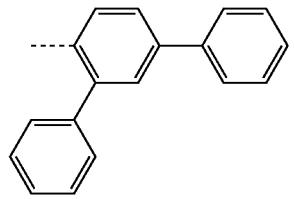 | 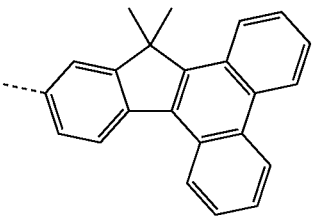 |
| 1-66 | 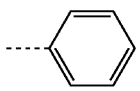 | 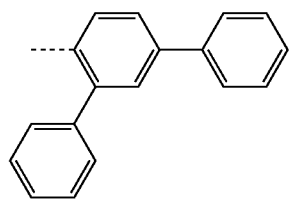 | 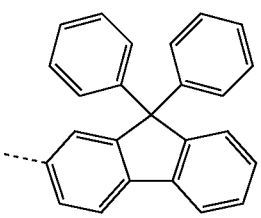 |
| 1-67 | 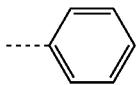 | 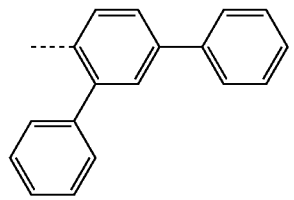 | 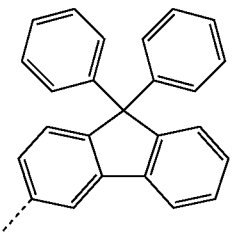 |
| 1-68 | 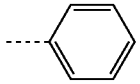 | 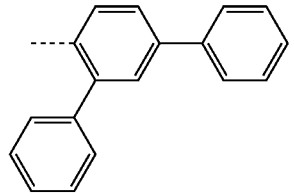 | 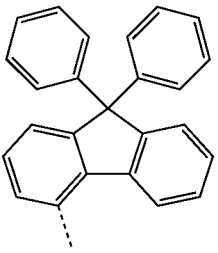 |
| 1-69 | 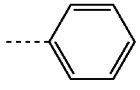 | 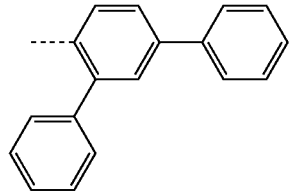 | 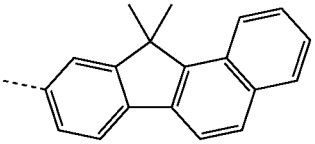 |

-continued
| Formula | ----Ar1 | ----Ar2 | ----Ar3 |
|---|---|---|---|
| 1-70 | 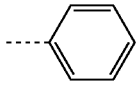 | 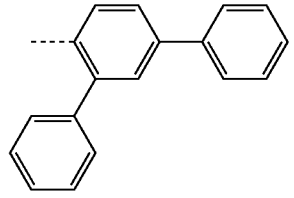 | 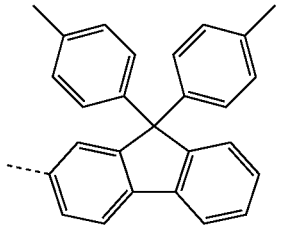 |
| 1-71 | 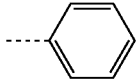 | 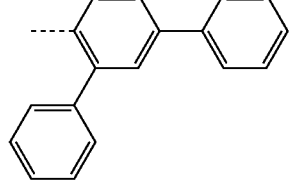 | 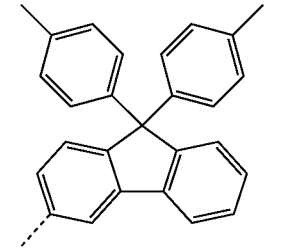 |
| 1-72 | 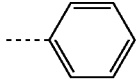 | 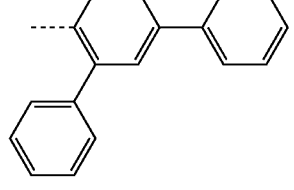 | 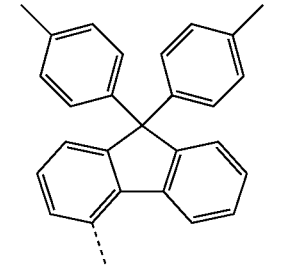 |
| 1-73 | 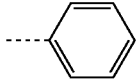 | 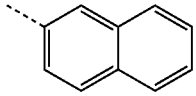 | 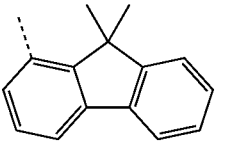 |
| 1-74 | 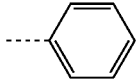 | 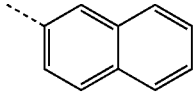 | 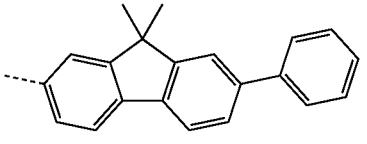 |
| 1-75 | 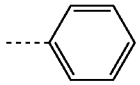 | 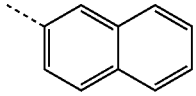 | 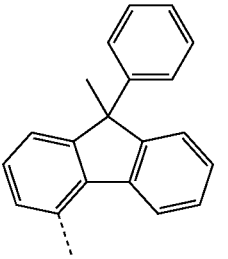 |
| 1-76 | 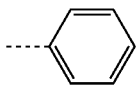 | 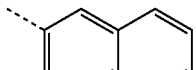 | 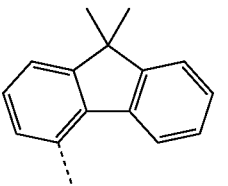 |

-continued
| Formula | ----Ar1 | ----Ar2 | ----Ar3 |
|---|---|---|---|
| 1-77 | 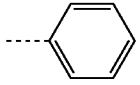 | 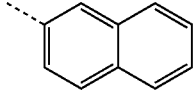 | 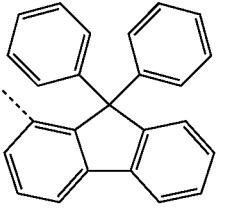 |
| 1-78 | 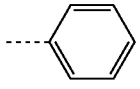 | 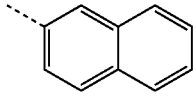 | 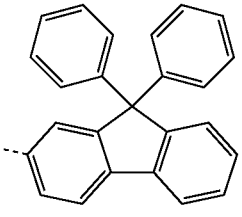 |
| 1-79 | 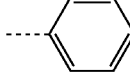 | 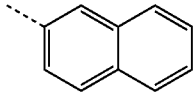 | 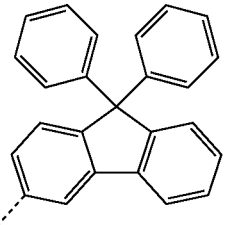 |
| 1-80 | 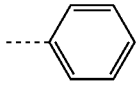 | 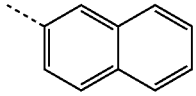 | 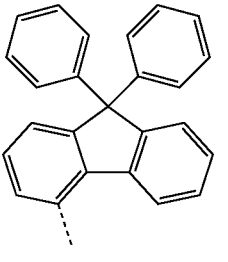 |
| 1-81 | 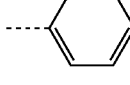 | 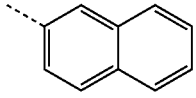 | 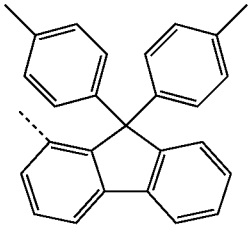 |
| 1-82 | 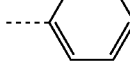 | 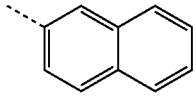 | 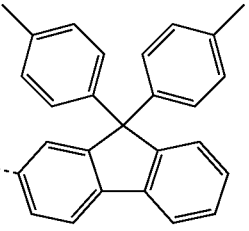 |

-continued
| Formula | ----Ar1 | ----Ar2 | ----Ar3 |
|---|---|---|---|
| 1-83 | 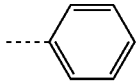 | 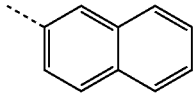 | 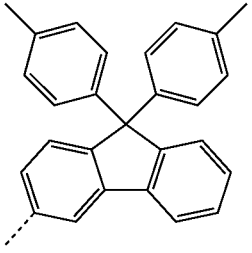 |
| 1-84 | 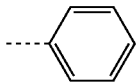 | 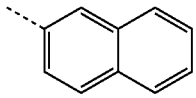 | 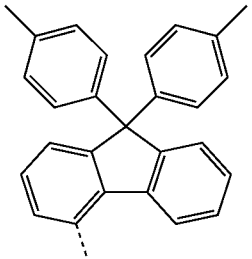 |
| 1-85 | 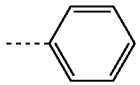 | 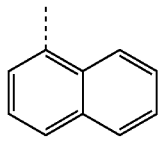 | 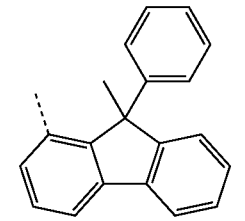 |
| 1-86 | 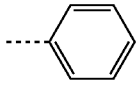 | 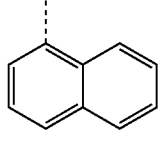 | 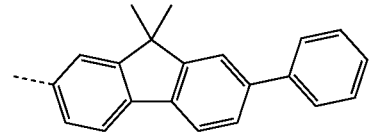 |
| 1-87 | 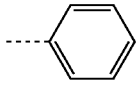 | 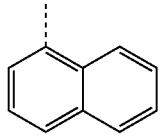 | 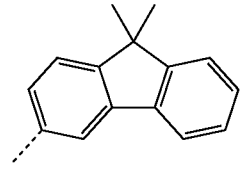 |
| 1-88 | 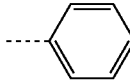 | 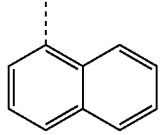 | 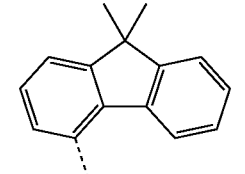 |
| 1-89 | 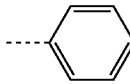 | 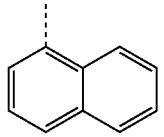 | 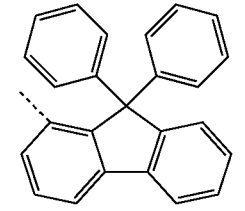 |

-continued
| Formula | ----Ar1 | ----Ar2 | ----Ar3 |
|---|---|---|---|
| 1-90 | 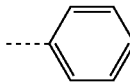 | 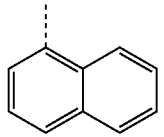 | 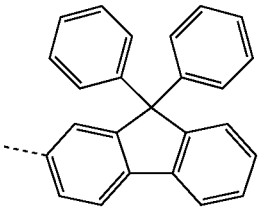 |
| 1-91 | 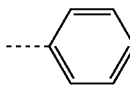 | 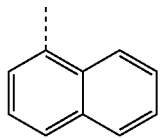 | 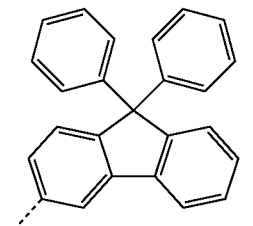 |
| 1-92 | 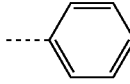 | 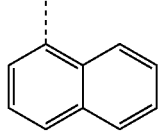 | 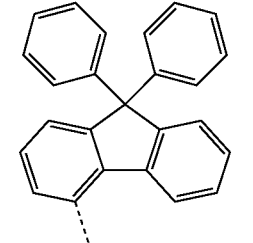 |
| 1-93 | 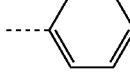 | 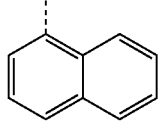 | 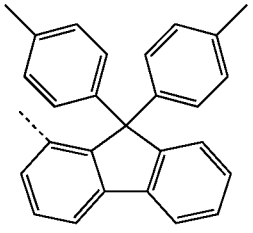 |
| 1-94 | 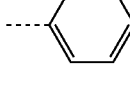 | 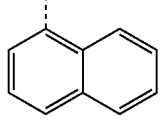 | 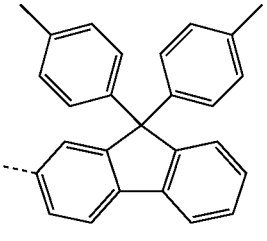 |
| 1-95 | 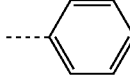 | 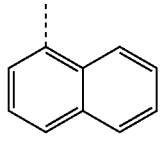 | 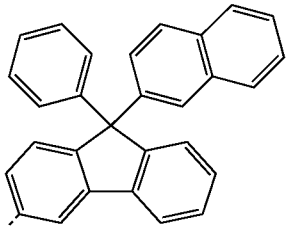 |

-continued
| Formula | ----Ar1 | ----Ar2 | ----Ar3 |
|---|---|---|---|
| 1-96 | 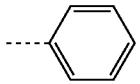 | 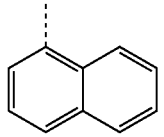 | 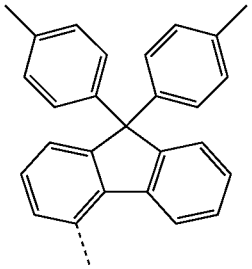 |
| 1-97 | 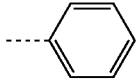 | 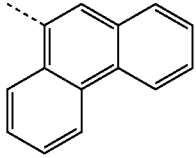 | 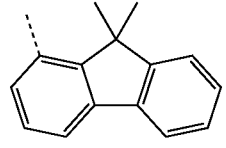 |
| 1-98 | 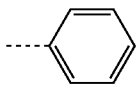 | 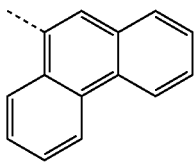 | 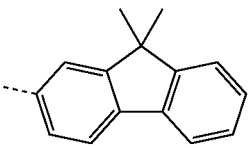 |
| 1-99 | 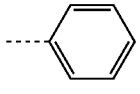 | 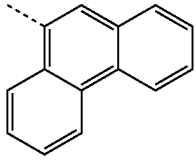 | 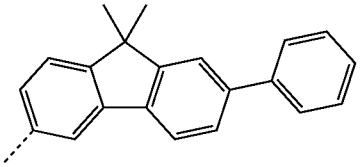 |
| 1-100 | 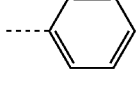 | 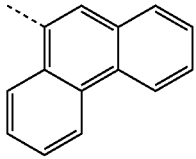 | 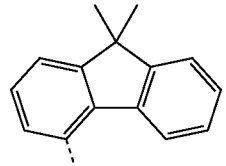 |
| 1-101 | 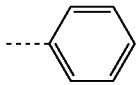 | 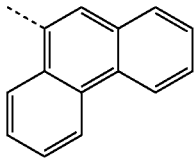 | 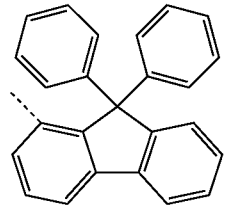 |
| 1-102 | 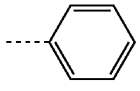 | 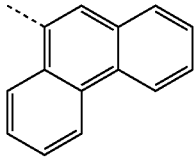 | 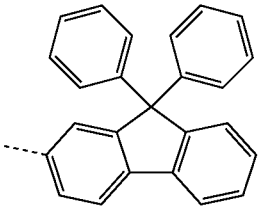 |

-continued
| Formula | ----Ar1 | ----Ar2 | ----Ar3 |
|---|---|---|---|
| 1-103 | 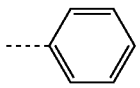 | 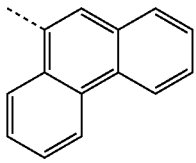 | 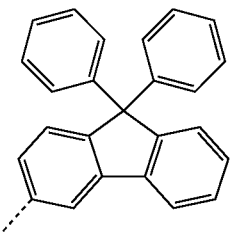 |
| 1-104 | 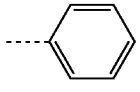 | 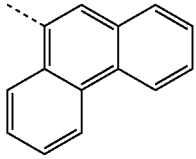 | 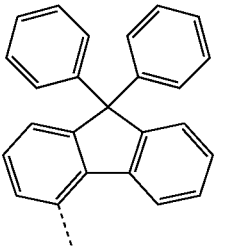 |
| 1-105 | 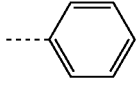 | 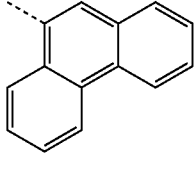 | 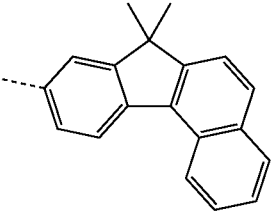 |
| 1-106 | 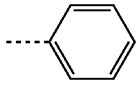 | 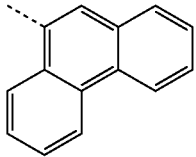 | 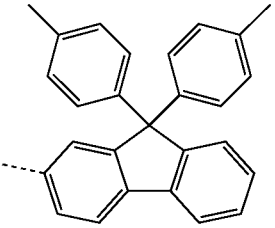 |
| 1-107 | 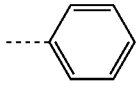 | 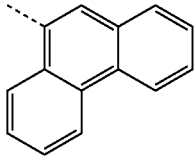 | 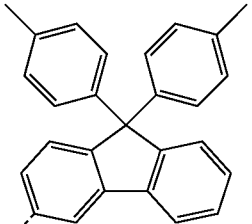 |
| 1-108 | 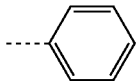 | 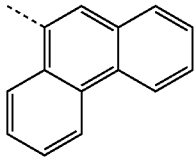 | 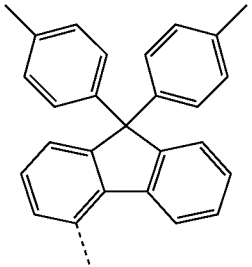 |

-continued
| Formula | ----Ar1 | ----Ar2 | ----Ar3 |
|---|---|---|---|
| 1-109 | 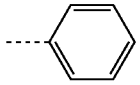 | 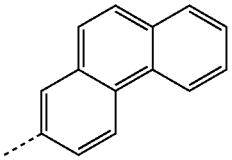 | 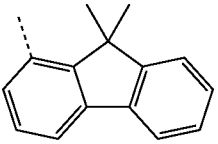 |
| 1-110 | 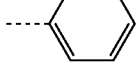 | 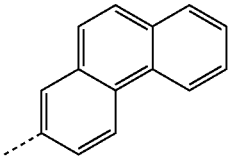 | 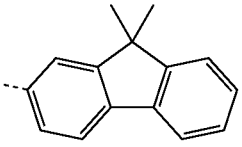 |
| 1-111 | 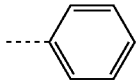 | 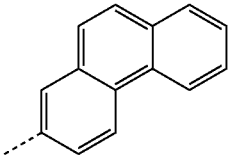 | 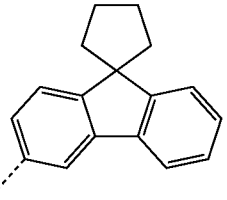 |
| 1-112 | 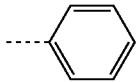 | 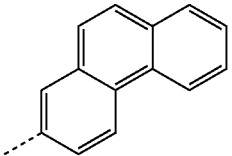 | 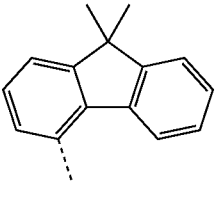 |
| 1-113 | 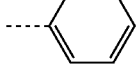 | 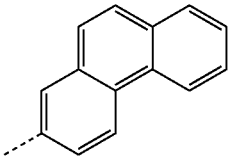 | 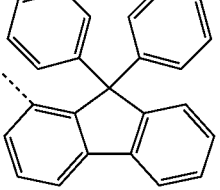 |
| 1-114 | 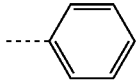 | 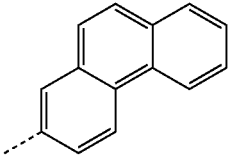 | 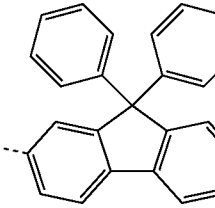 |
| 1-115 | 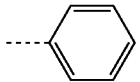 | 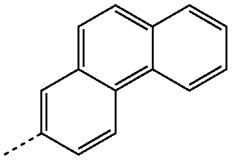 | 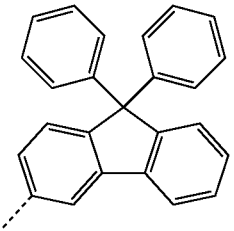 |

-continued

| Formula | ----Ar1 | ----Ar2 | ----Ar3 |
|---|---|---|---|
| 1-116 | phenyl | phenanthrenyl | 9,9-diphenylfluorenyl |
| 1-117 | phenyl | phenanthrenyl | 9,9-bis(methylphenyl)fluorenyl |
| 1-118 | phenyl | phenanthrenyl | 9,9-bis(methylphenyl)fluorenyl |
| 1-119 | phenyl | phenanthrenyl | dimethyl-benzofluorenyl |
| 1-120 | phenyl | phenanthrenyl | 9,9-bis(methylphenyl)fluorenyl |
| 1-121 | phenyl | phenanthrenyl | 9,9-dimethylfluorenyl |

-continued
| Formula | ----Ar1 | ----Ar2 | ----Ar3 |
|---|---|---|---|
| 1-122 | 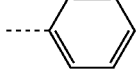 | 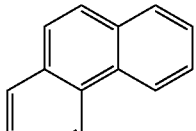 | 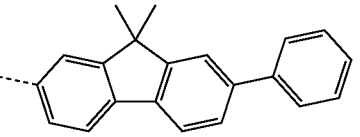 |
| 1-123 | 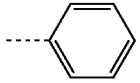 | 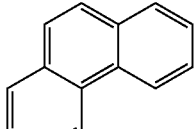 | 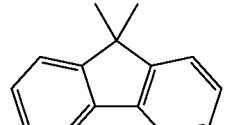 |
| 1-124 | 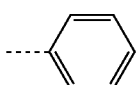 | 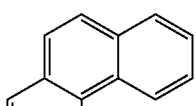 | 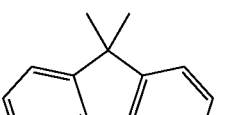 |
| 1-125 | 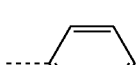 | 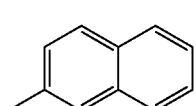 | 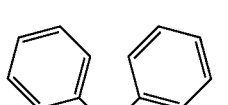 |
| 1-126 | 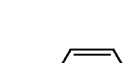 | 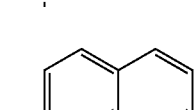 | 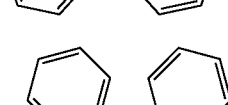 |
| 1-127 | 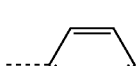 | 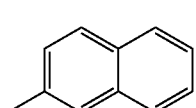 | 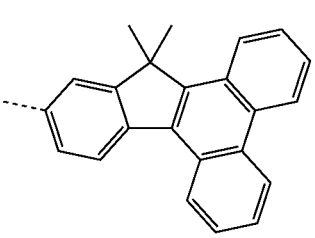 |
| 1-128 | 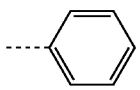 | 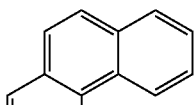 | 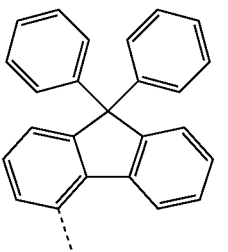 |

-continued

| Formula | ----Ar1 | ----Ar2 | ----Ar3 |
|---------|---------|---------|---------|
| 1-129 | | | |
| 1-130 | | | |
| 1-131 | | | |
| 1-132 | | | |
| 1-133 | | | |
| 1-134 | | | |

-continued

| Formula | ----Ar1 | ----Ar2 | ----Ar3 |
|---|---|---|---|
| 1-135 | biphenyl | biphenyl | 9,9-dimethylfluorene |
| 1-136 | biphenyl | biphenyl | 9,9-dimethylfluorene |
| 1-137 | biphenyl | biphenyl | 9,9-diphenylfluorene |
| 1-138 | phenyl | naphthylphenyl | 9,9-diphenylfluorene |
| 1-139 | biphenyl | biphenyl | 9,9-diphenylfluorene |
| 1-140 | biphenyl | biphenyl | 9,9-diphenylfluorene |
| 1-141 | biphenyl | biphenyl | 9,9-di(p-tolyl)fluorene |

-continued
| Formula | ----Ar1 | ----Ar2 | ----Ar3 |
|---|---|---|---|
| 1-142 | 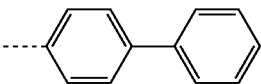 | 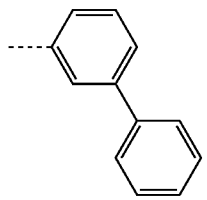 | 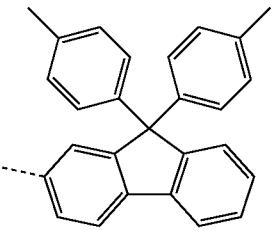 |
| 1-143 | 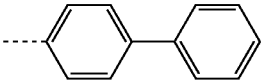 | 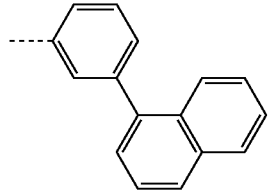 | 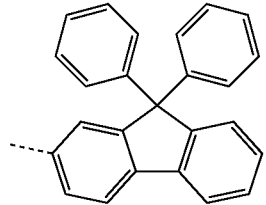 |
| 1-144 | 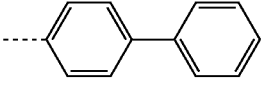 | 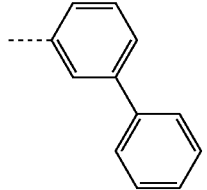 | 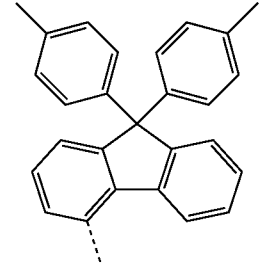 |
| 1-145 | 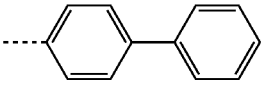 | 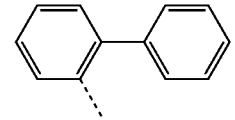 | 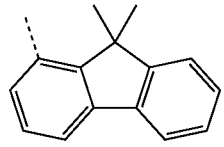 |
| 1-146 | 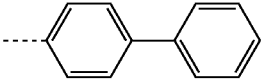 | 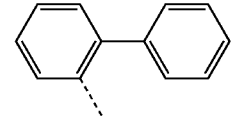 | 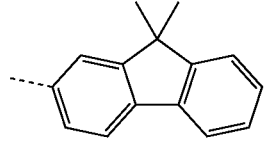 |
| 1-147 | 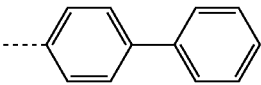 | 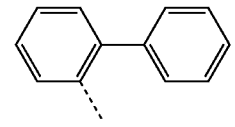 | 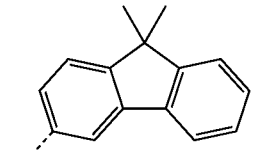 |
| 1-148 | 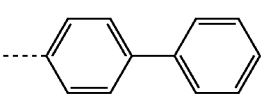 | 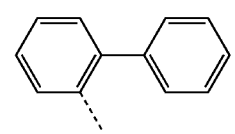 | 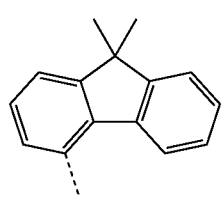 |

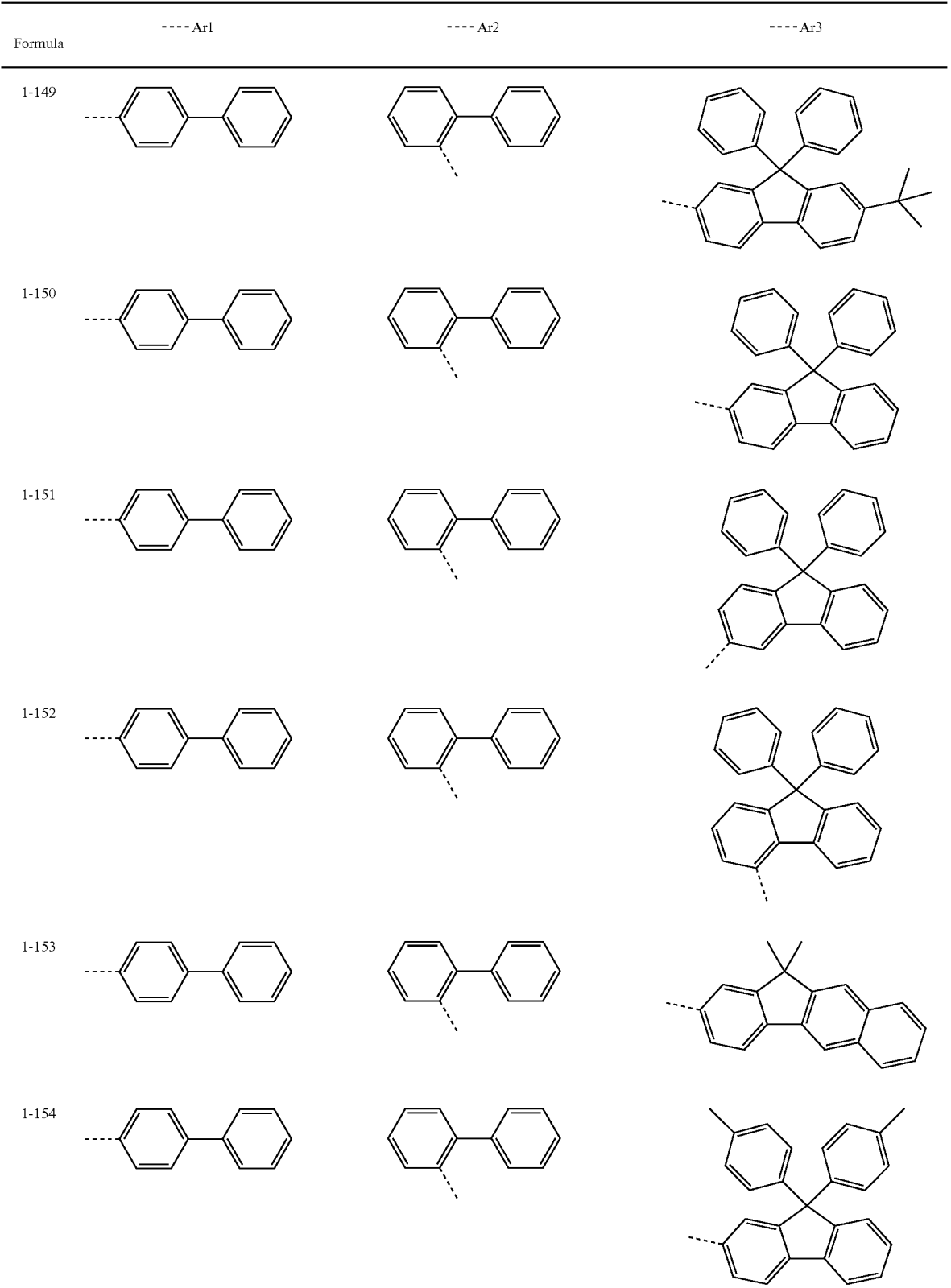

-continued

| Formula | ----Ar1 | ----Ar2 | ----Ar3 |
|---|---|---|---|
| 1-155 | | | |
| 1-156 | | | |
| 1-157 | | | |
| 1-158 | | | |
| 1-159 | | | |
| 1-160 | | | |
| 1-161 | | | |

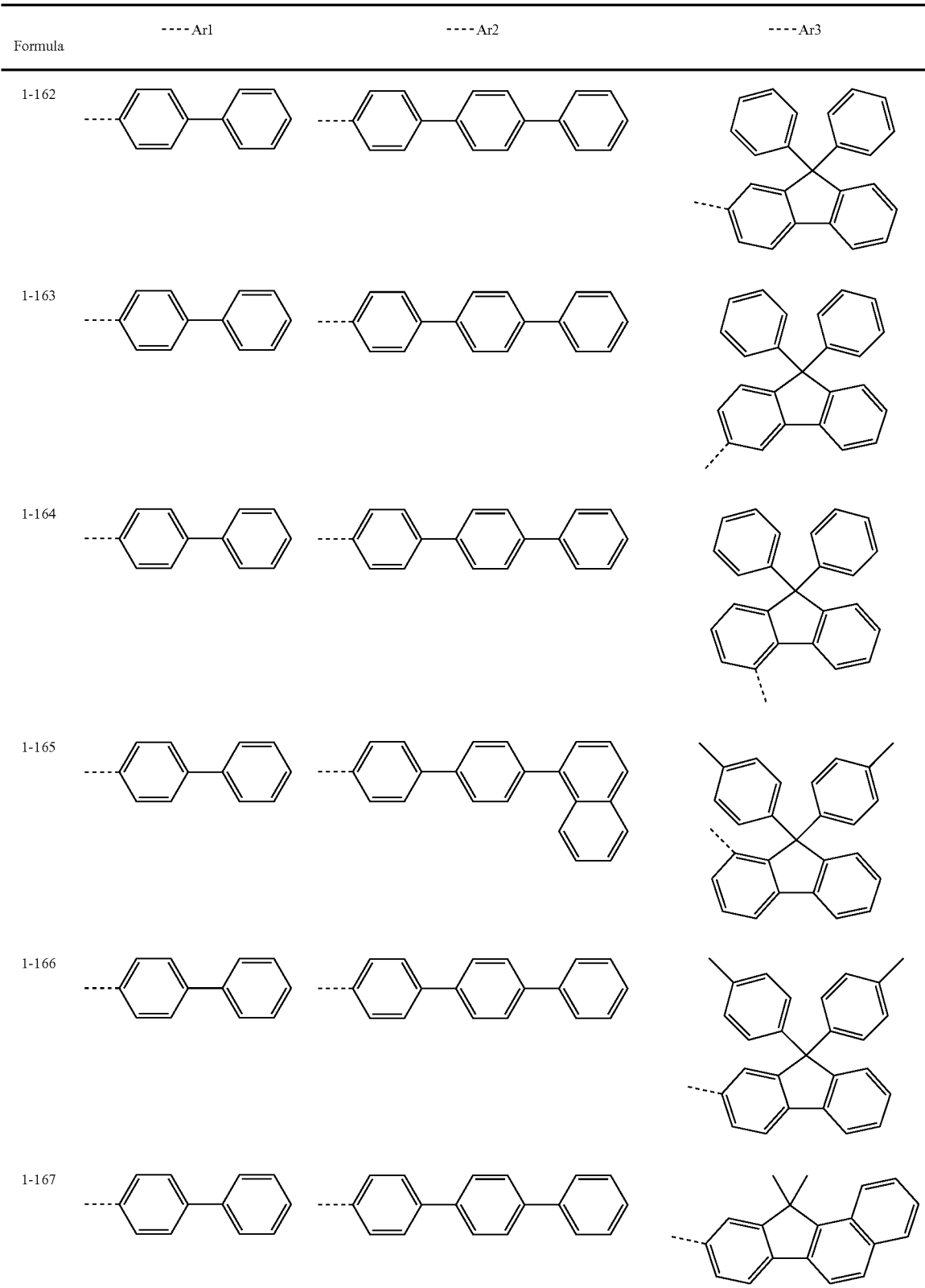

-continued

| Formula | ----Ar1 | ----Ar2 | ----Ar3 |
|---|---|---|---|
| 1-168 | | | |
| 1-169 | | | |
| 1-170 | | | |
| 1-171 | | | |
| 1-172 | | | |

-continued

| Formula | ----Ar1 | ----Ar2 | ----Ar3 |
|---|---|---|---|
| 1-173 | | | |
| 1-174 | | | |
| 1-175 | | | |
| 1-176 | | | |
| 1-177 | | | |

-continued

| Formula | ----Ar1 | ----Ar2 | ----Ar3 |
|---|---|---|---|
| 1-178 | | | |
| 1-179 | | | |
| 1-180 | | | |
| 1-181 | | | |
| 1-182 | | | |
| 1-183 | | | |

-continued

| Formula | ----Ar1 | ----Ar2 | ----Ar3 |
|---|---|---|---|
| 1-184 | | | |
| 1-185 | | | |
| 1-186 | | | |
| 1-187 | | | |
| 1-188 | | | |
| 1-189 | | | |

-continued

| Formula | ----Ar1 | ----Ar2 | ----Ar3 |
|---|---|---|---|
| 1-190 | | | |
| 1-191 | | | |
| 1-192 | | | |
| 1-193 | | | |
| 1-194 | | | |
| 1-195 | | | |
| 1-196 | | | |

-continued

| Formula | ----Ar1 | ----Ar2 | ----Ar3 |
|---|---|---|---|
| 1-197 | biphenyl | 2-naphthyl | 9,9-diphenylfluoren-1-yl |
| 1-198 | biphenyl | 2-naphthyl | 9,9-diphenylfluoren-2-yl |
| 1-199 | biphenyl | 6-phenylnaphthalen-2-yl | 9,9-diphenylfluoren-3-yl |
| 1-200 | biphenyl | 6-phenylnaphthalen-2-yl | 9,9-diphenylfluoren-4-yl |
| 1-201 | biphenyl | 2-naphthyl | 9,9-di(p-tolyl)fluoren-1-yl |
| 1-202 | biphenyl | 2-naphthyl | 9,9-di(p-tolyl)fluoren-2-yl |

-continued

| Formula | ----Ar1 | ----Ar2 | ----Ar3 |
|---|---|---|---|
| 1-203 | | | |
| 1-204 | | | |
| 1-205 | | | |
| 1-206 | | | |
| 1-207 | | | |
| 1-208 | | | |
| 1-209 | | | |

-continued

| Formula | ----Ar1 | ----Ar2 | ----Ar3 |
|---|---|---|---|
| 1-210 | biphenyl | 1-naphthyl | 9,9-diphenylfluoren-2-yl |
| 1-211 | biphenyl | 1-naphthyl | 9,9-diphenylfluoren-3-yl |
| 1-212 | biphenyl | 1-naphthyl | 9,9-diphenylfluoren-4-yl |
| 1-213 | biphenyl | 4-phenyl-1-naphthyl | 9,9-di(p-tolyl)fluoren-1-yl |
| 1-214 | biphenyl | 1-naphthyl | 9,9-di(p-tolyl)fluoren-2-yl |
| 1-215 | biphenyl | 1-naphthyl | 9,9-di(p-tolyl)fluoren-3-yl |

-continued

| Formula | ----Ar1 | ----Ar2 | ----Ar3 |
|---|---|---|---|
| 1-216 | biphenyl | 1-naphthyl | 9,9-di(p-tolyl)fluoren-4-yl |
| 1-217 | biphenyl | phenanthrenyl | 9,9-dimethylfluoren-1-yl |
| 1-218 | biphenyl | phenanthrenyl | 9,9-dimethylfluoren-2-yl |
| 1-219 | biphenyl | phenanthrenyl | 9,9-dimethylfluoren-3-yl |
| 1-220 | biphenyl | 10-phenylphenanthrenyl | 9,9-dimethylfluoren-4-yl |
| 1-221 | biphenyl | phenanthrenyl | 9,9-diphenylfluoren-1-yl |
| 1-222 | biphenyl | phenanthrenyl | 9,9-diphenylfluoren-2-yl |

-continued

| Formula | ----Ar1 | ----Ar2 | ----Ar3 |
|---|---|---|---|
| 1-223 | | | |
| 1-224 | | | |
| 1-225 | | | |
| 1-226 | | | |
| 1-227 | | | |
| 1-228 | | | |

-continued

| Formula | ----Ar1 | ----Ar2 | ----Ar3 |
| --- | --- | --- | --- |
| 1-229 | biphenyl | phenanthrene | 9,9-dimethylfluorene (1-position) |
| 1-230 | biphenyl | phenanthrene | 9,9-dimethylfluorene (2-position) |
| 1-231 | biphenyl | phenanthrene | 9,9-dimethylfluorene (3-position) |
| 1-232 | biphenyl | phenanthrene | 9,9-dimethylfluorene (4-position) |
| 1-233 | biphenyl | phenanthrene | 9,9-diphenylfluorene (1-position) |
| 1-234 | biphenyl | phenanthrene | 9,9-diphenylfluorene (2-position) |
| 1-235 | biphenyl | phenanthrene | 9,9-diphenylfluorene (3-position) |

-continued
| Formula | ----Ar1 | ----Ar2 | ----Ar3 |
|---|---|---|---|
| 1-236 |  |  | 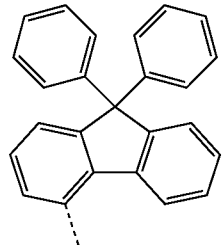 |
| 1-237 |  | 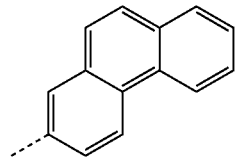 | 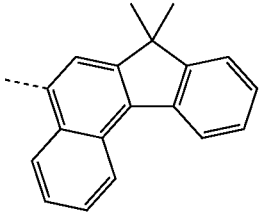 |
| 1-238 |  | 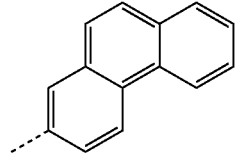 | 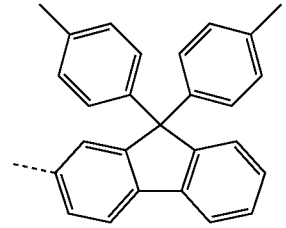 |
| 1-239 |  | 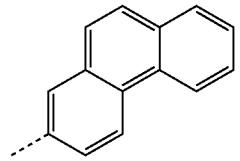 | 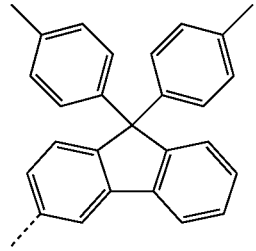 |
| 1-240 | 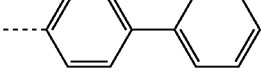 | 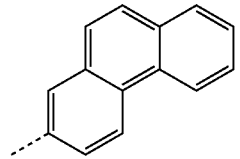 | 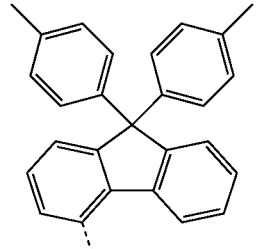 |
| 1-241 | 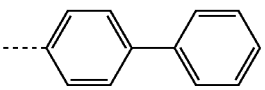 | 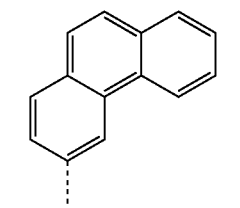 | 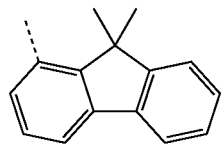 |

-continued

| Formula | ----Ar1 | ----Ar2 | ----Ar3 |
|---|---|---|---|
| 1-242 | biphenyl | phenanthrene | 9,9-dimethylfluorene |
| 1-243 | biphenyl | phenanthrene | 9,9-dimethylfluorene |
| 1-244 | biphenyl | phenanthrene | 9,9-dimethylfluorene |
| 1-245 | biphenyl | phenanthrene | 9,9-diphenylfluorene |
| 1-246 | biphenyl | phenanthrene | 9,9-diphenylfluorene |
| 1-247 | biphenyl | phenanthrene | 9,9-diphenyl-t-butylfluorene |
| 1-248 | biphenyl | phenanthrene | 9,9-diphenylfluorene |

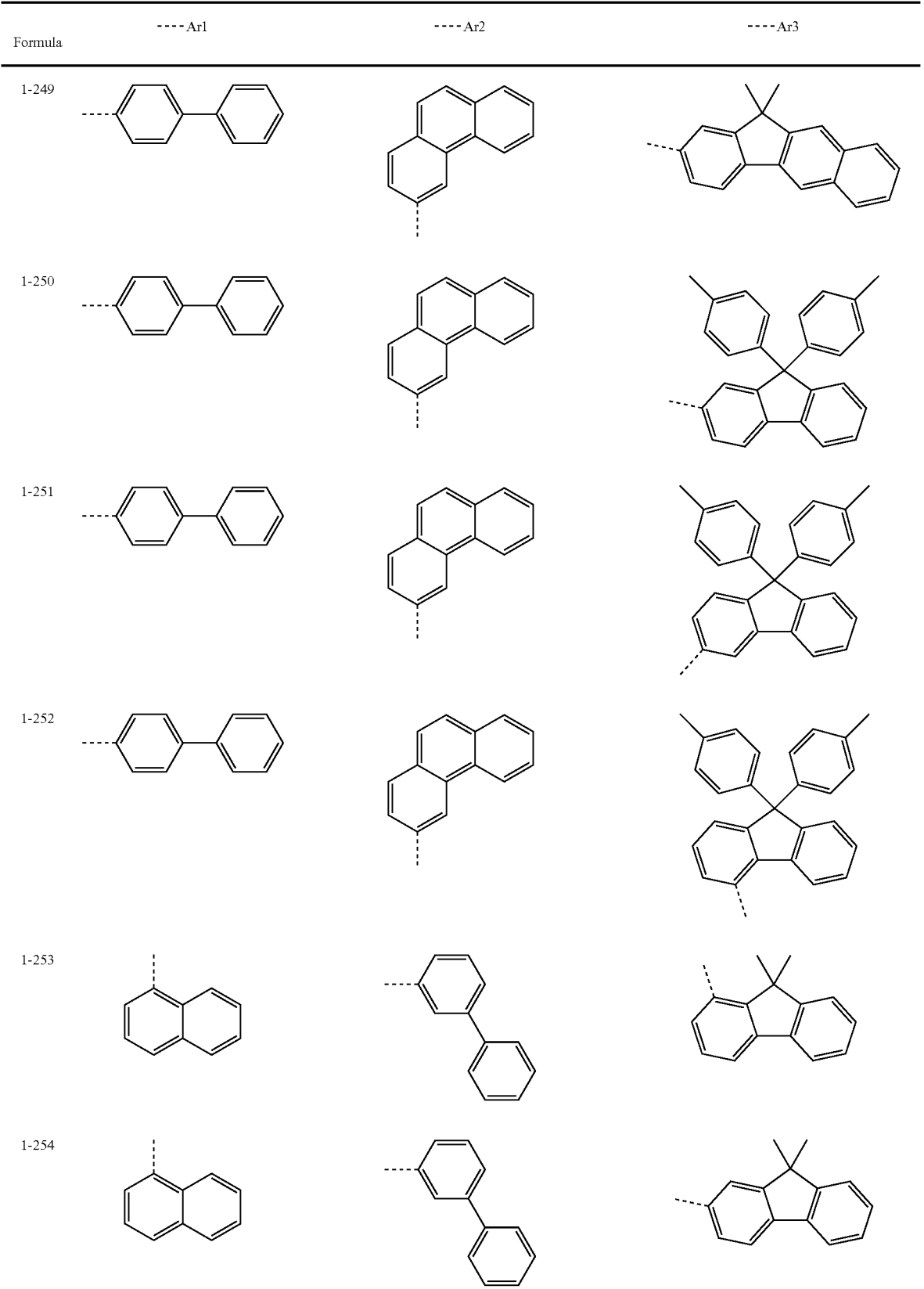

-continued
| Formula | ----Ar1 | ----Ar2 | ----Ar3 |
|---|---|---|---|
| 1-255 | 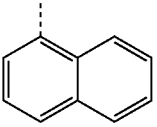 | 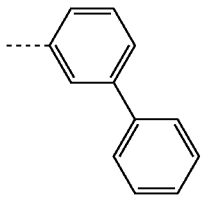 | 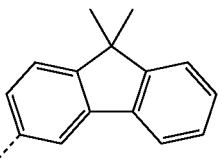 |
| 1-256 | 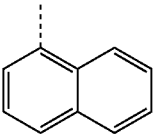 | 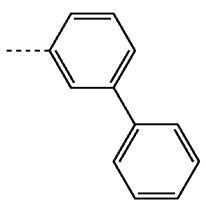 | 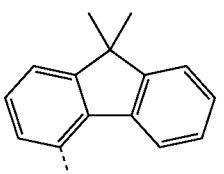 |
| 1-257 | 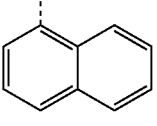 | 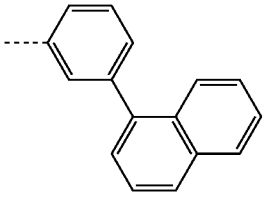 | 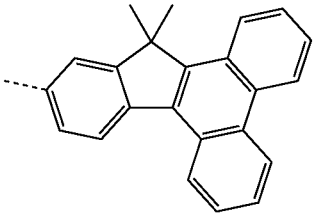 |
| 1-258 | 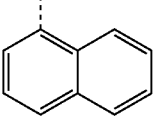 | 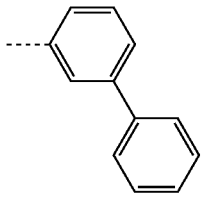 | 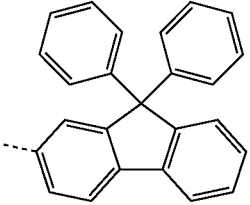 |
| 1-259 | 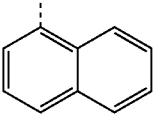 | 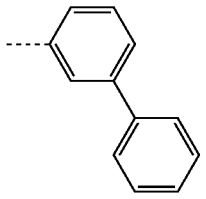 | 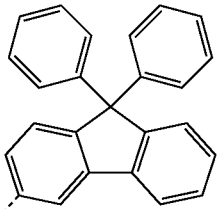 |
| 1-260 | 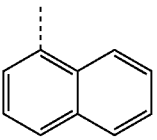 | 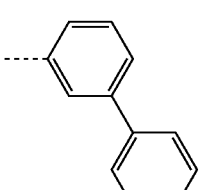 | 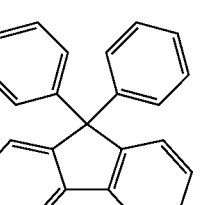 |
| 1-261 | 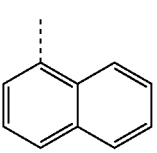 | 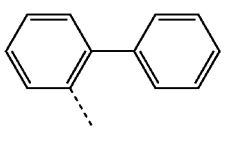 | 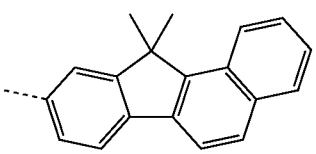 |

497                                                                                      498
-continued
| Formula | ----Ar1 | ----Ar2 | ----Ar3 |
|---|---|---|---|
| 1-262 | 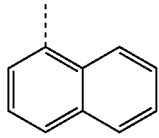 | 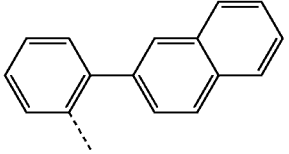 | 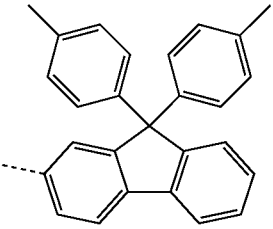 |
| 1-263 | 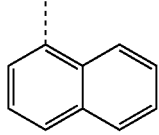 | 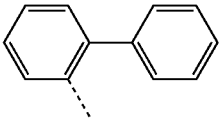 | 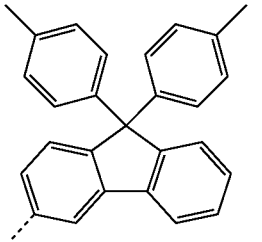 |
| 1-264 | 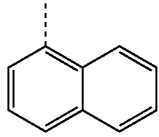 | 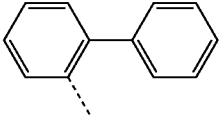 | 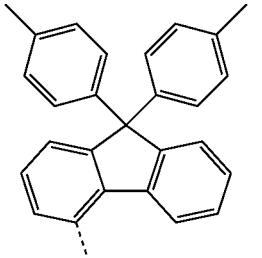 |
| 1-265 | 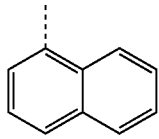 | 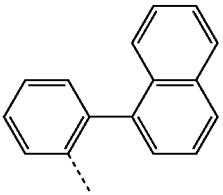 | 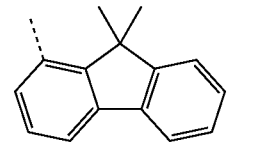 |
| 1-266 | 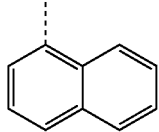 | 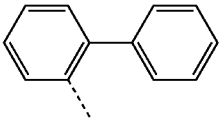 | 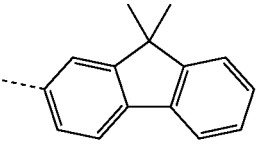 |
| 1-267 | 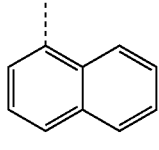 | 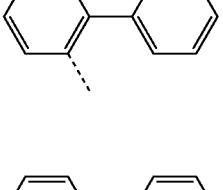 | 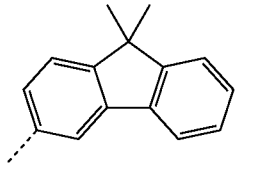 |
| 1-268 | 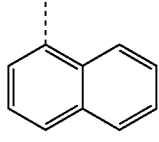 | 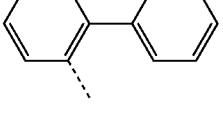 | 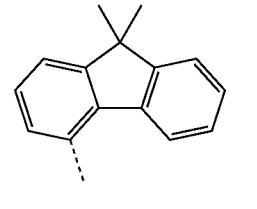 |

-continued

| Formula | ----Ar1 | ----Ar2 | ----Ar3 |
|---|---|---|---|
| 1-269 | 1-naphthyl | 2-biphenyl | 9,9-diphenyl-fluoren-1-yl |
| 1-270 | 1-naphthyl | 2-biphenyl | 9,9-diphenyl-fluoren-2-yl |
| 1-271 | 1-naphthyl | 2-biphenyl | 9,9-diphenyl-fluoren-3-yl |
| 1-272 | 1-naphthyl | 2-(anthracen-9-yl)phenyl | 9,9-diphenyl-fluoren-4-yl |
| 1-273 | 1-naphthyl | 2-biphenyl | 9,9-dimethyl-benzo[a]fluorenyl |
| 1-274 | 1-naphthyl | 2-biphenyl | 9,9-di(p-tolyl)-fluoren-2-yl |

-continued
| Formula | ----Ar1 | ----Ar2 | ----Ar3 |
|---|---|---|---|
| 1-275 | 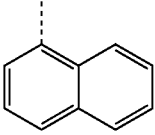 | 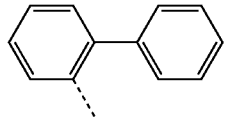 | 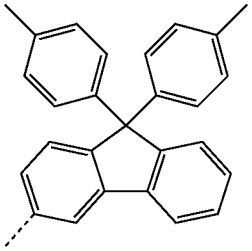 |
| 1-276 | 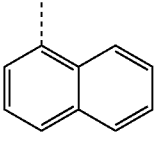 | 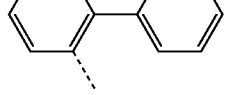 | 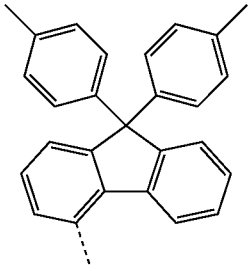 |
| 1-277 | 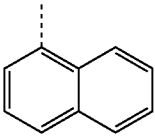 | 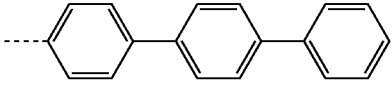 | 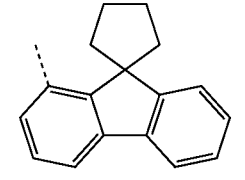 |
| 1-278 | 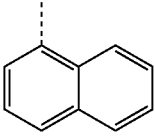 | 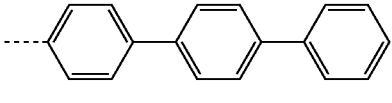 | 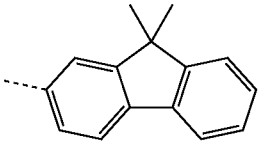 |
| 1-279 | 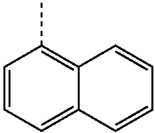 | 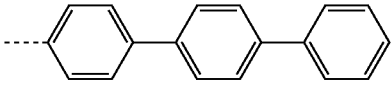 | 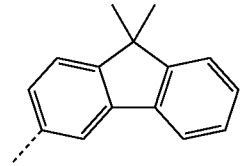 |
| 1-280 | 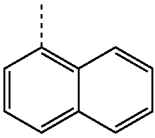 | 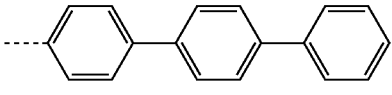 | 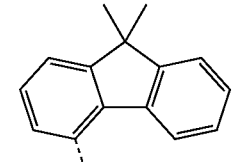 |
| 1-281 | 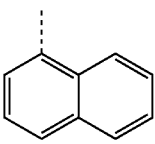 | 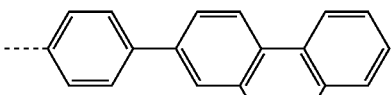 | 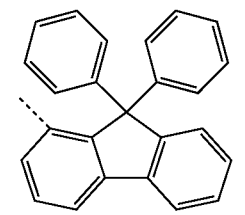 |

-continued

| Formula | ----Ar1 | ----Ar2 | ----Ar3 |
|---|---|---|---|
| 1-282 | 1-naphthyl | p-terphenyl-4-yl | 9,9-diphenylfluoren-2-yl |
| 1-283 | 1-naphthyl | p-terphenyl-4-yl | 9,9-diphenylfluoren-3-yl |
| 1-284 | 1-naphthyl | p-terphenyl-4-yl | 9,9-diphenylfluoren-4-yl |
| 1-285 | 1-naphthyl | p-terphenyl-4-yl | 9,9-di(p-tolyl)fluoren-1-yl |
| 1-286 | 1-naphthyl | p-terphenyl-4-yl | 9,9-di(p-tolyl)fluoren-2-yl |
| 1-287 | 1-naphthyl | 4-(phenanthren-2-yl)phenyl | 9,9-di(p-tolyl)fluoren-3-yl |

-continued

| Formula | ----Ar1 | ----Ar2 | ----Ar3 |
|---|---|---|---|
| 1-288 | 1-naphthyl | p-terphenyl-4-yl | 9,9-di(p-tolyl)fluoren-4-yl |
| 1-289 | 1-naphthyl | 3,5-diphenylphenyl | 9,9-dimethylfluoren-1-yl |
| 1-290 | 1-naphthyl | 3,5-diphenylphenyl | 9,9-dimethylfluoren-2-yl |
| 1-291 | 1-naphthyl | 3,5-diphenylphenyl | spiro[cyclopentane-1,9'-fluoren]-3'-yl |
| 1-292 | 1-naphthyl | 3,5-diphenylphenyl | 9,9-dimethylfluoren-4-yl |

-continued

| Formula | ----Ar1 | ----Ar2 | ----Ar3 |
|---|---|---|---|
| 1-293 | 1-naphthyl | 3,5-diphenylphenyl | 9,9-diphenylfluoren-1-yl |
| 1-294 | 1-naphthyl | 3,5-diphenylphenyl | 9,9-diphenylfluoren-2-yl |
| 1-295 | 1-naphthyl | 3,5-diphenylphenyl | 9,9-diphenylfluoren-3-yl |
| 1-296 | 1-naphthyl | 3,5-diphenylphenyl | 9,9-diphenylfluoren-4-yl |
| 1-297 | 1-naphthyl | 3,5-diphenylphenyl | 7-tert-butyl-9,9-diphenylfluoren-2-yl |

-continued
| Formula | ----Ar1 | ----Ar2 | ----Ar3 |
|---|---|---|---|
| 1-298 | 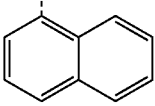 | 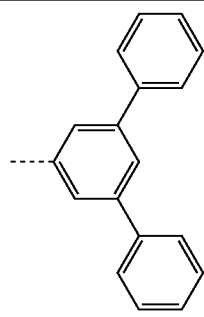 | 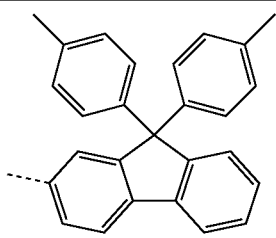 |
| 1-299 | 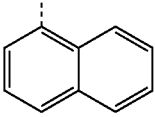 | 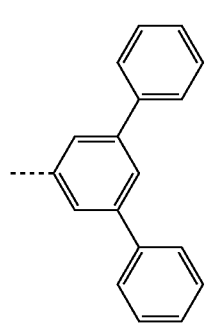 | 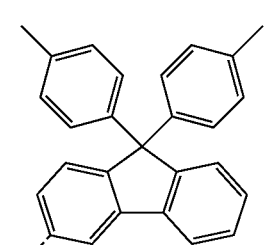 |
| 1-300 | 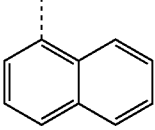 | 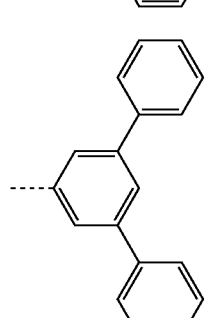 | 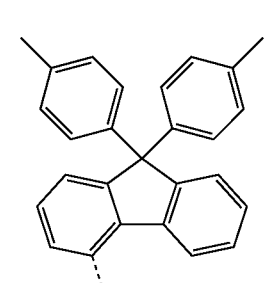 |
| 1-301 | 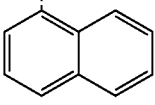 | 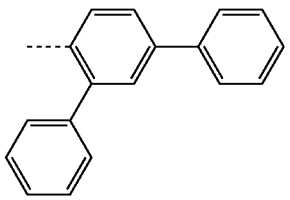 | 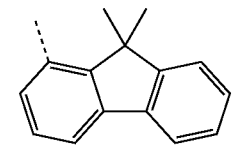 |
| 1-302 | 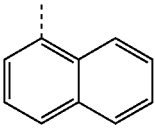 | 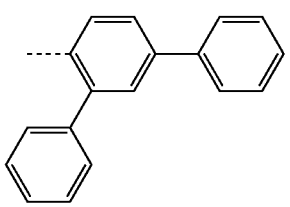 | 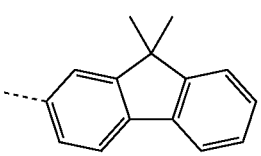 |
| 1-303 | 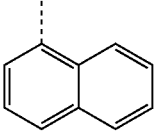 | 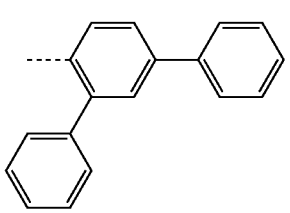 | 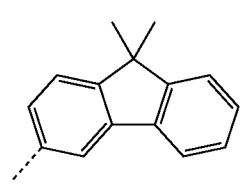 |

-continued
| Formula | ----Ar1 | ----Ar2 | ----Ar3 |
|---|---|---|---|
| 1-304 | 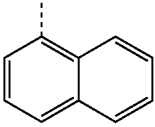 | 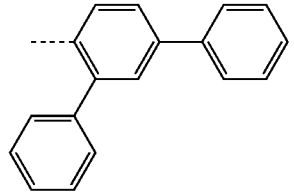 | 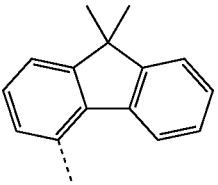 |
| 1-305 | 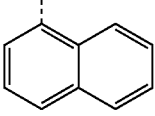 | 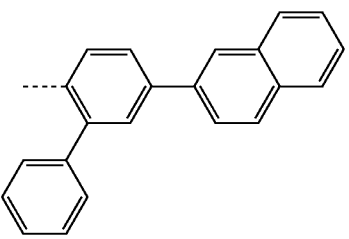 | 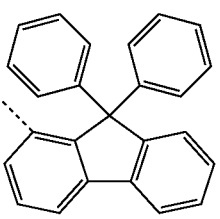 |
| 1-306 | 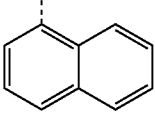 | 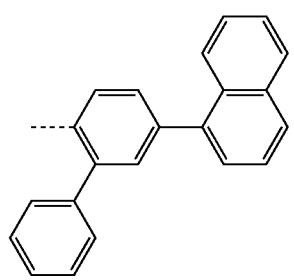 | 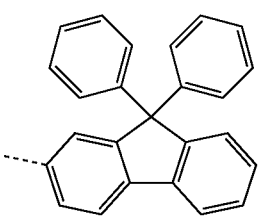 |
| 1-307 | 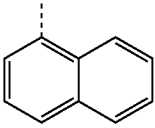 | 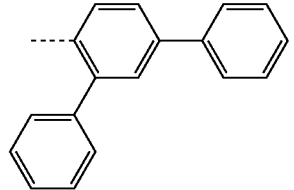 | 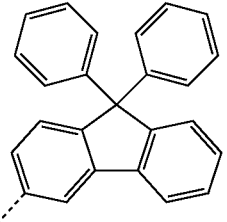 |
| 1-308 | 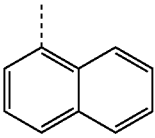 | 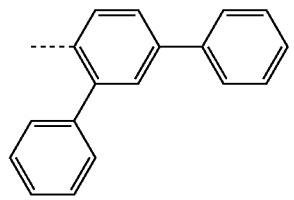 | 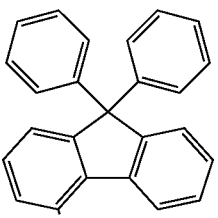 |
| 1-309 | 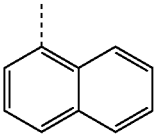 | 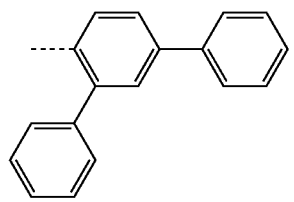 | 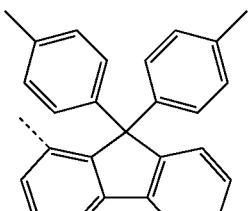 |

-continued
| Formula | ----Ar1 | ----Ar2 | ----Ar3 |
|---|---|---|---|
| 1-310 | 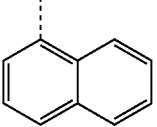 | 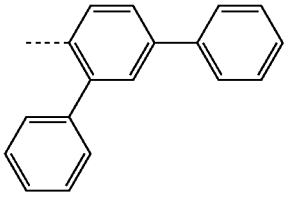 | 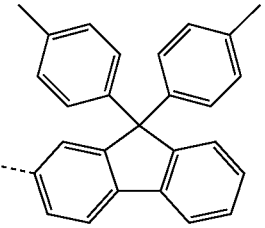 |
| 1-311 | 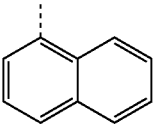 | 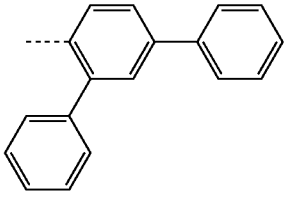 | 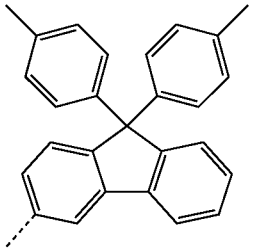 |
| 1-312 | 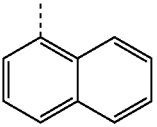 | 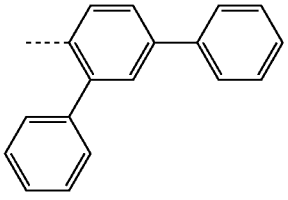 | 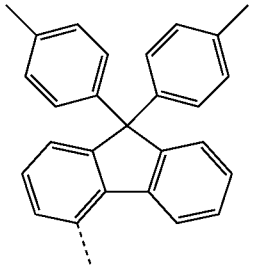 |
| 1-313 | 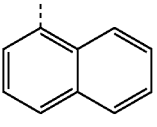 | 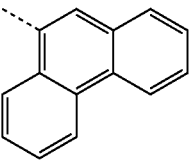 | 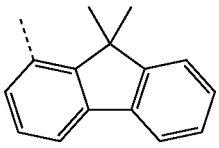 |
| 1-314 | 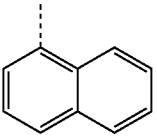 | 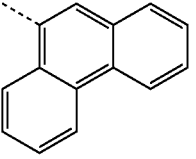 | 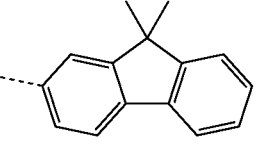 |
| 1-315 | 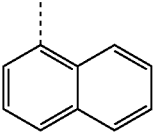 | 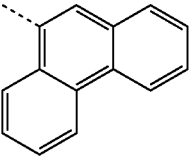 | 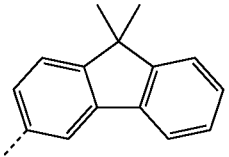 |
| 1-316 | 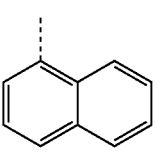 | 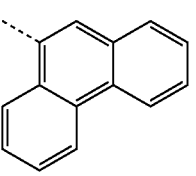 | 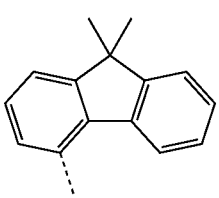 |

-continued
| Formula | ----Ar1 | ----Ar2 | ----Ar3 |
|---|---|---|---|
| 1-317 | 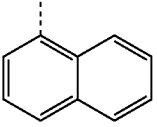 | 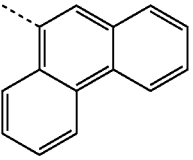 | 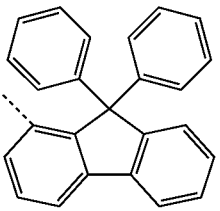 |
| 1-318 | 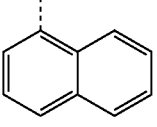 | 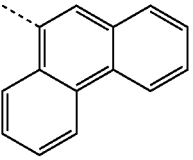 | 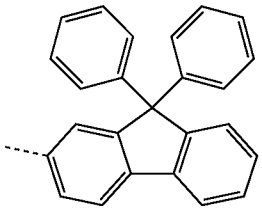 |
| 1-319 | 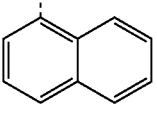 | 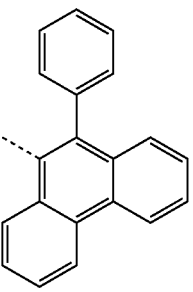 | 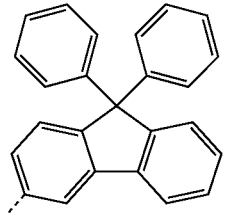 |
| 1-320 | 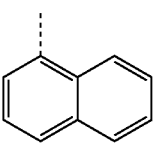 | 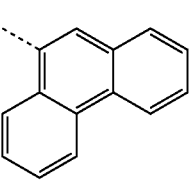 | 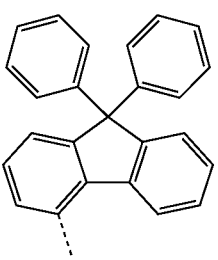 |
| 1-321 | 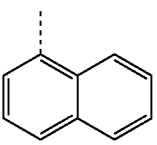 | 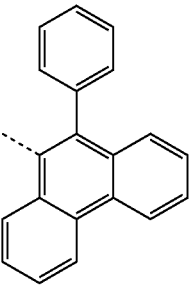 | 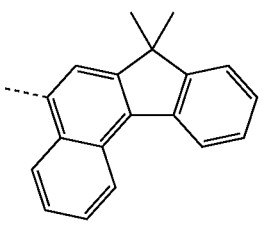 |
| 1-322 | 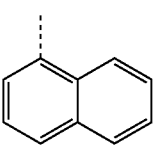 | 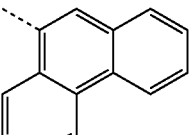 | 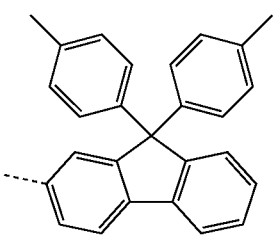 |

-continued
| Formula | ----Ar1 | ----Ar2 | ----Ar3 |
|---|---|---|---|
| 1-323 | 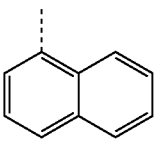 | 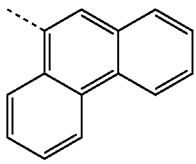 | 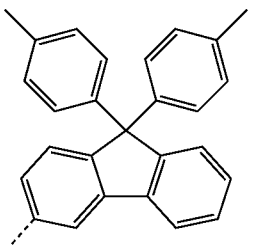 |
| 1-324 | 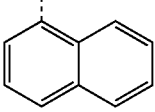 | 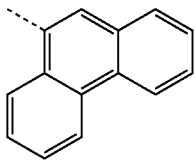 | 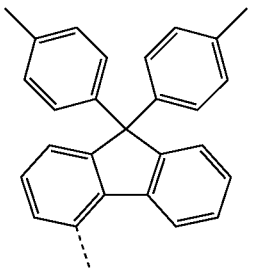 |
| 1-325 | 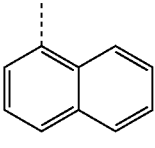 | 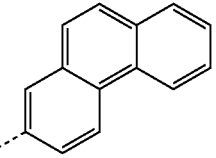 | 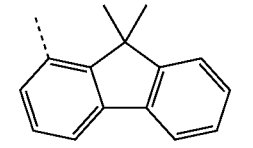 |
| 1-326 | 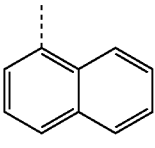 | 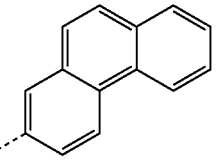 | 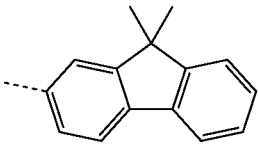 |
| 1-327 | 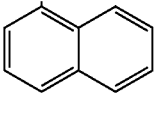 | 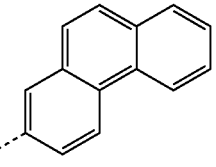 | 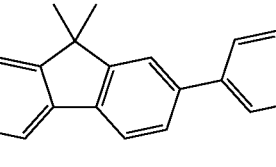 |
| 1-328 | 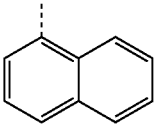 | 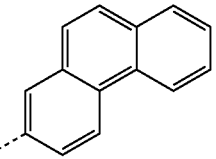 | 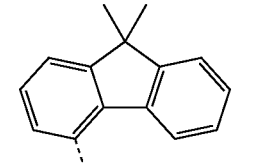 |
| 1-329 | 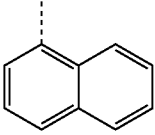 | 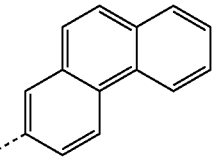 | 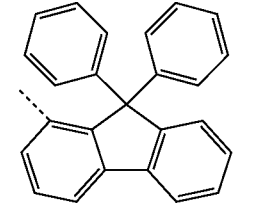 |

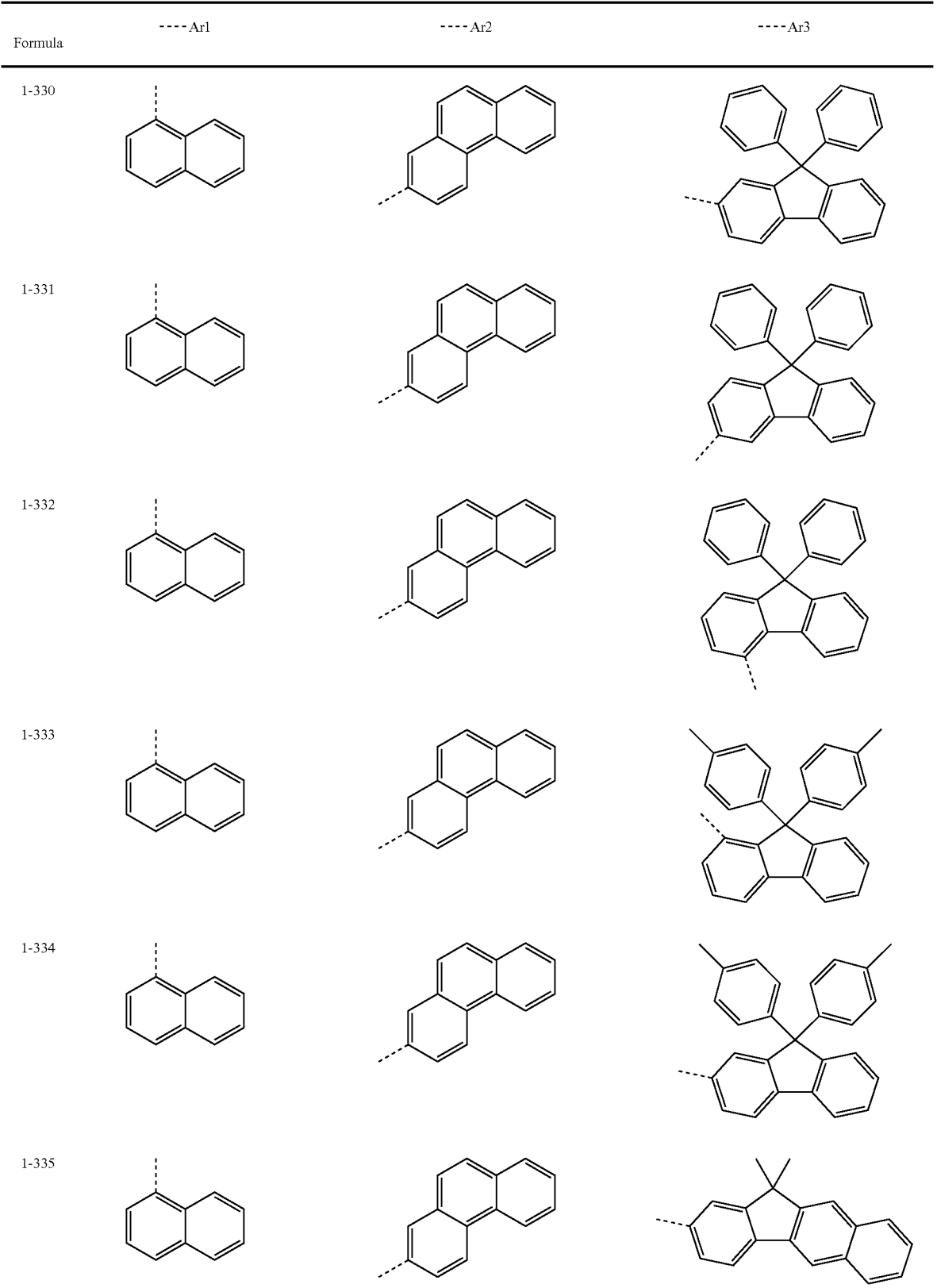

US 9,640,766 B2
521 522
-continued
| Formula | ----Ar1 | ----Ar2 | ----Ar3 |
|---|---|---|---|
| 1-336 | 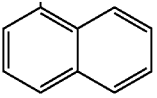 | 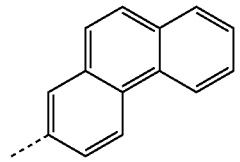 | 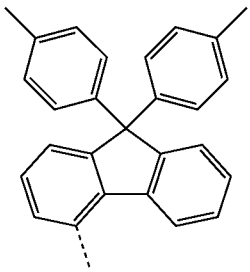 |
| 1-337 | 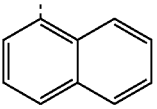 | 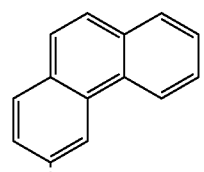 | 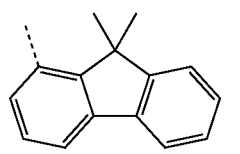 |
| 1-338 | 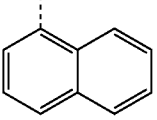 | 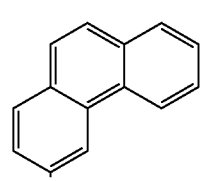 | 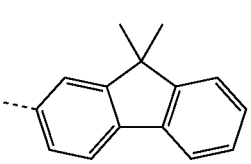 |
| 1-339 | 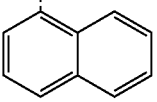 | 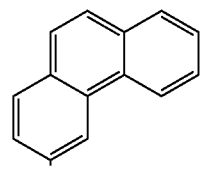 | 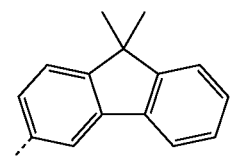 |
| 1-340 | 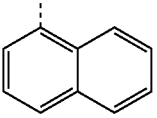 | 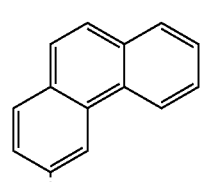 | 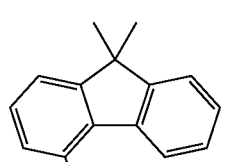 |
| 1-341 | 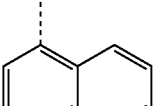 | 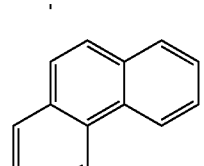 | 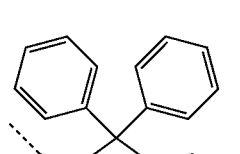 |
| 1-342 | 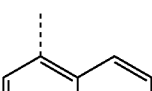 | 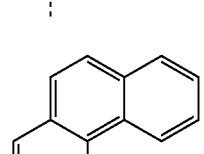 | 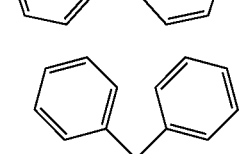 |

-continued
| Formula | ----Ar1 | ----Ar2 | ----Ar3 |
|---|---|---|---|
| 1-343 | 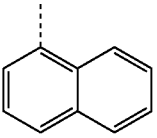 | 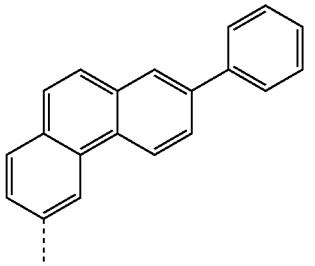 | 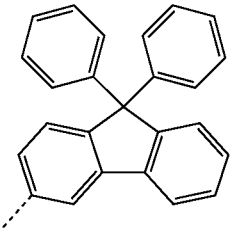 |
| 1-344 | 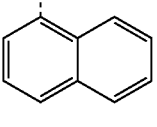 | 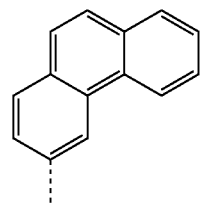 | 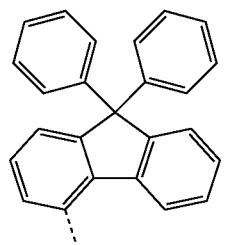 |
| 1-345 | 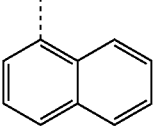 | 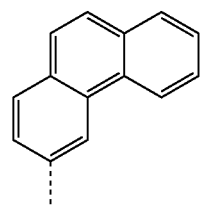 | 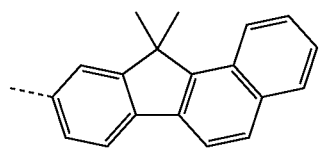 |
| 1-346 | 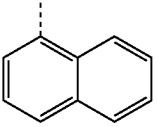 | 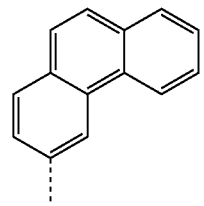 | 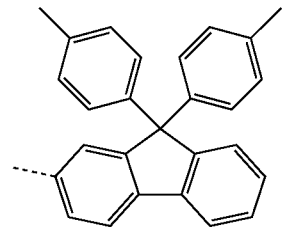 |
| 1-347 | 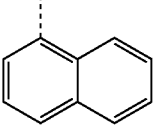 | 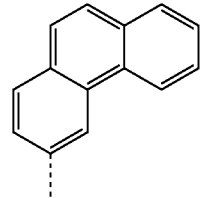 | 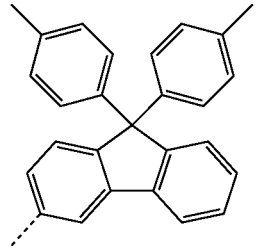 |
| 1-348 | 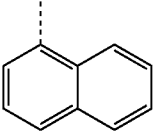 | 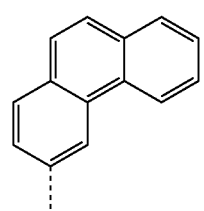 | 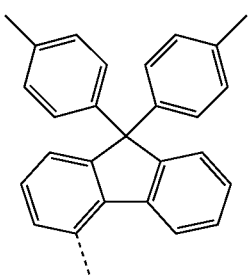 |

-continued
| Formula | ----Ar1 | ----Ar2 | ----Ar3 |
|---|---|---|---|
| 1-349 | 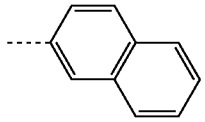 | 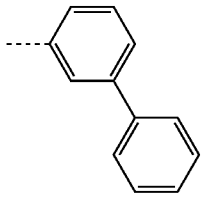 | 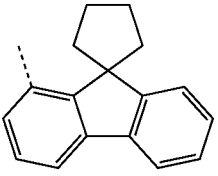 |
| 1-350 | 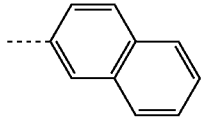 | 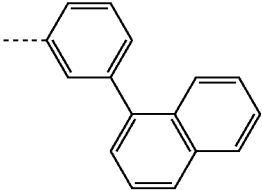 | 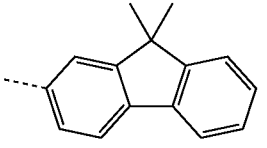 |
| 1-351 | 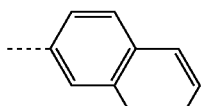 | 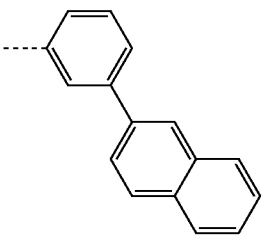 | 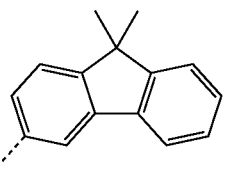 |
| 1-352 | 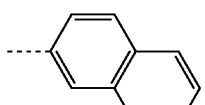 | 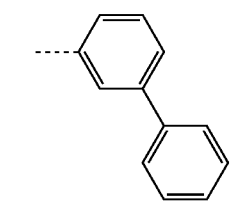 | 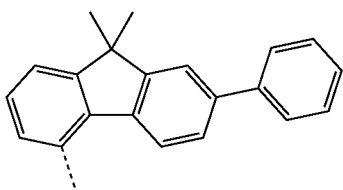 |
| 1-353 | 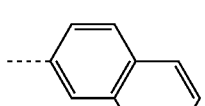 | 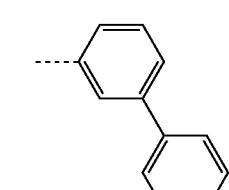 | 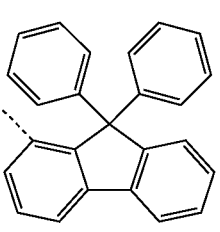 |
| 1-354 | 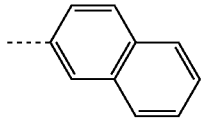 | 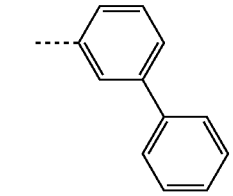 | 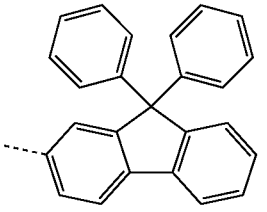 |
| 1-355 | 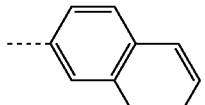 | 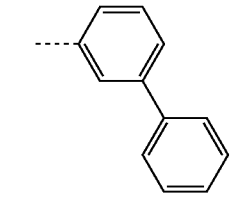 | 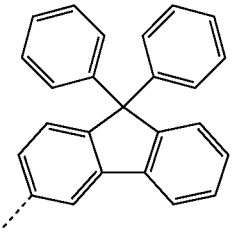 |

-continued
| Formula | ----Ar1 | ----Ar2 | ----Ar3 |
|---|---|---|---|
| 1-356 | 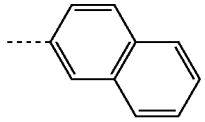 | 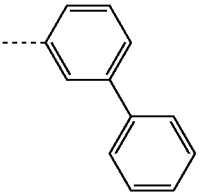 | 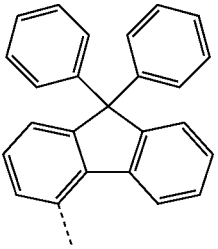 |
| 1-357 | 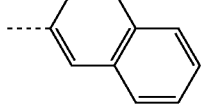 | 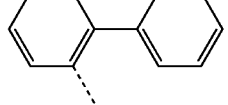 | 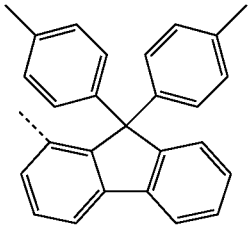 |
| 1-358 | 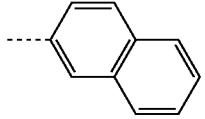 | 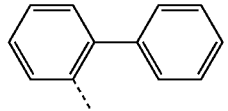 | 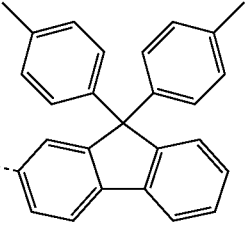 |
| 1-359 | 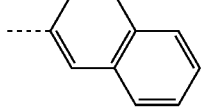 | 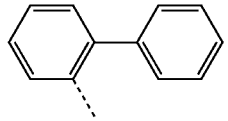 | 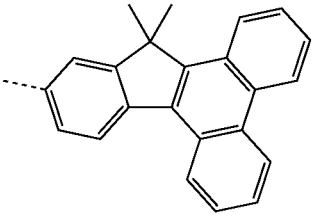 |
| 1-360 | 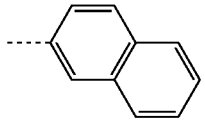 | 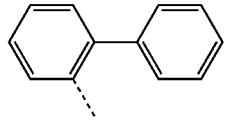 | 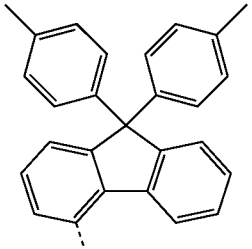 |
| 1-361 | 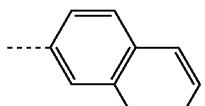 | 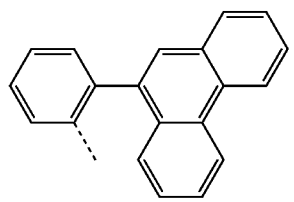 | 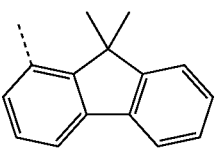 |

-continued
| Formula | ----Ar1 | ----Ar2 | ----Ar3 |
|---|---|---|---|
| 1-362 | 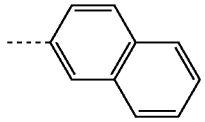 | 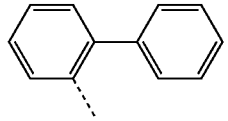 | 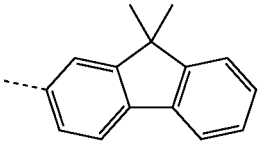 |
| 1-363 | 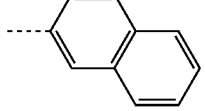 | 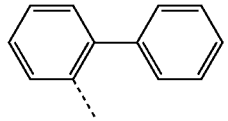 | 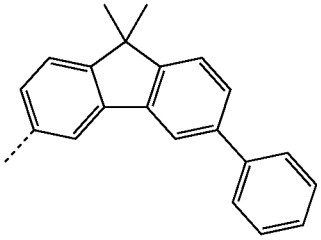 |
| 1-364 | 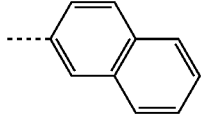 | 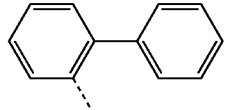 | 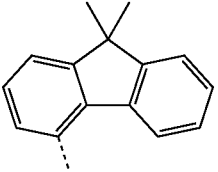 |
| 1-365 | 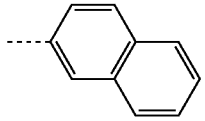 | 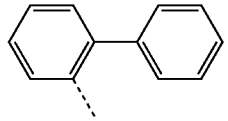 | 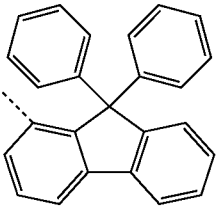 |
| 1-366 | 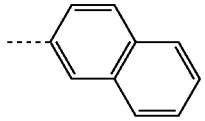 | 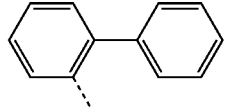 | 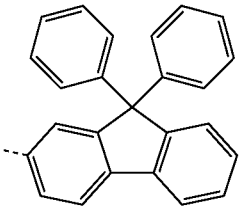 |
| 1-367 | 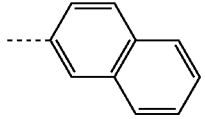 | 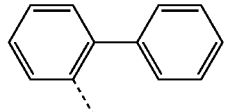 | 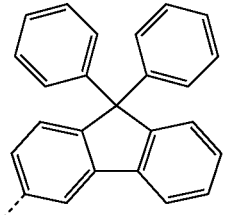 |
| 1-368 | 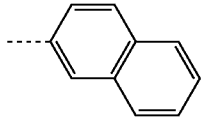 | 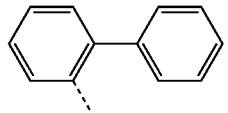 | 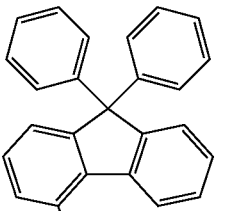 |

-continued
| Formula | ----Ar1 | ----Ar2 | ----Ar3 |
|---|---|---|---|
| 1-369 | 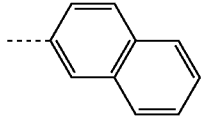 | 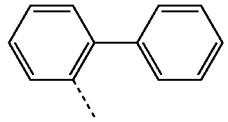 | 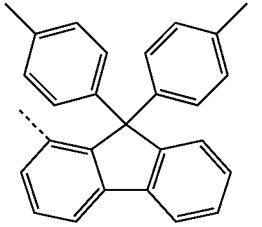 |
| 1-370 | 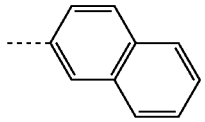 | 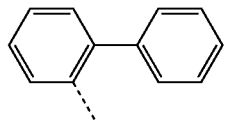 | 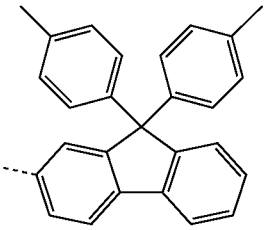 |
| 1-371 | 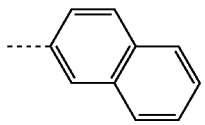 | 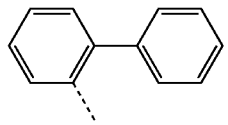 | 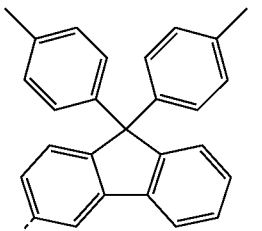 |
| 1-372 | 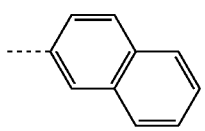 | 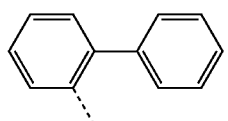 | 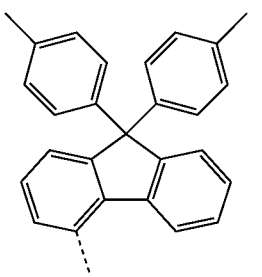 |
| 1-373 | 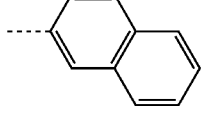 | 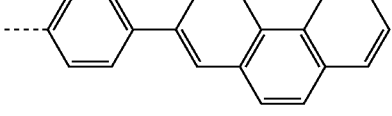 | 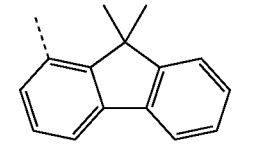 |
| 1-374 | 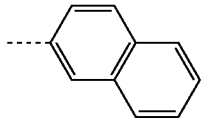 | 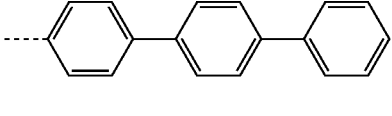 | 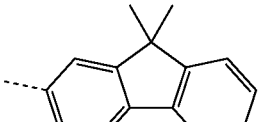 |
| 1-375 | 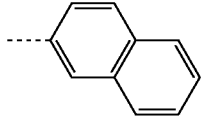 | 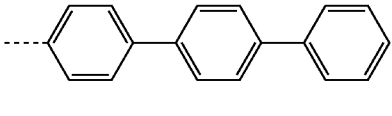 | 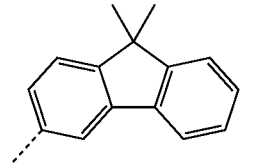 |

533                                                                                                              534
-continued
| Formula | ----Ar1 | ----Ar2 | ----Ar3 |
|---|---|---|---|
| 1-376 | 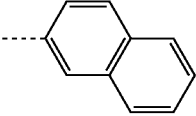 | 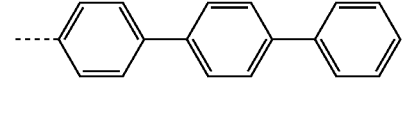 | 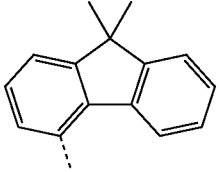 |
| 1-377 | 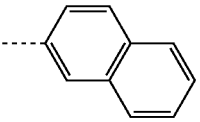 | 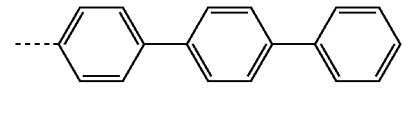 | 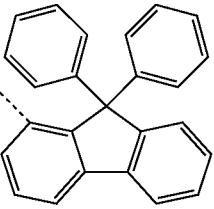 |
| 1-378 | 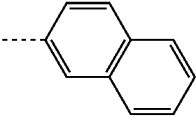 | 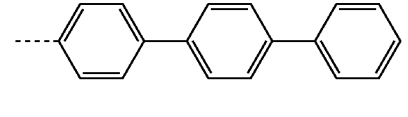 | 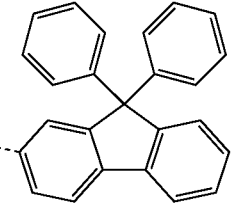 |
| 1-379 | 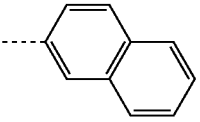 | 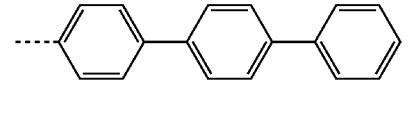 | 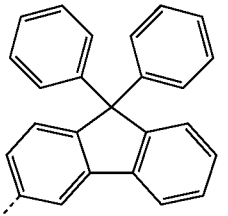 |
| 1-380 | 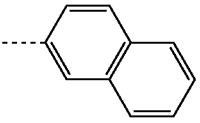 | 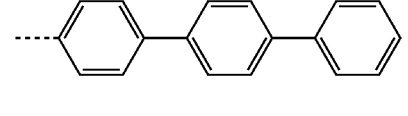 | 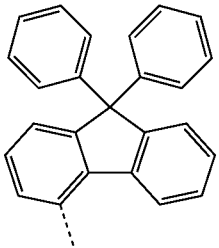 |
| 1-381 | 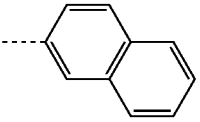 | 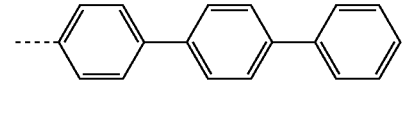 |  |
| 1-382 | 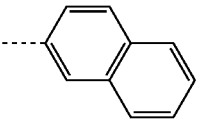 | 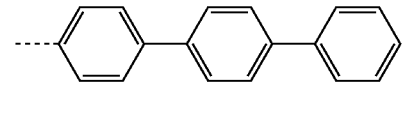 | 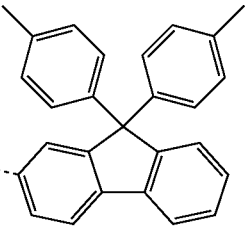 |

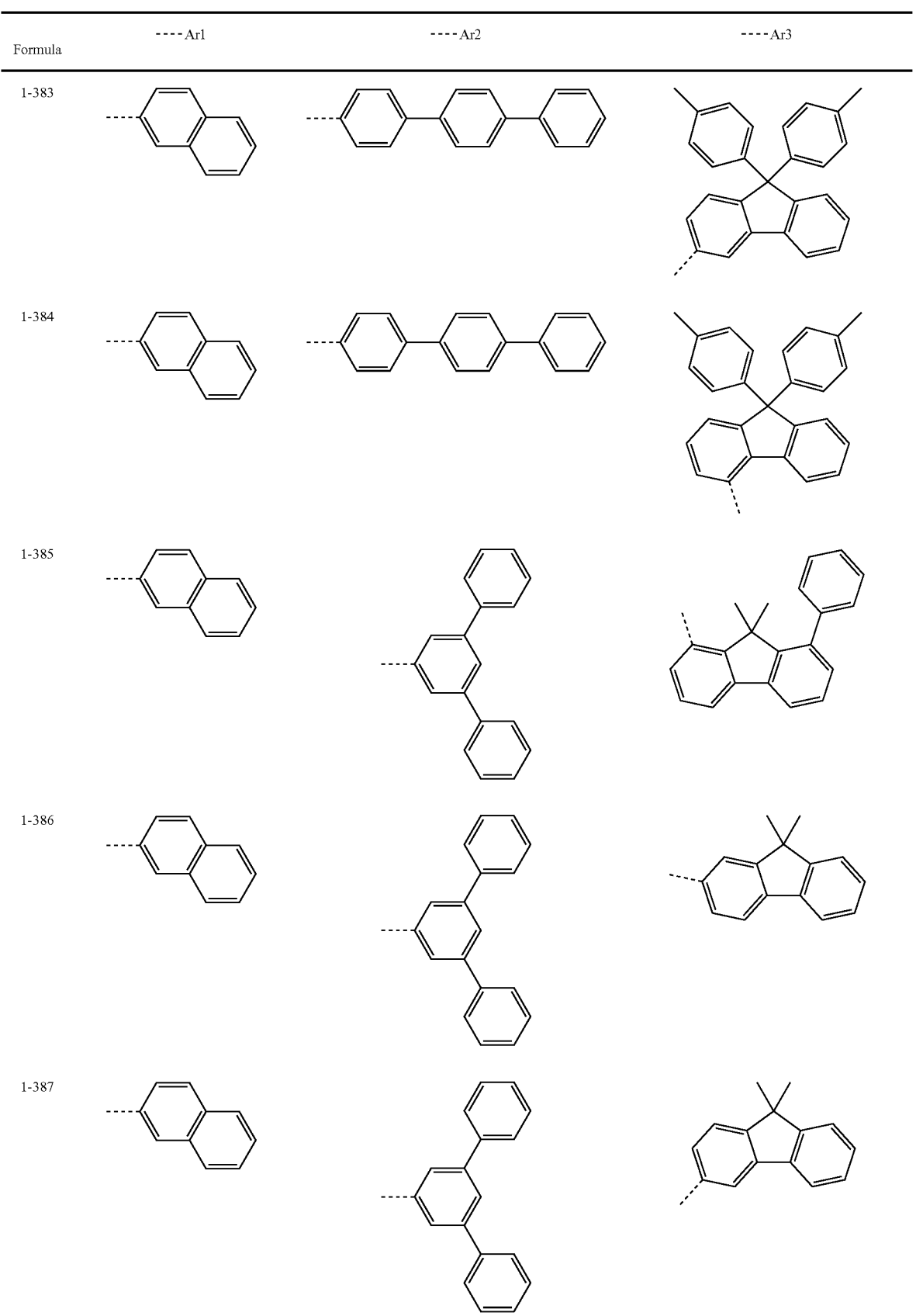

-continued

| Formula | ----Ar1 | ----Ar2 | ----Ar3 |
|---|---|---|---|
| 1-388 | 2-naphthyl | 3,5-bis(phenyl)-4'-phenyl (1,1':3',1''-terphenyl) | 9,9-dimethylfluoren-4-yl |
| 1-389 | 2-naphthyl | 3,5-diphenylphenyl | 2-tert-butyl-9,9-diphenylfluoren-7-yl |
| 1-390 | 2-naphthyl | 3,5-diphenylphenyl | 9,9-diphenylfluoren-2-yl |
| 1-391 | 2-naphthyl | 3,5-diphenylphenyl | 9,9-diphenylfluoren-3-yl |
| 1-392 | 2-naphthyl | 3,5-diphenylphenyl | 9,9-diphenylfluoren-4-yl |

-continued
| Formula | ----Ar1 | ----Ar2 | ----Ar3 |
|---|---|---|---|
| 1-393 | 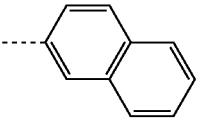 | 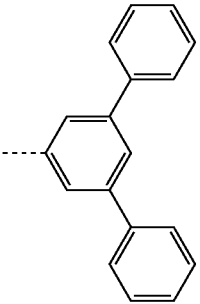 | 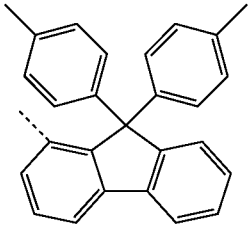 |
| 1-394 | 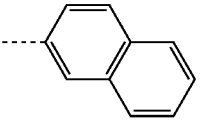 | 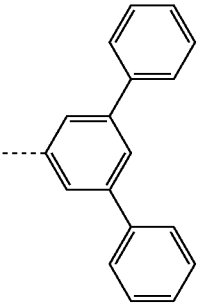 | 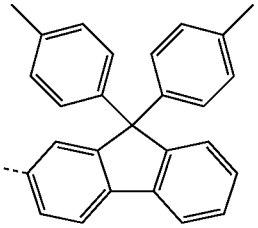 |
| 1-395 | 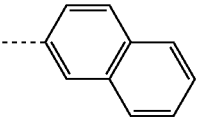 | 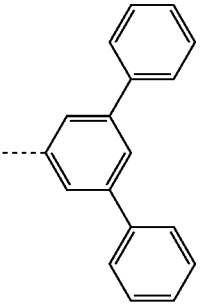 | 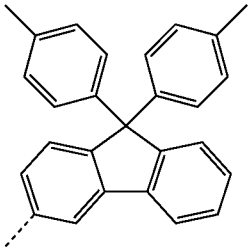 |
| 1-396 | 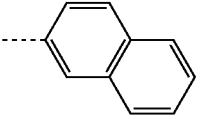 | 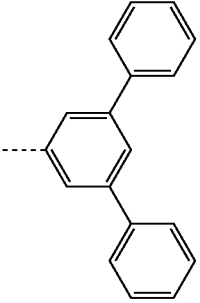 | 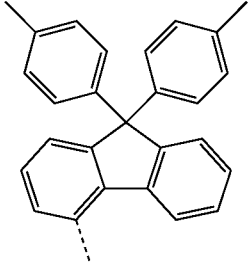 |
| 1-397 | 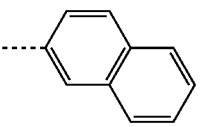 | 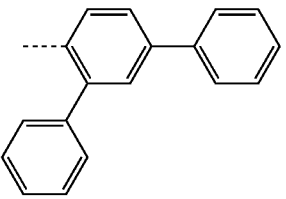 | 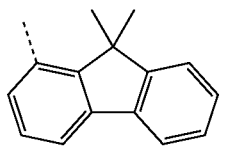 |

-continued
| Formula | ----Ar1 | ----Ar2 | ----Ar3 |
|---|---|---|---|
| 1-398 |  |  | 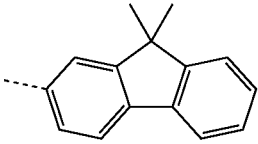 |
| 1-399 |  | 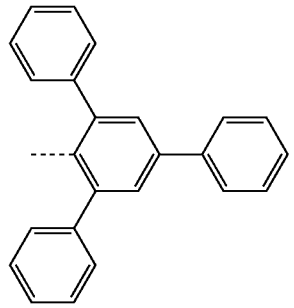 | 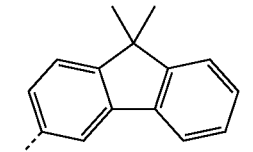 |
| 1-400 |  |  | 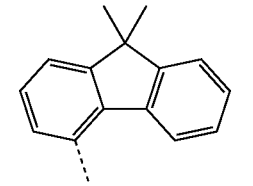 |
| 1-401 |  |  | 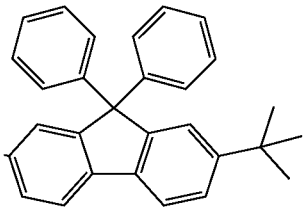 |
| 1-402 |  |  |  |
| 1-403 | 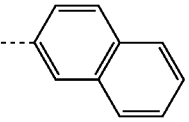 | 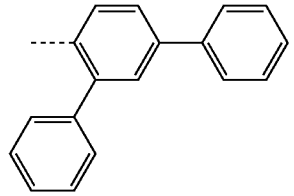 | 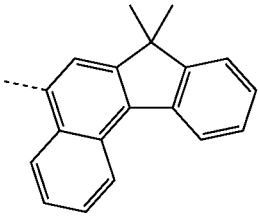 |

| Formula | ----Ar1 | ----Ar2 | ----Ar3 |
|---|---|---|---|
| 1-404 | 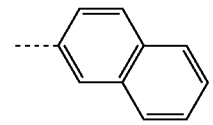 | 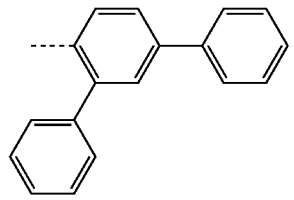 | 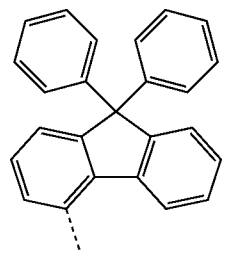 |
| 1-405 | 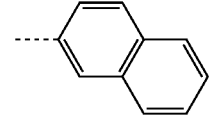 | 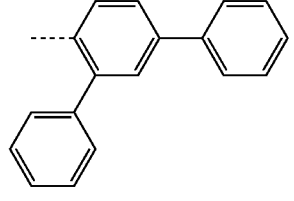 | 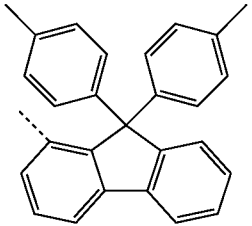 |
| 1-406 | 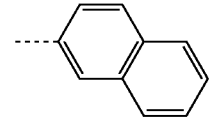 | 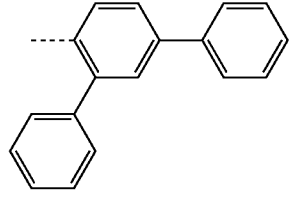 | 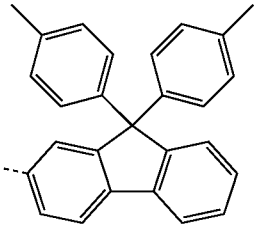 |
| 1-407 | 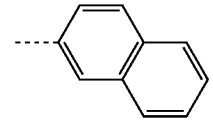 | 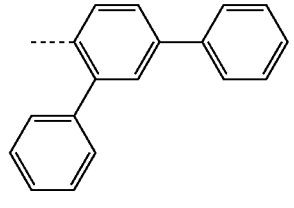 | 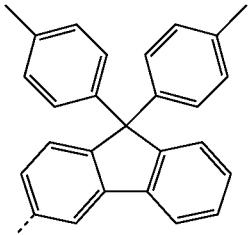 |
| 1-408 | 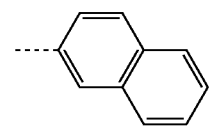 | 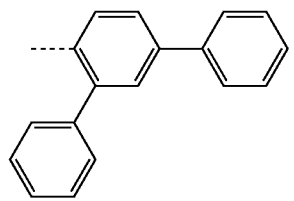 | 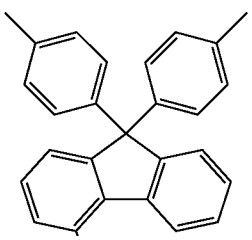 |
| 1-409 | 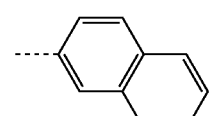 | 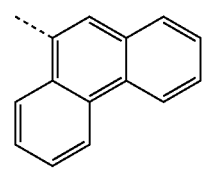 | 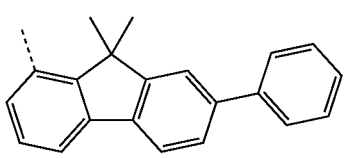 |

-continued
| Formula | ----Ar1 | ----Ar2 | ----Ar3 |
|---|---|---|---|
| 1-410 | 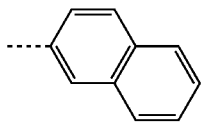 | 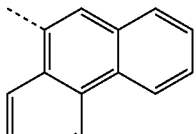 | 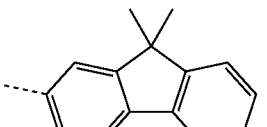 |
| 1-411 | 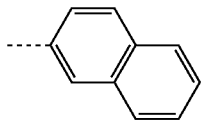 | 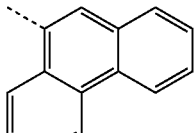 | 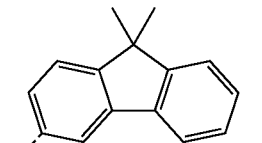 |
| 1-412 | 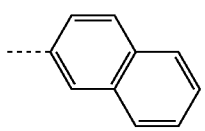 | 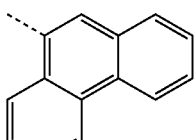 | 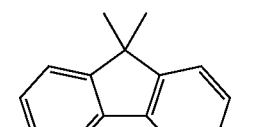 |
| 1-413 | 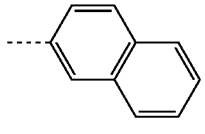 | 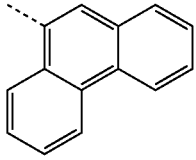 | 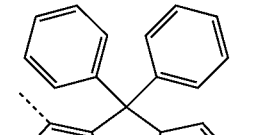 |
| 1-414 | 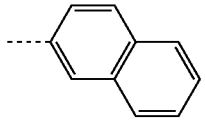 | 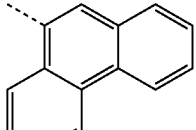 |  |
| 1-415 | 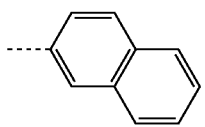 | 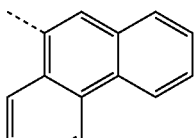 | 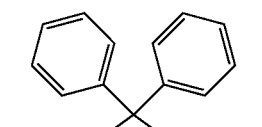 |
| 1-416 | 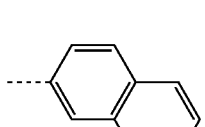 | 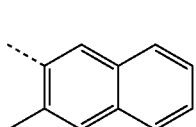 | 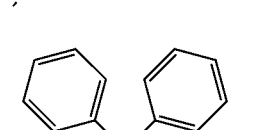 |

| Formula | ----Ar1 | ----Ar2 | ----Ar3 |
|---|---|---|---|
| 1-417 | 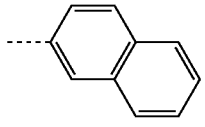 | 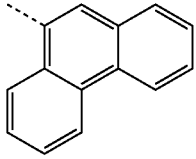 | 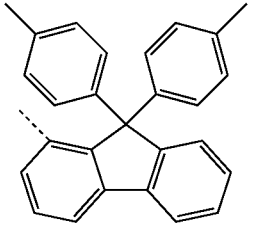 |
| 1-418 | 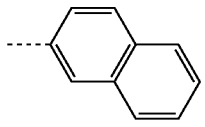 | 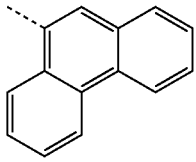 | 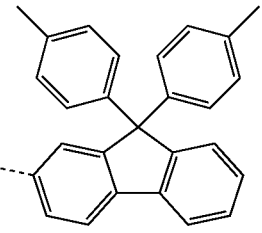 |
| 1-419 | 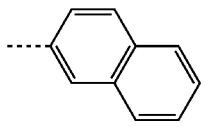 | 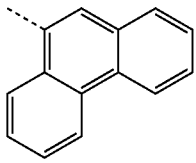 | 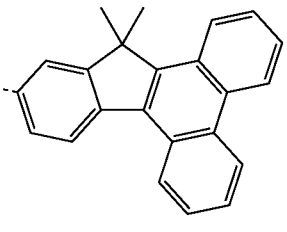 |
| 1-420 | 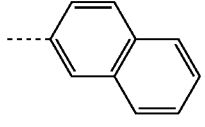 | 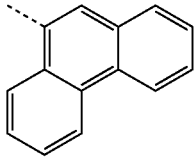 | 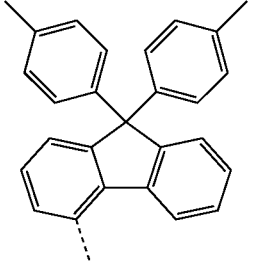 |
| 1-421 | 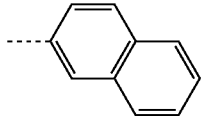 | 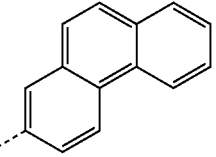 | 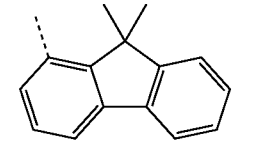 |
| 1-422 | 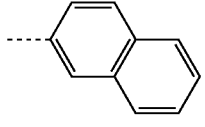 | 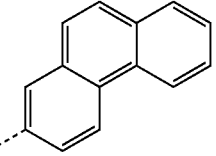 | 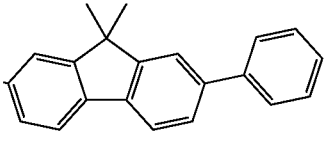 |
| 1-423 | 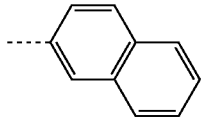 | 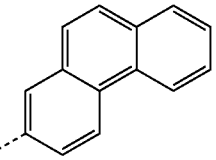 | 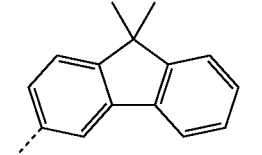 |

-continued
| Formula | ----Ar1 | ----Ar2 | ----Ar3 |
|---|---|---|---|
| 1-424 | 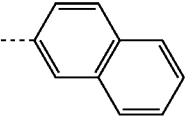 | 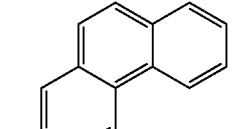 | 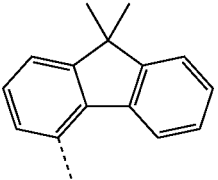 |
| 1-425 | 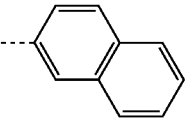 | 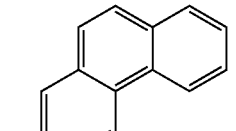 | 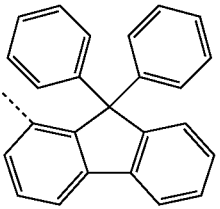 |
| 1-426 | 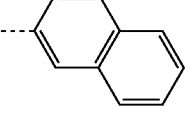 | 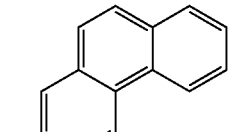 | 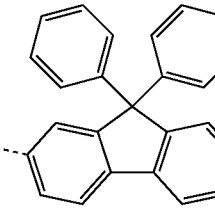 |
| 1-427 | 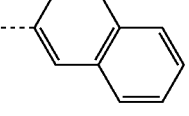 | 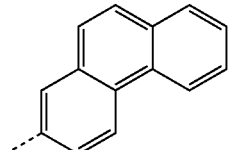 | 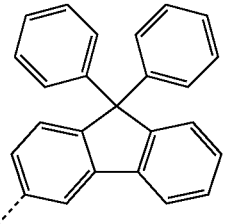 |
| 1-428 | 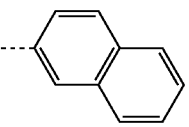 | 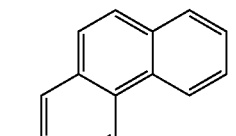 | 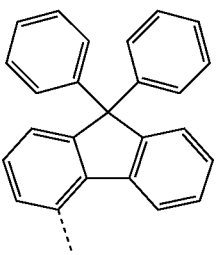 |
| 1-429 | 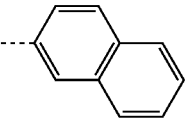 | 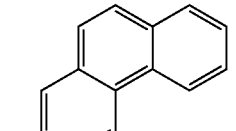 | 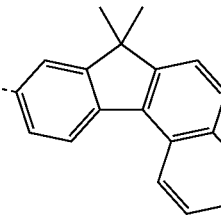 |

551 552
-continued
| Formula | ----Ar1 | ----Ar2 | ----Ar3 |
|---|---|---|---|
| 1-430 | | | |
| 1-431 | | | |
| 1-432 | | | |
| 1-433 | | | |
| 1-434 | | | |
| 1-435 | | | |
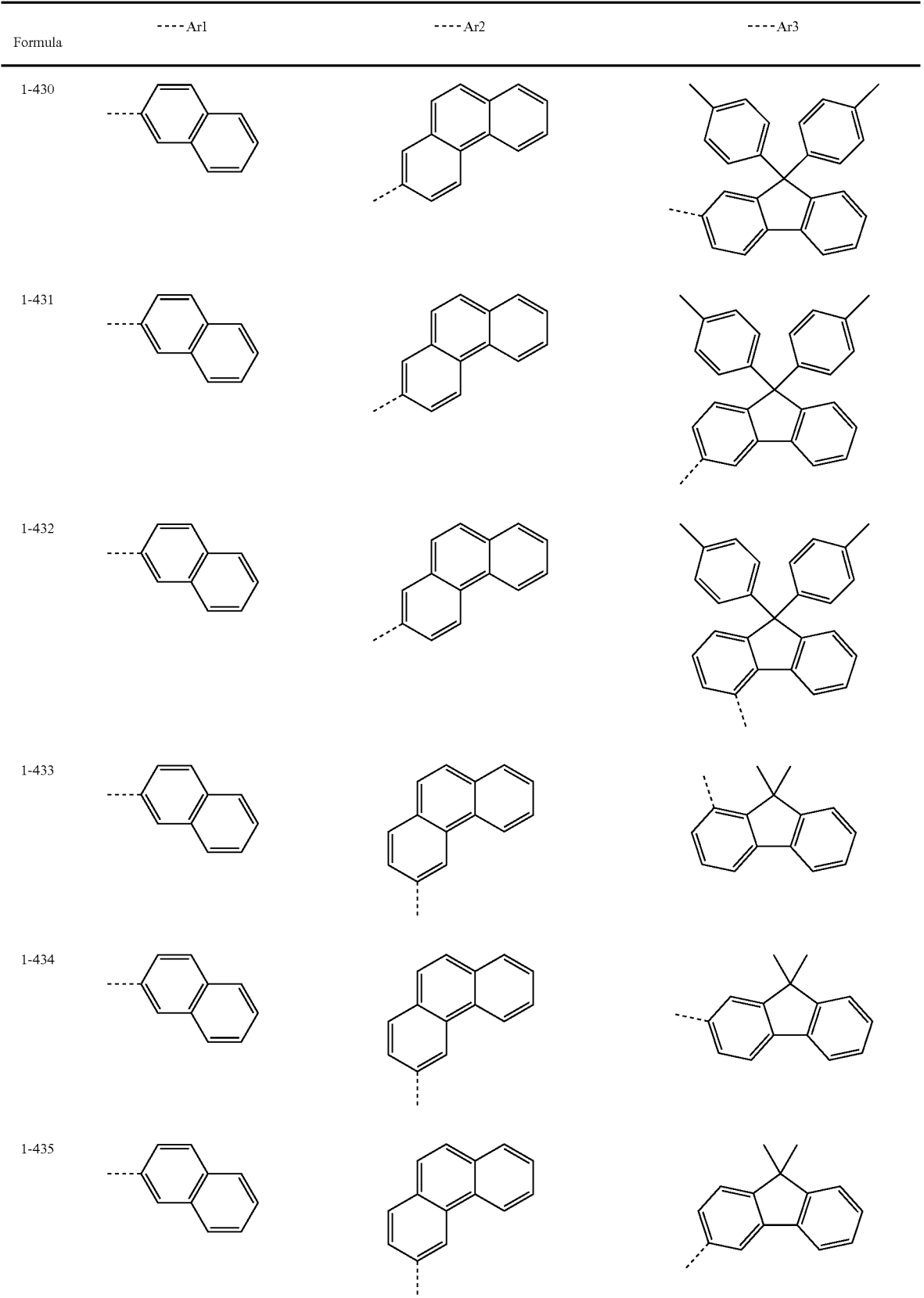

-continued
| Formula | ----Ar1 | ----Ar2 | ----Ar3 |
|---|---|---|---|
| 1-436 | 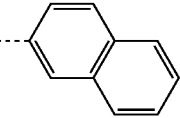 | 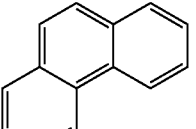 | 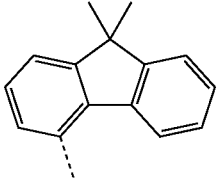 |
| 1-437 | 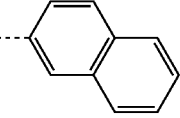 | 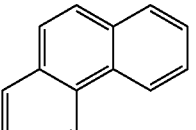 | 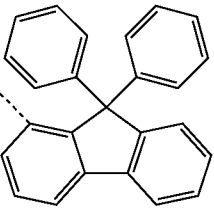 |
| 1-438 | 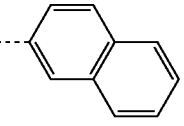 | 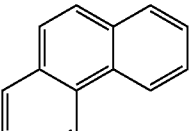 | 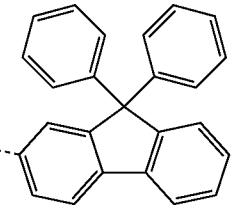 |
| 1-439 | 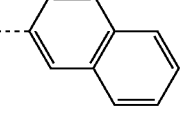 | 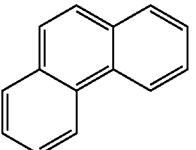 | 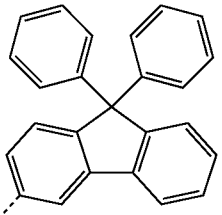 |
| 1-440 | 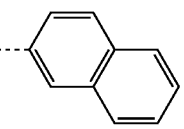 | 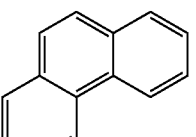 | 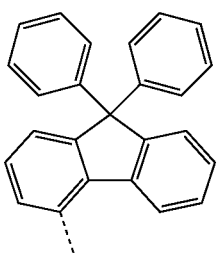 |
| 1-441 | 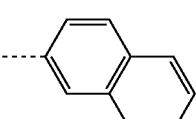 | 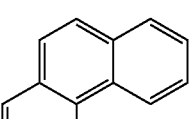 | 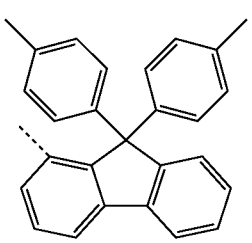 |

-continued

| Formula | ----Ar1 | ----Ar2 | ----Ar3 |
|---|---|---|---|
| 1-442 | | | |
| 1-443 | | | |
| 1-444 | | | |
| 1-445 | | | |
| 1-446 | | | |
| 1-447 | | | |

-continued

| Formula | ----Ar1 | ----Ar2 | ----Ar3 |
|---|---|---|---|
| 1-448 | | | |
| 1-449 | | | |
| 1-450 | | | |
| 1-451 | | | |
| 1-452 | | | |
| 1-453 | | | |

-continued

| Formula | ----Ar1 | ----Ar2 | ----Ar3 |
|---|---|---|---|
| 1-454 | phenanthrene | biphenyl (meta) | 9,9-di(p-tolyl)fluorene (2-position) |
| 1-455 | phenanthrene | biphenyl (meta) | 9,9-di(p-tolyl)fluorene (3-position) |
| 1-456 | phenanthrene | biphenyl (meta) | 9,9-di(p-tolyl)fluorene (4-position) |
| 1-457 | phenanthrene | biphenyl (ortho) | 9,9-dimethylfluorene |
| 1-458 | phenanthrene | biphenyl (ortho) | 9,9-spirocyclopentylfluorene |
| 1-459 | phenanthrene | 9-phenylphenanthrene | 9,9-dimethylfluorene |
| 1-460 | phenanthrene | 1-phenylnaphthalene | 9,9-dimethylfluorene |

-continued

| Formula | ----Ar1 | ----Ar2 | ----Ar3 |
|---|---|---|---|
| 1-461 | phenanthrenyl | 2-biphenyl | 9,9-diphenylfluoren-1-yl |
| 1-462 | phenanthrenyl | 2-biphenyl | 9,9-diphenylfluoren-2-yl |
| 1-463 | phenanthrenyl | 2-biphenyl | 11,11-dimethyl-11H-benzo[b]fluorenyl |
| 1-464 | phenanthrenyl | 2-biphenyl | 9,9-diphenylfluoren-4-yl |
| 1-465 | phenanthrenyl | 2-biphenyl | 9,9-di(p-tolyl)fluoren-1-yl |
| 1-466 | phenanthrenyl | 2-biphenyl | 9,9-di(p-tolyl)fluoren-2-yl |

-continued
| Formula | ----Ar1 | ----Ar2 | ----Ar3 |
|---|---|---|---|
| 1-467 | 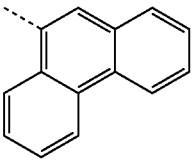 | 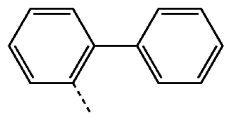 | 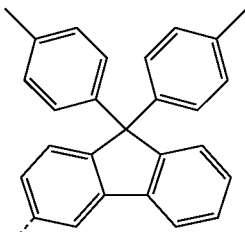 |
| 1-468 | 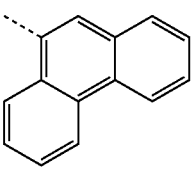 | 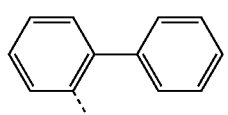 | 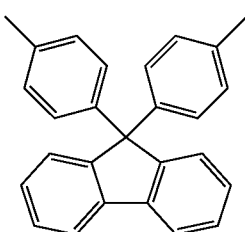 |
| 1-469 | 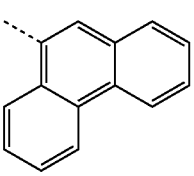 | 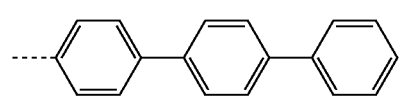 | 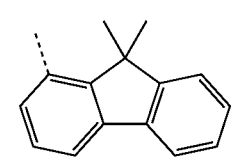 |
| 1-470 | 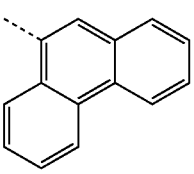 | 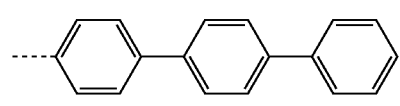 | 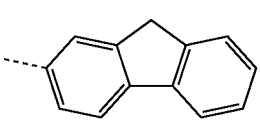 |
| 1-471 | 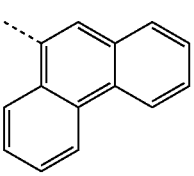 | 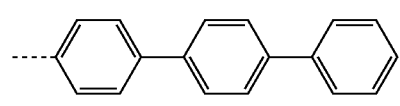 | 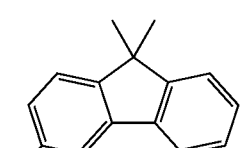 |
| 1-472 | 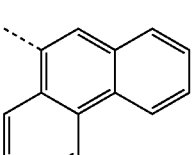 | 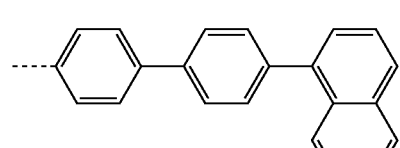 | 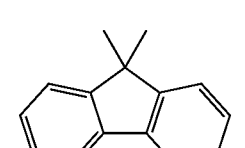 |
| 1-473 | 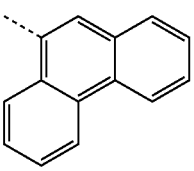 | 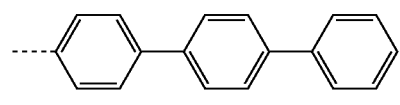 | 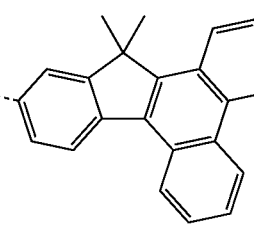 |

-continued
| Formula | ----Ar1 | ----Ar2 | ----Ar3 |
|---|---|---|---|
| 1-474 | 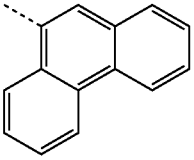 | 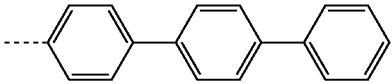 | 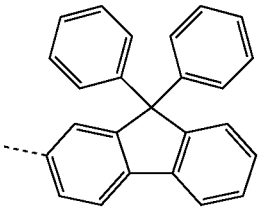 |
| 1-475 | 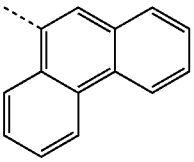 | 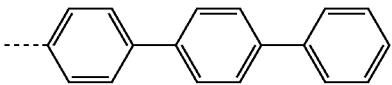 | 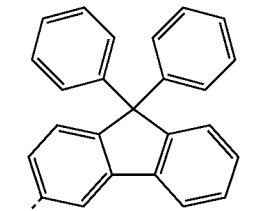 |
| 1-476 | 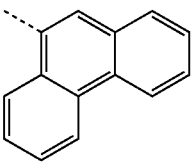 | 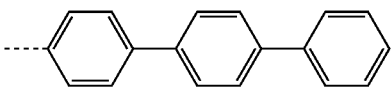 | 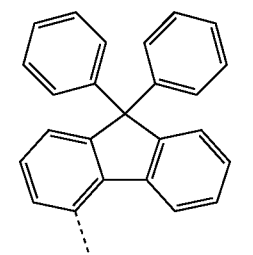 |
| 1-477 | 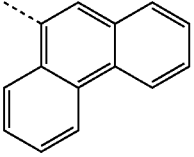 | 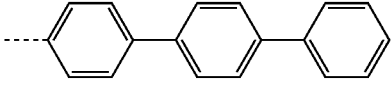 | 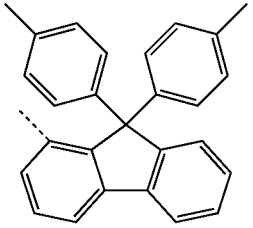 |
| 1-478 | 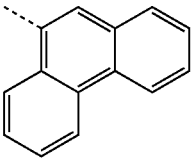 | 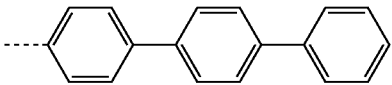 | 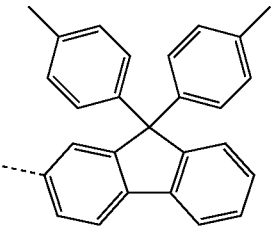 |
| 1-479 | 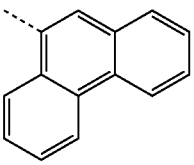 | 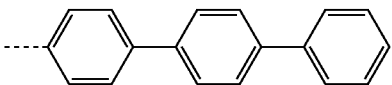 | 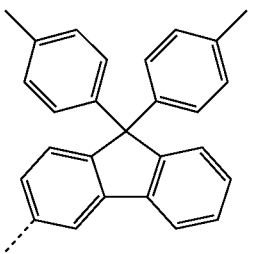 |

-continued

| Formula | ----Ar1 | ----Ar2 | ----Ar3 |
|---|---|---|---|
| 1-480 | | | |
| 1-481 | | | |
| 1-482 | | | |
| 1-483 | | | |
| 1-484 | | | |

-continued
| Formula | ----Ar1 | ----Ar2 | ----Ar3 |
|---|---|---|---|
| 1-485 | 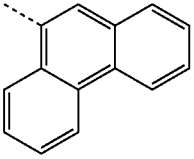 | 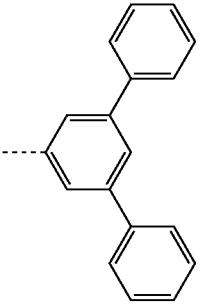 | 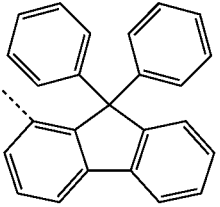 |
| 1-486 | 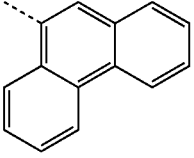 | 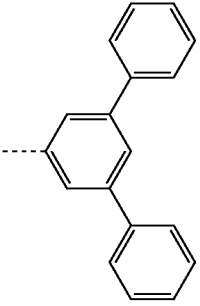 | 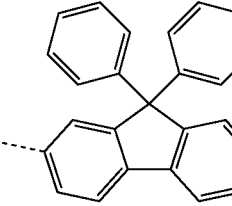 |
| 1-487 | 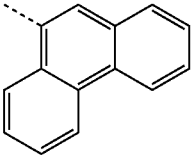 | 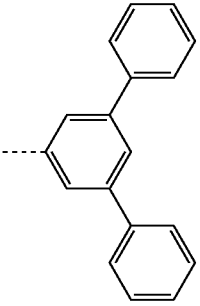 | 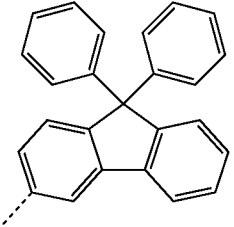 |
| 1-488 | 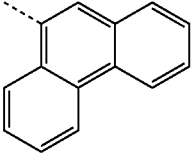 | 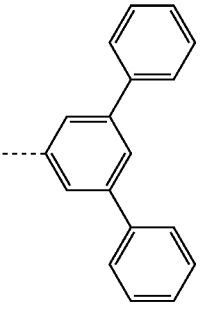 | 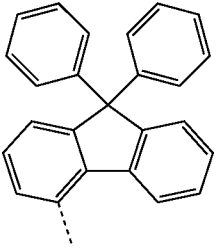 |
| 1-489 | 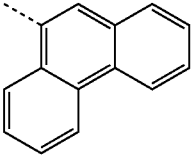 | 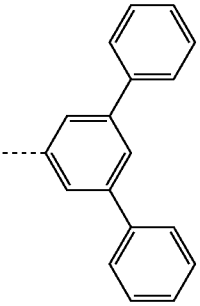 | 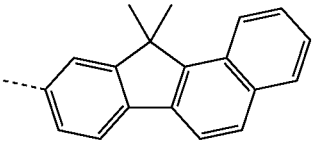 |

-continued
| Formula | ----Ar1 | ----Ar2 | ----Ar3 |
| --- | --- | --- | --- |
| 1-490 | 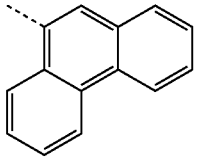 | 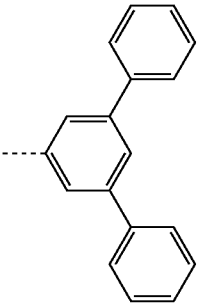 | 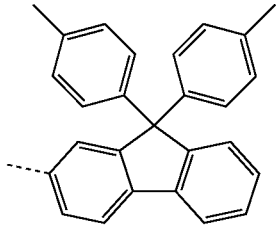 |
| 1-491 | 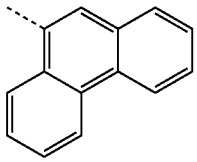 | 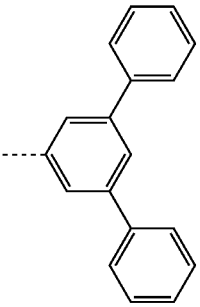 | 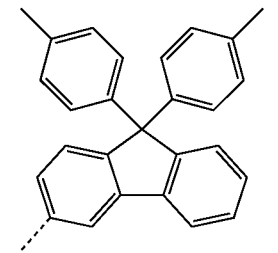 |
| 1-492 | 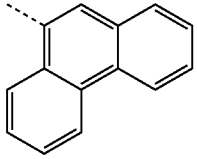 | 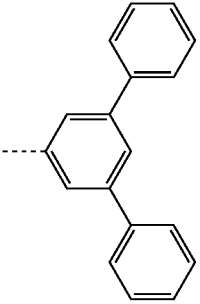 | 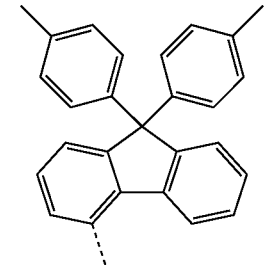 |
| 1-493 | 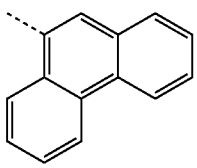 | 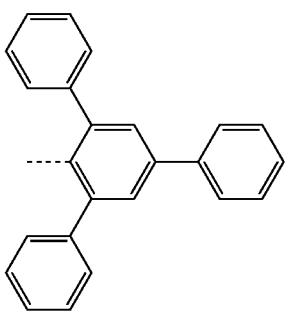 | 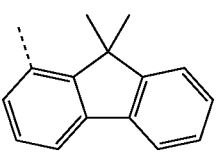 |
| 1-494 | 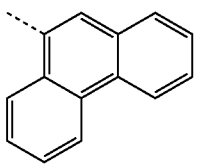 | 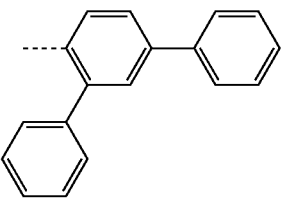 | 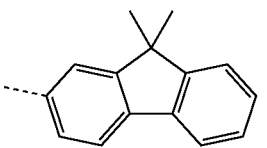 |

-continued
| Formula | ----Ar1 | ----Ar2 | ----Ar3 |
|---|---|---|---|
| 1-495 | 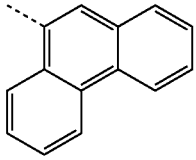 | 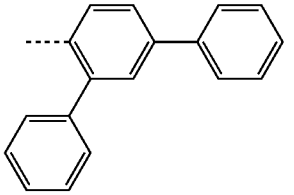 | 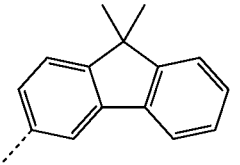 |
| 1-496 | 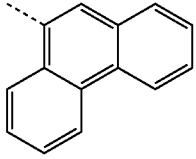 | 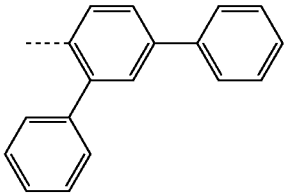 | 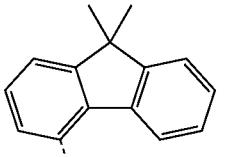 |
| 1-497 | 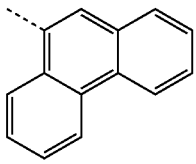 | 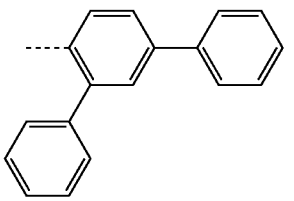 | 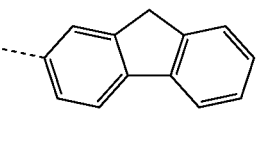 |
| 1-498 | 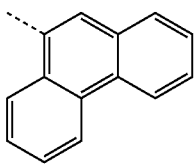 | 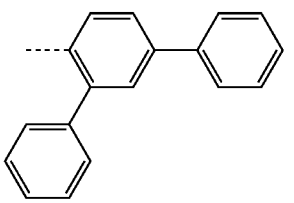 | 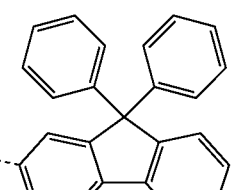 |
| 1-499 | 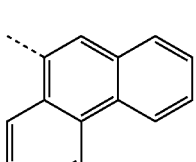 | 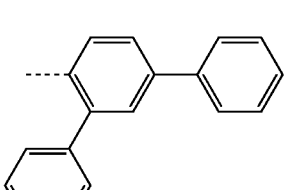 | 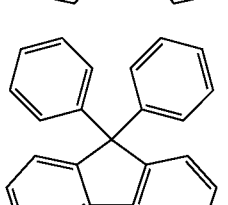 |
| 1-500 | 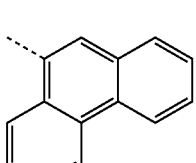 | 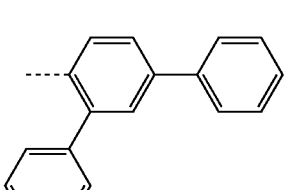 | 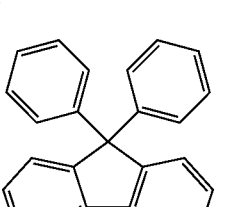 |
| 1-501 | 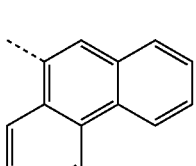 | 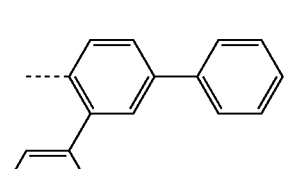 | 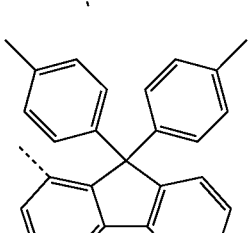 |

-continued
| Formula | ----Ar1 | ----Ar2 | ----Ar3 |
|---|---|---|---|
| 1-502 | 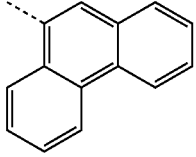 | 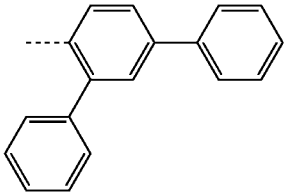 | 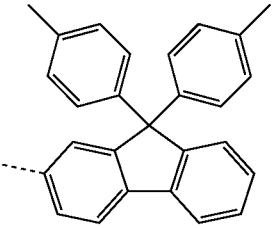 |
| 1-503 | 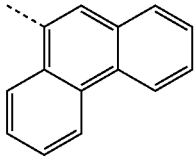 | 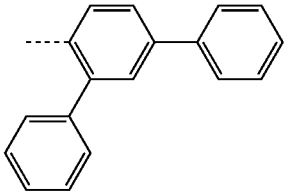 | 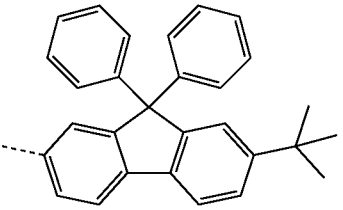 |
| 1-504 | 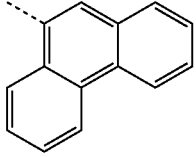 | 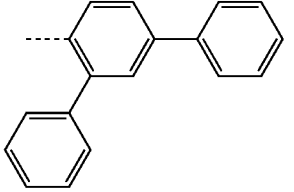 | 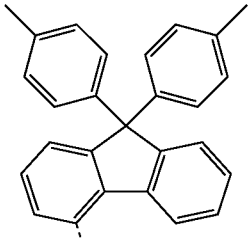 |
| 1-505 | 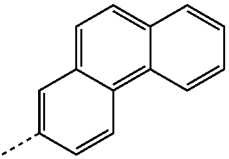 | 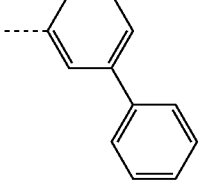 | 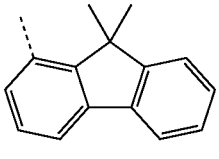 |
| 1-506 | 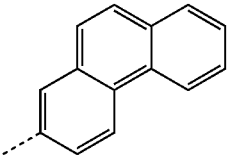 | 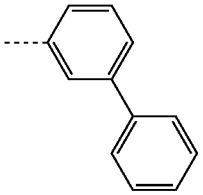 | 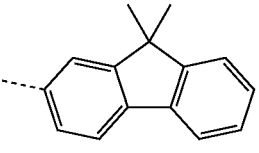 |
| 1-507 | 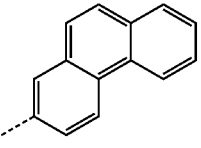 | 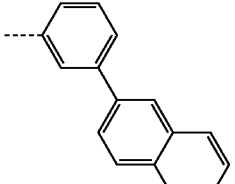 | 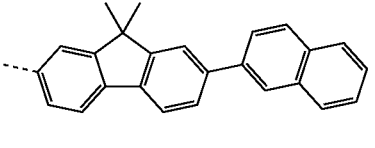 |
| 1-508 | 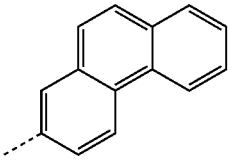 | 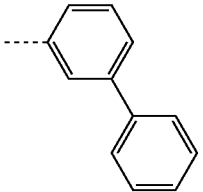 | 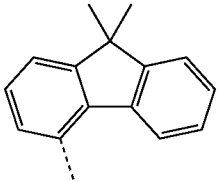 |

-continued

| Formula | ----Ar1 | ----Ar2 | ----Ar3 |
|---|---|---|---|
| 1-509 | phenanthrene | biphenyl (meta) | 9,9-diphenylfluorene |
| 1-510 | phenanthrene | biphenyl (meta) | 9,9-diphenylfluorene |
| 1-511 | phenanthrene | biphenyl (meta) | 9,9-diphenylfluorene |
| 1-512 | phenanthrene | biphenyl (meta) | 9,9-diphenylfluorene |
| 1-513 | phenanthrene | biphenyl (meta) | 9,9-di(p-tolyl)fluorene |
| 1-514 | phenanthrene | biphenyl (meta) | 9,9-di(p-tolyl)fluorene |

-continued
| Formula | ----Ar1 | ----Ar2 | ----Ar3 |
|---|---|---|---|
| 1-515 | 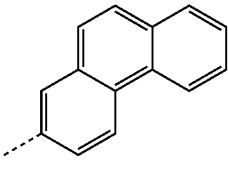 | 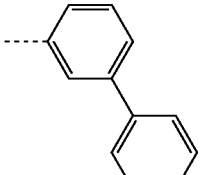 | 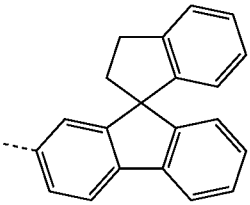 |
| 1-516 | 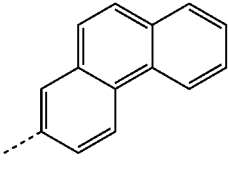 | 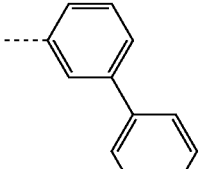 | 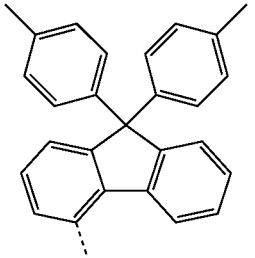 |
| 1-517 | 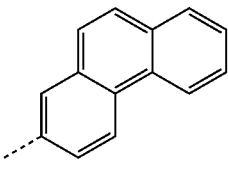 | 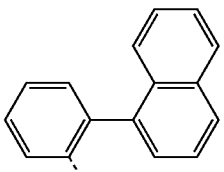 | 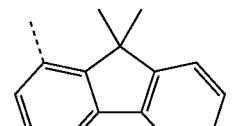 |
| 1-518 | 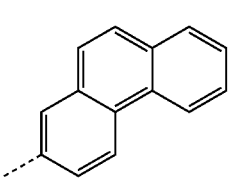 | 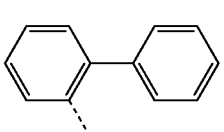 | 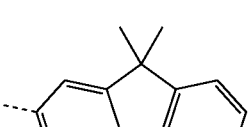 |
| 1-519 | 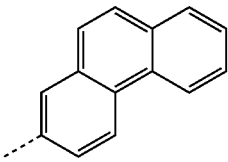 | 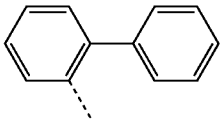 | 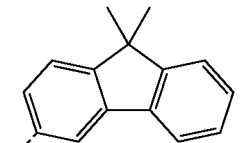 |
| 1-520 | 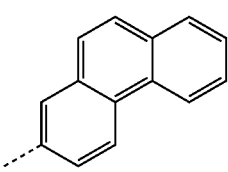 | 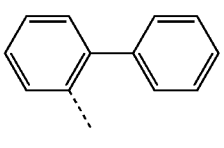 | 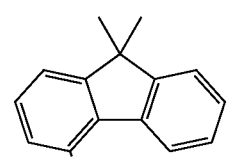 |
| 1-521 | 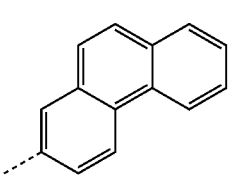 | 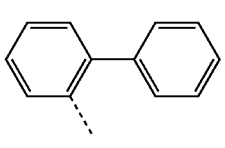 | 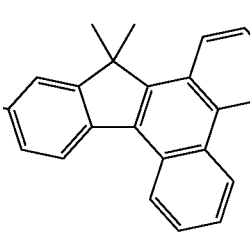 |

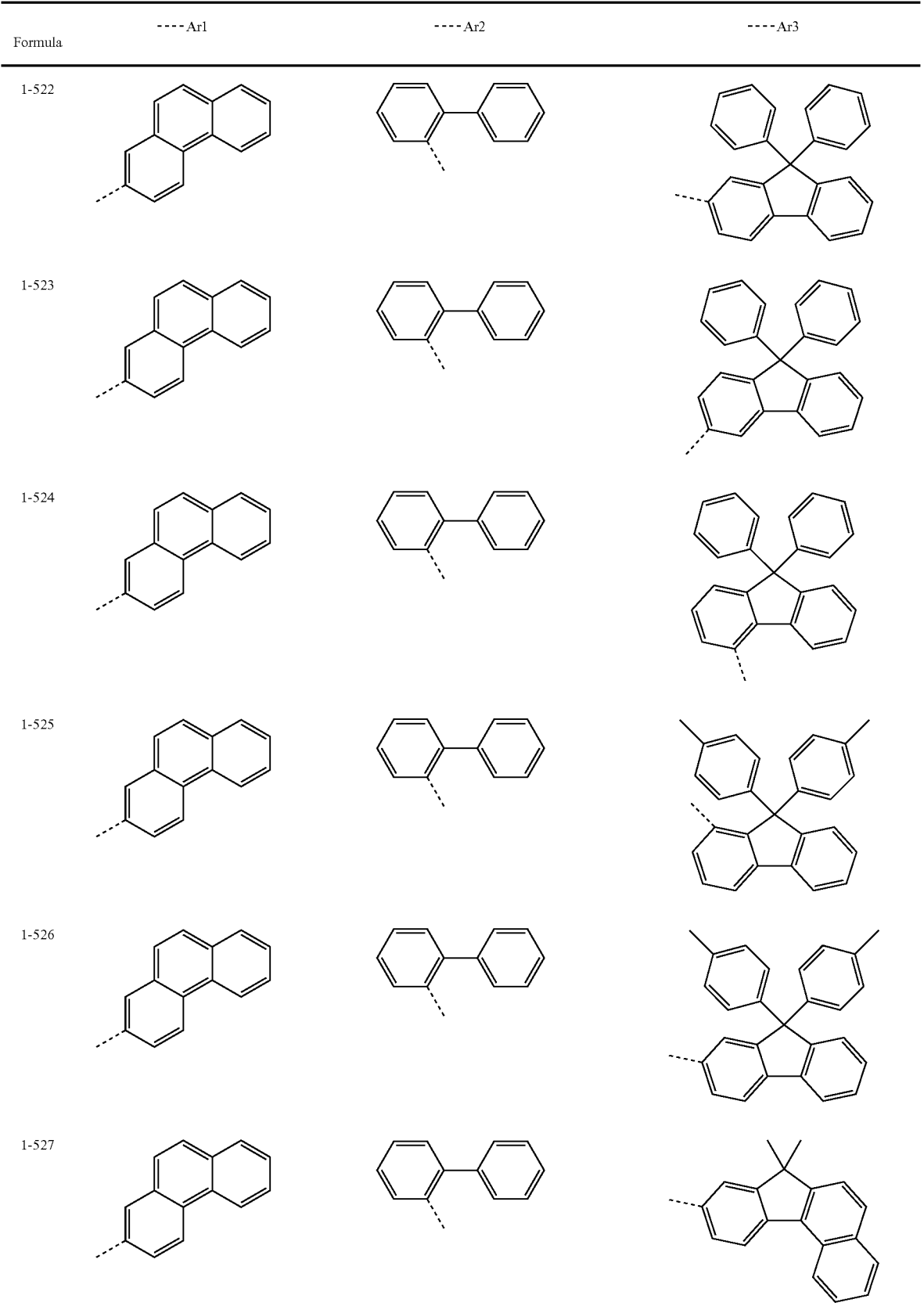

-continued
| Formula | ----Ar1 | ----Ar2 | ----Ar3 |
|---|---|---|---|
| 1-528 | 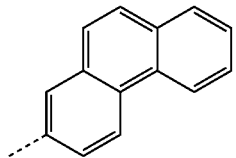 | 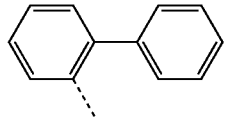 | 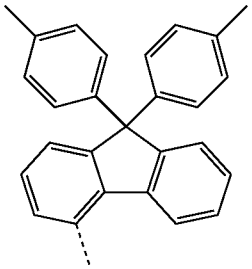 |
| 1-529 | 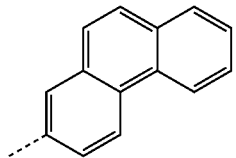 | 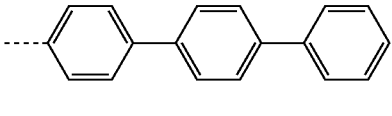 | 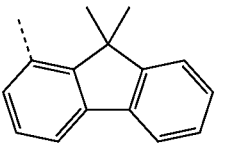 |
| 1-530 | 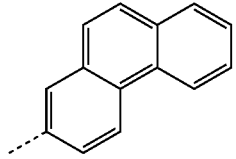 | 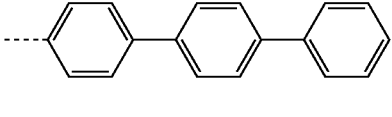 | 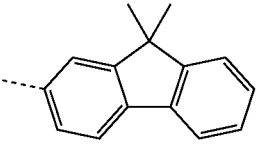 |
| 1-531 | 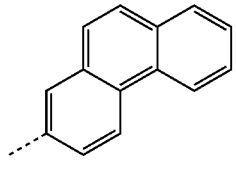 | 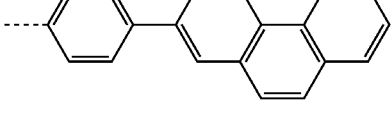 | 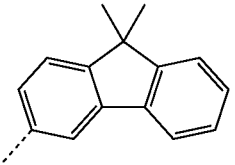 |
| 1-532 | 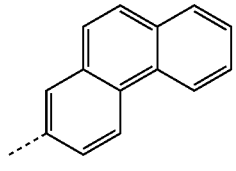 | 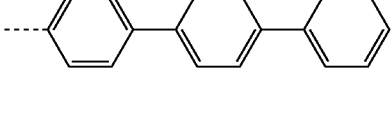 | 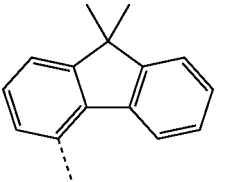 |
| 1-533 | 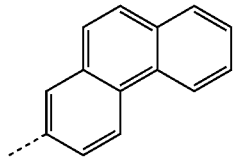 | 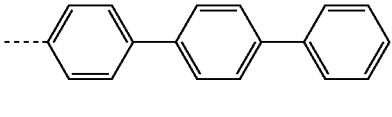 | 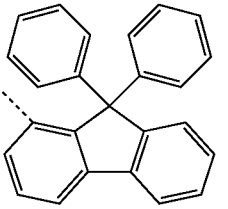 |
| 1-534 | 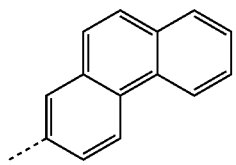 | 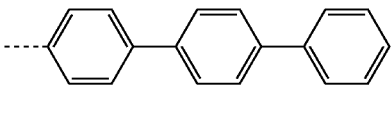 | 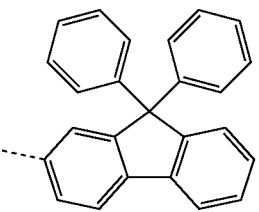 |

-continued
| Formula | ----Ar1 | ----Ar2 | ----Ar3 |
|---|---|---|---|
| 1-535 | 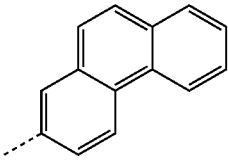 | 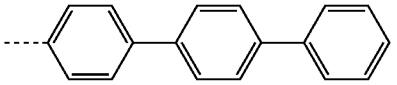 | 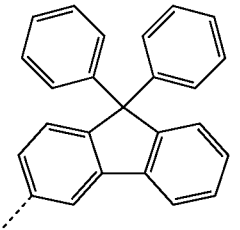 |
| 1-536 | 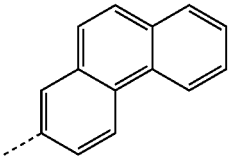 | 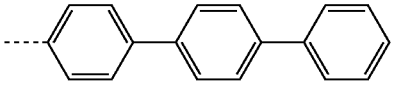 | 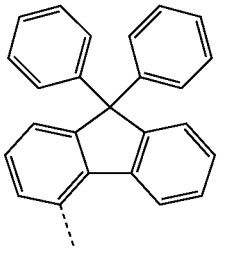 |
| 1-537 | 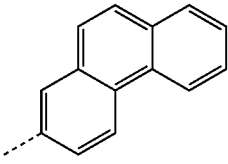 | 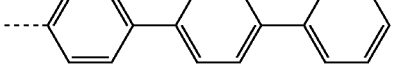 | 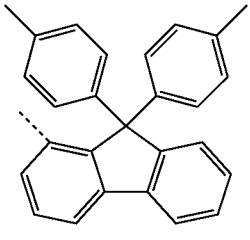 |
| 1-538 | 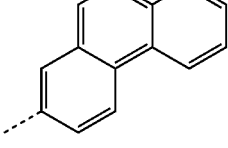 | 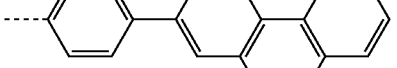 | 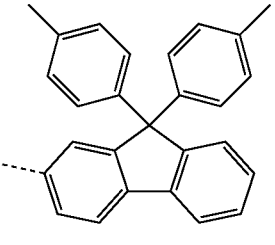 |
| 1-539 | 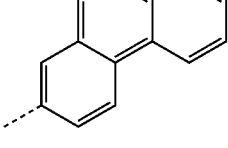 | 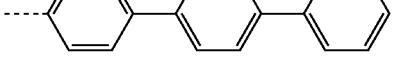 | 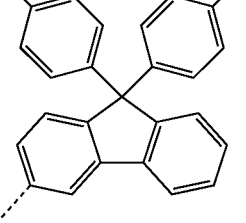 |
| 1-540 | 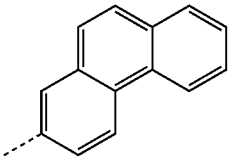 | 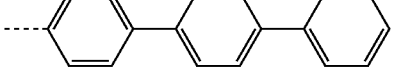 | 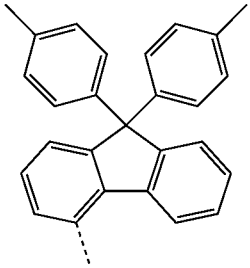 |

-continued
| Formula | ----Ar1 | ----Ar2 | ----Ar3 |
|---|---|---|---|
| 1-541 | 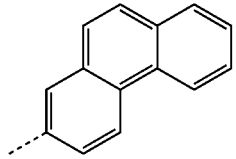 | 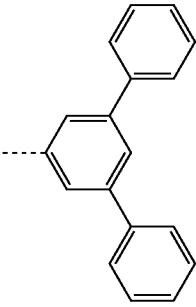 | 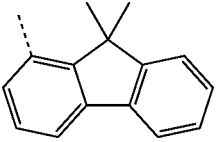 |
| 1-542 | 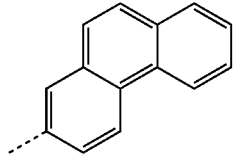 | 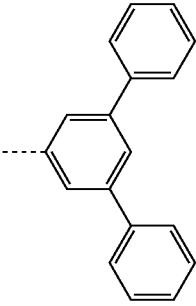 | 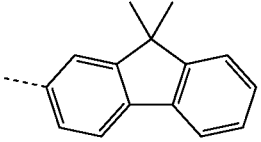 |
| 1-543 | 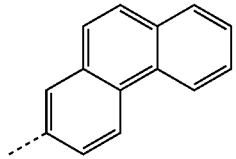 | 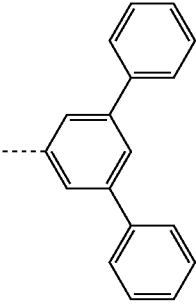 | 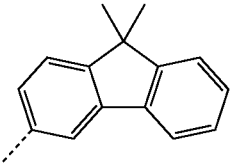 |
| 1-544 | 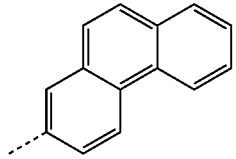 | 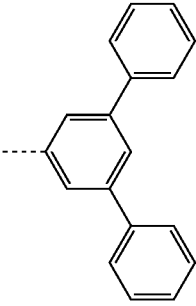 | 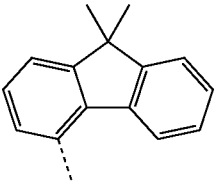 |
| 1-545 | 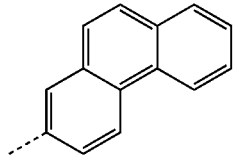 | 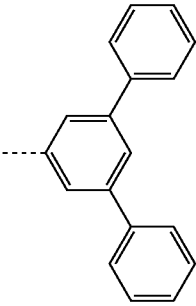 | 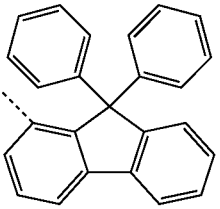 |

-continued
| Formula | ----Ar1 | ----Ar2 | ----Ar3 |
|---|---|---|---|
| 1-546 | 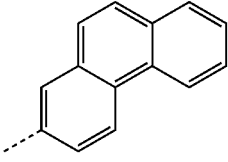 | 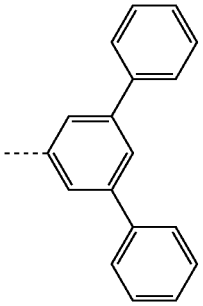 | 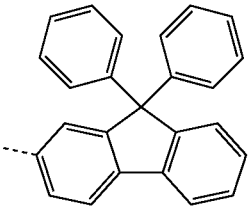 |
| 1-547 | 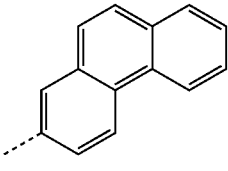 | 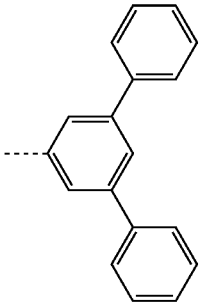 | 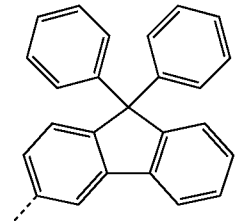 |
| 1-548 | 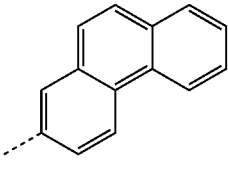 | 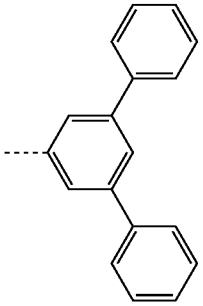 | 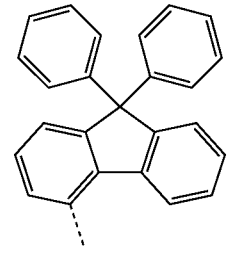 |
| 1-549 | 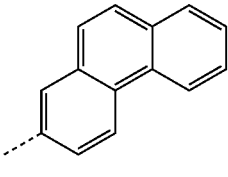 | 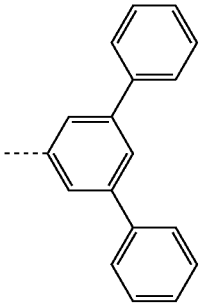 | 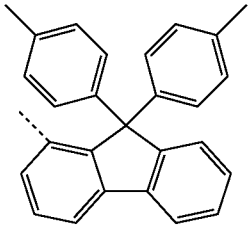 |
| 1-550 | 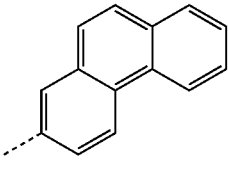 | 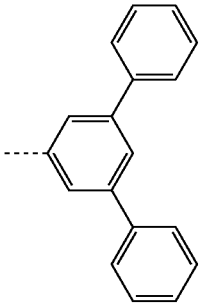 | 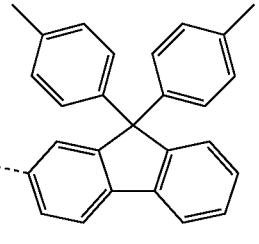 |

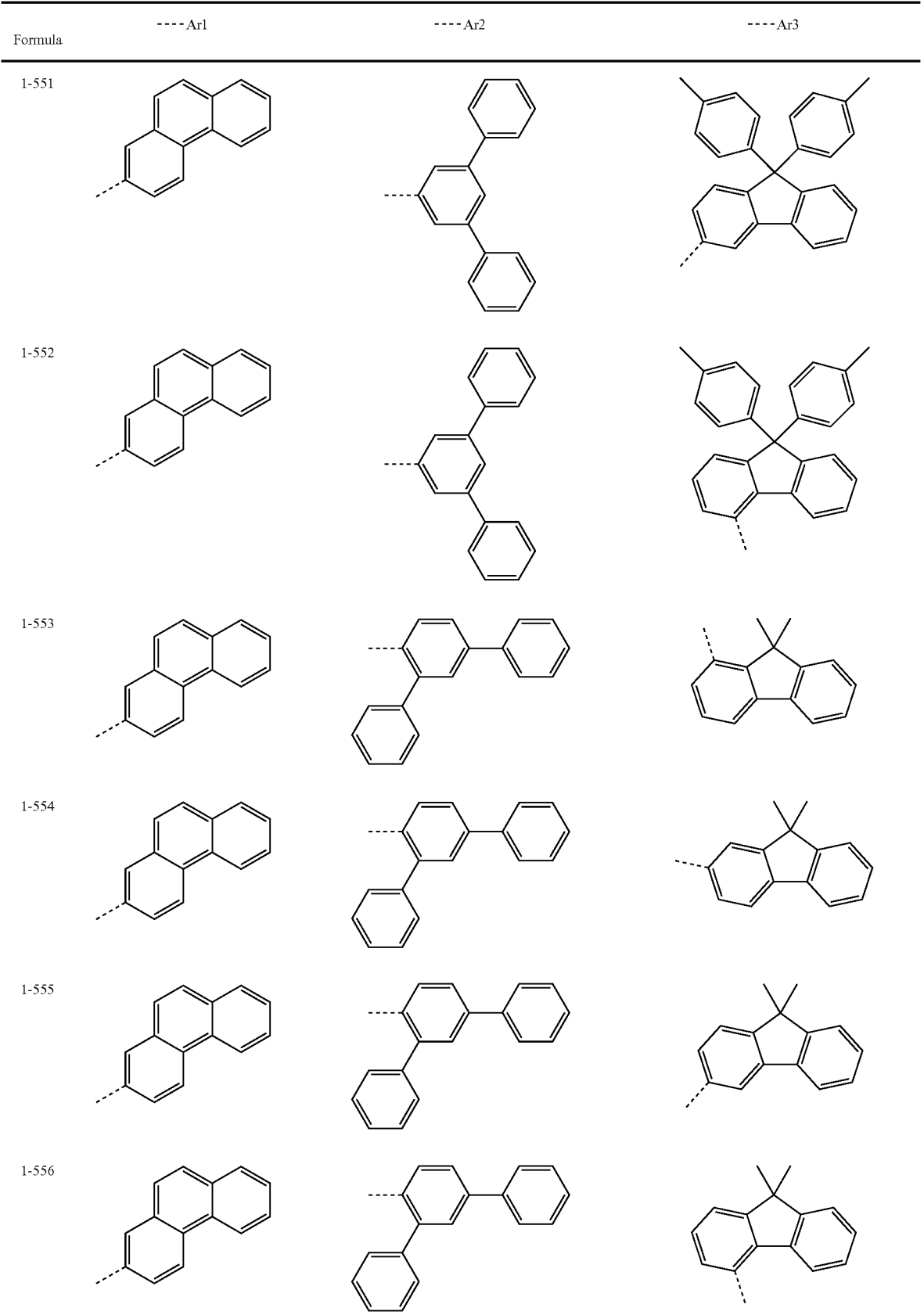

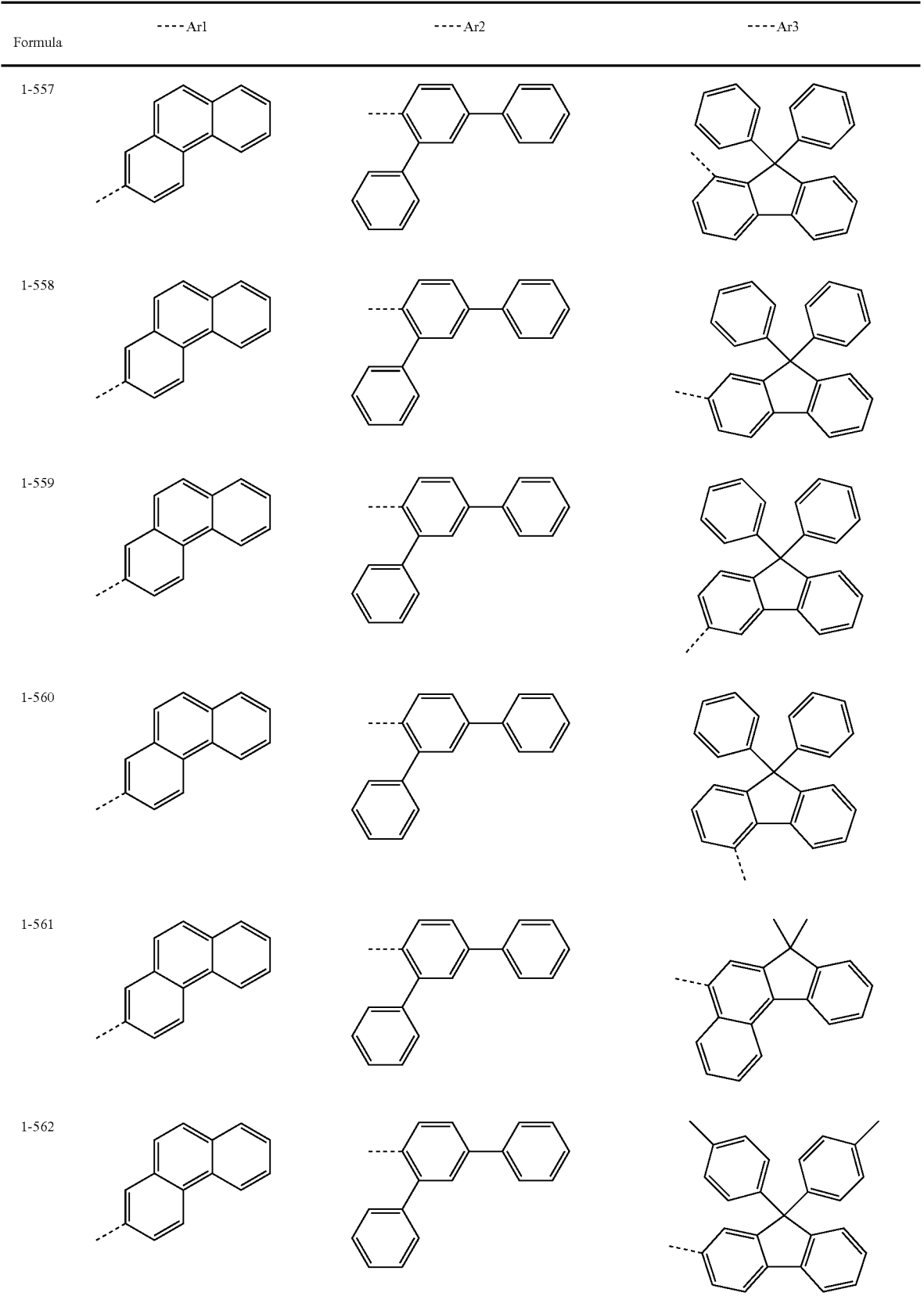

-continued
| Formula | ----Ar1 | ----Ar2 | ----Ar3 |
|---|---|---|---|
| 1-563 | | | 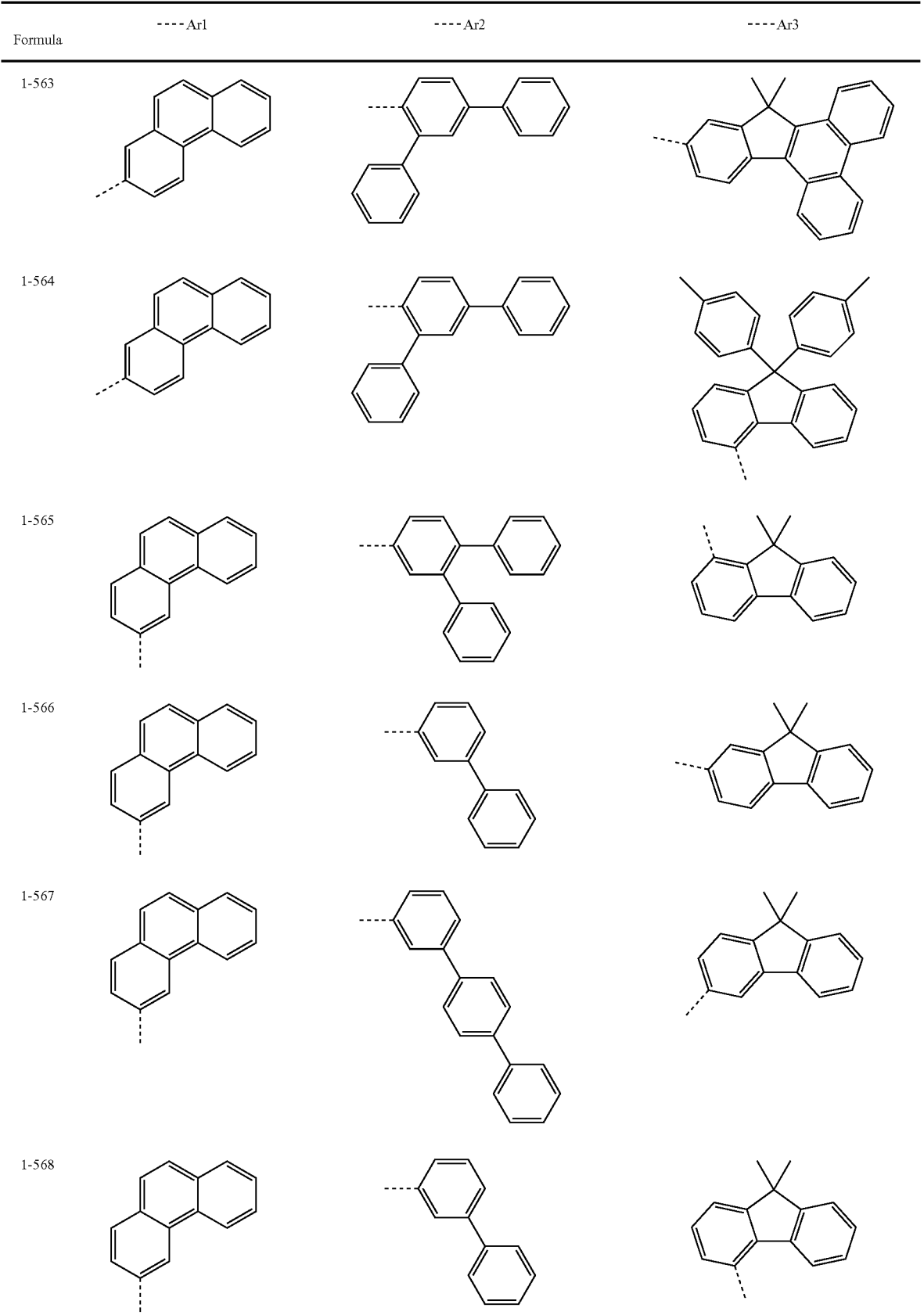 |
| 1-564 | | | |
| 1-565 | | | |
| 1-566 | | | |
| 1-567 | | | |
| 1-568 | | | |

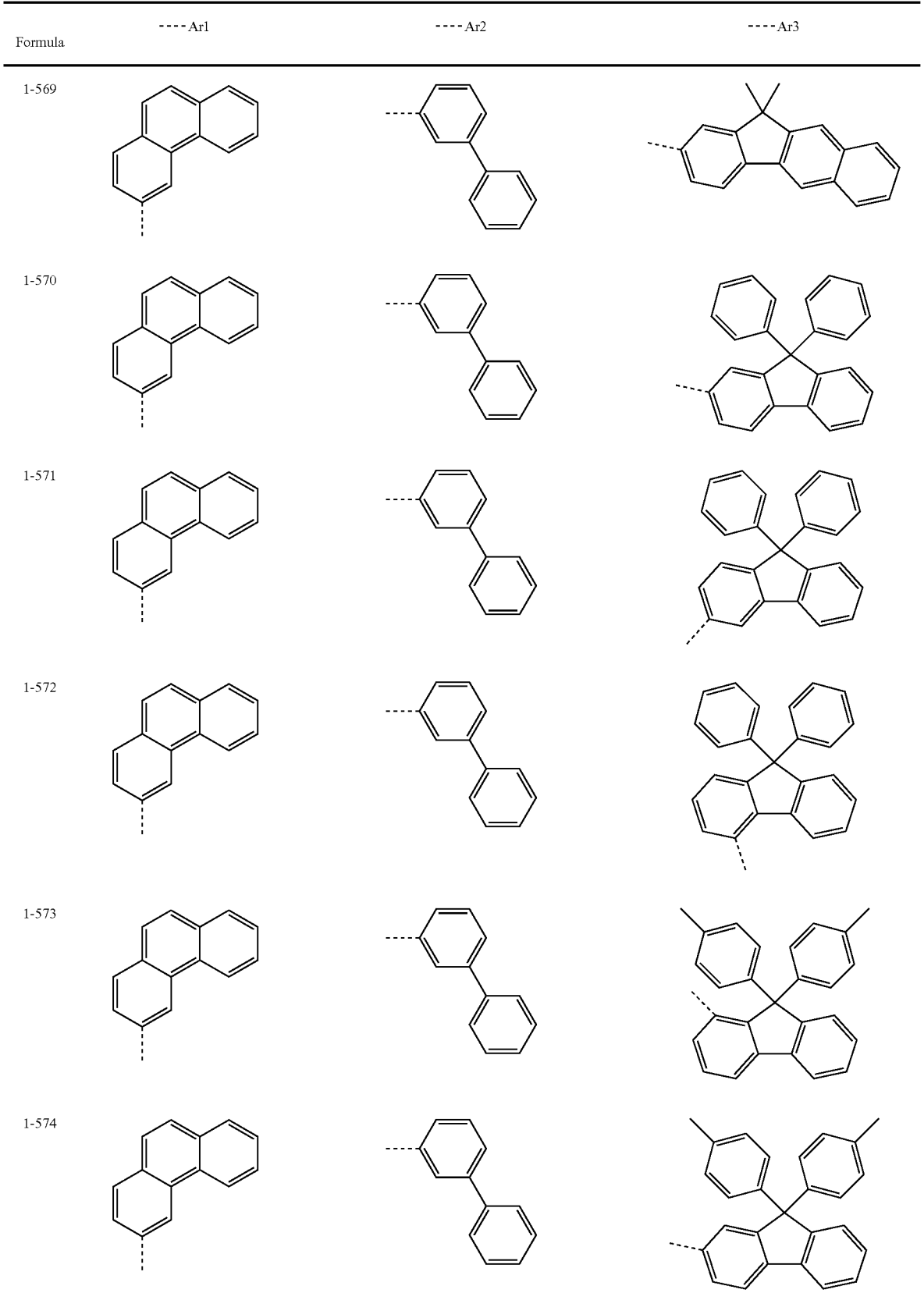

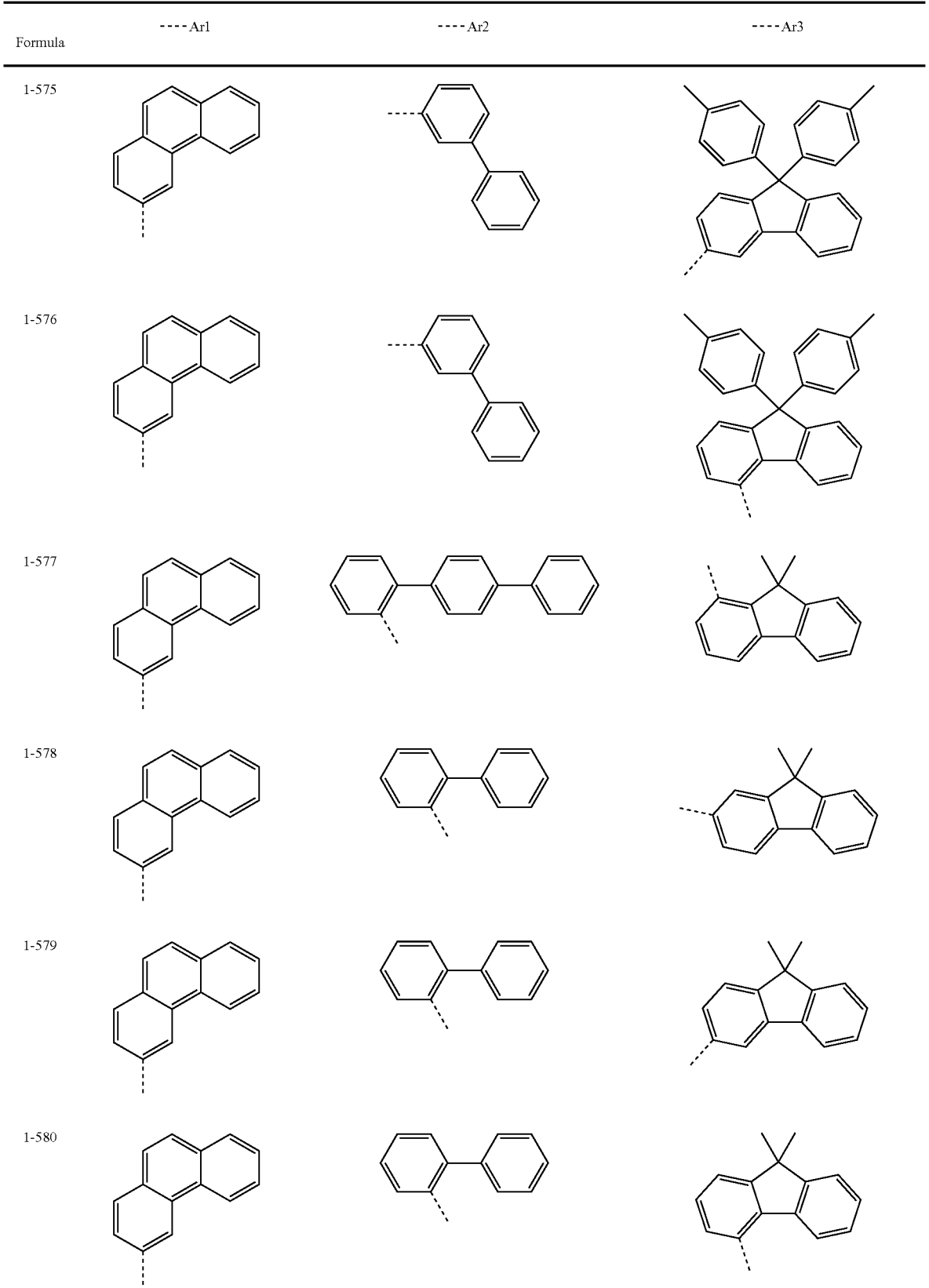

-continued
| Formula | ----Ar1 | ----Ar2 | ----Ar3 |
|---|---|---|---|
| 1-581 | 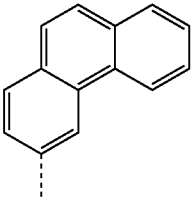 | 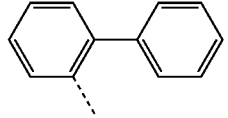 | 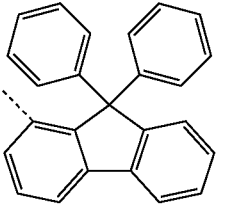 |
| 1-582 | 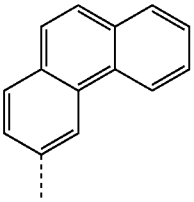 | 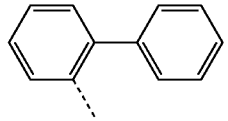 | 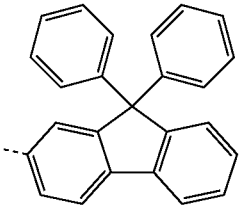 |
| 1-583 | 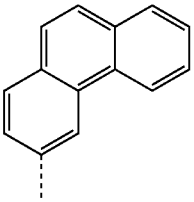 | 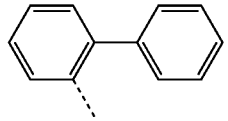 | 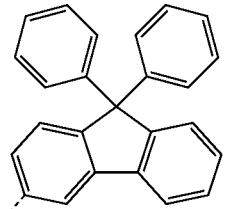 |
| 1-584 | 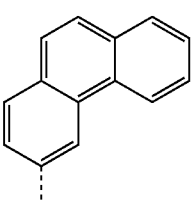 | 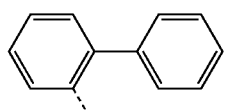 | 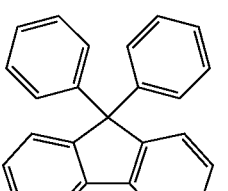 |
| 1-585 | 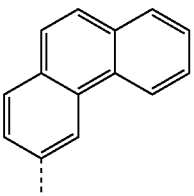 | 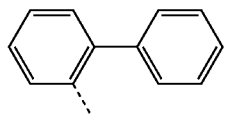 | 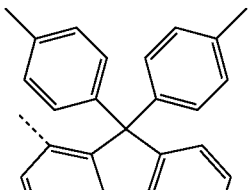 |
| 1-586 | 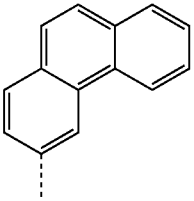 | 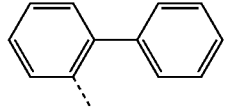 | 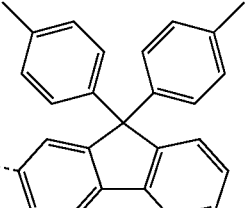 |

-continued
| Formula | ----Ar1 | ----Ar2 | ----Ar3 |
|---|---|---|---|
| 1-587 | 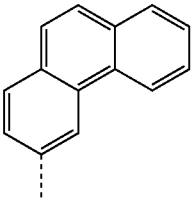 | 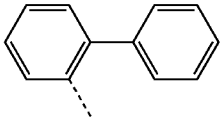 | 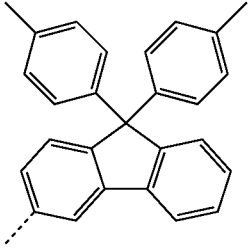 |
| 1-588 | 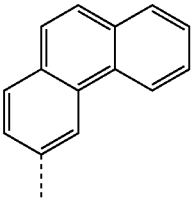 | 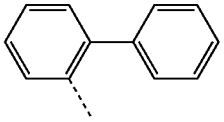 | 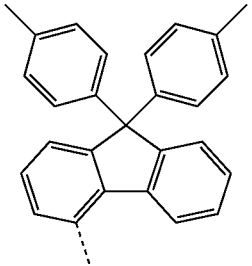 |
| 1-589 | 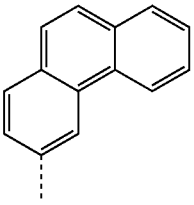 | 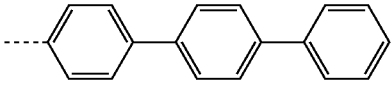 | 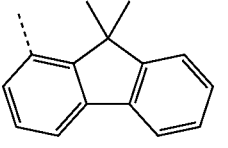 |
| 1-590 | 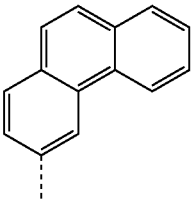 | 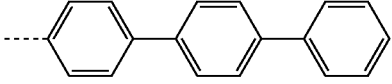 | 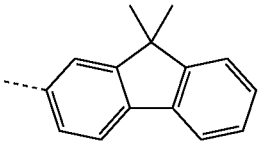 |
| 1-591 | 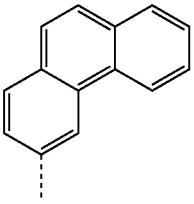 | 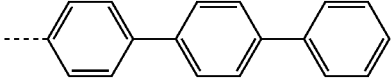 | 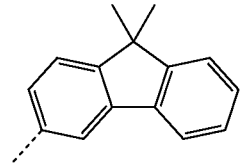 |
| 1-592 | 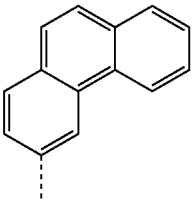 | 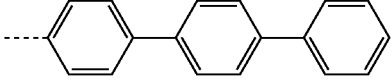 | 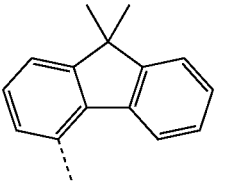 |

-continued
| Formula | ----Ar1 | ----Ar2 | ----Ar3 |
|---|---|---|---|
| 1-593 | 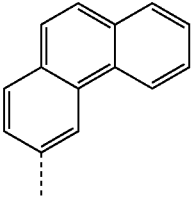 | 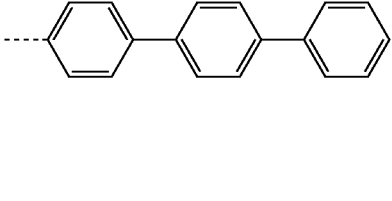 | 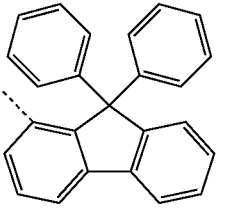 |
| 1-594 | 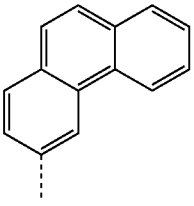 | 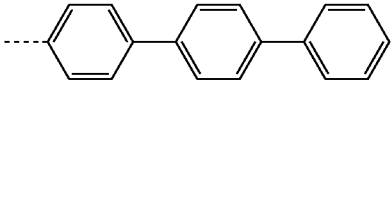 | 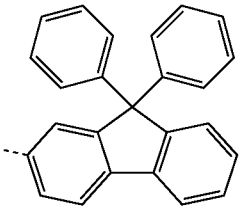 |
| 1-595 | 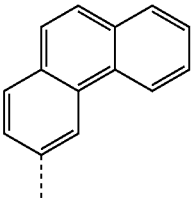 | 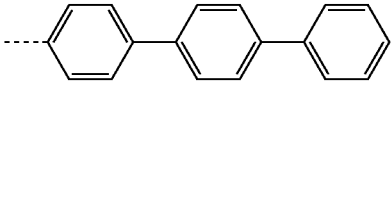 | 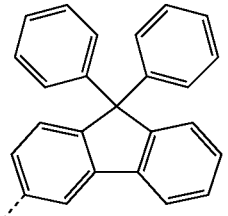 |
| 1-596 | 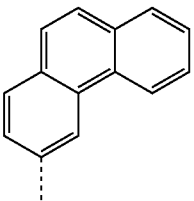 | 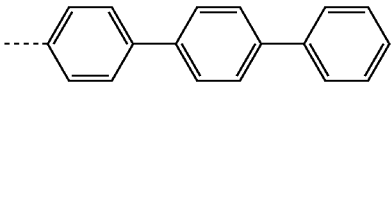 | 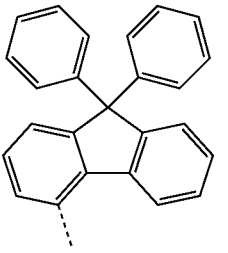 |
| 1-597 | 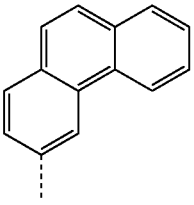 | 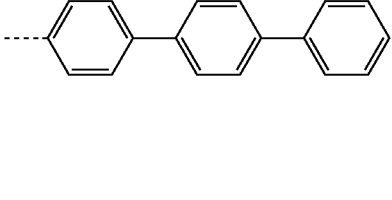 | 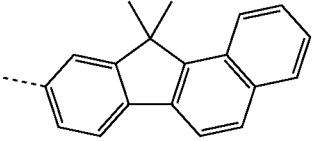 |
| 1-598 | 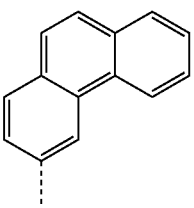 | 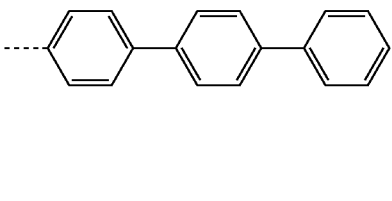 | 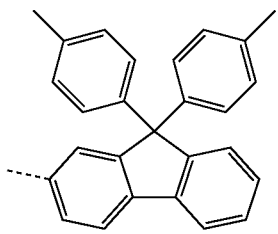 |

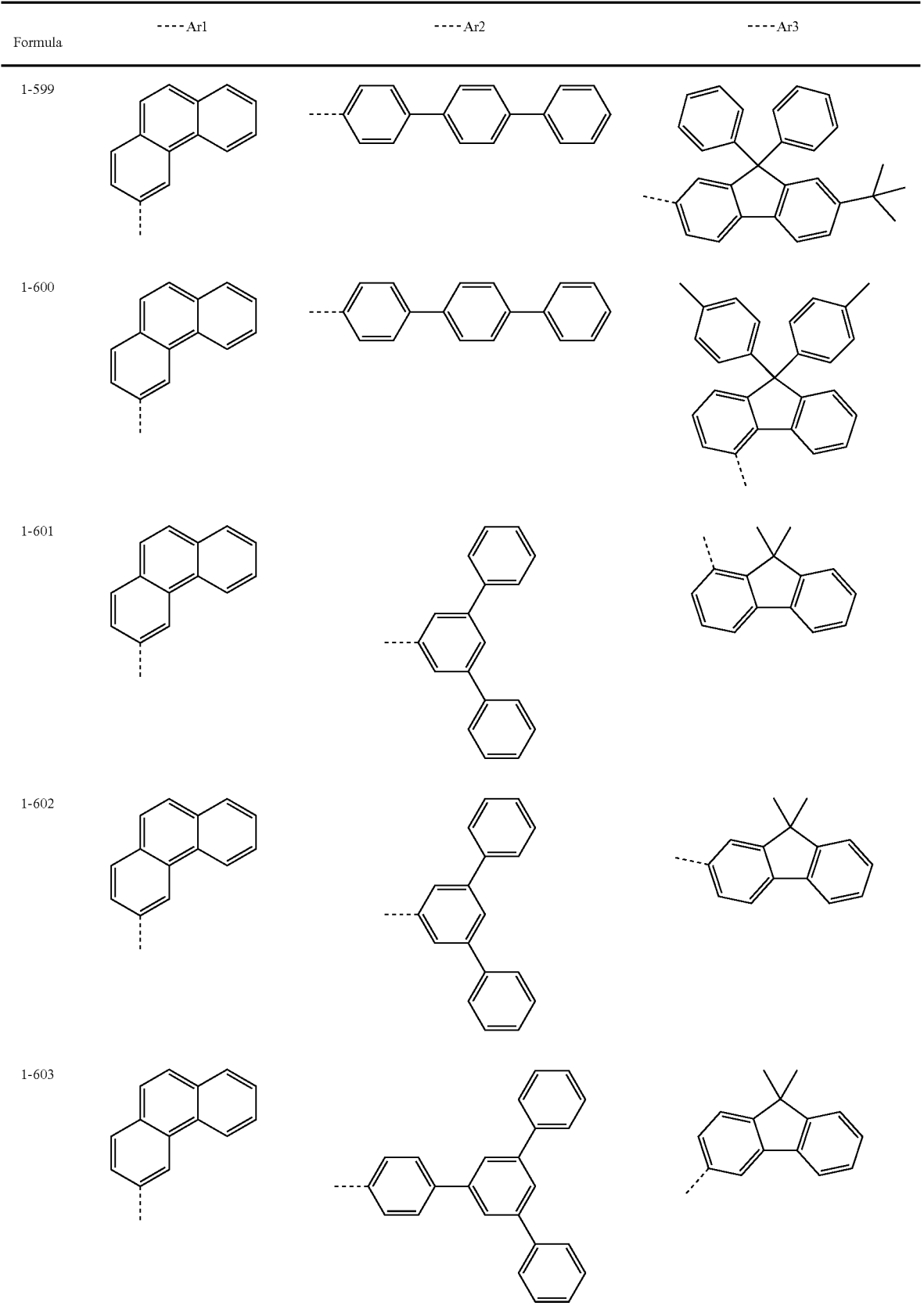

-continued

| Formula | ----Ar1 | ----Ar2 | ----Ar3 |
| --- | --- | --- | --- |
| 1-604 | | | |
| 1-605 | | | |
| 1-606 | | | |
| 1-607 | | | |
| 1-608 | | | |

-continued
| Formula | ----Ar1 | ----Ar2 | ----Ar3 |
|---|---|---|---|
| 1-609 | 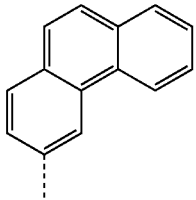 | 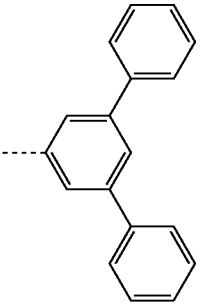 | 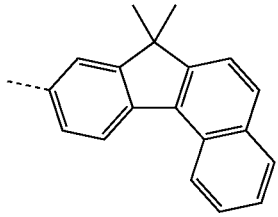 |
| 1-610 | 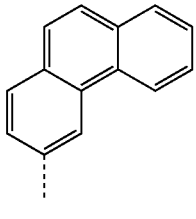 | 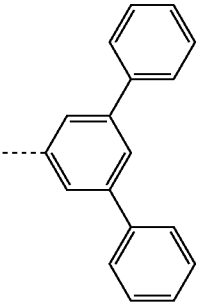 | 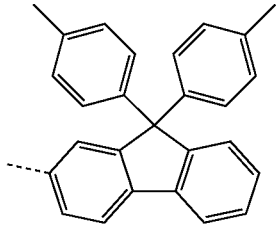 |
| 1-611 | 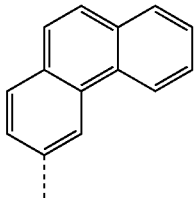 | 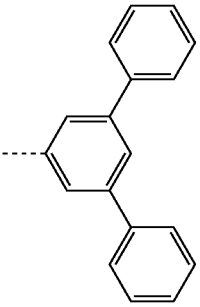 | 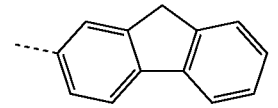 |
| 1-612 | 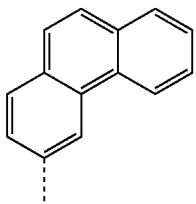 | 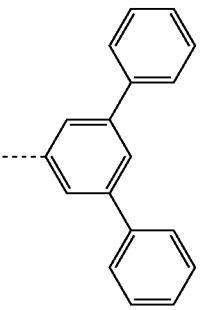 | 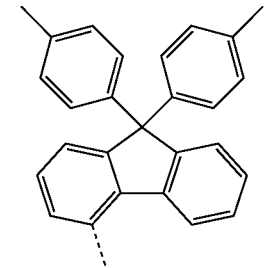 |
| 1-613 | 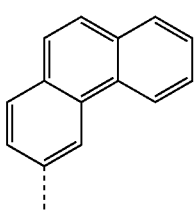 | 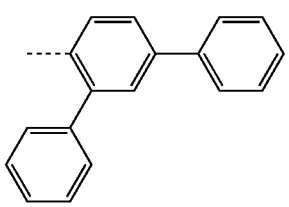 | 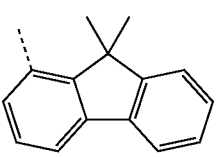 |

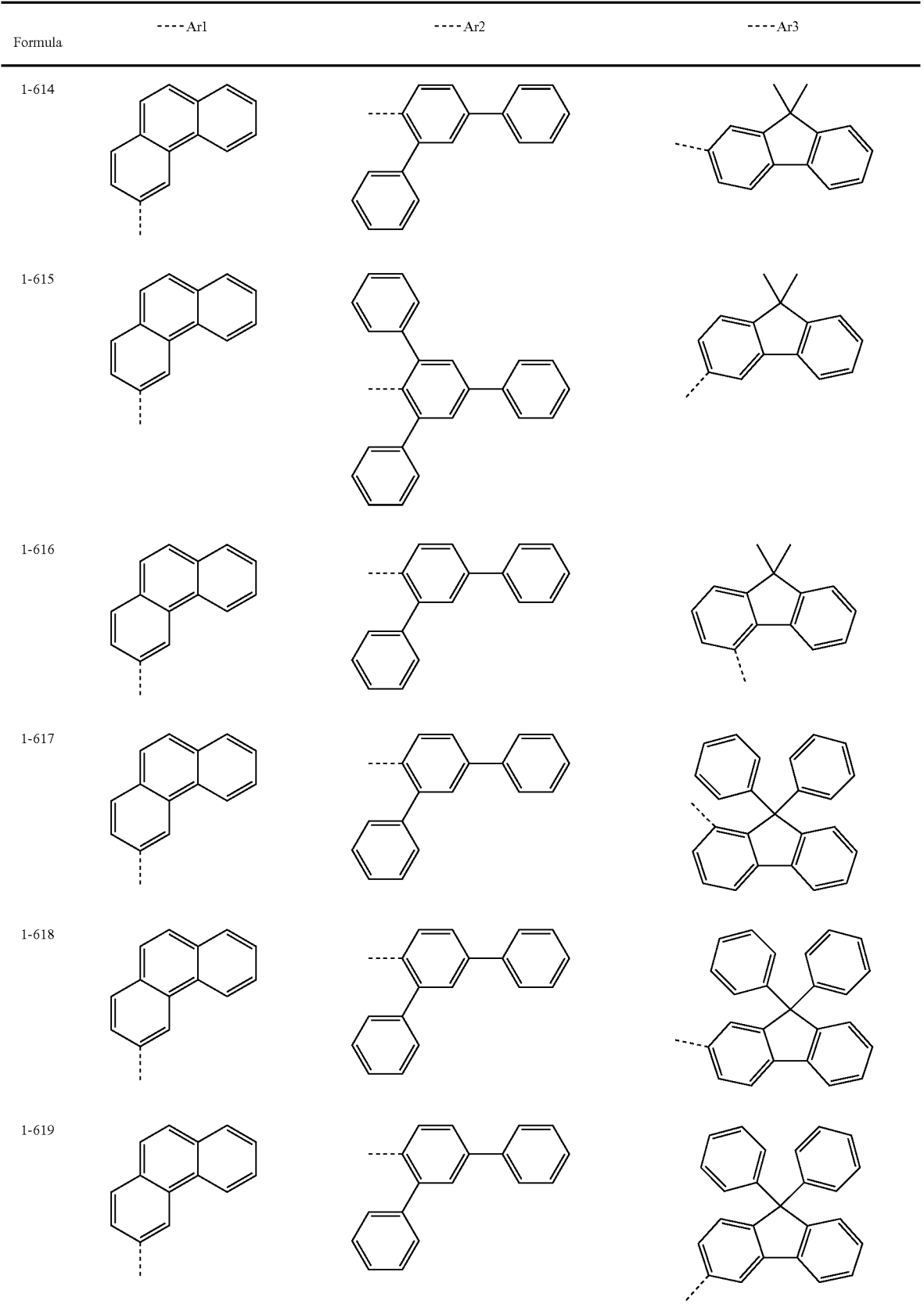

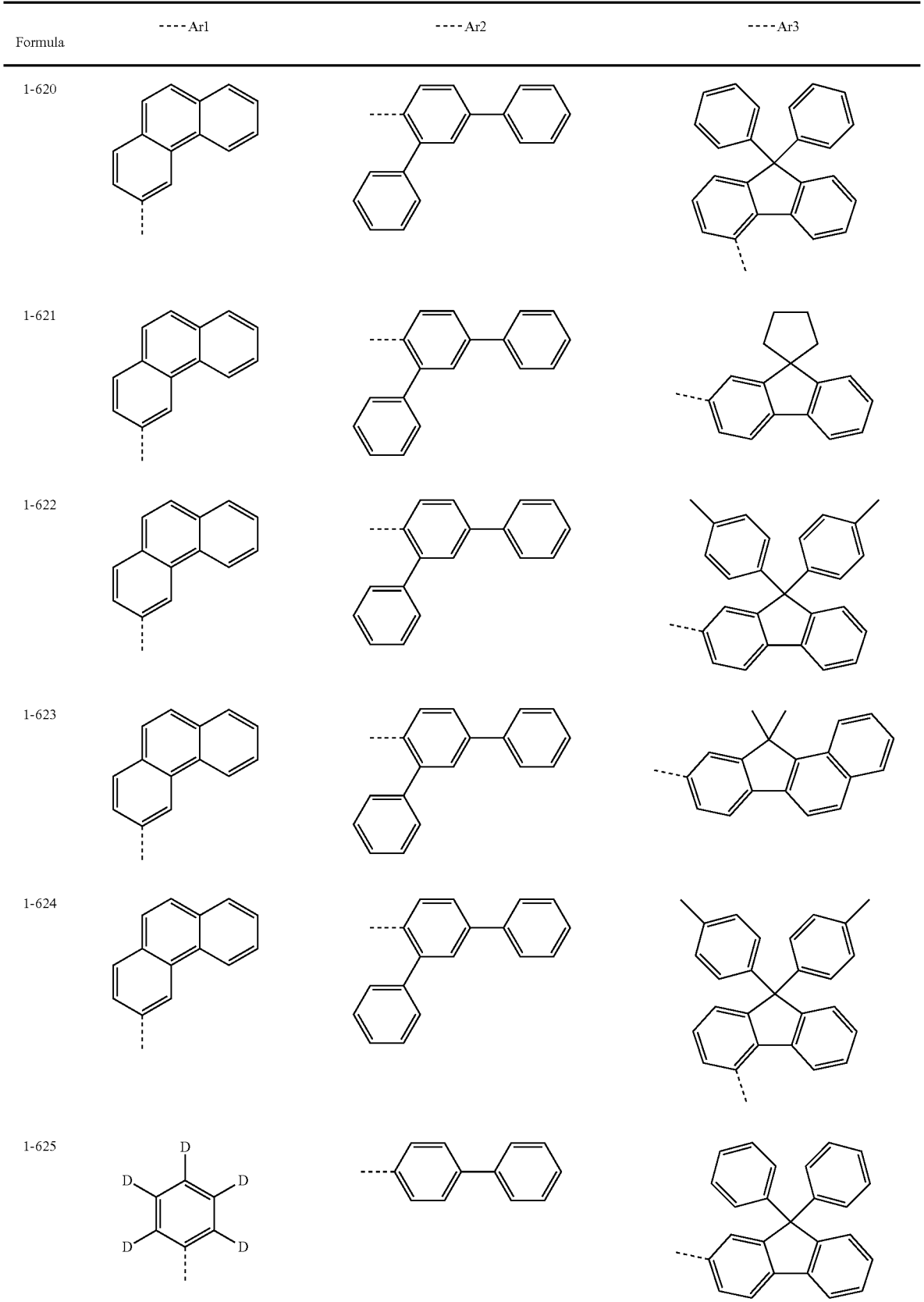

-continued
| Formula | ----Ar1 | ----Ar2 | ----Ar3 |
|---|---|---|---|
| 1-626 | 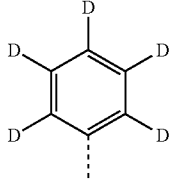 | 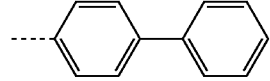 | 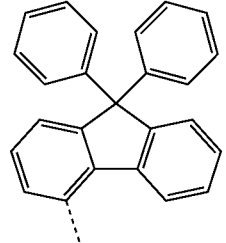 |
| 1-627 | 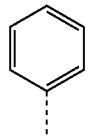 | 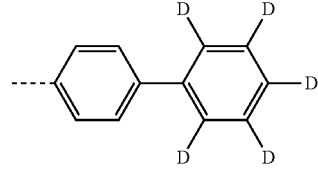 | 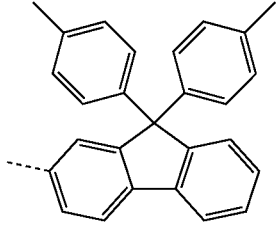 |
| Formula | ---Ar1 | ---Ar2 | ---Ar3 |
|---|---|---|---|
| 2-1 | 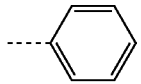 | 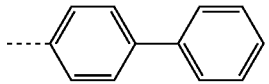 | 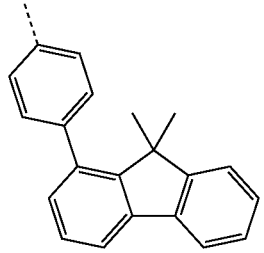 |
| 2-2 | 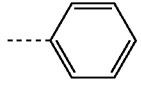 | 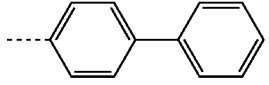 | 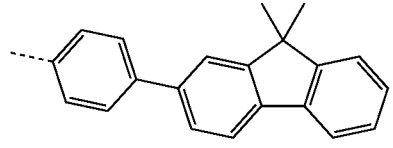 |
| 2-3 | 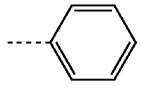 | 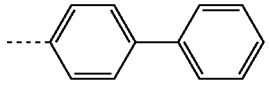 | 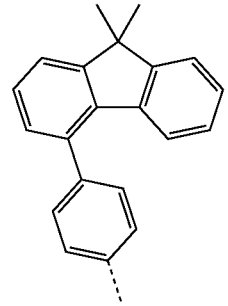 |
| 2-4 | 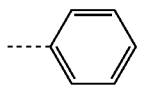 | 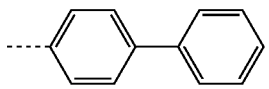 | 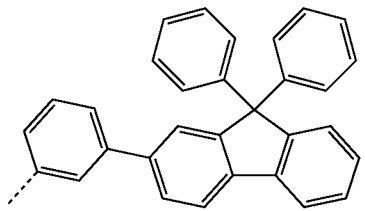 |

-continued
| Formula | ---Ar1 | ---Ar2 | ---Ar3 |
|---|---|---|---|
| 2-5 | 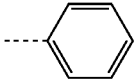 | 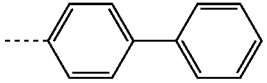 | 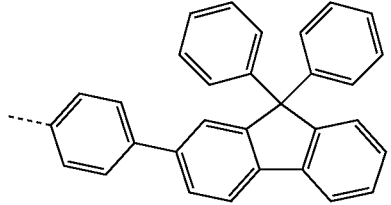 |
| 2-6 | 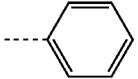 | 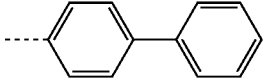 | 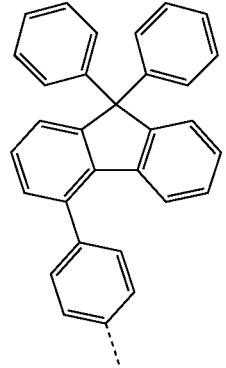 |
| 2-7 | 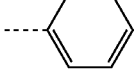 | 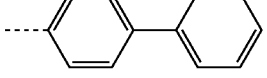 | 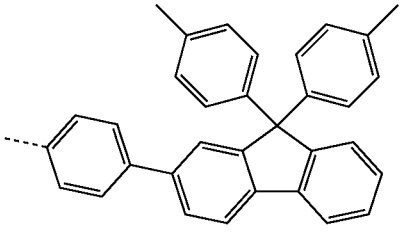 |
| 2-8 | 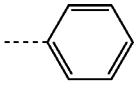 | 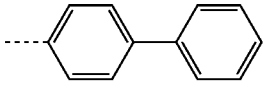 | 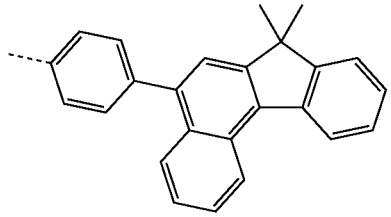 |
| 2-9 | 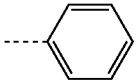 | 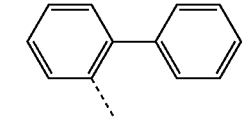 | 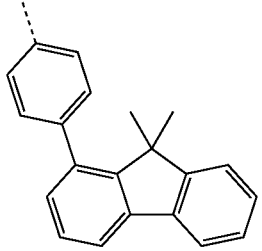 |
| 2-10 | 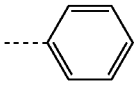 | 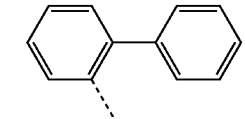 | 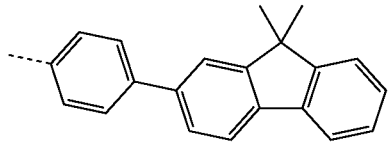 |

-continued

| Formula | ---Ar1 | ---Ar2 | ---Ar3 |
|---|---|---|---|
| 2-11 | phenyl | biphenyl-2-yl | 9,9-dimethyl-fluorene substituted at 3-position with p-phenylene linker |
| 2-12 | phenyl | biphenyl-2-yl | 9,9-dimethyl-fluorene substituted at 4-position with p-phenylene linker |
| 2-13 | phenyl | biphenyl-2-yl | 9,9-diphenyl-fluorene substituted at 2-position with p-phenylene linker |
| 2-14 | phenyl | biphenyl-2-yl | 9,9-diphenyl-fluorene substituted at 4-position with p-phenylene linker |
| 2-15 | phenyl | biphenyl-2-yl | 11,11-dimethyl-benzo[a]fluorene substituted with p-phenylene linker |

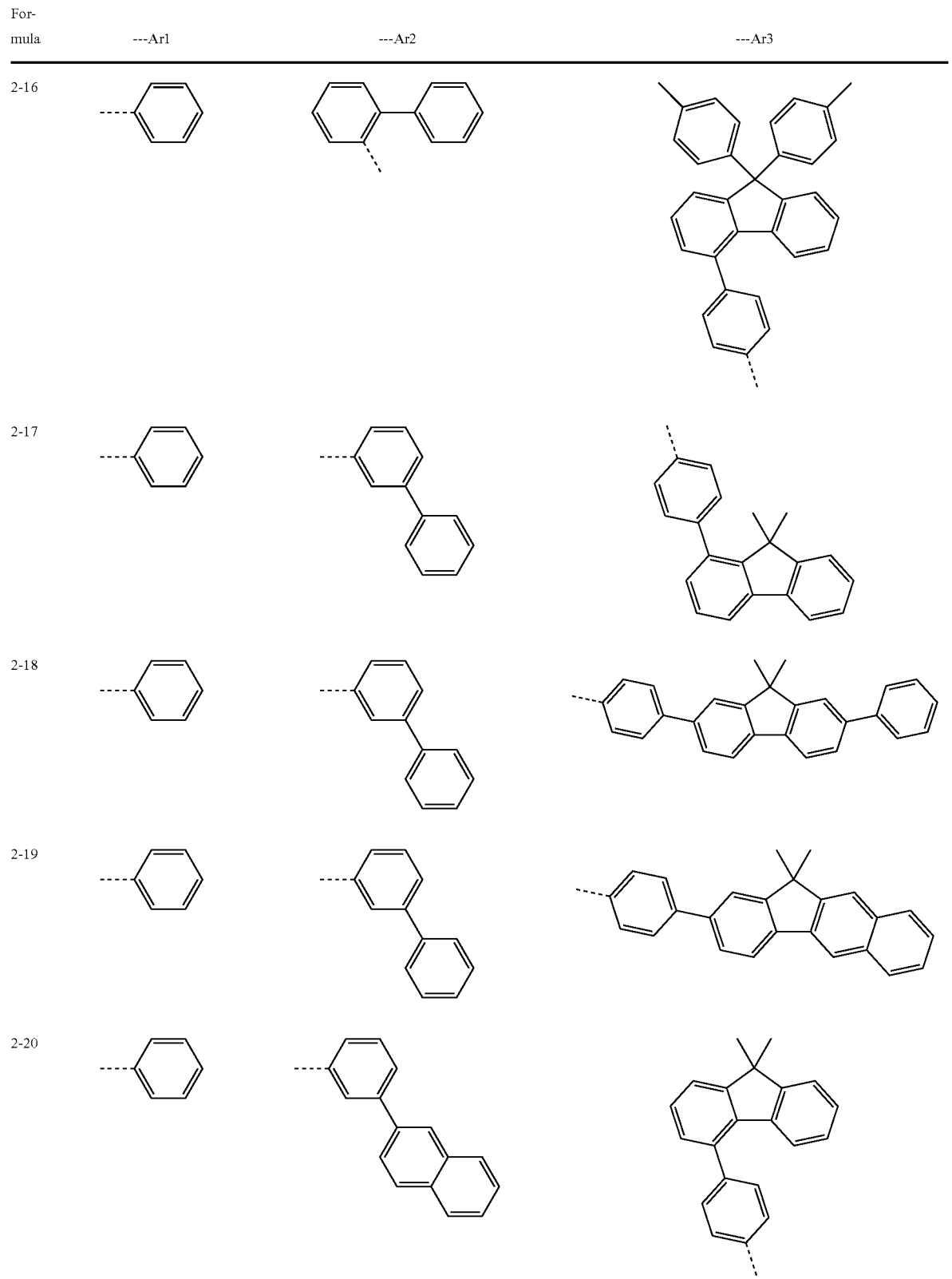

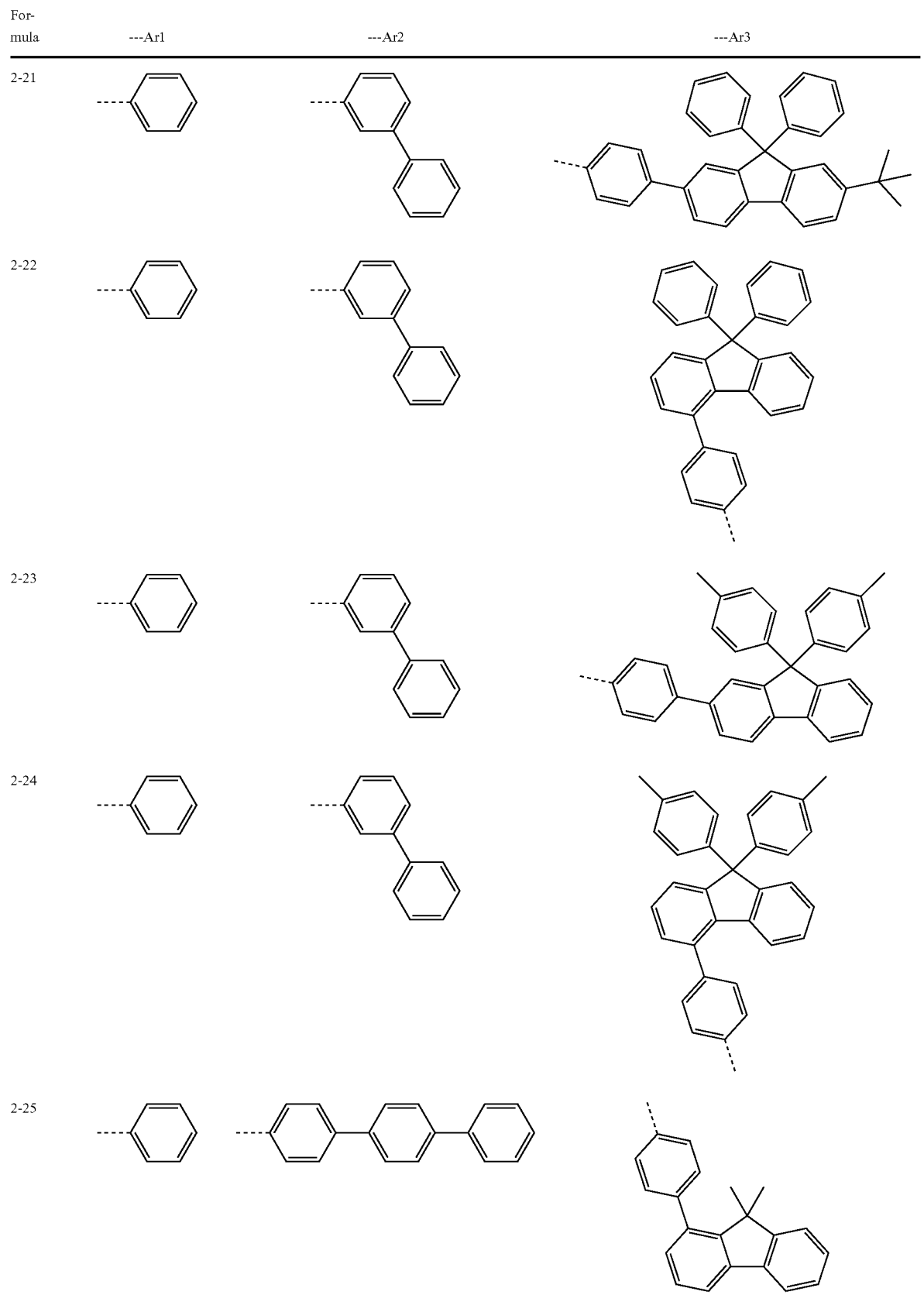

| Formula | ---Ar1 | ---Ar2 | ---Ar3 |
|---|---|---|---|
| 2-26 | 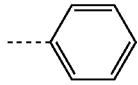 | 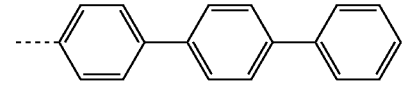 | 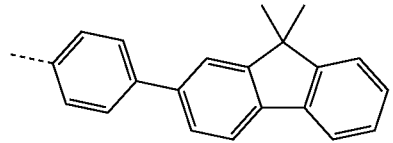 |
| 2-27 | 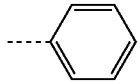 | 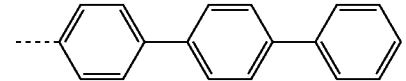 | 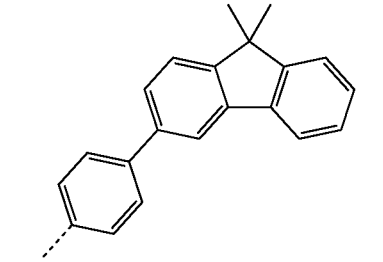 |
| 2-28 | 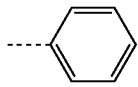 | 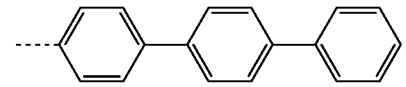 | 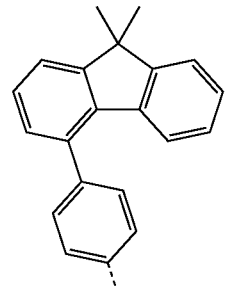 |
| 2-29 | 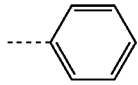 | 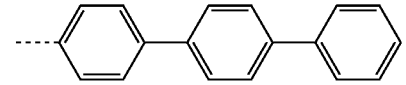 | 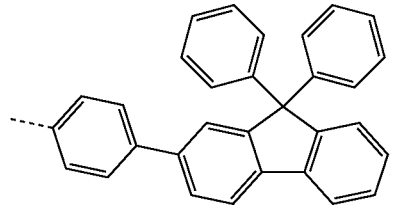 |
| 2-30 | 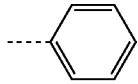 | 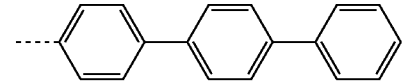 | 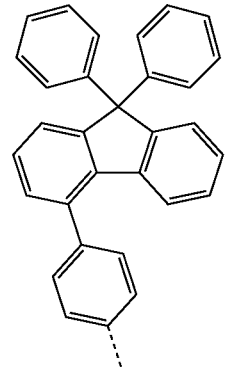 |
| 2-31 | 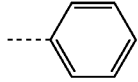 | 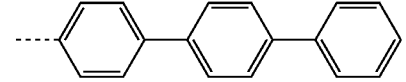 | 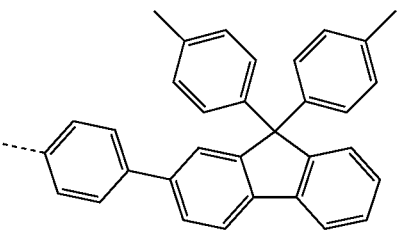 |

-continued
| Formula | ---Ar1 | ---Ar2 | ---Ar3 |
|---|---|---|---|
| 2-32 | | | 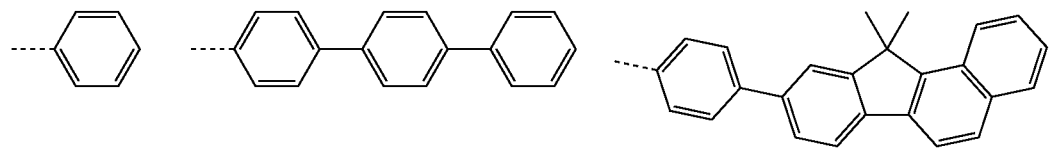 |
| 2-33 | | | 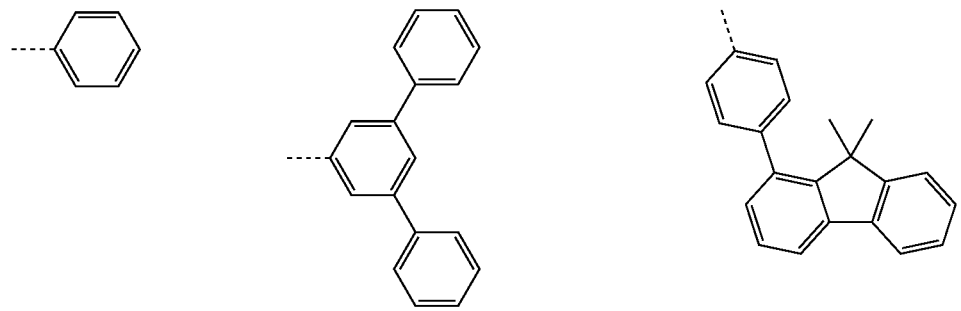 |
| 2-34 | | | 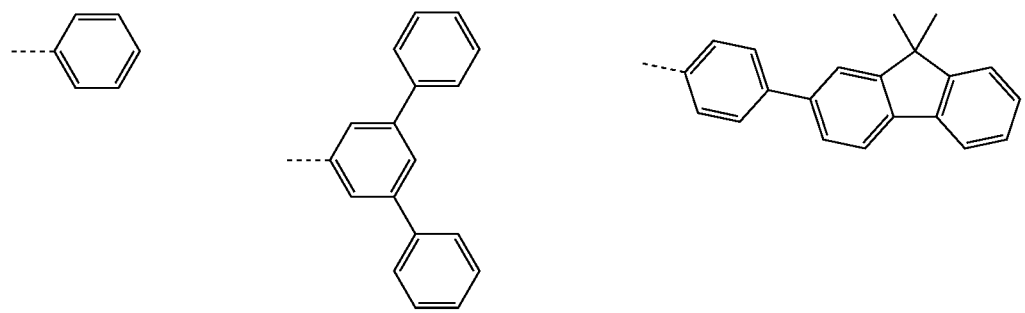 |
| 2-35 | | | 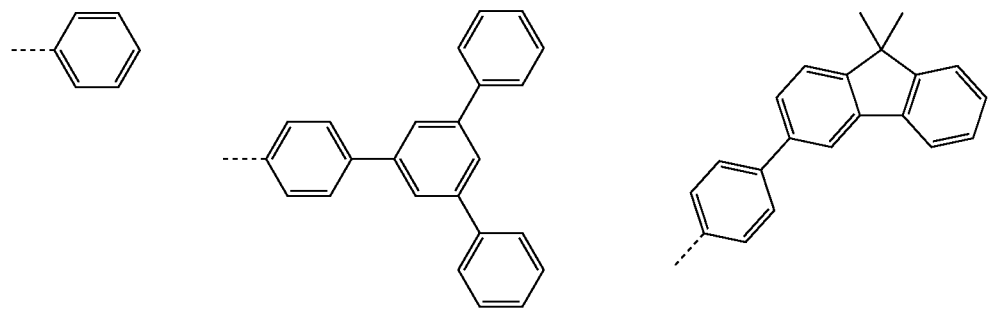 |
| 2-36 | | | 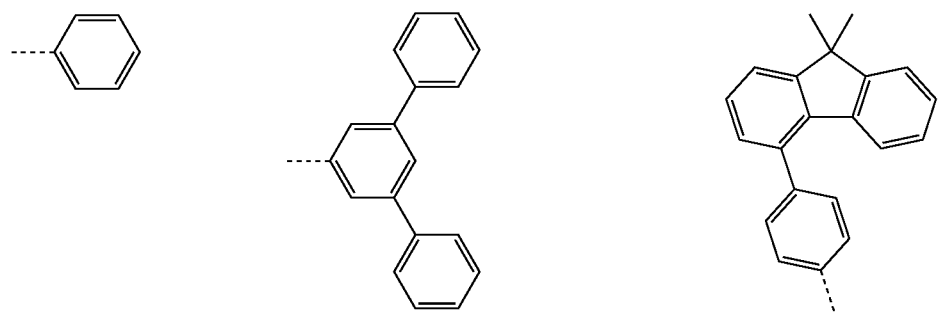 |

-continued
| Formula | ---Ar1 | ---Ar2 | ---Ar3 |
|---|---|---|---|
| 2-37 | 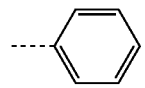 | 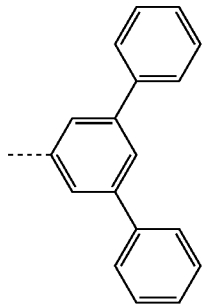 | 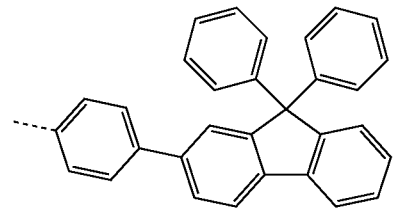 |
| 2-38 | 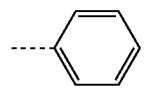 | 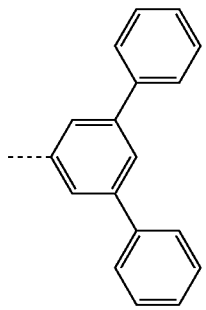 | 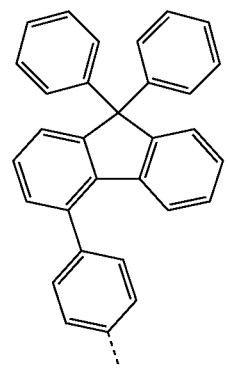 |
| 2-39 | 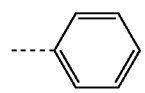 | 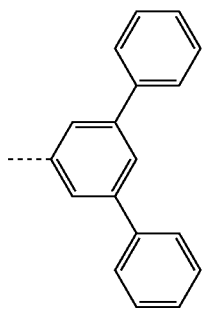 | 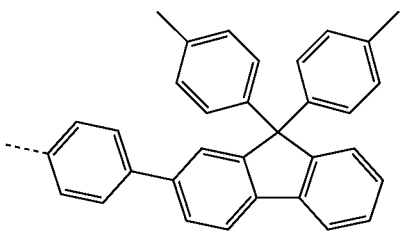 |
| 2-40 | 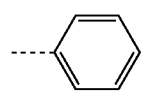 | 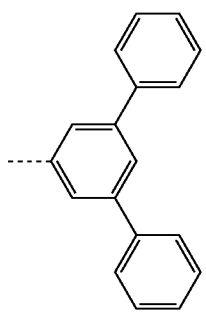 | 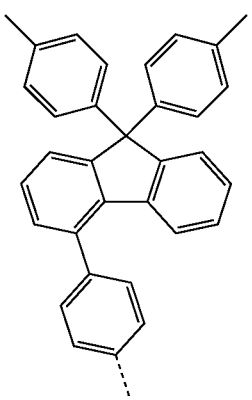 |

-continued

| Formula | ---Ar1 | ---Ar2 | ---Ar3 |
|---|---|---|---|
| 2-41 | phenyl | m-terphenyl | 4-(9,9-dimethylfluoren-1-yl)phenyl |
| 2-42 | phenyl | m-terphenyl | 4-(9,9-dimethylfluoren-2-yl)phenyl |
| 2-43 | phenyl | m-terphenyl | 4-(9,9-dimethylfluoren-3-yl)phenyl |
| 2-44 | phenyl | m-terphenyl | 4-(9,9-dimethylfluoren-4-yl)phenyl |
| 2-45 | phenyl | m-terphenyl | 4-(9,9-diphenylfluoren-2-yl)phenyl |
| 2-46 | phenyl | m-terphenyl | 4-(benzo[c]fluorenyl)phenyl |

-continued
| Formula | ---Ar1 | ---Ar2 | ---Ar3 |
|---|---|---|---|
| 2-47 | 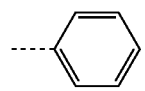 | 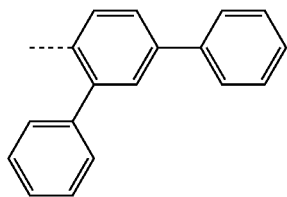 | 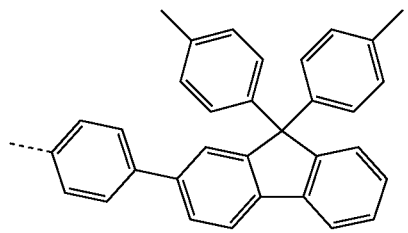 |
| 2-48 | 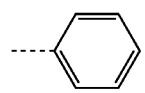 | 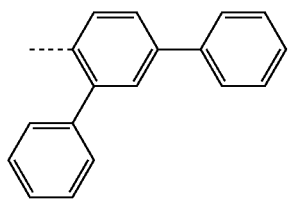 | 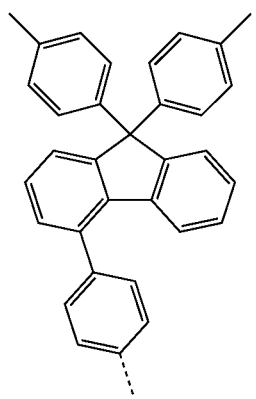 |
| 2-49 | 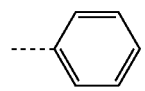 | 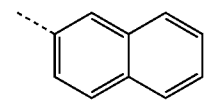 | 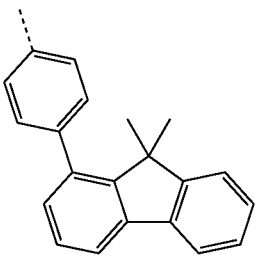 |
| 2-50 | 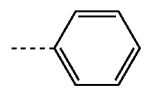 | 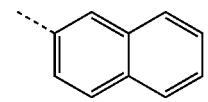 | 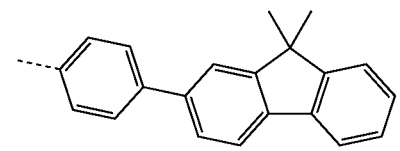 |
| 2-51 | 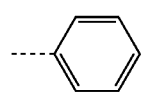 | 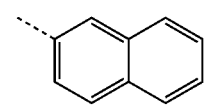 | 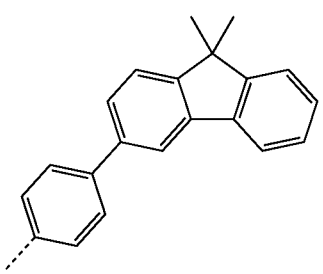 |

-continued

| Formula | ---Ar1 | ---Ar2 | ---Ar3 |
|---|---|---|---|
| 2-52 | phenyl | naphthyl | 9,9-dimethylfluorene-phenyl |
| 2-53 | phenyl | naphthyl | 9,9-diphenylfluorene-phenyl |
| 2-54 | phenyl | naphthyl | 9,9-diphenylfluorene-phenyl (meta) |
| 2-55 | phenyl | naphthyl | 9,9-di(p-tolyl)fluorene-phenyl |
| 2-56 | phenyl | naphthyl | 9,9-di(p-tolyl)fluorene-phenyl |

-continued

| Formula | ---Ar1 | ---Ar2 | ---Ar3 |
|---|---|---|---|
| 2-57 | phenyl | naphthyl | 9,9-dimethylfluorenyl-phenyl |
| 2-58 | phenyl | naphthyl | 9,9-dimethylfluorenyl-phenyl |
| 2-59 | phenyl | naphthyl | 9,9-dimethylfluorenyl-phenyl |
| 2-60 | phenyl | naphthyl | fluorenyl-biphenyl |
| 2-61 | phenyl | naphthyl | 9,9-diphenylfluorenyl-phenyl |

-continued
| Formula | ---Ar1 | ---Ar2 | ---Ar3 |
|---|---|---|---|
| 2-62 | 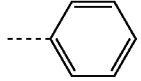 | 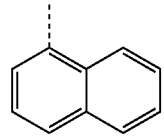 | 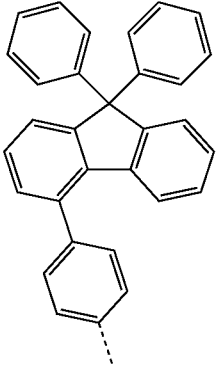 |
| 2-63 | 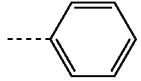 | 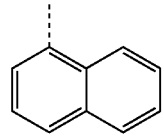 | 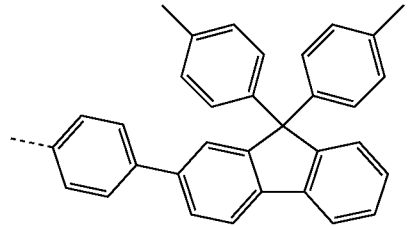 |
| 2-64 | 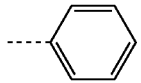 | 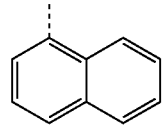 | 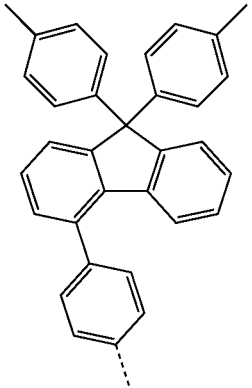 |
| 2-65 | 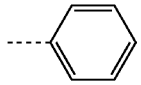 | 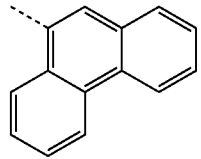 | 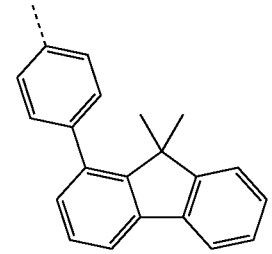 |
| 2-66 | 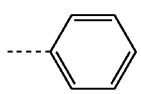 | 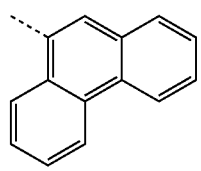 | 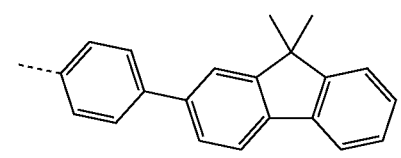 |

| Formula | ---Ar1 | ---Ar2 | ---Ar3 |
|---|---|---|---|
| 2-67 | | | |
| 2-68 | | | |
| 2-69 | | | |
| 2-70 | | | |
| 2-71 | | | |

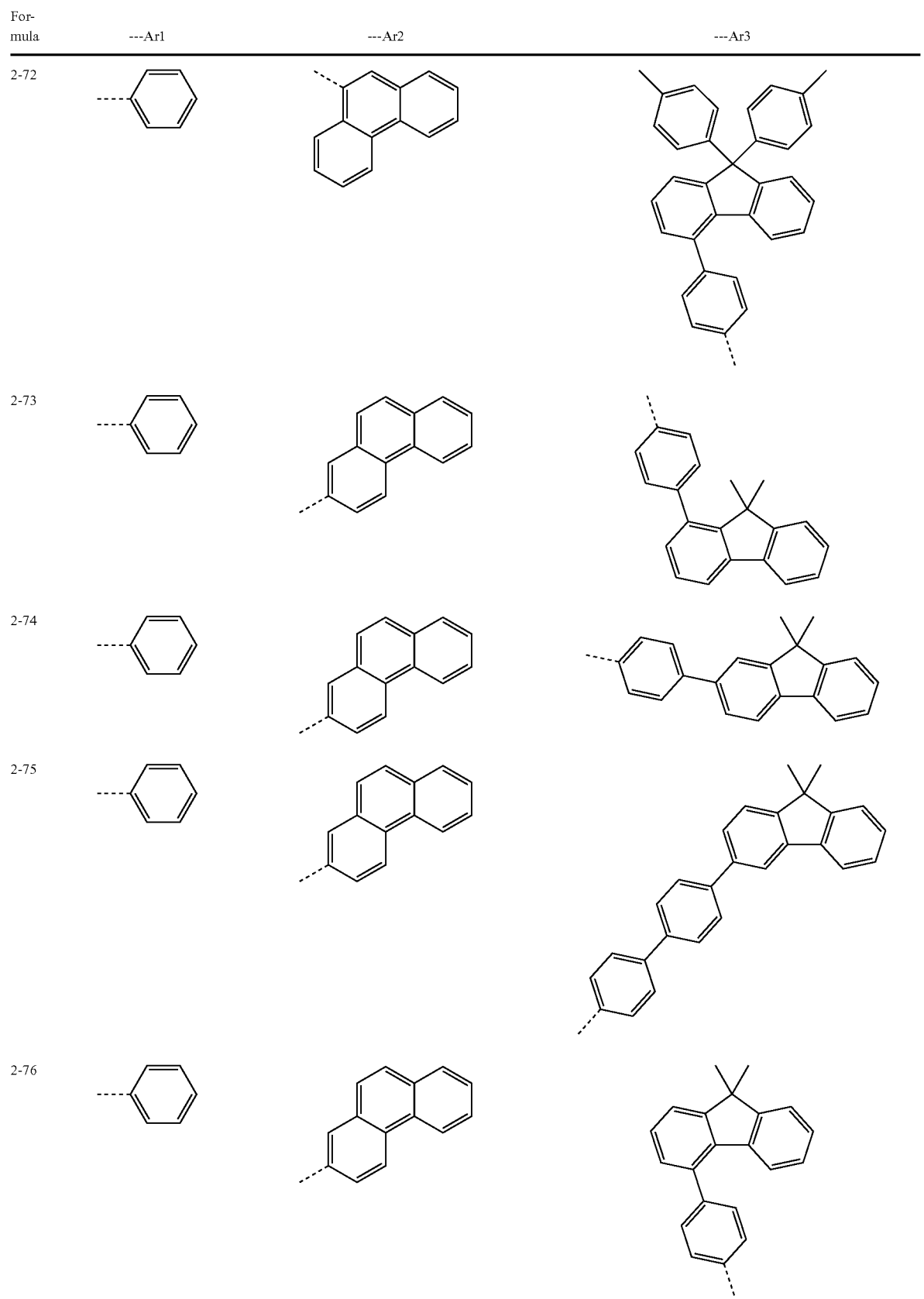

-continued

| Formula | ---Ar1 | ---Ar2 | ---Ar3 |
|---|---|---|---|
| 2-77 | phenyl | phenanthrenyl | 9,9-diphenylfluorenyl-phenyl |
| 2-78 | phenyl | phenanthrenyl | 9,9-diphenylfluorenyl-phenyl |
| 2-79 | phenyl | phenanthrenyl | 9,9-di(p-tolyl)fluorenyl-phenyl |
| 2-80 | phenyl | phenanthrenyl | 9,9-dimethyl-benzofluorenyl-phenyl |
| 2-81 | phenyl | phenanthrenyl | 9,9-dimethylfluorenyl-phenyl |
| 2-82 | phenyl | phenanthrenyl | 9,9-dimethylfluorenyl-phenyl |

| Formula | ---Ar1 | ---Ar2 | ---Ar3 |
|---|---|---|---|
| 2-83 | 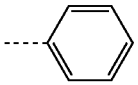 | 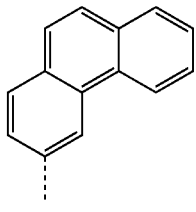 | 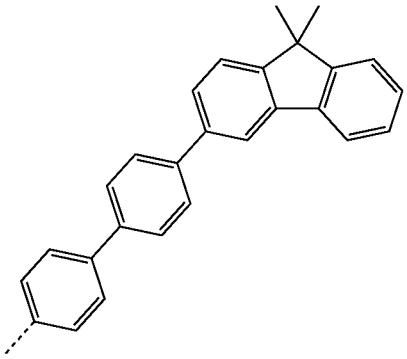 |
| 2-84 | 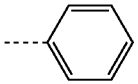 | 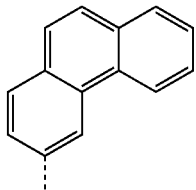 | 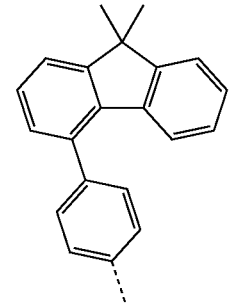 |
| 2-85 | 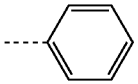 | 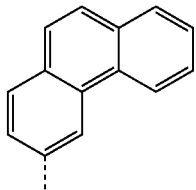 | 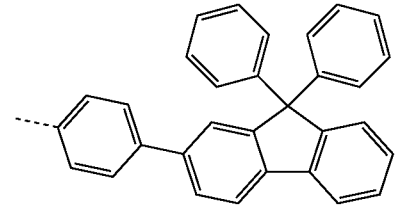 |
| 2-86 | 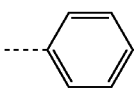 | 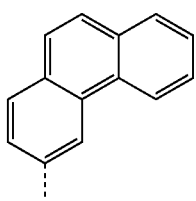 | 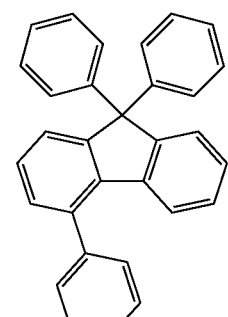 |
| 2-87 | 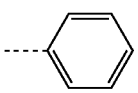 | 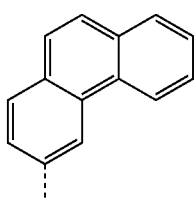 | 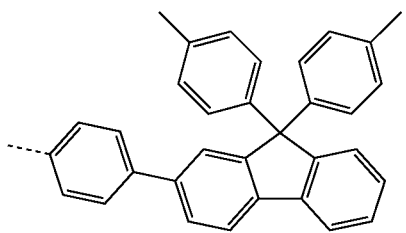 |

-continued

| Formula | ---Ar1 | ---Ar2 | ---Ar3 |
|---|---|---|---|
| 2-88 | phenyl | phenanthrenyl | 9,9-di(p-tolyl)fluorenyl-phenyl |
| 2-89 | phenyl | biphenyl | 9,9-dimethylfluorenyl-naphthyl |
| 2-90 | phenyl | biphenyl | 9,9-dimethylfluorenyl-naphthyl |
| 2-91 | phenyl | biphenyl | 9,9-dimethylfluorenyl-naphthyl |
| 2-92 | phenyl | biphenyl | 9,9-dimethylfluorenyl-naphthyl |

-continued
| Formula | ---Ar1 | ---Ar2 | ---Ar3 |
|---|---|---|---|
| 2-93 | 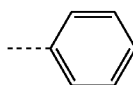 | 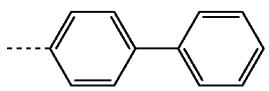 | 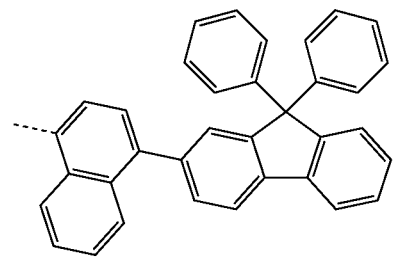 |
| 2-94 | 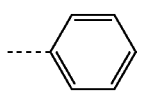 | 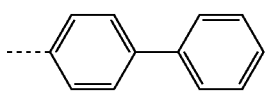 | 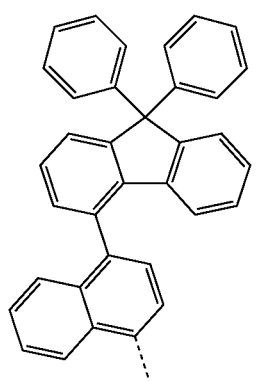 |
| 2-95 | 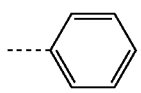 | 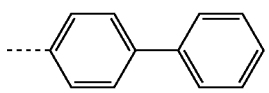 | 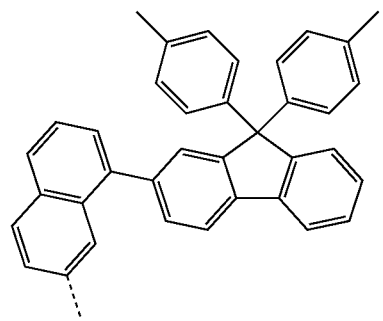 |
| 2-96 | 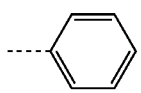 | 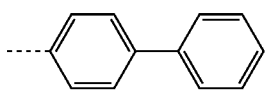 | 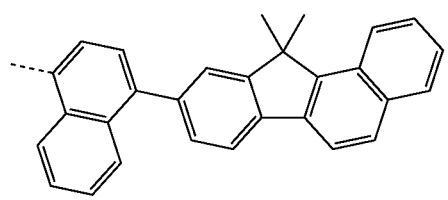 |
| 2-97 | 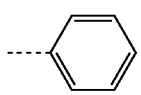 | 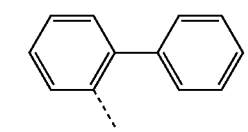 | 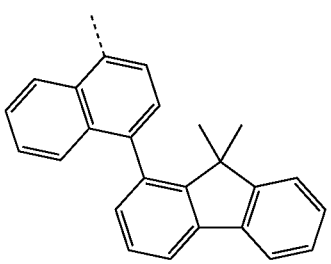 |

-continued

| Formula | ---Ar1 | ---Ar2 | ---Ar3 |
|---|---|---|---|
| 2-98 | phenyl | biphenyl | naphthyl-(9,9-dimethylfluorenyl) |
| 2-99 | phenyl | biphenyl | naphthyl-(9,9-dimethylfluorenyl) |
| 2-100 | phenyl | biphenyl | naphthyl-(9,9-dimethylfluorenyl) |
| 2-101 | phenyl | biphenyl | naphthyl-(9,9-diphenylfluorenyl) |
| 2-102 | phenyl | biphenyl | naphthyl-(9,9-diphenylfluorenyl) |

-continued
| Formula | ---Ar1 | ---Ar2 | ---Ar3 |
|---|---|---|---|
| 2-103 | 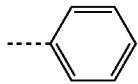 | 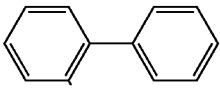 | 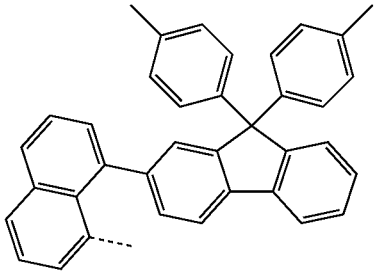 |
| 2-104 | 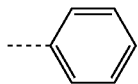 | 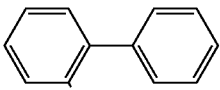 | 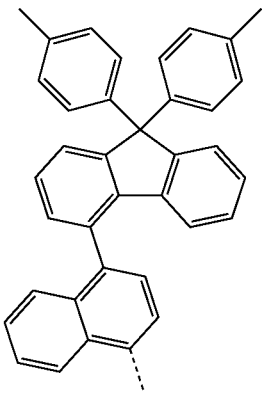 |
| 2-105 | 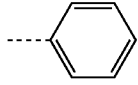 | 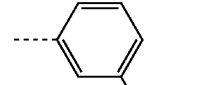 | 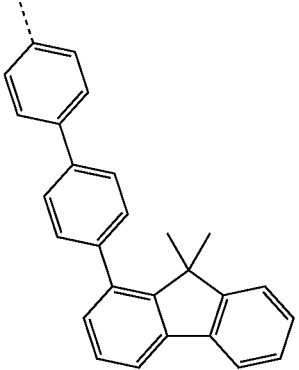 |
| 2-106 | 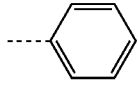 | 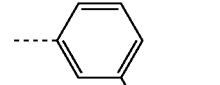 | 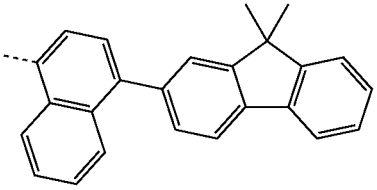 |
| 2-107 | 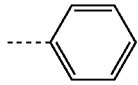 | 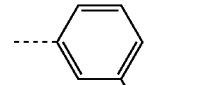 | 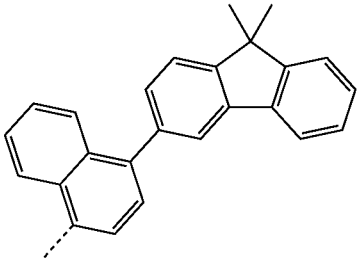 |

-continued
| Formula | ---Ar1 | ---Ar2 | ---Ar3 |
|---|---|---|---|
| 2-108 | 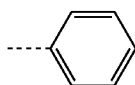 | 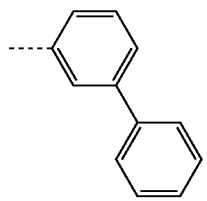 | 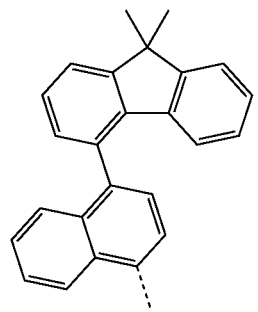 |
| 2-109 | 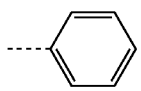 | 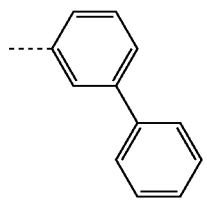 | 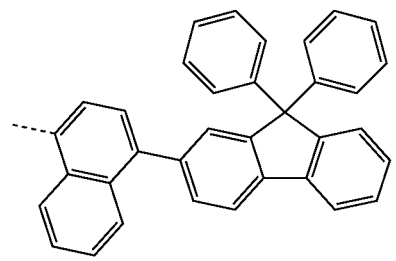 |
| 2-110 | 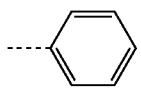 | 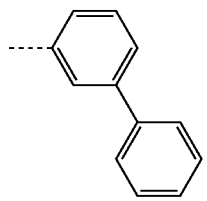 | 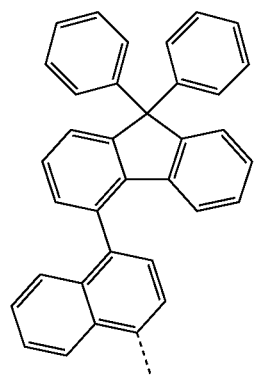 |
| 2-111 | 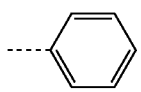 | 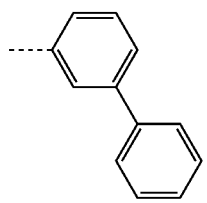 | 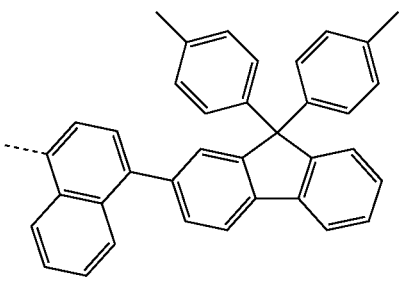 |

-continued
| Formula | ---Ar1 | ---Ar2 | ---Ar3 |
|---|---|---|---|
| 2-112 | 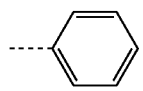 | 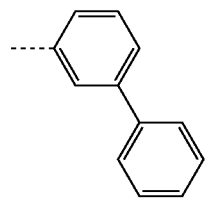 | 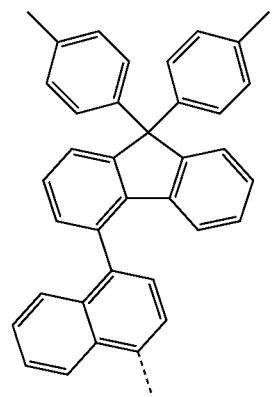 |
| 2-113 | 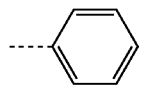 | 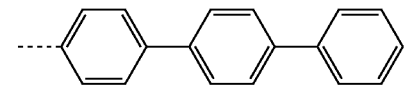 | 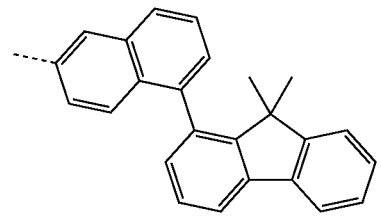 |
| 2-114 | 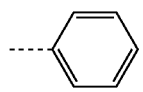 | 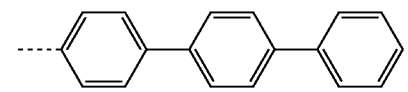 | 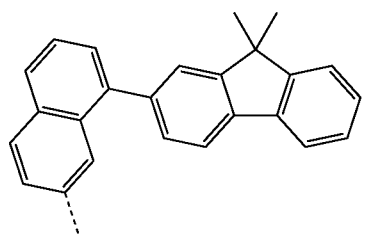 |
| 2-115 | 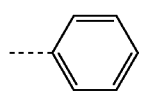 | 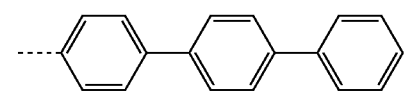 | 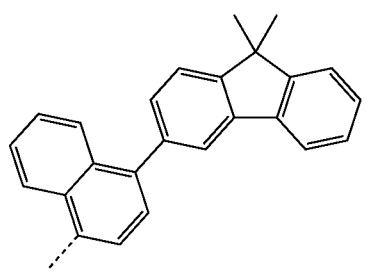 |
| 2-116 | 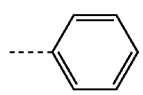 | 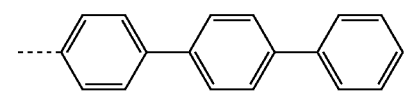 | 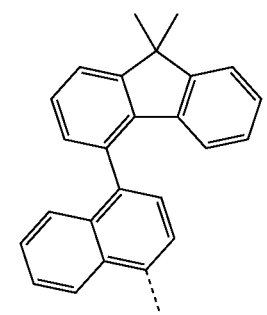 |

-continued
| Formula | ---Ar1 | ---Ar2 | ---Ar3 |
|---|---|---|---|
| 2-117 | 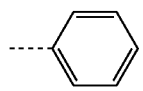 | 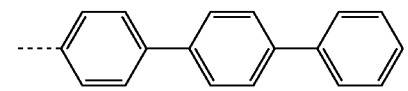 | 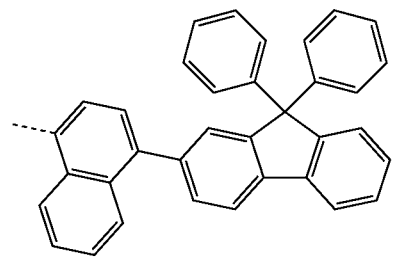 |
| 2-118 | 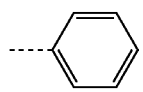 | 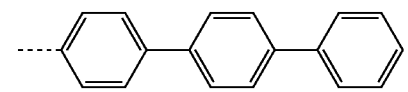 | 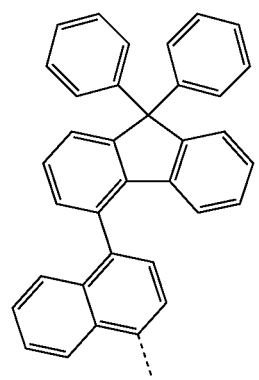 |
| 2-119 | 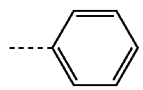 | 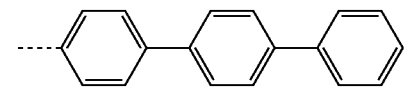 | 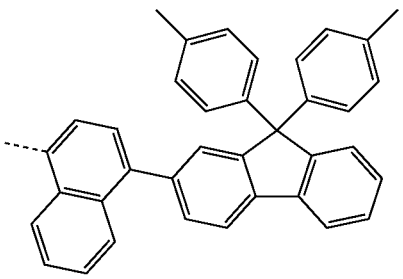 |
| 2-120 | 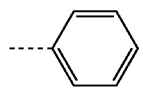 | 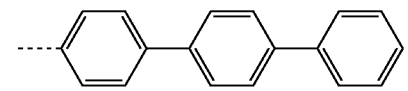 | 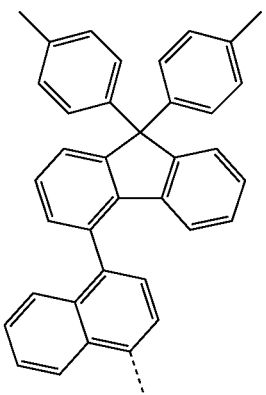 |

-continued
| Formula | ---Ar1 | ---Ar2 | ---Ar3 |
|---|---|---|---|
| 2-121 | 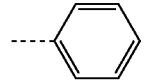 | 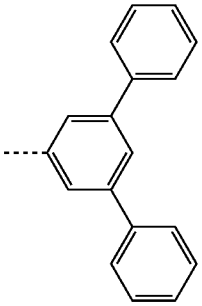 | 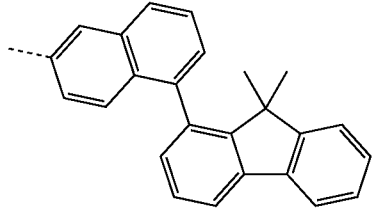 |
| 2-122 | 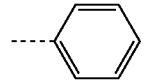 | 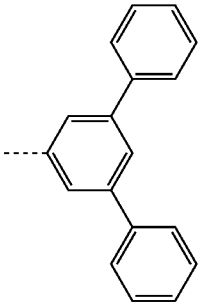 | 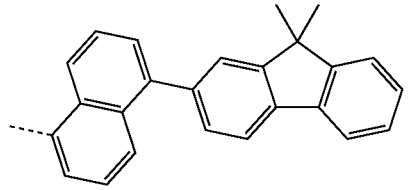 |
| 2-123 | 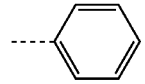 | 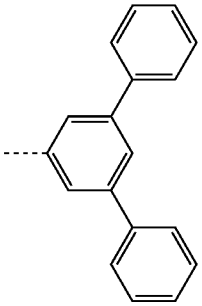 | 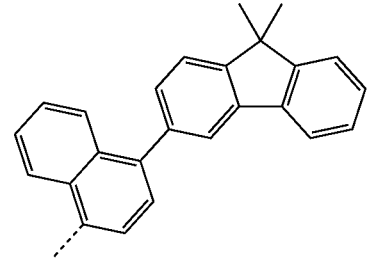 |
| 2-124 | 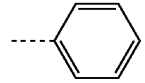 | 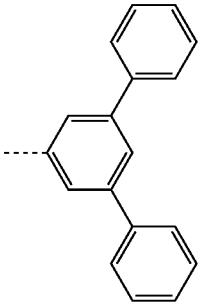 | 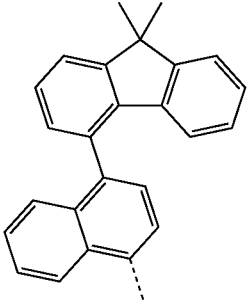 |
| 2-125 | 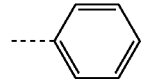 | 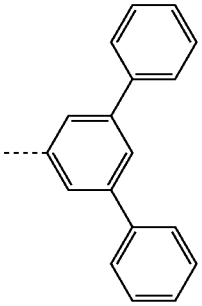 | 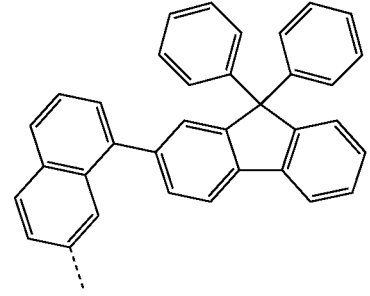 |

-continued
| Formula | ---Ar1 | ---Ar2 | ---Ar3 |
|---|---|---|---|
| 2-126 | 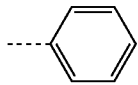 | 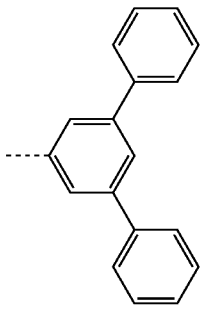 | 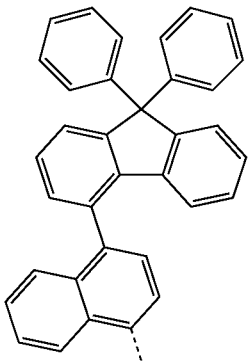 |
| 2-127 | 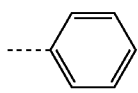 | 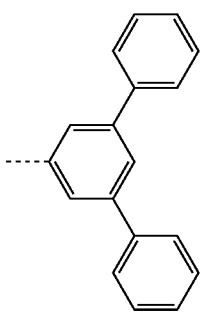 | 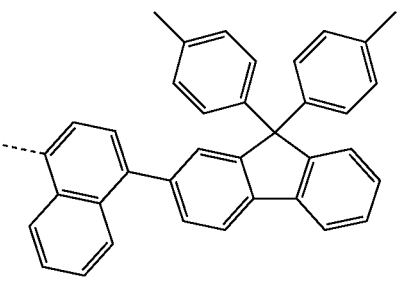 |
| 2-128 | 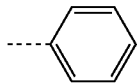 | 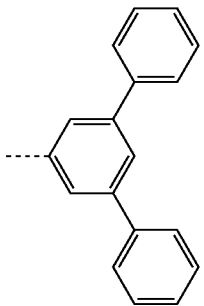 | 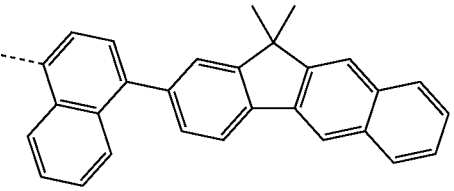 |
| 2-129 | 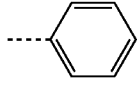 | 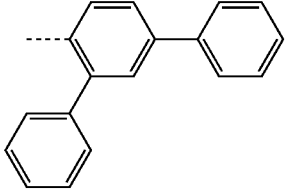 | 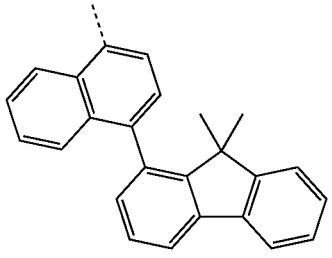 |
| 2-130 | 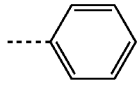 | 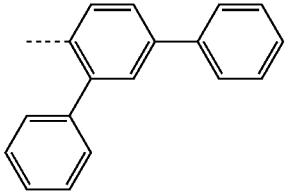 | 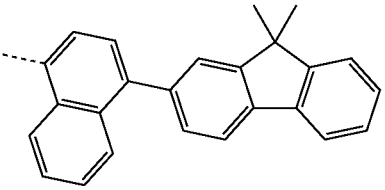 |

-continued

| Formula | ---Ar1 | ---Ar2 | ---Ar3 |
|---|---|---|---|
| 2-131 | phenyl | m-terphenyl (branched) | 4-(9,9-dimethylfluoren-3-yl)naphthalen-1-yl |
| 2-132 | phenyl | m-terphenyl (branched) | 4-(9,9-dimethylfluoren-4-yl)naphthalen-1-yl |
| 2-133 | phenyl | m-terphenyl (branched) | 4-(9,9-diphenylfluoren-2-yl)naphthalen-1-yl |
| 2-134 | phenyl | m-terphenyl (branched) | 4-(9,9-diphenylfluoren-4-yl)naphthalen-1-yl |
| 2-135 | phenyl | m-terphenyl (branched) | 3-(9,9-di-p-tolylfluoren-2-yl)naphthalen-2-yl |

-continued

| Formula | ---Ar1 | ---Ar2 | ---Ar3 |
|---|---|---|---|
| 2-136 | phenyl | 3,5-diphenylphenyl | (9,9-dimethylfluorenyl)-substituted naphthyl fused system |
| 2-137 | phenyl | 2-naphthyl | 1-(9,9-dimethylfluoren-1-yl)naphthyl |
| 2-138 | phenyl | 2-naphthyl | 1-(9,9-dimethylfluoren-2-yl)naphthyl |
| 2-139 | phenyl | 2-naphthyl | 4-(9,9-dimethylfluoren-2-yl)naphth-1-yl |
| 2-140 | phenyl | 2-naphthyl | 4-(9,9-dimethylfluoren-4-yl)naphth-1-yl |
| 2-141 | phenyl | 2-naphthyl | 3-(9,9-diphenylfluoren-2-yl)naphth-2-yl |

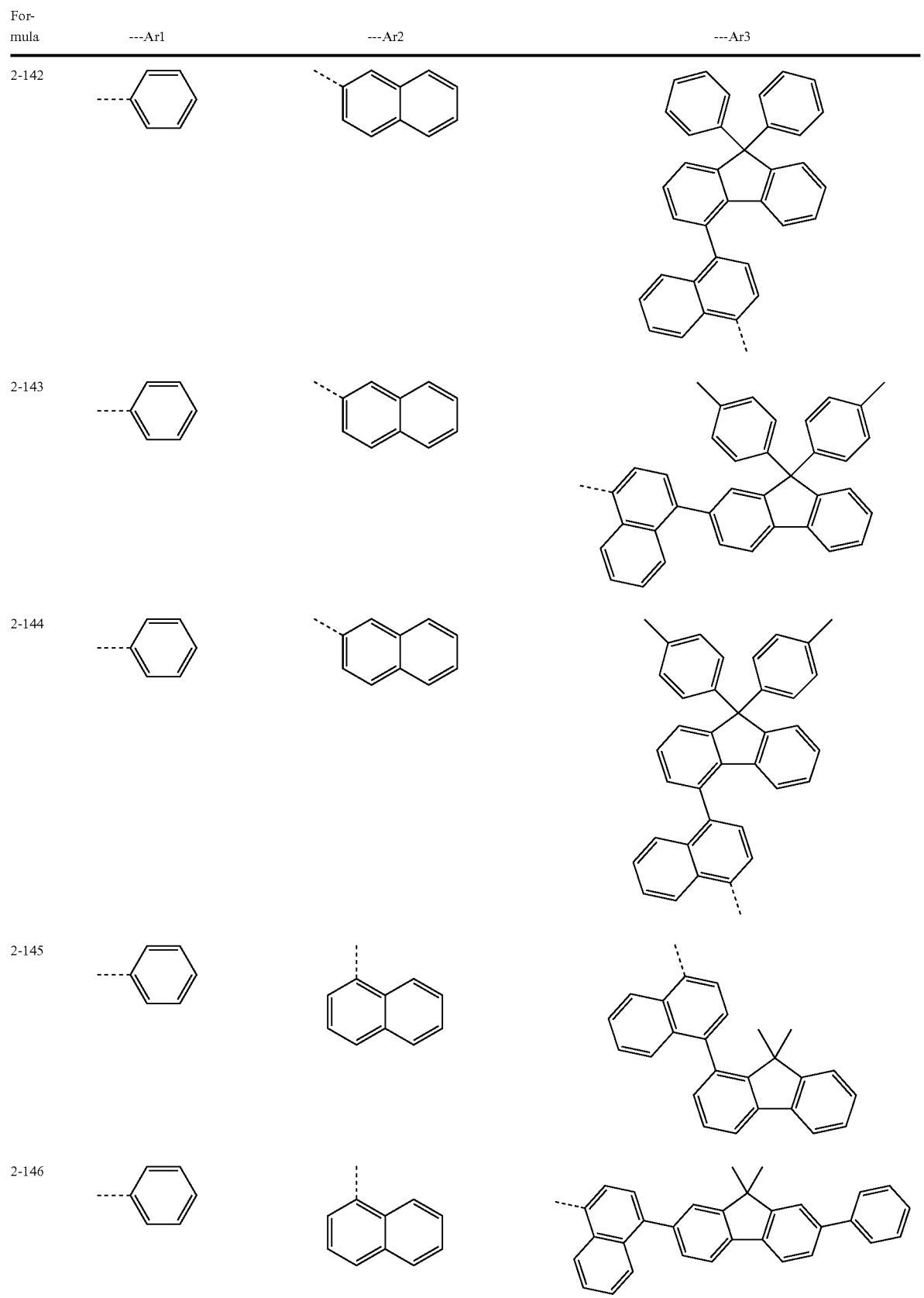

| Formula | ---Ar1 | ---Ar2 | ---Ar3 |
|---|---|---|---|
| 2-147 | 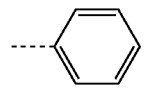 | 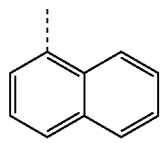 | 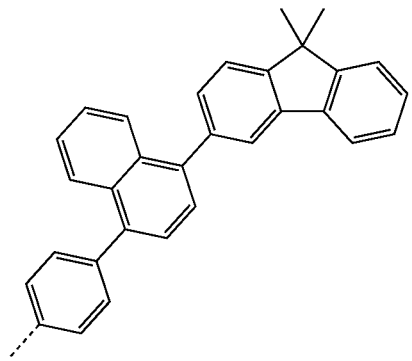 |
| 2-148 | 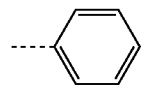 | 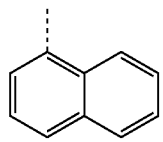 | 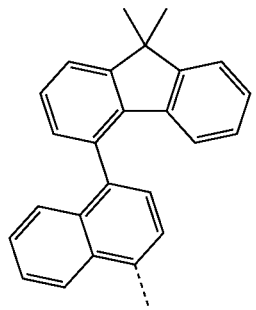 |
| 2-149 | 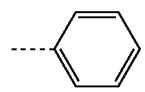 | 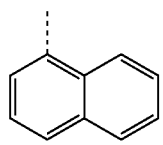 | 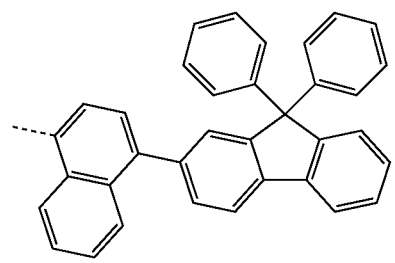 |
| 2-150 | 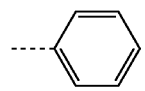 | 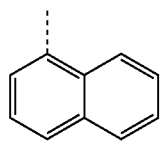 | 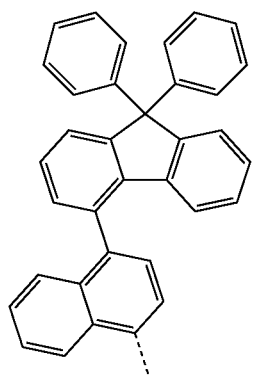 |

-continued

| Formula | ---Ar1 | ---Ar2 | ---Ar3 |
| --- | --- | --- | --- |
| 2-151 | | | |
| 2-152 | | | |
| 2-153 | | | |
| 2-154 | | | |
| 2-155 | | | |

-continued
| Formula | ---Ar1 | ---Ar2 | ---Ar3 |
|---|---|---|---|
| 2-156 | 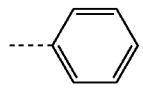 | 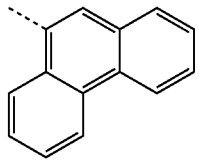 | 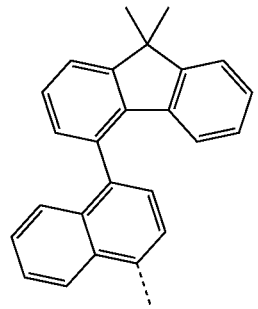 |
| 2-157 | 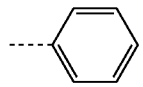 | 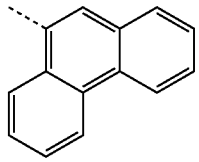 | 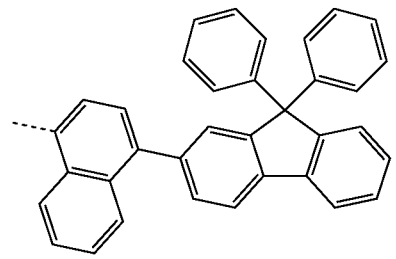 |
| 2-158 | 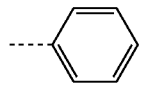 | 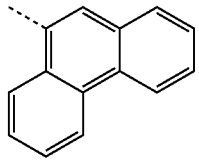 | 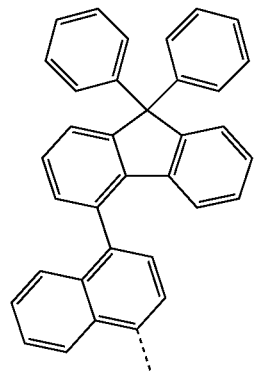 |
| 2-159 | 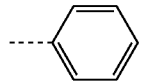 | 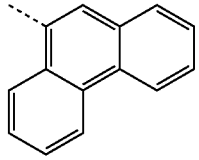 | 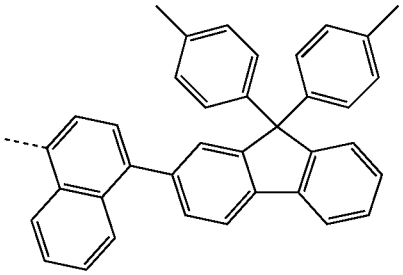 |

-continued

| Formula | ---Ar1 | ---Ar2 | ---Ar3 |
|---|---|---|---|
| 2-160 | phenyl | phenanthrenyl | 9,9-di(p-tolyl)fluorenyl-naphthyl |
| 2-161 | phenyl | phenanthrenyl | 9,9-dimethylfluorenyl-naphthyl |
| 2-162 | phenyl | phenanthrenyl | naphthyl-9,9-dimethylfluorenyl |
| 2-163 | phenyl | phenanthrenyl | 9,9-dimethylfluorenyl-naphthyl |
| 2-164 | phenyl | phenanthrenyl | 9,9-dimethylfluorenyl-naphthyl |

-continued

| Formula | ---Ar1 | ---Ar2 | ---Ar3 |
|---|---|---|---|
| 2-165 | phenyl | phenanthrenyl | 4-(9,9-diphenyl-9H-fluoren-2-yl)naphthalen-1-yl |
| 2-166 | phenyl | phenanthrenyl | 4-(9,9-diphenyl-9H-fluoren-4-yl)naphthalen-1-yl |
| 2-167 | phenyl | phenanthrenyl | 4-(9,9-di-p-tolyl-9H-fluoren-2-yl)naphthalen-1-yl |
| 2-168 | phenyl | phenanthrenyl | 4-(9,9-di-p-tolyl-9H-fluoren-4-yl)naphthalen-1-yl |
| 2-169 | phenyl | phenanthrenyl | 4-(7,7-dimethyl-7H-benzo[c]fluoren-yl)naphthalen-1-yl |

-continued
| Formula | ---Ar1 | ---Ar2 | ---Ar3 |
|---|---|---|---|
| 2-170 | 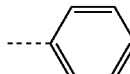 | 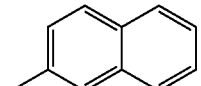 | 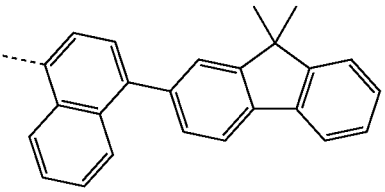 |
| 2-171 | 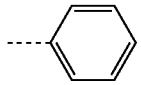 | 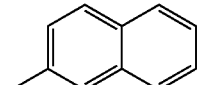 | 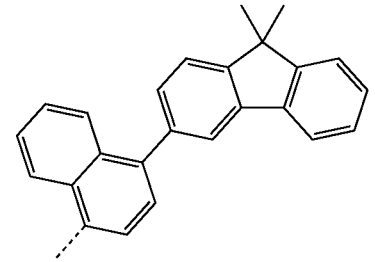 |
| 2-172 | 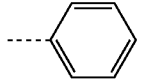 | 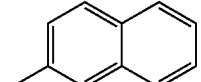 | 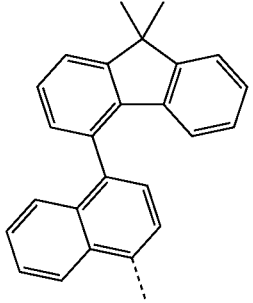 |
| 2-173 | 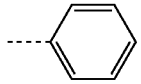 | 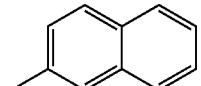 | 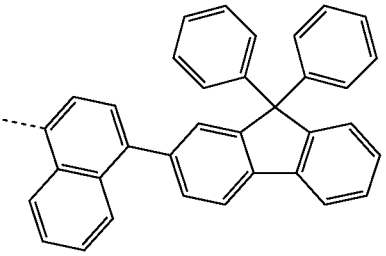 |
| 2-174 | 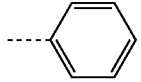 | 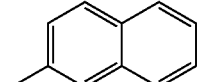 | 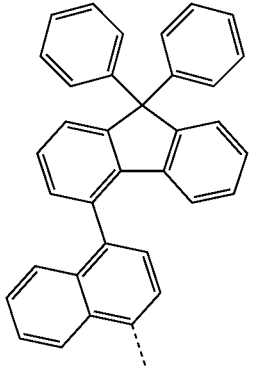 |

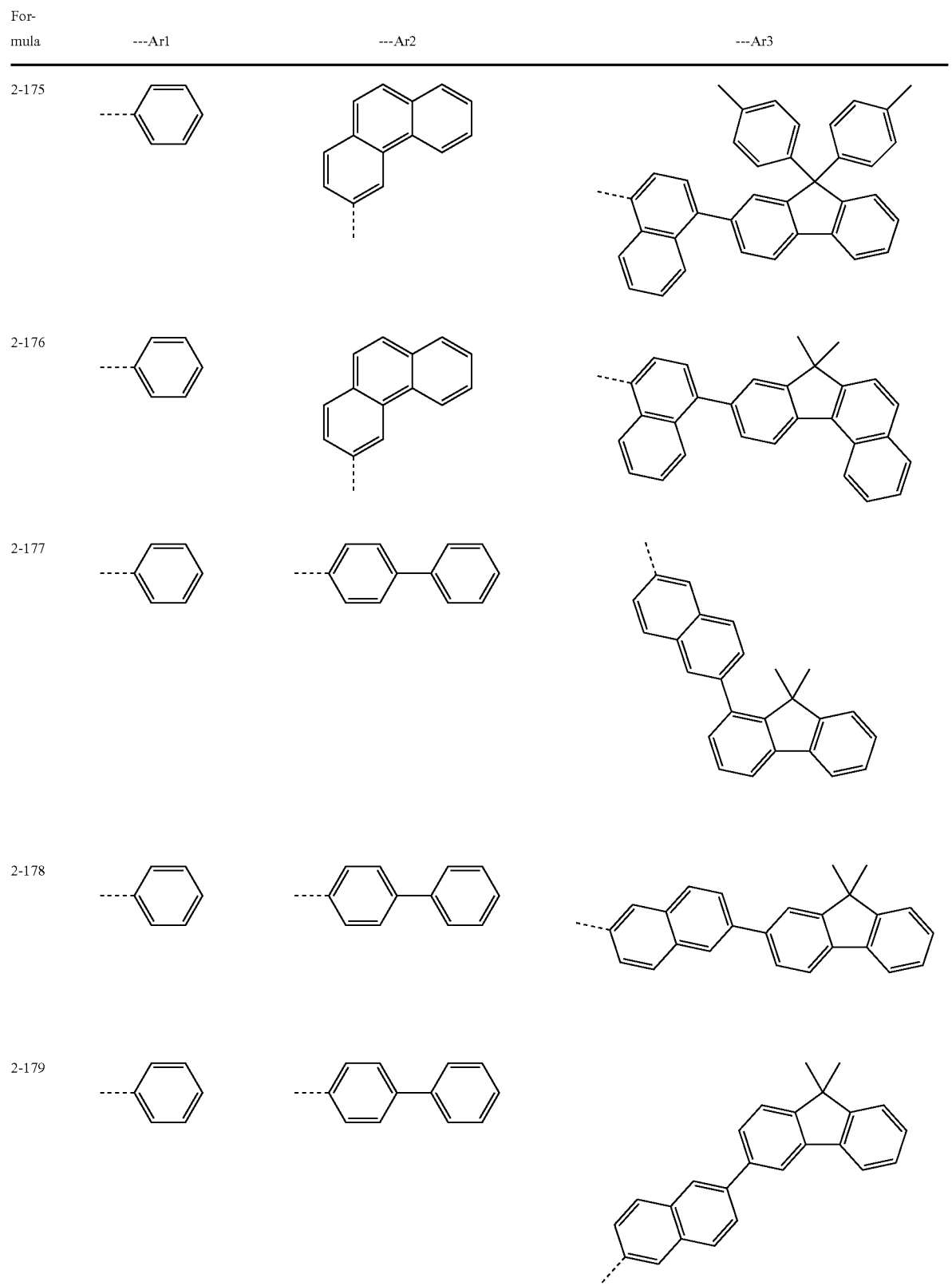

-continued
| Formula | ---Ar1 | ---Ar2 | ---Ar3 |
|---|---|---|---|
| 2-180 |  |  | 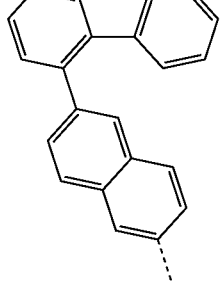 |
| 2-181 |  | 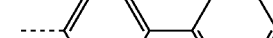 | 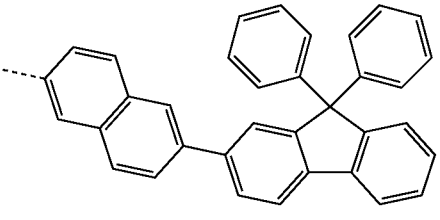 |
| 2-182 |  | 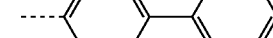 | 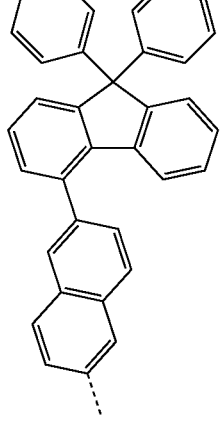 |
| 2-183 |  | 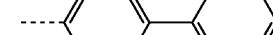 | 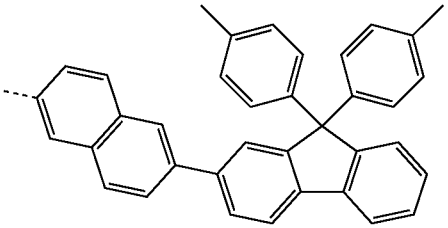 |

-continued
| Formula | ---Ar1 | ---Ar2 | ---Ar3 |
|---|---|---|---|
| 2-184 | 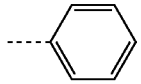 | 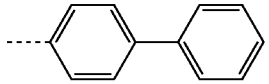 | 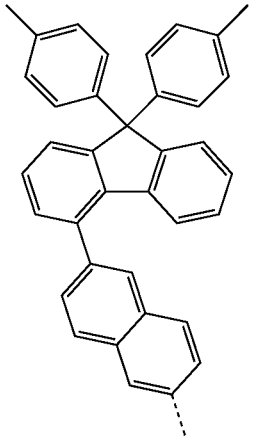 |
| 2-185 | 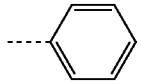 | 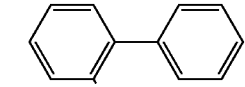 | 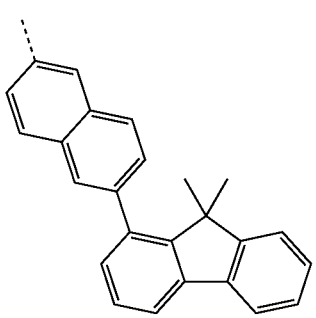 |
| 2-186 | 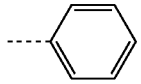 | 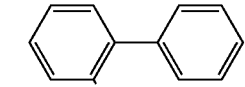 | 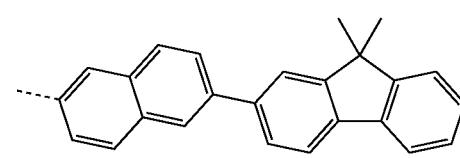 |
| 2-187 | 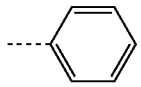 | 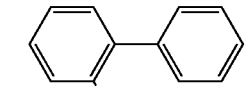 | 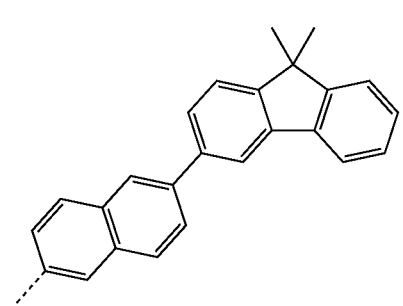 |
| 2-188 | 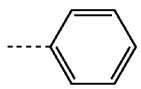 | 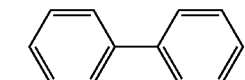 | 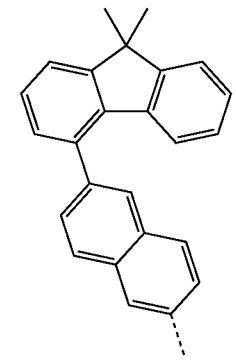 |

-continued

| Formula | ---Ar1 | ---Ar2 | ---Ar3 |
|---|---|---|---|
| 2-189 | phenyl | 2-biphenyl | 9,9-diphenylfluorenyl-naphthyl |
| 2-190 | phenyl | 2-biphenyl | 9,9-diphenylfluorenyl-naphthyl |
| 2-191 | phenyl | 2-biphenyl | 9,9-di(p-tolyl)fluorenyl-naphthyl |
| 2-192 | phenyl | 2-biphenyl | 9,9-dimethylbenzofluorenyl-naphthyl |
| 2-193 | phenyl | 3-biphenyl | 9,9-dimethylfluorenyl-naphthyl |

-continued
| Formula | ---Ar1 | ---Ar2 | ---Ar3 |
|---|---|---|---|
| 2-194 | 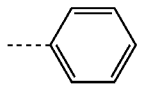 | 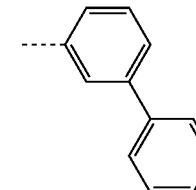 | 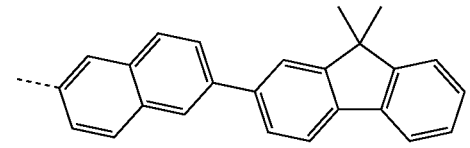 |
| 2-195 | 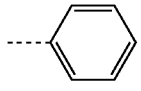 | 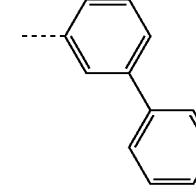 | 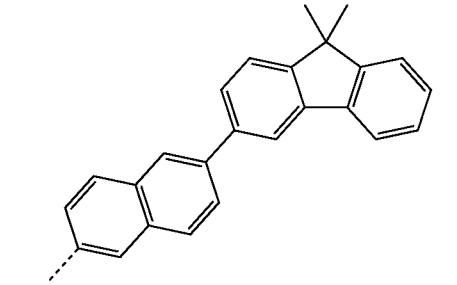 |
| 2-196 | 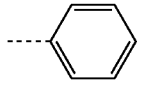 | 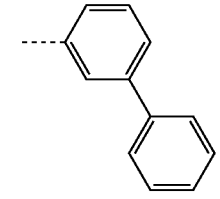 | 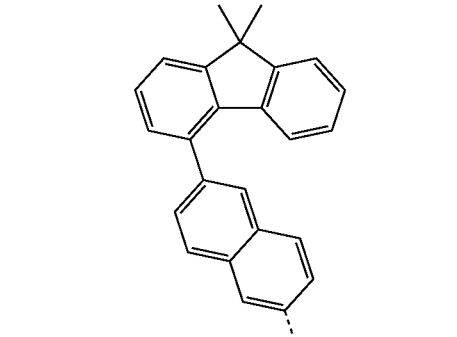 |
| 2-197 | 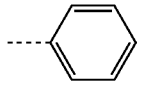 | 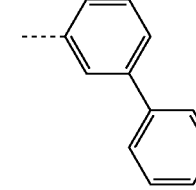 | 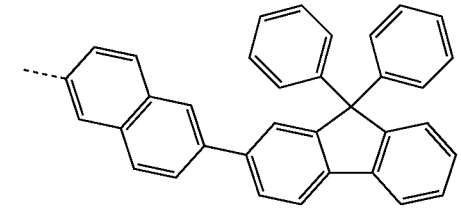 |
| 2-198 | 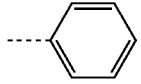 | 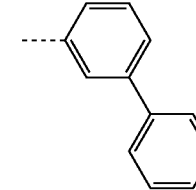 | 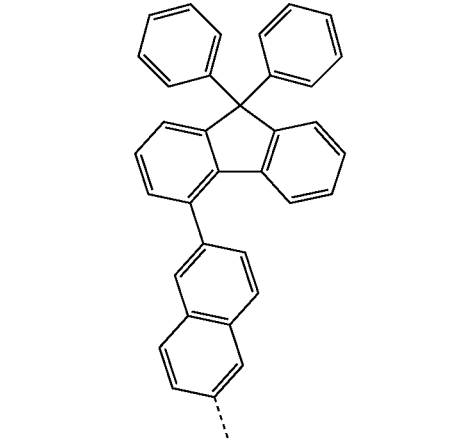 |

-continued
| Formula | ---Ar1 | ---Ar2 | ---Ar3 |
|---|---|---|---|
| 2-199 | 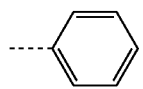 | 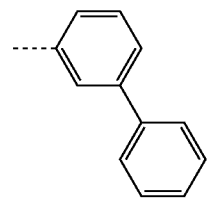 | 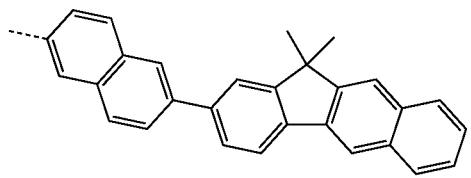 |
| 2-200 | 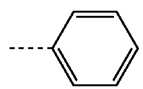 | 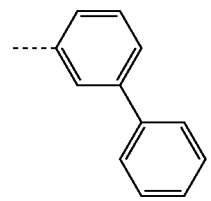 | 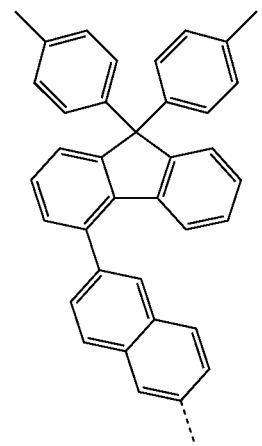 |
| 2-201 | 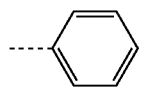 | 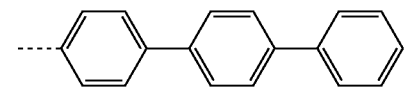 | 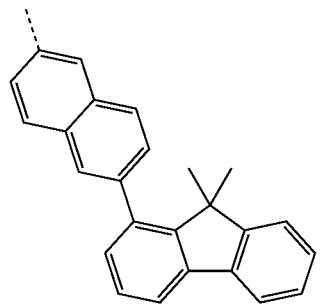 |
| 2-202 | 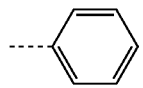 | 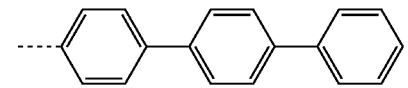 | 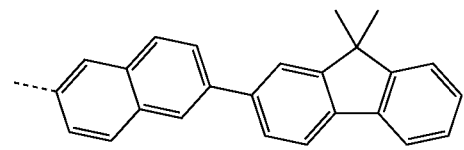 |
| 2-203 | 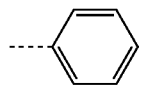 | 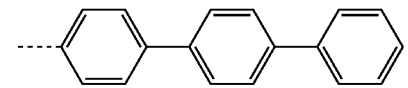 | 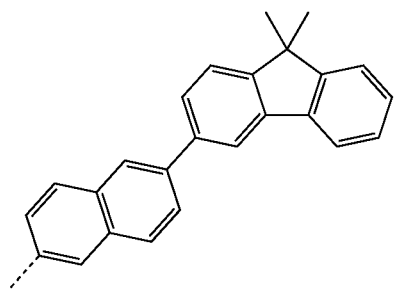 |

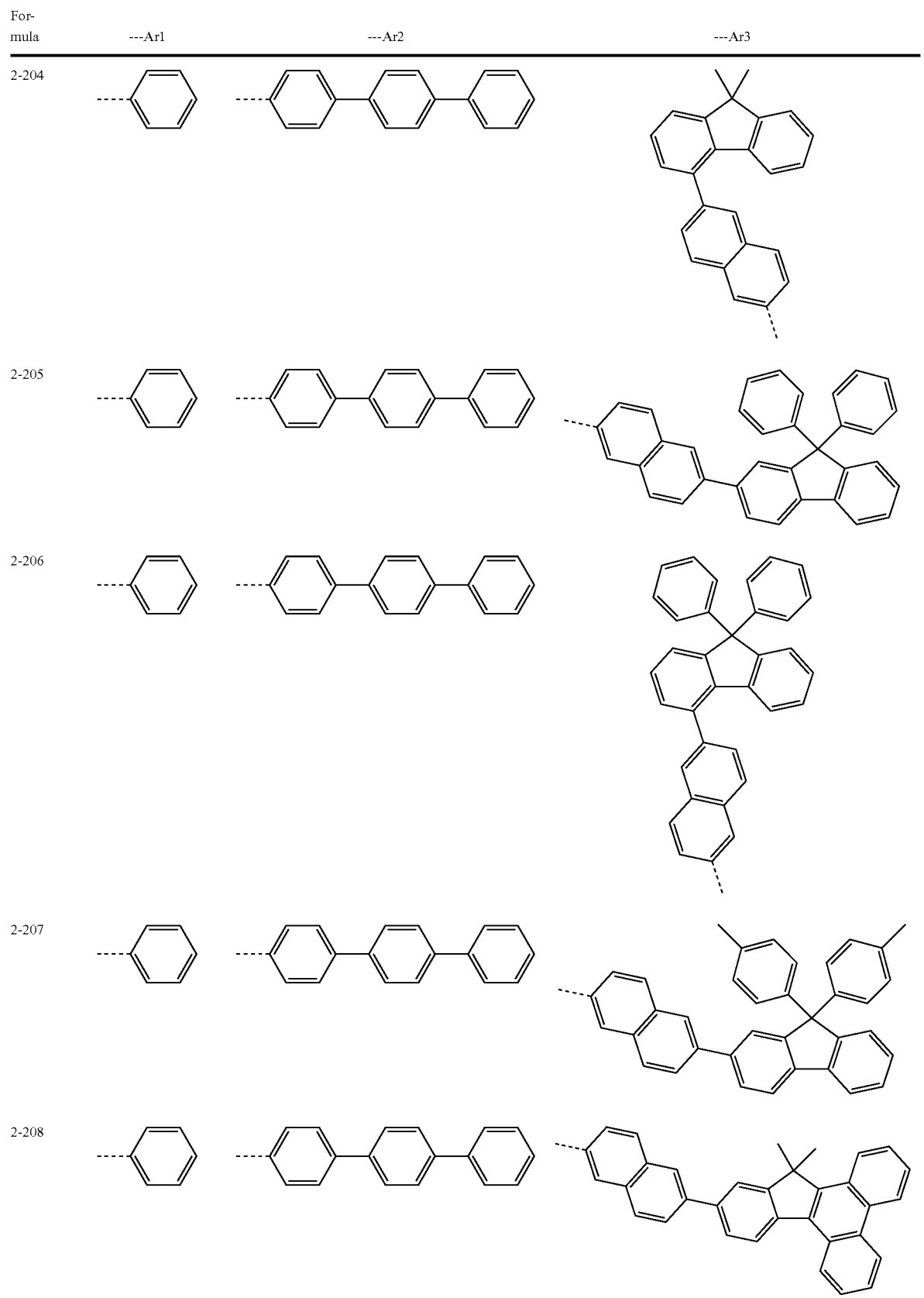

-continued
| Formula | ---Ar1 | ---Ar2 | ---Ar3 |
|---|---|---|---|
| 2-209 | 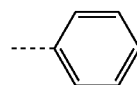 | 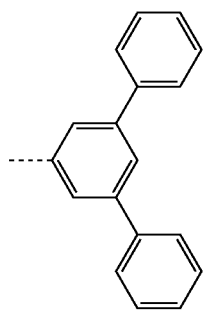 | 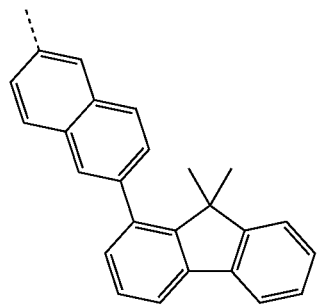 |
| 2-210 | 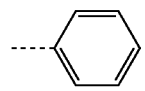 | 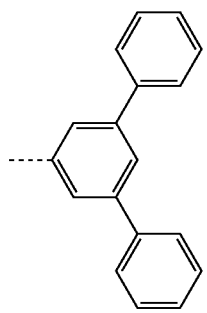 | 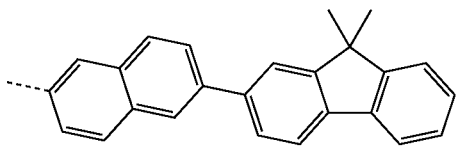 |
| 2-211 | 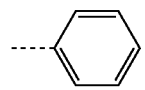 | 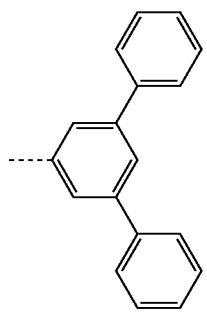 | 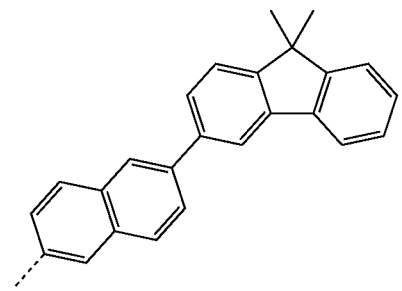 |
| 2-212 | 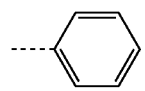 | 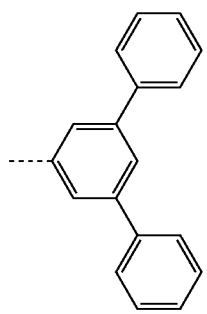 | 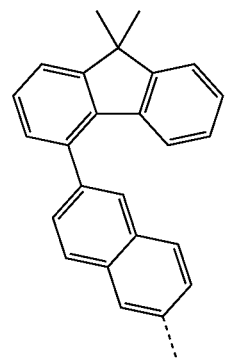 |

-continued
| Formula | ---Ar1 | ---Ar2 | ---Ar3 |
|---|---|---|---|
| 2-213 | | | |
| 2-214 | | | |
| 2-215 | | | |
| 2-216 | | | |
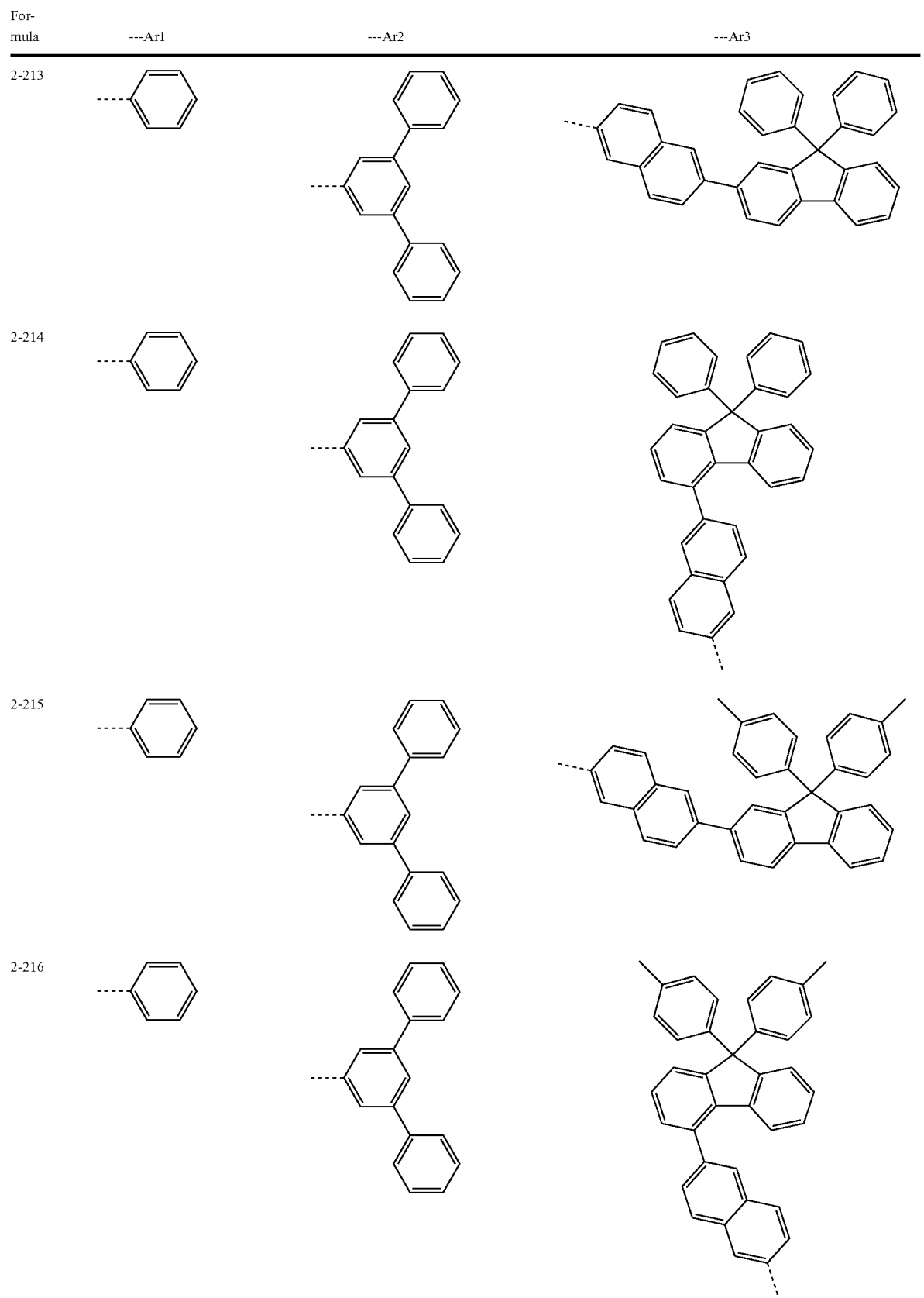

-continued
| Formula | ---Ar1 | ---Ar2 | ---Ar3 |
|---|---|---|---|
| 2-217 | 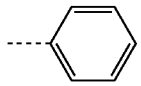 | 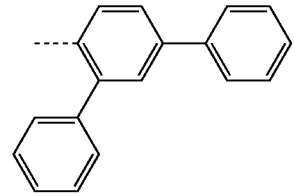 | 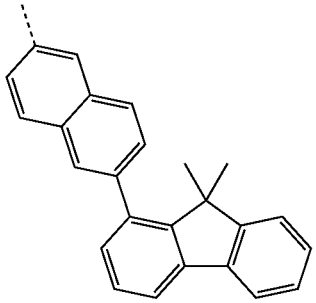 |
| 2-218 | 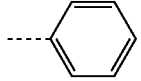 | 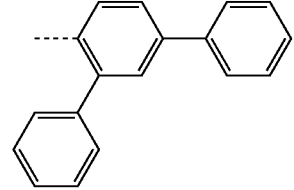 | 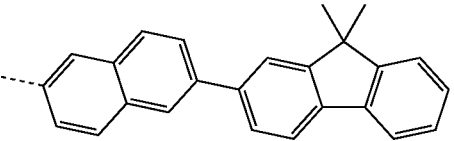 |
| 2-219 | 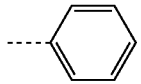 | 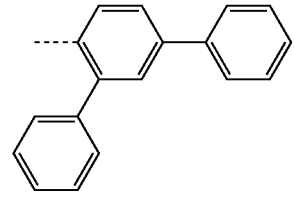 | 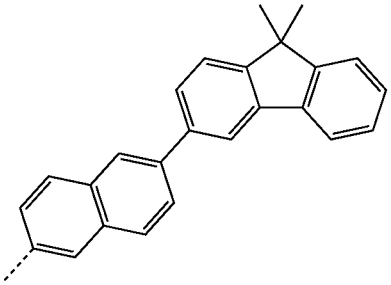 |
| 2-220 | 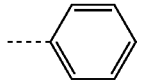 | 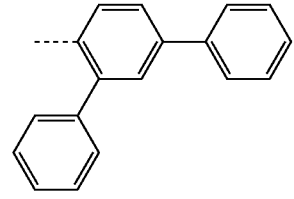 | 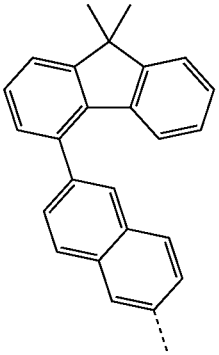 |
| 2-221 | 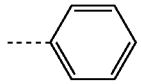 | 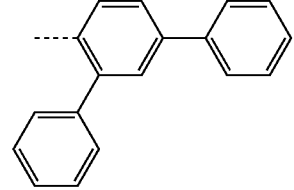 | 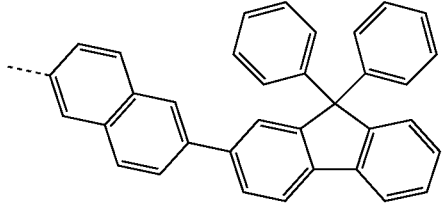 |

-continued
| Formula | ---Ar1 | ---Ar2 | ---Ar3 |
|---|---|---|---|
| 2-222 | 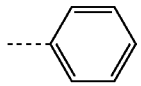 | 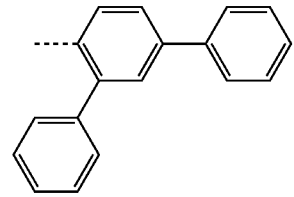 | 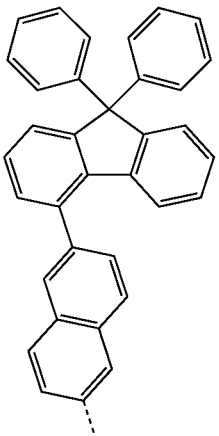 |
| 2-223 | 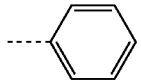 | 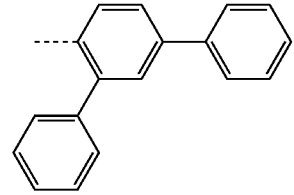 | 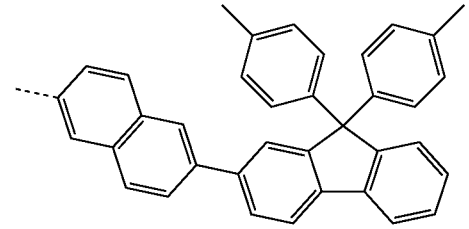 |
| 2-224 | 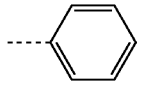 | 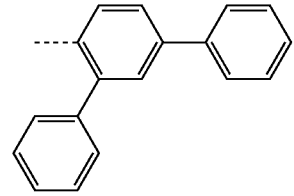 | 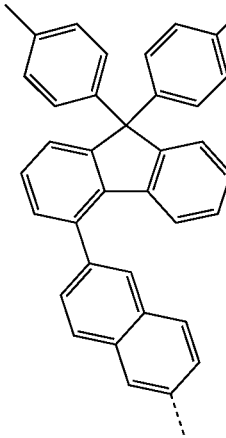 |
| 2-225 | 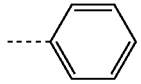 | 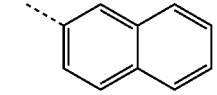 | 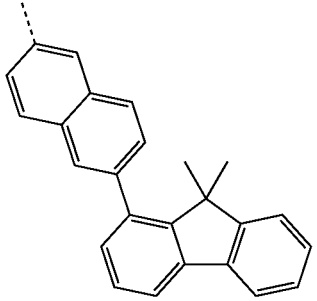 |
| 2-226 | 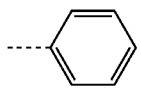 | 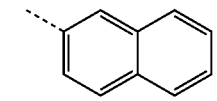 | 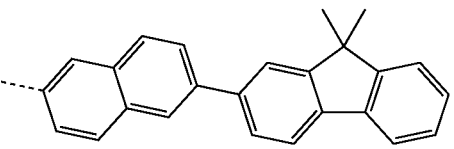 |

-continued
| Formula | ---Ar1 | ---Ar2 | ---Ar3 |
|---|---|---|---|
| 2-227 | 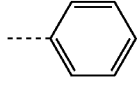 | 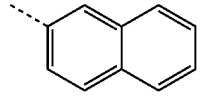 | 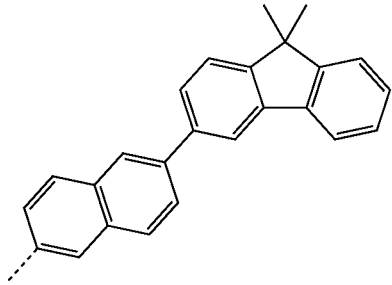 |
| 2-228 | 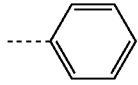 | 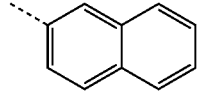 | 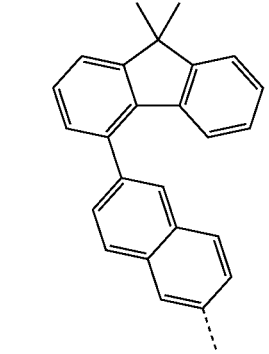 |
| 2-229 | 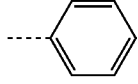 | 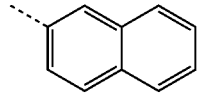 | 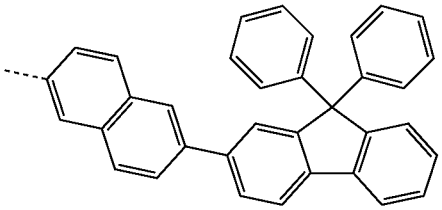 |
| 2-230 | 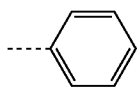 | 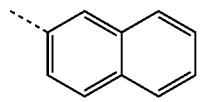 | 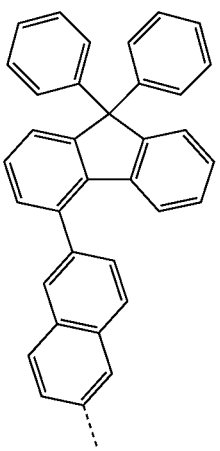 |
| 2-231 | 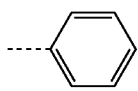 | 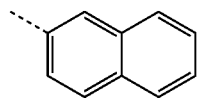 | 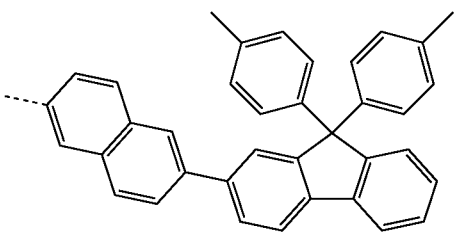 |

| Formula | ---Ar1 | ---Ar2 | ---Ar3 |
|---|---|---|---|
| 2-232 | phenyl | 2-naphthyl | 2-naphthyl-(9,9-dimethyl-benzo-fluorenyl) |
| 2-233 | phenyl | 1-naphthyl | 1-naphthyl-(9,9-dimethylfluorenyl) |
| 2-234 | phenyl | 1-naphthyl | 2-naphthyl-(9,9-dimethylfluorenyl) |
| 2-235 | phenyl | 1-naphthyl | 2-naphthyl-(9,9-dimethylfluorenyl) |
| 2-236 | phenyl | 1-naphthyl | 2-naphthyl-(9,9-dimethylfluorenyl) |
| 2-237 | phenyl | 1-naphthyl | 2-naphthyl-(9,9-diphenylfluorenyl) |

-continued
| Formula | ---Ar1 | ---Ar2 | ---Ar3 |
|---|---|---|---|
| 2-238 | 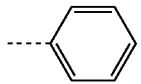 | 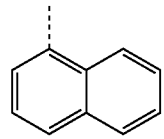 | 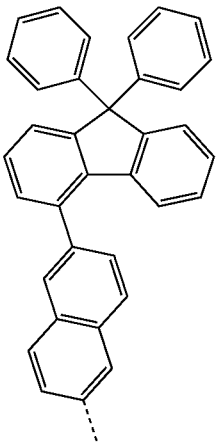 |
| 2-239 | 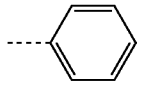 | 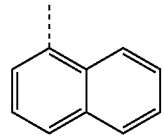 | 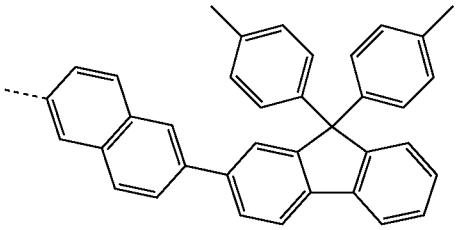 |
| 2-240 | 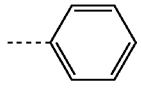 | 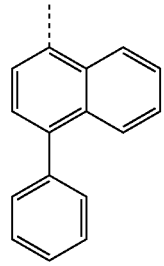 | 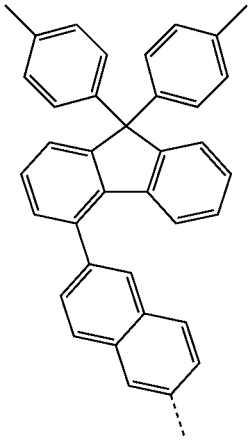 |
| 2-241 | 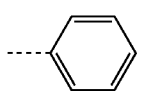 | 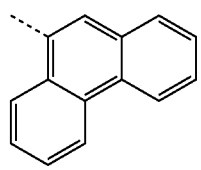 | 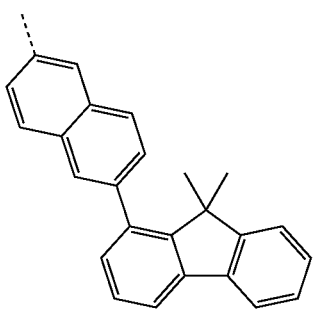 |

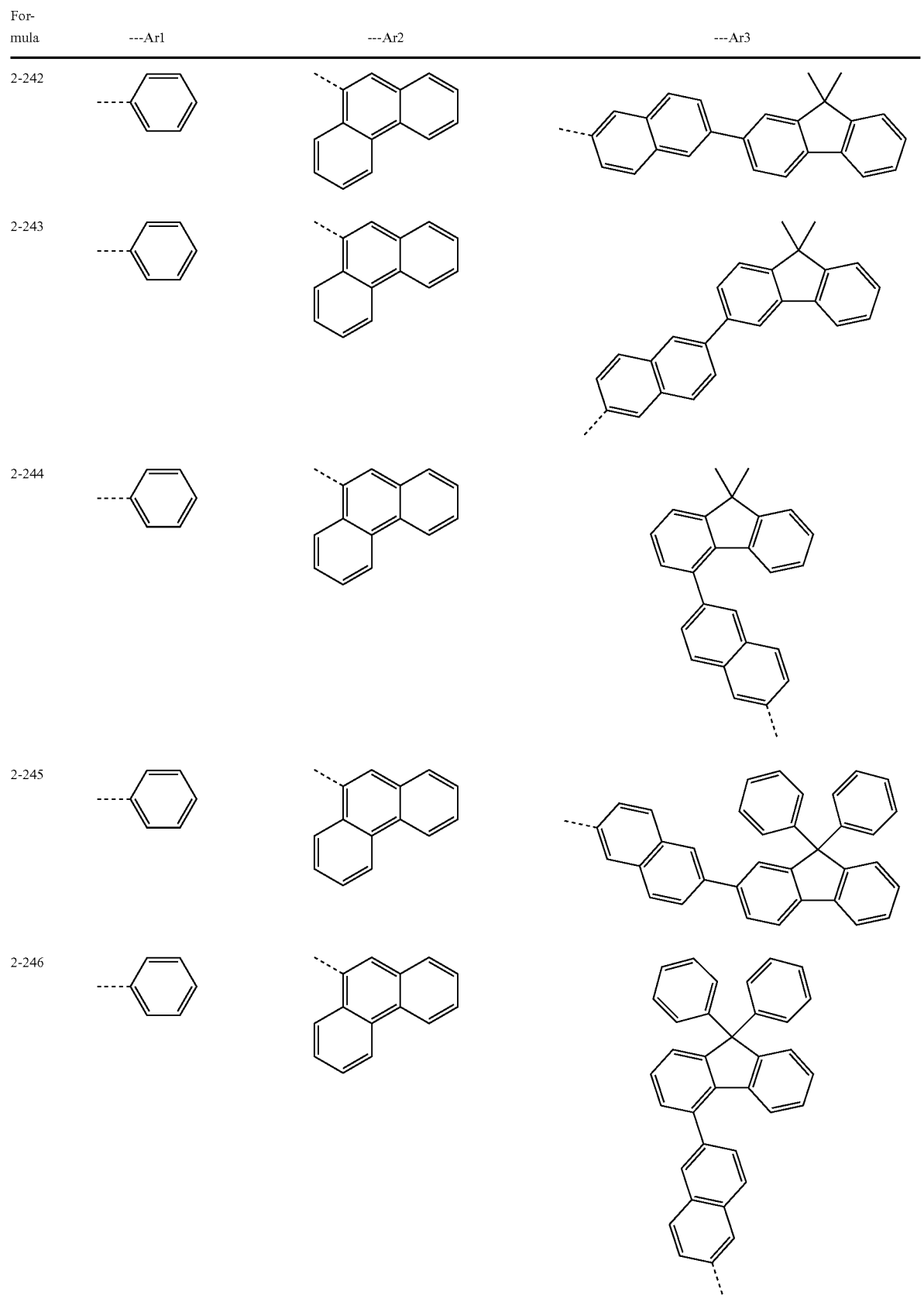

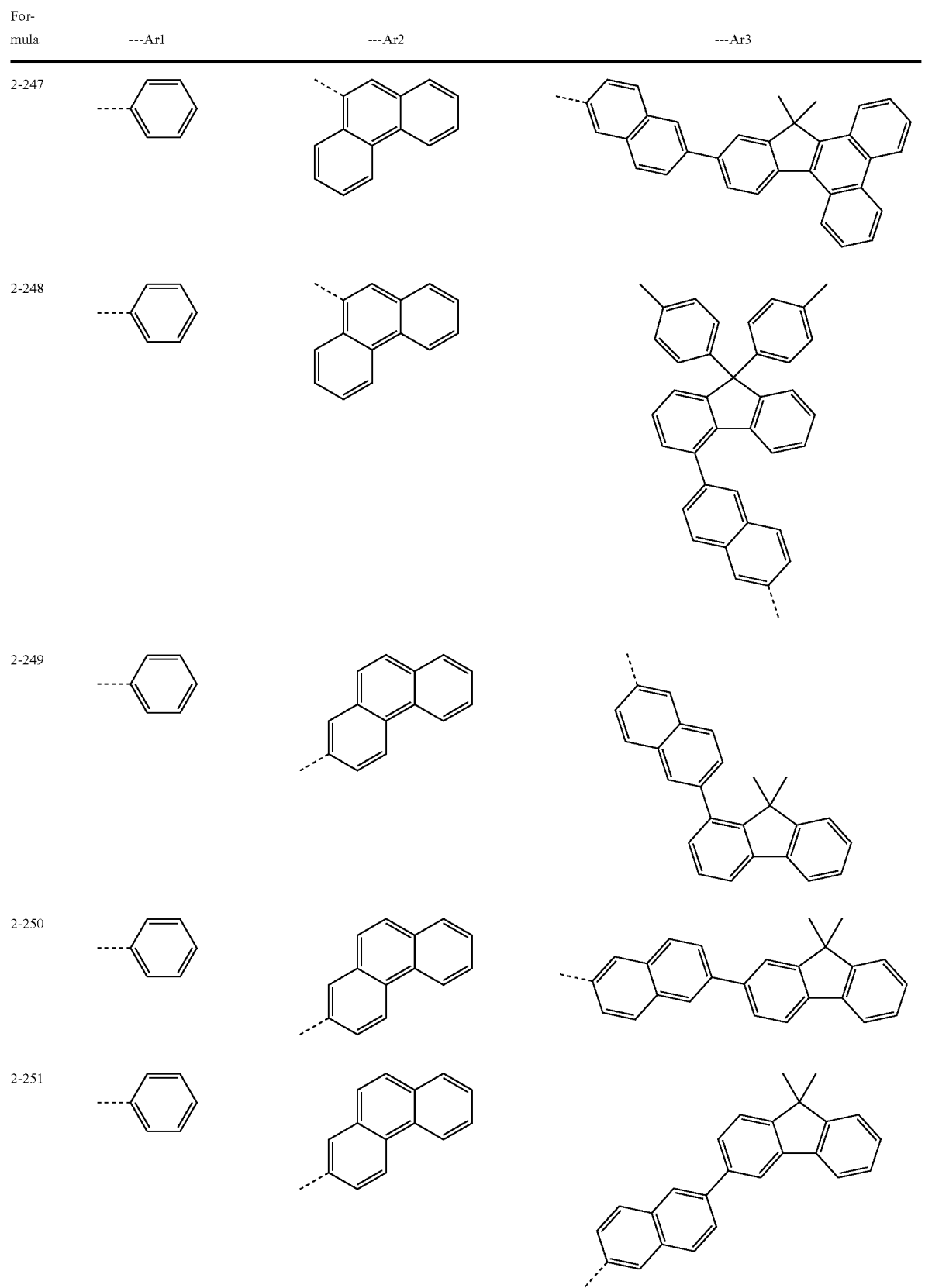

-continued
| Formula | ---Ar1 | ---Ar2 | ---Ar3 |
|---|---|---|---|
| 2-252 | 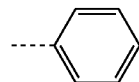 | 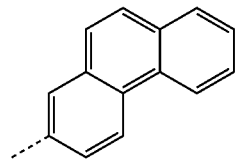 | 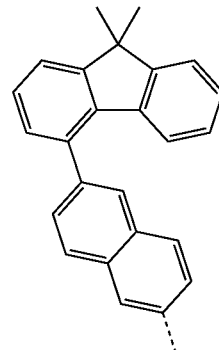 |
| 2-253 | 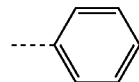 | 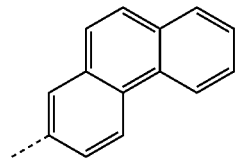 | 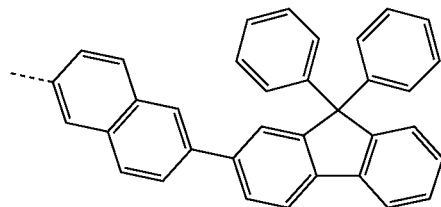 |
| 2-254 | 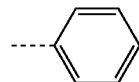 | 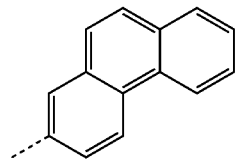 | 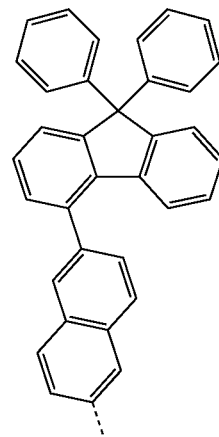 |
| 2-255 | 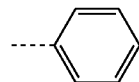 | 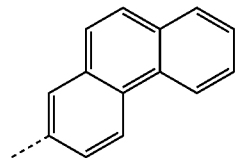 | 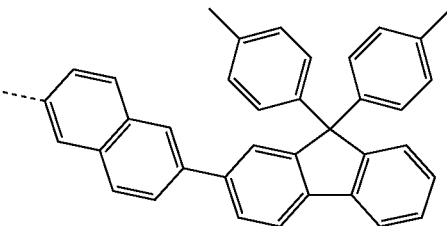 |

-continued
| Formula | ---Ar1 | ---Ar2 | ---Ar3 |
|---|---|---|---|
| 2-256 | 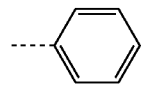 | 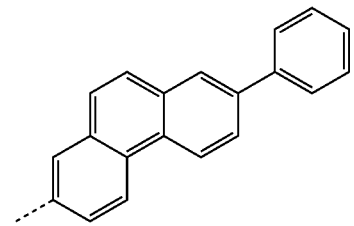 | 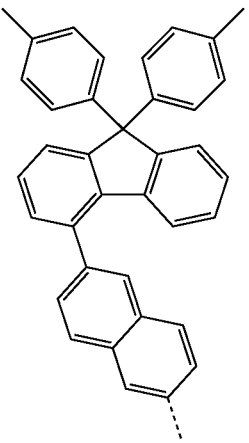 |
| 2-257 | 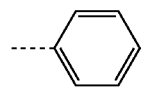 | 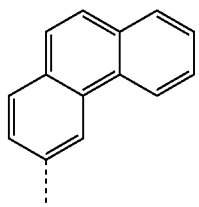 | 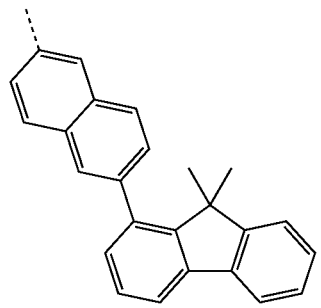 |
| 2-258 | 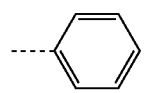 | 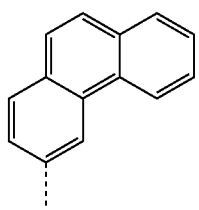 | 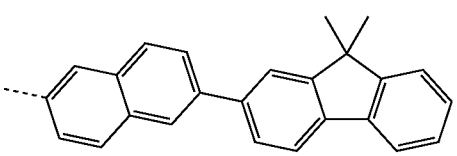 |
| 2-259 | 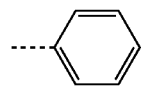 | 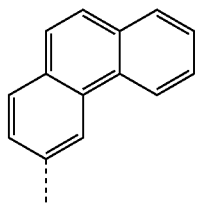 | 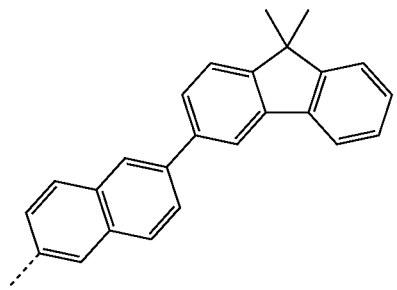 |

-continued
| Formula | ---Ar1 | ---Ar2 | ---Ar3 |
|---|---|---|---|
| 2-260 | 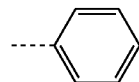 | 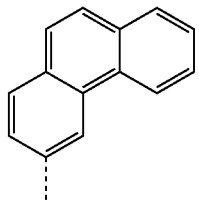 | 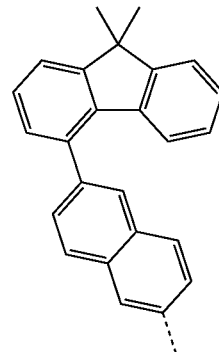 |
| 2-261 | 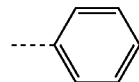 | 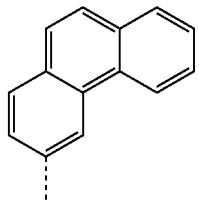 | 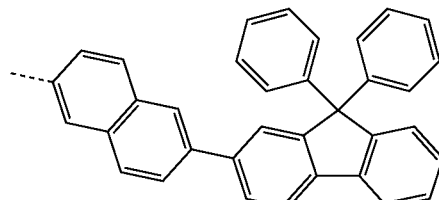 |
| 2-262 | 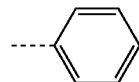 | 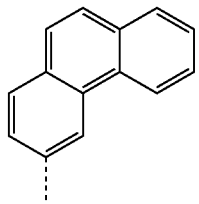 | 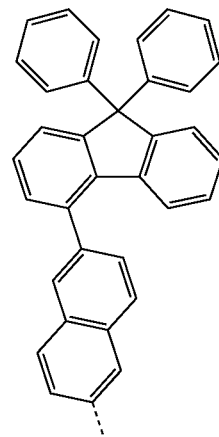 |
| 2-263 | 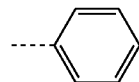 | 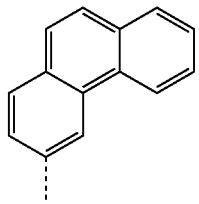 | 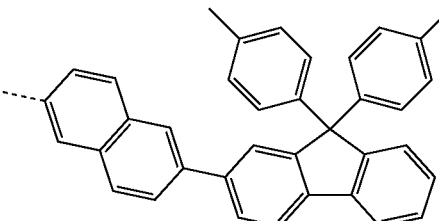 |

US 9,640,766 B2
-continued
| Formula | ---Ar1 | ---Ar2 | ---Ar3 |
|---|---|---|---|
| 2-264 | 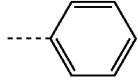 | 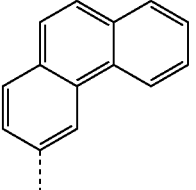 | 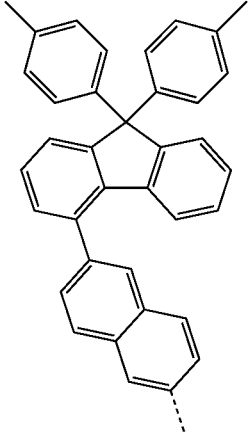 |
| 2-265 | 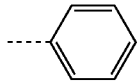 | 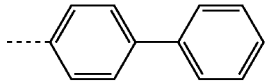 | 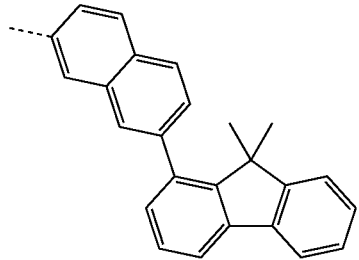 |
| 2-266 | 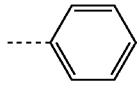 | 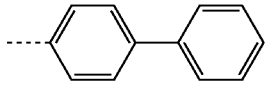 | 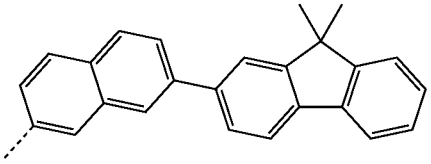 |
| 2-267 | 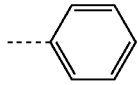 | 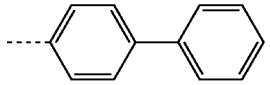 | 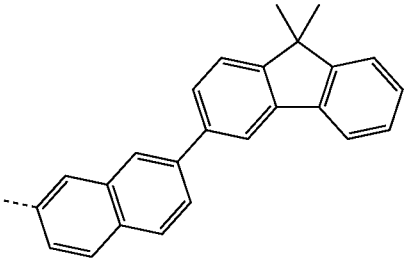 |
| 2-268 | 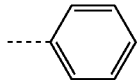 | 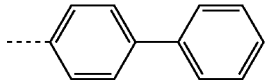 | 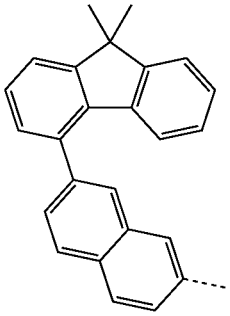 |

-continued
| Formula | ---Ar1 | ---Ar2 | ---Ar3 |
|---|---|---|---|
| 2-269 | 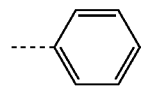 | 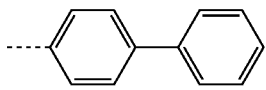 | 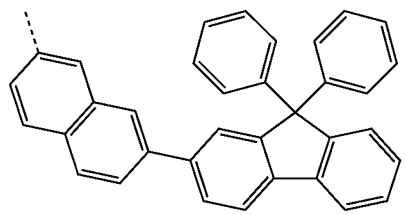 |
| 2-270 | 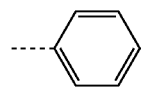 | 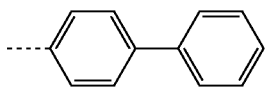 | 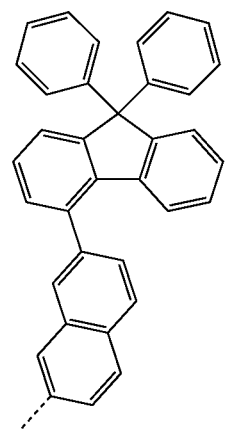 |
| 2-271 | 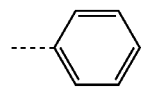 | 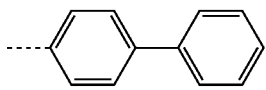 | 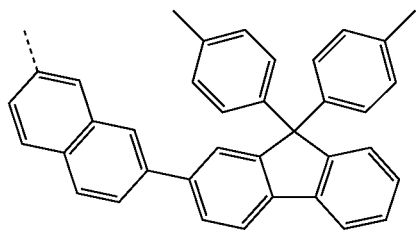 |
| 2-272 | 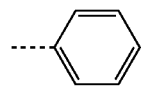 | 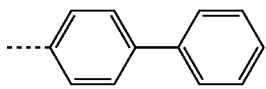 | 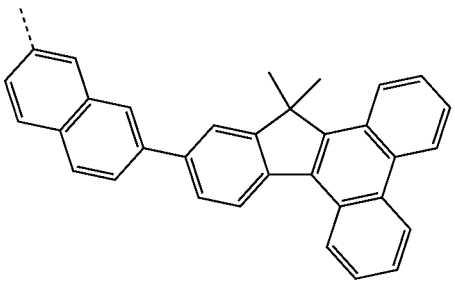 |
| 2-273 | 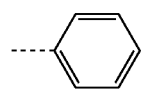 | 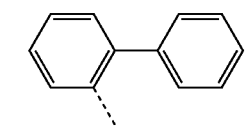 | 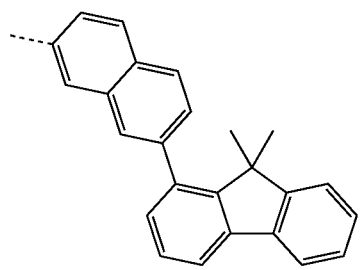 |

-continued
| Formula | ---Ar1 | ---Ar2 | ---Ar3 |
|---|---|---|---|
| 2-274 | 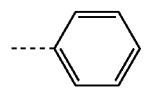 | 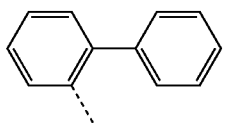 | 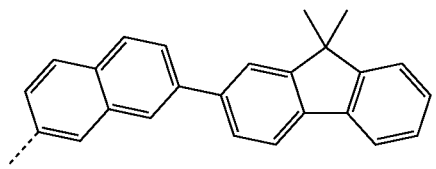 |
| 2-275 | 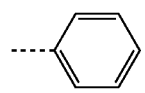 | 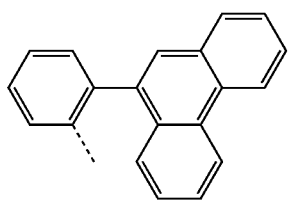 | 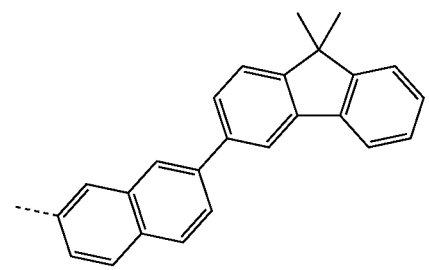 |
| 2-276 | 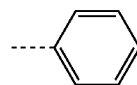 | 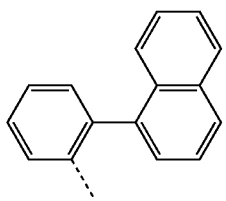 | 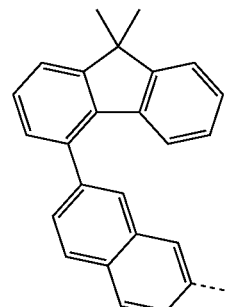 |
| 2-277 | 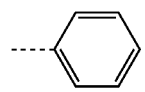 | 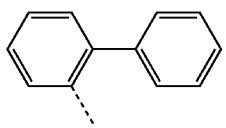 | 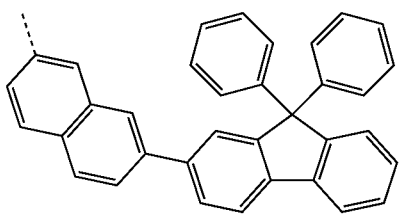 |
| 2-278 | 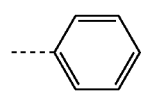 | 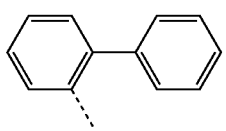 | 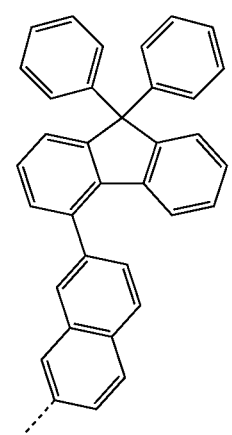 |

-continued

| Formula | ---Ar1 | ---Ar2 | ---Ar3 |
|---|---|---|---|
| 2-279 | phenyl | 2-biphenyl | 9,9-di(p-tolyl)-2-(naphthalen-2-yl)fluorene |
| 2-280 | phenyl | 2-biphenyl | benzo-fused fluorene-naphthalene |
| 2-281 | phenyl | 3-biphenyl | 9,9-dimethylfluorene-naphthalene |
| 2-282 | phenyl | 3-biphenyl | 9,9-dimethylfluorene-naphthalene |
| 2-283 | phenyl | 3-biphenyl | 9,9-dimethylfluorene-naphthalene |
| 2-284 | phenyl | 3-biphenyl | 9,9-dimethylfluorene-naphthalene |

-continued

| Formula | ---Ar1 | ---Ar2 | ---Ar3 |
|---|---|---|---|
| 2-285 | phenyl | biphenyl | 2-(9,9-diphenylfluoren-2-yl)naphthalen-6-yl |
| 2-286 | phenyl | biphenyl | 4-(6-substituted-naphthalen-2-yl)-9,9-diphenylfluoren-yl |
| 2-287 | phenyl | biphenyl | 2-(9,9-di-p-tolylfluoren-2-yl)naphthalen-6-yl |
| 2-288 | phenyl | biphenyl | 4-(6-substituted-naphthalen-2-yl)-9,9-di-p-tolylfluoren-yl |
| 2-289 | phenyl | p-terphenyl | 1-(9,9-dimethylfluoren-4-yl)naphthalen-6-yl |

-continued
| Formula | ---Ar1 | ---Ar2 | ---Ar3 |
|---|---|---|---|
| 2-290 | 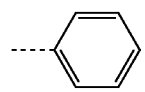 | 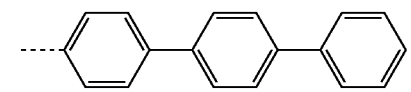 | 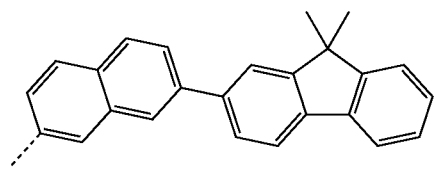 |
| 2-291 | 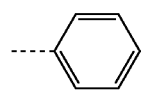 | 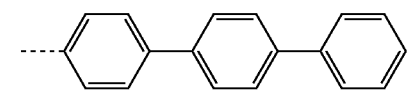 | 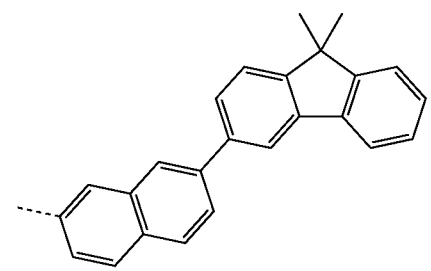 |
| 2-292 | 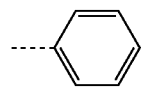 | 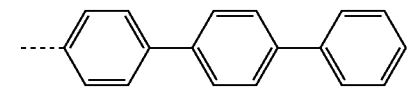 | 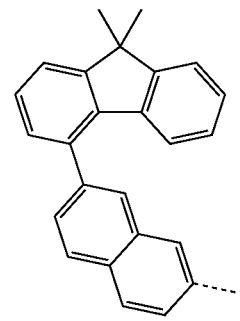 |
| 2-293 | 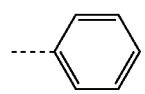 | 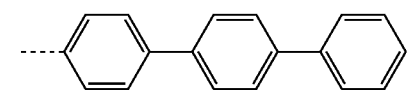 | 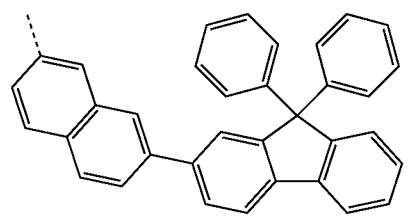 |
| 2-294 | 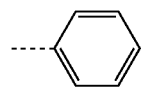 | 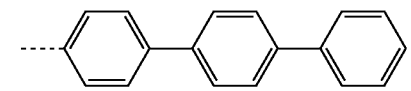 | 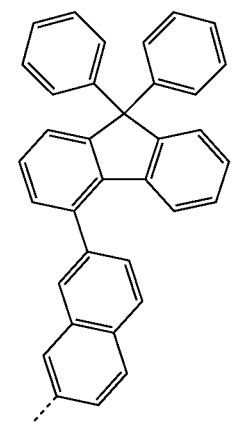 |

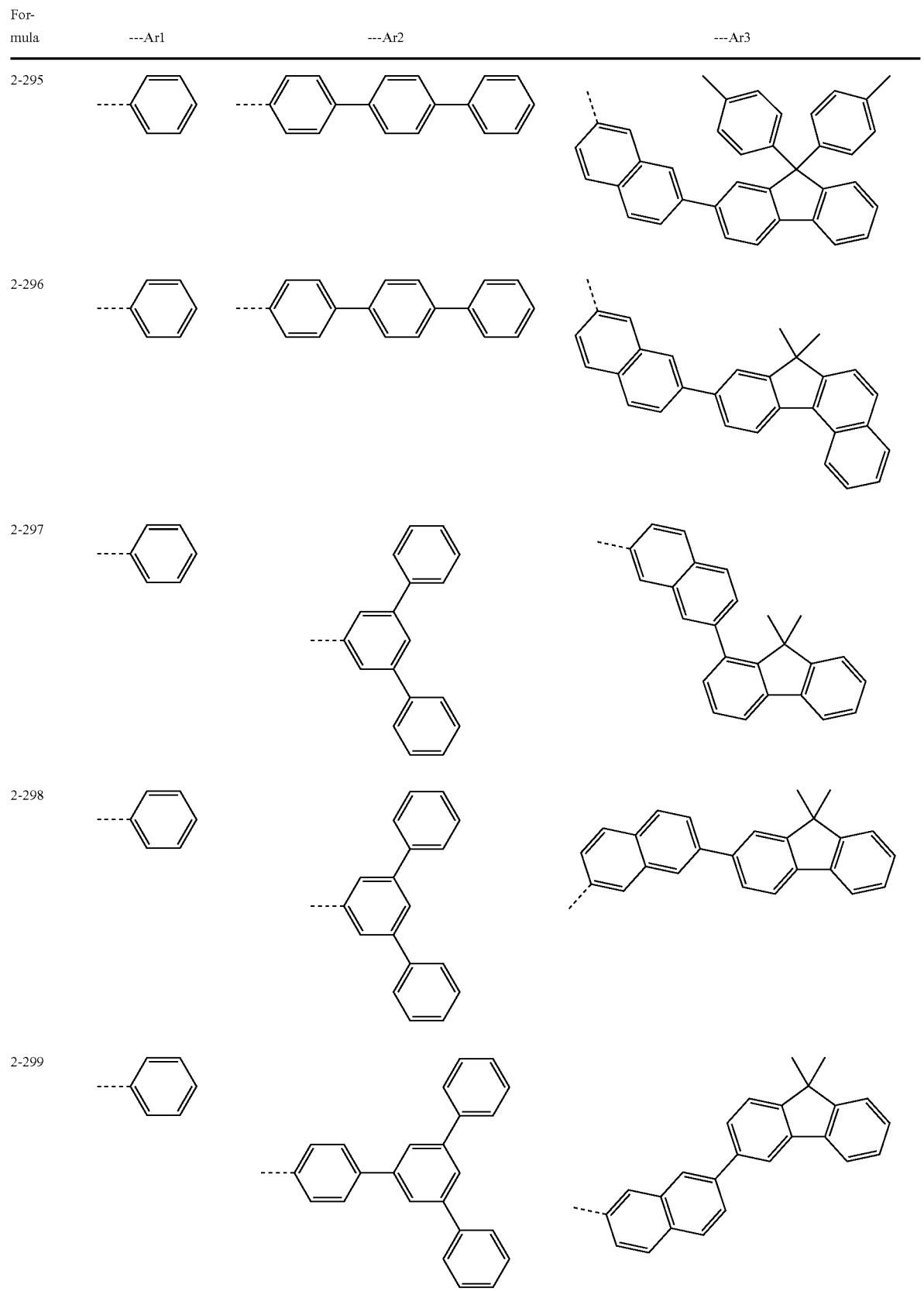

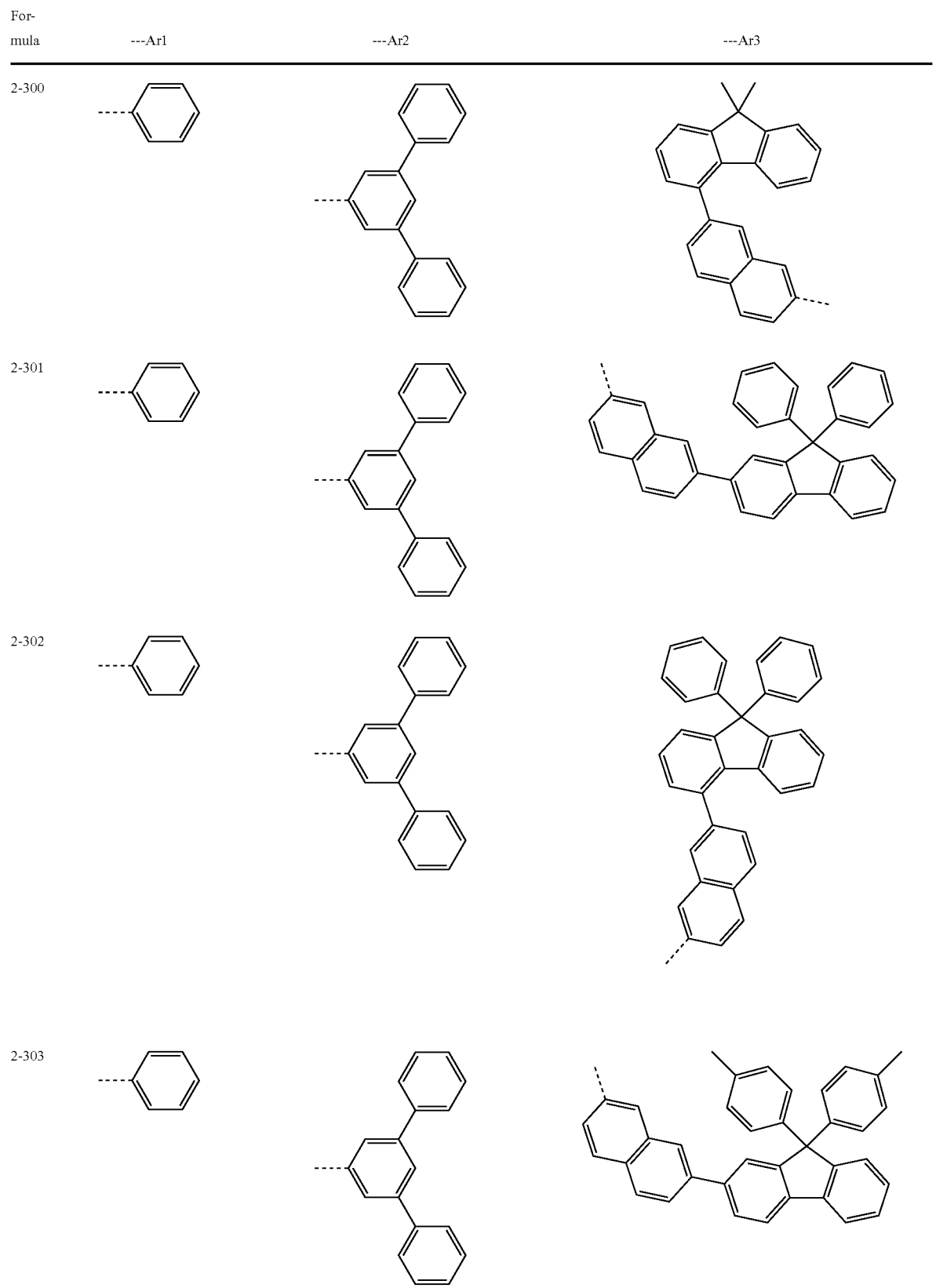

| Formula | ---Ar1 | ---Ar2 | ---Ar3 |
|---|---|---|---|
| 2-304 |  |  | 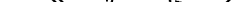 |
| 2-305 |  | 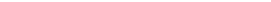 | 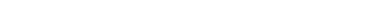 |
| 2-306 |  |  | 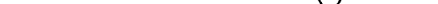 |
| 2-307 |  |  | 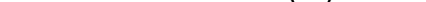 |
| 2-308 |  |  |  |

-continued
| Formula | ---Ar1 | ---Ar2 | ---Ar3 |
|---|---|---|---|
| 2-309 | 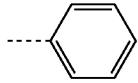 | 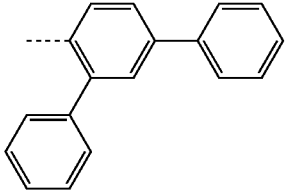 | 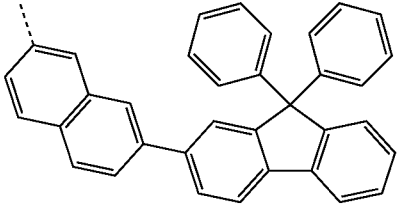 |
| 2-310 | 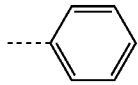 | 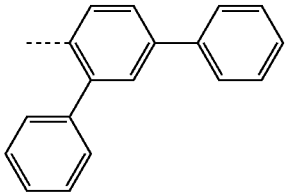 | 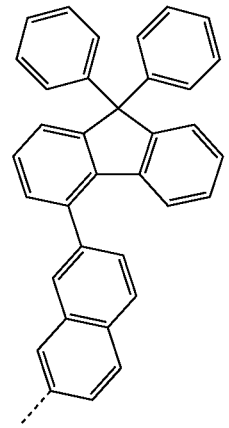 |
| 2-311 | 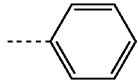 | 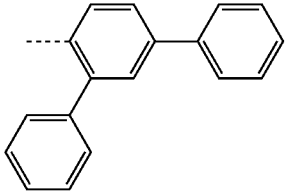 | 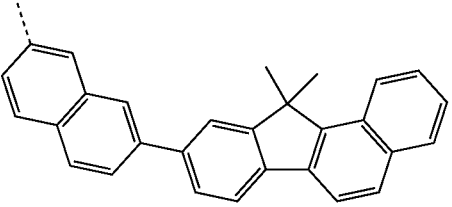 |
| 2-312 | 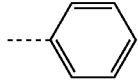 | 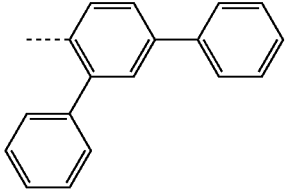 | 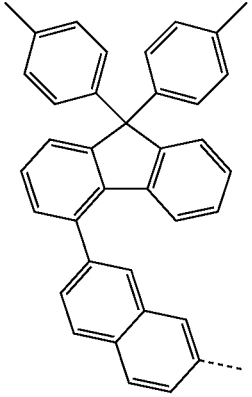 |
| 2-313 | 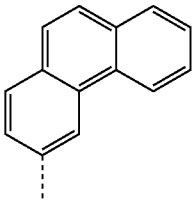 | 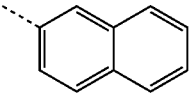 | 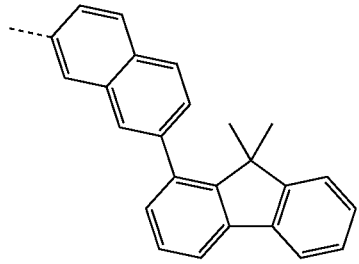 |

-continued
| Formula | ---Ar1 | ---Ar2 | ---Ar3 |
| --- | --- | --- | --- |
| 2-314 | 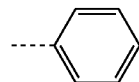 | 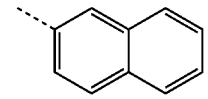 | 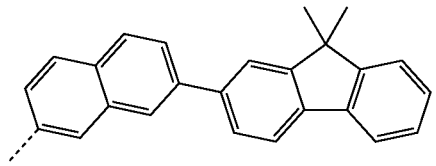 |
| 2-315 | 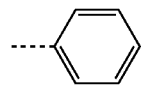 | 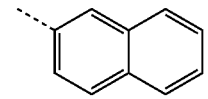 | 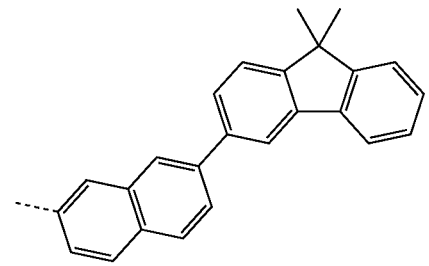 |
| 2-316 | 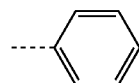 | 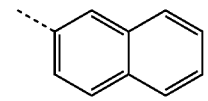 | 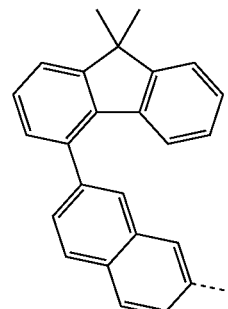 |
| 2-317 | 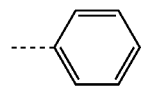 | 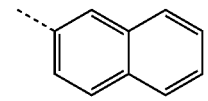 | 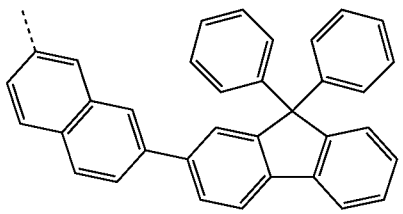 |
| 2-318 | 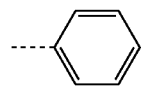 | 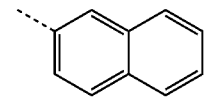 | 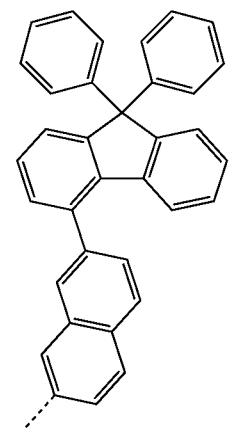 |

-continued

| Formula | ---Ar1 | ---Ar2 | ---Ar3 |
|---|---|---|---|
| 2-319 | phenyl | 2-naphthyl | 2-naphthyl-9,9-di(p-tolyl)fluorene |
| 2-320 | phenyl | 2-naphthyl | 9,9-di(p-tolyl)fluorene-4-yl linked to 2-naphthyl |
| 2-321 | phenyl | 1-naphthyl | 9,9-dimethylfluorene linked to 2-naphthyl |
| 2-322 | phenyl | 1-naphthyl | 2-naphthyl-9,9-dimethylfluorene |
| 2-323 | phenyl | 1-naphthyl | 9,9-dimethylfluorene linked to 2-naphthyl |

-continued
| Formula | ---Ar1 | ---Ar2 | ---Ar3 |
|---|---|---|---|
| 2-324 | 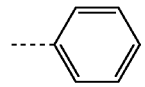 | 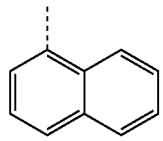 | 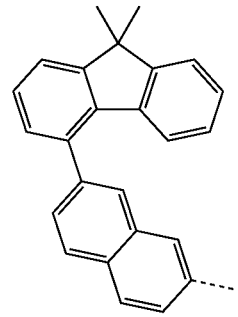 |
| 2-325 | 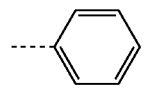 | 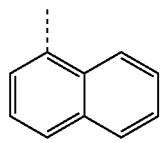 | 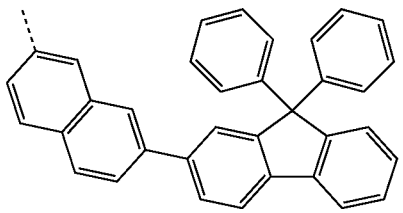 |
| 2-326 | 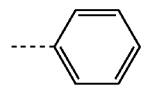 | 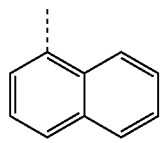 | 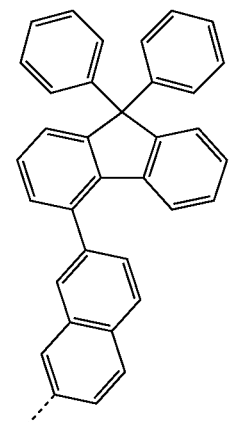 |
| 2-327 | 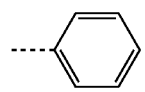 | 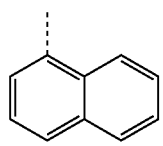 | 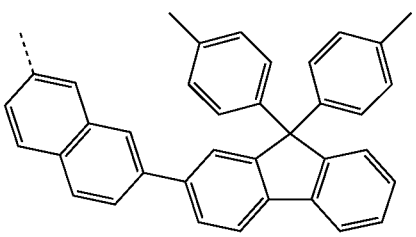 |

751 752
-continued
| Formula | ---Ar1 | ---Ar2 | ---Ar3 |
|---|---|---|---|
| 2-328 | 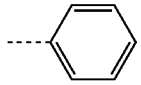 | 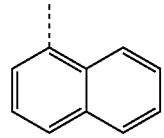 | 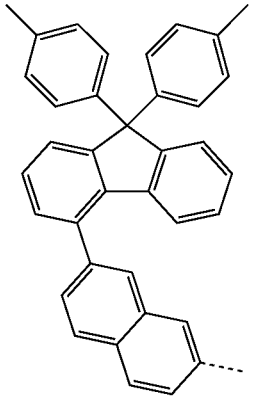 |
| 2-329 | 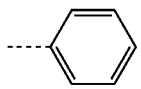 | 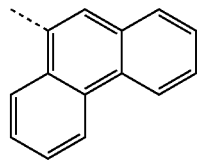 | 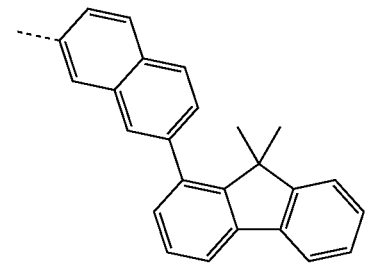 |
| 2-330 | 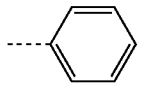 | 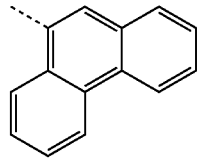 | 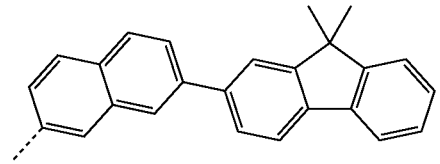 |
| 2-331 | 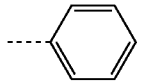 | 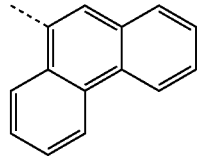 | 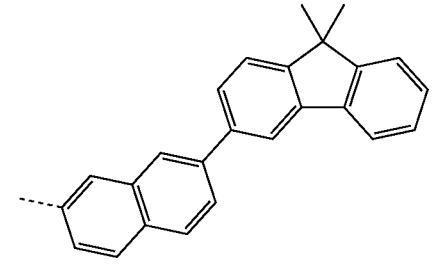 |
| 2-332 | 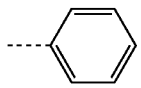 | 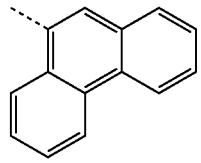 | 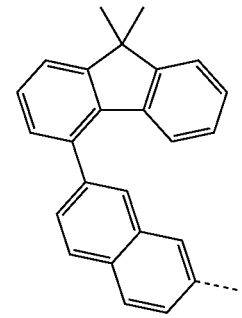 |

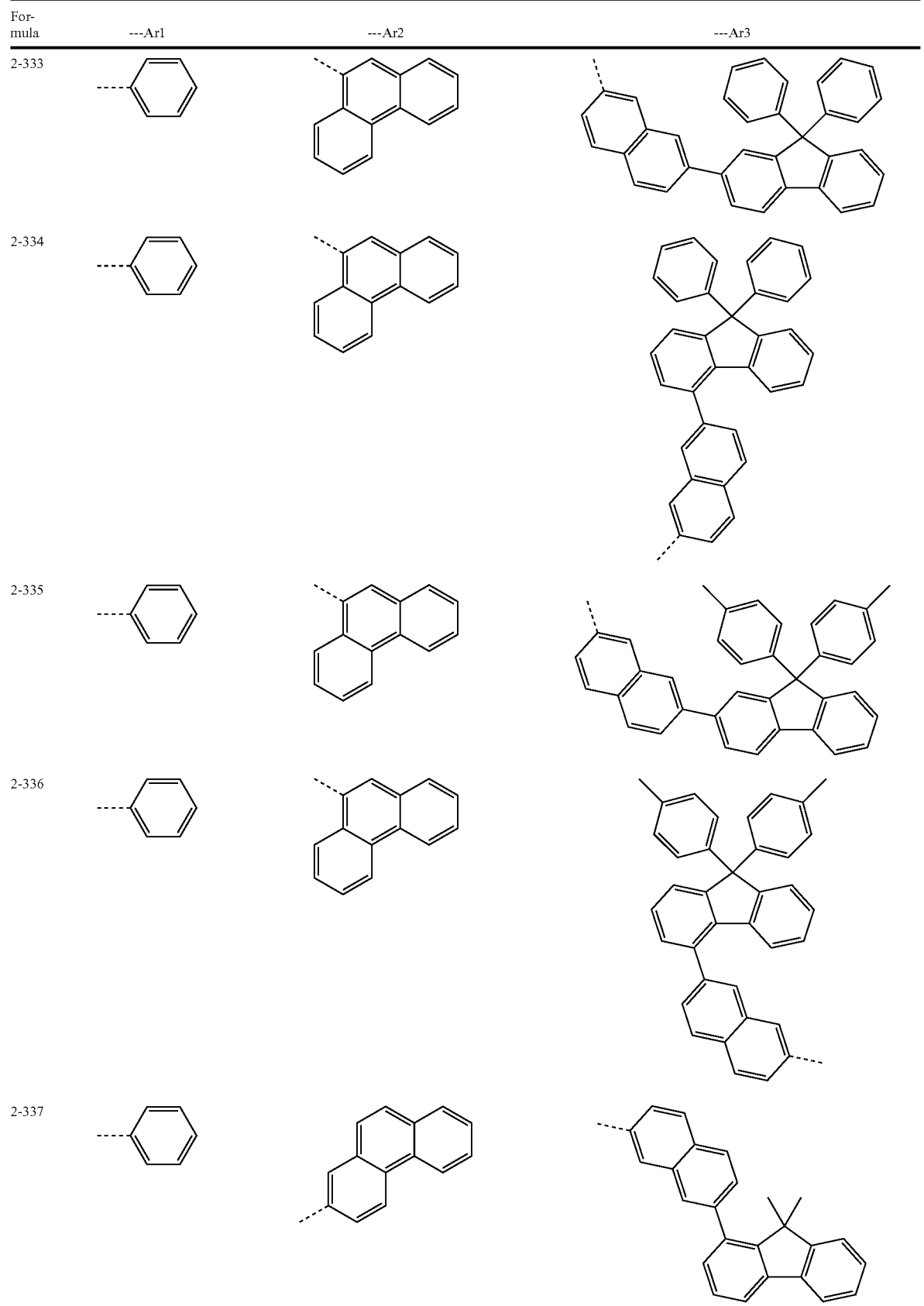

-continued
| Formula | ---Ar1 | ---Ar2 | ---Ar3 |
|---|---|---|---|
| 2-338 | 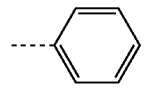 | 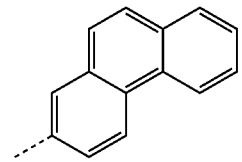 | 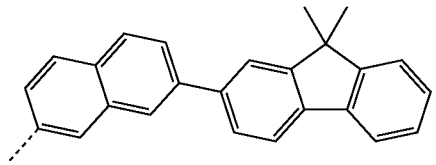 |
| 2-339 | 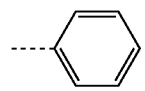 | 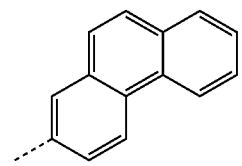 | 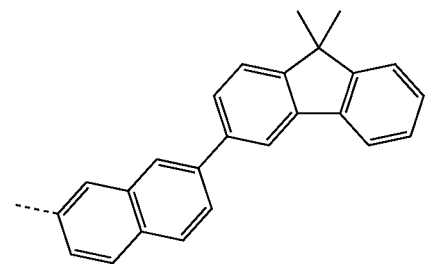 |
| 2-340 | 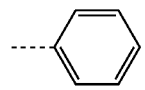 | 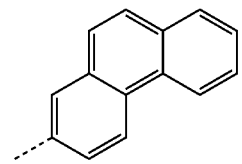 | 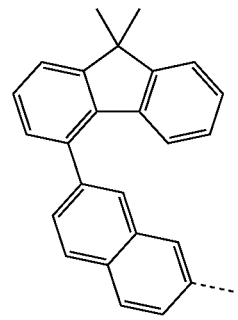 |
| 2-341 | 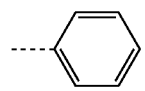 | 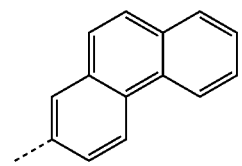 | 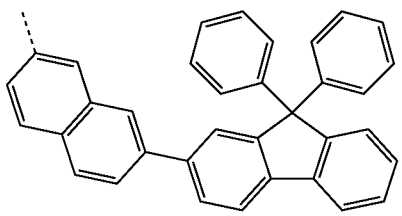 |
| 2-342 | 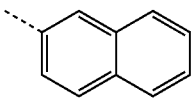 | 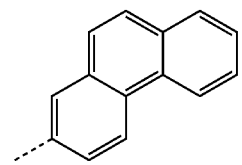 | 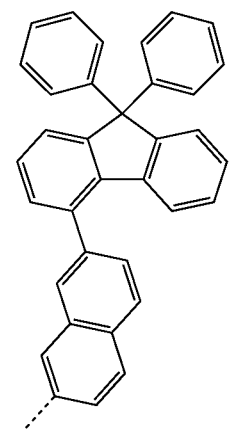 |

-continued

| Formula | ---Ar1 | ---Ar2 | ---Ar3 |
|---|---|---|---|
| 2-343 | | | |
| 2-344 | | | |
| 2-345 | | | |
| 2-346 | | | |
| 2-347 | | | |

-continued

| Formula | ---Ar1 | ---Ar2 | ---Ar3 |
|---|---|---|---|
| 2-348 | | | |
| 2-349 | | | |
| 2-350 | | | |
| 2-351 | | | |
| 2-352 | | | |

-continued

| Formula | ---Ar1 | ---Ar2 | ---Ar3 |
|---|---|---|---|
| 2-353 | | | |
| 2-354 | | | |
| 2-355 | | | |
| 2-356 | | | |
| 2-357 | | | |
| 2-358 | | | |

| Formula | ---Ar1 | ---Ar2 | ---Ar3 |
|---|---|---|---|
| 2-359 | | | |
| 2-360 | | | |
| 2-361 | | | |
| 2-362 | | | |
| 2-363 | | | |

15. The organic light emitting diode of claim 1, wherein the organic material layer comprising the carbazole derivative represented by Formula 3 is a hole transporting layer, a hole injection layer, or a layer which simultaneously transports and injects holes.

16. The organic light emitting diode of claim 1, wherein a hole mobility of the compound represented by Formula 3 is $5 \times 10^{-6}$ cm$^2$/Vs or more.

17. The organic light emitting diode of claim 1, wherein Ar4 and Ar5 are the same as or different from each other, and each independently a substituted or unsubstituted phenyl group; a substituted or unsubstituted biphenyl group; or a substituted or unsubstituted fluorenyl group.

18. The organic light emitting diode of claim 1, wherein L2 is a direct bond; a substituted or unsubstituted phenylene group; a substituted or unsubstituted biphenylylene group; or a substituted or unsubstituted naphthalene group.

19. The organic light emitting diode of claim 1, wherein Y1 and Y2 are the same as or different from each other, and each independently a substituted or unsubstituted alkyl group having 1 to 10 carbon atoms; or a substituted or unsubstituted phenyl group, or combine with each other to form a substituted or unsubstituted fluorene structure.

20. The organic light emitting diode of claim 1, wherein the carbazole derivative represented by Formula 3 is represented by any one of the following Formulae 3-1 to 3-22
Formula 3-1
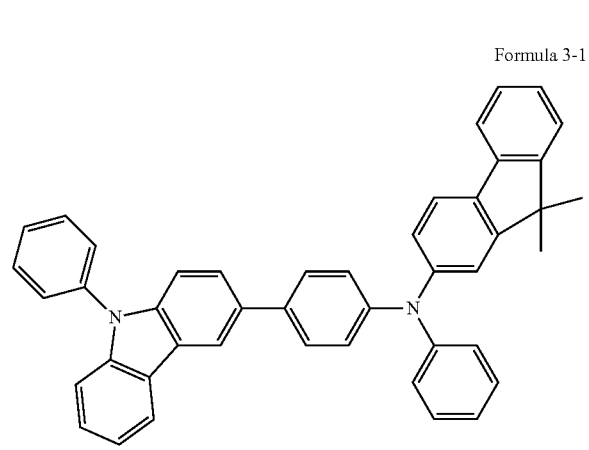
Formula 3-2
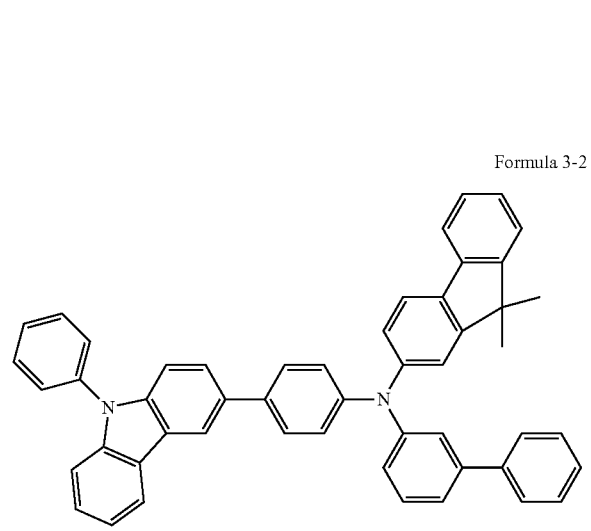
Formula 3-3
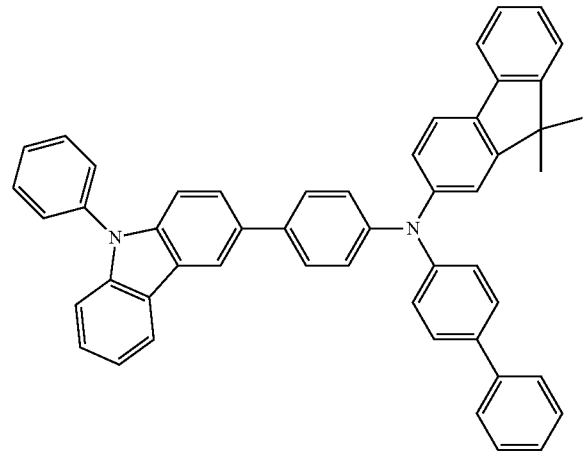
Formula 3-4
Formula 3-5
Formula 3-6
Formula 3-7
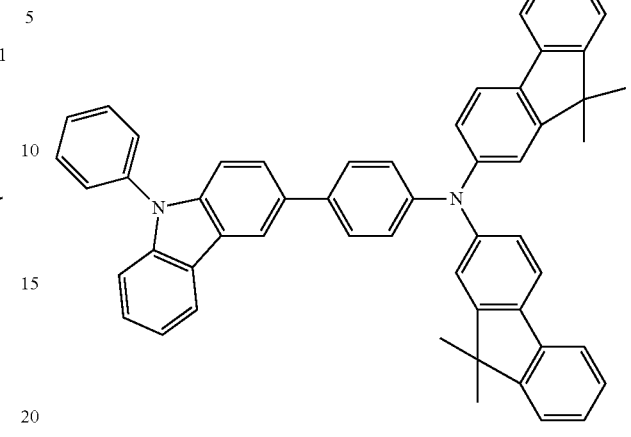
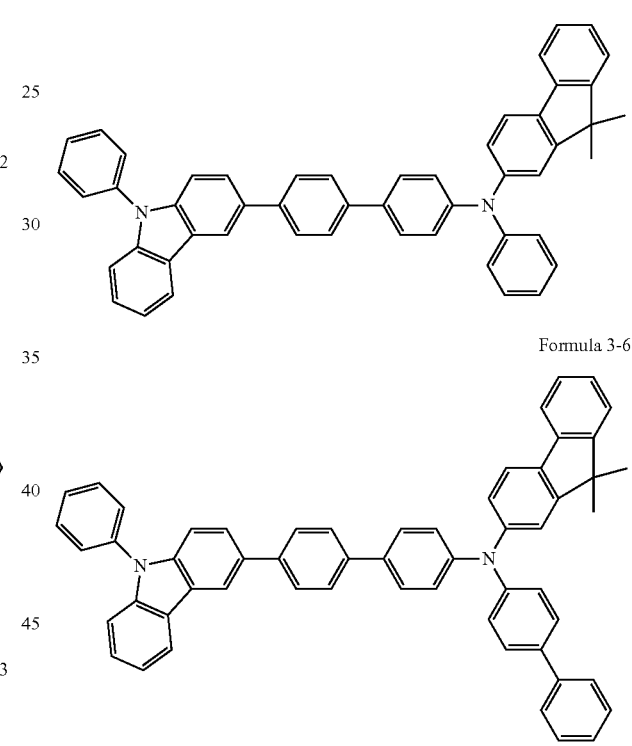

-continued
Formula 3-8
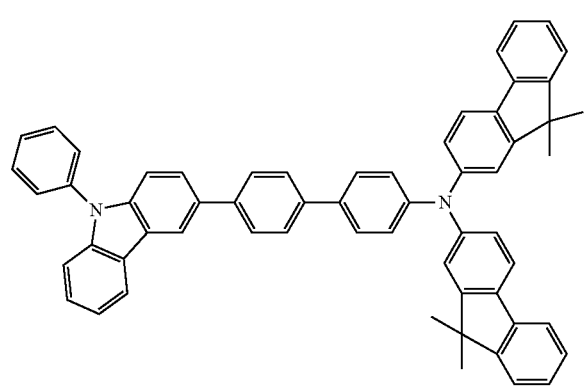
Formula 3-9
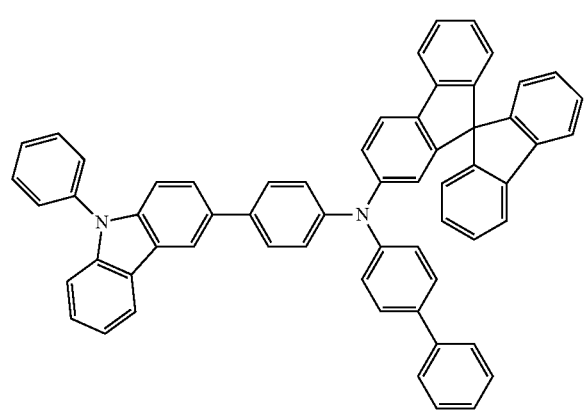
Formula 3-10
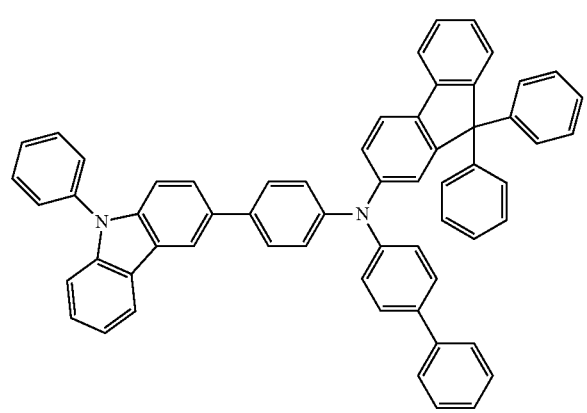
-continued
Formula 3-11
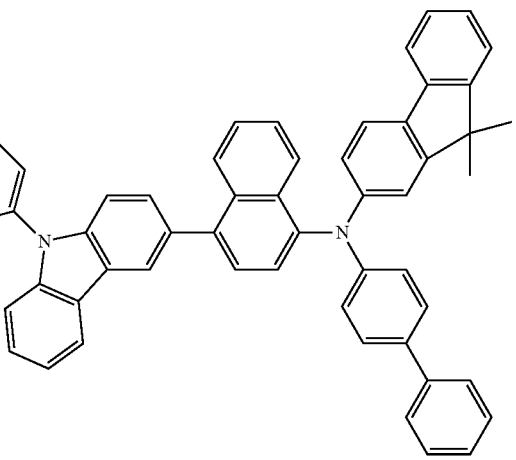
Formula 3-12
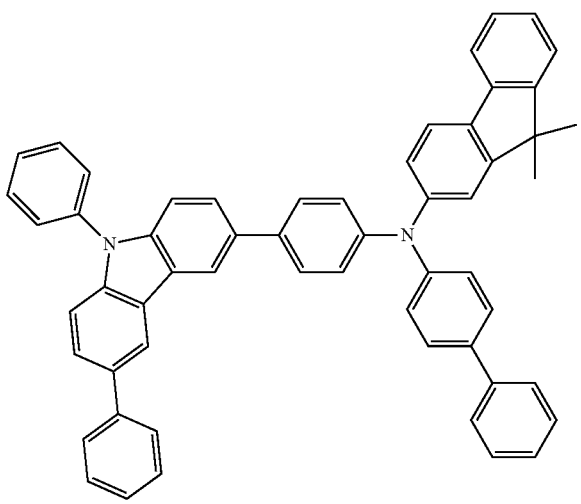
Formula 3-13
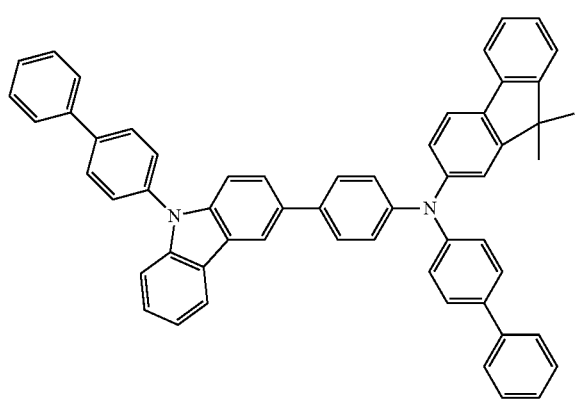

769
-continued
Formula 3-14
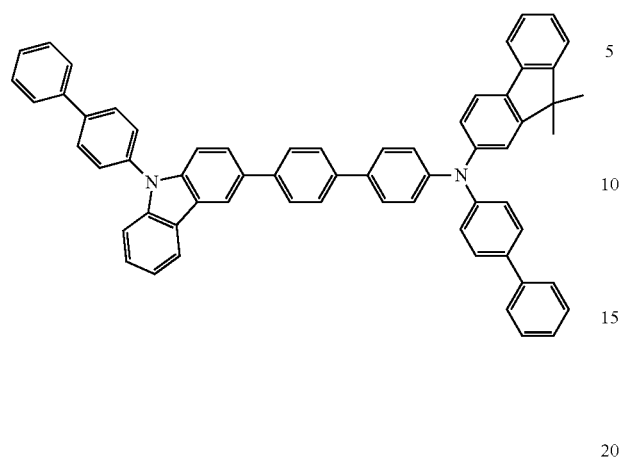
Formula 3-15
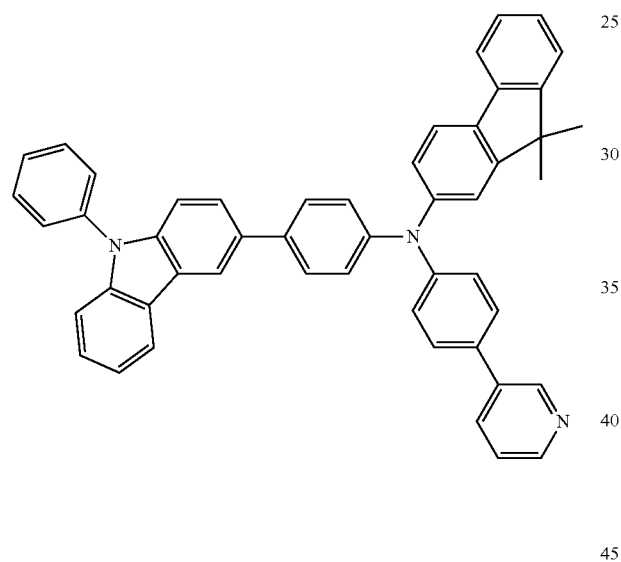
Formula 3-16
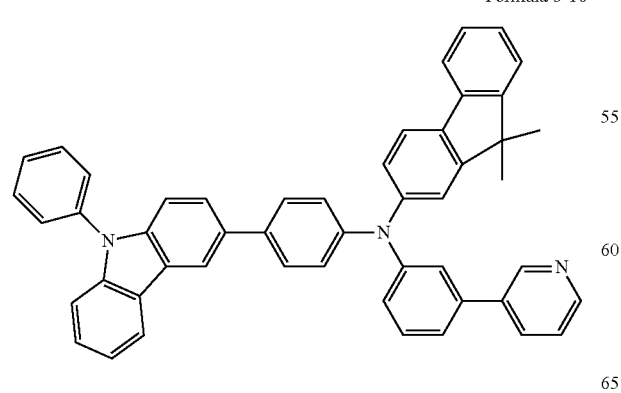
770
-continued
Formula 3-17
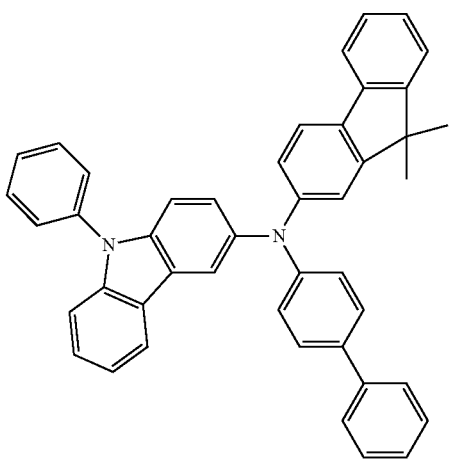
Formula 3-18
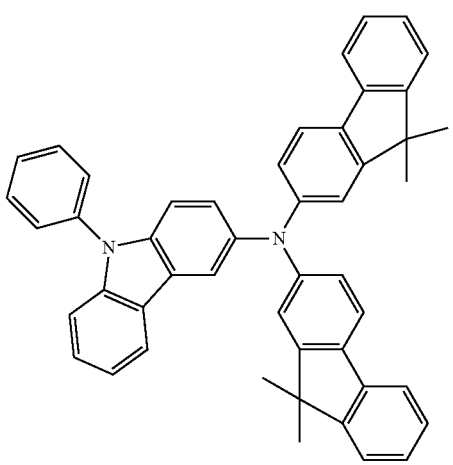
Formula 3-19
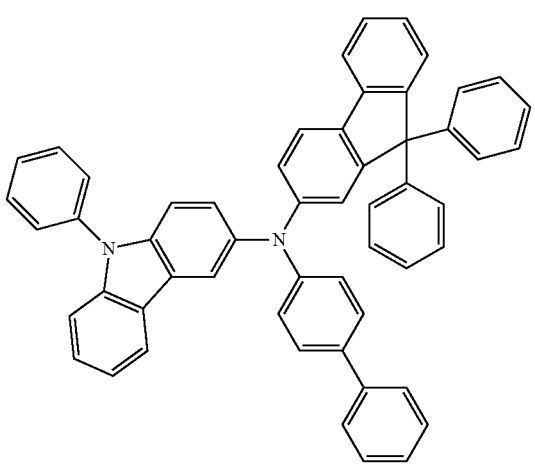

Formula 3-20

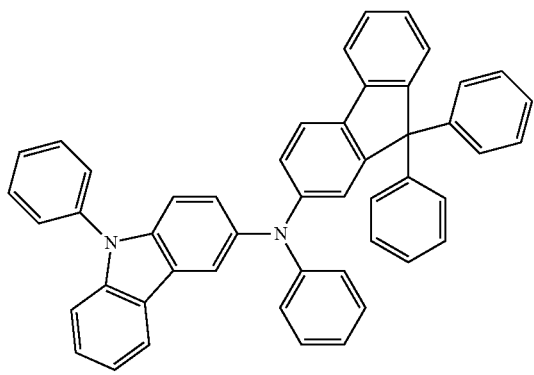

Formula 3-21

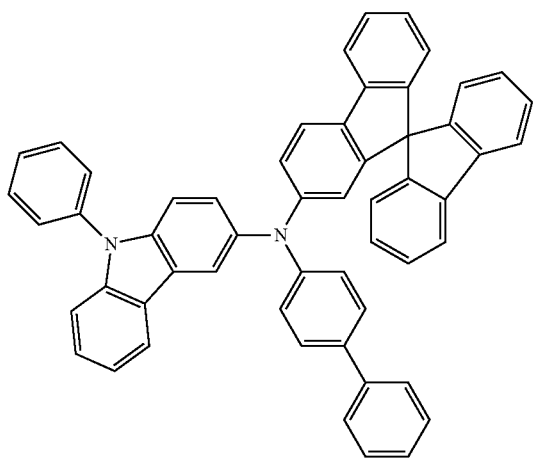

Formula 3-22

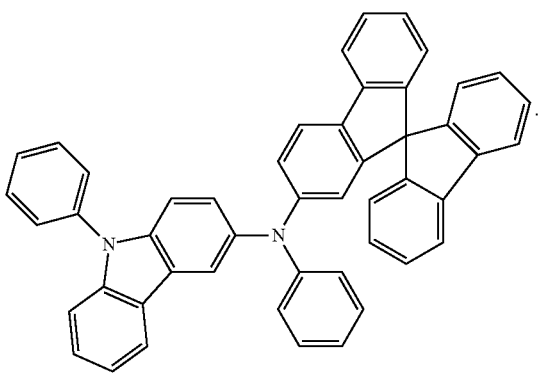

21. The organic light emitting diode of claim 1, wherein the organic light emitting diode emits blue fluorescent light.

22. The organic light emitting diode of claim 1, wherein the organic light emitting diode further comprises an acceptor layer comprising an acceptor material represented by the following Formula 4 between the anode and the organic material layer comprising the carbazole derivative represented by Formula 3:

[Formula 4]

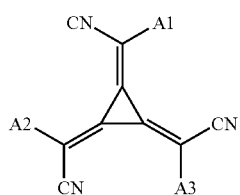

in Formula 4,

A1 to A3 are the same as or different from each other, and each independently an aryl group, which is unsubstituted or substituted with one or two or more substituents selected from the group consisting of a cyano group, a halogen group, and a haloalkyl group; or a heterocyclic group, which is unsubstituted or substituted with one or two or more substituents selected from the group consisting of a cyano group, a halogen group, and a haloalkyl group.

23. The organic light emitting diode of claim 22, wherein the acceptor layer further comprises the carbazole derivative represented by Formula 3.

24. The organic light emitting diode of claim 22, wherein the acceptor material represented by Formula 4 is present in an amount of 1 wt % to 30 wt % based on a total weight of the acceptor layer.

* * * * *